US012441803B2

(12) United States Patent
Greving et al.

(10) Patent No.: US 12,441,803 B2
(45) Date of Patent: Oct. 14, 2025

(54) ENGINEERED CD25 POLYPEPTIDES AND USES THEREOF

(71) Applicant: iBio, Inc., Bryan, TX (US)

(72) Inventors: Matthew P. Greving, San Carlos, CA (US); Phung Tu Gip, San Francisco, CA (US); Mohan Srinivasan, Cupertino, CA (US); Andrew Morin, San Mateo, CA (US); Kevin Eduard Hauser, Jupiter, FL (US); Jordan R. Willis, Hayward, CA (US); Cody A. Moore, San Francisco, CA (US); Christian Barrett, San Diego, CA (US); Alex T. Taguchi, San Mateo, CA (US); Angeles Estelles, Belmont, CA (US)

(73) Assignee: iBio, Inc., San Diego, CA (US)

( * ) Notice: Subject to any disclaimer, the term of this patent is extended or adjusted under 35 U.S.C. 154(b) by 1035 days.

(21) Appl. No.: 17/320,118

(22) Filed: May 13, 2021

(65) Prior Publication Data

US 2023/0016112 A1 Jan. 19, 2023

Related U.S. Application Data

(63) Continuation of application No. PCT/US2019/061567, filed on Nov. 14, 2019.

(60) Provisional application No. 62/902,334, filed on Sep. 18, 2019, provisional application No. 62/767,431, filed on Nov. 14, 2018.

(51) Int. Cl.
*C07K 16/28* (2006.01)

(52) U.S. Cl.
CPC ...... *C07K 16/2866* (2013.01); *C07K 2317/34* (2013.01); *C07K 2317/565* (2013.01)

(58) Field of Classification Search
CPC ...................... C07K 2317/34; C07K 2317/565
See application file for complete search history.

(56) References Cited

U.S. PATENT DOCUMENTS

| | | | |
|---|---|---|---|
| 7,438,907 B2 | 10/2008 | Schuurman et al. | |
| 2012/0276125 A1 | 11/2012 | Ast et al. | |
| 2017/0342112 A1 | 11/2017 | Altermann et al. | |
| 2018/0141999 A1 | 5/2018 | Chandran et al. | |
| 2019/0300592 A1* | 10/2019 | Struthers ............ | C07K 14/7155 |
| 2020/0010554 A1 | 1/2020 | Goubier et al. | |

FOREIGN PATENT DOCUMENTS

| | | | |
|---|---|---|---|
| CN | 1279057 | C | 10/2006 |
| WO | WO-2011/051327 | A2 | 5/2011 |
| WO | WO-2011/051327 | A3 | 5/2011 |
| WO | WO-2014/028776 | A1 | 2/2014 |
| WO | WO-2014/145907 | A1 | 9/2014 |
| WO | 2014160463 | A1 | 10/2014 |
| WO | 2016040110 | A1 | 3/2016 |
| WO | WO-2018/089829 | A1 | 5/2018 |
| WO | WO-2018/167104 | A1 | 9/2018 |
| WO | WO-2018/195226 | A1 | 10/2018 |
| WO | WO-2020/102591 | A1 | 5/2020 |
| WO | WO-2020/242765 | A1 | 12/2020 |

OTHER PUBLICATIONS

Japan Patent Office, Examination Report for Japanese Patent Appl. No. 2021-526460 dated Dec. 18, 2023, 12 pp.

International Search Report mailed on Apr. 27, 2020, for PCT Application No. PCT/US2019/061552, filed on Nov. 14, 2019, 5 pages.

International Search Report mailed on Apr. 21, 2020, for PCT Application No. PCT/US2019/061567, filed on Nov. 14, 2019, 5 pages.

Wilkinson, D.S. et al. (2017). "Partial CD25 Antagonism Enables Dominance of Antigen-Inducible $CD25^{high}$ FOXP3+ Regulatory T Cells as a Basis for a Regulatory T Cell-Based Adoptive Immunotherapy," Frontiers in Immunology 8:1-21.

Written Opinion of the International Searching Authority mailed on Apr. 27, 2020, for PCT Application No. PCT/US2019/061552, filed on Nov. 14, 2019, 7 pages.

Written Opinion of the International Searching Authority mailed on Apr. 21, 2020, for PCT Application No. PCT/US2019/061567, filed on Nov. 14, 2019, 7 pages.

U.S. Appl. No. 17/320,125, filed May 13, 2021, by Li et al.

European Patent Office, Communication pursuant to Rule 164(1) EPC, Partial supplementary search report for Appl. No. 19885972.0 dated Aug. 1, 2022, 17 pp.

European Patent Office, Extended Search Report for Appl. No. 19885972.0 dated Nov. 2, 2022, 15 pp.

Gip, et al. "Discovery of epitope-selective anti-CD25 targeting therapeutic antibodies for effective Treg cell depletion in cancer using a novel AI/ML based platform" Cancer Res (2020) 80 (16_Supplement): 6055 https://doi.org/10.1158/1538-7445.AM2020-6055, Abstract Only.

Trier, et al. "Production and characterization of peptide antiboies", Methods 56 (2012) 136-144, available online Dec. 8, 2011.

China Intellectual Property Office, Examination Report for Chinese Patent Appl. NO. 201980088633.3 dated Sep. 27, 2023, 36 pp.

* cited by examiner

*Primary Examiner* — Gyan Chandra
(74) *Attorney, Agent, or Firm* — Edwin S. Flores; Daniel J. Chalker; Chalker Flores, LLP

(57) ABSTRACT

Provided herein engineered polypeptides that comprise a combination of spatially-associated topological constraints, wherein at least one constraint is derived from a CD25 reference target, and methods of selecting said engineered polypeptides. Further provided are methods of using the engineered polypeptides, including as positive and/or negative selection molecules in methods of screening a library of binding molecules such as antibodies. Further provided herein are CD25 antibodies selected using these engineered polypeptides.

10 Claims, 38 Drawing Sheets

Specification includes a Sequence Listing.

Step 1: Reference target

Step 2: Spatially constrained amino acid & Atomic distance reference topology

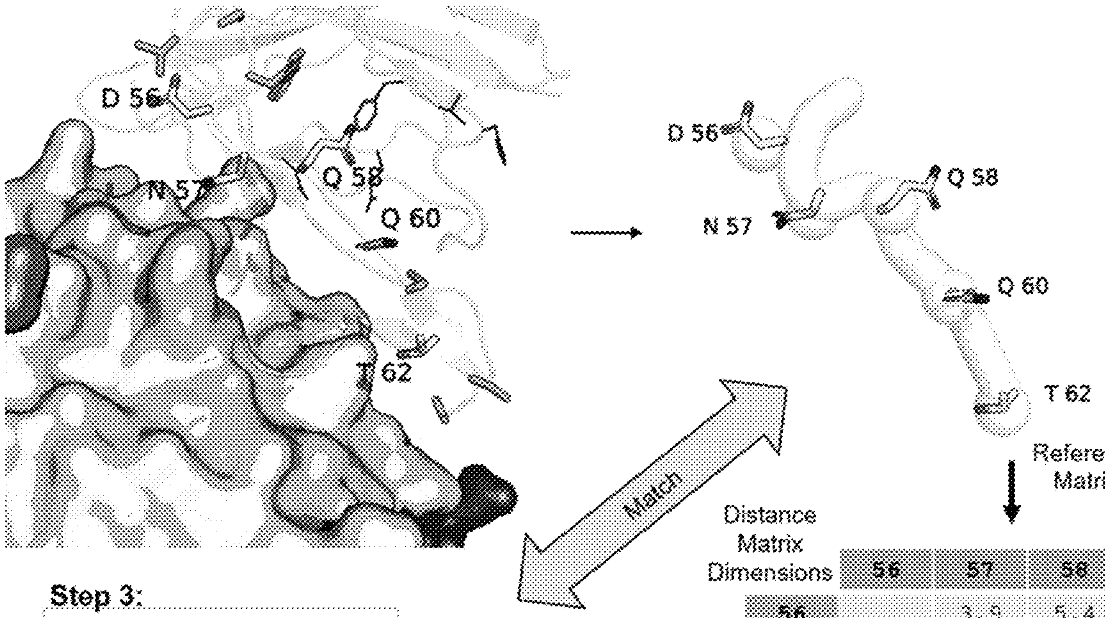

Amino Acid Descriptor Lookup Table

| NUMERIC | LETTER CODE |
|---|---|
| 1 | M |
| 2 | A |
| 3 | V |
| 4 | F |
| 5 | L |
| 6 | I |
| 7 | G |
| 8 | W |
| 9 | Y |
| 10 | P |
| 11 | S |
| 12 | T |
| 13 | C |
| 14 | N |
| 15 | Q |
| 16 | K |
| 17 | R |
| 18 | H |
| 19 | D |
| 20 | E |

Distance Matrix Dimensions

| | 56 | 57 | 58 | 60 | 62 |
|---|---|---|---|---|---|
| 56 | | 3.9 | 5.4 | 12.3 | 19.1 |
| 57 | | | 3.8 | 9.6 | 16.0 |
| 58 | | | | 7.6 | 14.4 |
| 60 | | | | | 6.9 |
| 62 | | | | | |

Amino Acid Matrix Dimension

| | |
|---|---|
| 56 | 19 |
| 57 | 14 |
| 58 | 15 |
| 60 | 15 |
| 62 | 12 |

Step 3:

*In silico* screen for engineered peptides with best-matched topology vs. reference topology Simulation Topologies

FIG. 4A

| Epitope(s) Covered | Double Alanine Mutation |
|---|---|
| 1 | D77A, Q79A |
| 1 | Q81A, T83A |
| 1 | D77A, N78A |
| 2 | T35A, Q151A |
| 2 | M39A, M147A |
| 2, 3, 7 | H33A, T35A |
| 2, 3 | K37A, Y149A |
| 3, 4, 7 | E30A, H33A |
| 3, 4 | D27A, E30A |
| 4 | R176A, Q179A |
| 4 | Q181A, I183A |
| 5 | E100A, R104A |
| 5 | Q101A, K105A |
| 5 | K102A, K105A |
| 6 | K169A, T171A |
| 6 | K174A, R176A |
| 6 | T175A, R176A |
| 6 | M170A, H172A |
| 8 | N70A, S71A |
| 8 | S72A, H73A |
| 8 | S74A, S75A |
| Basiliximab, Daclizumab | L23A, D25A |

CD25 Global Stability

| Mutations | Mutant Global RMSD (Å) |
|---|---|
| K174A, R176A | 2.3 ± 0.4 |
| T175A, R176A | 2.5 ± 0.8 |
| M170A, H172A | 2.1 ± 0.5 |
| K169A, T171A | 2.3 ± 0.6 |

| Wild-Type Global RMSD |
|---|
| 2.4 ±0.6 |

Epitope Local Stability

SEQUENCE LISTING

<160> NUMBER OF SEQ ID NOS: 846

<210> SEQ ID NO 1
<211> LENGTH: 23
<212> TYPE: PRT
<213> ORGANISM: Mus musculus

<400> SEQUENCE: 1

```
Cys Asp Cys Gln Ala Gln Trp Thr Pro Gly Met Arg Ala Pro Gly Tyr
1               5                   10                  15

Asp Pro Tyr Cys Leu Asn Cys
            20
```

<210> SEQ ID NO 2
<211> LENGTH: 29
<212> TYPE: PRT
<213> ORGANISM: Mus musculus

<400> SEQUENCE: 2

```
Met Val Tyr Cys Gln Pro Asp Cys Thr Ala Lys Cys Met His Gly Cys
1               5                   10                  15
```

Asp Arg Asp Thr Met Lys Glu Cys Cys Asp Arg Leu Lys
20 25

<210> SEQ ID NO 3
<211> LENGTH: 28
<212> TYPE: PRT
<213> ORGANISM: Mus musculus

<400> SEQUENCE: 3

Asp Asp Cys Pro Glu Val Pro His Ala Thr Phe Lys Gly Pro Gly Gln
1 5 10 15

Lys Trp Glu Gly Pro Gly Gly Gly Asp Cys Ser Lys
20 25

<210> SEQ ID NO 4
<211> LENGTH: 30
<212> TYPE: PRT
<213> ORGANISM: Mus musculus

<400> SEQUENCE: 4

Asp Asp Cys Ile Glu Val Pro Gly Pro Ala Glu Cys Ala Glu Arg Ala
1 5 10 15

Cys Arg Ala Gln Glu Glu Arg Gln Arg Gln Pro Gln Cys Ile
20 25 30

<210> SEQ ID NO 5
<211> LENGTH: 24
<212> TYPE: PRT
<213> ORGANISM: Mus musculus

<400> SEQUENCE: 5

Ala Glu Glu Glu Lys Ile Lys Ile Glu Gln Lys Glu Arg Lys Thr Thr
1 5 10 15

Ile Lys Leu Ala Lys Glu Ala Lys
20

<210> SEQ ID NO 6
<211> LENGTH: 16
<212> TYPE: PRT
<213> ORGANISM: Mus musculus

<400> SEQUENCE: 6

Cys His Leu Gln Ile Met Thr His Gly Lys Ile Ile Tyr Val Pro Cys
1 5 10 15

<210> SEQ ID NO 7
<211> LENGTH: 26
<212> TYPE: PRT
<213> ORGANISM: Mus musculus

<400> SEQUENCE: 7

Asp Asp Gly Asp Arg Cys Ala Lys Glu His Glu Ile Pro His Ala Thr
1 5 10 15

Gly Glu Glu Cys Gln Lys Arg Asp Lys Ser
20 25

<210> SEQ ID NO 8
<211> LENGTH: 24
<212> TYPE: PRT
<213> ORGANISM: Mus musculus

<400> SEQUENCE: 8

Cys Lys Gln Leu Val Ile Tyr Phe Thr Gly Asn Ser Ser His Ser Ser

```
1               5                   10                  15

Val Phe Tyr Ile Tyr Tyr Asp Cys
            20


<210> SEQ ID NO 9
<211> LENGTH: 33
<212> TYPE: PRT
<213> ORGANISM: Mus musculus

<400> SEQUENCE: 9

Gly Ser Gly Asp Glu Asp Cys Lys Lys Phe Gln Ser Asp Asp Asn Trp
1               5                   10                  15

Glu Asn Tyr Thr Ser Thr Arg His Leu Thr Phe Cys Asp Glu Lys Arg
            20                  25                  30

Ser


<210> SEQ ID NO 10
<211> LENGTH: 33
<212> TYPE: PRT
<213> ORGANISM: Mus musculus

<400> SEQUENCE: 10

Gly Ser Gly Asn Glu Glu Ile Glu Lys Lys Ile Lys Asp Cys Thr Gly
1               5                   10                  15

Asn Ser Ser His Ser Ser Trp Glu Glu Ala Leu Glu Cys Ala Leu Lys
            20                  25                  30

Lys


<210> SEQ ID NO 11
<211> LENGTH: 33
<212> TYPE: PRT
<213> ORGANISM: Mus musculus

<400> SEQUENCE: 11

Gly Ser Gly Asp Glu Arg Ile Glu Arg Leu Ile Lys Glu Cys Thr Gly
1               5                   10                  15

Asn Ser Ser His Ser Ser Trp Glu Glu Ala Leu Glu Cys Ala Leu Arg
            20                  25                  30

Arg


<210> SEQ ID NO 12
<211> LENGTH: 33
<212> TYPE: PRT
<213> ORGANISM: Mus musculus

<400> SEQUENCE: 12

Gly Ser Gly Ser His Pro Cys Ala Tyr Trp Arg Trp Val Ile Lys Met
1               5                   10                  15

Thr His Gly Lys Thr Arg Trp Val Leu Glu Leu Val Phe Cys Tyr Arg
            20                  25                  30

Asp


<210> SEQ ID NO 13
<211> LENGTH: 33
<212> TYPE: PRT
<213> ORGANISM: Mus musculus

<400> SEQUENCE: 13

Gly Ser Gly Lys Cys Glu Glu Glu Ala Lys Lys Ile Ala Ser Lys Met
1               5                   10                  15
```

```
Thr His Gly Lys Thr Arg Glu Glu Glu Ala Glu Glu Tyr Leu Lys Lys
            20                  25                  30

Cys


<210> SEQ ID NO 14
<211> LENGTH: 33
<212> TYPE: PRT
<213> ORGANISM: Mus musculus

<400> SEQUENCE: 14

Gly Ser Gly Asp Asp Glu Ser Glu Lys Arg Thr Thr Glu Arg Asp Thr
1               5                   10                  15

Arg Lys Cys Thr Lys Ala Lys Ala Asn Asp Asn Gln Cys Gln Pro Thr
            20                  25                  30

Glu


<210> SEQ ID NO 15
<211> LENGTH: 33
<212> TYPE: PRT
<213> ORGANISM: Mus musculus

<400> SEQUENCE: 15

Gly Ser Gly Ser Ser Glu Trp Asp Lys Trp Val Glu Glu Trp Tyr Lys
1               5                   10                  15

Lys Met Cys Thr Glu Ala Lys Lys Asn Asp Asn Gln Cys Gln Pro Thr
            20                  25                  30

Lys


<210> SEQ ID NO 16
<211> LENGTH: 33
<212> TYPE: PRT
<213> ORGANISM: Mus musculus

<400> SEQUENCE: 16

Gly Ser Gly Gln Cys Arg Val Trp Val Phe Arg Asn Gly Asp Lys Ile
1               5                   10                  15

Leu Tyr Ile Tyr Glu Asp Cys Asp Asn Asp Asn Gln His Gln Gln Thr
            20                  25                  30

Leu


<210> SEQ ID NO 17
<211> LENGTH: 29
<212> TYPE: PRT
<213> ORGANISM: Mus musculus

<400> SEQUENCE: 17

Thr Val Tyr Pro Gln Pro Asp Ala Thr Ala Lys Cys Val His Gly Cys
1               5                   10                  15

Asp Pro Arg Glu Tyr Thr Lys Ala Val Glu Asp Ala Lys
            20                  25


<210> SEQ ID NO 18
<211> LENGTH: 26
<212> TYPE: PRT
<213> ORGANISM: Mus musculus

<400> SEQUENCE: 18

Asp Trp Gly Asp Asp Cys Lys Lys Lys His Glu Ile Thr His Ala Thr
1               5                   10                  15
```

-continued

```
Gly Asp Tyr Cys Glu Lys Leu Asp Lys Ser
            20                  25


<210> SEQ ID NO 19
<211> LENGTH: 30
<212> TYPE: PRT
<213> ORGANISM: Mus musculus

<400> SEQUENCE: 19

Asp Asp Cys Ile Lys Val Thr Gly Pro Ala Glu Cys Ala Glu Arg Ala
1               5                   10                  15

Cys Arg Ala Gln Glu Glu Arg Gln Arg Gln Pro Gln Cys Ile
            20                  25                  30


<210> SEQ ID NO 20
<211> LENGTH: 25
<212> TYPE: PRT
<213> ORGANISM: Mus musculus

<400> SEQUENCE: 20

Cys Asp Cys Gln Ala Gln Trp Thr Pro Gly Met Arg Ala Pro Gly Tyr
1               5                   10                  15

Asp Pro Tyr Cys Leu Asn Cys Gly Ser
            20                  25


<210> SEQ ID NO 21
<211> LENGTH: 18
<212> TYPE: PRT
<213> ORGANISM: Mus musculus

<400> SEQUENCE: 21

Cys His Leu Gln Ile Met Thr His Gly Lys Ile Ile Tyr Val Pro Cys
1               5                   10                  15

Gly Ser


<210> SEQ ID NO 22
<211> LENGTH: 9
<212> TYPE: PRT
<213> ORGANISM: Mus musculus

<400> SEQUENCE: 22

Ser Trp Asp Asn Gln Cys Gln Cys Thr
1               5


<210> SEQ ID NO 23
<211> LENGTH: 7
<212> TYPE: PRT
<213> ORGANISM: Mus musculus

<400> SEQUENCE: 23

Ala Thr Phe Lys Ala Met Ala
1               5


<210> SEQ ID NO 24
<211> LENGTH: 6
<212> TYPE: PRT
<213> ORGANISM: Mus musculus

<400> SEQUENCE: 24

Met Val Tyr Tyr Gln Cys
1               5


<210> SEQ ID NO 25
```

<211> LENGTH: 13
<212> TYPE: PRT
<213> ORGANISM: Mus musculus

<400> SEQUENCE: 25

Asp Asp Pro Pro Glu Ile Pro His Ala Thr Phe Lys Ala
1               5                   10

<210> SEQ ID NO 26
<211> LENGTH: 7
<212> TYPE: PRT
<213> ORGANISM: Mus musculus

<400> SEQUENCE: 26

Asp Asp Pro Pro Glu Ile Pro
1               5

<210> SEQ ID NO 27
<211> LENGTH: 8
<212> TYPE: PRT
<213> ORGANISM: Mus musculus

<400> SEQUENCE: 27

Arg Trp Thr Gln Pro Gln Leu Ile
1               5

<210> SEQ ID NO 28
<211> LENGTH: 13
<212> TYPE: PRT
<213> ORGANISM: Mus musculus

<400> SEQUENCE: 28

Gln Pro Glu Glu Gln Lys Glu Arg Lys Thr Thr Glu Met
1               5                   10

<210> SEQ ID NO 29
<211> LENGTH: 11
<212> TYPE: PRT
<213> ORGANISM: Mus musculus

<400> SEQUENCE: 29

Val Cys Lys Met Thr His Gly Lys Thr Arg Trp
1               5                   10

<210> SEQ ID NO 30
<211> LENGTH: 4
<212> TYPE: PRT
<213> ORGANISM: Mus musculus

<400> SEQUENCE: 30

Ile Pro His Ala
1

<210> SEQ ID NO 31
<211> LENGTH: 13
<212> TYPE: PRT
<213> ORGANISM: Mus musculus

<400> SEQUENCE: 31

Tyr Met Leu Cys Thr Gly Ser Ser Ser His Ser Ser Trp
1               5                   10

<210> SEQ ID NO 32
<211> LENGTH: 3
<212> TYPE: PRT

<213> ORGANISM: Artificial Sequence
<220> FEATURE:
<223> OTHER INFORMATION: linker

<400> SEQUENCE: 32

Gly Ser Gly
1

<210> SEQ ID NO 33
<211> LENGTH: 50
<212> TYPE: PRT
<213> ORGANISM: Artificial Sequence
<220> FEATURE:
<223> OTHER INFORMATION: linker
<220> FEATURE:
<221> NAME/KEY: SITE
<222> LOCATION: (6)..(10)
<223> OTHER INFORMATION: May be present or absent
<220> FEATURE:
<221> NAME/KEY: SITE
<222> LOCATION: (11)..(15)
<223> OTHER INFORMATION: May be present or absent
<220> FEATURE:
<221> NAME/KEY: SITE
<222> LOCATION: (16)..(20)
<223> OTHER INFORMATION: May be present or absent
<220> FEATURE:
<221> NAME/KEY: SITE
<222> LOCATION: (21)..(25)
<223> OTHER INFORMATION: May be present or absent
<220> FEATURE:
<221> NAME/KEY: SITE
<222> LOCATION: (26)..(30)
<223> OTHER INFORMATION: May be present or absent
<220> FEATURE:
<221> NAME/KEY: SITE
<222> LOCATION: (31)..(35)
<223> OTHER INFORMATION: May be present or absent
<220> FEATURE:
<221> NAME/KEY: SITE
<222> LOCATION: (36)..(40)
<223> OTHER INFORMATION: May be present or absent
<220> FEATURE:
<221> NAME/KEY: SITE
<222> LOCATION: (41)..(45)
<223> OTHER INFORMATION: May be present or absent
<220> FEATURE:
<221> NAME/KEY: SITE
<222> LOCATION: (46)..(50)
<223> OTHER INFORMATION: May be present or absent

<400> SEQUENCE: 33

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50
```

<210> SEQ ID NO 34
<211> LENGTH: 30
<212> TYPE: PRT
<213> ORGANISM: Artificial Sequence
<220> FEATURE:
<223> OTHER INFORMATION: linker
<220> FEATURE:
<221> NAME/KEY: SITE
<222> LOCATION: (4)..(6)
<223> OTHER INFORMATION: May be present or absent
<220> FEATURE:

<221> NAME/KEY: SITE
<222> LOCATION: (7)..(9)
<223> OTHER INFORMATION: May be present or absent
<220> FEATURE:
<221> NAME/KEY: SITE
<222> LOCATION: (10)..(12)
<223> OTHER INFORMATION: May be present or absent
<220> FEATURE:
<221> NAME/KEY: SITE
<222> LOCATION: (13)..(15)
<223> OTHER INFORMATION: May be present or absent
<220> FEATURE:
<221> NAME/KEY: SITE
<222> LOCATION: (16)..(18)
<223> OTHER INFORMATION: May be present or absent
<220> FEATURE:
<221> NAME/KEY: SITE
<222> LOCATION: (19)..(21)
<223> OTHER INFORMATION: May be present or absent
<220> FEATURE:
<221> NAME/KEY: SITE
<222> LOCATION: (22)..(24)
<223> OTHER INFORMATION: May be present or absent
<220> FEATURE:
<221> NAME/KEY: SITE
<222> LOCATION: (25)..(27)
<223> OTHER INFORMATION: May be present or absent
<220> FEATURE:
<221> NAME/KEY: SITE
<222> LOCATION: (28)..(30)
<223> OTHER INFORMATION: May be present or absent

<400> SEQUENCE: 34

```
Gly Ser Gly Gly Ser Gly Gly Ser Gly Gly Ser Gly Gly Ser Gly Gly
1               5                   10                  15

Ser Gly Gly Ser Gly Gly Ser Gly Gly Ser Gly Gly Ser Gly
            20                  25                  30
```

<210> SEQ ID NO 35
<211> LENGTH: 9
<212> TYPE: PRT
<213> ORGANISM: Artificial Sequence
<220> FEATURE:
<223> OTHER INFORMATION: linker

<400> SEQUENCE: 35

```
Gly Gly Gly Ser Gly Gly Gly Gly Ser
1               5
```

<210> SEQ ID NO 36
<211> LENGTH: 9
<212> TYPE: PRT
<213> ORGANISM: Artificial Sequence
<220> FEATURE:
<223> OTHER INFORMATION: linker

<400> SEQUENCE: 36

```
Gly Gly Gly Gly Ser Gly Gly Gly Ser
1               5
```

<210> SEQ ID NO 37
<211> LENGTH: 40
<212> TYPE: PRT
<213> ORGANISM: Artificial Sequence
<220> FEATURE:
<223> OTHER INFORMATION: linker
<220> FEATURE:
<221> NAME/KEY: SITE
<222> LOCATION: (5)..(8)
<223> OTHER INFORMATION: May be present or absent
<220> FEATURE:
<221> NAME/KEY: SITE
<222> LOCATION: (9)..(12)
<223> OTHER INFORMATION: May be present or absent
<220> FEATURE:
<221> NAME/KEY: SITE
<222> LOCATION: (13)..(16)
<223> OTHER INFORMATION: May be present or absent
<220> FEATURE:
<221> NAME/KEY: SITE
<222> LOCATION: (17)..(20)
<223> OTHER INFORMATION: May be present or absent
<220> FEATURE:
<221> NAME/KEY: SITE
<222> LOCATION: (21)..(24)
<223> OTHER INFORMATION: May be present or absent
<220> FEATURE:
<221> NAME/KEY: SITE
<222> LOCATION: (25)..(28)
<223> OTHER INFORMATION: May be present or absent
<220> FEATURE:
<221> NAME/KEY: SITE
<222> LOCATION: (29)..(32)
<223> OTHER INFORMATION: May be present or absent
<220> FEATURE:
<221> NAME/KEY: SITE
<222> LOCATION: (33)..(36)
<223> OTHER INFORMATION: May be present or absent
<220> FEATURE:
<221> NAME/KEY: SITE
<222> LOCATION: (37)..(40)
<223> OTHER INFORMATION: May be present or absent

<400> SEQUENCE: 37

```
Pro Gly Ser Gly Pro Gly Ser Gly Pro Gly Ser Gly Pro Gly Ser Gly
1               5                   10                  15

Pro Gly Ser Gly Pro Gly Ser Gly Pro Gly Ser Gly Pro Gly Ser Gly
            20                  25                  30

Pro Gly Ser Gly Pro Gly Ser Gly
        35                  40
```

<210> SEQ ID NO 38
<211> LENGTH: 6
<212> TYPE: PRT
<213> ORGANISM: Artificial Sequence
<220> FEATURE:
<223> OTHER INFORMATION: linker

<400> SEQUENCE: 38

```
Pro Gly Ser Gly Ser Gly
1               5
```

<210> SEQ ID NO 39
<211> LENGTH: 3
<212> TYPE: PRT
<213> ORGANISM: Artificial Sequence
<220> FEATURE:
<223> OTHER INFORMATION: linker

<400> SEQUENCE: 39

```
Gly Ser Ser
1
```

<210> SEQ ID NO 40
<211> LENGTH: 3
<212> TYPE: PRT
<213> ORGANISM: Artificial Sequence
<220> FEATURE:
<223> OTHER INFORMATION: linker

<400> SEQUENCE: 40

```
Gly Gly Ser
```

-continued

1

<210> SEQ ID NO 41
<211> LENGTH: 6
<212> TYPE: PRT
<213> ORGANISM: Artificial Sequence
<220> FEATURE:
<223> OTHER INFORMATION: linker

<400> SEQUENCE: 41

Gly Gly Ser Gly Gly Ser
1               5

<210> SEQ ID NO 42
<211> LENGTH: 6
<212> TYPE: PRT
<213> ORGANISM: Artificial Sequence
<220> FEATURE:
<223> OTHER INFORMATION: linker

<400> SEQUENCE: 42

Gly Ser Ser Gly Ser Ser
1               5

<210> SEQ ID NO 43
<211> LENGTH: 4
<212> TYPE: PRT
<213> ORGANISM: Artificial Sequence
<220> FEATURE:
<223> OTHER INFORMATION: linker

<400> SEQUENCE: 43

Gly Ser Gly Lys
1

<210> SEQ ID NO 44
<211> LENGTH: 4
<212> TYPE: PRT
<213> ORGANISM: Artificial Sequence
<220> FEATURE:
<223> OTHER INFORMATION: linker

<400> SEQUENCE: 44

Gly Ser Ser Lys
1

<210> SEQ ID NO 45
<211> LENGTH: 4
<212> TYPE: PRT
<213> ORGANISM: Artificial Sequence
<220> FEATURE:
<223> OTHER INFORMATION: linker

<400> SEQUENCE: 45

Gly Gly Ser Lys
1

<210> SEQ ID NO 46
<211> LENGTH: 7
<212> TYPE: PRT
<213> ORGANISM: Artificial Sequence
<220> FEATURE:
<223> OTHER INFORMATION: linker

<400> SEQUENCE: 46

Gly Gly Ser Gly Gly Ser Lys
1               5

-continued

<210> SEQ ID NO 47
<211> LENGTH: 7
<212> TYPE: PRT
<213> ORGANISM: Artificial Sequence
<220> FEATURE:
<223> OTHER INFORMATION: linker

<400> SEQUENCE: 47

Gly Ser Ser Gly Ser Ser Lys
1               5

<210> SEQ ID NO 48
<211> LENGTH: 6
<212> TYPE: PRT
<213> ORGANISM: Artificial Sequence
<220> FEATURE:
<223> OTHER INFORMATION: linker
<220> FEATURE:
<221> NAME/KEY: SITE
<222> LOCATION: (6)..(6)
<223> OTHER INFORMATION: PEG4-biotin moiety is attached

<400> SEQUENCE: 48

Gly Ser Gly Ser Gly Lys
1               5

<210> SEQ ID NO 49
<211> LENGTH: 3
<212> TYPE: PRT
<213> ORGANISM: Mus musculus

<400> SEQUENCE: 49

Ala Ala Ser
1

<210> SEQ ID NO 50
<211> LENGTH: 3
<212> TYPE: PRT
<213> ORGANISM: Mus musculus

<400> SEQUENCE: 50

Ala Ala Thr
1

<210> SEQ ID NO 51
<211> LENGTH: 11
<212> TYPE: PRT
<213> ORGANISM: Mus musculus

<400> SEQUENCE: 51

Ala Ala Trp Asp Asp Ser Leu Ile Gly His Val
1               5                   10

<210> SEQ ID NO 52
<211> LENGTH: 11
<212> TYPE: PRT
<213> ORGANISM: Mus musculus

<400> SEQUENCE: 52

Ala Ala Trp Asp Asp Ser Leu Asn Gly Pro Val
1               5                   10

<210> SEQ ID NO 53
<211> LENGTH: 11
<212> TYPE: PRT

<213> ORGANISM: Mus musculus

<400> SEQUENCE: 53

Ala Ala Trp Asp Asp Ser Leu Asn Gly Val Val
1 5 10

<210> SEQ ID NO 54
<211> LENGTH: 11
<212> TYPE: PRT
<213> ORGANISM: Mus musculus

<400> SEQUENCE: 54

Ala Ala Trp Asp Asp Ser Leu Asn Gly Tyr Val
1 5 10

<210> SEQ ID NO 55
<211> LENGTH: 11
<212> TYPE: PRT
<213> ORGANISM: Mus musculus

<400> SEQUENCE: 55

Ala Ala Trp Asp Asp Ser Leu Arg Ser Tyr Val
1 5 10

<210> SEQ ID NO 56
<211> LENGTH: 11
<212> TYPE: PRT
<213> ORGANISM: Mus musculus

<400> SEQUENCE: 56

Ala Ala Trp Asp Asp Ser Leu Ser Gly Val Val
1 5 10

<210> SEQ ID NO 57
<211> LENGTH: 8
<212> TYPE: PRT
<213> ORGANISM: Mus musculus

<400> SEQUENCE: 57

Ala Ile His Gly Tyr Phe Asp Tyr
1 5

<210> SEQ ID NO 58
<211> LENGTH: 15
<212> TYPE: PRT
<213> ORGANISM: Mus musculus

<400> SEQUENCE: 58

Ala Ile Leu Glu Tyr Ser Ser Ser Gly Ala Glu Tyr Phe Gln His
1 5 10 15

<210> SEQ ID NO 59
<211> LENGTH: 15
<212> TYPE: PRT
<213> ORGANISM: Mus musculus

<400> SEQUENCE: 59

Ala Ile Pro Trp Asp Ala Glu Leu Gly Asn Tyr Gly Met Asp Val
1 5 10 15

<210> SEQ ID NO 60
<211> LENGTH: 10
<212> TYPE: PRT
<213> ORGANISM: Mus musculus

<400> SEQUENCE: 60

Ala Lys Ala Ile Thr Ser Ile Glu Pro Tyr
1 5 10

<210> SEQ ID NO 61
<211> LENGTH: 13
<212> TYPE: PRT
<213> ORGANISM: Mus musculus

<400> SEQUENCE: 61

Ala Lys Asp Leu Leu Gly Glu Leu Ser Phe Phe Asp Tyr
1 5 10

<210> SEQ ID NO 62
<211> LENGTH: 12
<212> TYPE: PRT
<213> ORGANISM: Mus musculus

<400> SEQUENCE: 62

Ala Lys Asp Leu Ser Gly Leu Pro Ile Ile Asp Tyr
1 5 10

<210> SEQ ID NO 63
<211> LENGTH: 16
<212> TYPE: PRT
<213> ORGANISM: Mus musculus

<400> SEQUENCE: 63

Ala Lys Glu Ile Ser Pro Arg Ser Ser Val Gly Trp Pro Leu Asp Tyr
1 5 10 15

<210> SEQ ID NO 64
<211> LENGTH: 11
<212> TYPE: PRT
<213> ORGANISM: Mus musculus

<400> SEQUENCE: 64

Ala Lys Glu Leu Leu Glu Gly Ala Phe Asp Ile
1 5 10

<210> SEQ ID NO 65
<211> LENGTH: 11
<212> TYPE: PRT
<213> ORGANISM: Mus musculus

<400> SEQUENCE: 65

Ala Lys Gly Asp Val Asn Tyr Gly Met Asp Val
1 5 10

<210> SEQ ID NO 66
<211> LENGTH: 10
<212> TYPE: PRT
<213> ORGANISM: Mus musculus

<400> SEQUENCE: 66

Ala Lys Gly Gln Gly Asp Gly Met Asp Val
1 5 10

<210> SEQ ID NO 67
<211> LENGTH: 11
<212> TYPE: PRT
<213> ORGANISM: Mus musculus

<400> SEQUENCE: 67

Ala Lys Gly Tyr Ser Ser Ser Pro Gly Asp Tyr
1 5 10

<210> SEQ ID NO 68
<211> LENGTH: 14
<212> TYPE: PRT
<213> ORGANISM: Mus musculus

<400> SEQUENCE: 68

Ala Lys Asn Pro Tyr Ser Asn Tyr Val Tyr Trp Phe Asp Pro
1 5 10

<210> SEQ ID NO 69
<211> LENGTH: 3
<212> TYPE: PRT
<213> ORGANISM: Mus musculus

<400> SEQUENCE: 69

Ala Asn Asp
1

<210> SEQ ID NO 70
<211> LENGTH: 11
<212> TYPE: PRT
<213> ORGANISM: Mus musculus

<400> SEQUENCE: 70

Ala Asn Leu Ala Met Gly Gln Tyr Phe Asp Tyr
1 5 10

<210> SEQ ID NO 71
<211> LENGTH: 11
<212> TYPE: PRT
<213> ORGANISM: Mus musculus

<400> SEQUENCE: 71

Ala Arg Ala Gly Tyr Tyr Tyr Gly Met Asp Val
1 5 10

<210> SEQ ID NO 72
<211> LENGTH: 11
<212> TYPE: PRT
<213> ORGANISM: Mus musculus

<400> SEQUENCE: 72

Ala Arg Ala Arg Gly Gly Arg Tyr Phe Asp Tyr
1 5 10

<210> SEQ ID NO 73
<211> LENGTH: 11
<212> TYPE: PRT
<213> ORGANISM: Mus musculus

<400> SEQUENCE: 73

Ala Arg Asp Ala Tyr Ala Tyr Gly Leu Asp Val
1 5 10

<210> SEQ ID NO 74
<211> LENGTH: 16
<212> TYPE: PRT
<213> ORGANISM: Mus musculus

<400> SEQUENCE: 74

Ala Arg Asp Phe Asn Pro Phe Ser Ile Thr Ile Phe Glu Met Asp Val
1 5 10 15

<210> SEQ ID NO 75
<211> LENGTH: 8
<212> TYPE: PRT
<213> ORGANISM: Mus musculus

<400> SEQUENCE: 75

Ala Arg Asp Phe Arg Met Asp Val
1               5

<210> SEQ ID NO 76
<211> LENGTH: 16
<212> TYPE: PRT
<213> ORGANISM: Mus musculus

<400> SEQUENCE: 76

Ala Arg Asp Phe Trp Ser Gly Tyr Asn Glu Leu Gly Gly Met Asp Val
1               5                   10                  15

<210> SEQ ID NO 77
<211> LENGTH: 21
<212> TYPE: PRT
<213> ORGANISM: Mus musculus

<400> SEQUENCE: 77

Ala Arg Asp Phe Tyr Tyr Gly Ser Gly Ser Tyr Pro Asn Gly Tyr Tyr
1               5                   10                  15

Tyr Gly Met Asp Val
            20

<210> SEQ ID NO 78
<211> LENGTH: 27
<212> TYPE: PRT
<213> ORGANISM: Mus musculus

<400> SEQUENCE: 78

Ala Arg Asp Gly Ala Gly Asn Tyr Asp Ile Leu Thr Gly Asp Arg Ser
1               5                   10                  15

Glu Asp Tyr Tyr Tyr Tyr Tyr Gly Met Asp Val
            20                  25

<210> SEQ ID NO 79
<211> LENGTH: 10
<212> TYPE: PRT
<213> ORGANISM: Mus musculus

<400> SEQUENCE: 79

Ala Arg Asp Gly Gly Tyr Tyr Phe Asp Asp
1               5                   10

<210> SEQ ID NO 80
<211> LENGTH: 12
<212> TYPE: PRT
<213> ORGANISM: Mus musculus

<400> SEQUENCE: 80

Ala Arg Asp Ile Gly Tyr Tyr Tyr Gly Met Asp Val
1               5                   10

<210> SEQ ID NO 81
<211> LENGTH: 9
<212> TYPE: PRT
<213> ORGANISM: Mus musculus

<400> SEQUENCE: 81

Ala Arg Asp Ile Leu Gly Leu Asp Tyr
1 5

<210> SEQ ID NO 82
<211> LENGTH: 14
<212> TYPE: PRT
<213> ORGANISM: Mus musculus

<400> SEQUENCE: 82

Ala Arg Asp Ile Leu Arg Gly Glu Ser Ser Ile Leu Asp His
1 5 10

<210> SEQ ID NO 83
<211> LENGTH: 11
<212> TYPE: PRT
<213> ORGANISM: Mus musculus

<400> SEQUENCE: 83

Ala Arg Asp Lys Gly Tyr Tyr Gly Met Asp Val
1 5 10

<210> SEQ ID NO 84
<211> LENGTH: 17
<212> TYPE: PRT
<213> ORGANISM: Mus musculus

<400> SEQUENCE: 84

Ala Arg Asp Leu Gly Glu Ala Lys Ser Ser Ser Pro His Glu Pro Asp
1 5 10 15

Tyr

<210> SEQ ID NO 85
<211> LENGTH: 19
<212> TYPE: PRT
<213> ORGANISM: Mus musculus

<400> SEQUENCE: 85

Ala Arg Asp Leu Gly Thr Met Val Arg Gly Val Ile Glu Pro Tyr Tyr
1 5 10 15

Phe Asp Tyr

<210> SEQ ID NO 86
<211> LENGTH: 14
<212> TYPE: PRT
<213> ORGANISM: Mus musculus

<400> SEQUENCE: 86

Ala Arg Asp Leu Leu Gly Ser Gly Tyr Asp Ile Ile Asp Tyr
1 5 10

<210> SEQ ID NO 87
<211> LENGTH: 11
<212> TYPE: PRT
<213> ORGANISM: Mus musculus

<400> SEQUENCE: 87

Ala Arg Asp Leu Met Asn Tyr Gly Met Asp Val
1 5 10

<210> SEQ ID NO 88
<211> LENGTH: 11
<212> TYPE: PRT

<213> ORGANISM: Mus musculus

<400> SEQUENCE: 88

Ala Arg Asp Gln Glu Met Tyr Tyr Phe Asp Tyr
1 5 10

<210> SEQ ID NO 89
<211> LENGTH: 17
<212> TYPE: PRT
<213> ORGANISM: Mus musculus

<400> SEQUENCE: 89

Ala Arg Asp Gln Leu Ala Ala Arg Arg Gly Tyr Tyr Tyr Gly Met Asp
1 5 10 15

Val

<210> SEQ ID NO 90
<211> LENGTH: 11
<212> TYPE: PRT
<213> ORGANISM: Mus musculus

<400> SEQUENCE: 90

Ala Arg Asp Arg Phe His Tyr Gly Met Asp Val
1 5 10

<210> SEQ ID NO 91
<211> LENGTH: 15
<212> TYPE: PRT
<213> ORGANISM: Mus musculus

<400> SEQUENCE: 91

Ala Arg Asp Arg Gly Asp Arg Val Gly Gly Leu Val Phe Asp Tyr
1 5 10 15

<210> SEQ ID NO 92
<211> LENGTH: 7
<212> TYPE: PRT
<213> ORGANISM: Mus musculus

<400> SEQUENCE: 92

Ala Arg Asp Arg Gly Asp Tyr
1 5

<210> SEQ ID NO 93
<211> LENGTH: 11
<212> TYPE: PRT
<213> ORGANISM: Mus musculus

<400> SEQUENCE: 93

Ala Arg Asp Arg Gly Tyr Tyr Gly Met Asp Val
1 5 10

<210> SEQ ID NO 94
<211> LENGTH: 10
<212> TYPE: PRT
<213> ORGANISM: Mus musculus

<400> SEQUENCE: 94

Ala Arg Asp Arg Asn Gly Tyr Phe Gln His
1 5 10

<210> SEQ ID NO 95
<211> LENGTH: 15
<212> TYPE: PRT

<213> ORGANISM: Mus musculus

<400> SEQUENCE: 95

Ala Arg Asp Arg Arg Gly Ser Gly Trp Tyr Glu Tyr Phe Asp Tyr
1 5 10 15

<210> SEQ ID NO 96
<211> LENGTH: 11
<212> TYPE: PRT
<213> ORGANISM: Mus musculus

<400> SEQUENCE: 96

Ala Arg Asp Arg Ser Tyr Tyr Gly Met Asp Val
1 5 10

<210> SEQ ID NO 97
<211> LENGTH: 14
<212> TYPE: PRT
<213> ORGANISM: Mus musculus

<400> SEQUENCE: 97

Ala Arg Asp Arg Val Thr Met Val Arg Gly Ala Leu Ala Tyr
1 5 10

<210> SEQ ID NO 98
<211> LENGTH: 11
<212> TYPE: PRT
<213> ORGANISM: Mus musculus

<400> SEQUENCE: 98

Ala Arg Asp Arg Tyr Tyr Tyr Gly Met Asp Val
1 5 10

<210> SEQ ID NO 99
<211> LENGTH: 16
<212> TYPE: PRT
<213> ORGANISM: Mus musculus

<400> SEQUENCE: 99

Ala Arg Asp Ser His Thr Val Tyr Tyr Gly Ser Gly Ser Gln Asp Tyr
1 5 10 15

<210> SEQ ID NO 100
<211> LENGTH: 13
<212> TYPE: PRT
<213> ORGANISM: Mus musculus

<400> SEQUENCE: 100

Ala Arg Asp Ser Ser Ser Gly Pro Tyr Gly Met Asp Val
1 5 10

<210> SEQ ID NO 101
<211> LENGTH: 11
<212> TYPE: PRT
<213> ORGANISM: Mus musculus

<400> SEQUENCE: 101

Ala Arg Asp Tyr Tyr Tyr Tyr Gly Met Asp Val
1 5 10

<210> SEQ ID NO 102
<211> LENGTH: 10
<212> TYPE: PRT
<213> ORGANISM: Mus musculus

<400> SEQUENCE: 102

Ala Arg Glu Lys Gly Ser Trp Phe Asp Pro
1 5 10

<210> SEQ ID NO 103
<211> LENGTH: 12
<212> TYPE: PRT
<213> ORGANISM: Mus musculus

<400> SEQUENCE: 103

Ala Arg Glu Met Tyr Tyr Tyr Tyr Gly Met Asp Val
1 5 10

<210> SEQ ID NO 104
<211> LENGTH: 15
<212> TYPE: PRT
<213> ORGANISM: Mus musculus

<400> SEQUENCE: 104

Ala Arg Glu Pro Leu Arg Tyr Tyr Tyr Tyr Tyr Gly Met Asp Val
1 5 10 15

<210> SEQ ID NO 105
<211> LENGTH: 11
<212> TYPE: PRT
<213> ORGANISM: Mus musculus

<400> SEQUENCE: 105

Ala Arg Glu Arg Ser Tyr Tyr Gly Met Asp Val
1 5 10

<210> SEQ ID NO 106
<211> LENGTH: 13
<212> TYPE: PRT
<213> ORGANISM: Mus musculus

<400> SEQUENCE: 106

Ala Arg Glu Arg Thr His Tyr Tyr Tyr Gly Met Asp Ile
1 5 10

<210> SEQ ID NO 107
<211> LENGTH: 13
<212> TYPE: PRT
<213> ORGANISM: Mus musculus

<400> SEQUENCE: 107

Ala Arg Glu Tyr Asp Tyr Gly Asp Tyr Val Phe Asp Tyr
1 5 10

<210> SEQ ID NO 108
<211> LENGTH: 13
<212> TYPE: PRT
<213> ORGANISM: Mus musculus

<400> SEQUENCE: 108

Ala Arg Gly Gly Leu Gly Gly Asp Asp Ala Phe Asp Ile
1 5 10

<210> SEQ ID NO 109
<211> LENGTH: 12
<212> TYPE: PRT
<213> ORGANISM: Mus musculus

<400> SEQUENCE: 109

-continued

Ala Arg Gly Gly Thr Ser Val Val His Phe Asp Tyr
1               5                   10

<210> SEQ ID NO 110
<211> LENGTH: 11
<212> TYPE: PRT
<213> ORGANISM: Mus musculus

<400> SEQUENCE: 110

Ala Arg Gly Lys Gly Ser Tyr Ala Phe Asp Ile
1               5                   10

<210> SEQ ID NO 111
<211> LENGTH: 11
<212> TYPE: PRT
<213> ORGANISM: Mus musculus

<400> SEQUENCE: 111

Ala Arg Gly Asn Leu Trp Ser Gly Tyr Tyr Phe
1               5                   10

<210> SEQ ID NO 112
<211> LENGTH: 15
<212> TYPE: PRT
<213> ORGANISM: Mus musculus

<400> SEQUENCE: 112

Ala Arg Gly Arg Leu Ala Tyr Gly Asp Thr Glu Gly Phe Asp Tyr
1               5                   10                  15

<210> SEQ ID NO 113
<211> LENGTH: 11
<212> TYPE: PRT
<213> ORGANISM: Mus musculus

<400> SEQUENCE: 113

Ala Arg Gly Arg Trp Ser Gly Leu Gly Asp Tyr
1               5                   10

<210> SEQ ID NO 114
<211> LENGTH: 8
<212> TYPE: PRT
<213> ORGANISM: Mus musculus

<400> SEQUENCE: 114

Ala Arg Gly Thr Ile Ile Asp Tyr
1               5

<210> SEQ ID NO 115
<211> LENGTH: 8
<212> TYPE: PRT
<213> ORGANISM: Mus musculus

<400> SEQUENCE: 115

Ala Arg Gly Thr Val Val Asp Tyr
1               5

<210> SEQ ID NO 116
<211> LENGTH: 14
<212> TYPE: PRT
<213> ORGANISM: Mus musculus

<400> SEQUENCE: 116

Ala Arg Gly Val Ile Ala Ala Ala Gly Thr Tyr Phe Asp Tyr
1               5                   10

<210> SEQ ID NO 117
<211> LENGTH: 8
<212> TYPE: PRT
<213> ORGANISM: Mus musculus

<400> SEQUENCE: 117

Ala Arg Gly Val Pro Phe Asp Tyr
1               5

<210> SEQ ID NO 118
<211> LENGTH: 11
<212> TYPE: PRT
<213> ORGANISM: Mus musculus

<400> SEQUENCE: 118

Ala Arg Gly Val Arg Gly Thr Gly Phe Asp Pro
1               5                   10

<210> SEQ ID NO 119
<211> LENGTH: 8
<212> TYPE: PRT
<213> ORGANISM: Mus musculus

<400> SEQUENCE: 119

Ala Arg Gly Val Ser Phe Asp Tyr
1               5

<210> SEQ ID NO 120
<211> LENGTH: 8
<212> TYPE: PRT
<213> ORGANISM: Mus musculus

<400> SEQUENCE: 120

Ala Arg Gly Val Thr Phe Asp Ile
1               5

<210> SEQ ID NO 121
<211> LENGTH: 8
<212> TYPE: PRT
<213> ORGANISM: Mus musculus

<400> SEQUENCE: 121

Ala Arg Gly Val Thr Phe Asp Ser
1               5

<210> SEQ ID NO 122
<211> LENGTH: 8
<212> TYPE: PRT
<213> ORGANISM: Mus musculus

<400> SEQUENCE: 122

Ala Arg Gly Val Thr Phe Asp Tyr
1               5

<210> SEQ ID NO 123
<211> LENGTH: 8
<212> TYPE: PRT
<213> ORGANISM: Mus musculus

<400> SEQUENCE: 123

Ala Arg Gly Val Thr Ser Asp Ser
1               5

<210> SEQ ID NO 124
<211> LENGTH: 8
<212> TYPE: PRT
<213> ORGANISM: Mus musculus

<400> SEQUENCE: 124

Ala Arg His Gly Tyr Phe Asp Tyr
1 5

<210> SEQ ID NO 125
<211> LENGTH: 8
<212> TYPE: PRT
<213> ORGANISM: Mus musculus
<220> FEATURE:
<221> NAME/KEY: SITE
<222> LOCATION: (4)..(4)
<223> OTHER INFORMATION: Xaa can be any naturally occurring amino acid

<400> SEQUENCE: 125

Ala Arg His Xaa Tyr Phe Asp Tyr
1 5

<210> SEQ ID NO 126
<211> LENGTH: 7
<212> TYPE: PRT
<213> ORGANISM: Mus musculus

<400> SEQUENCE: 126

Ala Arg Ile Thr Pro Ala Ser
1 5

<210> SEQ ID NO 127
<211> LENGTH: 15
<212> TYPE: PRT
<213> ORGANISM: Mus musculus

<400> SEQUENCE: 127

Ala Arg Leu Glu Asn Asn Trp Asp Tyr Gly Gly Trp Phe Asp Pro
1 5 10 15

<210> SEQ ID NO 128
<211> LENGTH: 15
<212> TYPE: PRT
<213> ORGANISM: Mus musculus

<400> SEQUENCE: 128

Ala Arg Leu Glu Asn Asn Trp Asn Tyr Gly Gly Trp Phe Asp Pro
1 5 10 15

<210> SEQ ID NO 129
<211> LENGTH: 9
<212> TYPE: PRT
<213> ORGANISM: Mus musculus

<400> SEQUENCE: 129

Ala Arg Leu Gly Trp Gly Met Asp Val
1 5

<210> SEQ ID NO 130
<211> LENGTH: 13
<212> TYPE: PRT
<213> ORGANISM: Mus musculus

<400> SEQUENCE: 130

Ala Arg Leu Ser Arg Tyr Tyr Tyr Tyr Gly Met Asp Val
1 5 10

-continued

<210> SEQ ID NO 131
<211> LENGTH: 10
<212> TYPE: PRT
<213> ORGANISM: Mus musculus

<400> SEQUENCE: 131

Ala Arg Gln Val Ala Gly Gly Leu Asp Tyr
1               5                   10

<210> SEQ ID NO 132
<211> LENGTH: 10
<212> TYPE: PRT
<213> ORGANISM: Mus musculus

<400> SEQUENCE: 132

Ala Arg Arg Arg Gly Gly Gly Phe Asp Tyr
1               5                   10

<210> SEQ ID NO 133
<211> LENGTH: 10
<212> TYPE: PRT
<213> ORGANISM: Mus musculus

<400> SEQUENCE: 133

Ala Arg Ser Arg Gly Ile Pro Phe Ala Tyr
1               5                   10

<210> SEQ ID NO 134
<211> LENGTH: 11
<212> TYPE: PRT
<213> ORGANISM: Mus musculus

<400> SEQUENCE: 134

Ala Arg Thr Trp Phe Gly Glu Phe Phe Asp Tyr
1               5                   10

<210> SEQ ID NO 135
<211> LENGTH: 11
<212> TYPE: PRT
<213> ORGANISM: Mus musculus

<400> SEQUENCE: 135

Ala Arg Val Gly Asp Gly Tyr Ser Leu Asp Tyr
1               5                   10

<210> SEQ ID NO 136
<211> LENGTH: 10
<212> TYPE: PRT
<213> ORGANISM: Mus musculus

<400> SEQUENCE: 136

Ala Arg Val Ile Gly Gly Trp Phe Asp Pro
1               5                   10

<210> SEQ ID NO 137
<211> LENGTH: 14
<212> TYPE: PRT
<213> ORGANISM: Mus musculus

<400> SEQUENCE: 137

Ala Arg Val Asn Tyr Gly Asp Tyr Asp Trp Tyr Phe Asp Leu
1               5                   10

<210> SEQ ID NO 138
<211> LENGTH: 7
<212> TYPE: PRT
<213> ORGANISM: Mus musculus

<400> SEQUENCE: 138

Ala Arg Val Ser Pro Ala Ser
1 5

<210> SEQ ID NO 139
<211> LENGTH: 7
<212> TYPE: PRT
<213> ORGANISM: Mus musculus

<400> SEQUENCE: 139

Ala Arg Val Thr Pro Ala Ser
1 5

<210> SEQ ID NO 140
<211> LENGTH: 7
<212> TYPE: PRT
<213> ORGANISM: Mus musculus

<400> SEQUENCE: 140

Ala Arg Val Thr Pro Ser Ser
1 5

<210> SEQ ID NO 141
<211> LENGTH: 15
<212> TYPE: PRT
<213> ORGANISM: Mus musculus

<400> SEQUENCE: 141

Ala Arg Val Trp Gly Asp Thr Thr Leu Gly Tyr Gly Met Asp Val
1 5 10 15

<210> SEQ ID NO 142
<211> LENGTH: 12
<212> TYPE: PRT
<213> ORGANISM: Mus musculus

<400> SEQUENCE: 142

Ala Arg Val Trp Gly Lys Asn Gly Asp Phe Asp Tyr
1 5 10

<210> SEQ ID NO 143
<211> LENGTH: 8
<212> TYPE: PRT
<213> ORGANISM: Mus musculus
<220> FEATURE:
<221> NAME/KEY: SITE
<222> LOCATION: (3)..(3)
<223> OTHER INFORMATION: Xaa can be any naturally occurring amino acid

<400> SEQUENCE: 143

Ala Arg Xaa Gly Tyr Phe Asp Tyr
1 5

<210> SEQ ID NO 144
<211> LENGTH: 8
<212> TYPE: PRT
<213> ORGANISM: Mus musculus
<220> FEATURE:
<221> NAME/KEY: SITE
<222> LOCATION: (3)..(3)
<223> OTHER INFORMATION: Xaa can be any naturally occurring amino acid

<400> SEQUENCE: 144

Ala Arg Xaa Val Thr Phe Asp Tyr
1               5

<210> SEQ ID NO 145
<211> LENGTH: 15
<212> TYPE: PRT
<213> ORGANISM: Mus musculus

<400> SEQUENCE: 145

Ala Ser Trp Ser Glu Arg Ile Gly Tyr Gln Tyr Gly Leu Asp Val
1               5                   10                  15

<210> SEQ ID NO 146
<211> LENGTH: 12
<212> TYPE: PRT
<213> ORGANISM: Mus musculus

<400> SEQUENCE: 146

Ala Thr Glu Asp Thr Ala Met Gly Gly Ile Asp Tyr
1               5                   10

<210> SEQ ID NO 147
<211> LENGTH: 10
<212> TYPE: PRT
<213> ORGANISM: Mus musculus

<400> SEQUENCE: 147

Ala Thr Glu Gly Arg Tyr Gly Met Asp Val
1               5                   10

<210> SEQ ID NO 148
<211> LENGTH: 8
<212> TYPE: PRT
<213> ORGANISM: Mus musculus

<400> SEQUENCE: 148

Ala Thr Gly Val Thr Phe Asp Tyr
1               5

<210> SEQ ID NO 149
<211> LENGTH: 11
<212> TYPE: PRT
<213> ORGANISM: Mus musculus

<400> SEQUENCE: 149

Ala Thr Trp Asp Asp Ala Leu Ser Gly Trp Val
1               5                   10

<210> SEQ ID NO 150
<211> LENGTH: 11
<212> TYPE: PRT
<213> ORGANISM: Mus musculus

<400> SEQUENCE: 150

Ala Thr Trp Asp Asp Ser Leu Asn Gly Pro Val
1               5                   10

<210> SEQ ID NO 151
<211> LENGTH: 11
<212> TYPE: PRT
<213> ORGANISM: Mus musculus

<400> SEQUENCE: 151

-continued

```
Ala Thr Trp Asp Asp Ser Leu Ser Gly Val Val
1               5                   10


<210> SEQ ID NO 152
<211> LENGTH: 8
<212> TYPE: PRT
<213> ORGANISM: Mus musculus
<220> FEATURE:
<221> NAME/KEY: SITE
<222> LOCATION: (3)..(3)
<223> OTHER INFORMATION: Xaa can be any naturally occurring amino acid

<400> SEQUENCE: 152

Ala Thr Xaa Val Thr Phe Asp Ser
1               5


<210> SEQ ID NO 153
<211> LENGTH: 20
<212> TYPE: PRT
<213> ORGANISM: Mus musculus

<400> SEQUENCE: 153

Ala Val Glu Gly Gly Arg Ala Pro Gly Thr Tyr Tyr Tyr Asp Ser Ser
1               5                   10                  15

Gly Leu Ala Tyr
            20


<210> SEQ ID NO 154
<211> LENGTH: 3
<212> TYPE: PRT
<213> ORGANISM: Mus musculus

<400> SEQUENCE: 154

Ala Val Ser
1


<210> SEQ ID NO 155
<211> LENGTH: 8
<212> TYPE: PRT
<213> ORGANISM: Mus musculus
<220> FEATURE:
<221> NAME/KEY: SITE
<222> LOCATION: (2)..(2)
<223> OTHER INFORMATION: Xaa can be any naturally occurring amino acid

<400> SEQUENCE: 155

Ala Xaa Gly Val Thr Phe Asp Tyr
1               5


<210> SEQ ID NO 156
<211> LENGTH: 3
<212> TYPE: PRT
<213> ORGANISM: Mus musculus

<400> SEQUENCE: 156

Asp Ala Phe
1


<210> SEQ ID NO 157
<211> LENGTH: 3
<212> TYPE: PRT
<213> ORGANISM: Mus musculus

<400> SEQUENCE: 157

Asp Ala Ser
1
```

<210> SEQ ID NO 158
<211> LENGTH: 3
<212> TYPE: PRT
<213> ORGANISM: Mus musculus

<400> SEQUENCE: 158

Asp Asp Asp
1

<210> SEQ ID NO 159
<211> LENGTH: 3
<212> TYPE: PRT
<213> ORGANISM: Mus musculus

<400> SEQUENCE: 159

Asp Asp Ser
1

<210> SEQ ID NO 160
<211> LENGTH: 3
<212> TYPE: PRT
<213> ORGANISM: Mus musculus

<400> SEQUENCE: 160

Asp Asp Thr
1

<210> SEQ ID NO 161
<211> LENGTH: 3
<212> TYPE: PRT
<213> ORGANISM: Mus musculus

<400> SEQUENCE: 161

Asp Asp Tyr
1

<210> SEQ ID NO 162
<211> LENGTH: 3
<212> TYPE: PRT
<213> ORGANISM: Mus musculus

<400> SEQUENCE: 162

Asp Gly Arg
1

<210> SEQ ID NO 163
<211> LENGTH: 6
<212> TYPE: PRT
<213> ORGANISM: Mus musculus

<400> SEQUENCE: 163

Asp Ile Glu Ser Glu Met
1               5

<210> SEQ ID NO 164
<211> LENGTH: 26
<212> TYPE: PRT
<213> ORGANISM: Mus musculus

<400> SEQUENCE: 164

Asp Ile Gly Met Thr Gln Ser Pro Ala Ser Leu Ser Ala Ser Val Gly
1               5                   10                  15

Glu Thr Val Thr Ile Thr Cys Arg Ala Ser 20 25

<210> SEQ ID NO 165
<211> LENGTH: 26
<212> TYPE: PRT
<213> ORGANISM: Mus musculus

<400> SEQUENCE: 165

Asp Ile Gln Met Thr Gln Ser Pro Ala Ser Leu Ser Ala Ser Val Gly
1 5 10 15

Glu Ser Val Thr Ile Thr Cys Arg Ala Ser
20 25

<210> SEQ ID NO 166
<211> LENGTH: 26
<212> TYPE: PRT
<213> ORGANISM: Mus musculus

<400> SEQUENCE: 166

Asp Ile Gln Met Thr Gln Ser Pro Ala Ser Leu Ser Ala Ser Val Gly
1 5 10 15

Glu Ser Val Thr Ile Thr Cys Arg Thr Ser
20 25

<210> SEQ ID NO 167
<211> LENGTH: 26
<212> TYPE: PRT
<213> ORGANISM: Mus musculus

<400> SEQUENCE: 167

Asp Ile Gln Met Thr Gln Ser Pro Ala Ser Leu Ser Ala Ser Val Gly
1 5 10 15

Glu Ser Val Thr Leu Thr Cys Gln Ala Ser
20 25

<210> SEQ ID NO 168
<211> LENGTH: 26
<212> TYPE: PRT
<213> ORGANISM: Mus musculus

<400> SEQUENCE: 168

Asp Ile Gln Met Thr Gln Ser Pro Ala Ser Leu Ser Ala Ser Val Gly
1 5 10 15

Glu Thr Val Thr Ile Thr Cys Arg Ala Ser
20 25

<210> SEQ ID NO 169
<211> LENGTH: 26
<212> TYPE: PRT
<213> ORGANISM: Mus musculus

<400> SEQUENCE: 169

Asp Ile Gln Met Thr Gln Ser Pro Lys Phe Leu Asp Val Ser Ala Gly
1 5 10 15

Asp Arg Val Thr Ile Thr Cys Lys Ala Ser
20 25

<210> SEQ ID NO 170
<211> LENGTH: 26
<212> TYPE: PRT
<213> ORGANISM: Mus musculus

<400> SEQUENCE: 170

Asp Ile Gln Met Thr Gln Ser Gln Lys Phe Met Ser Ala Ser Val Gly
1 5 10 15

Asp Arg Val Ser Val Thr Cys Lys Ala Ser
20 25

<210> SEQ ID NO 171
<211> LENGTH: 26
<212> TYPE: PRT
<213> ORGANISM: Mus musculus

<400> SEQUENCE: 171

Asp Ile Gln Met Thr Gln Ser Gln Lys Phe Met Ser Thr Ser Ala Gly
1 5 10 15

Asp Arg Val Ser Val Thr Cys Lys Ala Ser
20 25

<210> SEQ ID NO 172
<211> LENGTH: 26
<212> TYPE: PRT
<213> ORGANISM: Mus musculus

<400> SEQUENCE: 172

Asp Ile Gln Met Thr Gln Ser Gln Lys Phe Met Ser Thr Ser Val Gly
1 5 10 15

Asp Arg Val Ser Val Thr Cys Lys Ala Ser
20 25

<210> SEQ ID NO 173
<211> LENGTH: 26
<212> TYPE: PRT
<213> ORGANISM: Mus musculus

<400> SEQUENCE: 173

Asp Ile Gln Met Thr Gln Ser Thr Ser Ser Leu Ser Ala Ser Leu Gly
1 5 10 15

Asp Arg Val Thr Ile Ser Cys Arg Ala Ser
20 25

<210> SEQ ID NO 174
<211> LENGTH: 26
<212> TYPE: PRT
<213> ORGANISM: Mus musculus

<400> SEQUENCE: 174

Asp Ile Gln Met Thr Gln Ser Thr Ser Ser Leu Ser Ala Ser Leu Gly
1 5 10 15

Asp Arg Val Thr Ile Thr Cys Arg Ala Ser
20 25

<210> SEQ ID NO 175
<211> LENGTH: 26
<212> TYPE: PRT
<213> ORGANISM: Mus musculus

<400> SEQUENCE: 175

Asp Ile Gln Met Thr Gln Thr Pro Ala Ser Leu Ser Ala Ser Val Gly
1 5 10 15

Glu Thr Val Thr Ile Thr Cys Arg Ala Ser
20 25

<210> SEQ ID NO 176

<211> LENGTH: 26
<212> TYPE: PRT
<213> ORGANISM: Mus musculus

<400> SEQUENCE: 176

Asp Ile Gln Met Thr Gln Thr Thr Ser Ser Leu Ser Ala Ser Leu Gly
1 5 10 15

Asp Arg Val Thr Ile Ser Cys Arg Ala Ser
20 25

<210> SEQ ID NO 177
<211> LENGTH: 26
<212> TYPE: PRT
<213> ORGANISM: Mus musculus

<400> SEQUENCE: 177

Asp Ile Gln Met Thr Gln Thr Thr Ser Ser Leu Ser Ala Ser Leu Gly
1 5 10 15

Asp Arg Val Thr Ile Thr Cys Arg Ala Ser
20 25

<210> SEQ ID NO 178
<211> LENGTH: 26
<212> TYPE: PRT
<213> ORGANISM: Mus musculus

<400> SEQUENCE: 178

Asp Ile Val Ile Thr Gln Ser Gln Lys Phe Met Ser Thr Ser Val Gly
1 5 10 15

Asp Arg Val Ser Val Thr Cys Lys Ala Ser
20 25

<210> SEQ ID NO 179
<211> LENGTH: 26
<212> TYPE: PRT
<213> ORGANISM: Mus musculus

<400> SEQUENCE: 179

Asp Ile Val Leu Thr Gln Ser Pro Ala Ser Leu Ser Ala Ser Val Gly
1 5 10 15

Glu Thr Val Thr Ile Thr Cys Arg Ala Ser
20 25

<210> SEQ ID NO 180
<211> LENGTH: 26
<212> TYPE: PRT
<213> ORGANISM: Mus musculus

<400> SEQUENCE: 180

Asp Ile Val Leu Thr Gln Ser Gln Lys Phe Met Ser Thr Ser Val Gly
1 5 10 15

Asp Arg Val Ser Val Thr Cys Lys Ala Ser
20 25

<210> SEQ ID NO 181
<211> LENGTH: 26
<212> TYPE: PRT
<213> ORGANISM: Mus musculus

<400> SEQUENCE: 181

Asp Ile Val Met Thr Gln Ser Pro Ala Ser Leu Ser Ala Ser Val Gly
1 5 10 15

-continued

```
Glu Ser Val Thr Ile Thr Cys Arg Ala Ser
            20                  25


<210> SEQ ID NO 182
<211> LENGTH: 26
<212> TYPE: PRT
<213> ORGANISM: Mus musculus

<400> SEQUENCE: 182

Asp Ile Val Met Thr Gln Ser Pro Ala Ser Leu Ser Ala Ser Val Gly
1               5                   10                  15

Glu Thr Val Thr Ile Thr Cys Arg Ala Ser
            20                  25


<210> SEQ ID NO 183
<211> LENGTH: 26
<212> TYPE: PRT
<213> ORGANISM: Mus musculus

<400> SEQUENCE: 183

Asp Ile Val Met Thr Gln Ser Pro Pro Thr Leu Ser Leu Ser Pro Gly
1               5                   10                  15

Glu Arg Val Thr Leu Ser Cys Gly Ala Ser
            20                  25


<210> SEQ ID NO 184
<211> LENGTH: 26
<212> TYPE: PRT
<213> ORGANISM: Mus musculus

<400> SEQUENCE: 184

Asp Ile Val Met Thr Gln Ser Gln Lys Phe Met Ser Thr Ser Val Gly
1               5                   10                  15

Asp Arg Val Ser Val Thr Cys Lys Ala Ser
            20                  25


<210> SEQ ID NO 185
<211> LENGTH: 26
<212> TYPE: PRT
<213> ORGANISM: Mus musculus

<400> SEQUENCE: 185

Asp Ile Val Met Thr Gln Thr Gln Lys Phe Met Ser Thr Ser Val Gly
1               5                   10                  15

Gly Arg Val Ser Val Thr Cys Lys Ala Ser
            20                  25


<210> SEQ ID NO 186
<211> LENGTH: 26
<212> TYPE: PRT
<213> ORGANISM: Mus musculus

<400> SEQUENCE: 186

Asp Ile Val Met Thr Gln Thr Thr Ser Ser Leu Ser Ala Ser Leu Gly
1               5                   10                  15

Asp Arg Val Thr Ile Ser Cys Arg Ala Ser
            20                  25


<210> SEQ ID NO 187
<211> LENGTH: 26
<212> TYPE: PRT
<213> ORGANISM: Mus musculus
```

-continued

<400> SEQUENCE: 187

Asp Ile Val Met Thr Gln Thr Thr Ser Ser Leu Ser Ala Ser Leu Gly
1 5 10 15

Asp Arg Val Thr Ile Thr Cys Gly Ala Ser
20 25

<210> SEQ ID NO 188
<211> LENGTH: 3
<212> TYPE: PRT
<213> ORGANISM: Mus musculus

<400> SEQUENCE: 188

Asp Asn Asp
1

<210> SEQ ID NO 189
<211> LENGTH: 6
<212> TYPE: PRT
<213> ORGANISM: Mus musculus

<400> SEQUENCE: 189

Asp Asn Ile Tyr Ser Tyr
1 5

<210> SEQ ID NO 190
<211> LENGTH: 3
<212> TYPE: PRT
<213> ORGANISM: Mus musculus

<400> SEQUENCE: 190

Asp Asn Asn
1

<210> SEQ ID NO 191
<211> LENGTH: 3
<212> TYPE: PRT
<213> ORGANISM: Mus musculus

<400> SEQUENCE: 191

Asp Ser Thr
1

<210> SEQ ID NO 192
<211> LENGTH: 26
<212> TYPE: PRT
<213> ORGANISM: Mus musculus

<400> SEQUENCE: 192

Asp Thr Thr Val Thr Gln Ser Pro Ser Ser Met Tyr Ala Ser Leu Gly
1 5 10 15

Glu Arg Val Thr Ile Thr Cys Lys Ala Ser
20 25

<210> SEQ ID NO 193
<211> LENGTH: 26
<212> TYPE: PRT
<213> ORGANISM: Mus musculus

<400> SEQUENCE: 193

Asp Thr Thr Val Thr Gln Ser Gln Lys Phe Met Ser Thr Ser Val Gly
1 5 10 15

Asp Arg Val Ser Val Thr Cys Lys Ala Ser
20 25

<210> SEQ ID NO 194
<211> LENGTH: 26
<212> TYPE: PRT
<213> ORGANISM: Mus musculus

<400> SEQUENCE: 194

```
Asp Val Gln Met Asn Gln Ser Pro Ser Ser Met Tyr Ala Ser Leu Gly
1               5                   10                  15

Glu Arg Val Thr Ile Thr Cys Lys Ala Ser
            20                  25
```

<210> SEQ ID NO 195
<211> LENGTH: 26
<212> TYPE: PRT
<213> ORGANISM: Mus musculus

<400> SEQUENCE: 195

```
Asp Val Gln Met Asn Gln Ser Gln Lys Phe Met Ser Thr Ser Val Gly
1               5                   10                  15

Asp Arg Val Ser Val Thr Cys Lys Ala Ser
            20                  25
```

<210> SEQ ID NO 196
<211> LENGTH: 26
<212> TYPE: PRT
<213> ORGANISM: Mus musculus

<400> SEQUENCE: 196

```
Asp Val Gln Met Thr Gln Ser Pro Ala Ser Leu Ser Ala Ser Val Gly
1               5                   10                  15

Glu Thr Val Thr Ile Thr Cys Arg Ala Ser
            20                  25
```

<210> SEQ ID NO 197
<211> LENGTH: 26
<212> TYPE: PRT
<213> ORGANISM: Mus musculus

<400> SEQUENCE: 197

```
Asp Val Gln Met Thr Gln Ser Pro Pro Ser Leu Ser Ala Ser Val Gly
1               5                   10                  15

Glu Thr Val Thr Ile Thr Cys Arg Ala Ser
            20                  25
```

<210> SEQ ID NO 198
<211> LENGTH: 26
<212> TYPE: PRT
<213> ORGANISM: Mus musculus

<400> SEQUENCE: 198

```
Asp Val Gln Met Thr Gln Ser Pro Ser Ser Met Tyr Ala Ser Leu Gly
1               5                   10                  15

Glu Arg Val Thr Phe Thr Cys Lys Ala Ser
            20                  25
```

<210> SEQ ID NO 199
<211> LENGTH: 26
<212> TYPE: PRT
<213> ORGANISM: Mus musculus

<400> SEQUENCE: 199

```
Asp Val Gln Met Thr Gln Ser Pro Ser Ser Met Tyr Ala Ser Leu Gly
1               5                   10                  15

Glu Arg Val Thr Ile Thr Cys Lys Ala Ser
            20                  25


<210> SEQ ID NO 200
<211> LENGTH: 26
<212> TYPE: PRT
<213> ORGANISM: Mus musculus

<400> SEQUENCE: 200

Asp Val Gln Met Thr Gln Ser Gln Lys Phe Met Ser Thr Ser Val Gly
1               5                   10                  15

Asp Arg Val Ser Val Thr Cys Lys Ala Ser
            20                  25


<210> SEQ ID NO 201
<211> LENGTH: 3
<212> TYPE: PRT
<213> ORGANISM: Mus musculus

<400> SEQUENCE: 201

Asp Val Ser
1


<210> SEQ ID NO 202
<211> LENGTH: 26
<212> TYPE: PRT
<213> ORGANISM: Mus musculus

<400> SEQUENCE: 202

Asp Val Val Leu Thr Gln Thr Pro Leu Ser Leu Pro Val Ser Leu Gly
1               5                   10                  15

Asp Gln Ala Ser Ile Ser Cys Arg Ser Ser
            20                  25


<210> SEQ ID NO 203
<211> LENGTH: 26
<212> TYPE: PRT
<213> ORGANISM: Mus musculus

<400> SEQUENCE: 203

Asp Val Val Met Thr Gln Ser Pro Ala Ser Leu Ser Ala Ser Val Gly
1               5                   10                  15

Glu Ser Val Thr Ile Thr Cys Arg Ala Ser
            20                  25


<210> SEQ ID NO 204
<211> LENGTH: 26
<212> TYPE: PRT
<213> ORGANISM: Mus musculus

<400> SEQUENCE: 204

Asp Val Val Met Thr Gln Ser Pro Ala Ser Leu Ser Ala Ser Val Gly
1               5                   10                  15

Glu Thr Val Thr Ile Thr Cys Arg Ala Ser
            20                  25


<210> SEQ ID NO 205
<211> LENGTH: 26
<212> TYPE: PRT
<213> ORGANISM: Mus musculus
```

<400> SEQUENCE: 205

Asp Val Val Met Thr Gln Ser Pro Pro Ser Leu Ser Ala Ser Val Gly
1 5 10 15

Glu Thr Val Thr Ile Ser Cys Arg Ala Ser
20 25

<210> SEQ ID NO 206
<211> LENGTH: 26
<212> TYPE: PRT
<213> ORGANISM: Mus musculus

<400> SEQUENCE: 206

Asp Val Val Met Thr Gln Ser Gln Lys Phe Met Ser Thr Ser Val Gly
1 5 10 15

Asp Arg Val Ser Val Thr Cys Lys Ala Ser
20 25

<210> SEQ ID NO 207
<211> LENGTH: 26
<212> TYPE: PRT
<213> ORGANISM: Mus musculus

<400> SEQUENCE: 207

Asp Val Val Met Thr Gln Thr Pro Ala Ser Leu Ser Ala Ser Val Gly
1 5 10 15

Glu Thr Val Thr Ile Thr Cys Arg Ala Ser
20 25

<210> SEQ ID NO 208
<211> LENGTH: 26
<212> TYPE: PRT
<213> ORGANISM: Mus musculus

<400> SEQUENCE: 208

Asp Val Val Met Thr Gln Thr Pro Leu Ser Leu Pro Val Asn Leu Gly
1 5 10 15

Asp Gln Ala Ser Ile Ser Cys Arg Ser Ser
20 25

<210> SEQ ID NO 209
<211> LENGTH: 26
<212> TYPE: PRT
<213> ORGANISM: Mus musculus

<400> SEQUENCE: 209

Asp Val Val Met Thr Gln Thr Pro Leu Ser Leu Pro Val Ser Leu Gly
1 5 10 15

Asp Gln Ala Ser Ile Ser Cys Arg Ser Ser
20 25

<210> SEQ ID NO 210
<211> LENGTH: 26
<212> TYPE: PRT
<213> ORGANISM: Mus musculus

<400> SEQUENCE: 210

Asp Val Val Met Thr Gln Thr Pro Ser Ser Leu Ser Ala Ser Leu Gly
1 5 10 15

Glu Arg Val Thr Ile Thr Cys Lys Ala Ser
20 25

<210> SEQ ID NO 211
<211> LENGTH: 26
<212> TYPE: PRT
<213> ORGANISM: Mus musculus

<400> SEQUENCE: 211

Asp Val Val Met Thr Gln Thr Thr Ser Ser Leu Ser Ala Ser Leu Gly
1 5 10 15

Asp Arg Val Thr Ile Thr Cys Arg Ala Ser
20 25

<210> SEQ ID NO 212
<211> LENGTH: 26
<212> TYPE: PRT
<213> ORGANISM: Mus musculus

<400> SEQUENCE: 212

Asp Val Val Val Thr Gln Thr Pro Leu Ser Leu Pro Val Ser Leu Gly
1 5 10 15

Asp Gln Ala Ser Ile Ser Cys Arg Ser Ser
20 25

<210> SEQ ID NO 213
<211> LENGTH: 38
<212> TYPE: PRT
<213> ORGANISM: Mus musculus

<400> SEQUENCE: 213

Asp Tyr Asn Glu Lys Phe Lys Asp Lys Ala Thr Leu Thr Ala Asp Lys
1 5 10 15

Ser Ser Ser Thr Ala Tyr Met Gln Leu Ser Ser Leu Thr Ser Asp Asp
20 25 30

Ser Ala Val Tyr Tyr Cys
35

<210> SEQ ID NO 214
<211> LENGTH: 3
<212> TYPE: PRT
<213> ORGANISM: Mus musculus

<400> SEQUENCE: 214

Glu Asp Asp
1

<210> SEQ ID NO 215
<211> LENGTH: 6
<212> TYPE: PRT
<213> ORGANISM: Mus musculus

<400> SEQUENCE: 215

Glu Asp Ile Arg Met Tyr
1 5

<210> SEQ ID NO 216
<211> LENGTH: 3
<212> TYPE: PRT
<213> ORGANISM: Mus musculus

<400> SEQUENCE: 216

Glu Asp Asn
1

<210> SEQ ID NO 217

<211> LENGTH: 34
<212> TYPE: PRT
<213> ORGANISM: Mus musculus

<400> SEQUENCE: 217

Glu Phe Lys Gly Lys Ala Thr Leu Thr Ala Asp Thr Ser Ser Ser Thr
1               5                   10                  15

Ala Tyr Met Gln Leu Ser Ser Leu Thr Ser Glu Asp Ser Ala Val Tyr
            20                  25                  30

Phe Cys

<210> SEQ ID NO 218
<211> LENGTH: 6
<212> TYPE: PRT
<213> ORGANISM: Mus musculus

<400> SEQUENCE: 218

Glu Gly Ile Arg Thr Ser
1               5

<210> SEQ ID NO 219
<211> LENGTH: 3
<212> TYPE: PRT
<213> ORGANISM: Mus musculus

<400> SEQUENCE: 219

Glu Gly Ser
1

<210> SEQ ID NO 220
<211> LENGTH: 38
<212> TYPE: PRT
<213> ORGANISM: Mus musculus

<400> SEQUENCE: 220

Glu His Asn Gln Lys Phe Lys Asp Lys Ala Thr Leu Thr Ala Asp Lys
1               5                   10                  15

Ser Ser Ser Thr Ala Tyr Met Gln Leu Ser Ser Leu Thr Ser Glu Asp
            20                  25                  30

Ser Ala Val Tyr Tyr Cys
        35

<210> SEQ ID NO 221
<211> LENGTH: 26
<212> TYPE: PRT
<213> ORGANISM: Mus musculus

<400> SEQUENCE: 221

Glu Ile Val Met Thr Gln Ser Pro Pro Thr Leu Ser Leu Ser Pro Gly
1               5                   10                  15

Glu Arg Val Thr Leu Ser Cys Lys Ala Ser
            20                  25

<210> SEQ ID NO 222
<211> LENGTH: 6
<212> TYPE: PRT
<213> ORGANISM: Mus musculus

<400> SEQUENCE: 222

Glu Asn Ile His Ser Tyr
1               5

<210> SEQ ID NO 223
<211> LENGTH: 6
<212> TYPE: PRT
<213> ORGANISM: Mus musculus

<400> SEQUENCE: 223

Glu Asn Ile Tyr Asn Tyr
1               5

<210> SEQ ID NO 224
<211> LENGTH: 6
<212> TYPE: PRT
<213> ORGANISM: Mus musculus

<400> SEQUENCE: 224

Glu Asn Ile Tyr Ser Tyr
1               5

<210> SEQ ID NO 225
<211> LENGTH: 6
<212> TYPE: PRT
<213> ORGANISM: Mus musculus

<400> SEQUENCE: 225

Glu Asn Ser Tyr Asn Tyr
1               5

<210> SEQ ID NO 226
<211> LENGTH: 6
<212> TYPE: PRT
<213> ORGANISM: Mus musculus

<400> SEQUENCE: 226

Glu Asn Ser Tyr Ser Tyr
1               5

<210> SEQ ID NO 227
<211> LENGTH: 11
<212> TYPE: PRT
<213> ORGANISM: Mus musculus

<400> SEQUENCE: 227

Glu Thr Trp Asp Asp Ser Leu Arg Gly Val Val
1               5                   10

<210> SEQ ID NO 228
<211> LENGTH: 25
<212> TYPE: PRT
<213> ORGANISM: Mus musculus

<400> SEQUENCE: 228

Glu Val His Leu Gln Gln Phe Gly Ala Glu Leu Val Arg Ser Gly Ala
1               5                   10                  15

Ser Val Lys Leu Ser Cys Thr Ala Ser
            20                  25

<210> SEQ ID NO 229
<211> LENGTH: 25
<212> TYPE: PRT
<213> ORGANISM: Mus musculus

<400> SEQUENCE: 229

Glu Val His Leu Gln Gln Ser Gly Ala Glu Leu Ala Lys Pro Gly Ala
1               5                   10                  15

Ser Val Lys Met Ser Cys Lys Ala Ser
            20                  25

<210> SEQ ID NO 230
<211> LENGTH: 25
<212> TYPE: PRT
<213> ORGANISM: Mus musculus

<400> SEQUENCE: 230

Glu Val His Leu Gln Gln Ser Gly Ala Glu Leu Val Arg Pro Gly Val
1               5                   10                  15

Ser Val Lys Ile Ser Cys Lys Gly Ser
            20                  25

<210> SEQ ID NO 231
<211> LENGTH: 25
<212> TYPE: PRT
<213> ORGANISM: Mus musculus

<400> SEQUENCE: 231

Glu Val His Leu Gln Gln Ser Gly Ala Glu Leu Val Arg Ser Gly Ala
1               5                   10                  15

Ser Val Lys Leu Ser Cys Thr Ala Ser
            20                  25

<210> SEQ ID NO 232
<211> LENGTH: 25
<212> TYPE: PRT
<213> ORGANISM: Mus musculus

<400> SEQUENCE: 232

Glu Val Leu Leu Gln Gln Ser Gly Ala Glu Leu Val Arg Pro Gly Val
1               5                   10                  15

Ser Val Lys Ile Ser Cys Lys Gly Ser
            20                  25

<210> SEQ ID NO 233
<211> LENGTH: 25
<212> TYPE: PRT
<213> ORGANISM: Mus musculus

<400> SEQUENCE: 233

Glu Val Leu Leu Gln Gln Ser Gly Ala Glu Leu Val Arg Ser Gly Ala
1               5                   10                  15

Ser Ala Lys Leu Ser Cys Thr Ala Ser
            20                  25

<210> SEQ ID NO 234
<211> LENGTH: 25
<212> TYPE: PRT
<213> ORGANISM: Mus musculus

<400> SEQUENCE: 234

Glu Val Gln Leu Gln Gln Ser Gly Ala Glu Leu Val Arg Pro Gly Val
1               5                   10                  15

Ser Leu Lys Ile Ser Cys Lys Gly Ser
            20                  25

<210> SEQ ID NO 235
<211> LENGTH: 25
<212> TYPE: PRT
<213> ORGANISM: Mus musculus

<400> SEQUENCE: 235

Glu Val Arg Leu Gln Gln Ser Gly Ala Asp Leu Met Lys Pro Gly Ala
1 5 10 15

Ser Val Lys Ile Ser Cys Lys Ala Ser
20 25

<210> SEQ ID NO 236
<211> LENGTH: 25
<212> TYPE: PRT
<213> ORGANISM: Mus musculus

<400> SEQUENCE: 236

Glu Val Arg Leu Gln Gln Ser Gly Ala Glu Leu Val Arg Ser Gly Ala
1 5 10 15

Ser Val Lys Leu Ser Cys Thr Ala Ser
20 25

<210> SEQ ID NO 237
<211> LENGTH: 3
<212> TYPE: PRT
<213> ORGANISM: Mus musculus

<400> SEQUENCE: 237

Glu Val Ser
1

<210> SEQ ID NO 238
<211> LENGTH: 38
<212> TYPE: PRT
<213> ORGANISM: Mus musculus

<400> SEQUENCE: 238

Glu Tyr Ala Pro Lys Phe Gln Gly Lys Ala Thr Met Thr Ala Asp Thr
1 5 10 15

Ser Ser Asn Thr Ala His Leu Gln Leu Ser Ser Leu Ala Pro Glu Asp
20 25 30

Thr Ala Val Tyr Tyr Cys
35

<210> SEQ ID NO 239
<211> LENGTH: 38
<212> TYPE: PRT
<213> ORGANISM: Mus musculus

<400> SEQUENCE: 239

Glu Tyr Ala Pro Lys Phe Gln Gly Lys Ala Thr Met Thr Ala Asp Thr
1 5 10 15

Ser Ser Asn Thr Ala His Leu Gln Leu Ser Ser Leu Thr Ser Glu Asp
20 25 30

Thr Ala Val Tyr Tyr Cys
35

<210> SEQ ID NO 240
<211> LENGTH: 38
<212> TYPE: PRT
<213> ORGANISM: Mus musculus

<400> SEQUENCE: 240

Glu Tyr Asn Gln Lys Phe Glu Asp Arg Ala Thr Leu Thr Ala Asp Lys
1 5 10 15

Ser Ser Ser Thr Ala Tyr Met Gln Leu Ser Ser Leu Thr Ser Asp Asp

```
            20                  25                  30

Ser Ala Val Tyr Tyr Cys
        35


<210> SEQ ID NO 241
<211> LENGTH: 38
<212> TYPE: PRT
<213> ORGANISM: Mus musculus

<400> SEQUENCE: 241

Glu Tyr Asn Gln Lys Phe Lys Asp Lys Ala Thr Leu Thr Ala Asp Lys
1               5                   10                  15

Ser Ser Ser Thr Ala Tyr Met Gln Leu Ser Ser Leu Ala Ser Asp Asp
            20                  25                  30

Ser Ala Val Tyr Tyr Cys
        35


<210> SEQ ID NO 242
<211> LENGTH: 38
<212> TYPE: PRT
<213> ORGANISM: Mus musculus

<400> SEQUENCE: 242

Glu Tyr Asn Gln Lys Phe Lys Asp Lys Ala Thr Leu Thr Ala Asp Lys
1               5                   10                  15

Ser Ser Ser Thr Ala Tyr Met Gln Leu Ser Ser Leu Thr Ser Asp Asp
            20                  25                  30

Ser Ala Val Tyr Tyr Cys
        35


<210> SEQ ID NO 243
<211> LENGTH: 38
<212> TYPE: PRT
<213> ORGANISM: Mus musculus

<400> SEQUENCE: 243

Glu Tyr Asn Gln Lys Phe Lys Asp Lys Ala Thr Leu Thr Ala Asn Lys
1               5                   10                  15

Ser Ser Ser Thr Ala Tyr Met Gln Leu Ser Ser Leu Thr Ser Asp Asp
            20                  25                  30

Ser Ala Val Tyr Tyr Cys
        35


<210> SEQ ID NO 244
<211> LENGTH: 38
<212> TYPE: PRT
<213> ORGANISM: Mus musculus

<400> SEQUENCE: 244

Glu Tyr Asn Gln Met Phe Glu Asp Arg Ala Thr Leu Thr Ala Asp Lys
1               5                   10                  15

Ser Ser Ser Thr Ala Tyr Ile Gln Leu Thr Ser Leu Thr Ser Glu Asp
            20                  25                  30

Ser Ala Val Tyr Tyr Cys
        35


<210> SEQ ID NO 245
<211> LENGTH: 38
<212> TYPE: PRT
<213> ORGANISM: Mus musculus
```

<400> SEQUENCE: 245

```
Glu Tyr Asn Gln Met Phe Glu Asp Arg Ala Thr Leu Thr Ala Asp Thr
1               5                   10                  15

Ser Ser Ser Thr Ala Tyr Ile Gln Leu Ser Ser Leu Thr Ser Glu Asp
            20                  25                  30

Ser Ala Val Tyr Tyr Cys
        35
```

<210> SEQ ID NO 246
<211> LENGTH: 10
<212> TYPE: PRT
<213> ORGANISM: Mus musculus

<400> SEQUENCE: 246

```
Phe Gly Ala Gly Thr Lys Leu Glu Ile Lys
1               5                   10
```

<210> SEQ ID NO 247
<211> LENGTH: 10
<212> TYPE: PRT
<213> ORGANISM: Mus musculus

<400> SEQUENCE: 247

```
Phe Gly Ala Gly Thr Lys Leu Glu Met Lys
1               5                   10
```

<210> SEQ ID NO 248
<211> LENGTH: 10
<212> TYPE: PRT
<213> ORGANISM: Mus musculus

<400> SEQUENCE: 248

```
Phe Gly Glu Gly Thr Lys Leu Glu Ile Lys
1               5                   10
```

<210> SEQ ID NO 249
<211> LENGTH: 10
<212> TYPE: PRT
<213> ORGANISM: Mus musculus

<400> SEQUENCE: 249

```
Phe Gly Gly Gly Thr Lys Leu Glu Ile Lys
1               5                   10
```

<210> SEQ ID NO 250
<211> LENGTH: 10
<212> TYPE: PRT
<213> ORGANISM: Mus musculus

<400> SEQUENCE: 250

```
Phe Gly Gly Gly Thr Lys Leu Glu Met Lys
1               5                   10
```

<210> SEQ ID NO 251
<211> LENGTH: 10
<212> TYPE: PRT
<213> ORGANISM: Mus musculus
<220> FEATURE:
<221> NAME/KEY: SITE
<222> LOCATION: (9)..(9)
<223> OTHER INFORMATION: Xaa can be any naturally occurring amino acid

<400> SEQUENCE: 251

```
Phe Gly Gly Gly Thr Lys Leu Glu Xaa Lys
```

```
1               5                   10


<210> SEQ ID NO 252
<211> LENGTH: 10
<212> TYPE: PRT
<213> ORGANISM: Mus musculus

<400> SEQUENCE: 252

Phe Gly Gly Gly Thr Lys Val Glu Ile Lys
1               5                   10


<210> SEQ ID NO 253
<211> LENGTH: 10
<212> TYPE: PRT
<213> ORGANISM: Mus musculus
<220> FEATURE:
<221> NAME/KEY: SITE
<222> LOCATION: (7)..(7)
<223> OTHER INFORMATION: Xaa can be any naturally occurring amino acid

<400> SEQUENCE: 253

Phe Gly Gly Gly Thr Lys Xaa Glu Met Lys
1               5                   10


<210> SEQ ID NO 254
<211> LENGTH: 10
<212> TYPE: PRT
<213> ORGANISM: Mus musculus

<400> SEQUENCE: 254

Phe Gly Gly Gly Thr Gln Leu Glu Ile Lys
1               5                   10


<210> SEQ ID NO 255
<211> LENGTH: 9
<212> TYPE: PRT
<213> ORGANISM: Mus musculus

<400> SEQUENCE: 255

Phe Gln Gly Ser His Val Pro Pro Thr
1               5


<210> SEQ ID NO 256
<211> LENGTH: 9
<212> TYPE: PRT
<213> ORGANISM: Mus musculus

<400> SEQUENCE: 256

Phe Gln Gly Ser His Val Pro Arg Thr
1               5


<210> SEQ ID NO 257
<211> LENGTH: 8
<212> TYPE: PRT
<213> ORGANISM: Mus musculus

<400> SEQUENCE: 257

Phe Gln Gly Ser His Val Pro Thr
1               5


<210> SEQ ID NO 258
<211> LENGTH: 9
<212> TYPE: PRT
<213> ORGANISM: Mus musculus

<400> SEQUENCE: 258
```

Phe Gln Gly Ser His Val Pro Thr Phe
1 5

<210> SEQ ID NO 259
<211> LENGTH: 9
<212> TYPE: PRT
<213> ORGANISM: Mus musculus

<400> SEQUENCE: 259

Phe Arg Phe Gly Glu Gly Phe Asp Tyr
1 5

<210> SEQ ID NO 260
<211> LENGTH: 3
<212> TYPE: PRT
<213> ORGANISM: Mus musculus

<400> SEQUENCE: 260

Gly Ala Ser
1

<210> SEQ ID NO 261
<211> LENGTH: 10
<212> TYPE: PRT
<213> ORGANISM: Mus musculus

<400> SEQUENCE: 261

Gly Asp Ser Ile Ser Ser Ser Ser Tyr Tyr
1 5 10

<210> SEQ ID NO 262
<211> LENGTH: 8
<212> TYPE: PRT
<213> ORGANISM: Mus musculus

<400> SEQUENCE: 262

Gly Phe Ala Phe Ser Ser Tyr Gly
1 5

<210> SEQ ID NO 263
<211> LENGTH: 8
<212> TYPE: PRT
<213> ORGANISM: Mus musculus

<400> SEQUENCE: 263

Gly Phe Asp Phe Asn Trp Tyr Gly
1 5

<210> SEQ ID NO 264
<211> LENGTH: 8
<212> TYPE: PRT
<213> ORGANISM: Mus musculus

<400> SEQUENCE: 264

Gly Phe Ile Phe Ser Arg His Ala
1 5

<210> SEQ ID NO 265
<211> LENGTH: 8
<212> TYPE: PRT
<213> ORGANISM: Mus musculus

<400> SEQUENCE: 265

Gly Phe Asn Ile Lys Asp Tyr Tyr 1 5

<210> SEQ ID NO 266
<211> LENGTH: 8
<212> TYPE: PRT
<213> ORGANISM: Mus musculus

<400> SEQUENCE: 266

Gly Phe Thr Phe Gly Asp Tyr Ala
1 5

<210> SEQ ID NO 267
<211> LENGTH: 8
<212> TYPE: PRT
<213> ORGANISM: Mus musculus

<400> SEQUENCE: 267

Gly Phe Thr Phe Asn Asn Ala Trp
1 5

<210> SEQ ID NO 268
<211> LENGTH: 8
<212> TYPE: PRT
<213> ORGANISM: Mus musculus

<400> SEQUENCE: 268

Gly Phe Thr Phe Arg Arg Tyr Trp
1 5

<210> SEQ ID NO 269
<211> LENGTH: 8
<212> TYPE: PRT
<213> ORGANISM: Mus musculus

<400> SEQUENCE: 269

Gly Phe Thr Phe Ser Gly Phe Trp
1 5

<210> SEQ ID NO 270
<211> LENGTH: 8
<212> TYPE: PRT
<213> ORGANISM: Mus musculus

<400> SEQUENCE: 270

Gly Phe Thr Phe Ser Asn Ala Trp
1 5

<210> SEQ ID NO 271
<211> LENGTH: 8
<212> TYPE: PRT
<213> ORGANISM: Mus musculus

<400> SEQUENCE: 271

Gly Phe Thr Phe Ser Asn Tyr Gly
1 5

<210> SEQ ID NO 272
<211> LENGTH: 8
<212> TYPE: PRT
<213> ORGANISM: Mus musculus

<400> SEQUENCE: 272

Gly Phe Thr Phe Ser Ser Ser Ala
1 5

<210> SEQ ID NO 273
<211> LENGTH: 8
<212> TYPE: PRT
<213> ORGANISM: Mus musculus

<400> SEQUENCE: 273

Gly Phe Thr Phe Ser Ser Tyr Ala
1 5

<210> SEQ ID NO 274
<211> LENGTH: 8
<212> TYPE: PRT
<213> ORGANISM: Mus musculus

<400> SEQUENCE: 274

Gly Phe Thr Phe Ser Ser Tyr Glu
1 5

<210> SEQ ID NO 275
<211> LENGTH: 8
<212> TYPE: PRT
<213> ORGANISM: Mus musculus

<400> SEQUENCE: 275

Gly Phe Thr Phe Ser Ser Tyr Gly
1 5

<210> SEQ ID NO 276
<211> LENGTH: 8
<212> TYPE: PRT
<213> ORGANISM: Mus musculus

<400> SEQUENCE: 276

Gly Phe Thr Phe Ser Ser Tyr Ser
1 5

<210> SEQ ID NO 277
<211> LENGTH: 8
<212> TYPE: PRT
<213> ORGANISM: Mus musculus

<400> SEQUENCE: 277

Gly Phe Thr Phe Ser Ser Tyr Trp
1 5

<210> SEQ ID NO 278
<211> LENGTH: 10
<212> TYPE: PRT
<213> ORGANISM: Mus musculus

<400> SEQUENCE: 278

Gly Gly Gly Gly Thr Lys Leu Glu Ile Lys
1 5 10

<210> SEQ ID NO 279
<211> LENGTH: 8
<212> TYPE: PRT
<213> ORGANISM: Mus musculus

<400> SEQUENCE: 279

Gly Gly Asn Ile Ala Arg Asn Tyr
1 5

<210> SEQ ID NO 280

-continued

<211> LENGTH: 8
<212> TYPE: PRT
<213> ORGANISM: Mus musculus

<400> SEQUENCE: 280

Gly Gly Asn Ile Ala Arg Asn Tyr
1 5

<210> SEQ ID NO 281
<211> LENGTH: 9
<212> TYPE: PRT
<213> ORGANISM: Mus musculus

<400> SEQUENCE: 281

Gly Gly Ser Ile Ser Arg Ser Asn Trp
1 5

<210> SEQ ID NO 282
<211> LENGTH: 10
<212> TYPE: PRT
<213> ORGANISM: Mus musculus

<400> SEQUENCE: 282

Gly Gly Ser Ile Ser Ser Gly Gly Tyr Ser
1 5 10

<210> SEQ ID NO 283
<211> LENGTH: 10
<212> TYPE: PRT
<213> ORGANISM: Mus musculus

<400> SEQUENCE: 283

Gly Gly Ser Ile Ser Ser Gly Gly Tyr Tyr
1 5 10

<210> SEQ ID NO 284
<211> LENGTH: 9
<212> TYPE: PRT
<213> ORGANISM: Mus musculus

<400> SEQUENCE: 284

Gly Gly Ser Ile Ser Ser Ser Asn Trp
1 5

<210> SEQ ID NO 285
<211> LENGTH: 10
<212> TYPE: PRT
<213> ORGANISM: Mus musculus

<400> SEQUENCE: 285

Gly Gly Ser Ile Ser Ser Ser Ser Tyr Tyr
1 5 10

<210> SEQ ID NO 286
<211> LENGTH: 8
<212> TYPE: PRT
<213> ORGANISM: Mus musculus

<400> SEQUENCE: 286

Gly Gly Thr Phe Ser Ser Tyr Ala
1 5

<210> SEQ ID NO 287
<211> LENGTH: 3
<212> TYPE: PRT

<213> ORGANISM: Mus musculus

<400> SEQUENCE: 287

Gly Lys Asn
1

<210> SEQ ID NO 288
<211> LENGTH: 6
<212> TYPE: PRT
<213> ORGANISM: Mus musculus

<400> SEQUENCE: 288

Gly Asn Val His Asn Phe
1 5

<210> SEQ ID NO 289
<211> LENGTH: 11
<212> TYPE: PRT
<213> ORGANISM: Mus musculus

<400> SEQUENCE: 289

Gly Ser Trp Asp Thr Asn Leu Ser Gly Tyr Val
1 5 10

<210> SEQ ID NO 290
<211> LENGTH: 11
<212> TYPE: PRT
<213> ORGANISM: Mus musculus

<400> SEQUENCE: 290

Gly Ser Trp Glu Ala Arg Glu Ser Val Phe Val
1 5 10

<210> SEQ ID NO 291
<211> LENGTH: 3
<212> TYPE: PRT
<213> ORGANISM: Mus musculus

<400> SEQUENCE: 291

Gly Thr Ser
1

<210> SEQ ID NO 292
<211> LENGTH: 11
<212> TYPE: PRT
<213> ORGANISM: Mus musculus

<400> SEQUENCE: 292

Gly Thr Trp Asp Ser Ser Leu Ser Ala Leu Val
1 5 10

<210> SEQ ID NO 293
<211> LENGTH: 11
<212> TYPE: PRT
<213> ORGANISM: Mus musculus

<400> SEQUENCE: 293

Gly Thr Trp Asp Ser Ser Leu Ser Ala Trp Val
1 5 10

<210> SEQ ID NO 294
<211> LENGTH: 11
<212> TYPE: PRT
<213> ORGANISM: Mus musculus

<400> SEQUENCE: 294

Gly Thr Trp Asp Ser Ser Leu Ser Ala Tyr Val
1 5 10

<210> SEQ ID NO 295
<211> LENGTH: 3
<212> TYPE: PRT
<213> ORGANISM: Mus musculus

<400> SEQUENCE: 295

Gly Val Ser
1

<210> SEQ ID NO 296
<211> LENGTH: 8
<212> TYPE: PRT
<213> ORGANISM: Mus musculus

<400> SEQUENCE: 296

Gly Tyr Lys Phe Ala Asn Tyr Trp
1 5

<210> SEQ ID NO 297
<211> LENGTH: 8
<212> TYPE: PRT
<213> ORGANISM: Mus musculus

<400> SEQUENCE: 297

Gly Tyr Ser Phe Asn Thr Tyr Trp
1 5

<210> SEQ ID NO 298
<211> LENGTH: 8
<212> TYPE: PRT
<213> ORGANISM: Mus musculus

<400> SEQUENCE: 298

Gly Tyr Ser Phe Ser Thr Tyr Trp
1 5

<210> SEQ ID NO 299
<211> LENGTH: 8
<212> TYPE: PRT
<213> ORGANISM: Mus musculus

<400> SEQUENCE: 299

Gly Tyr Ser Phe Thr Ser Tyr Trp
1 5

<210> SEQ ID NO 300
<211> LENGTH: 8
<212> TYPE: PRT
<213> ORGANISM: Mus musculus

<400> SEQUENCE: 300

Gly Tyr Ser Phe Thr Thr Tyr Trp
1 5

<210> SEQ ID NO 301
<211> LENGTH: 8
<212> TYPE: PRT
<213> ORGANISM: Mus musculus

<400> SEQUENCE: 301

Gly Tyr Thr Phe Lys Asn Phe Gly
1 5

<210> SEQ ID NO 302
<211> LENGTH: 8
<212> TYPE: PRT
<213> ORGANISM: Mus musculus

<400> SEQUENCE: 302

Gly Tyr Thr Phe Asn Asn Tyr Gly
1 5

<210> SEQ ID NO 303
<211> LENGTH: 8
<212> TYPE: PRT
<213> ORGANISM: Mus musculus

<400> SEQUENCE: 303

Gly Tyr Thr Phe Asn Arg Phe Trp
1 5

<210> SEQ ID NO 304
<211> LENGTH: 8
<212> TYPE: PRT
<213> ORGANISM: Mus musculus

<400> SEQUENCE: 304

Gly Tyr Thr Phe Ser Asn Tyr Trp
1 5

<210> SEQ ID NO 305
<211> LENGTH: 8
<212> TYPE: PRT
<213> ORGANISM: Mus musculus

<400> SEQUENCE: 305

Gly Tyr Thr Phe Thr Asp Tyr Ala
1 5

<210> SEQ ID NO 306
<211> LENGTH: 8
<212> TYPE: PRT
<213> ORGANISM: Mus musculus

<400> SEQUENCE: 306

Gly Tyr Thr Phe Thr Asp Tyr Tyr
1 5

<210> SEQ ID NO 307
<211> LENGTH: 8
<212> TYPE: PRT
<213> ORGANISM: Mus musculus

<400> SEQUENCE: 307

Gly Tyr Thr Phe Thr Gly Tyr Tyr
1 5

<210> SEQ ID NO 308
<211> LENGTH: 8
<212> TYPE: PRT
<213> ORGANISM: Mus musculus

<400> SEQUENCE: 308

Gly Tyr Thr Phe Thr Lys Tyr Trp
1 5

<210> SEQ ID NO 309
<211> LENGTH: 8
<212> TYPE: PRT
<213> ORGANISM: Mus musculus

<400> SEQUENCE: 309

Gly Tyr Thr Phe Thr Asn Tyr Trp
1 5

<210> SEQ ID NO 310
<211> LENGTH: 8
<212> TYPE: PRT
<213> ORGANISM: Mus musculus

<400> SEQUENCE: 310

Gly Tyr Thr Phe Thr Arg Phe Trp
1 5

<210> SEQ ID NO 311
<211> LENGTH: 8
<212> TYPE: PRT
<213> ORGANISM: Mus musculus

<400> SEQUENCE: 311

Gly Tyr Thr Phe Thr Arg Tyr Trp
1 5

<210> SEQ ID NO 312
<211> LENGTH: 8
<212> TYPE: PRT
<213> ORGANISM: Mus musculus

<400> SEQUENCE: 312

Gly Tyr Thr Phe Thr Ser Tyr Gly
1 5

<210> SEQ ID NO 313
<211> LENGTH: 8
<212> TYPE: PRT
<213> ORGANISM: Mus musculus

<400> SEQUENCE: 313

Gly Tyr Thr Phe Thr Ser Tyr Tyr
1 5

<210> SEQ ID NO 314
<211> LENGTH: 8
<212> TYPE: PRT
<213> ORGANISM: Mus musculus

<400> SEQUENCE: 314

Gly Tyr Thr Phe Thr Thr Tyr Ala
1 5

<210> SEQ ID NO 315
<211> LENGTH: 26
<212> TYPE: PRT
<213> ORGANISM: Mus musculus

<400> SEQUENCE: 315

His Ile Gln Met Thr His Ser Pro Pro Pro Leu Ser Ala Ser Val Gly
1 5 10 15

Glu Thr Val Thr Leu Thr Cys Arg Ala Ser 20 25

<210> SEQ ID NO 316
<211> LENGTH: 9
<212> TYPE: PRT
<213> ORGANISM: Mus musculus

<400> SEQUENCE: 316

His Gln Tyr Asn Asn Tyr Pro Tyr Thr
1 5

<210> SEQ ID NO 317
<211> LENGTH: 3
<212> TYPE: PRT
<213> ORGANISM: Mus musculus

<400> SEQUENCE: 317

His Thr Ser
1

<210> SEQ ID NO 318
<211> LENGTH: 8
<212> TYPE: PRT
<213> ORGANISM: Mus musculus

<400> SEQUENCE: 318

Ile Asp Pro Asp Asn Gly Glu Thr
1 5

<210> SEQ ID NO 319
<211> LENGTH: 12
<212> TYPE: PRT
<213> ORGANISM: Mus musculus

<400> SEQUENCE: 319

Ile Asp Pro Asp Asn Gly Glu Thr Glu Tyr Ala Pro
1 5 10

<210> SEQ ID NO 320
<211> LENGTH: 17
<212> TYPE: PRT
<213> ORGANISM: Mus musculus

<400> SEQUENCE: 320

Ile Glu Trp Ile Lys Gln Arg Pro Gly His Gly Leu Glu Trp Ile Gly
1 5 10 15

Glu

<210> SEQ ID NO 321
<211> LENGTH: 17
<212> TYPE: PRT
<213> ORGANISM: Mus musculus

<400> SEQUENCE: 321

Ile Glu Trp Ile Lys Gln Arg Pro Gly His Gly Leu Glu Trp Val Gly
1 5 10 15

Glu

<210> SEQ ID NO 322
<211> LENGTH: 12
<212> TYPE: PRT
<213> ORGANISM: Mus musculus

<400> SEQUENCE: 322

Ile His Pro Ser Asp Ser Glu Thr Arg Leu Asn Gln
1               5                   10

<210> SEQ ID NO 323
<211> LENGTH: 17
<212> TYPE: PRT
<213> ORGANISM: Mus musculus

<400> SEQUENCE: 323

Ile His Trp Ile Arg Gln Arg Pro Gly Gln Ser Leu Glu Trp Ile Gly
1               5                   10                  15

Tyr

<210> SEQ ID NO 324
<211> LENGTH: 17
<212> TYPE: PRT
<213> ORGANISM: Mus musculus

<400> SEQUENCE: 324

Ile His Trp Val Lys Gln Arg Pro Glu Gln Gly Leu Glu Trp Ile Gly
1               5                   10                  15

Trp

<210> SEQ ID NO 325
<211> LENGTH: 17
<212> TYPE: PRT
<213> ORGANISM: Mus musculus

<400> SEQUENCE: 325

Ile His Trp Val Lys Gln Arg Pro Gly Gln Asp Leu Glu Trp Ile Gly
1               5                   10                  15

Tyr

<210> SEQ ID NO 326
<211> LENGTH: 8
<212> TYPE: PRT
<213> ORGANISM: Mus musculus

<400> SEQUENCE: 326

Ile Ile Pro Ile Phe Gly Thr Ala
1               5

<210> SEQ ID NO 327
<211> LENGTH: 8
<212> TYPE: PRT
<213> ORGANISM: Mus musculus

<400> SEQUENCE: 327

Ile Ile Pro Ile Phe Gly Thr Ala
1               5

<210> SEQ ID NO 328
<211> LENGTH: 8
<212> TYPE: PRT
<213> ORGANISM: Mus musculus

<400> SEQUENCE: 328

Ile Lys Gln Asp Gly Ser Glu Lys
1               5

<210> SEQ ID NO 329
<211> LENGTH: 10

<212> TYPE: PRT
<213> ORGANISM: Mus musculus

<400> SEQUENCE: 329

Ile Lys Ser Lys Asn Asp Gly Gly Thr Thr
1 5 10

<210> SEQ ID NO 330
<211> LENGTH: 10
<212> TYPE: PRT
<213> ORGANISM: Mus musculus

<400> SEQUENCE: 330

Ile Lys Ser Lys Thr Asp Gly Gly Thr Thr
1 5 10

<210> SEQ ID NO 331
<211> LENGTH: 12
<212> TYPE: PRT
<213> ORGANISM: Mus musculus

<400> SEQUENCE: 331

Ile Leu Pro Gly Ser Gly Phe Thr Asn Tyr Asn Glu
1 5 10

<210> SEQ ID NO 332
<211> LENGTH: 8
<212> TYPE: PRT
<213> ORGANISM: Mus musculus

<400> SEQUENCE: 332

Ile Met Pro Ile Phe Asp Thr Ala
1 5

<210> SEQ ID NO 333
<211> LENGTH: 7
<212> TYPE: PRT
<213> ORGANISM: Mus musculus

<400> SEQUENCE: 333

Ile Asn His Ser Gly Ser Thr
1 5

<210> SEQ ID NO 334
<211> LENGTH: 8
<212> TYPE: PRT
<213> ORGANISM: Mus musculus

<400> SEQUENCE: 334

Ile Asn Pro Gly Ser Asp Tyr Thr
1 5

<210> SEQ ID NO 335
<211> LENGTH: 8
<212> TYPE: PRT
<213> ORGANISM: Mus musculus

<400> SEQUENCE: 335

Ile Asn Pro Asn Ser Asp Tyr Ile
1 5

<210> SEQ ID NO 336
<211> LENGTH: 8
<212> TYPE: PRT
<213> ORGANISM: Mus musculus

<400> SEQUENCE: 336

Ile Asn Pro Asn Ser Gly Asp Thr
1 5

<210> SEQ ID NO 337
<211> LENGTH: 8
<212> TYPE: PRT
<213> ORGANISM: Mus musculus

<400> SEQUENCE: 337

Ile Asn Pro Arg Thr Asp Tyr Thr
1 5

<210> SEQ ID NO 338
<211> LENGTH: 12
<212> TYPE: PRT
<213> ORGANISM: Mus musculus

<400> SEQUENCE: 338

Ile Asn Pro Arg Thr Asp Tyr Thr Glu Tyr Asn Gln
1 5 10

<210> SEQ ID NO 339
<211> LENGTH: 8
<212> TYPE: PRT
<213> ORGANISM: Mus musculus

<400> SEQUENCE: 339

Ile Asn Pro Ser Gly Gly Ser Thr
1 5

<210> SEQ ID NO 340
<211> LENGTH: 8
<212> TYPE: PRT
<213> ORGANISM: Mus musculus

<400> SEQUENCE: 340

Ile Asn Pro Ser Thr Asp Tyr Ile
1 5

<210> SEQ ID NO 341
<211> LENGTH: 8
<212> TYPE: PRT
<213> ORGANISM: Mus musculus

<400> SEQUENCE: 341

Ile Asn Pro Ser Thr Gly Tyr Ile
1 5

<210> SEQ ID NO 342
<211> LENGTH: 12
<212> TYPE: PRT
<213> ORGANISM: Mus musculus

<400> SEQUENCE: 342

Ile Asn Ser Asp Gly Ser Ala Ile Asn Tyr Ala Pro
1 5 10

<210> SEQ ID NO 343
<211> LENGTH: 8
<212> TYPE: PRT
<213> ORGANISM: Mus musculus

<400> SEQUENCE: 343

Ile Asn Thr Asp Gly Ser Ile Thr
1 5

<210> SEQ ID NO 344
<211> LENGTH: 8
<212> TYPE: PRT
<213> ORGANISM: Mus musculus

<400> SEQUENCE: 344

Ile Asn Thr Asn Thr Gly Asp Pro
1 5

<210> SEQ ID NO 345
<211> LENGTH: 8
<212> TYPE: PRT
<213> ORGANISM: Mus musculus

<400> SEQUENCE: 345

Ile Asn Thr Tyr Ser Gly Asp Ala
1 5

<210> SEQ ID NO 346
<211> LENGTH: 8
<212> TYPE: PRT
<213> ORGANISM: Mus musculus

<400> SEQUENCE: 346

Ile Ser Ala Tyr Asn Gly Asn Thr
1 5

<210> SEQ ID NO 347
<211> LENGTH: 8
<212> TYPE: PRT
<213> ORGANISM: Mus musculus

<400> SEQUENCE: 347

Ile Ser Gly Arg Lys Gly Asn Thr
1 5

<210> SEQ ID NO 348
<211> LENGTH: 8
<212> TYPE: PRT
<213> ORGANISM: Mus musculus

<400> SEQUENCE: 348

Ile Ser Gly Ser Gly Gly Ser Thr
1 5

<210> SEQ ID NO 349
<211> LENGTH: 8
<212> TYPE: PRT
<213> ORGANISM: Mus musculus

<400> SEQUENCE: 349

Ile Ser His Asp Gly His Val Lys
1 5

<210> SEQ ID NO 350
<211> LENGTH: 8
<212> TYPE: PRT
<213> ORGANISM: Mus musculus

<400> SEQUENCE: 350

Ile Ser Ser Arg Gly Ser Thr Ile 1 5

<210> SEQ ID NO 351
<211> LENGTH: 8
<212> TYPE: PRT
<213> ORGANISM: Mus musculus

<400> SEQUENCE: 351

Ile Ser Ser Ser Gly Ser Thr Ile
1 5

<210> SEQ ID NO 352
<211> LENGTH: 8
<212> TYPE: PRT
<213> ORGANISM: Mus musculus

<400> SEQUENCE: 352

Ile Ser Ser Ser Ser Ser Tyr Ile
1 5

<210> SEQ ID NO 353
<211> LENGTH: 8
<212> TYPE: PRT
<213> ORGANISM: Mus musculus

<400> SEQUENCE: 353

Ile Ser Thr Tyr Ser Gly Asp Ala
1 5

<210> SEQ ID NO 354
<211> LENGTH: 12
<212> TYPE: PRT
<213> ORGANISM: Mus musculus

<400> SEQUENCE: 354

Ile Ser Thr Tyr Ser Gly Asp Ala Ile Tyr Asn Gln
1 5 10

<210> SEQ ID NO 355
<211> LENGTH: 12
<212> TYPE: PRT
<213> ORGANISM: Mus musculus

<400> SEQUENCE: 355

Ile Ser Thr Tyr Ser Gly Asp Ala Leu Tyr Asn Gln
1 5 10

<210> SEQ ID NO 356
<211> LENGTH: 8
<212> TYPE: PRT
<213> ORGANISM: Mus musculus

<400> SEQUENCE: 356

Ile Ser Thr Tyr Ser Gly Asp Val
1 5

<210> SEQ ID NO 357
<211> LENGTH: 12
<212> TYPE: PRT
<213> ORGANISM: Mus musculus

<400> SEQUENCE: 357

Ile Ser Thr Tyr Ser Gly Asp Val Asn Tyr Asn Gln
1 5 10

<210> SEQ ID NO 358
<211> LENGTH: 12
<212> TYPE: PRT
<213> ORGANISM: Mus musculus

<400> SEQUENCE: 358

Ile Ser Thr Tyr Ser Gly Asp Val Ser Tyr Asn Gln
1 5 10

<210> SEQ ID NO 359
<211> LENGTH: 8
<212> TYPE: PRT
<213> ORGANISM: Mus musculus

<400> SEQUENCE: 359

Ile Ser Val Tyr Asn Gly Asp Ile
1 5

<210> SEQ ID NO 360
<211> LENGTH: 8
<212> TYPE: PRT
<213> ORGANISM: Mus musculus

<400> SEQUENCE: 360

Ile Ser Tyr Asp Gly Asn Asn Lys
1 5

<210> SEQ ID NO 361
<211> LENGTH: 8
<212> TYPE: PRT
<213> ORGANISM: Mus musculus

<400> SEQUENCE: 361

Ile Ser Tyr Asp Gly Ser Asp Lys
1 5

<210> SEQ ID NO 362
<211> LENGTH: 8
<212> TYPE: PRT
<213> ORGANISM: Mus musculus

<400> SEQUENCE: 362

Ile Ser Tyr Asp Gly Ser Asn Lys
1 5

<210> SEQ ID NO 363
<211> LENGTH: 8
<212> TYPE: PRT
<213> ORGANISM: Mus musculus

<400> SEQUENCE: 363

Ile Trp Tyr Asp Gly Ser Asn Glu
1 5

<210> SEQ ID NO 364
<211> LENGTH: 38
<212> TYPE: PRT
<213> ORGANISM: Mus musculus

<400> SEQUENCE: 364

Ile Tyr Asp Gln Lys Phe Gln Gly Lys Ala Thr Met Thr Val Asp Lys
1 5 10 15

Ser Ser Ser Thr Ala Tyr Leu Gly Leu Ala Arg Leu Thr Ser Asp Asp
20 25 30

```
Ser Ala Ile Tyr Tyr Cys
        35


<210> SEQ ID NO 365
<211> LENGTH: 7
<212> TYPE: PRT
<213> ORGANISM: Mus musculus

<400> SEQUENCE: 365

Ile Tyr His Ser Gly Ser Thr
1               5


<210> SEQ ID NO 366
<211> LENGTH: 7
<212> TYPE: PRT
<213> ORGANISM: Mus musculus

<400> SEQUENCE: 366

Ile Tyr His Thr Gly Ser Thr
1               5


<210> SEQ ID NO 367
<211> LENGTH: 38
<212> TYPE: PRT
<213> ORGANISM: Mus musculus

<400> SEQUENCE: 367

Ile Tyr Asn Gln Lys Phe Lys Asp Lys Ala Thr Met Thr Val Asp Lys
1               5                   10                  15

Ser Ser Ser Thr Ala Tyr Leu Glu Leu Ala Arg Leu Thr Ser Glu Asp
            20                  25                  30

Ser Ala Ile Tyr Tyr Cys
        35


<210> SEQ ID NO 368
<211> LENGTH: 38
<212> TYPE: PRT
<213> ORGANISM: Mus musculus

<400> SEQUENCE: 368

Ile Tyr Asn Gln Lys Phe Lys Gly Lys Ala Thr Met Thr Val Asp Lys
1               5                   10                  15

Ser Ser Ile Thr Ala Tyr Leu Glu Leu Ala Arg Leu Thr Ser Asp Asp
            20                  25                  30

Ser Ala Val Tyr Tyr Cys
        35


<210> SEQ ID NO 369
<211> LENGTH: 38
<212> TYPE: PRT
<213> ORGANISM: Mus musculus

<400> SEQUENCE: 369

Ile Tyr Asn Gln Lys Phe Lys Gly Lys Ala Thr Met Thr Val Asp Lys
1               5                   10                  15

Ser Ser Asn Thr Ala Tyr Leu Glu Leu Ala Arg Leu Thr Ser Asp Asp
            20                  25                  30

Ser Ala Ile Tyr Tyr Cys
        35


<210> SEQ ID NO 370
```

<211> LENGTH: 38
<212> TYPE: PRT
<213> ORGANISM: Mus musculus

<400> SEQUENCE: 370

Ile Tyr Asn Gln Lys Phe Lys Gly Lys Ala Thr Met Thr Val Asp Lys
1 5 10 15

Ser Ser Asn Thr Ala Tyr Arg Glu Leu Ala Lys Leu Thr Ser Glu Asp
20 25 30

Ser Ala Ile Tyr Tyr Cys
35

<210> SEQ ID NO 371
<211> LENGTH: 38
<212> TYPE: PRT
<213> ORGANISM: Mus musculus

<400> SEQUENCE: 371

Ile Tyr Asn Gln Lys Phe Lys Gly Lys Ala Thr Met Thr Val Asp Lys
1 5 10 15

Ser Ser Ser Thr Ala Tyr Leu Glu Leu Ala Arg Leu Thr Ser Asp Asp
20 25 30

Ser Ala Ile Tyr Tyr Cys
35

<210> SEQ ID NO 372
<211> LENGTH: 38
<212> TYPE: PRT
<213> ORGANISM: Mus musculus

<400> SEQUENCE: 372

Ile Tyr Asn Gln Lys Phe Lys Gly Lys Ala Thr Met Thr Val Asp Lys
1 5 10 15

Ser Ser Ser Thr Ala Tyr Leu Glu Leu Ala Arg Leu Thr Ser Asp His
20 25 30

Ser Ala Ile Tyr Tyr Cys
35

<210> SEQ ID NO 373
<211> LENGTH: 38
<212> TYPE: PRT
<213> ORGANISM: Mus musculus

<400> SEQUENCE: 373

Ile Tyr Asn Gln Lys Phe Lys Gly Lys Ala Thr Met Thr Val Asp Lys
1 5 10 15

Ser Ser Ser Thr Ala Tyr Leu Glu Leu Ala Arg Leu Thr Ser Asp Asn
20 25 30

Ser Ala Ile Tyr Tyr Cys
35

<210> SEQ ID NO 374
<211> LENGTH: 38
<212> TYPE: PRT
<213> ORGANISM: Mus musculus

<400> SEQUENCE: 374

Ile Tyr Asn Gln Lys Phe Lys Gly Lys Ala Thr Met Thr Val Asp Lys
1 5 10 15

Ser Ser Ser Thr Ala Tyr Leu Glu Leu Ala Arg Leu Thr Ser Glu Asp
20 25 30

Ser Ala Ile Tyr Tyr Cys
35

<210> SEQ ID NO 375
<211> LENGTH: 38
<212> TYPE: PRT
<213> ORGANISM: Mus musculus

<400> SEQUENCE: 375

Ile Tyr Asn Gln Lys Phe Lys Gly Lys Ala Thr Met Thr Val Asn Lys
1 5 10 15

Ser Ser Ser Thr Ala Tyr Leu Glu Leu Ala Arg Leu Thr Ser Asp Asp
20 25 30

Ser Ala Ile Tyr Tyr Cys
35

<210> SEQ ID NO 376
<211> LENGTH: 38
<212> TYPE: PRT
<213> ORGANISM: Mus musculus

<400> SEQUENCE: 376

Ile Tyr Asn Gln Lys Phe Lys Ser Lys Ala Thr Met Thr Val Asp Lys
1 5 10 15

Ser Ser Ser Thr Ala Tyr Leu Glu Leu Ala Arg Leu Thr Ser Glu Asp
20 25 30

Ser Ala Ile Tyr Tyr Cys
35

<210> SEQ ID NO 377
<211> LENGTH: 8
<212> TYPE: PRT
<213> ORGANISM: Mus musculus

<400> SEQUENCE: 377

Ile Tyr Pro Gly Asp Ser Asp Thr
1 5

<210> SEQ ID NO 378
<211> LENGTH: 8
<212> TYPE: PRT
<213> ORGANISM: Mus musculus

<400> SEQUENCE: 378

Ile Tyr Pro Gly Gly Asp Tyr Thr
1 5

<210> SEQ ID NO 379
<211> LENGTH: 12
<212> TYPE: PRT
<213> ORGANISM: Mus musculus

<400> SEQUENCE: 379

Ile Tyr Pro Gly Gly Asp Tyr Thr Asn Tyr Asn Glu
1 5 10

<210> SEQ ID NO 380
<211> LENGTH: 8
<212> TYPE: PRT
<213> ORGANISM: Mus musculus

<400> SEQUENCE: 380

Ile Tyr Pro Gly Gly Gly Tyr Ala
1               5

<210> SEQ ID NO 381
<211> LENGTH: 8
<212> TYPE: PRT
<213> ORGANISM: Mus musculus

<400> SEQUENCE: 381

Ile Tyr Pro Gly Gly Gly Tyr Thr
1               5

<210> SEQ ID NO 382
<211> LENGTH: 12
<212> TYPE: PRT
<213> ORGANISM: Mus musculus

<400> SEQUENCE: 382

Ile Tyr Pro Gly Gly Gly Tyr Thr Asn Tyr Asn Glu
1               5                   10

<210> SEQ ID NO 383
<211> LENGTH: 8
<212> TYPE: PRT
<213> ORGANISM: Mus musculus

<400> SEQUENCE: 383

Ile Tyr Pro Ser Asp Ser Asp Thr
1               5

<210> SEQ ID NO 384
<211> LENGTH: 7
<212> TYPE: PRT
<213> ORGANISM: Mus musculus

<400> SEQUENCE: 384

Ile Tyr Tyr Ser Gly Ser Thr
1               5

<210> SEQ ID NO 385
<211> LENGTH: 3
<212> TYPE: PRT
<213> ORGANISM: Mus musculus

<400> SEQUENCE: 385

Lys Ala Ser
1

<210> SEQ ID NO 386
<211> LENGTH: 3
<212> TYPE: PRT
<213> ORGANISM: Mus musculus

<400> SEQUENCE: 386

Lys Asp Asn
1

<210> SEQ ID NO 387
<211> LENGTH: 34
<212> TYPE: PRT
<213> ORGANISM: Mus musculus

<400> SEQUENCE: 387

Lys Phe Glu Asp Lys Ala Thr Leu Thr Ala Asp Lys Ser Ser Ser Thr
1               5                   10                  15

Ala Tyr Met Gln Leu Ser Ser Leu Thr Ser Asp Asp Ser Ala Val Tyr
20 25 30

Tyr Cys

<210> SEQ ID NO 388
<211> LENGTH: 34
<212> TYPE: PRT
<213> ORGANISM: Mus musculus

<400> SEQUENCE: 388

Lys Phe Lys Asp Lys Ala Thr Leu Thr Ala Asp Lys Ser Ser Ser Thr
1 5 10 15

Ala Tyr Met Gln Leu Ser Ser Leu Ala Ser Asp Asp Ser Ala Val Tyr
20 25 30

Tyr Cys

<210> SEQ ID NO 389
<211> LENGTH: 34
<212> TYPE: PRT
<213> ORGANISM: Mus musculus

<400> SEQUENCE: 389

Lys Phe Lys Asp Lys Ala Thr Leu Thr Ala Asp Lys Ser Ser Ser Thr
1 5 10 15

Ala Tyr Met Gln Leu Ser Ser Leu Thr Ser Asp Asp Ser Ala Val Tyr
20 25 30

Tyr Cys

<210> SEQ ID NO 390
<211> LENGTH: 34
<212> TYPE: PRT
<213> ORGANISM: Mus musculus

<400> SEQUENCE: 390

Lys Phe Lys Asp Lys Ala Thr Leu Thr Val Asp Lys Ser Ser Ser Thr
1 5 10 15

Ala Tyr Met Gln Leu Ser Ser Pro Thr Ser Glu Asp Ser Ala Val Tyr
20 25 30

Tyr Cys

<210> SEQ ID NO 391
<211> LENGTH: 34
<212> TYPE: PRT
<213> ORGANISM: Mus musculus

<400> SEQUENCE: 391

Lys Phe Lys Asp Lys Ala Thr Met Thr Val Asp Lys Ser Ser Ser Thr
1 5 10 15

Ala Tyr Leu Glu Leu Ala Arg Leu Thr Ser Glu Asp Ser Ala Ile Tyr
20 25 30

Tyr Cys

<210> SEQ ID NO 392
<211> LENGTH: 34
<212> TYPE: PRT
<213> ORGANISM: Mus musculus

<400> SEQUENCE: 392

Lys Phe Lys Asp Lys Ala Thr Met Thr Val Asp Lys Ser Ser Ser Thr 1 5 10 15

Ala Tyr Met Glu Leu Ala Arg Leu Thr Ser Glu Asp Ser Ala Ile Tyr
20 25 30

Tyr Cys

<210> SEQ ID NO 393
<211> LENGTH: 34
<212> TYPE: PRT
<213> ORGANISM: Mus musculus

<400> SEQUENCE: 393

Lys Phe Lys Gly Lys Ala Thr Leu Thr Ala Asp Thr Ser Ser Ser Thr
1 5 10 15

Ala Tyr Met Gln Leu Asn Ser Leu Thr Ser Glu Asp Ser Ala Val Tyr
20 25 30

Phe Cys

<210> SEQ ID NO 394
<211> LENGTH: 34
<212> TYPE: PRT
<213> ORGANISM: Mus musculus

<400> SEQUENCE: 394

Lys Phe Lys Gly Lys Ala Thr Leu Thr Ala Asp Thr Ser Ser Ser Thr
1 5 10 15

Ala Tyr Met Gln Leu Ser Ser Leu Thr Ser Glu Asp Ser Ala Ala Tyr
20 25 30

Phe Cys

<210> SEQ ID NO 395
<211> LENGTH: 34
<212> TYPE: PRT
<213> ORGANISM: Mus musculus

<400> SEQUENCE: 395

Lys Phe Lys Gly Lys Ala Thr Leu Thr Ala Asp Thr Ser Ser Ser Thr
1 5 10 15

Ala Tyr Met Gln Leu Ser Ser Leu Thr Ser Glu Asp Ser Ala Val Tyr
20 25 30

Phe Cys

<210> SEQ ID NO 396
<211> LENGTH: 34
<212> TYPE: PRT
<213> ORGANISM: Mus musculus
<220> FEATURE:
<221> NAME/KEY: SITE
<222> LOCATION: (22)..(22)
<223> OTHER INFORMATION: Xaa can be any naturally occurring amino acid

<400> SEQUENCE: 396

Lys Phe Lys Gly Lys Ala Thr Leu Thr Ala Asp Thr Ser Ser Ser Thr
1 5 10 15

Ala Tyr Met Gln Leu Xaa Ser Leu Thr Ser Glu Asp Ser Ala Val Tyr
20 25 30

Phe Cys

<210> SEQ ID NO 397
<211> LENGTH: 34
<212> TYPE: PRT

<213> ORGANISM: Mus musculus

<400> SEQUENCE: 397

Lys Phe Lys Gly Lys Ala Thr Met Thr Val Asp Lys Ser Ser Asn Thr
1 5 10 15

Ala Tyr Met Glu Leu Ala Arg Leu Thr Ser Glu Asp Ser Ala Ile Tyr
20 25 30

Tyr Cys

<210> SEQ ID NO 398
<211> LENGTH: 34
<212> TYPE: PRT
<213> ORGANISM: Mus musculus

<400> SEQUENCE: 398

Lys Phe Lys Gly Lys Ala Thr Met Thr Val Asp Lys Ser Ser Ser Thr
1 5 10 15

Ala Tyr Leu Glu Leu Ala Arg Leu Thr Ser Asp Asp Ser Ala Ile Tyr
20 25 30

Tyr Cys

<210> SEQ ID NO 399
<211> LENGTH: 34
<212> TYPE: PRT
<213> ORGANISM: Mus musculus

<400> SEQUENCE: 399

Lys Phe Lys Gly Lys Ala Thr Met Thr Val Asp Lys Ser Ser Ser Thr
1 5 10 15

Ala Tyr Leu Glu Leu Ala Arg Leu Thr Ser Glu Asp Ser Ala Ile Tyr
20 25 30

Tyr Cys

<210> SEQ ID NO 400
<211> LENGTH: 34
<212> TYPE: PRT
<213> ORGANISM: Mus musculus

<400> SEQUENCE: 400

Lys Phe Lys Gly Lys Ala Thr Met Thr Val Asp Lys Ser Ser Ser Thr
1 5 10 15

Ala Tyr Met Glu Leu Ala Arg Leu Thr Ser Glu Asp Ser Ala Ile Tyr
20 25 30

Tyr Cys

<210> SEQ ID NO 401
<211> LENGTH: 34
<212> TYPE: PRT
<213> ORGANISM: Mus musculus
<220> FEATURE:
<221> NAME/KEY: SITE
<222> LOCATION: (15)..(15)
<223> OTHER INFORMATION: Xaa can be any naturally occurring amino acid

<400> SEQUENCE: 401

Lys Phe Lys Gly Lys Ala Thr Met Thr Val Asp Lys Ser Ser Xaa Thr
1 5 10 15

Ala Tyr Leu Glu Leu Ala Arg Leu Thr Ser Asp Asp Ser Ala Ile Tyr
20 25 30

Tyr Cys

<210> SEQ ID NO 402
<211> LENGTH: 34
<212> TYPE: PRT
<213> ORGANISM: Mus musculus

<400> SEQUENCE: 402

Lys Phe Lys Ser Lys Ala Thr Met Thr Val Asp Lys Ser Ser Ser Thr
1 5 10 15

Ala Tyr Leu Glu Leu Ala Arg Leu Thr Ser Glu Asp Ser Ala Ile Tyr
20 25 30

Tyr Cys

<210> SEQ ID NO 403
<211> LENGTH: 34
<212> TYPE: PRT
<213> ORGANISM: Mus musculus

<400> SEQUENCE: 403

Lys Phe Gln Gly Lys Ala Thr Met Thr Ala Asp Thr Ser Ser Asn Thr
1 5 10 15

Ala His Leu Gln Leu Ser Ser Leu Thr Ser Glu Asp Thr Ala Val Tyr
20 25 30

Tyr Cys

<210> SEQ ID NO 404
<211> LENGTH: 6
<212> TYPE: PRT
<213> ORGANISM: Mus musculus

<400> SEQUENCE: 404

Lys Leu Gly Asp Lys Tyr
1 5

<210> SEQ ID NO 405
<211> LENGTH: 6
<212> TYPE: PRT
<213> ORGANISM: Mus musculus

<400> SEQUENCE: 405

Lys Leu Gly Glu Arg Phe
1 5

<210> SEQ ID NO 406
<211> LENGTH: 3
<212> TYPE: PRT
<213> ORGANISM: Mus musculus

<400> SEQUENCE: 406

Lys Val Ser
1

<210> SEQ ID NO 407
<211> LENGTH: 17
<212> TYPE: PRT
<213> ORGANISM: Mus musculus

<400> SEQUENCE: 407

Leu Glu Trp Ser Gln Gln Lys Gln Gly Lys Ser Pro Gln Leu Leu Val
1 5 10 15

Tyr

<210> SEQ ID NO 408
<211> LENGTH: 17
<212> TYPE: PRT
<213> ORGANISM: Mus musculus

<400> SEQUENCE: 408

Leu Glu Trp Tyr Leu Gln Lys Pro Gly Gln Pro Pro Lys Leu Leu Ile
1 5 10 15

Tyr

<210> SEQ ID NO 409
<211> LENGTH: 17
<212> TYPE: PRT
<213> ORGANISM: Mus musculus

<400> SEQUENCE: 409

Leu Glu Trp Tyr Leu Gln Lys Pro Gly Gln Ser Pro Lys Leu Leu Ile
1 5 10 15

Tyr

<210> SEQ ID NO 410
<211> LENGTH: 17
<212> TYPE: PRT
<213> ORGANISM: Mus musculus

<400> SEQUENCE: 410

Leu Glu Trp Tyr Leu Gln Arg Pro Gly Gln Ser Pro Lys Leu Leu Ile
1 5 10 15

Tyr

<210> SEQ ID NO 411
<211> LENGTH: 17
<212> TYPE: PRT
<213> ORGANISM: Mus musculus

<400> SEQUENCE: 411

Leu Glu Trp Tyr Gln Gln Lys Lys Gly Lys Ser Pro Gln Leu Leu Val
1 5 10 15

Tyr

<210> SEQ ID NO 412
<211> LENGTH: 17
<212> TYPE: PRT
<213> ORGANISM: Mus musculus

<400> SEQUENCE: 412

Leu Glu Trp Tyr Gln Gln Lys Gln Gly Lys Ser Pro His Leu Leu Val
1 5 10 15

Tyr

<210> SEQ ID NO 413
<211> LENGTH: 17
<212> TYPE: PRT
<213> ORGANISM: Mus musculus

<400> SEQUENCE: 413

Leu Glu Trp Tyr Gln Gln Lys Gln Gly Lys Ser Pro Gln Leu Leu Val
1 5 10 15

Tyr

<210> SEQ ID NO 414
<211> LENGTH: 17
<212> TYPE: PRT
<213> ORGANISM: Mus musculus

<400> SEQUENCE: 414

Leu Gly Trp Ile Lys Gln Arg Pro Gly His Gly Leu Glu Trp Ile Gly
1 5 10 15

Asp

<210> SEQ ID NO 415
<211> LENGTH: 17
<212> TYPE: PRT
<213> ORGANISM: Mus musculus

<400> SEQUENCE: 415

Leu Gly Trp Val Lys Gln Gly Pro Gly His Gly Leu Glu Trp Ile Gly
1 5 10 15

Asp

<210> SEQ ID NO 416
<211> LENGTH: 17
<212> TYPE: PRT
<213> ORGANISM: Mus musculus

<400> SEQUENCE: 416

Leu Gly Trp Val Lys Gln Arg Pro Gly His Gly Leu Glu Trp Ile Gly
1 5 10 15

Asp

<210> SEQ ID NO 417
<211> LENGTH: 17
<212> TYPE: PRT
<213> ORGANISM: Mus musculus

<400> SEQUENCE: 417

Leu His Trp Tyr Leu Gln Lys Pro Gly Gln Ser Pro Lys Leu Leu Ile
1 5 10 15

Tyr

<210> SEQ ID NO 418
<211> LENGTH: 17
<212> TYPE: PRT
<213> ORGANISM: Mus musculus

<400> SEQUENCE: 418

Leu Asn Trp Tyr Gln Gln Lys Pro Asp Gly Thr Val Lys Leu Leu Ile
1 5 10 15

Tyr

<210> SEQ ID NO 419
<211> LENGTH: 17
<212> TYPE: PRT
<213> ORGANISM: Mus musculus

<400> SEQUENCE: 419

Leu Asn Trp Tyr Gln Gln Lys Gln Asp Gly Thr Val Lys Leu Leu Ile
1 5 10 15

Tyr

<210> SEQ ID NO 420

<211> LENGTH: 17
<212> TYPE: PRT
<213> ORGANISM: Mus musculus

<400> SEQUENCE: 420

Leu Asn Trp Tyr Gln Gln Arg Pro Asp Gly Thr Val Lys Leu Leu Ile
1 5 10 15

Tyr

<210> SEQ ID NO 421
<211> LENGTH: 17
<212> TYPE: PRT
<213> ORGANISM: Mus musculus

<400> SEQUENCE: 421

Leu Asn Trp Tyr Gln Gln Arg Gln Asp Gly Thr Val Lys Leu Leu Ile
1 5 10 15

Tyr

<210> SEQ ID NO 422
<211> LENGTH: 9
<212> TYPE: PRT
<213> ORGANISM: Mus musculus

<400> SEQUENCE: 422

Leu Gln Asp Tyr Asn Tyr Pro Pro Ala
1 5

<210> SEQ ID NO 423
<211> LENGTH: 9
<212> TYPE: PRT
<213> ORGANISM: Mus musculus

<400> SEQUENCE: 423

Leu Gln His Asn Thr Phe Pro Tyr Thr
1 5

<210> SEQ ID NO 424
<211> LENGTH: 9
<212> TYPE: PRT
<213> ORGANISM: Mus musculus

<400> SEQUENCE: 424

Leu Gln Tyr Asp Glu Phe Pro Trp Thr
1 5

<210> SEQ ID NO 425
<211> LENGTH: 9
<212> TYPE: PRT
<213> ORGANISM: Mus musculus

<400> SEQUENCE: 425

Leu Gln Tyr Asp Glu Phe Pro Tyr Thr
1 5

<210> SEQ ID NO 426
<211> LENGTH: 9
<212> TYPE: PRT
<213> ORGANISM: Mus musculus

<400> SEQUENCE: 426

Leu Gln Tyr Asp Arg Tyr Ser Gly Ala
1 5

<210> SEQ ID NO 427
<211> LENGTH: 17
<212> TYPE: PRT
<213> ORGANISM: Mus musculus

<400> SEQUENCE: 427

Leu Ser Trp Phe Gln Gln Lys Pro Gly Lys Ser Pro Lys Thr Leu Ile
1 5 10 15

Tyr

<210> SEQ ID NO 428
<211> LENGTH: 17
<212> TYPE: PRT
<213> ORGANISM: Mus musculus

<400> SEQUENCE: 428

Leu Ser Trp Phe Gln Gln Lys Pro Gly Lys Ser Pro Gln Thr Leu Ile
1 5 10 15

Tyr

<210> SEQ ID NO 429
<211> LENGTH: 17
<212> TYPE: PRT
<213> ORGANISM: Mus musculus

<400> SEQUENCE: 429

Leu Ser Trp Phe Gln Gln Lys Gln Gly Lys Ser Pro Gln Thr Leu Ile
1 5 10 15

Tyr

<210> SEQ ID NO 430
<211> LENGTH: 17
<212> TYPE: PRT
<213> ORGANISM: Mus musculus

<400> SEQUENCE: 430

Leu Thr Trp Tyr Gln Gln Lys Gln Gly Lys Ser Pro Gln Leu Leu Val
1 5 10 15

Tyr

<210> SEQ ID NO 431
<211> LENGTH: 38
<212> TYPE: PRT
<213> ORGANISM: Mus musculus

<400> SEQUENCE: 431

Leu Tyr Asn Gln Lys Phe Lys Gly Lys Ala Thr Met Thr Val Asp Lys
1 5 10 15

Ser Ser Ser Thr Ala Tyr Leu Glu Leu Ala Arg Leu Thr Ser Asp Asp
20 25 30

Ser Ala Ile Tyr Tyr Cys
35

<210> SEQ ID NO 432
<211> LENGTH: 17
<212> TYPE: PRT
<213> ORGANISM: Mus musculus

<400> SEQUENCE: 432

Met His Trp Val Lys Gln Arg Pro Gly Gln Asp Leu Glu Trp Ile Gly
1 5 10 15

Tyr

<210> SEQ ID NO 433
<211> LENGTH: 17
<212> TYPE: PRT
<213> ORGANISM: Mus musculus

<400> SEQUENCE: 433

Met His Trp Val Lys Gln Arg Pro Gly Gln Gly Leu Glu Trp Ile Gly
1 5 10 15

Tyr

<210> SEQ ID NO 434
<211> LENGTH: 17
<212> TYPE: PRT
<213> ORGANISM: Mus musculus

<400> SEQUENCE: 434

Met His Trp Val Lys Gln Ser His Ala Lys Ser Leu Glu Trp Ile Gly
1 5 10 15

Val

<210> SEQ ID NO 435
<211> LENGTH: 17
<212> TYPE: PRT
<213> ORGANISM: Mus musculus

<400> SEQUENCE: 435

Met His Trp Val Arg Pro Ser His Ala Lys Ser Leu Glu Trp Ile Gly
1 5 10 15

Val

<210> SEQ ID NO 436
<211> LENGTH: 17
<212> TYPE: PRT
<213> ORGANISM: Mus musculus

<400> SEQUENCE: 436

Met His Trp Val Arg Gln Ser His Ala Lys Ser Leu Glu Trp Ile Gly
1 5 10 15

Val

<210> SEQ ID NO 437
<211> LENGTH: 17
<212> TYPE: PRT
<213> ORGANISM: Mus musculus

<400> SEQUENCE: 437

Met His Trp Val Arg Gln Ser His Ala Lys Ser Leu Glu Trp Ile Val
1 5 10 15

Val

<210> SEQ ID NO 438
<211> LENGTH: 17
<212> TYPE: PRT
<213> ORGANISM: Mus musculus

<400> SEQUENCE: 438

Met His Trp Val Arg Gln Ser His Ala Lys Ser Leu Lys Trp Ile Gly
1 5 10 15

Val

<210> SEQ ID NO 439
<211> LENGTH: 17
<212> TYPE: PRT
<213> ORGANISM: Mus musculus

<400> SEQUENCE: 439

Met His Trp Val Arg Gln Ser His Ala Lys Ser Pro Glu Trp Ile Gly
1 5 10 15

Val

<210> SEQ ID NO 440
<211> LENGTH: 17
<212> TYPE: PRT
<213> ORGANISM: Mus musculus

<400> SEQUENCE: 440

Met His Trp Val Arg Gln Thr His Ala Lys Ser Leu Lys Trp Ile Gly
1 5 10 15

Val

<210> SEQ ID NO 441
<211> LENGTH: 26
<212> TYPE: PRT
<213> ORGANISM: Mus musculus

<400> SEQUENCE: 441

Met Leu Val Met Thr Gln Thr Pro Leu Ser Leu Pro Val Ser Leu Gly
1 5 10 15

Asp Gln Ala Ser Ile Ser Cys Arg Ser Ser
20 25

<210> SEQ ID NO 442
<211> LENGTH: 17
<212> TYPE: PRT
<213> ORGANISM: Mus musculus

<400> SEQUENCE: 442

Met Asn Trp Val Lys Gln Arg Pro Gly Gln Gly Leu Glu Trp Ile Gly
1 5 10 15

Ile

<210> SEQ ID NO 443
<211> LENGTH: 9
<212> TYPE: PRT
<213> ORGANISM: Mus musculus

<400> SEQUENCE: 443

Met Gln Thr Lys Gln Leu Pro Leu Thr
1 5

<210> SEQ ID NO 444
<211> LENGTH: 17
<212> TYPE: PRT
<213> ORGANISM: Mus musculus

<400> SEQUENCE: 444

Met Gln Trp Val Lys Gln Ser His Ala Lys Ser Leu Glu Trp Ile Gly
1 5 10 15

Val

<210> SEQ ID NO 445
<211> LENGTH: 17
<212> TYPE: PRT
<213> ORGANISM: Mus musculus

<400> SEQUENCE: 445

Met Gln Trp Val Arg Gln Ser His Ala Lys Ser Leu Glu Trp Ile Gly
1 5 10 15

Val

<210> SEQ ID NO 446
<211> LENGTH: 17
<212> TYPE: PRT
<213> ORGANISM: Mus musculus

<400> SEQUENCE: 446

Met Arg Trp Val Lys Gln Arg Pro Gly Gln Asp Leu Glu Trp Ile Gly
1 5 10 15

Tyr

<210> SEQ ID NO 447
<211> LENGTH: 12
<212> TYPE: PRT
<213> ORGANISM: Mus musculus

<400> SEQUENCE: 447

Met Arg Tyr Asp Gly Tyr Tyr Trp Tyr Phe Asp Val
1 5 10

<210> SEQ ID NO 448
<211> LENGTH: 17
<212> TYPE: PRT
<213> ORGANISM: Mus musculus

<400> SEQUENCE: 448

Met Ser Trp Val Arg Gln Thr Pro Gly Lys Thr Leu Glu Trp Ile Gly
1 5 10 15

Asp

<210> SEQ ID NO 449
<211> LENGTH: 3
<212> TYPE: PRT
<213> ORGANISM: Mus musculus

<400> SEQUENCE: 449

Asn Ala Glu
1

<210> SEQ ID NO 450
<211> LENGTH: 3
<212> TYPE: PRT
<213> ORGANISM: Mus musculus

<400> SEQUENCE: 450

Asn Ala Lys
1

<210> SEQ ID NO 451
<211> LENGTH: 34
<212> TYPE: PRT
<213> ORGANISM: Mus musculus

<400> SEQUENCE: 451

Asn Phe Lys Gly Lys Ala Thr Phe Thr Ala Asp Thr Ser Ser Asn Thr
1               5                   10                  15

Thr Tyr Met Gln Leu Ser Ser Leu Ser Ser Glu Asp Ser Ala Val Tyr
            20                  25                  30

Tyr Cys

<210> SEQ ID NO 452
<211> LENGTH: 34
<212> TYPE: PRT
<213> ORGANISM: Mus musculus

<400> SEQUENCE: 452

Asn Phe Lys Gly Lys Ala Thr Phe Thr Ala Asp Thr Ser Ser Asn Thr
1               5                   10                  15

Thr Tyr Met Gln Leu Ser Ser Leu Thr Ser Glu Asp Ser Ala Val Tyr
            20                  25                  30

Tyr Cys

<210> SEQ ID NO 453
<211> LENGTH: 8
<212> TYPE: PRT
<213> ORGANISM: Mus musculus

<400> SEQUENCE: 453

Asn Phe Asn Ile Gly Asn Asn Leu
1               5

<210> SEQ ID NO 454
<211> LENGTH: 6
<212> TYPE: PRT
<213> ORGANISM: Mus musculus

<400> SEQUENCE: 454

Asn Ile Glu Ser Glu Ser
1               5

<210> SEQ ID NO 455
<211> LENGTH: 6
<212> TYPE: PRT
<213> ORGANISM: Mus musculus

<400> SEQUENCE: 455

Asn Ile Glu Thr Lys Ser
1               5

<210> SEQ ID NO 456
<211> LENGTH: 6
<212> TYPE: PRT
<213> ORGANISM: Mus musculus

<400> SEQUENCE: 456

Asn Ile Gly Ser Lys Ser
1               5

<210> SEQ ID NO 457
<211> LENGTH: 6
<212> TYPE: PRT
<213> ORGANISM: Mus musculus

<400> SEQUENCE: 457

Asn Ile Gly Ser Lys Thr
1               5

<210> SEQ ID NO 458
<211> LENGTH: 6
<212> TYPE: PRT
<213> ORGANISM: Mus musculus

<400> SEQUENCE: 458

Asn Ile Gly Ser Gln Ser
1               5

<210> SEQ ID NO 459
<211> LENGTH: 6
<212> TYPE: PRT
<213> ORGANISM: Mus musculus

<400> SEQUENCE: 459

Asn Ile Gly Thr Lys Ser
1               5

<210> SEQ ID NO 460
<211> LENGTH: 36
<212> TYPE: PRT
<213> ORGANISM: Mus musculus

<400> SEQUENCE: 460

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Ile Tyr Tyr Cys
        35

<210> SEQ ID NO 461
<211> LENGTH: 36
<212> TYPE: PRT
<213> ORGANISM: Mus musculus

<400> SEQUENCE: 461

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Tyr Cys
        35

<210> SEQ ID NO 462
<211> LENGTH: 36
<212> TYPE: PRT
<213> ORGANISM: Mus musculus

<400> SEQUENCE: 462

Asn Arg Phe Ser Gly Val Pro Asp Arg Phe Ser Gly Ser Gly Ser Gly
1               5                   10                  15

Thr Asp Phe Thr Leu Lys Ile Ser Arg Val Gly Ala Glu Asp Leu Gly
            20                  25                  30

Val Tyr Tyr Cys
        35

<210> SEQ ID NO 463
<211> LENGTH: 36
<212> TYPE: PRT
<213> ORGANISM: Mus musculus

<400> SEQUENCE: 463

Asn Arg Phe Ser Gly Val Pro Asp Arg Phe Ser Val Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 464
<211> LENGTH: 36
<212> TYPE: PRT
<213> ORGANISM: Mus musculus

<400> SEQUENCE: 464

Asn Arg Tyr Thr Gly Val Pro Asp Arg Phe Thr Gly Ser Gly Tyr Gly
1               5                   10                  15

Thr Asp Phe Thr Phe Thr Ile Ser Thr Val Gln Ala Glu Asp Leu Ala
            20                  25                  30

Val Tyr Phe Cys
        35

<210> SEQ ID NO 465
<211> LENGTH: 8
<212> TYPE: PRT
<213> ORGANISM: Mus musculus

<400> SEQUENCE: 465

Asn Ser Asn Val Gly Asn Asn Tyr
1               5

<210> SEQ ID NO 466
<211> LENGTH: 11
<212> TYPE: PRT
<213> ORGANISM: Mus musculus

<400> SEQUENCE: 466

Asn Ser Arg Asp Ser Ser Gly Asn His Val Val
1               5                   10

<210> SEQ ID NO 467
<211> LENGTH: 3
<212> TYPE: PRT
<213> ORGANISM: Mus musculus

<400> SEQUENCE: 467

Asn Thr Asp
1

<210> SEQ ID NO 468
<211> LENGTH: 38
<212> TYPE: PRT
<213> ORGANISM: Mus musculus

<400> SEQUENCE: 468

Asn Tyr Asn Glu Lys Phe Lys Gly Lys Ala Thr Leu Thr Ala Asp Thr
1               5                   10                  15

Ser Ser Asn Thr Ala Tyr Met Gln Leu Ser Ser Leu Thr Ser Glu Asp
            20                  25                  30

Ser Ala Val Tyr Phe Cys
        35

<210> SEQ ID NO 469
<211> LENGTH: 38
<212> TYPE: PRT
<213> ORGANISM: Mus musculus

<400> SEQUENCE: 469

Asn Tyr Asn Glu Lys Phe Lys Gly Lys Ala Thr Leu Thr Ala Asp Thr
1               5                   10                  15

Ser Ser Ser Thr Ala Tyr Met Gln Leu Ser Ser Leu Thr Ser Glu Asp
            20                  25                  30

Ser Ala Val Tyr Phe Cys
        35

<210> SEQ ID NO 470
<211> LENGTH: 38
<212> TYPE: PRT
<213> ORGANISM: Mus musculus

<400> SEQUENCE: 470

Asn Tyr Asn Glu Lys Phe Gln Gly Lys Ala Thr Leu Thr Ala Asp Thr
1               5                   10                  15

Ser Ser Ser Thr Ala Tyr Met Gln Leu Ser Ser Leu Thr Ser Glu Asp
            20                  25                  30

Ser Ala Val Tyr Phe Cys
        35

<210> SEQ ID NO 471
<211> LENGTH: 38
<212> TYPE: PRT
<213> ORGANISM: Mus musculus

<400> SEQUENCE: 471

Asn Tyr Asn Glu Lys Phe Arg Gly Lys Ala Thr Leu Thr Ala Asp Thr
1               5                   10                  15

Ser Ser Ser Thr Ala Tyr Met Gln Leu Ser Ser Leu Thr Ser Glu Asp
            20                  25                  30

Ser Ala Val Tyr Phe Cys
        35

<210> SEQ ID NO 472
<211> LENGTH: 6
<212> TYPE: PRT
<213> ORGANISM: Mus musculus

<400> SEQUENCE: 472

Gln Ala Val Arg Ile Asp
1               5

<210> SEQ ID NO 473
<211> LENGTH: 9
<212> TYPE: PRT
<213> ORGANISM: Mus musculus

<400> SEQUENCE: 473

Gln Ala Trp Asp Ser Ser Thr Tyr Val
1               5

<210> SEQ ID NO 474
<211> LENGTH: 25
<212> TYPE: PRT
<213> ORGANISM: Mus musculus

<400> SEQUENCE: 474

Gln Ala Tyr Leu Gln Gln Ser Gly Ala Glu Leu Val Arg Pro Gly Thr
1 5 10 15

Ser Val Lys Ile Ser Cys Lys Ala Ser
20 25

<210> SEQ ID NO 475
<211> LENGTH: 25
<212> TYPE: PRT
<213> ORGANISM: Mus musculus

<400> SEQUENCE: 475

Gln Ala Tyr Leu Gln Gln Ser Gly Ala Glu Leu Val Arg Pro Gly Val
1 5 10 15

Ser Leu Lys Ile Ser Cys Lys Gly Ser
20 25

<210> SEQ ID NO 476
<211> LENGTH: 25
<212> TYPE: PRT
<213> ORGANISM: Mus musculus

<400> SEQUENCE: 476

Gln Ala Tyr Leu Gln Gln Ser Gly Ala Glu Leu Val Arg Pro Gly Val
1 5 10 15

Ser Val Lys Ile Ser Cys Lys Gly Ser
20 25

<210> SEQ ID NO 477
<211> LENGTH: 25
<212> TYPE: PRT
<213> ORGANISM: Mus musculus

<400> SEQUENCE: 477

Gln Ala Tyr Leu Gln Gln Ser Gly Ala Glu Leu Val Arg Ser Gly Ala
1 5 10 15

Ser Val Lys Leu Ser Cys Thr Ala Ser
20 25

<210> SEQ ID NO 478
<211> LENGTH: 25
<212> TYPE: PRT
<213> ORGANISM: Mus musculus

<400> SEQUENCE: 478

Gln Ala Tyr Leu Gln Gln Ser Gly Ala Glu Met Val Arg Pro Gly Val
1 5 10 15

Ser Val Lys Ile Ser Cys Lys Gly Ser
20 25

<210> SEQ ID NO 479
<211> LENGTH: 3
<212> TYPE: PRT
<213> ORGANISM: Mus musculus

<400> SEQUENCE: 479

Gln Asp Asp
1

<210> SEQ ID NO 480
<211> LENGTH: 6
<212> TYPE: PRT

<213> ORGANISM: Mus musculus

<400> SEQUENCE: 480

Gln Asp Ile Lys Arg Arg
1 5

<210> SEQ ID NO 481
<211> LENGTH: 6
<212> TYPE: PRT
<213> ORGANISM: Mus musculus

<400> SEQUENCE: 481

Gln Asp Ile Asn Asn Phe
1 5

<210> SEQ ID NO 482
<211> LENGTH: 6
<212> TYPE: PRT
<213> ORGANISM: Mus musculus

<400> SEQUENCE: 482

Gln Asp Ile Asn Asn Tyr
1 5

<210> SEQ ID NO 483
<211> LENGTH: 6
<212> TYPE: PRT
<213> ORGANISM: Mus musculus

<400> SEQUENCE: 483

Gln Asp Ile Asn Arg Tyr
1 5

<210> SEQ ID NO 484
<211> LENGTH: 6
<212> TYPE: PRT
<213> ORGANISM: Mus musculus

<400> SEQUENCE: 484

Gln Asp Ile Asn Ser Tyr
1 5

<210> SEQ ID NO 485
<211> LENGTH: 6
<212> TYPE: PRT
<213> ORGANISM: Mus musculus

<400> SEQUENCE: 485

Gln Asp Ile Ser Asn Tyr
1 5

<210> SEQ ID NO 486
<211> LENGTH: 6
<212> TYPE: PRT
<213> ORGANISM: Mus musculus

<400> SEQUENCE: 486

Gln Asp Val Asn Thr Ala
1 5

<210> SEQ ID NO 487
<211> LENGTH: 6
<212> TYPE: PRT
<213> ORGANISM: Mus musculus

<400> SEQUENCE: 487

Gln Gly Ile Asn Ser Tyr
1 5

<210> SEQ ID NO 488
<211> LENGTH: 6
<212> TYPE: PRT
<213> ORGANISM: Mus musculus

<400> SEQUENCE: 488

Gln Gly Ile Ser Asn Ser
1 5

<210> SEQ ID NO 489
<211> LENGTH: 6
<212> TYPE: PRT
<213> ORGANISM: Mus musculus

<400> SEQUENCE: 489

Gln Gly Ile Ser Ser Trp
1 5

<210> SEQ ID NO 490
<211> LENGTH: 6
<212> TYPE: PRT
<213> ORGANISM: Mus musculus

<400> SEQUENCE: 490

Gln Gly Ile Ser Thr Tyr
1 5

<210> SEQ ID NO 491
<211> LENGTH: 6
<212> TYPE: PRT
<213> ORGANISM: Mus musculus

<400> SEQUENCE: 491

Gln Gly Thr Ser Ser Trp
1 5

<210> SEQ ID NO 492
<211> LENGTH: 9
<212> TYPE: PRT
<213> ORGANISM: Mus musculus

<400> SEQUENCE: 492

Gln His Phe Trp Asn Thr Pro Pro Thr
1 5

<210> SEQ ID NO 493
<211> LENGTH: 9
<212> TYPE: PRT
<213> ORGANISM: Mus musculus

<400> SEQUENCE: 493

Gln His His Tyr Asp Thr Pro Tyr Thr
1 5

<210> SEQ ID NO 494
<211> LENGTH: 9
<212> TYPE: PRT
<213> ORGANISM: Mus musculus

<400> SEQUENCE: 494

Gln His His Tyr Gly Ile Pro Tyr Thr
1 5

<210> SEQ ID NO 495
<211> LENGTH: 9
<212> TYPE: PRT
<213> ORGANISM: Mus musculus

<400> SEQUENCE: 495

Gln His His Tyr Gly Ser Pro Tyr Thr
1 5

<210> SEQ ID NO 496
<211> LENGTH: 9
<212> TYPE: PRT
<213> ORGANISM: Mus musculus

<400> SEQUENCE: 496

Gln His His Tyr Gly Thr Pro Tyr Thr
1 5

<210> SEQ ID NO 497
<211> LENGTH: 9
<212> TYPE: PRT
<213> ORGANISM: Mus musculus

<400> SEQUENCE: 497

Gln His His Tyr Ser Ser Pro Trp Thr
1 5

<210> SEQ ID NO 498
<211> LENGTH: 9
<212> TYPE: PRT
<213> ORGANISM: Mus musculus

<400> SEQUENCE: 498

Gln His His Tyr Ser Thr Pro Tyr Thr
1 5

<210> SEQ ID NO 499
<211> LENGTH: 25
<212> TYPE: PRT
<213> ORGANISM: Mus musculus

<400> SEQUENCE: 499

Gln Ile Gln Leu Lys Glu Ser Gly Ala Glu Leu Ala Lys Pro Gly Ala
1 5 10 15

Ser Val Lys Met Ser Cys Lys Ala Ser
20 25

<210> SEQ ID NO 500
<211> LENGTH: 25
<212> TYPE: PRT
<213> ORGANISM: Mus musculus

<400> SEQUENCE: 500

Gln Ile Gln Leu Gln Gln Pro Gly Ala Glu Leu Ala Lys Pro Gly Ala
1 5 10 15

Ser Val Lys Met Ser Cys Lys Ala Ser
20 25

<210> SEQ ID NO 501
<211> LENGTH: 25
<212> TYPE: PRT

<213> ORGANISM: Mus musculus

<400> SEQUENCE: 501

Gln Ile Gln Leu Gln Gln Pro Gly Ala Glu Leu Val Arg Pro Gly Thr
1               5                   10                  15

Ser Val Lys Ile Ser Cys Lys Ala Ser
            20                  25

<210> SEQ ID NO 502
<211> LENGTH: 25
<212> TYPE: PRT
<213> ORGANISM: Mus musculus

<400> SEQUENCE: 502

Gln Ile Gln Leu Gln Gln Pro Gly Ala Glu Leu Val Arg Pro Gly Val
1               5                   10                  15

Ser Leu Lys Ile Ser Cys Lys Gly Ser
            20                  25

<210> SEQ ID NO 503
<211> LENGTH: 25
<212> TYPE: PRT
<213> ORGANISM: Mus musculus

<400> SEQUENCE: 503

Gln Ile Gln Leu Gln Gln Ser Gly Ala Glu Leu Ala Lys Pro Gly Ala
1               5                   10                  15

Ser Val Lys Met Ser Cys Lys Ala Ser
            20                  25

<210> SEQ ID NO 504
<211> LENGTH: 25
<212> TYPE: PRT
<213> ORGANISM: Mus musculus

<400> SEQUENCE: 504

Gln Ile Gln Leu Gln Gln Ser Gly Ala Glu Leu Val Arg Pro Gly Thr
1               5                   10                  15

Ser Val Lys Ile Ser Cys Lys Ala Ser
            20                  25

<210> SEQ ID NO 505
<211> LENGTH: 25
<212> TYPE: PRT
<213> ORGANISM: Mus musculus

<400> SEQUENCE: 505

Gln Ile Gln Leu Gln Gln Ser Gly Ala Glu Leu Val Arg Pro Gly Thr
1               5                   10                  15

Ser Val Lys Ile Ser Cys Arg Ala Ser
            20                  25

<210> SEQ ID NO 506
<211> LENGTH: 25
<212> TYPE: PRT
<213> ORGANISM: Mus musculus

<400> SEQUENCE: 506

Gln Ile Gln Leu Gln Gln Ser Gly Ala Glu Leu Val Arg Pro Gly Val
1               5                   10                  15

Ser Leu Lys Ile Ser Cys Lys Gly Ser
            20                  25

<210> SEQ ID NO 507
<211> LENGTH: 25
<212> TYPE: PRT
<213> ORGANISM: Mus musculus

<400> SEQUENCE: 507

Gln Ile Gln Leu Gln Gln Ser Gly Ala Glu Leu Val Arg Pro Gly Val
1               5                   10                  15

Ser Val Lys Ile Ser Cys Lys Gly Ser
            20                  25

<210> SEQ ID NO 508
<211> LENGTH: 25
<212> TYPE: PRT
<213> ORGANISM: Mus musculus

<400> SEQUENCE: 508

Gln Ile Gln Leu Gln Gln Ser Gly Ala Glu Met Val Arg Pro Gly Thr
1               5                   10                  15

Ser Val Lys Ile Ser Cys Lys Ala Ser
            20                  25

<210> SEQ ID NO 509
<211> LENGTH: 25
<212> TYPE: PRT
<213> ORGANISM: Mus musculus

<400> SEQUENCE: 509

Gln Ile Gln Leu Gln Gln Ser Gly Ala Glu Met Val Arg Pro Gly Val
1               5                   10                  15

Ser Val Lys Ile Ser Cys Lys Gly Ser
            20                  25

<210> SEQ ID NO 510
<211> LENGTH: 11
<212> TYPE: PRT
<213> ORGANISM: Mus musculus

<400> SEQUENCE: 510

Gln Ile Trp Asp Ser Ser Ser Ala His Val Val
1               5                   10

<210> SEQ ID NO 511
<211> LENGTH: 6
<212> TYPE: PRT
<213> ORGANISM: Mus musculus

<400> SEQUENCE: 511

Gln Asn Val Gly Ile Asn
1               5

<210> SEQ ID NO 512
<211> LENGTH: 6
<212> TYPE: PRT
<213> ORGANISM: Mus musculus

<400> SEQUENCE: 512

Gln Asn Val Gly Thr Asn
1               5

<210> SEQ ID NO 513
<211> LENGTH: 6

<212> TYPE: PRT
<213> ORGANISM: Mus musculus

<400> SEQUENCE: 513

Gln Asn Val Ser Thr Asn
1 5

<210> SEQ ID NO 514
<211> LENGTH: 9
<212> TYPE: PRT
<213> ORGANISM: Mus musculus

<400> SEQUENCE: 514

Gln Gln Ala Asn Ser Phe Pro Leu Thr
1 5

<210> SEQ ID NO 515
<211> LENGTH: 9
<212> TYPE: PRT
<213> ORGANISM: Mus musculus

<400> SEQUENCE: 515

Gln Gln Ala Asn Ser Phe Pro Pro Thr
1 5

<210> SEQ ID NO 516
<211> LENGTH: 9
<212> TYPE: PRT
<213> ORGANISM: Mus musculus

<400> SEQUENCE: 516

Gln Gln Ala Asn Thr Phe Pro Gln Thr
1 5

<210> SEQ ID NO 517
<211> LENGTH: 9
<212> TYPE: PRT
<213> ORGANISM: Mus musculus

<400> SEQUENCE: 517

Gln Gln Ala Tyr Trp Ser Pro Tyr Thr
1 5

<210> SEQ ID NO 518
<211> LENGTH: 10
<212> TYPE: PRT
<213> ORGANISM: Mus musculus

<400> SEQUENCE: 518

Gln Gln Phe Asp Ile Ser Gly Gly Leu Ile
1 5 10

<210> SEQ ID NO 519
<211> LENGTH: 9
<212> TYPE: PRT
<213> ORGANISM: Mus musculus

<400> SEQUENCE: 519

Gln Gln Gly Asn Thr Leu Pro Leu Thr
1 5

<210> SEQ ID NO 520
<211> LENGTH: 9
<212> TYPE: PRT
<213> ORGANISM: Mus musculus

<400> SEQUENCE: 520

Gln Gln Gly Asn Thr Leu Pro Pro Thr
1               5

<210> SEQ ID NO 521
<211> LENGTH: 9
<212> TYPE: PRT
<213> ORGANISM: Mus musculus

<400> SEQUENCE: 521

Gln Gln Gly Asn Thr Leu Pro Ser Thr
1               5

<210> SEQ ID NO 522
<211> LENGTH: 9
<212> TYPE: PRT
<213> ORGANISM: Mus musculus

<400> SEQUENCE: 522

Gln Gln Gly Asn Thr Leu Pro Trp Thr
1               5

<210> SEQ ID NO 523
<211> LENGTH: 9
<212> TYPE: PRT
<213> ORGANISM: Mus musculus

<400> SEQUENCE: 523

Gln Gln His Tyr Gly Thr Pro Tyr Thr
1               5

<210> SEQ ID NO 524
<211> LENGTH: 9
<212> TYPE: PRT
<213> ORGANISM: Mus musculus

<400> SEQUENCE: 524

Gln Gln His Tyr Ser Ser Pro Trp Thr
1               5

<210> SEQ ID NO 525
<211> LENGTH: 9
<212> TYPE: PRT
<213> ORGANISM: Mus musculus

<400> SEQUENCE: 525

Gln Gln Leu Asn Gly Tyr Pro Thr Thr
1               5

<210> SEQ ID NO 526
<211> LENGTH: 9
<212> TYPE: PRT
<213> ORGANISM: Mus musculus

<400> SEQUENCE: 526

Gln Gln Ser His Ser Thr Pro Ile Thr
1               5

<210> SEQ ID NO 527
<211> LENGTH: 9
<212> TYPE: PRT
<213> ORGANISM: Mus musculus

<400> SEQUENCE: 527

Gln Gln Ser His Ser Thr Pro Leu Thr
1 5

<210> SEQ ID NO 528
<211> LENGTH: 9
<212> TYPE: PRT
<213> ORGANISM: Mus musculus

<400> SEQUENCE: 528

Gln Gln Ser Lys Gln Ile Pro Tyr Thr
1 5

<210> SEQ ID NO 529
<211> LENGTH: 9
<212> TYPE: PRT
<213> ORGANISM: Mus musculus

<400> SEQUENCE: 529

Gln Gln Ser Asn Ser Leu Pro Pro Thr
1 5

<210> SEQ ID NO 530
<211> LENGTH: 9
<212> TYPE: PRT
<213> ORGANISM: Mus musculus

<400> SEQUENCE: 530

Gln Gln Ser Asn Thr Leu Pro Pro Thr
1 5

<210> SEQ ID NO 531
<211> LENGTH: 9
<212> TYPE: PRT
<213> ORGANISM: Mus musculus

<400> SEQUENCE: 531

Gln Gln Ser Tyr Ser Leu Pro Leu Thr
1 5

<210> SEQ ID NO 532
<211> LENGTH: 9
<212> TYPE: PRT
<213> ORGANISM: Mus musculus

<400> SEQUENCE: 532

Gln Gln Ser Tyr Ser Thr Pro Leu Thr
1 5

<210> SEQ ID NO 533
<211> LENGTH: 9
<212> TYPE: PRT
<213> ORGANISM: Mus musculus

<400> SEQUENCE: 533

Gln Gln Ser Tyr Ser Thr Pro Pro Ala
1 5

<210> SEQ ID NO 534
<211> LENGTH: 9
<212> TYPE: PRT
<213> ORGANISM: Mus musculus

<400> SEQUENCE: 534

Gln Gln Ser Tyr Ser Thr Pro Pro Thr 1 5

<210> SEQ ID NO 535
<211> LENGTH: 9
<212> TYPE: PRT
<213> ORGANISM: Mus musculus

<400> SEQUENCE: 535

Gln Gln Ser Tyr Ser Thr Pro Trp Thr
1 5

<210> SEQ ID NO 536
<211> LENGTH: 9
<212> TYPE: PRT
<213> ORGANISM: Mus musculus

<400> SEQUENCE: 536

Gln Gln Ser Tyr Ser Thr Pro Tyr Thr
1 5

<210> SEQ ID NO 537
<211> LENGTH: 9
<212> TYPE: PRT
<213> ORGANISM: Mus musculus

<400> SEQUENCE: 537

Gln Gln Ser Tyr Thr Thr Pro Leu Thr
1 5

<210> SEQ ID NO 538
<211> LENGTH: 9
<212> TYPE: PRT
<213> ORGANISM: Mus musculus

<400> SEQUENCE: 538

Gln Gln Thr His Thr Trp Pro Trp Thr
1 5

<210> SEQ ID NO 539
<211> LENGTH: 9
<212> TYPE: PRT
<213> ORGANISM: Mus musculus

<400> SEQUENCE: 539

Gln Gln Thr Tyr Asn Asp Pro Pro Thr
1 5

<210> SEQ ID NO 540
<211> LENGTH: 9
<212> TYPE: PRT
<213> ORGANISM: Mus musculus

<400> SEQUENCE: 540

Gln Gln Thr Tyr Ser Thr Pro Leu Thr
1 5

<210> SEQ ID NO 541
<211> LENGTH: 9
<212> TYPE: PRT
<213> ORGANISM: Mus musculus

<400> SEQUENCE: 541

Gln Gln Val His Ser Phe Pro Phe Thr
1 5

<210> SEQ ID NO 542
<211> LENGTH: 9
<212> TYPE: PRT
<213> ORGANISM: Mus musculus

<400> SEQUENCE: 542

Gln Gln Tyr Asp Asn Leu Pro Leu Thr
1 5

<210> SEQ ID NO 543
<211> LENGTH: 9
<212> TYPE: PRT
<213> ORGANISM: Mus musculus

<400> SEQUENCE: 543

Gln Gln Tyr Asp Asn Leu Pro Tyr Thr
1 5

<210> SEQ ID NO 544
<211> LENGTH: 9
<212> TYPE: PRT
<213> ORGANISM: Mus musculus

<400> SEQUENCE: 544

Gln Gln Tyr Asn His Trp Pro Pro Leu
1 5

<210> SEQ ID NO 545
<211> LENGTH: 8
<212> TYPE: PRT
<213> ORGANISM: Mus musculus

<400> SEQUENCE: 545

Gln Gln Tyr Asn Asn Trp Trp Thr
1 5

<210> SEQ ID NO 546
<211> LENGTH: 9
<212> TYPE: PRT
<213> ORGANISM: Mus musculus

<400> SEQUENCE: 546

Gln Gln Tyr Asn Asn Tyr Pro Tyr Thr
1 5

<210> SEQ ID NO 547
<211> LENGTH: 11
<212> TYPE: PRT
<213> ORGANISM: Mus musculus

<400> SEQUENCE: 547

Gln Gln Tyr Asn Ser Ser Pro Leu Met Tyr Thr
1 5 10

<210> SEQ ID NO 548
<211> LENGTH: 9
<212> TYPE: PRT
<213> ORGANISM: Mus musculus

<400> SEQUENCE: 548

Gln Gln Tyr Asn Ser Tyr Pro Phe Thr
1 5

<210> SEQ ID NO 549

<211> LENGTH: 9
<212> TYPE: PRT
<213> ORGANISM: Mus musculus

<400> SEQUENCE: 549

Gln Gln Tyr Asn Ser Tyr Pro Leu Thr
1 5

<210> SEQ ID NO 550
<211> LENGTH: 9
<212> TYPE: PRT
<213> ORGANISM: Mus musculus

<400> SEQUENCE: 550

Gln Gln Tyr Asn Ser Tyr Pro Tyr Thr
1 5

<210> SEQ ID NO 551
<211> LENGTH: 9
<212> TYPE: PRT
<213> ORGANISM: Mus musculus

<400> SEQUENCE: 551

Gln Gln Tyr Asn Ser Tyr Ser Arg Thr
1 5

<210> SEQ ID NO 552
<211> LENGTH: 9
<212> TYPE: PRT
<213> ORGANISM: Mus musculus

<400> SEQUENCE: 552

Gln Gln Tyr Asn Thr Tyr Pro Tyr Thr
1 5

<210> SEQ ID NO 553
<211> LENGTH: 10
<212> TYPE: PRT
<213> ORGANISM: Mus musculus

<400> SEQUENCE: 553

Gln Gln Tyr Ser Gly Asp Ser Met Tyr Thr
1 5 10

<210> SEQ ID NO 554
<211> LENGTH: 9
<212> TYPE: PRT
<213> ORGANISM: Mus musculus

<400> SEQUENCE: 554

Gln Gln Tyr Thr Asn Trp Pro Gln Thr
1 5

<210> SEQ ID NO 555
<211> LENGTH: 8
<212> TYPE: PRT
<213> ORGANISM: Mus musculus

<400> SEQUENCE: 555

Gln Gln Tyr Tyr Asp Asp Pro Gln
1 5

<210> SEQ ID NO 556
<211> LENGTH: 9
<212> TYPE: PRT

-continued

<213> ORGANISM: Mus musculus

<400> SEQUENCE: 556

Gln Gln Tyr Tyr Ser Thr Pro Pro His
1               5

<210> SEQ ID NO 557
<211> LENGTH: 8
<212> TYPE: PRT
<213> ORGANISM: Mus musculus

<400> SEQUENCE: 557

Gln Arg Tyr Gly Ser Ser Pro Arg
1               5

<210> SEQ ID NO 558
<211> LENGTH: 6
<212> TYPE: PRT
<213> ORGANISM: Mus musculus

<400> SEQUENCE: 558

Gln Ser Ile Gly Asn Tyr
1               5

<210> SEQ ID NO 559
<211> LENGTH: 6
<212> TYPE: PRT
<213> ORGANISM: Mus musculus

<400> SEQUENCE: 559

Gln Ser Ile Gly Tyr Trp
1               5

<210> SEQ ID NO 560
<211> LENGTH: 6
<212> TYPE: PRT
<213> ORGANISM: Mus musculus

<400> SEQUENCE: 560

Gln Ser Ile Ile Thr Tyr
1               5

<210> SEQ ID NO 561
<211> LENGTH: 6
<212> TYPE: PRT
<213> ORGANISM: Mus musculus

<400> SEQUENCE: 561

Gln Ser Ile Lys Asn Tyr
1               5

<210> SEQ ID NO 562
<211> LENGTH: 6
<212> TYPE: PRT
<213> ORGANISM: Mus musculus

<400> SEQUENCE: 562

Gln Ser Ile Asn Ser Tyr
1               5

<210> SEQ ID NO 563
<211> LENGTH: 6
<212> TYPE: PRT
<213> ORGANISM: Mus musculus

<400> SEQUENCE: 563

Gln Ser Ile Ser Asn Tyr
1 5

<210> SEQ ID NO 564
<211> LENGTH: 6
<212> TYPE: PRT
<213> ORGANISM: Mus musculus

<400> SEQUENCE: 564

Gln Ser Ile Ser Arg Tyr
1 5

<210> SEQ ID NO 565
<211> LENGTH: 6
<212> TYPE: PRT
<213> ORGANISM: Mus musculus

<400> SEQUENCE: 565

Gln Ser Ile Ser Ser His
1 5

<210> SEQ ID NO 566
<211> LENGTH: 6
<212> TYPE: PRT
<213> ORGANISM: Mus musculus

<400> SEQUENCE: 566

Gln Ser Ile Ser Ser Trp
1 5

<210> SEQ ID NO 567
<211> LENGTH: 6
<212> TYPE: PRT
<213> ORGANISM: Mus musculus

<400> SEQUENCE: 567

Gln Ser Ile Ser Ser Tyr
1 5

<210> SEQ ID NO 568
<211> LENGTH: 6
<212> TYPE: PRT
<213> ORGANISM: Mus musculus

<400> SEQUENCE: 568

Gln Ser Ile Ser Ser Tyr
1 5

<210> SEQ ID NO 569
<211> LENGTH: 11
<212> TYPE: PRT
<213> ORGANISM: Mus musculus

<400> SEQUENCE: 569

Gln Ser Ile Val His Ser Asn Gly Asn Thr Tyr
1 5 10

<210> SEQ ID NO 570
<211> LENGTH: 11
<212> TYPE: PRT
<213> ORGANISM: Mus musculus

<400> SEQUENCE: 570

-continued

Gln Ser Leu Leu His Ser Asp Gly Lys Thr Tyr
1 5 10

<210> SEQ ID NO 571
<211> LENGTH: 11
<212> TYPE: PRT
<213> ORGANISM: Mus musculus

<400> SEQUENCE: 571

Gln Ser Leu Val His Ser Asn Gly Asn Thr Tyr
1 5 10

<210> SEQ ID NO 572
<211> LENGTH: 6
<212> TYPE: PRT
<213> ORGANISM: Mus musculus

<400> SEQUENCE: 572

Gln Ser Val Asn Asn Asp
1 5

<210> SEQ ID NO 573
<211> LENGTH: 7
<212> TYPE: PRT
<213> ORGANISM: Mus musculus

<400> SEQUENCE: 573

Gln Ser Val Ser Asn Asn Tyr
1 5

<210> SEQ ID NO 574
<211> LENGTH: 6
<212> TYPE: PRT
<213> ORGANISM: Mus musculus

<400> SEQUENCE: 574

Gln Ser Val Ser Asn Tyr
1 5

<210> SEQ ID NO 575
<211> LENGTH: 6
<212> TYPE: PRT
<213> ORGANISM: Mus musculus

<400> SEQUENCE: 575

Gln Ser Val Ser Ser Asn
1 5

<210> SEQ ID NO 576
<211> LENGTH: 6
<212> TYPE: PRT
<213> ORGANISM: Mus musculus

<400> SEQUENCE: 576

Gln Ser Val Ser Ser Arg
1 5

<210> SEQ ID NO 577
<211> LENGTH: 7
<212> TYPE: PRT
<213> ORGANISM: Mus musculus

<400> SEQUENCE: 577

Gln Ser Val Ser Ser Thr Tyr
1 5

<210> SEQ ID NO 578
<211> LENGTH: 10
<212> TYPE: PRT
<213> ORGANISM: Mus musculus

<400> SEQUENCE: 578

Gln Ser Tyr Asp Gly Asn Asn His Met Val
1 5 10

<210> SEQ ID NO 579
<211> LENGTH: 9
<212> TYPE: PRT
<213> ORGANISM: Mus musculus

<400> SEQUENCE: 579

Gln Ser Tyr Asp Gly Ser Ser Val Val
1 5

<210> SEQ ID NO 580
<211> LENGTH: 9
<212> TYPE: PRT
<213> ORGANISM: Mus musculus

<400> SEQUENCE: 580

Gln Ser Tyr Asp Ser Thr Thr Leu Val
1 5

<210> SEQ ID NO 581
<211> LENGTH: 6
<212> TYPE: PRT
<213> ORGANISM: Mus musculus

<400> SEQUENCE: 581

Gln Thr Ile Ser Gly Leu
1 5

<210> SEQ ID NO 582
<211> LENGTH: 6
<212> TYPE: PRT
<213> ORGANISM: Mus musculus

<400> SEQUENCE: 582

Gln Thr Ile Ser Gln Trp
1 5

<210> SEQ ID NO 583
<211> LENGTH: 9
<212> TYPE: PRT
<213> ORGANISM: Mus musculus

<400> SEQUENCE: 583

Gln Thr Trp Asp Gly Ser Ile Val Val
1 5

<210> SEQ ID NO 584
<211> LENGTH: 25
<212> TYPE: PRT
<213> ORGANISM: Mus musculus

<400> SEQUENCE: 584

Gln Val Gln Leu Ile Gln Ser Gly Ala Glu Leu Val Arg Pro Gly Val
1 5 10 15

Ser Leu Lys Ile Ser Cys Lys Gly Ser 20                  25

<210> SEQ ID NO 585
<211> LENGTH: 25
<212> TYPE: PRT
<213> ORGANISM: Mus musculus

<400> SEQUENCE: 585

Gln Val Gln Leu Lys Gln Ser Gly Ala Glu Leu Val Arg Pro Gly Val
1               5                   10                  15

Ser Leu Lys Ile Ser Cys Lys Gly Ser
            20                  25

<210> SEQ ID NO 586
<211> LENGTH: 24
<212> TYPE: PRT
<213> ORGANISM: Mus musculus

<400> SEQUENCE: 586

Gln Val Gln Leu Gln Pro Gly Ala Glu Leu Val Arg Pro Gly Thr Ser
1               5                   10                  15

Val Lys Ile Ser Cys Lys Ala Ser
            20

<210> SEQ ID NO 587
<211> LENGTH: 25
<212> TYPE: PRT
<213> ORGANISM: Mus musculus

<400> SEQUENCE: 587

Gln Val Gln Leu Gln Gln Pro Gly Ala Asp Leu Met Lys Pro Gly Ala
1               5                   10                  15

Ser Val Lys Ile Ser Cys Lys Ala Ser
            20                  25

<210> SEQ ID NO 588
<211> LENGTH: 25
<212> TYPE: PRT
<213> ORGANISM: Mus musculus

<400> SEQUENCE: 588

Gln Val Gln Leu Gln Gln Pro Gly Ala Glu Leu Ala Lys Pro Gly Ala
1               5                   10                  15

Ser Val Lys Met Ser Cys Lys Ala Ser
            20                  25

<210> SEQ ID NO 589
<211> LENGTH: 25
<212> TYPE: PRT
<213> ORGANISM: Mus musculus

<400> SEQUENCE: 589

Gln Val Gln Leu Gln Gln Pro Gly Ala Glu Leu Val Arg Pro Gly Ala
1               5                   10                  15

Ser Val Lys Leu Ser Cys Lys Ala Ser
            20                  25

<210> SEQ ID NO 590
<211> LENGTH: 25
<212> TYPE: PRT
<213> ORGANISM: Mus musculus

<400> SEQUENCE: 590

```
Gln Val Gln Leu Gln Gln Pro Gly Ala Glu Leu Val Arg Pro Gly Thr
1               5                   10                  15

Ser Val Lys Ile Ser Cys Lys Ala Ser
            20                  25


<210> SEQ ID NO 591
<211> LENGTH: 25
<212> TYPE: PRT
<213> ORGANISM: Mus musculus

<400> SEQUENCE: 591

Gln Val Gln Leu Gln Gln Pro Gly Ala Glu Leu Val Arg Pro Gly Val
1               5                   10                  15

Ser Leu Lys Ile Ser Cys Lys Gly Ser
            20                  25


<210> SEQ ID NO 592
<211> LENGTH: 25
<212> TYPE: PRT
<213> ORGANISM: Mus musculus

<400> SEQUENCE: 592

Gln Val Gln Leu Gln Gln Pro Gly Ala Glu Leu Val Arg Pro Gly Val
1               5                   10                  15

Ser Val Lys Ile Ser Cys Lys Gly Ser
            20                  25


<210> SEQ ID NO 593
<211> LENGTH: 25
<212> TYPE: PRT
<213> ORGANISM: Mus musculus

<400> SEQUENCE: 593

Gln Val Gln Leu Gln Gln Ser Gly Ala Glu Leu Ala Lys Pro Gly Ala
1               5                   10                  15

Ser Val Lys Met Ser Cys Lys Ala Ser
            20                  25


<210> SEQ ID NO 594
<211> LENGTH: 25
<212> TYPE: PRT
<213> ORGANISM: Mus musculus

<400> SEQUENCE: 594

Gln Val Gln Leu Gln Gln Ser Gly Ala Glu Leu Met Arg Pro Gly Val
1               5                   10                  15

Ser Leu Lys Ile Ser Cys Lys Gly Ser
            20                  25


<210> SEQ ID NO 595
<211> LENGTH: 25
<212> TYPE: PRT
<213> ORGANISM: Mus musculus

<400> SEQUENCE: 595

Gln Val Gln Leu Gln Gln Ser Gly Ala Glu Leu Val Arg Pro Gly Ile
1               5                   10                  15

Ser Val Lys Ile Ser Cys Lys Ala Ser
            20                  25


<210> SEQ ID NO 596
```

<211> LENGTH: 25
<212> TYPE: PRT
<213> ORGANISM: Mus musculus

<400> SEQUENCE: 596

Gln Val Gln Leu Gln Gln Ser Gly Ala Glu Leu Val Arg Pro Gly Thr
1 5 10 15

Ser Val Lys Ile Ser Cys Lys Ala Ser
20 25

<210> SEQ ID NO 597
<211> LENGTH: 25
<212> TYPE: PRT
<213> ORGANISM: Mus musculus

<400> SEQUENCE: 597

Gln Val Gln Leu Gln Gln Ser Gly Ala Glu Leu Val Arg Pro Gly Thr
1 5 10 15

Ser Val Lys Ile Ser Cys Arg Ala Ser
20 25

<210> SEQ ID NO 598
<211> LENGTH: 25
<212> TYPE: PRT
<213> ORGANISM: Mus musculus

<400> SEQUENCE: 598

Gln Val Gln Leu Gln Gln Ser Gly Ala Glu Leu Val Arg Pro Gly Val
1 5 10 15

Ser Leu Lys Ile Ser Cys Lys Gly Ser
20 25

<210> SEQ ID NO 599
<211> LENGTH: 25
<212> TYPE: PRT
<213> ORGANISM: Mus musculus

<400> SEQUENCE: 599

Gln Val Gln Leu Gln Gln Ser Gly Ala Glu Leu Val Arg Pro Gly Val
1 5 10 15

Ser Val Lys Ile Ser Cys Lys Gly Ser
20 25

<210> SEQ ID NO 600
<211> LENGTH: 25
<212> TYPE: PRT
<213> ORGANISM: Mus musculus

<400> SEQUENCE: 600

Gln Val Gln Leu Gln Gln Ser Gly Ala Glu Met Val Arg Pro Gly Thr
1 5 10 15

Ser Val Lys Ile Ser Cys Lys Ala Ser
20 25

<210> SEQ ID NO 601
<211> LENGTH: 25
<212> TYPE: PRT
<213> ORGANISM: Mus musculus

<400> SEQUENCE: 601

Gln Val Gln Leu Gln Gln Ser Gly Ala Glu Met Val Arg Pro Gly Val
1 5 10 15

```
Ser Val Lys Ile Ser Cys Lys Gly Ser
            20                  25


<210> SEQ ID NO 602
<211> LENGTH: 25
<212> TYPE: PRT
<213> ORGANISM: Mus musculus

<400> SEQUENCE: 602

Gln Val Gln Leu Gln Gln Ser Gly Ala Gly Leu Val Arg Pro Gly Val
1               5                   10                  15

Ser Leu Lys Ile Ser Cys Lys Gly Ser
            20                  25


<210> SEQ ID NO 603
<211> LENGTH: 25
<212> TYPE: PRT
<213> ORGANISM: Mus musculus

<400> SEQUENCE: 603

Gln Val Gln Leu Val Glu Thr Gly Gly Gly Leu Val Gln Pro Gly Gly
1               5                   10                  15

Ser Arg Gly Leu Ser Cys Glu Gly Ser
            20                  25


<210> SEQ ID NO 604
<211> LENGTH: 25
<212> TYPE: PRT
<213> ORGANISM: Mus musculus

<400> SEQUENCE: 604

Gln Val Gln Met Lys Gln Ser Gly Ala Glu Leu Ala Lys Pro Gly Ala
1               5                   10                  15

Ser Val Lys Met Ser Cys Lys Ala Ser
            20                  25


<210> SEQ ID NO 605
<211> LENGTH: 25
<212> TYPE: PRT
<213> ORGANISM: Mus musculus

<400> SEQUENCE: 605

Gln Val Gln Met Lys Gln Ser Gly Ala Glu Leu Val Arg Pro Gly Val
1               5                   10                  15

Ser Leu Lys Ile Ser Cys Lys Gly Ser
            20                  25


<210> SEQ ID NO 606
<211> LENGTH: 25
<212> TYPE: PRT
<213> ORGANISM: Mus musculus

<400> SEQUENCE: 606

Gln Val Gln Met Gln Gln Ser Gly Ala Glu Leu Val Arg Pro Gly Val
1               5                   10                  15

Ser Leu Lys Ile Ser Cys Lys Gly Ser
            20                  25


<210> SEQ ID NO 607
<211> LENGTH: 25
<212> TYPE: PRT
<213> ORGANISM: Mus musculus
```

<400> SEQUENCE: 607

Gln Val Gln Met Gln Gln Ser Gly Ala Glu Leu Val Arg Pro Gly Val
1 5 10 15

Ser Val Lys Ile Ser Cys Lys Gly Ser
20 25

<210> SEQ ID NO 608
<211> LENGTH: 12
<212> TYPE: PRT
<213> ORGANISM: Mus musculus

<400> SEQUENCE: 608

Gln Val Trp Asp Ser Ser Ser Asp His Pro Val Val
1 5 10

<210> SEQ ID NO 609
<211> LENGTH: 12
<212> TYPE: PRT
<213> ORGANISM: Mus musculus

<400> SEQUENCE: 609

Gln Val Trp Asp Ser Ser Ser Asp His Thr Val Ala
1 5 10

<210> SEQ ID NO 610
<211> LENGTH: 11
<212> TYPE: PRT
<213> ORGANISM: Mus musculus

<400> SEQUENCE: 610

Gln Val Trp Asp Ser Ser Ser Asp His Val Val
1 5 10

<210> SEQ ID NO 611
<211> LENGTH: 11
<212> TYPE: PRT
<213> ORGANISM: Mus musculus

<400> SEQUENCE: 611

Gln Val Trp Asp Ser Ser Ser Asp His Trp Val
1 5 10

<210> SEQ ID NO 612
<211> LENGTH: 12
<212> TYPE: PRT
<213> ORGANISM: Mus musculus

<400> SEQUENCE: 612

Gln Val Trp Asp Ser Ser Ser Asp Leu Leu Trp Val
1 5 10

<210> SEQ ID NO 613
<211> LENGTH: 12
<212> TYPE: PRT
<213> ORGANISM: Mus musculus

<400> SEQUENCE: 613

Gln Val Trp Asp Ser Ser Ser Gly His Arg Glu Val
1 5 10

<210> SEQ ID NO 614
<211> LENGTH: 12
<212> TYPE: PRT
<213> ORGANISM: Mus musculus

<400> SEQUENCE: 614

Gln Val Trp Asp Thr Ser Gly Asp Leu His Trp Ala
1 5 10

<210> SEQ ID NO 615
<211> LENGTH: 11
<212> TYPE: PRT
<213> ORGANISM: Mus musculus

<400> SEQUENCE: 615

Gln Val Trp His Thr Thr Asn Asp His Val Leu
1 5 10

<210> SEQ ID NO 616
<211> LENGTH: 3
<212> TYPE: PRT
<213> ORGANISM: Mus musculus

<400> SEQUENCE: 616

Gln Tyr Ile
1

<210> SEQ ID NO 617
<211> LENGTH: 6
<212> TYPE: PRT
<213> ORGANISM: Mus musculus

<400> SEQUENCE: 617

Gln Tyr Ile Ser Asn Tyr
1 5

<210> SEQ ID NO 618
<211> LENGTH: 3
<212> TYPE: PRT
<213> ORGANISM: Mus musculus

<400> SEQUENCE: 618

Arg Ala Asn
1

<210> SEQ ID NO 619
<211> LENGTH: 3
<212> TYPE: PRT
<213> ORGANISM: Mus musculus

<400> SEQUENCE: 619

Arg Ala Ser
1

<210> SEQ ID NO 620
<211> LENGTH: 6
<212> TYPE: PRT
<213> ORGANISM: Mus musculus

<400> SEQUENCE: 620

Arg Asp Val Asn Thr Ala
1 5

<210> SEQ ID NO 621
<211> LENGTH: 26
<212> TYPE: PRT
<213> ORGANISM: Mus musculus

<400> SEQUENCE: 621

Arg His Cys Glu Ser Gln Ser Gln Lys Phe Met Ser Thr Ser Val Gly
1               5                   10                  15

Asp Arg Val Ser Val Thr Cys Lys Ala Ser
            20                  25

<210> SEQ ID NO 622
<211> LENGTH: 36
<212> TYPE: PRT
<213> ORGANISM: Mus musculus

<400> SEQUENCE: 622

Arg Leu His Ile Gly Ile Pro Ser Arg Phe Ser Gly Ser Gly Ser Gly
1               5                   10                  15

Thr Asp Tyr Ser Leu Thr Ile Ser Asn Leu Glu Gln Glu Asp Ile Ala
            20                  25                  30

Thr Tyr Phe Cys
        35

<210> SEQ ID NO 623
<211> LENGTH: 36
<212> TYPE: PRT
<213> ORGANISM: Mus musculus

<400> SEQUENCE: 623

Arg Leu His Ser Gly Val Pro Ser Arg Phe Ser Gly Ser Glu Pro Gly
1               5                   10                  15

Thr Asp Tyr Ser Leu Thr Ile Ser Asn Leu Glu Gln Glu Asp Ile Ala
            20                  25                  30

Thr Tyr Phe Cys
        35

<210> SEQ ID NO 624
<211> LENGTH: 36
<212> TYPE: PRT
<213> ORGANISM: Mus musculus

<400> SEQUENCE: 624

Arg Leu His Ser Gly Val Pro Ser Arg Phe Ser Gly Ser Glu Ser Gly
1               5                   10                  15

Thr Asp Tyr Ser Leu Thr Ile Ser Asn Leu Glu Gln Glu Asp Ile Ala
            20                  25                  30

Thr Tyr Phe Cys
        35

<210> SEQ ID NO 625
<211> LENGTH: 36
<212> TYPE: PRT
<213> ORGANISM: Mus musculus

<400> SEQUENCE: 625

Arg Leu His Ser Gly Val Pro Ser Arg Phe Ser Gly Ser Gly Ser Gly
1               5                   10                  15

Ala Asp Tyr Ser Leu Thr Ile Ser Asn Leu Glu Gln Glu Asp Ile Ala
            20                  25                  30

Thr Tyr Phe Cys
        35

<210> SEQ ID NO 626
<211> LENGTH: 36
<212> TYPE: PRT

<213> ORGANISM: Mus musculus

<400> SEQUENCE: 626

Arg Leu His Ser Gly Val Pro Ser Arg Phe Ser Gly Ser Gly Ser Gly
1 5 10 15

Thr Asp Tyr Ser Leu Thr Ile Ser Asn Leu Glu Gln Glu Asp Ile Ala
20 25 30

Thr Tyr Phe Cys
35

<210> SEQ ID NO 627
<211> LENGTH: 36
<212> TYPE: PRT
<213> ORGANISM: Mus musculus

<400> SEQUENCE: 627

Arg Leu Gln Ser Gly Val Pro Ser Arg Phe Thr Gly Ser Gly Ser Gly
1 5 10 15

Thr Asp Tyr Ser Leu Thr Ile Ser Asn Leu Glu Gln Glu Asp Ile Ala
20 25 30

Thr Tyr Phe Cys
35

<210> SEQ ID NO 628
<211> LENGTH: 36
<212> TYPE: PRT
<213> ORGANISM: Mus musculus

<400> SEQUENCE: 628

Arg Leu Val Asp Gly Ala Pro Ser Arg Phe Ser Gly Ser Gly Ser Gly
1 5 10 15

Gln Asp Tyr Ser Leu Thr Ile Ser Ser Leu Glu Tyr Glu Asp Met Gly
20 25 30

Ile Tyr Tyr Cys
35

<210> SEQ ID NO 629
<211> LENGTH: 36
<212> TYPE: PRT
<213> ORGANISM: Mus musculus

<400> SEQUENCE: 629

Arg Leu Val Asp Gly Val Pro Ser Arg Phe Ser Gly Ser Gly Ser Gly
1 5 10 15

Gln Asp Tyr Ser Leu Thr Ile Ser Ser Leu Glu Tyr Glu Asp Leu Gly
20 25 30

Ile Tyr Tyr Cys
35

<210> SEQ ID NO 630
<211> LENGTH: 36
<212> TYPE: PRT
<213> ORGANISM: Mus musculus

<400> SEQUENCE: 630

Arg Leu Val Asp Gly Val Pro Ser Arg Phe Ser Gly Ser Gly Ser Gly
1 5 10 15

Gln Asp Tyr Ser Leu Thr Ile Ser Ser Leu Glu Tyr Glu Asp Met Gly
20 25 30

Ile Tyr Tyr Cys

35

<210> SEQ ID NO 631
<211> LENGTH: 36
<212> TYPE: PRT
<213> ORGANISM: Mus musculus

<400> SEQUENCE: 631

Arg Leu Val Asp Gly Val Pro Ser Arg Phe Ser Gly Ser Gly Ser Gly
1               5                   10                  15

Gln His Tyr Ser Leu Thr Ile Ser Gly Leu Glu Tyr Glu Asp Leu Gly
            20                  25                  30

Ile Tyr Tyr Cys
        35

<210> SEQ ID NO 632
<211> LENGTH: 36
<212> TYPE: PRT
<213> ORGANISM: Mus musculus

<400> SEQUENCE: 632

Arg Leu Val Asp Gly Val Pro Ser Arg Phe Ser Gly Ser Gly Ser Gly
1               5                   10                  15

Gln Asn Tyr Ser Leu Thr Ile Ser Ser Leu Glu Tyr Glu Asp Met Gly
            20                  25                  30

Ile Tyr Tyr Cys
        35

<210> SEQ ID NO 633
<211> LENGTH: 3
<212> TYPE: PRT
<213> ORGANISM: Mus musculus

<400> SEQUENCE: 633

Arg Asn His
1

<210> SEQ ID NO 634
<211> LENGTH: 6
<212> TYPE: PRT
<213> ORGANISM: Mus musculus

<400> SEQUENCE: 634

Arg Asn Ile Trp Ser Tyr
1               5

<210> SEQ ID NO 635
<211> LENGTH: 3
<212> TYPE: PRT
<213> ORGANISM: Mus musculus

<400> SEQUENCE: 635

Arg Asn Asn
1

<210> SEQ ID NO 636
<211> LENGTH: 8
<212> TYPE: PRT
<213> ORGANISM: Mus musculus

<400> SEQUENCE: 636

Arg Pro Asn Val Ala Ser Asn Ser
1               5

<210> SEQ ID NO 637
<211> LENGTH: 3
<212> TYPE: PRT
<213> ORGANISM: Mus musculus

<400> SEQUENCE: 637

Ser Ala Ser
1

<210> SEQ ID NO 638
<211> LENGTH: 3
<212> TYPE: PRT
<213> ORGANISM: Mus musculus

<400> SEQUENCE: 638

Ser Asp Asn
1

<210> SEQ ID NO 639
<211> LENGTH: 8
<212> TYPE: PRT
<213> ORGANISM: Mus musculus

<400> SEQUENCE: 639

Ser Gly Arg Ile Ala Ser Asn Tyr
1               5

<210> SEQ ID NO 640
<211> LENGTH: 8
<212> TYPE: PRT
<213> ORGANISM: Mus musculus

<400> SEQUENCE: 640

Ser Gly Ser Ile Ala Ser Ser Tyr
1               5

<210> SEQ ID NO 641
<211> LENGTH: 9
<212> TYPE: PRT
<213> ORGANISM: Mus musculus

<400> SEQUENCE: 641

Ser Gly Ser Val Ser Thr Ser Tyr Tyr
1               5

<210> SEQ ID NO 642
<211> LENGTH: 34
<212> TYPE: PRT
<213> ORGANISM: Mus musculus

<400> SEQUENCE: 642

Ser Ile Lys Asp Arg Phe Thr Ile Phe Arg Asp Asn Asp Lys Ser Thr
1               5                   10                  15

Leu Tyr Leu Gln Met Ser Asn Val Arg Ser Glu Asp Thr Ala Thr Tyr
            20                  25                  30

Phe Cys

<210> SEQ ID NO 643
<211> LENGTH: 6
<212> TYPE: PRT
<213> ORGANISM: Mus musculus

<400> SEQUENCE: 643

Ser Leu Arg Ser Tyr Tyr
1 5

<210> SEQ ID NO 644
<211> LENGTH: 3
<212> TYPE: PRT
<213> ORGANISM: Mus musculus

<400> SEQUENCE: 644

Ser Asn Asn
1

<210> SEQ ID NO 645
<211> LENGTH: 9
<212> TYPE: PRT
<213> ORGANISM: Mus musculus

<400> SEQUENCE: 645

Ser Gln Ser Thr His Val Pro Pro Thr
1 5

<210> SEQ ID NO 646
<211> LENGTH: 12
<212> TYPE: PRT
<213> ORGANISM: Mus musculus

<400> SEQUENCE: 646

Ser Arg Gly Gly Thr Ser Phe Val His Phe Asp Tyr
1 5 10

<210> SEQ ID NO 647
<211> LENGTH: 9
<212> TYPE: PRT
<213> ORGANISM: Mus musculus

<400> SEQUENCE: 647

Ser Ser Asp Val Gly Ala Tyr Asn Tyr
1 5

<210> SEQ ID NO 648
<211> LENGTH: 9
<212> TYPE: PRT
<213> ORGANISM: Mus musculus

<400> SEQUENCE: 648

Ser Ser Asp Val Gly Gly Tyr Asn Phe
1 5

<210> SEQ ID NO 649
<211> LENGTH: 9
<212> TYPE: PRT
<213> ORGANISM: Mus musculus

<400> SEQUENCE: 649

Ser Ser Asp Val Gly Gly Tyr Asn Tyr
1 5

<210> SEQ ID NO 650
<211> LENGTH: 8
<212> TYPE: PRT
<213> ORGANISM: Mus musculus

<400> SEQUENCE: 650

Ser Ser Asn Ile Gly Asn Asn Phe 1 5

<210> SEQ ID NO 651
<211> LENGTH: 8
<212> TYPE: PRT
<213> ORGANISM: Mus musculus

<400> SEQUENCE: 651

Ser Ser Asn Ile Gly Asn Asn Tyr
1 5

<210> SEQ ID NO 652
<211> LENGTH: 8
<212> TYPE: PRT
<213> ORGANISM: Mus musculus

<400> SEQUENCE: 652

Ser Ser Asn Ile Gly Arg Asn Tyr
1 5

<210> SEQ ID NO 653
<211> LENGTH: 8
<212> TYPE: PRT
<213> ORGANISM: Mus musculus

<400> SEQUENCE: 653

Ser Ser Asn Ile Gly Ser Asn Phe
1 5

<210> SEQ ID NO 654
<211> LENGTH: 8
<212> TYPE: PRT
<213> ORGANISM: Mus musculus

<400> SEQUENCE: 654

Ser Ser Asn Ile Gly Ser Asn Thr
1 5

<210> SEQ ID NO 655
<211> LENGTH: 8
<212> TYPE: PRT
<213> ORGANISM: Mus musculus

<400> SEQUENCE: 655

Ser Ser Asn Ile Gly Ser Asn Tyr
1 5

<210> SEQ ID NO 656
<211> LENGTH: 8
<212> TYPE: PRT
<213> ORGANISM: Mus musculus

<400> SEQUENCE: 656

Ser Ser Asn Val Gly Ser Asn Tyr
1 5

<210> SEQ ID NO 657
<211> LENGTH: 8
<212> TYPE: PRT
<213> ORGANISM: Mus musculus

<400> SEQUENCE: 657

Ser Ser Asn Val Gly Ser Arg Thr
1 5

<210> SEQ ID NO 658
<211> LENGTH: 10
<212> TYPE: PRT
<213> ORGANISM: Mus musculus

<400> SEQUENCE: 658

Ser Ser Tyr Thr Lys Asn Asn Ser Val Val
1               5                   10

<210> SEQ ID NO 659
<211> LENGTH: 10
<212> TYPE: PRT
<213> ORGANISM: Mus musculus

<400> SEQUENCE: 659

Ser Ser Tyr Thr Ser Ser Ser Thr Leu Val
1               5                   10

<210> SEQ ID NO 660
<211> LENGTH: 11
<212> TYPE: PRT
<213> ORGANISM: Mus musculus

<400> SEQUENCE: 660

Ser Ser Tyr Thr Ser Ser Ser Thr Leu Val Val
1               5                   10

<210> SEQ ID NO 661
<211> LENGTH: 11
<212> TYPE: PRT
<213> ORGANISM: Mus musculus

<400> SEQUENCE: 661

Ser Ser Tyr Thr Ser Ser Ser Thr Leu Trp Val
1               5                   10

<210> SEQ ID NO 662
<211> LENGTH: 10
<212> TYPE: PRT
<213> ORGANISM: Mus musculus

<400> SEQUENCE: 662

Ser Ser Tyr Thr Ser Ser Ser Thr Pro Val
1               5                   10

<210> SEQ ID NO 663
<211> LENGTH: 10
<212> TYPE: PRT
<213> ORGANISM: Mus musculus

<400> SEQUENCE: 663

Ser Ser Tyr Thr Ser Ser Ser Thr Trp Val
1               5                   10

<210> SEQ ID NO 664
<211> LENGTH: 10
<212> TYPE: PRT
<213> ORGANISM: Mus musculus

<400> SEQUENCE: 664

Ser Ser Tyr Thr Ser Ser Ser Thr Tyr Val
1               5                   10

<210> SEQ ID NO 665

<211> LENGTH: 10
<212> TYPE: PRT
<213> ORGANISM: Mus musculus

<400> SEQUENCE: 665

Ser Ser Tyr Thr Thr Thr Asp Thr Phe Val
1               5                   10

<210> SEQ ID NO 666
<211> LENGTH: 38
<212> TYPE: PRT
<213> ORGANISM: Mus musculus

<400> SEQUENCE: 666

Ser Tyr Asn Gln Lys Phe Lys Gly Lys Ala Thr Met Thr Val Asp Lys
1               5                   10                  15

Ser Ser Ser Thr Ala Tyr Met Glu Leu Ala Arg Leu Thr Ser Glu Asp
            20                  25                  30

Ser Ala Ile Tyr Tyr Cys
        35

<210> SEQ ID NO 667
<211> LENGTH: 3
<212> TYPE: PRT
<213> ORGANISM: Mus musculus

<400> SEQUENCE: 667

Thr Ala Ser
1

<210> SEQ ID NO 668
<211> LENGTH: 36
<212> TYPE: PRT
<213> ORGANISM: Mus musculus

<400> SEQUENCE: 668

Thr Leu Ala Asp Gly Val Pro Ser Arg Phe Ser Gly Ser Gly Ser Arg
1               5                   10                  15

Ser Gln Tyr Ser Leu Met Ile Asn Ser Leu Gln Pro Glu Asp Phe Gly
            20                  25                  30

Thr Tyr Tyr Cys
        35

<210> SEQ ID NO 669
<211> LENGTH: 36
<212> TYPE: PRT
<213> ORGANISM: Mus musculus

<400> SEQUENCE: 669

Thr Leu Ala Glu Gly Val Pro Ser Arg Phe Ser Gly Ser Gly Phe Gly
1               5                   10                  15

Thr Gln Phe Ser Leu Lys Ile Asn Ser Leu Gln Pro Glu Asp Phe Gly
            20                  25                  30

Thr Tyr Tyr Cys
        35

<210> SEQ ID NO 670
<211> LENGTH: 36
<212> TYPE: PRT
<213> ORGANISM: Mus musculus

<400> SEQUENCE: 670

Thr Leu Ala Glu Gly Val Pro Ser Arg Phe Ser Gly Ser Gly Ser Gly
1 5 10 15

Thr Gln Phe Ser Leu Lys Ile Asn Ser Leu Gln Pro Glu Asp Phe Gly
20 25 30

Ser Tyr Tyr Cys
35

<210> SEQ ID NO 671
<211> LENGTH: 36
<212> TYPE: PRT
<213> ORGANISM: Mus musculus

<400> SEQUENCE: 671

Thr Leu Ala Glu Gly Val Pro Ser Arg Phe Ser Gly Ser Gly Ser Gly
1 5 10 15

Thr Gln Phe Ser Leu Lys Ile Asn Ser Leu Gln Pro Glu Asp Phe Gly
20 25 30

Thr Tyr Tyr Cys
35

<210> SEQ ID NO 672
<211> LENGTH: 36
<212> TYPE: PRT
<213> ORGANISM: Mus musculus

<400> SEQUENCE: 672

Thr Leu Ala Glu Gly Val Pro Ser Arg Phe Ser Gly Ser Gly Ser Gly
1 5 10 15

Thr Gln Phe Ser Leu Lys Ile Asn Ser Leu Gln Ser Glu Asp Phe Gly
20 25 30

Ser Tyr Tyr Cys
35

<210> SEQ ID NO 673
<211> LENGTH: 36
<212> TYPE: PRT
<213> ORGANISM: Mus musculus

<400> SEQUENCE: 673

Thr Leu Ala Glu Gly Val Pro Ser Arg Phe Ser Gly Ser Gly Ser Gly
1 5 10 15

Thr Gln Phe Ser Leu Arg Ile Asn Ser Leu Gln Pro Glu Asp Phe Gly
20 25 30

Thr Tyr Tyr Cys
35

<210> SEQ ID NO 674
<211> LENGTH: 36
<212> TYPE: PRT
<213> ORGANISM: Mus musculus

<400> SEQUENCE: 674

Thr Leu Ala Glu Gly Val Pro Ser Arg Phe Ser Gly Ser Gly Ser Gly
1 5 10 15

Thr Arg Phe Ser Leu Lys Ile Asn Ser Leu Gln Pro Glu Asp Phe Gly
20 25 30

Ser Tyr Tyr Cys
35

<210> SEQ ID NO 675

<211> LENGTH: 36
<212> TYPE: PRT
<213> ORGANISM: Mus musculus
<220> FEATURE:
<221> NAME/KEY: SITE
<222> LOCATION: (4)..(4)
<223> OTHER INFORMATION: Xaa can be any naturally occurring amino acid
<220> FEATURE:
<221> NAME/KEY: SITE
<222> LOCATION: (11)..(11)
<223> OTHER INFORMATION: Xaa can be any naturally occurring amino acid

<400> SEQUENCE: 675

```
Thr Leu Ala Xaa Gly Val Pro Ser Arg Phe Xaa Gly Ser Gly Ser Gly
1               5                   10                  15

Thr Gln Phe Ser Leu Lys Ile Asn Ser Leu Gln Pro Glu Asp Phe Gly
            20                  25                  30

Ser Tyr Tyr Cys
        35
```

<210> SEQ ID NO 676
<211> LENGTH: 36
<212> TYPE: PRT
<213> ORGANISM: Mus musculus

<400> SEQUENCE: 676

```
Thr Leu Pro Glu Gly Val Pro Ser Arg Phe Ser Gly Ser Gly Ser Gly
1               5                   10                  15

Thr Gln Phe Ser Leu Lys Ile Ser Ser Leu Gln Pro Glu Asp Phe Gly
            20                  25                  30

Thr Tyr Tyr Cys
        35
```

<210> SEQ ID NO 677
<211> LENGTH: 36
<212> TYPE: PRT
<213> ORGANISM: Mus musculus

<400> SEQUENCE: 677

```
Thr Leu Thr Glu Gly Val Pro Ser Arg Phe Ser Gly Ser Gly Ser Gly
1               5                   10                  15

Thr Gln Phe Ser Leu Lys Ile Asn Ser Leu Gln Pro Glu Asp Phe Gly
            20                  25                  30

Thr Tyr Tyr Cys
        35
```

<210> SEQ ID NO 678
<211> LENGTH: 36
<212> TYPE: PRT
<213> ORGANISM: Mus musculus

<400> SEQUENCE: 678

```
Thr Leu Val Glu Gly Val Pro Ser Arg Phe Ser Gly Ser Gly Ser Gly
1               5                   10                  15

Thr Gln Phe Ser Leu Lys Ile Asn Ser Leu Gln Pro Glu Asp Phe Gly
            20                  25                  30

Ser Tyr Tyr Cys
        35
```

<210> SEQ ID NO 679
<211> LENGTH: 36
<212> TYPE: PRT
<213> ORGANISM: Mus musculus

<400> SEQUENCE: 679

Thr Leu Val Glu Gly Val Pro Ser Arg Phe Ser Gly Ser Gly Ser Gly
1 5 10 15

Thr Gln Phe Ser Leu Lys Ile Asn Ser Leu Gln Pro Glu Asp Phe Gly
20 25 30

Thr Tyr Tyr Cys
35

<210> SEQ ID NO 680
<211> LENGTH: 36
<212> TYPE: PRT
<213> ORGANISM: Mus musculus

<400> SEQUENCE: 680

Thr Arg His Thr Gly Val Pro Ser Arg Phe Gly Gly Gly Gly Ser Gly
1 5 10 15

Thr Asp Phe Thr Leu Thr Ile Ser Arg Leu Gln Pro Glu Asn Phe Ala
20 25 30

Thr Tyr Tyr Cys
35

<210> SEQ ID NO 681
<211> LENGTH: 36
<212> TYPE: PRT
<213> ORGANISM: Mus musculus

<400> SEQUENCE: 681

Thr Arg His Thr Gly Val Pro Ser Arg Phe Ser Gly Ser Gly Ser Gly
1 5 10 15

Thr Asp Phe Thr Leu Thr Ile Ser Ser Leu Gln Pro Glu Asp Phe Ala
20 25 30

Thr Tyr Tyr Cys
35

<210> SEQ ID NO 682
<211> LENGTH: 9
<212> TYPE: PRT
<213> ORGANISM: Mus musculus

<400> SEQUENCE: 682

Thr Thr Ala Pro Ser Leu Met Asp Val
1 5

<210> SEQ ID NO 683
<211> LENGTH: 17
<212> TYPE: PRT
<213> ORGANISM: Mus musculus

<400> SEQUENCE: 683

Thr Thr Glu Gly Val Glu Leu Leu Ser Phe Gly Gly Ala Pro Phe Asp
1 5 10 15

Tyr

<210> SEQ ID NO 684
<211> LENGTH: 14
<212> TYPE: PRT
<213> ORGANISM: Mus musculus

<400> SEQUENCE: 684

Thr Val Phe Trp Tyr Gly Asn Asn Tyr Ala Gly Phe Ala Tyr 1 5 10

<210> SEQ ID NO 685
<211> LENGTH: 17
<212> TYPE: PRT
<213> ORGANISM: Mus musculus

<400> SEQUENCE: 685

Val Ala Trp Tyr Gln Gln Glu Pro Gly Gln Ser Pro Lys Ala Leu Ile
1 5 10 15

Tyr

<210> SEQ ID NO 686
<211> LENGTH: 17
<212> TYPE: PRT
<213> ORGANISM: Mus musculus

<400> SEQUENCE: 686

Val Ala Trp Tyr Gln Gln Lys Ile Gly Gln Ser Pro Lys Ala Leu Ile
1 5 10 15

Tyr

<210> SEQ ID NO 687
<211> LENGTH: 17
<212> TYPE: PRT
<213> ORGANISM: Mus musculus

<400> SEQUENCE: 687

Val Ala Trp Tyr Gln Gln Lys Pro Gly Gln Ala Pro Arg Leu Leu Ile
1 5 10 15

Tyr

<210> SEQ ID NO 688
<211> LENGTH: 17
<212> TYPE: PRT
<213> ORGANISM: Mus musculus

<400> SEQUENCE: 688

Val Ala Trp Tyr Gln Gln Lys Pro Gly Gln Cys Pro Lys Ala Leu Ile
1 5 10 15

Tyr

<210> SEQ ID NO 689
<211> LENGTH: 17
<212> TYPE: PRT
<213> ORGANISM: Mus musculus

<400> SEQUENCE: 689

Val Ala Trp Tyr Gln Gln Lys Pro Gly Gln Ser Pro Lys Ala Leu Ile
1 5 10 15

Tyr

<210> SEQ ID NO 690
<211> LENGTH: 17
<212> TYPE: PRT
<213> ORGANISM: Mus musculus

<400> SEQUENCE: 690

Val Ala Trp Tyr Gln Gln Lys Gln Gly Gln Ala Pro Arg Leu Leu Ile
1 5 10 15

Tyr

<210> SEQ ID NO 691
<211> LENGTH: 17
<212> TYPE: PRT
<213> ORGANISM: Mus musculus

<400> SEQUENCE: 691

Val Ala Trp Tyr Gln Gln Lys Gln Gly Gln Ser Pro Lys Ala Leu Ile
1 5 10 15

Tyr

<210> SEQ ID NO 692
<211> LENGTH: 17
<212> TYPE: PRT
<213> ORGANISM: Mus musculus

<400> SEQUENCE: 692

Val Ala Trp Tyr Gln Gln Arg Pro Gly Gln Ser Pro Lys Ala Leu Ile
1 5 10 15

Tyr

<210> SEQ ID NO 693
<211> LENGTH: 8
<212> TYPE: PRT
<213> ORGANISM: Mus musculus

<400> SEQUENCE: 693

Val Asp Pro Glu Asp Gly Glu Thr
1 5

<210> SEQ ID NO 694
<211> LENGTH: 10
<212> TYPE: PRT
<213> ORGANISM: Mus musculus

<400> SEQUENCE: 694

Val Leu Tyr Met Gly Ser Gly Ile Trp Val
1 5 10

<210> SEQ ID NO 695
<211> LENGTH: 17
<212> TYPE: PRT
<213> ORGANISM: Mus musculus

<400> SEQUENCE: 695

Val Gln Trp Val Arg Gln Ser His Ala Lys Ser Leu Glu Trp Ile Gly
1 5 10 15

Val

<210> SEQ ID NO 696
<211> LENGTH: 17
<212> TYPE: PRT
<213> ORGANISM: Mus musculus

<400> SEQUENCE: 696

Val Val Trp Tyr Gln Gln Lys Pro Gly Gln Ser Pro Lys Leu Leu Ile
1 5 10 15

Tyr

<210> SEQ ID NO 697
<211> LENGTH: 11
<212> TYPE: PRT

<213> ORGANISM: Mus musculus

<400> SEQUENCE: 697

Trp Ala Gln Ser Thr Ile Leu Thr Val Ser Ser
1 5 10

<210> SEQ ID NO 698
<211> LENGTH: 3
<212> TYPE: PRT
<213> ORGANISM: Mus musculus

<400> SEQUENCE: 698

Trp Ala Ser
1

<210> SEQ ID NO 699
<211> LENGTH: 11
<212> TYPE: PRT
<213> ORGANISM: Mus musculus

<400> SEQUENCE: 699

Trp Gly Ala Gly Thr Ser Leu Thr Val Ser Ser
1 5 10

<210> SEQ ID NO 700
<211> LENGTH: 11
<212> TYPE: PRT
<213> ORGANISM: Mus musculus

<400> SEQUENCE: 700

Trp Gly Ala Gly Thr Thr Val Thr Val Ser Ser
1 5 10

<210> SEQ ID NO 701
<211> LENGTH: 11
<212> TYPE: PRT
<213> ORGANISM: Mus musculus

<400> SEQUENCE: 701

Trp Gly Gln Gly Thr Ile Leu Thr Val Ser Ser
1 5 10

<210> SEQ ID NO 702
<211> LENGTH: 9
<212> TYPE: PRT
<213> ORGANISM: Mus musculus

<400> SEQUENCE: 702

Trp Gly Gln Gly Thr Leu Val Thr Val
1 5

<210> SEQ ID NO 703
<211> LENGTH: 11
<212> TYPE: PRT
<213> ORGANISM: Mus musculus

<400> SEQUENCE: 703

Trp Gly Gln Gly Thr Leu Val Thr Val Ser Ala
1 5 10

<210> SEQ ID NO 704
<211> LENGTH: 11
<212> TYPE: PRT
<213> ORGANISM: Mus musculus

<400> SEQUENCE: 704

Trp Gly Gln Gly Thr Leu Val Thr Val Ser Ser
1 5 10

<210> SEQ ID NO 705
<211> LENGTH: 11
<212> TYPE: PRT
<213> ORGANISM: Mus musculus

<400> SEQUENCE: 705

Trp Gly Gln Gly Thr Pro Val Thr Val Ser Ser
1 5 10

<210> SEQ ID NO 706
<211> LENGTH: 9
<212> TYPE: PRT
<213> ORGANISM: Mus musculus

<400> SEQUENCE: 706

Trp Gly Gln Gly Thr Ser Leu Thr Val
1 5

<210> SEQ ID NO 707
<211> LENGTH: 11
<212> TYPE: PRT
<213> ORGANISM: Mus musculus

<400> SEQUENCE: 707

Trp Gly Gln Gly Thr Ser Leu Thr Val Ser Ala
1 5 10

<210> SEQ ID NO 708
<211> LENGTH: 11
<212> TYPE: PRT
<213> ORGANISM: Mus musculus

<400> SEQUENCE: 708

Trp Gly Gln Gly Thr Ser Leu Thr Val Ser Ser
1 5 10

<210> SEQ ID NO 709
<211> LENGTH: 11
<212> TYPE: PRT
<213> ORGANISM: Mus musculus

<400> SEQUENCE: 709

Trp Gly Gln Gly Thr Thr Leu Thr Val Ser Ser
1 5 10

<210> SEQ ID NO 710
<211> LENGTH: 11
<212> TYPE: PRT
<213> ORGANISM: Mus musculus
<220> FEATURE:
<221> NAME/KEY: SITE
<222> LOCATION: (9)..(9)
<223> OTHER INFORMATION: Xaa can be any naturally occurring amino acid

<400> SEQUENCE: 710

Trp Gly Gln Gly Thr Thr Leu Thr Xaa Ser Ser
1 5 10

<210> SEQ ID NO 711
<211> LENGTH: 9
<212> TYPE: PRT

<213> ORGANISM: Mus musculus

<400> SEQUENCE: 711

Trp Gly Gln Gly Thr Thr Val Thr Val
1 5

<210> SEQ ID NO 712
<211> LENGTH: 11
<212> TYPE: PRT
<213> ORGANISM: Mus musculus

<400> SEQUENCE: 712

Trp Gly Gln Gly Thr Thr Val Thr Val Ser Ala
1 5 10

<210> SEQ ID NO 713
<211> LENGTH: 11
<212> TYPE: PRT
<213> ORGANISM: Mus musculus

<400> SEQUENCE: 713

Trp Gly Gln Gly Thr Thr Val Thr Val Ser Ser
1 5 10

<210> SEQ ID NO 714
<211> LENGTH: 11
<212> TYPE: PRT
<213> ORGANISM: Mus musculus

<400> SEQUENCE: 714

Trp Gly Gln Gly Thr Thr Val Thr Val Tyr Ser
1 5 10

<210> SEQ ID NO 715
<211> LENGTH: 11
<212> TYPE: PRT
<213> ORGANISM: Mus musculus
<220> FEATURE:
<221> NAME/KEY: SITE
<222> LOCATION: (6)..(6)
<223> OTHER INFORMATION: Xaa can be any naturally occurring amino acid

<400> SEQUENCE: 715

Trp Gly Gln Gly Thr Xaa Leu Thr Val Ser Ser
1 5 10

<210> SEQ ID NO 716
<211> LENGTH: 11
<212> TYPE: PRT
<213> ORGANISM: Mus musculus

<400> SEQUENCE: 716

Trp Gly Arg Gly Thr Thr Val Thr Val Ser Ser
1 5 10

<210> SEQ ID NO 717
<211> LENGTH: 3
<212> TYPE: PRT
<213> ORGANISM: Mus musculus

<400> SEQUENCE: 717

Tyr Ala Ser
1

<210> SEQ ID NO 718

<211> LENGTH: 36
<212> TYPE: PRT
<213> ORGANISM: Mus musculus

<400> SEQUENCE: 718

```
Tyr Arg Tyr Ser Gly Val Pro Asp Arg Phe Thr Gly Ser Gly Ser Gly
1               5                   10                  15

Thr Asp Phe Ala Leu Thr Ile Ser Asn Val Gln Ser Glu Asp Leu Ala
            20                  25                  30

Glu Tyr Phe Cys
        35
```

<210> SEQ ID NO 719
<211> LENGTH: 36
<212> TYPE: PRT
<213> ORGANISM: Mus musculus

<400> SEQUENCE: 719

```
Tyr Arg Tyr Ser Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Glu Tyr Phe Cys
        35
```

<210> SEQ ID NO 720
<211> LENGTH: 36
<212> TYPE: PRT
<213> ORGANISM: Mus musculus

<400> SEQUENCE: 720

```
Tyr Arg Tyr Ser Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Lys Tyr Phe Cys
        35
```

<210> SEQ ID NO 721
<211> LENGTH: 36
<212> TYPE: PRT
<213> ORGANISM: Mus musculus

<400> SEQUENCE: 721

```
Tyr Arg Tyr Ser Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Val
            20                  25                  30

Glu Tyr Phe Cys
        35
```

<210> SEQ ID NO 722
<211> LENGTH: 36
<212> TYPE: PRT
<213> ORGANISM: Mus musculus

<400> SEQUENCE: 722

```
Tyr Arg Tyr Ser Gly Val Pro Asp Arg Phe Thr Gly Ser Gly Ser Gly
1               5                   10                  15

Thr Asp Phe Thr Leu Thr Ile Ser Asn Val Gln Ser Gly Asp Leu Ala
            20                  25                  30
```

```
Glu Tyr Phe Cys
        35


<210> SEQ ID NO 723
<211> LENGTH: 36
<212> TYPE: PRT
<213> ORGANISM: Mus musculus

<400> SEQUENCE: 723

Tyr Arg Tyr Ser Gly Val Pro Asp Arg Phe Thr Gly Ser Gly Ser Gly
1               5                   10                  15

Thr Asp Phe Thr Leu Thr Ile Ser Ser Val Lys Ser Glu Asp Leu Ala
            20                  25                  30

Glu Tyr Phe Cys
        35


<210> SEQ ID NO 724
<211> LENGTH: 36
<212> TYPE: PRT
<213> ORGANISM: Mus musculus

<400> SEQUENCE: 724

Tyr Arg Tyr Ser Gly Val Pro Asp Arg Ile Thr Gly Arg Gly Ser Gly
1               5                   10                  15

Thr Asp Phe Thr Leu Thr Ile Ser Asn Val Gln Ser Glu Asp Leu Ala
            20                  25                  30

Asp Tyr Phe Cys
        35


<210> SEQ ID NO 725
<211> LENGTH: 36
<212> TYPE: PRT
<213> ORGANISM: Mus musculus

<400> SEQUENCE: 725

Tyr Arg Tyr Thr Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Glu Tyr Phe Cys
        35


<210> SEQ ID NO 726
<211> LENGTH: 8
<212> TYPE: PRT
<213> ORGANISM: Mus musculus

<400> SEQUENCE: 726

Tyr Ser Asn Ile Gly Ser Asn Thr
1               5


<210> SEQ ID NO 727
<211> LENGTH: 3
<212> TYPE: PRT
<213> ORGANISM: Mus musculus

<400> SEQUENCE: 727

Tyr Thr Ser
1


<210> SEQ ID NO 728
```

<211> LENGTH: 238
<212> TYPE: PRT
<213> ORGANISM: Mus musculus

<400> SEQUENCE: 728

```
Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Gln Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Ser Tyr Leu Asn Trp Tyr Gln Gln Lys Pro
145                 150                 155                 160

Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Thr Lys Val
    210                 215                 220

Glu Ile Lys Cys Gln Gln Ser Tyr Ser Thr Pro Pro Thr Phe
225                 230                 235
```

<210> SEQ ID NO 729
<211> LENGTH: 238
<212> TYPE: PRT
<213> ORGANISM: Mus musculus

<400> SEQUENCE: 729

```
Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110
```

```
Tyr Tyr Tyr Gly Met Asp Val Trp Glu Ile Val Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Ser Tyr Leu Asn Trp Tyr Gln Gln Lys Pro
145                 150                 155                 160

Gly Lys Ala Pro Lys Leu Leu Thr Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Pro Gly Thr Lys Val
    210                 215                 220

Asp Ile Lys Cys Gln Gln Ser Tyr Ser Thr Pro Pro Thr Phe
225                 230                 235


<210> SEQ ID NO 730
<211> LENGTH: 242
<212> TYPE: PRT
<213> ORGANISM: Mus musculus

<400> SEQUENCE: 730

Pro Ser Gln Thr Leu Ser Leu Thr Cys Thr Val Ser Gly Gly Ser Ile
1               5                   10                  15

Ser Ser Gly Gly Tyr Tyr Trp Ser Trp Ile Arg Gln His Pro Gly Lys
            20                  25                  30

Gly Leu Glu Trp Ile Gly Tyr Ile Tyr Tyr Ser Gly Ser Thr Tyr Tyr
        35                  40                  45

Asn Pro Ser Leu Lys Ser Arg Val Thr Ile Ser Val Asp Thr Ser Lys
    50                  55                  60

Asn Gln Phe Ser Leu Lys Leu Ser Ser Val Thr Ala Ala Asp Thr Ala
65                  70                  75                  80

Val Tyr Tyr Cys Ala Arg Gly Asn Leu Trp Ser Gly Tyr Tyr Phe Trp
                85                  90                  95

Gly Gln Gly Thr Leu Val Thr Val Ser Ser Cys Ala Arg Gly Asn Leu
            100                 105                 110

Trp Ser Gly Tyr Tyr Phe Trp Gln Ser Val Leu Thr Gln Pro Pro Ser
        115                 120                 125

Val Ser Ala Ala Pro Gly Gln Lys Val Thr Ile Ser Cys Ser Gly Ser
    130                 135                 140

Ser Ser Asn Ile Gly Asn Asn Phe Val Ser Trp Tyr Gln Gln Val Pro
145                 150                 155                 160

Gly Thr Ala Pro Lys Leu Leu Thr Tyr Asp Ser Thr Lys Arg Pro Ala
                165                 170                 175

Gly Ile Pro Asp Arg Phe Ser Gly Ser Lys Ser Gly Thr Ser Ala Thr
            180                 185                 190

Leu Glu Ile Ala Gly Leu Gln Thr Gly Asp Glu Ala Asp Tyr Tyr Cys
        195                 200                 205

Gly Ser Trp Asp Thr Asn Leu Ser Gly Tyr Val Phe Gly Thr Gly Thr
    210                 215                 220

Lys Val Thr Val Leu Cys Gly Ser Trp Asp Thr Asn Leu Ser Gly Tyr
225                 230                 235                 240

Val Phe
```

<210> SEQ ID NO 731
<211> LENGTH: 238
<212> TYPE: PRT
<213> ORGANISM: Mus musculus

<400> SEQUENCE: 731

```
Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Gln Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Ser Tyr Leu Asn Trp Tyr Gln Gln Lys Pro
145                 150                 155                 160

Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Thr Lys Val
    210                 215                 220

Glu Ile Lys Cys Gln Gln Ser Tyr Ser Thr Pro Pro Thr Phe
225                 230                 235
```

<210> SEQ ID NO 732
<211> LENGTH: 238
<212> TYPE: PRT
<213> ORGANISM: Mus musculus

<400> SEQUENCE: 732

```
Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95
```

```
Gly Gln Gly Thr Thr Val Thr Val Ser Ser Cys Ala Arg Glu Met Tyr
            100                 105                 110

Tyr Tyr Tyr Gly Met Asp Val Trp Asp Ile Gln Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Ser Tyr Leu Asn Trp Tyr Gln Gln Lys Pro
145                 150                 155                 160

Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Thr Lys Val
    210                 215                 220

Glu Thr Asn Cys Gln Gln Ser Tyr Ser Thr Pro Pro Thr Phe
225                 230                 235


<210> SEQ ID NO 733
<211> LENGTH: 238
<212> TYPE: PRT
<213> ORGANISM: Mus musculus

<400> SEQUENCE: 733

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Gln Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Ser Tyr Leu Asn Trp Tyr Gln Gln Lys Pro
145                 150                 155                 160

Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Thr Lys Val
    210                 215                 220

Glu Thr Lys Cys Gln Gln Ser Tyr Ser Thr Pro Pro Thr Phe
```

225 230 235

<210> SEQ ID NO 734
<211> LENGTH: 238
<212> TYPE: PRT
<213> ORGANISM: Mus musculus

<400> SEQUENCE: 734

Pro Gly Ser Ser Val Lys Val Ser Cys Lys Ala Ser Gly Gly Thr Phe
1 5 10 15

Ser Ser Tyr Ala Ile Ser Trp Val Arg Gln Ala Pro Gly Gln Gly Leu
20 25 30

Glu Trp Met Gly Gly Ile Ile Pro Ile Phe Gly Thr Ala Asn Tyr Ala
35 40 45

Gln Lys Phe Gln Gly Arg Val Thr Ile Thr Ala Asp Glu Ser Thr Ser
50 55 60

Thr Ala Tyr Met Glu Leu Ser Ser Leu Arg Ser Glu Asp Thr Ala Val
65 70 75 80

Tyr Tyr Cys Ala Arg Glu Met Tyr Tyr Tyr Tyr Gly Met Asp Val Trp
85 90 95

Gly Gln Gly Thr Thr Val Thr Val Ser Ser Cys Ala Arg Glu Met Tyr
100 105 110

Tyr Tyr Tyr Gly Met Asp Val Trp Glu Ile Val Met Thr Gln Ser Pro
115 120 125

Ser Ser Leu Ser Ala Ser Val Gly Asp Arg Val Thr Ile Thr Cys Arg
130 135 140

Ala Ser Gln Ser Ile Ser Ser Tyr Leu Asn Trp Tyr Gln Gln Lys Pro
145 150 155 160

Gly Lys Ala Pro Lys Leu Leu Ile Tyr Ala Ala Ser Ser Leu Gln Ser
165 170 175

Gly Val Pro Ser Arg Phe Ser Gly Ser Gly Ser Gly Thr Asp Phe Thr
180 185 190

Leu Thr Ile Ser Ser Leu Gln Pro Glu Asp Phe Ala Thr Tyr Tyr Cys
195 200 205

Gln Gln Ser Tyr Ser Thr Pro Pro Thr Phe Gly Gln Gly Thr Lys Leu
210 215 220

Glu Ile Lys Cys Gln Gln Ser Tyr Ser Thr Pro Pro Thr Phe
225 230 235

<210> SEQ ID NO 735
<211> LENGTH: 238
<212> TYPE: PRT
<213> ORGANISM: Mus musculus

<400> SEQUENCE: 735

Pro Gly Ser Ser Val Lys Val Ser Cys Lys Ala Ser Gly Gly Thr Phe
1 5 10 15

Ser Ser Tyr Ala Ile Ser Trp Val Arg Gln Ala Pro Gly Gln Gly Leu
20 25 30

Glu Trp Met Gly Gly Ile Ile Pro Ile Phe Gly Thr Ala Asn Tyr Ala
35 40 45

Gln Lys Phe Gln Gly Arg Val Thr Ile Thr Ala Asp Glu Ser Thr Ser
50 55 60

Thr Ala Tyr Met Glu Leu Ser Ser Leu Arg Ser Glu Asp Thr Ala Val
65 70 75 80

Tyr Tyr Cys Ala Arg Glu Met Tyr Tyr Tyr Tyr Gly Met Asp Val Trp

```
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Gln Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Asn Tyr Leu Asn Trp Tyr Gln Gln Lys Pro
145                 150                 155                 160

Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Thr Lys Leu
    210                 215                 220

Glu Ile Lys Cys Gln Gln Ser Tyr Ser Thr Pro Pro Thr Phe
225                 230                 235


<210> SEQ ID NO 736
<211> LENGTH: 241
<212> TYPE: PRT
<213> ORGANISM: Mus musculus

<400> SEQUENCE: 736

Pro Gly Arg Ser Leu Arg Leu Ser Cys Ala Ala Ser Gly Phe Thr Phe
1               5                   10                  15

Ser Ser Tyr Gly Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Lys Glu Leu Leu Glu Gly Ala Phe Asp Ile Trp Gly
                85                  90                  95

Gln Gly Thr Met Val Thr Val Ser Ser Cys Ala Lys Glu Leu Leu Glu
            100                 105                 110

Gly Ala Phe Asp Ile Trp Ser Tyr Val Leu Thr Gln Pro Pro Ser Leu
        115                 120                 125

Ser Val Ala Pro Gly Gln Thr Ala Arg Ile Thr Cys Gly Gly Asp Asn
    130                 135                 140

Ile Glu Thr Lys Ser Val His Trp Tyr Gln Gln Arg Pro Gly Gln Ala
145                 150                 155                 160

Pro Val Leu Val Val Tyr Asp Asp Asp Asp Arg Pro Ser Gly Ile Pro
                165                 170                 175

Glu Arg Phe Ser Gly Ser Asn Ser Gly Asn Thr Ala Thr Leu Thr Ile
            180                 185                 190

Ser Arg Val Glu Ala Gly Asp Glu Ala Asp Tyr Tyr Cys Gln Val Trp
        195                 200                 205

Asp Ser Ser Ser Gly His Arg Glu Val Phe Gly Gly Arg Thr Lys Pro
    210                 215                 220
```

```
Ala Leu Leu Cys Gln Val Trp Asp Ser Ser Ser Gly His Arg Glu Val
225                 230                 235                 240

Phe


<210> SEQ ID NO 737
<211> LENGTH: 241
<212> TYPE: PRT
<213> ORGANISM: Mus musculus

<400> SEQUENCE: 737

Pro Gly Ala Ser Val Lys Val Ser Cys Lys Ala Ser Gly Tyr Thr Phe
1               5                   10                  15

Thr Ser Tyr Tyr Met His Trp Val Arg Gln Ala Pro Gly Gln Gly Leu
            20                  25                  30

Glu Trp Met Gly Ile Ile Asn Pro Ser Gly Gly Ser Thr Ser Tyr Ala
        35                  40                  45

Gln Lys Phe Gln Gly Arg Val Thr Met Thr Arg Asp Thr Ser Thr Ser
    50                  55                  60

Thr Val Tyr Met Glu Leu Ser Ser Leu Arg Ser Glu Asp Thr Ala Val
65                  70                  75                  80

Tyr Tyr Cys Ala Arg Asp Arg Val Thr Met Val Arg Gly Ala Leu Ala
                85                  90                  95

Tyr Trp Gly Gln Gly Thr Leu Val Thr Val Ser Ser Cys Ala Arg Asp
            100                 105                 110

Arg Val Thr Met Val Arg Gly Ala Leu Ala Tyr Trp Ser Tyr Glu Leu
        115                 120                 125

Thr Gln Pro Pro Ser Val Ser Val Ser Pro Gly His Thr Ala Thr Ile
    130                 135                 140

Thr Cys Ser Gly Glu Lys Leu Gly Asp Lys Tyr Val Tyr Trp Tyr Gln
145                 150                 155                 160

Gln Lys Pro Gly Gln Ser Pro Leu Leu Val Met Tyr Lys Asp Asn Lys
                165                 170                 175

Arg Pro Ser Ala Thr Pro Glu Arg Phe Ser Gly Ser Asn Ser Gly Asp
            180                 185                 190

Thr Ala Thr Leu Thr Ile Arg Gly Thr Gln Ala Met Asp Glu Ala Asp
        195                 200                 205

Tyr Tyr Cys Gln Ala Trp Asp Ser Ser Thr Tyr Val Phe Gly Ser Gly
    210                 215                 220

Thr Lys Val Thr Val Leu Cys Gln Ala Trp Asp Ser Ser Thr Tyr Val
225                 230                 235                 240

Phe


<210> SEQ ID NO 738
<211> LENGTH: 241
<212> TYPE: PRT
<213> ORGANISM: Mus musculus

<400> SEQUENCE: 738

Pro Gly Arg Ser Leu Arg Leu Ser Cys Ala Ala Ser Gly Phe Thr Phe
1               5                   10                  15

Ser Ser Tyr Gly Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60
```

-continued

Thr Leu Tyr Leu Gln Met Asn Ser Leu Arg Ala Glu Asp Thr Ala Val
65 70 75 80

Tyr Tyr Cys Ala Lys Glu Leu Leu Glu Gly Ala Phe Asp Ile Trp Gly
85 90 95

Gln Gly Thr Met Val Thr Val Ser Ser Cys Ala Lys Glu Leu Leu Glu
100 105 110

Gly Ala Phe Asp Ile Trp Ser Tyr Val Leu Thr Gln Pro Pro Ser Leu
115 120 125

Ser Val Ala Pro Gly Gln Thr Ala Arg Ile Thr Cys Gly Gly Asp Asn
130 135 140

Ile Glu Thr Lys Ser Val His Trp Tyr Gln Gln Arg Pro Gly Gln Ala
145 150 155 160

Pro Val Leu Val Val Tyr Asp Asp Asp Asp Arg Pro Ser Gly Ile Pro
165 170 175

Glu Arg Phe Ser Gly Ser Asn Ser Gly Asn Thr Ala Thr Leu Thr Ile
180 185 190

Ser Arg Val Glu Ala Gly Asp Glu Ala Asp Tyr Tyr Cys Gln Val Trp
195 200 205

Asp Ser Ser Ser Gly His Arg Glu Val Phe Gly Gly Gly Thr Lys Leu
210 215 220

Thr Val Leu Cys Gln Val Trp Asp Ser Ser Ser Gly His Arg Glu Val
225 230 235 240

Phe

<210> SEQ ID NO 739
<211> LENGTH: 238
<212> TYPE: PRT
<213> ORGANISM: Mus musculus

<400> SEQUENCE: 739

Pro Gly Ser Ser Val Lys Val Ser Cys Lys Ala Ser Gly Gly Thr Phe
1 5 10 15

Ser Ser Tyr Ala Ile Ser Trp Val Arg Gln Ala Pro Gly Gln Gly Leu
20 25 30

Glu Trp Met Gly Gly Ile Ile Pro Ile Phe Gly Thr Ala Asn Tyr Ala
35 40 45

Gln Lys Phe Gln Gly Arg Val Thr Ile Thr Ala Asp Glu Ser Thr Ser
50 55 60

Thr Ala Tyr Met Glu Leu Ser Ser Leu Arg Ser Glu Asp Thr Ala Val
65 70 75 80

Tyr Tyr Cys Ala Arg Glu Met Tyr Tyr Tyr Tyr Gly Met Asp Val Trp
85 90 95

Gly Gln Gly Thr Thr Val Thr Val Ser Ser Cys Ala Arg Glu Met Tyr
100 105 110

Tyr Tyr Tyr Gly Met Asp Val Trp Asp Ile Gln Met Thr Gln Ser Pro
115 120 125

Ser Ser Leu Ser Ala Ser Val Gly Asp Arg Val Thr Ile Thr Cys Arg
130 135 140

Ala Ser Gln Ser Ile Ser Ser Tyr Leu Asn Trp Tyr Gln Gln Lys Pro
145 150 155 160

Gly Lys Ala Pro Lys Leu Leu Ile Tyr Ala Ala Ser Ser Leu Gln Ser
165 170 175

Gly Val Pro Ser Arg Phe Ser Gly Ser Gly Ser Gly Thr Asp Phe Thr
180 185 190

```
Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Pro Lys Val
    210                 215                 220

Glu Ile Lys Cys Gln Gln Ser Tyr Ser Thr Pro Pro Thr Phe
225                 230                 235


<210> SEQ ID NO 740
<211> LENGTH: 232
<212> TYPE: PRT
<213> ORGANISM: Mus musculus

<400> SEQUENCE: 740

Pro Gly Ala Ser Ala Lys Val Ser Cys Lys Ala Ser Gly Tyr Thr Phe
1               5                   10                  15

Thr Ser Tyr Gly Ile Ser Trp Val Arg Gln Ala Pro Gly Gln Gly Leu
            20                  25                  30

Glu Trp Met Gly Trp Ile Ser Ala Tyr Asn Gly Asn Thr Asn Tyr Ala
        35                  40                  45

Gln Lys Leu Gln Gly Arg Val Thr Met Thr Thr Asp Thr Ser Thr Ser
    50                  55                  60

Thr Ala Tyr Met Glu Leu Arg Ser Leu Arg Ser Asp Asp Thr Ala Val
65                  70                  75                  80

Tyr Tyr Cys Ala Arg Glu Arg Ser Tyr Tyr Gly Met Asp Val Trp Gly
                85                  90                  95

Gln Gly Thr Thr Val Thr Val Ser Ser Cys Ala Arg Glu Arg Ser Tyr
            100                 105                 110

Tyr Gly Met Asp Val Trp Thr Gln Ser Pro Ala Thr Leu Ser Val Ser
        115                 120                 125

Pro Gly Glu Ser Ala Thr Leu Ser Cys Arg Ala Ser Gln Ser Val Ser
    130                 135                 140

Asn Tyr Leu Ala Trp Tyr Gln Gln Lys Pro Gly Gln Ala Pro Arg Leu
145                 150                 155                 160

Leu Ile Tyr Gly Ala Ser Thr Arg Ala Thr Gly Ile Pro Ala Arg Phe
                165                 170                 175

Ser Gly Ser Gly Ser Gly Thr Glu Phe Thr Leu Thr Ile Ser Ser Leu
            180                 185                 190

Gln Ser Glu Asp Phe Ala Val Tyr Tyr Cys Gln Gln Tyr Asn His Trp
        195                 200                 205

Pro Pro Leu Phe Gly Gly Gly Thr Lys Val Glu Thr Lys Cys Gln Gln
    210                 215                 220

Tyr Asn His Trp Pro Pro Leu Phe
225                 230


<210> SEQ ID NO 741
<211> LENGTH: 238
<212> TYPE: PRT
<213> ORGANISM: Mus musculus

<400> SEQUENCE: 741

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45
```

```
Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Gln Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Ser Tyr Leu Asn Trp Tyr Gln Gln Lys Pro
145                 150                 155                 160

Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Pro Lys Val
    210                 215                 220

Glu Leu Lys Cys Gln Gln Ser Tyr Ser Thr Pro Pro Thr Phe
225                 230                 235


<210> SEQ ID NO 742
<211> LENGTH: 246
<212> TYPE: PRT
<213> ORGANISM: Mus musculus

<400> SEQUENCE: 742

Pro Gly Ser Ser Val Lys Val Ser Cys Lys Val Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Met Pro Ile Phe Asp Thr Ala Glu Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Thr Leu Arg Ser Glu Asp Thr Ala Val
65                  70                  75                  80

Tyr Tyr Cys Ala Ser Trp Ser Glu Arg Ile Gly Tyr Gln Tyr Gly Leu
                85                  90                  95

Asp Val Trp Gly Gln Gly Thr Thr Val Thr Val Ser Ser Cys Ala Ser
            100                 105                 110

Trp Ser Glu Arg Ile Gly Tyr Gln Tyr Gly Leu Asp Val Trp Asp Ile
        115                 120                 125

Arg Met Thr Gln Ser Pro Ser Thr Leu Ser Ala Ser Val Gly Asp Arg
    130                 135                 140

Val Ser Ile Thr Cys Arg Ala Ser Gln Thr Ile Ser Gln Trp Leu Ala
145                 150                 155                 160

Trp Phe His Gln Lys Pro Gly Lys Ala Pro Lys Leu Leu Ile Tyr Lys
                165                 170                 175

Ala Ser Arg Leu Glu Ser Gly Val Ser Ser Arg Phe Ser Gly Ser Gly
```

```
            180                 185                 190

Ser Gly Thr Glu Phe Thr Leu Thr Ile Thr Ser Leu Gln Pro Asp Asp
        195                 200                 205

Ile Gly Thr Tyr Tyr Cys Gln Gln Tyr Ser Gly Asp Ser Met Tyr Thr
    210                 215                 220

Phe Gly Gln Gly Thr Arg Leu Glu Ile Arg Cys Gln Gln Tyr Ser Gly
225                 230                 235                 240

Asp Ser Met Tyr Thr Phe
                245


<210> SEQ ID NO 743
<211> LENGTH: 237
<212> TYPE: PRT
<213> ORGANISM: Mus musculus

<400> SEQUENCE: 743

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Gln Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Ser Tyr Leu Asn Trp Tyr Gln Gln Lys Pro
145                 150                 155                 160

Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Thr Lys Val
    210                 215                 220

Glu Thr Cys Gln Gln Ser Tyr Ser Thr Pro Pro Thr Phe
225                 230                 235


<210> SEQ ID NO 744
<211> LENGTH: 232
<212> TYPE: PRT
<213> ORGANISM: Mus musculus

<400> SEQUENCE: 744

Pro Gly Ala Ser Ala Lys Val Ser Cys Lys Ala Ser Gly Tyr Thr Phe
1               5                   10                  15

Thr Ser Tyr Gly Ile Ser Trp Val Arg Gln Ala Pro Gly Gln Gly Leu
```

```
            20                  25                  30

Glu Trp Met Gly Trp Ile Ser Ala Tyr Asn Gly Asn Thr Asn Tyr Ala
        35                  40                  45

Gln Lys Leu Gln Gly Arg Val Thr Met Thr Thr Asp Thr Ser Thr Ser
    50                  55                  60

Thr Ala Tyr Met Glu Leu Arg Ser Leu Arg Ser Asp Asp Thr Ala Val
65                  70                  75                  80

Tyr Tyr Cys Ala Arg Glu Arg Ser Tyr Tyr Gly Met Asp Val Trp Gly
                85                  90                  95

Gln Gly Thr Thr Val Thr Val Ser Ser Cys Ala Arg Glu Arg Ser Tyr
            100                 105                 110

Tyr Gly Met Asp Val Trp Thr Gln Ser Pro Ala Thr Leu Ser Val Ser
        115                 120                 125

Pro Gly Glu Ser Ala Thr Leu Ser Cys Arg Ala Ser Gln Ser Val Ser
    130                 135                 140

Asn Tyr Leu Ala Trp Tyr Gln Gln Lys Pro Gly Gln Ala Pro Arg Leu
145                 150                 155                 160

Leu Ile Tyr Gly Ala Ser Thr Arg Ala Thr Gly Ile Pro Ala Arg Phe
                165                 170                 175

Ser Gly Ser Gly Ser Gly Thr Glu Phe Thr Leu Thr Ile Ser Ser Leu
            180                 185                 190

Gln Ser Glu Asp Phe Ala Val Tyr Tyr Cys Gln Gln Tyr Asn His Trp
        195                 200                 205

Pro Pro Leu Phe Gly Gly Gly Thr Lys Val Glu Ile Lys Cys Gln Gln
    210                 215                 220

Tyr Asn His Trp Pro Pro Leu Phe
225                 230


<210> SEQ ID NO 745
<211> LENGTH: 238
<212> TYPE: PRT
<213> ORGANISM: Mus musculus

<400> SEQUENCE: 745

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Gln Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Ser Tyr Leu Asn Trp Tyr Gln Gln Lys Pro
145                 150                 155                 160
```

```
Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Thr Lys Val
    210                 215                 220

Glu Leu Lys Cys Gln Gln Ser Tyr Ser Thr Pro Pro Thr Phe
225                 230                 235
```

<210> SEQ ID NO 746
<211> LENGTH: 232
<212> TYPE: PRT
<213> ORGANISM: Mus musculus

<400> SEQUENCE: 746

```
Pro Gly Ala Ser Ala Lys Val Ser Cys Lys Ala Ser Gly Tyr Thr Phe
1               5                   10                  15

Thr Ser Tyr Gly Ile Ser Trp Val Arg Gln Ala Pro Gly Gln Gly Leu
            20                  25                  30

Glu Trp Met Gly Trp Ile Ser Ala Tyr Asn Gly Asn Thr Asn Tyr Ala
        35                  40                  45

Gln Lys Leu Gln Gly Arg Val Thr Met Thr Thr Asp Thr Ser Thr Ser
    50                  55                  60

Thr Ala Tyr Met Glu Leu Arg Ser Leu Arg Ser Asp Asp Thr Ala Val
65                  70                  75                  80

Tyr Tyr Cys Ala Arg Glu Arg Ser Tyr Tyr Gly Met Asp Val Trp Gly
                85                  90                  95

Gln Gly Thr Thr Val Thr Val Ser Ser Cys Ala Arg Glu Arg Ser Tyr
            100                 105                 110

Tyr Gly Met Asp Val Trp Thr Gln Ser Pro Ala Thr Leu Ser Val Ser
        115                 120                 125

Pro Gly Glu Ser Ala Thr Leu Ser Cys Arg Ala Ser Gln Ser Val Ser
    130                 135                 140

Asn Tyr Leu Ala Trp Tyr Gln Gln Lys Pro Gly Gln Ala Pro Arg Leu
145                 150                 155                 160

Leu Ile Tyr Gly Ala Ser Thr Arg Ala Thr Gly Ile Pro Ala Arg Phe
                165                 170                 175

Ser Gly Ser Gly Ser Gly Thr Glu Phe Thr Leu Thr Ile Ser Ser Leu
            180                 185                 190

Gln Ser Glu Asp Phe Ala Val Tyr Tyr Cys Gln Gln Tyr Asn His Trp
        195                 200                 205

Pro Pro Leu Phe Gly Gly Gly Asn Gly Gly Glu Ile Lys Cys Gln Gln
    210                 215                 220

Tyr Asn His Trp Pro Pro Leu Phe
225                 230
```

<210> SEQ ID NO 747
<211> LENGTH: 236
<212> TYPE: PRT
<213> ORGANISM: Mus musculus

<400> SEQUENCE: 747

```
Pro Gly Ala Ser Val Lys Val Ser Cys Lys Ala Ser Gly Tyr Thr Phe
1               5                   10                  15
```

```
Thr Ser Tyr Tyr Met His Trp Val Arg Gln Ala Pro Gly Gln Gly Leu
            20                  25                  30

Glu Trp Met Gly Ile Ile Asn Pro Ser Gly Gly Ser Thr Ser Tyr Ala
        35                  40                  45

Gln Lys Phe Gln Gly Arg Val Thr Met Thr Arg Asp Thr Ser Thr Ser
    50                  55                  60

Thr Val Tyr Met Glu Leu Ser Ser Leu Arg Ser Glu Asp Thr Ala Val
65                  70                  75                  80

Tyr Tyr Cys Ala Arg Asp Ile Leu Gly Leu Asp Tyr Trp Gly Gln Gly
                85                  90                  95

Thr Leu Val Thr Val Ser Ser Cys Ala Arg Asp Ile Leu Gly Leu Asp
            100                 105                 110

Tyr Trp Gln Pro Gly Leu Thr Gln Pro Pro Ser Ala Ser Glu Thr Pro
        115                 120                 125

Gly Gln Arg Val Thr Ile Ser Cys Ser Gly Ser Ser Ser Asn Ile Gly
    130                 135                 140

Ser Asn Tyr Val Tyr Trp Tyr Gln Gln Leu Pro Gly Thr Ala Pro Lys
145                 150                 155                 160

Leu Leu Ile Tyr Arg Asn Asn Gln Arg Pro Ser Gly Val Pro Gly Arg
                165                 170                 175

Phe Ser Gly Ser Lys Ser Gly Thr Ser Ala Ser Leu Ala Ile Ser Gly
            180                 185                 190

Leu Arg Ser Glu Asp Glu Ala Asp Tyr Tyr Cys Ala Ala Trp Asp Asp
        195                 200                 205

Ser Leu Ser Gly Val Val Phe Gly Gly Gly Thr Lys Leu Thr Val Cys
    210                 215                 220

Ala Ala Trp Asp Asp Ser Leu Ser Gly Val Val Phe
225                 230                 235


<210> SEQ ID NO 748
<211> LENGTH: 243
<212> TYPE: PRT
<213> ORGANISM: Mus musculus

<400> SEQUENCE: 748

Pro Gly Ala Thr Val Lys Ile Ser Cys Lys Val Ser Gly Tyr Thr Phe
1               5                   10                  15

Thr Asp Tyr Tyr Met His Trp Val Gln Gln Ala Pro Gly Lys Gly Leu
            20                  25                  30

Glu Trp Met Gly Leu Val Asp Pro Glu Asp Gly Glu Thr Ile Tyr Ala
        35                  40                  45

Glu Lys Phe Gln Gly Arg Val Thr Ile Thr Ala Asp Thr Ser Thr Asp
    50                  55                  60

Thr Ala Tyr Met Glu Leu Ser Ser Leu Arg Ser Glu Asp Thr Ala Val
65                  70                  75                  80

Tyr Tyr Cys Ala Thr Glu Asp Thr Ala Met Gly Gly Ile Asp Tyr Trp
                85                  90                  95

Gly Gln Gly Thr Leu Val Thr Val Ser Ser Cys Ala Thr Glu Asp Thr
            100                 105                 110

Ala Met Gly Gly Ile Asp Tyr Trp Gln Pro Val Leu Thr Gln Ser Pro
        115                 120                 125

Ser Ala Ser Gly Thr Pro Gly Gln Arg Val Thr Ile Ser Cys Ser Gly
    130                 135                 140

Ser Ser Ser Asn Ile Gly Ser Asn Tyr Val Tyr Trp Tyr Gln Gln Leu
145                 150                 155                 160
```

```
Pro Gly Thr Ala Pro Lys Leu Leu Ile Tyr Ser Asn Asn Gln Arg Pro
                165                 170                 175

Ser Gly Val Pro Asp Arg Phe Ser Gly Ser Lys Ser Gly Thr Ser Ala
            180                 185                 190

Ser Leu Ala Ile Ser Gly Leu Gln Ser Glu Asp Glu Ala Asp Tyr Tyr
        195                 200                 205

Cys Ala Ala Trp Asp Asp Ser Leu Asn Gly Val Val Phe Gly Gly Gly
    210                 215                 220

Thr Lys Leu Thr Val Leu Cys Ala Ala Trp Asp Asp Ser Leu Asn Gly
225                 230                 235                 240

Val Val Phe


<210> SEQ ID NO 749
<211> LENGTH: 239
<212> TYPE: PRT
<213> ORGANISM: Mus musculus

<400> SEQUENCE: 749

Pro Gly Ala Thr Val Lys Ile Ser Cys Lys Val Ser Gly Tyr Thr Phe
1               5                   10                  15

Thr Asp Tyr Tyr Met His Trp Val Gln Gln Ala Pro Gly Lys Gly Leu
            20                  25                  30

Glu Trp Met Gly Leu Val Asp Pro Glu Asp Gly Glu Thr Ile Tyr Ala
        35                  40                  45

Glu Lys Phe Gln Gly Arg Val Thr Ile Thr Ala Asp Thr Ser Thr Asp
    50                  55                  60

Thr Ala Tyr Met Glu Leu Ser Ser Leu Arg Ser Glu Asp Thr Ala Val
65                  70                  75                  80

Tyr Tyr Cys Ala Thr Glu Gly Arg Tyr Gly Met Asp Val Trp Gly Gln
                85                  90                  95

Gly Thr Thr Val Thr Val Ser Ser Cys Ala Thr Glu Gly Arg Tyr Gly
            100                 105                 110

Met Asp Val Trp Gln Ala Val Leu Thr Gln Pro Pro Ser Val Ser Gly
        115                 120                 125

Thr Pro Gly Gln Arg Val Thr Ile Ser Cys Ser Gly Asn Asn Phe Asn
    130                 135                 140

Ile Gly Asn Asn Leu Val Tyr Trp Tyr Gln Gln Leu Pro Gly Thr Ala
145                 150                 155                 160

Pro Lys Leu Leu Ile Tyr Ala Asn Asp Glu Arg Pro Ser Gly Val Pro
                165                 170                 175

Asp Arg Phe Ser Gly Ser Lys Ser Gly Thr Ser Ala Ser Leu Ala Ile
            180                 185                 190

Ser Gly Leu Arg Ser Glu Asp Asp Ala Asp Tyr Tyr Cys Ala Thr Trp
        195                 200                 205

Asp Asp Ser Leu Ser Gly Val Val Phe Gly Gly Gly Thr Lys Leu Thr
    210                 215                 220

Ala Leu Cys Ala Thr Trp Asp Asp Ser Leu Ser Gly Val Val Phe
225                 230                 235


<210> SEQ ID NO 750
<211> LENGTH: 259
<212> TYPE: PRT
<213> ORGANISM: Mus musculus

<400> SEQUENCE: 750
```

-continued

```
Pro Gly Ala Thr Val Lys Ile Ser Cys Lys Val Ser Gly Tyr Thr Phe
1               5                   10                  15

Thr Asp Tyr Tyr Met His Trp Val Gln Gln Ala Pro Gly Lys Gly Leu
            20                  25                  30

Glu Trp Met Gly Leu Val Asp Pro Glu Asp Gly Glu Thr Ile Tyr Ala
        35                  40                  45

Glu Lys Phe Gln Gly Arg Val Thr Ile Thr Ala Asp Thr Ser Thr Asp
    50                  55                  60

Thr Ala Tyr Met Glu Leu Ser Ser Leu Arg Ser Glu Asp Thr Ala Val
65                  70                  75                  80

Tyr Tyr Cys Ala Val Glu Gly Gly Arg Ala Pro Gly Thr Tyr Tyr Tyr
                85                  90                  95

Asp Ser Ser Gly Leu Ala Tyr Trp Gly Gln Gly Thr Leu Val Thr Val
            100                 105                 110

Ser Ser Cys Ala Val Glu Gly Gly Arg Ala Pro Gly Thr Tyr Tyr Tyr
        115                 120                 125

Asp Ser Ser Gly Leu Ala Tyr Trp Gln Ala Gly Leu Thr Gln Pro Pro
    130                 135                 140

Ser Ala Ser Gly Thr Pro Gly Gln Arg Val Thr Ile Ser Cys Ser Gly
145                 150                 155                 160

Ser Ser Ser Asn Ile Gly Ser Asn Tyr Val Tyr Trp Tyr Gln Gln Leu
                165                 170                 175

Pro Gly Thr Ala Pro Lys Leu Leu Ile Tyr Ser Asn Asn Gln Arg Pro
            180                 185                 190

Ser Gly Val Pro Asp Arg Phe Ser Gly Ser Lys Ser Gly Thr Ser Ala
        195                 200                 205

Ser Leu Ala Ile Ser Gly Leu Arg Ser Glu Asp Glu Ala Asp Tyr Tyr
    210                 215                 220

Cys Ala Thr Trp Asp Asp Ser Leu Ser Gly Val Val Phe Gly Gly Gly
225                 230                 235                 240

Thr Lys Leu Thr Val Leu Cys Ala Thr Trp Asp Asp Ser Leu Ser Gly
                245                 250                 255

Val Val Phe


<210> SEQ ID NO 751
<211> LENGTH: 237
<212> TYPE: PRT
<213> ORGANISM: Mus musculus

<400> SEQUENCE: 751

Pro Ser Gln Thr Leu Ser Leu Thr Cys Ala Val Ser Gly Gly Ser Ile
1               5                   10                  15

Ser Ser Gly Gly Tyr Ser Trp Ser Trp Ile Arg Gln Pro Pro Gly Lys
            20                  25                  30

Gly Leu Glu Trp Ile Gly Tyr Ile Tyr His Ser Gly Ser Thr Tyr Tyr
        35                  40                  45

Asn Pro Ser Leu Lys Ser Arg Val Thr Ile Ser Val Asp Arg Ser Lys
    50                  55                  60

Asn Gln Phe Ser Leu Lys Leu Ser Ser Val Thr Ala Ala Asp Thr Ala
65                  70                  75                  80

Val Tyr Tyr Cys Ala Arg Ala Gly Tyr Tyr Tyr Gly Met Asp Val Trp
                85                  90                  95

Gly Gln Gly Thr Thr Val Thr Val Ser Ser Cys Ala Arg Ala Gly Tyr
            100                 105                 110
```

-continued

```
Tyr Tyr Gly Met Asp Val Trp Asp Ile Val Met Thr Gln Thr Pro Ser
        115                 120                 125

Ser Leu Ser Ala Ser Val Gly Asp Arg Val Ala Ile Thr Cys Gln Ala
    130                 135                 140

Ser Arg Asn Ile Trp Ser Tyr Val Asn Trp Tyr Gln Gln Lys Pro Gly
145                 150                 155                 160

Glu Ala Pro Arg Leu Leu Ile Tyr Gly Ala Ser Thr Leu Gln Arg Gly
                165                 170                 175

Val Pro Ser Arg Phe Ser Gly Ser Gly Ser Gly Thr Gly Phe Thr Leu
            180                 185                 190

Thr Ile Asn Ser Leu Gln Pro Glu Asp Phe Ala Thr Tyr Phe Cys Gln
        195                 200                 205

Gln Ser His Ser Thr Pro Ile Thr Phe Gly Gly Gly Thr Arg Val Asp
    210                 215                 220

Ile Lys Cys Gln Gln Ser His Ser Thr Pro Ile Thr Phe
225                 230                 235
```

<210> SEQ ID NO 752
<211> LENGTH: 252
<212> TYPE: PRT
<213> ORGANISM: Mus musculus

<400> SEQUENCE: 752

```
Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Lys Ser Thr Ser
    50                  55                  60

Thr Ala Tyr Met Glu Leu Ser Ser Leu Arg Ser Asp Asp Thr Ala Val
65                  70                  75                  80

Tyr Tyr Cys Ala Arg Asp Leu Gly Thr Met Val Arg Gly Val Ile Glu
                85                  90                  95

Pro Tyr Tyr Phe Asp Tyr Trp Gly Gln Gly Thr Leu Val Thr Val Ser
            100                 105                 110

Ser Cys Ala Arg Asp Leu Gly Thr Met Val Arg Gly Val Ile Glu Pro
        115                 120                 125

Tyr Tyr Phe Asp Tyr Trp Asp Ile Gln Met Thr Gln Ser Pro Ser Thr
    130                 135                 140

Leu Ser Ala Ser Val Gly Asp Arg Val Thr Ile Thr Cys Arg Ala Ser
145                 150                 155                 160

Gln Ser Ile Ser Ser Trp Leu Ala Trp Tyr Gln Gln Lys Pro Gly Lys
                165                 170                 175

Ala Pro Lys Leu Leu Ile Tyr Asp Ala Phe Ser Leu Glu Ser Gly Val
            180                 185                 190

Pro Ser Arg Phe Ser Gly Ser Gly Ser Gly Thr Glu Phe Thr Leu Thr
        195                 200                 205

Ile Ser Ser Leu Gln Pro Asp Asp Phe Ala Thr Tyr Tyr Cys Gln Gln
    210                 215                 220

Tyr Asn Ser Tyr Ser Arg Thr Phe Gly Gln Gly Thr Lys Val Glu Ile
225                 230                 235                 240

Lys Cys Gln Gln Tyr Asn Ser Tyr Ser Arg Thr Phe
                245                 250
```

<210> SEQ ID NO 753
<211> LENGTH: 232
<212> TYPE: PRT
<213> ORGANISM: Mus musculus

<400> SEQUENCE: 753

Pro Ser Gly Thr Leu Ser Leu Thr Cys Ala Val Ser Gly Gly Ser Ile
1 5 10 15

Ser Ser Ser Asn Trp Trp Ser Trp Val Arg Gln Pro Pro Gly Lys Gly
20 25 30

Leu Glu Trp Ile Gly Glu Ile Tyr His Ser Gly Ser Thr Asn Tyr Asn
35 40 45

Pro Ser Leu Lys Ser Arg Val Thr Ile Ser Val Asp Lys Ser Lys Asn
50 55 60

Gln Phe Ser Leu Lys Leu Ser Ser Val Thr Ala Ala Asp Thr Ala Val
65 70 75 80

Tyr Tyr Cys Ala Arg Gly Val Arg Gly Thr Gly Phe Asp Pro Trp Gly
85 90 95

Gln Gly Thr Leu Val Thr Val Ser Ser Cys Ala Arg Gly Val Arg Gly
100 105 110

Thr Gly Phe Asp Pro Trp Thr Gln Ser Pro Gly Thr Leu Ser Val Ser
115 120 125

Pro Gly Glu Arg Ala Thr Leu Ser Cys Arg Ala Ser Gln Ser Val Ser
130 135 140

Ser Arg Leu Ala Trp Tyr Gln Gln Lys Pro Gly Gln Ala Pro Arg Leu
145 150 155 160

Leu Ile Tyr Gly Ala Ser Thr Arg Ala Thr Gly Ile Pro Ala Arg Phe
165 170 175

Ser Gly Ser Gly Ser Gly Thr Glu Phe Thr Leu Thr Ile Ser Ser Leu
180 185 190

Gln Ser Glu Asp Phe Ala Val Tyr Phe Cys Gln Gln Tyr Thr Asn Trp
195 200 205

Pro Gln Thr Phe Gly Gln Gly Thr Lys Val Glu Ile Lys Cys Gln Gln
210 215 220

Tyr Thr Asn Trp Pro Gln Thr Phe
225 230

<210> SEQ ID NO 754
<211> LENGTH: 234
<212> TYPE: PRT
<213> ORGANISM: Mus musculus

<400> SEQUENCE: 754

Pro Gly Ala Ser Val Lys Val Ser Cys Lys Ala Ser Gly Tyr Thr Phe
1 5 10 15

Thr Ser Tyr Gly Ile Ser Trp Val Arg Gln Ala Pro Gly Gln Gly Leu
20 25 30

Glu Trp Met Gly Trp Ile Ser Ala Tyr Asn Gly Asn Thr Asn Tyr Ala
35 40 45

Gln Lys Leu Gln Gly Arg Val Thr Met Thr Thr Asp Thr Ser Thr Ser
50 55 60

Thr Ala Tyr Met Glu Leu Arg Ser Leu Arg Ser Asp Asp Thr Ala Val
65 70 75 80

Tyr Tyr Cys Ala Arg Asp Arg Asn Gly Tyr Phe Gln His Trp Gly Gln
85 90 95

```
Gly Thr Leu Val Thr Val Ser Ser Cys Ala Arg Asp Arg Asn Gly Tyr
            100                 105                 110

Phe Gln His Trp Asp Ile Val Met Thr Gln Thr Pro Ser Thr Leu Ser
        115                 120                 125

Ala Ser Val Gly Asp Arg Val Thr Ile Thr Cys Arg Ala Ser Gln Thr
    130                 135                 140

Ile Ser Gly Leu Leu Ala Trp Tyr Gln Gln Lys Pro Gly Lys Ala Pro
145                 150                 155                 160

Asn Leu Leu Ile Tyr Gly Ala Ser Asn Ser Gln Ser Gly Val Pro Ser
                165                 170                 175

Arg Phe Thr Gly Ser Gly Ser Gly Thr Glu Phe Thr Leu Thr Ile Thr
            180                 185                 190

Asn Leu Gln Pro Asp Asp Phe Ala Thr Tyr Tyr Cys Leu Gln Tyr Asp
        195                 200                 205

Arg Tyr Ser Gly Ala Phe Gly Gln Gly Thr Lys Leu Glu Ile Lys Cys
    210                 215                 220

Leu Gln Tyr Asp Arg Tyr Ser Gly Ala Phe
225                 230


<210> SEQ ID NO 755
<211> LENGTH: 242
<212> TYPE: PRT
<213> ORGANISM: Mus musculus

<400> SEQUENCE: 755

Pro Gly Arg Ser Leu Arg Leu Ser Cys Ala Ala Ser Gly Phe Thr Phe
1               5                   10                  15

Ser Ser Tyr Gly Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Lys Asp Leu Leu Gly Glu Leu Ser Phe Phe Asp Tyr
                85                  90                  95

Trp Gly Gln Gly Thr Leu Val Thr Val Ser Ser Cys Ala Lys Asp Leu
            100                 105                 110

Leu Gly Glu Leu Ser Phe Phe Asp Tyr Trp Ser Val Leu Thr Gln Pro
        115                 120                 125

Pro Ser Val Ser Val Ala Pro Gly Gln Thr Ala Arg Ile Pro Cys Gly
    130                 135                 140

Gly Asp Asp Ile Glu Ser Glu Met Val His Trp Tyr Gln Gln Lys Pro
145                 150                 155                 160

Gly Gln Ala Pro Val Leu Val Val Tyr Asp Asp Ser Val Arg Pro Ser
                165                 170                 175

Gly Ile Pro Glu Arg Phe Ser Gly Ser Asn Ser Gly Asn Thr Ala Thr
            180                 185                 190

Leu Ile Ile Ser Gly Val Glu Ala Gly Asp Glu Ala Ala Tyr Tyr Cys
        195                 200                 205

Gln Val Trp His Thr Thr Asn Asp His Val Leu Phe Gly Gly Gly Thr
    210                 215                 220

Asn Leu Thr Val Leu Cys Gln Val Trp His Thr Thr Asn Asp His Val
```

-continued

```
225                 230                 235                 240

Leu Phe


<210> SEQ ID NO 756
<211> LENGTH: 247
<212> TYPE: PRT
<213> ORGANISM: Mus musculus

<400> SEQUENCE: 756

Pro Gly Asp Leu Trp Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asp Tyr Gly Gly Trp Phe
                85                  90                  95

Asp Pro Trp Gly Gln Gly Thr Leu Val Thr Val Ser Ser Cys Ala Arg
            100                 105                 110

Leu Glu Asn Asn Trp Asp Tyr Gly Gly Trp Phe Asp Pro Trp Ser Tyr
        115                 120                 125

Val Leu Thr Gln Pro Pro Ser Val Ser Val Ala Pro Gly Gln Thr Ala
    130                 135                 140

Arg Ile Thr Cys Gly Gly Asn Asn Ile Gly Ser Lys Ser Val His Trp
145                 150                 155                 160

Tyr Gln Gln Lys Pro Gly Gln Ala Pro Val Leu Val Val Tyr Asp Asp
                165                 170                 175

Ser Asp Arg Pro Ser Gly Ile Pro Glu Arg Phe Ser Gly Ser Asn Ser
            180                 185                 190

Gly Asn Thr Ala Thr Leu Thr Ile Ser Arg Val Glu Ala Gly Asp Glu
        195                 200                 205

Ala Asp Tyr Tyr Cys Gln Val Trp Asp Ser Ser Ser Asp His Trp Val
    210                 215                 220

Phe Gly Gly Gly Thr Lys Leu Thr Val Leu Cys Gln Val Trp Asp Ser
225                 230                 235                 240

Ser Ser Asp His Trp Val Phe
                245


<210> SEQ ID NO 757
<211> LENGTH: 247
<212> TYPE: PRT
<213> ORGANISM: Mus musculus

<400> SEQUENCE: 757

Pro Gly Glu Ser Leu Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60
```

```
Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asp Tyr Gly Gly Trp Phe
                85                  90                  95

Asp Pro Trp Gly Gln Gly Thr Leu Val Thr Val Ser Ser Cys Ala Arg
            100                 105                 110

Leu Glu Asn Asn Trp Asp Tyr Gly Gly Trp Phe Asp Pro Trp Ser Tyr
        115                 120                 125

Val Leu Thr Gln Pro Pro Ser Val Ser Val Ala Pro Gly Gln Thr Ala
    130                 135                 140

Arg Ile Thr Cys Gly Gly Asn Asn Ile Gly Ser Lys Ser Val His Trp
145                 150                 155                 160

Tyr Gln Gln Lys Pro Gly Gln Ala Pro Val Leu Val Val Tyr Asp Asp
                165                 170                 175

Ser Asp Arg Pro Ser Gly Ile Pro Glu Arg Phe Ser Gly Ser Asn Ser
            180                 185                 190

Gly Asn Thr Ala Thr Leu Thr Ile Ser Arg Val Glu Ala Gly Asp Glu
        195                 200                 205

Ala Asp Tyr Tyr Cys Gln Val Trp Asp Ser Ser Ser Asp His Trp Val
    210                 215                 220

Phe Gly Gly Gly Thr Lys Leu Thr Val Leu Cys Gln Val Trp Asp Ser
225                 230                 235                 240

Ser Ser Asp His Trp Val Phe
                245


<210> SEQ ID NO 758
<211> LENGTH: 236
<212> TYPE: PRT
<213> ORGANISM: Mus musculus

<400> SEQUENCE: 758

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Lys Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Asp Arg Ser Tyr Tyr Gly Met Asp Val Trp Gly
                85                  90                  95

Gln Gly Thr Thr Val Thr Val Ser Ser Cys Ala Arg Asp Arg Ser Tyr
            100                 105                 110

Tyr Gly Met Asp Val Trp Asp Ile Arg Leu Thr Gln Ser Pro Ser Ser
        115                 120                 125

Leu Ser Ala Ser Val Gly Asp Arg Val Thr Ile Thr Cys Arg Ala Ser
    130                 135                 140

Gln Ser Ile Gly Asn Tyr Leu Asn Trp Tyr Gln Gln Arg Leu Gly Glu
145                 150                 155                 160

Ala Pro Lys Val Leu Ile Tyr Ala Ala Thr Arg Leu Gln Arg Gly Val
                165                 170                 175

Pro Ser Arg Phe Ser Ala Ser Ala Ser Gly Thr Asp Phe Thr Leu Thr
```

```
            180                 185                 190

Ile Ser Ser Leu Gln Pro Glu Asp Phe Thr Thr Tyr Tyr Cys Gln Gln
        195                 200                 205

Ser Lys Gln Ile Pro Tyr Thr Phe Gly Gln Gly Thr Lys Leu Gln Ile
    210                 215                 220

Lys Cys Gln Gln Ser Lys Gln Ile Pro Tyr Thr Phe
225                 230                 235


<210> SEQ ID NO 759
<211> LENGTH: 236
<212> TYPE: PRT
<213> ORGANISM: Mus musculus

<400> SEQUENCE: 759

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Lys Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Asp Lys Gly Tyr Tyr Gly Met Asp Val Trp Gly
                85                  90                  95

Gln Gly Thr Thr Val Thr Val Ser Ser Cys Ala Arg Asp Lys Gly Tyr
            100                 105                 110

Tyr Gly Met Asp Val Trp Asp Ile Gln Met Thr Gln Ser Pro Ser Ser
        115                 120                 125

Val Ser Ala Ser Val Gly Asp Arg Val Thr Ile Thr Cys Arg Ala Ser
    130                 135                 140

Gln Gly Ile Ser Ser Trp Leu Ala Trp Tyr Gln Gln Lys Pro Gly Lys
145                 150                 155                 160

Ala Pro Lys Leu Leu Ile Tyr Ala Val Ser Ser Leu Gln Ser Gly Val
                165                 170                 175

Pro Ser Arg Phe Ser Gly Ser Gly Ser Gly Thr Asp Phe Thr Leu Thr
            180                 185                 190

Ile Ser Ser Leu Gln Pro Glu Asp Phe Ala Thr Tyr Tyr Cys Gln Gln
        195                 200                 205

Ser Tyr Ser Leu Pro Leu Thr Phe Gly Gly Gly Thr Glu Val Leu Ile
    210                 215                 220

Lys Cys Gln Gln Ser Tyr Ser Leu Pro Leu Thr Phe
225                 230                 235


<210> SEQ ID NO 760
<211> LENGTH: 236
<212> TYPE: PRT
<213> ORGANISM: Mus musculus

<400> SEQUENCE: 760

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
```

-continued

```
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Asp Arg Ser Tyr Tyr Gly Met Asp Val Trp Gly
                85                  90                  95

Gln Gly Thr Thr Val Thr Val Ser Ser Cys Ala Arg Asp Arg Ser Tyr
            100                 105                 110

Tyr Gly Met Asp Val Trp Asp Ile Gln Met Thr Gln Ser Pro Ser Ser
        115                 120                 125

Leu Ser Ala Ser Val Gly Asp Arg Val Thr Ile Thr Cys Arg Ala Ser
    130                 135                 140

Gln Ser Ile Gly Asn Tyr Leu Asn Trp Tyr Gln Gln Arg Leu Gly Glu
145                 150                 155                 160

Ala Pro Lys Val Leu Ile Tyr Ala Ala Thr Arg Leu Gln Arg Gly Val
                165                 170                 175

Pro Ser Arg Phe Ser Ala Gly Ala Ser Gly Thr Asp Phe Thr Leu Thr
            180                 185                 190

Ile Ser Ser Leu Gln Pro Glu Asp Phe Thr Thr Tyr Tyr Cys Gln Gln
        195                 200                 205

Ser Lys Gln Ile Pro Tyr Thr Phe Gly Gln Gly Thr Lys Leu Gln Ile
    210                 215                 220

Lys Cys Gln Gln Ser Lys Gln Ile Pro Tyr Thr Phe
225                 230                 235


<210> SEQ ID NO 761
<211> LENGTH: 245
<212> TYPE: PRT
<213> ORGANISM: Mus musculus

<400> SEQUENCE: 761

Pro Gly Arg Ser Leu Arg Leu Ser Cys Ala Ala Ser Gly Phe Thr Phe
1               5                   10                  15

Ser Asn Tyr Gly Met His Trp Val Arg Gln Ala Pro Gly Lys Gly Leu
            20                  25                  30

Glu Trp Val Ala Val Ile Ser His Asp Gly His Val Lys Trp His Gly
        35                  40                  45

Asp Ser Val Lys Gly Arg Phe Thr Ile Ser Arg Asp Asn Ser Lys Asn
    50                  55                  60

Thr Leu Tyr Leu Gln Leu Asp Ser Leu Arg Thr Glu Asp Thr Ala Val
65                  70                  75                  80

Tyr Tyr Cys Ala Lys Glu Ile Ser Pro Arg Ser Ser Val Gly Trp Pro
                85                  90                  95

Leu Asp Tyr Trp Gly Gln Gly Thr Leu Val Thr Val Ser Ser Cys Ala
            100                 105                 110

Lys Glu Ile Ser Pro Arg Ser Ser Val Gly Trp Pro Leu Asp Tyr Trp
        115                 120                 125

Thr Gln Ser Pro Gly Thr Leu Ser Leu Ser Pro Gly Glu Arg Ala Thr
    130                 135                 140

Leu Ser Cys Arg Ala Asp Gln Ser Val Ser Ser Thr Tyr Leu Ala Trp
145                 150                 155                 160

Tyr Gln Gln Arg Pro Gly Gln Ala Pro Arg Leu Leu Ile Tyr Gly Ala
                165                 170                 175
```

```
Ser Asn Arg Ala Thr Gly Ile Pro Asp Arg Phe Ser Gly Ser Gly Ser
            180                 185                 190

Gly Ser Asp Phe Thr Leu Thr Ile Ser Arg Leu Glu Pro Glu Asp Phe
        195                 200                 205

Ala Val Tyr Tyr Cys Gln Gln Phe Asp Ile Ser Gly Gly Leu Ile Phe
    210                 215                 220

Gly Pro Gly Thr Lys Val Asp Ile Lys Cys Gln Gln Phe Asp Ile Ser
225                 230                 235                 240

Gly Gly Leu Ile Phe
                245


<210> SEQ ID NO 762
<211> LENGTH: 246
<212> TYPE: PRT
<213> ORGANISM: Mus musculus

<400> SEQUENCE: 762

Pro Gly Arg Ser Leu Arg Leu Ser Cys Ala Ala Ser Gly Phe Thr Phe
1               5                   10                  15

Ser Ser Ser Ala Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Lys Ala Lys Asn
    50                  55                  60

Ser Leu Tyr Leu Gln Met Asn Ser Leu Arg Ala Glu Asp Thr Ala Val
65                  70                  75                  80

Tyr Tyr Cys Ala Arg Asp Phe Trp Ser Gly Tyr Asn Glu Leu Gly Gly
                85                  90                  95

Met Asp Val Trp Gly Gln Gly Thr Thr Val Thr Val Ser Ser Cys Ala
            100                 105                 110

Arg Asp Phe Trp Ser Gly Tyr Asn Glu Leu Gly Gly Met Asp Val Trp
        115                 120                 125

Glu Ile Val Met Thr Gln Ser Pro Ser Ser Leu Ser Ala Ser Val Gly
    130                 135                 140

Asp Arg Val Thr Ile Thr Cys Gln Ala Ser Gln Asp Ile Ser Asn Tyr
145                 150                 155                 160

Leu Asn Trp Tyr Gln Gln Lys Pro Gly Lys Ala Pro Lys Leu Leu Ile
                165                 170                 175

Tyr Asp Ala Ser Asn Leu Glu Thr Gly Val Pro Ser Arg Phe Ser Gly
            180                 185                 190

Ser Gly Ser Gly Thr Asp Phe Thr Phe Thr Ile Ser Ser Leu Gln Pro
        195                 200                 205

Glu Asp Ile Ala Thr Tyr Tyr Cys Gln Gln Tyr Asp Asn Leu Pro Leu
    210                 215                 220

Thr Phe Gly Gly Gly Thr Lys Val Glu Ile Lys Cys Gln Gln Tyr Asp
225                 230                 235                 240

Asn Leu Pro Leu Thr Phe
                245


<210> SEQ ID NO 763
<211> LENGTH: 240
<212> TYPE: PRT
<213> ORGANISM: Mus musculus

<400> SEQUENCE: 763
```

-continued

Pro Gly Gly Ser Leu Arg Leu Ser Cys Ala Ala Ser Gly Phe Thr Phe
1 5 10 15

Ser Ser Tyr Trp Met Ser Trp Val Arg Gln Ala Pro Gly Lys Gly Leu
20 25 30

Glu Trp Val Ala Asn Ile Lys Gln Asp Gly Ser Glu Lys Tyr Tyr Val
35 40 45

Asp Ser Val Lys Gly Arg Phe Thr Ile Ser Arg Asp Asn Ala Lys Asn
50 55 60

Ser Leu Tyr Leu Gln Met Asn Ser Leu Arg Ala Glu Asp Thr Ala Val
65 70 75 80

Tyr Tyr Cys Ala Arg Thr Trp Phe Gly Glu Phe Phe Asp Tyr Trp Gly
85 90 95

Gln Gly Thr Leu Val Thr Val Ser Ser Cys Ala Arg Thr Trp Phe Gly
100 105 110

Glu Phe Phe Asp Tyr Trp Ser Val Leu Thr Gln Pro Pro Ser Val Ser
115 120 125

Val Ala Pro Gly Gln Thr Ala Arg Val Thr Cys Gly Gly Asn Asn Ile
130 135 140

Glu Ser Glu Ser Val His Trp Tyr Gln Gln Lys Pro Gly Gln Ala Pro
145 150 155 160

Val Leu Val Val Tyr Asp Asp Ser Ala Arg Pro Ser Gly Ile Pro Glu
165 170 175

Arg Phe Ser Gly Ser Asn Ser Gly Asn Thr Ala Thr Leu Thr Ile Ser
180 185 190

Arg Val Glu Ala Gly Asp Glu Ala Asp Tyr Tyr Cys Gln Val Trp Asp
195 200 205

Ser Ser Ser Asp His Thr Val Ala Phe Gly Gly Gly Thr Lys Leu Ala
210 215 220

Val Leu Cys Gln Val Trp Asp Ser Ser Ser Asp His Thr Val Ala Phe
225 230 235 240

<210> SEQ ID NO 764
<211> LENGTH: 238
<212> TYPE: PRT
<213> ORGANISM: Mus musculus

<400> SEQUENCE: 764

Pro Gly Ala Ser Val Lys Val Ser Cys Lys Ala Ser Gly Tyr Thr Phe
1 5 10 15

Thr Ser Tyr Gly Ile Ser Trp Val Arg Gln Ala Pro Gly Gln Gly Leu
20 25 30

Glu Trp Met Gly Trp Ile Ser Ala Tyr Asn Gly Asn Thr Asn Tyr Ala
35 40 45

Gln Lys Leu Gln Gly Arg Val Thr Met Thr Thr Asp Thr Ser Thr Ser
50 55 60

Thr Ala Tyr Met Glu Leu Arg Ser Leu Arg Ser Asp Asp Thr Ala Val
65 70 75 80

Tyr Tyr Cys Ala Arg Val Ile Gly Gly Trp Phe Asp Pro Trp Gly Gln
85 90 95

Gly Thr Leu Val Thr Val Ser Ser Cys Ala Arg Val Ile Gly Gly Trp
100 105 110

Phe Asp Pro Trp Gln Ser Ala Leu Thr Gln Pro Ala Ser Val Ser Gly
115 120 125

Ser Pro Gly Gln Ser Ile Thr Ile Ser Cys Thr Gly Thr Ser Ser Asp
130 135 140

Val Gly Ala Tyr Asn Tyr Val Ser Trp Tyr Gln Gln Gln Pro Gly Lys
145 150 155 160

Ala Pro Glu Leu Met Ile Tyr Gly Val Ser His Arg Pro Ser Arg Val
165 170 175

Ser Asn Arg Phe Ser Gly Ser Lys Ser Gly Asn Thr Ala Ser Leu Thr
180 185 190

Ile Ser Gly Leu Gln Thr Glu Asp Glu Ala Asp Tyr Tyr Cys Ser Ser
195 200 205

Tyr Thr Thr Thr Asp Thr Phe Val Leu Gly Ser Gly Thr Lys Val Thr
210 215 220

Val Leu Cys Ser Ser Tyr Thr Thr Thr Asp Thr Phe Val Leu
225 230 235

<210> SEQ ID NO 765
<211> LENGTH: 244
<212> TYPE: PRT
<213> ORGANISM: Mus musculus

<400> SEQUENCE: 765

Pro Gly Arg Ser Leu Arg Leu Ser Cys Ala Ala Ser Gly Phe Ile Phe
1 5 10 15

Ser Arg His Ala Met His Trp Val Arg Gln Ala Pro Asp Lys Gly Leu
20 25 30

Glu Trp Val Ala Val Ile Ser Tyr Asp Gly Ser Asn Lys Tyr Tyr Ala
35 40 45

Asp Ser Val Lys Gly Arg Phe Thr Ile Ser Arg Asp Asn Pro Lys Asn
50 55 60

Thr Leu Tyr Leu Gln Met Asn Ser Leu Arg Ala Glu Asp Thr Ala Val
65 70 75 80

Tyr Tyr Cys Ala Arg Gly Arg Leu Ala Tyr Gly Asp Thr Glu Gly Phe
85 90 95

Asp Tyr Trp Gly Gln Gly Thr Leu Val Thr Val Ser Ser Cys Ala Arg
100 105 110

Gly Arg Leu Ala Tyr Gly Asp Thr Glu Gly Phe Asp Tyr Trp Asp Ile
115 120 125

Val Met Thr Gln Ser Pro Ser Ser Leu Ser Ala Ser Val Gly Asp Arg
130 135 140

Val Thr Ile Thr Cys Gln Ala Ser Gln Asp Ile Asn Asn Tyr Leu Ser
145 150 155 160

Trp Phe Gln His Lys Pro Gly Lys Ala Pro Lys Leu Leu Ile Tyr Asp
165 170 175

Ala Ser Asp Leu Glu Thr Gly Val Pro Ser Arg Phe Ser Gly Ser Gly
180 185 190

Ser Gly Pro Glu Phe Ser Phe Thr Ile Thr Asn Leu Gln Pro Glu Asp
195 200 205

Val Ala Thr Tyr Tyr Cys Gln Gln Tyr Asp Asn Leu Pro Tyr Thr Phe
210 215 220

Gly Gln Gly Thr Lys Val Glu Ile Arg Cys Gln Gln Tyr Asp Asn Leu
225 230 235 240

Pro Tyr Thr Phe

<210> SEQ ID NO 766
<211> LENGTH: 241
<212> TYPE: PRT
<213> ORGANISM: Mus musculus

<400> SEQUENCE: 766

Pro Gly Ala Ser Val Lys Val Ser Cys Lys Ala Ser Gly Tyr Thr Phe
1 5 10 15

Asn Asn Tyr Gly Leu Ala Trp Val Arg Gln Ala Pro Gly Gln Gly Leu
20 25 30

Glu Trp Met Gly Trp Ile Ser Val Tyr Asn Gly Asp Ile Asn Tyr Ala
35 40 45

Gln Lys Phe Gln Gly Arg Val Thr Met Thr Thr Asp Arg Ala Thr Arg
50 55 60

Thr Ala Tyr Met Glu Leu Arg Ser Leu Ile Ser Asp Asp Thr Ala Val
65 70 75 80

Tyr Tyr Cys Ala Arg Asp Ile Leu Arg Gly Glu Ser Ser Ile Leu Asp
85 90 95

His Trp Gly Gln Gly Thr Leu Val Thr Val Ser Cys Ala Arg Asp Ile
100 105 110

Leu Arg Gly Glu Ser Ser Ile Leu Asp His Trp Asp Ile Val Met Thr
115 120 125

Gln Ser Pro Ser Ser Leu Ser Ala Ser Val Gly Asp Arg Val Thr Ile
130 135 140

Thr Cys Arg Ala Ser Gln Gly Ile Ser Asn Ser Leu Ala Trp Tyr Gln
145 150 155 160

Gln Lys Pro Gly Lys Ala Pro Lys Leu Leu Leu Tyr Ala Ala Ser Arg
165 170 175

Leu Glu Ser Gly Val Pro Ser Arg Phe Ser Gly Ser Gly Ser Gly Thr
180 185 190

Asp Tyr Thr Leu Thr Ile Ser Ser Leu Gln Pro Glu Asp Phe Ala Thr
195 200 205

Tyr Tyr Cys Gln Gln Tyr Tyr Ser Thr Pro Pro His Phe Gly Gly Gly
210 215 220

Thr Lys Val Glu Ile Lys Cys Gln Gln Tyr Tyr Ser Thr Pro Pro His
225 230 235 240

Phe

<210> SEQ ID NO 767
<211> LENGTH: 236
<212> TYPE: PRT
<213> ORGANISM: Mus musculus

<400> SEQUENCE: 767

Pro Gly Ser Ser Val Lys Val Ser Cys Lys Ala Ser Gly Gly Thr Phe
1 5 10 15

Ser Ser Tyr Ala Ile Ser Trp Val Arg Gln Ala Pro Gly Gln Gly Leu
20 25 30

Glu Trp Met Gly Gly Ile Ile Pro Ile Phe Gly Thr Ala Asn Tyr Ala
35 40 45

Gln Lys Phe Gln Gly Arg Val Thr Ile Thr Ala Asp Glu Ser Thr Ser
50 55 60

Thr Ala Tyr Met Glu Leu Ser Ser Leu Arg Ser Asp Asp Thr Ala Val
65 70 75 80

Tyr Tyr Cys Ala Arg Asp Arg Tyr Tyr Tyr Gly Met Asp Val Trp Gly
85 90 95

Gln Gly Thr Thr Val Thr Val Ser Ser Cys Ala Arg Asp Arg Tyr Tyr
100 105 110

-continued

```
Tyr Gly Met Asp Val Trp Ala Ile Arg Met Thr Gln Ser Pro Ser Ser
        115                 120                 125

Leu Ser Ala Ser Val Gly Asp Arg Val Thr Ile Thr Cys Arg Ala Ser
    130                 135                 140

Gln Ser Ile Ser Ser Tyr Leu Asn Trp Tyr Gln Gln Lys Pro Gly Lys
145                 150                 155                 160

Ala Pro Lys Leu Leu Ile Tyr Ala Ala Ser Ser Leu Gln Ser Gly Val
                165                 170                 175

Pro Ser Arg Phe Ser Gly Ser Gly Ser Gly Thr Asp Phe Thr Leu Thr
            180                 185                 190

Ile Ser Ser Leu Gln Pro Glu Asp Phe Ala Thr Tyr Tyr Cys Gln Gln
        195                 200                 205

Ser Tyr Ser Thr Pro Leu Thr Phe Gly Gly Gly Thr Lys Val Glu Ile
    210                 215                 220

Lys Cys Gln Gln Ser Tyr Ser Thr Pro Leu Thr Phe
225                 230                 235


<210> SEQ ID NO 768
<211> LENGTH: 245
<212> TYPE: PRT
<213> ORGANISM: Mus musculus

<400> SEQUENCE: 768

Pro Gly Arg Ser Leu Arg Leu Ser Cys Ala Ala Ser Gly Phe Thr Phe
1               5                   10                  15

Ser Ser Tyr Ala Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Arg Asp Leu Leu Gly Ser Gly Tyr Asp Ile Ile Asp
                85                  90                  95

Tyr Trp Gly Gln Gly Thr Leu Val Thr Val Ser Ser Cys Ala Arg Asp
            100                 105                 110

Leu Leu Gly Ser Gly Tyr Asp Ile Ile Asp Tyr Trp Ser Tyr Val Leu
        115                 120                 125

Thr Gln Pro Pro Ser Val Ser Val Ala Pro Gly Gln Thr Ala Arg Ile
    130                 135                 140

Thr Cys Gly Gly Asn Asn Ile Gly Ser Lys Ser Val His Trp Tyr Gln
145                 150                 155                 160

Gln Lys Pro Gly Gln Ala Pro Val Leu Val Val Tyr Asp Asp Ser Asp
                165                 170                 175

Arg Pro Ser Gly Ile Pro Glu Arg Phe Ser Gly Ser Asn Ser Gly Asn
            180                 185                 190

Thr Ala Thr Leu Thr Ile Ser Arg Val Glu Ala Gly Asp Glu Ala Asp
        195                 200                 205

Tyr Tyr Cys Gln Val Trp Asp Ser Ser Ser Asp His Val Val Phe Gly
    210                 215                 220

Gly Gly Thr Lys Leu Thr Val Leu Cys Gln Val Trp Asp Ser Ser Ser
225                 230                 235                 240

Asp His Val Val Phe
                245
```

<210> SEQ ID NO 769
<211> LENGTH: 243
<212> TYPE: PRT
<213> ORGANISM: Mus musculus

<400> SEQUENCE: 769

Pro Gly Ala Ser Val Lys Val Ser Cys Lys Ala Ser Gly Tyr Thr Phe
1               5                   10                  15

Thr Ser Tyr Gly Ile Ser Trp Val Arg Gln Ala Pro Gly Gln Gly Leu
            20                  25                  30

Glu Trp Met Gly Trp Ile Ser Ala Tyr Asn Gly Asn Thr Asn Tyr Ala
        35                  40                  45

Gln Lys Leu Gln Gly Arg Val Thr Met Thr Thr Asp Thr Ser Thr Ser
    50                  55                  60

Thr Ala Tyr Met Glu Leu Arg Ser Leu Arg Ser Asp Asp Thr Ala Val
65                  70                  75                  80

Tyr Tyr Cys Ala Arg Val Trp Gly Lys Asn Gly Asp Phe Asp Tyr Trp
                85                  90                  95

Gly Gln Gly Thr Leu Val Thr Val Ser Ser Cys Ala Arg Val Trp Gly
            100                 105                 110

Lys Asn Gly Asp Phe Asp Tyr Trp Gln Ser Val Leu Thr Gln Pro Pro
        115                 120                 125

Ser Val Ser Ala Ala Pro Gly Gln Lys Val Thr Ile Ser Cys Ser Gly
    130                 135                 140

Ser Ser Ser Asn Ile Gly Asn Asn Tyr Val Ser Trp Tyr Gln Gln Leu
145                 150                 155                 160

Pro Gly Thr Ala Pro Lys Leu Leu Ile Tyr Asp Asn Asn Lys Arg Pro
                165                 170                 175

Ser Gly Ile Pro Asp Arg Phe Ser Gly Ser Lys Ser Gly Thr Ser Ala
            180                 185                 190

Thr Leu Gly Ile Thr Gly Leu Gln Thr Gly Asp Glu Ala Asp Tyr Tyr
        195                 200                 205

Cys Gly Thr Trp Asp Ser Ser Leu Ser Ala Tyr Val Phe Gly Thr Gly
    210                 215                 220

Thr Lys Val Thr Val Leu Cys Gly Thr Trp Asp Ser Ser Leu Ser Ala
225                 230                 235                 240

Tyr Val Phe

<210> SEQ ID NO 770
<211> LENGTH: 232
<212> TYPE: PRT
<213> ORGANISM: Mus musculus

<400> SEQUENCE: 770

Pro Gly Ala Ser Val Lys Val Ser Cys Lys Ala Ser Gly Tyr Thr Phe
1               5                   10                  15

Thr Thr Tyr Ala Met Asn Trp Val Arg Gln Ala Pro Gly Gln Gly Leu
            20                  25                  30

Glu Trp Met Gly Gly Ile Asn Thr Asn Thr Gly Asp Pro Thr Tyr Ala
        35                  40                  45

Gln Gly Ser Thr Gly Arg Phe Val Phe Ser Ser Asp Thr Ser Val Ser
    50                  55                  60

Thr Ala Tyr Leu Gln Ile Ser Ser Leu Lys Pro Glu Asp Thr Ala Val
65                  70                  75                  80

-continued

```
Tyr Tyr Cys Ala Arg Asp Arg Phe His Tyr Gly Met Asp Val Trp Gly
                85                  90                  95

Gln Gly Thr Thr Val Thr Val Ser Ser Cys Ala Arg Asp Arg Phe His
            100                 105                 110

Tyr Gly Met Asp Val Trp Thr Gln Ser Pro Asp Thr Leu Ser Val Ser
        115                 120                 125

Pro Gly Asp Gly Ala Thr Leu Ser Cys Arg Ala Ser Glu Gly Ile Arg
    130                 135                 140

Thr Ser Val Ala Trp Tyr Gln Gln Arg Pro Gly Gln Ala Pro Arg Leu
145                 150                 155                 160

Leu Ile Tyr Gly Ala Ser Thr Arg Ala Ala Gly Val Pro Ala Arg Phe
                165                 170                 175

Ser Gly Ser Gly Ser Gly Thr Glu Phe Thr Leu Thr Ile Ser Ser Leu
            180                 185                 190

Gln Ser Asp Asp Phe Ala Val Tyr Tyr Cys Gln Gln Thr His Thr Trp
        195                 200                 205

Pro Trp Thr Phe Gly Gln Gly Thr Lys Ala Glu Ile Lys Cys Gln Gln
    210                 215                 220

Thr His Thr Trp Pro Trp Thr Phe
225                 230


<210> SEQ ID NO 771
<211> LENGTH: 228
<212> TYPE: PRT
<213> ORGANISM: Mus musculus

<400> SEQUENCE: 771

Pro Gly Ala Ser Val Lys Val Ser Cys Lys Ala Ser Gly Tyr Thr Phe
1               5                   10                  15

Thr Ser Tyr Gly Ile Ser Trp Val Arg Gln Ala Pro Gly Gln Gly Leu
            20                  25                  30

Glu Trp Met Gly Trp Ile Ser Ala Tyr Asn Gly Asn Thr Asn Tyr Ala
        35                  40                  45

Gln Lys Leu Gln Gly Arg Val Thr Met Thr Thr Asp Thr Ser Thr Ser
    50                  55                  60

Thr Ala Tyr Met Glu Leu Arg Ser Leu Arg Ser Asp Asp Thr Ala Val
65                  70                  75                  80

Tyr Tyr Cys Ala Arg Asp Arg Gly Asp Tyr Trp Gly Gln Gly Thr Leu
                85                  90                  95

Val Thr Val Ser Ser Cys Ala Arg Asp Arg Gly Asp Tyr Trp Asp Ile
            100                 105                 110

Gln Met Thr Gln Ser Pro Ser Ser Val Ser Ala Ser Val Gly Asp Arg
        115                 120                 125

Val Thr Ile Thr Cys Arg Ala Ser Gln Gly Thr Ser Ser Trp Leu Ala
    130                 135                 140

Trp Tyr Gln Gln Lys Pro Gly Lys Ala Pro Lys Leu Leu Ile Tyr Ala
145                 150                 155                 160

Ala Ser Ser Leu Gln Ser Gly Val Pro Ser Arg Phe Ser Gly Ser Gly
                165                 170                 175

Ser Gly Thr Asp Phe Thr Leu Thr Ile Ser Ser Leu Gln Pro Glu Asp
            180                 185                 190

Phe Ala Thr Tyr Tyr Cys Gln Gln Ala Asn Ser Phe Pro Leu Thr Phe
        195                 200                 205

Gly Gly Gly Thr Lys Val Glu Ile Lys Cys Gln Gln Ala Asn Ser Phe
    210                 215                 220
```

Pro Leu Thr Phe
225

<210> SEQ ID NO 772
<211> LENGTH: 250
<212> TYPE: PRT
<213> ORGANISM: Mus musculus

<400> SEQUENCE: 772

Pro Gly Gly Ser Leu Arg Leu Ser Cys Ala Ala Ser Gly Phe Thr Phe
1 5 10 15

Asn Asn Ala Trp Met Ser Trp Val Arg Gln Ala Pro Gly Lys Gly Leu
20 25 30

Glu Trp Val Gly Arg Ile Lys Ser Lys Thr Asp Gly Gly Thr Thr Asp
35 40 45

Tyr Gly Ala Pro Val Lys Gly Arg Phe Thr Ile Ser Arg Asp Asp Ser
50 55 60

Lys Asn Thr Leu Tyr Leu Gln Met Asn Ser Leu Lys Thr Glu Asp Thr
65 70 75 80

Ala Val Tyr Tyr Cys Thr Thr Glu Gly Val Glu Leu Leu Ser Phe Gly
85 90 95

Gly Ala Pro Phe Asp Tyr Trp Gly Gln Gly Thr Leu Val Thr Val Ser
100 105 110

Ser Cys Thr Thr Glu Gly Val Glu Leu Leu Ser Phe Gly Gly Ala Pro
115 120 125

Phe Asp Tyr Trp Asp Ile Gln Met Thr Gln Ser Pro Ser Ser Leu Ser
130 135 140

Ala Ser Val Gly Asp Arg Val Thr Ile Thr Cys Arg Ala Ser Gln Ser
145 150 155 160

Ile Ser Ser Tyr Leu Asn Trp Tyr Gln Gln Lys Pro Gly Lys Ala Pro
165 170 175

Lys Leu Leu Ile Tyr Ala Ala Ser Ser Leu Gln Ser Gly Val Pro Ser
180 185 190

Arg Phe Ser Gly Ser Gly Ser Gly Thr Asp Phe Thr Leu Thr Ile Ser
195 200 205

Ser Leu Gln Pro Glu Asp Phe Ala Thr Tyr Tyr Cys Gln Gln Ser Tyr
210 215 220

Ser Thr Pro Tyr Thr Phe Gly Gln Gly Thr Lys Leu Glu Ile Lys Cys
225 230 235 240

Gln Gln Ser Tyr Ser Thr Pro Tyr Thr Phe
245 250

<210> SEQ ID NO 773
<211> LENGTH: 238
<212> TYPE: PRT
<213> ORGANISM: Mus musculus

<400> SEQUENCE: 773

Pro Gly Gly Ser Leu Arg Leu Ser Cys Ala Ala Ser Gly Phe Thr Phe
1 5 10 15

Ser Ser Tyr Glu Met Asn Trp Val Arg Gln Ala Pro Gly Lys Gly Leu
20 25 30

Glu Trp Val Ser Tyr Ile Ser Ser Ser Gly Ser Thr Ile Tyr Tyr Ala
35 40 45

Asp Ser Val Lys Gly Arg Phe Thr Ile Ser Arg Asp Asn Ala Lys Asn
50 55 60

```
Ser Leu Tyr Leu Gln Met Asn Ser Leu Arg Ala Glu Asp Thr Ala Val
65                  70                  75                  80

Tyr Tyr Cys Ala Arg Arg Arg Gly Gly Gly Phe Asp Tyr Trp Gly Gln
                85                  90                  95

Gly Thr Leu Val Thr Val Ser Ser Cys Ala Arg Arg Arg Gly Gly Gly
            100                 105                 110

Phe Asp Tyr Trp Gln Ser Ala Leu Thr Gln Pro Ala Ser Val Ser Gly
        115                 120                 125

Ser Pro Gly Gln Ser Ile Thr Ile Ser Cys Thr Gly Thr Ser Ser Asp
    130                 135                 140

Val Gly Gly Tyr Asn Tyr Val Ser Trp Tyr Gln Gln His Pro Gly Lys
145                 150                 155                 160

Ala Pro Lys Leu Met Ile Tyr Asp Val Ser Asn Arg Pro Ser Gly Val
                165                 170                 175

Ser Asn Arg Phe Ser Gly Ser Lys Ser Gly Asn Thr Ala Ser Leu Thr
            180                 185                 190

Ile Ser Gly Leu Gln Ala Glu Asp Glu Ala Asp Tyr Tyr Cys Ser Ser
        195                 200                 205

Tyr Thr Ser Ser Ser Thr Tyr Val Phe Gly Thr Gly Thr Lys Val Thr
    210                 215                 220

Val Leu Cys Ser Ser Tyr Thr Ser Ser Ser Thr Tyr Val Phe
225                 230                 235


<210> SEQ ID NO 774
<211> LENGTH: 229
<212> TYPE: PRT
<213> ORGANISM: Mus musculus

<400> SEQUENCE: 774

Pro Gly Gly Ser Leu Arg Leu Ser Cys Ala Ala Ser Gly Phe Thr Phe
1               5                   10                  15

Ser Ser Tyr Trp Met Ser Trp Val Arg Gln Ala Pro Gly Lys Gly Leu
            20                  25                  30

Glu Trp Val Ala Asn Ile Lys Gln Asp Gly Ser Glu Lys Tyr Tyr Val
        35                  40                  45

Asp Ser Val Gly Gly Arg Phe Thr Ile Ser Arg Asp Asn Ala Lys Asn
    50                  55                  60

Ser Leu Tyr Leu Gln Met Asn Ser Leu Arg Ala Glu Asp Thr Ala Val
65                  70                  75                  80

Tyr Tyr Cys Ala Arg Glu Lys Gly Ser Trp Phe Asp Pro Trp Gly Gln
                85                  90                  95

Gly Thr Leu Val Thr Val Ser Ser Cys Ala Arg Glu Lys Gly Ser Trp
            100                 105                 110

Phe Asp Pro Trp Thr Gln Ser Pro Gly Thr Leu Ser Leu Ser Pro Gly
        115                 120                 125

Glu Arg Ala Thr Leu Ser Cys Arg Ala Ser Gln Ser Val Ser Asn Asn
    130                 135                 140

Tyr Leu Ala Trp Tyr Gln Gln Lys Pro Gly Gln Ala Pro Arg Leu Leu
145                 150                 155                 160

Ile Tyr Gly Ala Ser Ser Arg Ala Thr Gly Ile Pro Asp Arg Phe Ser
                165                 170                 175

Gly Asn Gly Ser Gly Thr Asp Phe Thr Leu Thr Ile Ser Arg Leu Glu
            180                 185                 190

Pro Glu Asp Phe Ala Val Tyr Tyr Cys Gln Arg Tyr Gly Ser Ser Pro
```

```
        195                 200                 205

Arg Phe Gly Gly Gly Thr Lys Val Glu Ile Lys Cys Gln Arg Tyr Gly
    210                 215                 220

Ser Ser Pro Arg Phe
225


<210> SEQ ID NO 775
<211> LENGTH: 233
<212> TYPE: PRT
<213> ORGANISM: Mus musculus

<400> SEQUENCE: 775

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Lys Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Asp Lys Gly Tyr Tyr Gly Met Asp Val Trp Gly
                85                  90                  95

Gln Gly Thr Thr Val Thr Val Ser Ser Cys Ala Arg Asp Lys Gly Tyr
            100                 105                 110

Tyr Gly Met Asp Val Trp Met Thr Gln Ser Pro Ser Phe Leu Ser Ala
        115                 120                 125

Ser Val Gly Asp Arg Val Thr Ile Thr Cys Arg Ala Ser Gln Gly Ile
    130                 135                 140

Asn Ser Tyr Leu Val Trp Tyr Lys Gln Lys Pro Gly Lys Ala Pro Asp
145                 150                 155                 160

Leu Leu Ile Tyr Ala Ala Ser Thr Leu Gln Ser Gly Val Pro Ser Arg
                165                 170                 175

Phe Ser Gly Ser Gly Ser Gly Thr Asp Phe Thr Leu Thr Ile Ser Ser
            180                 185                 190

Leu Gln Pro Glu Asp Phe Ala Thr Tyr Tyr Cys Gln Gln Val His Ser
        195                 200                 205

Phe Pro Phe Thr Phe Gly Pro Gly Thr Lys Val Glu Ile Lys Cys Gln
    210                 215                 220

Gln Val His Ser Phe Pro Phe Thr Phe
225                 230


<210> SEQ ID NO 776
<211> LENGTH: 245
<212> TYPE: PRT
<213> ORGANISM: Mus musculus

<400> SEQUENCE: 776

Pro Gly Gly Ser Leu Arg Leu Ser Cys Ala Ala Ser Gly Phe Thr Phe
1               5                   10                  15

Ser Ser Tyr Gly Ile Asn Trp Val Arg Gln Ala Pro Gly Lys Gly Leu
            20                  25                  30

Glu Trp Val Ser Tyr Ile Ser Ser Arg Gly Ser Thr Ile Leu Tyr Ala
        35                  40                  45

Asp Ser Val Lys Gly Arg Phe Thr Ile Ser Arg Asp Asn Ala Arg Asn
```

```
    50                  55                  60

Ser Val His Leu Gln Met Asn Ser Leu Arg Asp Glu Asp Thr Ala Val
65                  70                  75                  80

Tyr Tyr Cys Ala Arg Asp Arg Gly Asp Arg Val Gly Gly Leu Val Phe
                85                  90                  95

Asp Tyr Trp Gly Gln Gly Ser Leu Val Thr Val Ser Ser Cys Ala Arg
            100                 105                 110

Asp Arg Gly Asp Arg Val Gly Gly Leu Val Phe Asp Tyr Trp Val Leu
        115                 120                 125

Thr Gln Pro Pro Ser Val Ser Val Ala Pro Gly Gln Thr Ala Arg Ile
    130                 135                 140

Thr Cys Gly Gly Asn Asn Ile Gly Ser Lys Ser Val His Trp Tyr Gln
145                 150                 155                 160

Gln Lys Pro Gly Gln Ala Pro Val Leu Val Val Tyr Asp Asp Ser Asp
                165                 170                 175

Arg Pro Ser Gly Ile Pro Glu Arg Phe Ser Gly Ser Asn Ser Gly Asn
            180                 185                 190

Thr Ala Thr Leu Thr Ile Ser Arg Val Glu Ala Gly Asp Glu Ala Asp
        195                 200                 205

Tyr Tyr Cys Gln Val Trp Asp Ser Ser Ser Asp His Val Val Phe Gly
    210                 215                 220

Gly Gly Thr Lys Leu Thr Val Leu Cys Gln Val Trp Asp Ser Ser Ser
225                 230                 235                 240

Asp His Val Val Phe
                245


<210> SEQ ID NO 777
<211> LENGTH: 234
<212> TYPE: PRT
<213> ORGANISM: Mus musculus

<400> SEQUENCE: 777

Pro Gly Glu Ser Leu Lys Ile Ser Cys Lys Gly Ser Gly Tyr Ser Phe
1               5                   10                  15

Thr Thr Tyr Trp Ile Ala Trp Val Arg Gln Met Pro Gly Lys Gly Leu
            20                  25                  30

Glu Trp Met Gly Ile Ile Tyr Pro Gly Asp Ser Asp Thr Thr Tyr Ser
        35                  40                  45

Pro Ser Phe Gln Gly Gln Val Thr Ile Ser Ala Asp Lys Ser Ile Thr
    50                  55                  60

Thr Thr Tyr Leu Gln Trp Ser Ser Leu Lys Ala Ser Asp Thr Ala Met
65                  70                  75                  80

Tyr Tyr Cys Ala Arg Gln Val Ala Gly Gly Leu Asp Tyr Trp Gly Gln
                85                  90                  95

Gly Thr Leu Val Thr Val Ser Ser Cys Ala Arg Gln Val Ala Gly Gly
            100                 105                 110

Leu Asp Tyr Trp Asp Ile Val Leu Thr Gln Ser Pro Ser Ser Leu Ser
        115                 120                 125

Ala Ser Val Gly Asp Arg Val Thr Ile Thr Cys Arg Ala Ser Gln Ala
    130                 135                 140

Val Arg Ile Asp Leu Ser Trp Tyr Gln Gln Lys Pro Gly Lys Ala Pro
145                 150                 155                 160

Glu Arg Leu Ile Phe Gly Ala Ser Gly Leu Gln Arg Gly Val Pro Ser
                165                 170                 175
```

```
Arg Phe Ser Gly Ser Gly Ser Gly Thr Glu Phe Thr Leu Thr Ile Ser
            180                 185                 190

Ser Leu Gln Pro Glu Asp Phe Ala Thr Tyr Tyr Cys Leu Gln His Asn
        195                 200                 205

Thr Phe Pro Tyr Thr Phe Gly Gln Gly Thr Lys Leu Glu Ile Lys Cys
    210                 215                 220

Leu Gln His Asn Thr Phe Pro Tyr Thr Phe
225                 230


<210> SEQ ID NO 778
<211> LENGTH: 236
<212> TYPE: PRT
<213> ORGANISM: Mus musculus

<400> SEQUENCE: 778

Pro Gly Ala Ser Val Lys Val Ser Cys Lys Ala Ser Gly Tyr Thr Phe
1               5                   10                  15

Thr Ser Tyr Gly Ile Ser Trp Val Arg Gln Ala Pro Gly Gln Gly Leu
            20                  25                  30

Glu Trp Met Gly Trp Ile Ser Ala Tyr Asn Gly Asn Thr Asn Tyr Ala
        35                  40                  45

Gln Lys Leu Gln Gly Arg Val Thr Met Thr Thr Asp Thr Ser Thr Ser
    50                  55                  60

Thr Ala Tyr Met Glu Leu Arg Ser Leu Arg Ser Asp Asp Thr Ala Val
65                  70                  75                  80

Tyr Tyr Cys Ala Arg Asp Arg Gly Tyr Tyr Gly Met Asp Val Trp Gly
                85                  90                  95

Gln Gly Thr Thr Val Thr Val Ser Ser Cys Ala Arg Asp Arg Gly Tyr
            100                 105                 110

Tyr Gly Met Asp Val Trp Asp Ile Gln Met Thr Gln Ser Pro Ser Ser
        115                 120                 125

Leu Ser Ala Ser Val Gly Asp Arg Val Thr Ile Thr Cys Arg Ala Ser
    130                 135                 140

Gln Ser Ile Ser Arg Tyr Leu Asn Trp Tyr Gln Gln Lys Pro Gly Lys
145                 150                 155                 160

Asp Pro Lys Leu Leu Ile Tyr Ala Ala Ser Ser Leu Gln Ser Gly Val
                165                 170                 175

Pro Ser Arg Phe Ser Gly Ser Gly Ser Gly Thr Asp Phe Thr Leu Thr
            180                 185                 190

Ile Ser Ser Leu Gln Pro Glu Asp Phe Ala Thr Tyr Tyr Cys Gln Gln
        195                 200                 205

Ser His Ser Thr Pro Leu Thr Phe Gly Gly Gly Thr Lys Val Glu Ile
    210                 215                 220

Lys Cys Gln Gln Ser His Ser Thr Pro Leu Thr Phe
225                 230                 235


<210> SEQ ID NO 779
<211> LENGTH: 229
<212> TYPE: PRT
<213> ORGANISM: Mus musculus

<400> SEQUENCE: 779

Pro Gly Glu Ser Leu Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
            20                  25                  30
```

-continued

```
Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Phe Arg Phe Gly Glu Gly Phe Asp Tyr Trp Gly Gln Gly
                85                  90                  95

Thr Leu Val Thr Val Ser Ser Cys Phe Arg Phe Gly Glu Gly Phe Asp
            100                 105                 110

Tyr Trp Met Thr Gln Ser Pro Ser Thr Leu Ser Ala Ser Val Gly Asp
        115                 120                 125

Arg Val Thr Ile Thr Cys Arg Ala Ser Gln Ser Ile Gly Tyr Trp Leu
    130                 135                 140

Ala Trp Tyr Gln Gln Arg Pro Gly Arg Ala Pro Lys Leu Leu Met Tyr
145                 150                 155                 160

Arg Ala Ser Asn Leu Lys Ser Gly Val Pro Ser Arg Phe Ser Gly Ser
                165                 170                 175

Gly Ser Gly Thr Glu Phe Thr Leu Thr Ile Ser Ser Leu Gln Pro Asp
            180                 185                 190

Asp Phe Ala Thr Tyr Tyr Cys Gln Gln Tyr Asn Ser Tyr Pro Phe Thr
        195                 200                 205

Phe Gly Pro Gly Thr Lys Val Asp Ile Lys Cys Gln Gln Tyr Asn Ser
    210                 215                 220

Tyr Pro Phe Thr Phe
225


<210> SEQ ID NO 780
<211> LENGTH: 239
<212> TYPE: PRT
<213> ORGANISM: Mus musculus

<400> SEQUENCE: 780

Pro Gly Glu Ser Leu Lys Ile Ser Cys Lys Gly Ser Gly Tyr Ser Phe
1               5                   10                  15

Thr Thr Tyr Trp Ile Ala Trp Val Arg Gln Met Pro Gly Lys Gly Leu
            20                  25                  30

Glu Trp Met Gly Ile Ile Tyr Pro Gly Asp Ser Asp Thr Thr Tyr Ser
        35                  40                  45

Pro Ser Phe Gln Gly Gln Val Thr Ile Ser Ala Asp Lys Ser Ile Thr
    50                  55                  60

Thr Thr Tyr Leu Gln Trp Ser Ser Leu Lys Ala Ser Asp Thr Ala Met
65                  70                  75                  80

Tyr Tyr Cys Ala Arg Gln Val Ala Gly Gly Leu Asp Tyr Trp Gly Gln
                85                  90                  95

Gly Thr Leu Val Thr Val Ser Ser Cys Ala Arg Gln Val Ala Gly Gly
            100                 105                 110

Leu Asp Tyr Trp Gln Ser Val Leu Thr Gln Pro Pro Ser Ala Ser Gly
        115                 120                 125

Thr Pro Gly Gln Arg Val Thr Ile Ser Cys Ser Gly Ser Ser Ser Asn
    130                 135                 140

Val Gly Ser Asn Tyr Val Ser Trp Tyr Gln Gln Leu Pro Gly Thr Ala
145                 150                 155                 160

Pro Lys Leu Leu Ile Gln Arg Asn Asn Arg Arg Pro Ser Gly Val Pro
                165                 170                 175
```

```
Asp Arg Phe Ser Gly Ser Lys Ser Gly Thr Ser Ala Ser Leu Ala Ile
            180                 185                 190

Ser Gly Leu Arg Ser Glu Asp Glu Ala Asp Tyr Tyr Cys Ala Ala Trp
        195                 200                 205

Asp Asp Ser Leu Ser Gly Val Val Phe Gly Gly Gly Thr Lys Leu Thr
    210                 215                 220

Val Leu Cys Ala Ala Trp Asp Asp Ser Leu Ser Gly Val Val Phe
225                 230                 235


<210> SEQ ID NO 781
<211> LENGTH: 235
<212> TYPE: PRT
<213> ORGANISM: Mus musculus

<400> SEQUENCE: 781

Pro Gly Glu Ser Leu Lys Ile Ser Cys Lys Ser Ser Gly Tyr Ser Phe
1               5                   10                  15

Asn Thr Tyr Trp Ile Gly Trp Val Arg Gln Met Pro Gly Lys Gly Leu
            20                  25                  30

Glu Trp Met Gly Ile Ile Tyr Pro Ser Asp Ser Asp Thr Arg Tyr Ser
        35                  40                  45

Pro Ser Phe Gln Gly Gln Val Thr Ile Ser Ala Asp Lys Ser Ile Asn
    50                  55                  60

Thr Ala Tyr Leu Gln Trp Ser Ser Leu Lys Ala Ser Asp Ser Ala Met
65                  70                  75                  80

Tyr Tyr Cys Ala Arg Asp Gly Gly Tyr Tyr Phe Asp Asp Trp Gly Gln
                85                  90                  95

Gly Thr Leu Val Thr Val Ser Ser Cys Ala Arg Asp Gly Gly Tyr Tyr
            100                 105                 110

Phe Asp Asp Trp Thr Gln Ser Pro Gly Thr Leu Ser Leu Ser Pro Gly
        115                 120                 125

Glu Arg Ala Thr Leu Ser Cys Arg Ala Ser Gln Ser Val Ser Ser Thr
    130                 135                 140

Tyr Leu Ala Trp Tyr Gln Gln Lys Pro Gly Gln Ala Pro Arg Leu Leu
145                 150                 155                 160

Ile Tyr Gly Thr Ser Arg Arg Ala Thr Gly Ile Pro Asp Arg Phe Ser
                165                 170                 175

Gly Ser Gly Ser Gly Thr Asp Phe Thr Leu Thr Ile Ser Arg Leu Glu
            180                 185                 190

Pro Glu Asp Phe Ala Val Tyr Tyr Cys Gln Gln Tyr Asn Ser Ser Pro
        195                 200                 205

Leu Met Tyr Thr Phe Gly Gln Gly Thr Arg Leu Glu Ile Lys Cys Gln
    210                 215                 220

Gln Tyr Asn Ser Ser Pro Leu Met Tyr Thr Phe
225                 230                 235


<210> SEQ ID NO 782
<211> LENGTH: 236
<212> TYPE: PRT
<213> ORGANISM: Mus musculus

<400> SEQUENCE: 782

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30
```

```
Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Lys Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Asp Lys Gly Tyr Tyr Gly Met Asp Val Trp Gly
                85                  90                  95

Gln Gly Thr Thr Val Thr Val Ser Pro Cys Ala Arg Asp Lys Gly Tyr
            100                 105                 110

Tyr Gly Met Asp Val Trp Asp Ile Val Met Thr Gln Ser Pro Ser Ser
        115                 120                 125

Leu Ser Ala Ser Ile Gly Asp Arg Val Thr Ile Thr Cys Arg Ala Ser
    130                 135                 140

Gln Ser Ile Lys Asn Tyr Leu Asn Trp Tyr Gln Gln Lys Pro Gly Lys
145                 150                 155                 160

Ala Pro Lys Leu Leu Ile Tyr Ala Ala Ser Ser Leu Gln Asn Gly Val
                165                 170                 175

Pro Ser Arg Phe Ser Gly Ser Gly Ser Gly Thr Asp Phe Thr Val Thr
            180                 185                 190

Ile Ser Ser Leu Gln Pro Glu Asp Phe Ala Ile Tyr Tyr Cys Gln Gln
        195                 200                 205

Thr Tyr Ser Thr Pro Leu Thr Phe Gly Gly Gly Thr Asn Val Glu Ile
    210                 215                 220

Lys Cys Gln Gln Thr Tyr Ser Thr Pro Leu Thr Phe
225                 230                 235


<210> SEQ ID NO 783
<211> LENGTH: 230
<212> TYPE: PRT
<213> ORGANISM: Mus musculus

<400> SEQUENCE: 783

Pro Gly Ser Ser Val Lys Val Ser Cys Lys Ala Ser Gly Tyr Thr Phe
1               5                   10                  15

Thr Ser Tyr Gly Ile Ser Trp Val Arg Gln Ala Pro Gly Gln Gly Leu
            20                  25                  30

Glu Trp Met Gly Trp Ile Ser Ala Tyr Asn Gly Asn Thr Asn Tyr Ala
        35                  40                  45

Gln Lys Leu Gln Gly Arg Val Thr Met Thr Thr Asp Thr Ser Thr Ser
    50                  55                  60

Thr Ala Tyr Met Glu Leu Arg Gly Leu Arg Ser Asp Asp Thr Ala Val
65                  70                  75                  80

Tyr Tyr Cys Ala Arg Asp Phe Arg Met Asp Val Trp Gly Gln Gly Thr
                85                  90                  95

Thr Val Thr Val Ser Ser Cys Ala Arg Asp Phe Arg Met Asp Val Trp
            100                 105                 110

Asp Ile Arg Leu Thr Gln Ser Pro Ser Ser Val Ala Ser Ser Val Gly
        115                 120                 125

Asp Ser Val Thr Val Thr Cys Arg Ala Ser Gln Asp Ile Lys Arg Arg
    130                 135                 140

Leu Ala Trp Tyr Leu Gln Lys Pro Gly Gln Ala Pro Lys Leu Leu Ile
145                 150                 155                 160

Phe Asp Ala Ser Arg Leu His Thr Gly Val Pro Ser Arg Phe Ser Gly
```

```
                165                 170                 175

Ser Gly Ser Gly Thr Asp Phe Thr Leu Ile Ile Asn Ser Leu Gln Pro
            180                 185                 190

Glu Asp Phe Gly Thr Tyr Tyr Cys Gln Gln Ala Asn Thr Phe Pro Gln
        195                 200                 205

Thr Phe Gly Gln Gly Thr Lys Val Glu Ile Lys Cys Gln Gln Ala Asn
    210                 215                 220

Thr Phe Pro Gln Thr Phe
225                 230


<210> SEQ ID NO 784
<211> LENGTH: 237
<212> TYPE: PRT
<213> ORGANISM: Mus musculus

<400> SEQUENCE: 784

Pro Gly Gly Ser Leu Arg Leu Ser Cys Ala Ala Ser Gly Phe Thr Phe
1               5                   10                  15

Arg Arg Tyr Trp Met Thr Trp Val Arg Gln Ala Pro Gly Lys Gly Leu
            20                  25                  30

Glu Trp Val Ala Asn Ile Lys Gln Asp Gly Ser Glu Lys Tyr Tyr Val
        35                  40                  45

Asp Ser Val Lys Gly Arg Phe Ala Val Ser Arg Asp Asn Ala Asn Asn
    50                  55                  60

Ser Leu Tyr Leu Arg Met Asn Ser Leu Arg Ala Glu Asp Thr Ala Val
65                  70                  75                  80

Tyr Tyr Cys Ala Arg Asp Ala Tyr Ala Tyr Gly Leu Asp Val Trp Gly
                85                  90                  95

Gln Gly Thr Ala Val Thr Val Ser Ser Cys Ala Arg Asp Ala Tyr Ala
            100                 105                 110

Tyr Gly Leu Asp Val Trp Val Leu Thr Gln Pro His Ser Val Ser Glu
        115                 120                 125

Ser Pro Gly Lys Thr Val Thr Ile Ser Cys Thr Gly Ser Ser Gly Ser
    130                 135                 140

Ile Ala Ser Ser Tyr Val His Trp Tyr Gln Gln Arg Pro Gly Arg Val
145                 150                 155                 160

Pro Thr Pro Val Ile Tyr Glu Asp Asn Gln Arg Pro Ser Gly Val Pro
                165                 170                 175

Asp Arg Phe Ser Gly Ser Ile Asp Ser Ser Ser Asn Ser Ala Ser Leu
            180                 185                 190

Thr Ile Ser Gly Leu Lys Thr Glu Asp Glu Ala Asp Tyr Tyr Cys Gln
        195                 200                 205

Ser Tyr Asp Gly Ser Ser Val Val Phe Gly Gly Gly Thr Lys Leu Thr
    210                 215                 220

Val Leu Cys Gln Ser Tyr Asp Gly Ser Ser Val Val Phe
225                 230                 235


<210> SEQ ID NO 785
<211> LENGTH: 247
<212> TYPE: PRT
<213> ORGANISM: Mus musculus

<400> SEQUENCE: 785

Pro Gly Asp Leu Arg Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
```

```
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asp Tyr Gly Gly Trp Phe
                85                  90                  95

Asp Pro Trp Gly Gln Gly Thr Leu Val Thr Val Ser Ser Cys Ala Arg
            100                 105                 110

Leu Glu Asn Asn Trp Asp Tyr Gly Gly Trp Phe Asp Pro Trp Ser Tyr
        115                 120                 125

Val Leu Thr Gln Pro Pro Ser Val Ser Val Ala Pro Gly Gln Thr Ala
    130                 135                 140

Arg Ile Thr Cys Gly Gly Asn Asn Ile Gly Ser Lys Ser Val His Trp
145                 150                 155                 160

Tyr Gln Gln Lys Pro Gly Gln Ala Pro Val Leu Val Val Tyr Asp Asp
                165                 170                 175

Ser Asp Arg Pro Ser Gly Ile Pro Glu Arg Phe Ser Gly Ser Asn Ser
            180                 185                 190

Gly Asn Thr Ala Thr Leu Thr Ile Ser Arg Val Glu Ala Gly Asp Glu
        195                 200                 205

Ala Asp Tyr Tyr Cys Gln Val Trp Asp Ser Ser Ser Asp His Trp Val
    210                 215                 220

Phe Gly Gly Gly Thr Lys Leu Thr Val Leu Cys Gln Val Trp Asp Ser
225                 230                 235                 240

Ser Ser Asp His Trp Val Phe
                245


<210> SEQ ID NO 786
<211> LENGTH: 247
<212> TYPE: PRT
<213> ORGANISM: Mus musculus

<400> SEQUENCE: 786

Pro Gly Asn Leu Trp Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asp Tyr Gly Gly Trp Phe
                85                  90                  95

Asp Pro Trp Gly Gln Gly Thr Leu Val Thr Val Ser Ser Cys Ala Arg
            100                 105                 110

Leu Glu Asn Asn Trp Asp Tyr Gly Gly Trp Phe Asp Pro Trp Ser Tyr
        115                 120                 125

Val Leu Thr Gln Pro Pro Ser Val Ser Val Ala Pro Gly Gln Thr Ala
    130                 135                 140
```

```
Arg Ile Thr Cys Gly Gly Asn Asn Ile Gly Ser Lys Ser Val His Trp
145                 150                 155                 160

Tyr Gln Gln Lys Pro Gly Gln Ala Pro Val Leu Val Val Tyr Asp Asp
                165                 170                 175

Ser Asp Arg Pro Ser Gly Ile Pro Glu Arg Phe Ser Gly Ser Asn Ser
            180                 185                 190

Gly Asn Thr Ala Thr Leu Thr Ile Ser Arg Val Glu Ala Gly Asp Glu
        195                 200                 205

Ala Asp Tyr Tyr Cys Gln Val Trp Asp Ser Ser Ser Asp His Trp Val
    210                 215                 220

Phe Gly Gly Gly Thr Lys Leu Thr Val Leu Cys Gln Val Trp Asp Ser
225                 230                 235                 240

Ser Ser Asp His Trp Val Phe
                245


<210> SEQ ID NO 787
<211> LENGTH: 247
<212> TYPE: PRT
<213> ORGANISM: Mus musculus

<400> SEQUENCE: 787

Pro Gly Asn Leu Leu Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asp Tyr Gly Gly Trp Phe
                85                  90                  95

Asp Pro Trp Gly Gln Gly Thr Leu Val Thr Val Ser Ser Cys Ala Arg
            100                 105                 110

Leu Glu Asn Asn Trp Asp Tyr Gly Gly Trp Phe Asp Pro Trp Ser Tyr
        115                 120                 125

Val Leu Thr Gln Pro Pro Ser Val Ser Val Ala Pro Gly Gln Thr Ala
    130                 135                 140

Arg Ile Thr Cys Gly Gly Asn Asn Ile Gly Ser Lys Ser Val His Trp
145                 150                 155                 160

Tyr Gln Gln Lys Pro Gly Gln Ala Pro Val Leu Val Val Tyr Asp Asp
                165                 170                 175

Ser Asp Arg Pro Ser Gly Ile Pro Glu Arg Phe Ser Gly Ser Asn Ser
            180                 185                 190

Gly Asn Thr Ala Thr Leu Thr Ile Ser Arg Val Glu Ala Gly Asp Glu
        195                 200                 205

Ala Asp Tyr Tyr Cys Gln Val Trp Asp Ser Ser Ser Asp His Trp Val
    210                 215                 220

Phe Gly Gly Gly Thr Lys Leu Thr Val Leu Cys Gln Val Trp Asp Ser
225                 230                 235                 240

Ser Ser Asp His Trp Val Phe
                245


<210> SEQ ID NO 788
```

<211> LENGTH: 233
<212> TYPE: PRT
<213> ORGANISM: Mus musculus

<400> SEQUENCE: 788

Pro Ser Gly Thr Leu Ser Leu Thr Cys Ala Val Ser Gly Gly Ser Ile
1 5 10 15

Ser Ser Ser Asn Trp Trp Ser Trp Val Arg Gln Pro Pro Gly Lys Gly
20 25 30

Leu Glu Trp Ile Gly Glu Ile Tyr His Ser Gly Ser Thr Asn Tyr Asn
35 40 45

Pro Ser Leu Lys Ser Arg Val Thr Ile Ser Val Asp Lys Ser Lys Asn
50 55 60

Gln Phe Ser Leu Lys Leu Ser Ser Val Thr Ala Ala Asp Thr Ala Val
65 70 75 80

Tyr Tyr Cys Ala Arg Asp Leu Met Asn Tyr Gly Met Asp Val Trp Gly
85 90 95

Gln Gly Thr Thr Val Thr Val Ser Ser Cys Ala Arg Asp Leu Met Asn
100 105 110

Tyr Gly Met Asp Val Trp Met Thr Gln Ser Pro Ser Ser Leu Ser Ala
115 120 125

Ser Val Gly Asp Arg Val Thr Ile Thr Cys Arg Ala Ser Gln Ser Ile
130 135 140

Ser Ser Tyr Leu Asn Trp Tyr Gln Gln Lys Pro Gly Lys Ala Pro Lys
145 150 155 160

Leu Leu Ile Tyr Ala Ala Ser Ser Leu Gln Ser Gly Val Pro Ser Arg
165 170 175

Phe Ser Gly Ser Gly Ser Gly Thr Asp Phe Thr Leu Thr Ile Ser Ser
180 185 190

Leu Gln Pro Glu Asp Phe Ala Thr Tyr Tyr Cys Gln Gln Ser Tyr Ser
195 200 205

Thr Pro Pro Thr Phe Gly Gln Gly Thr Lys Val Glu Ile Lys Cys Gln
210 215 220

Gln Ser Tyr Ser Thr Pro Pro Thr Phe
225 230

<210> SEQ ID NO 789
<211> LENGTH: 243
<212> TYPE: PRT
<213> ORGANISM: Mus musculus

<400> SEQUENCE: 789

Pro Gly Arg Ser Leu Arg Leu Ser Cys Ala Ala Ser Gly Phe Thr Phe
1 5 10 15

Ser Ser Tyr Ala Met His Trp Val Arg Gln Ala Pro Gly Lys Gly Leu
20 25 30

Glu Trp Val Ala Val Ile Ser Tyr Asp Gly Ser Asn Lys Tyr Tyr Ala
35 40 45

Asp Ser Val Lys Gly Arg Phe Thr Ile Ser Arg Asp Ser Ser Lys Asn
50 55 60

Thr Leu Tyr Leu Gln Met Asn Ser Leu Arg Ala Glu Asp Thr Ala Val
65 70 75 80

Tyr Tyr Cys Ala Arg Asp Leu Leu Gly Ser Gly Tyr Asp Ile Ile Asp
85 90 95

Tyr Trp Gly Gln Gly Thr Leu Val Thr Val Ser Ser Cys Ala Arg Asp
100 105 110

```
Leu Leu Gly Ser Gly Tyr Asp Ile Ile Asp Tyr Trp Val Leu Thr Gln
        115                 120                 125

Ser Pro Ser Val Ser Val Ala Pro Gly Lys Thr Ala Arg Ile Thr Cys
    130                 135                 140

Gly Gly Asn Asn Ile Gly Ser Lys Ser Val His Trp Tyr Gln Gln Lys
145                 150                 155                 160

Pro Gly Gln Ala Pro Val Leu Val Val Tyr Asp Asp Ser Asp Arg Pro
                165                 170                 175

Ser Gly Ile Pro Glu Arg Phe Ser Gly Ser Asn Ser Gly Asn Thr Ala
            180                 185                 190

Thr Leu Thr Ile Ser Arg Val Glu Ala Gly Asp Glu Ala Asp Tyr Tyr
        195                 200                 205

Cys Gln Val Trp Asp Ser Ser Ser Asp His Val Val Phe Gly Gly Gly
    210                 215                 220

Thr Lys Leu Thr Val Leu Cys Gln Val Trp Asp Ser Ser Ser Asp His
225                 230                 235                 240

Val Val Phe


<210> SEQ ID NO 790
<211> LENGTH: 246
<212> TYPE: PRT
<213> ORGANISM: Mus musculus

<400> SEQUENCE: 790

Pro Gly Asp Leu Lys Ile Ser Cys Lys Gly Ser Gly Tyr Ser Phe Thr
1               5                   10                  15

Ser Tyr Trp Ile Gly Trp Val Arg Gln Met Pro Gly Lys Gly Leu Glu
            20                  25                  30

Trp Met Gly Ile Ile Tyr Pro Gly Asp Ser Asp Thr Arg Tyr Ser Pro
        35                  40                  45

Ser Phe Gln Gly Gln Val Thr Ile Ser Ala Asp Lys Ser Ile Ser Thr
    50                  55                  60

Ala Tyr Leu Gln Trp Ser Ser Leu Lys Ala Ser Asp Thr Ala Met Tyr
65                  70                  75                  80

Tyr Cys Ala Arg Leu Glu Asn Asn Trp Asp Tyr Gly Gly Trp Phe Asp
                85                  90                  95

Pro Trp Gly Gln Gly Thr Leu Val Thr Val Ser Ser Cys Ala Arg Leu
            100                 105                 110

Glu Asn Asn Trp Asp Tyr Gly Gly Trp Phe Asp Pro Trp Ser Tyr Val
        115                 120                 125

Leu Thr Gln Pro Pro Ser Val Ser Val Ala Pro Gly Gln Thr Ala Arg
    130                 135                 140

Ile Thr Cys Gly Gly Asn Asn Ile Gly Ser Lys Ser Val His Trp Tyr
145                 150                 155                 160

Gln Gln Lys Pro Gly Gln Ala Pro Val Leu Val Val Tyr Asp Asp Ser
                165                 170                 175

Asp Arg Pro Ser Gly Ile Pro Glu Arg Phe Ser Gly Ser Asn Ser Gly
            180                 185                 190

Asn Thr Ala Thr Leu Thr Ile Ser Arg Val Glu Ala Gly Asp Glu Ala
        195                 200                 205

Asp Tyr Tyr Cys Gln Val Trp Asp Ser Ser Ser Asp His Trp Val Phe
    210                 215                 220

Gly Gly Gly Thr Lys Leu Thr Val Leu Cys Gln Val Trp Asp Ser Ser
225                 230                 235                 240
```

Ser Asp His Trp Val Phe
245

<210> SEQ ID NO 791
<211> LENGTH: 243
<212> TYPE: PRT
<213> ORGANISM: Mus musculus

<400> SEQUENCE: 791

Pro Gly Gly Ser Leu Arg Leu Ser Cys Ala Ala Ser Gly Phe Thr Phe
1 5 10 15

Ser Ser Tyr Trp Met Ser Trp Val Arg Gln Ala Pro Gly Lys Gly Leu
20 25 30

Glu Trp Val Ala Asn Ile Lys Gln Asp Gly Ser Glu Lys Tyr Tyr Val
35 40 45

Asp Ser Val Lys Gly Arg Phe Thr Ile Ser Arg Asp Asn Ala Lys Asn
50 55 60

Ser Leu Tyr Leu Gln Met Asn Ser Leu Arg Ala Glu Asp Thr Ala Val
65 70 75 80

Tyr Tyr Cys Ala Arg Glu Tyr Asp Tyr Gly Asp Tyr Val Phe Asp Tyr
85 90 95

Trp Gly Gln Gly Thr Leu Val Thr Val Ser Ser Cys Ala Arg Glu Tyr
100 105 110

Asp Tyr Gly Asp Tyr Val Phe Asp Tyr Trp Tyr Glu Leu Thr Gln Pro
115 120 125

Pro Ser Met Ser Ala Thr Pro Gly Gln Lys Val Thr Ile Thr Cys Ser
130 135 140

Gly Ser Asn Ser Asn Val Gly Asn Asn Tyr Val Ser Trp Tyr Gln Gln
145 150 155 160

Val Pro Gly Thr Ala Pro Lys Leu Leu Ile Tyr Asp Asn Asp Arg Arg
165 170 175

Pro Ser Gly Ile Pro Asp Arg Phe Ser Gly Ala Lys Ser Gly Thr Ser
180 185 190

Ala Thr Leu Gly Ile Thr Gly Leu Gln Thr Gly Asp Glu Ala Asp Tyr
195 200 205

Tyr Cys Gly Ser Trp Glu Ala Arg Glu Ser Val Phe Val Phe Gly Gly
210 215 220

Gly Thr Lys Leu Thr Val Cys Gly Ser Trp Glu Ala Arg Glu Ser Val
225 230 235 240

Phe Val Phe

<210> SEQ ID NO 792
<211> LENGTH: 247
<212> TYPE: PRT
<213> ORGANISM: Mus musculus

<400> SEQUENCE: 792

Pro Gly Asp Leu Leu Lys Ile Ser Cys Lys Gly Ser Gly Tyr Ser Phe
1 5 10 15

Thr Ser Tyr Trp Ile Gly Trp Val Arg Gln Met Pro Gly Lys Gly Leu
20 25 30

Glu Trp Met Gly Ile Ile Tyr Pro Gly Asp Ser Asp Thr Arg Tyr Ser
35 40 45

Pro Ser Phe Gln Gly Gln Val Thr Ile Ser Ala Asp Lys Ser Ile Ser
50 55 60

-continued

```
Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asp Tyr Gly Gly Trp Phe
                85                  90                  95

Asp Pro Trp Gly Gln Gly Thr Leu Val Thr Val Ser Ser Cys Ala Arg
            100                 105                 110

Leu Glu Asn Asn Trp Asp Tyr Gly Gly Trp Phe Asp Pro Trp Ser Tyr
        115                 120                 125

Val Leu Thr Gln Pro Pro Ser Val Ser Val Ala Pro Gly Gln Thr Ala
    130                 135                 140

Arg Ile Thr Cys Gly Gly Asn Asn Ile Gly Ser Lys Ser Val His Trp
145                 150                 155                 160

Tyr Gln Gln Lys Pro Gly Gln Ala Pro Val Leu Val Val Tyr Asp Asp
                165                 170                 175

Ser Asp Arg Pro Ser Gly Ile Pro Glu Arg Phe Ser Gly Ser Asn Ser
            180                 185                 190

Gly Asn Thr Ala Thr Leu Thr Ile Ser Arg Val Glu Ala Gly Asp Glu
        195                 200                 205

Ala Asp Tyr Tyr Cys Gln Val Trp Asp Ser Ser Ser Asp His Trp Val
    210                 215                 220

Phe Gly Gly Gly Thr Lys Leu Thr Val Leu Cys Gln Val Trp Asp Ser
225                 230                 235                 240

Ser Ser Asp His Trp Val Phe
                245


<210> SEQ ID NO 793
<211> LENGTH: 247
<212> TYPE: PRT
<213> ORGANISM: Mus musculus

<400> SEQUENCE: 793

Arg Gly Asp Leu Leu Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asp Tyr Gly Gly Trp Phe
                85                  90                  95

Asp Pro Trp Gly Gln Gly Thr Leu Val Thr Val Ser Ser Cys Ala Arg
            100                 105                 110

Leu Glu Asn Asn Trp Asp Tyr Gly Gly Trp Phe Asp Pro Trp Ser Tyr
        115                 120                 125

Val Leu Thr Gln Pro Pro Ser Val Ser Val Ala Pro Gly Gln Thr Ala
    130                 135                 140

Arg Ile Thr Cys Gly Gly Asn Asn Ile Gly Ser Lys Ser Val His Trp
145                 150                 155                 160

Tyr Gln Gln Lys Pro Gly Gln Ala Pro Val Leu Val Val Tyr Asp Asp
                165                 170                 175

Ser Asp Arg Pro Ser Gly Ile Pro Glu Arg Phe Ser Gly Ser Asn Ser
            180                 185                 190
```

Gly Asn Thr Ala Thr Leu Thr Ile Ser Arg Val Glu Ala Gly Asp Glu
195 200 205

Ala Asp Tyr Tyr Cys Gln Val Trp Asp Ser Ser Ser Asp His Trp Val
210 215 220

Phe Gly Gly Gly Thr Lys Leu Thr Val Leu Cys Gln Val Trp Asp Ser
225 230 235 240

Ser Ser Asp His Trp Val Phe
245

<210> SEQ ID NO 794
<211> LENGTH: 238
<212> TYPE: PRT
<213> ORGANISM: Mus musculus

<400> SEQUENCE: 794

Pro Gly Ser Ser Val Lys Val Ser Cys Lys Ala Ser Gly Gly Thr Phe
1 5 10 15

Ser Ser Tyr Ala Ile Ser Trp Val Arg Gln Ala Pro Gly Gln Gly Leu
20 25 30

Glu Trp Met Gly Gly Ile Ile Pro Ile Phe Gly Thr Ala Asn Tyr Ala
35 40 45

Gln Lys Phe Gln Gly Arg Val Thr Ile Thr Ala Asp Glu Ser Thr Ser
50 55 60

Thr Ala Tyr Met Glu Leu Ser Ser Leu Arg Ser Glu Asp Thr Ala Val
65 70 75 80

Tyr Tyr Cys Ala Arg Glu Met Tyr Tyr Tyr Tyr Gly Met Asp Val Trp
85 90 95

Gly Gln Gly Thr Thr Val Thr Val Ser Ser Cys Ala Arg Glu Met Tyr
100 105 110

Tyr Tyr Tyr Gly Met Asp Val Trp Asp Ile Val Met Thr Gln Ser Pro
115 120 125

Ser Ser Leu Ser Ala Ser Val Gly Asp Arg Val Thr Ile Thr Cys Arg
130 135 140

Ala Ser Gln Ser Ile Ser Ser Tyr Leu Asn Trp Tyr Gln Gln Lys Pro
145 150 155 160

Gly Lys Ala Pro Lys Leu Leu Ile Tyr Ala Ala Ser Ser Leu Gln Ser
165 170 175

Gly Val Pro Ser Arg Phe Ser Gly Ser Gly Ser Gly Thr Asp Phe Thr
180 185 190

Leu Thr Ile Ser Ser Leu Gln Pro Glu Asp Phe Ala Thr Tyr Tyr Cys
195 200 205

Gln Gln Ser Tyr Ser Thr Pro Pro Thr Phe Gly Gln Gly Thr Lys Val
210 215 220

Glu Ile Lys Cys Gln Gln Ser Tyr Ser Thr Pro Pro Thr Phe
225 230 235

<210> SEQ ID NO 795
<211> LENGTH: 247
<212> TYPE: PRT
<213> ORGANISM: Mus musculus

<400> SEQUENCE: 795

Pro Gly Asp Pro Leu Lys Ile Ser Cys Lys Gly Ser Gly Tyr Ser Phe
1 5 10 15

Thr Ser Tyr Trp Ile Gly Trp Val Arg Gln Met Pro Gly Lys Gly Leu
20 25 30

```
Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asp Tyr Gly Gly Trp Phe
                85                  90                  95

Asp Pro Trp Gly Gln Gly Thr Leu Val Thr Val Ser Ser Cys Ala Arg
            100                 105                 110

Leu Glu Asn Asn Trp Asp Tyr Gly Gly Trp Phe Asp Pro Trp Ser Tyr
        115                 120                 125

Val Leu Thr Gln Pro Pro Ser Val Ser Val Ala Pro Gly Gln Thr Ala
    130                 135                 140

Arg Ile Thr Cys Gly Gly Asn Asn Ile Gly Ser Lys Ser Val His Trp
145                 150                 155                 160

Tyr Gln Gln Lys Pro Gly Gln Ala Pro Val Leu Val Val Tyr Asp Asp
                165                 170                 175

Ser Asp Arg Pro Ser Gly Ile Pro Glu Arg Phe Ser Gly Ser Asn Ser
            180                 185                 190

Gly Asn Thr Ala Thr Leu Thr Ile Ser Arg Val Glu Ala Gly Asp Glu
        195                 200                 205

Ala Asp Tyr Tyr Cys Gln Val Trp Asp Ser Ser Ser Asp His Trp Val
    210                 215                 220

Phe Gly Gly Gly Thr Lys Leu Thr Val Leu Cys Gln Val Trp Asp Ser
225                 230                 235                 240

Ser Ser Asp His Trp Val Phe
                245


<210> SEQ ID NO 796
<211> LENGTH: 247
<212> TYPE: PRT
<213> ORGANISM: Mus musculus

<400> SEQUENCE: 796

Pro Gly Asp Phe Leu Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asp Tyr Gly Gly Trp Phe
                85                  90                  95

Asp Pro Trp Gly Gln Gly Thr Leu Val Thr Val Ser Ser Cys Ala Arg
            100                 105                 110

Leu Glu Asn Asn Trp Asp Tyr Gly Gly Trp Phe Asp Pro Trp Ser Tyr
        115                 120                 125

Val Leu Thr Gln Pro Pro Ser Val Ser Val Ala Pro Gly Gln Thr Ala
    130                 135                 140

Arg Ile Thr Cys Gly Gly Asn Asn Ile Gly Ser Lys Ser Val His Trp
```

145 150 155 160

Tyr Gln Gln Lys Pro Gly Gln Ala Pro Val Leu Val Val Tyr Asp Asp
165 170 175

Ser Asp Arg Pro Ser Gly Ile Pro Glu Arg Phe Ser Gly Ser Asn Ser
180 185 190

Gly Asn Thr Ala Thr Leu Thr Ile Ser Arg Val Glu Ala Gly Asp Glu
195 200 205

Ala Asp Tyr Tyr Cys Gln Val Trp Asp Ser Ser Ser Asp His Trp Val
210 215 220

Phe Gly Gly Gly Thr Lys Leu Thr Val Leu Cys Gln Val Trp Asp Ser
225 230 235 240

Ser Ser Asp His Trp Val Phe
245

<210> SEQ ID NO 797
<211> LENGTH: 247
<212> TYPE: PRT
<213> ORGANISM: Mus musculus

<400> SEQUENCE: 797

Pro Gly Glu Phe Arg Lys Ile Ser Cys Lys Gly Ser Gly Tyr Ser Phe
1 5 10 15

Thr Ser Tyr Trp Ile Gly Trp Val Arg Gln Met Pro Gly Lys Gly Leu
20 25 30

Glu Trp Met Gly Ile Ile Tyr Pro Gly Asp Ser Asp Thr Arg Tyr Ser
35 40 45

Pro Ser Phe Gln Gly Gln Val Thr Ile Ser Ala Asp Lys Ser Ile Ser
50 55 60

Thr Ala Tyr Leu Gln Trp Ser Ser Leu Lys Ala Ser Asp Thr Ala Met
65 70 75 80

Tyr Tyr Cys Ala Arg Leu Glu Asn Asn Trp Asp Tyr Gly Gly Trp Phe
85 90 95

Asp Pro Trp Gly Gln Gly Thr Leu Val Thr Val Ser Ser Cys Ala Arg
100 105 110

Leu Glu Asn Asn Trp Asp Tyr Gly Gly Trp Phe Asp Pro Trp Ser Tyr
115 120 125

Val Leu Thr Gln Pro Pro Ser Val Ser Val Ala Pro Gly Gln Thr Ala
130 135 140

Arg Ile Thr Cys Gly Gly Asn Asn Ile Gly Ser Lys Ser Val His Trp
145 150 155 160

Tyr Gln Gln Lys Pro Gly Gln Ala Pro Val Leu Val Val Tyr Asp Asp
165 170 175

Ser Asp Arg Pro Ser Gly Ile Pro Glu Arg Phe Ser Gly Ser Asn Ser
180 185 190

Gly Asn Thr Ala Thr Leu Thr Ile Ser Arg Val Glu Ala Gly Asp Glu
195 200 205

Ala Asp Tyr Tyr Cys Gln Val Trp Asp Ser Ser Ser Asp His Trp Val
210 215 220

Phe Gly Gly Gly Thr Lys Leu Thr Val Leu Cys Gln Val Trp Asp Ser
225 230 235 240

Ser Ser Asp His Trp Val Phe
245

<210> SEQ ID NO 798
<211> LENGTH: 245

<212> TYPE: PRT
<213> ORGANISM: Mus musculus

<400> SEQUENCE: 798

```
Arg Gly Asp Leu Leu Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asn Tyr Gly Gly Trp Phe
                85                  90                  95

Asp Pro Trp Gly Gln Gly Thr Leu Val Thr Val Ser Ser Cys Ala Arg
            100                 105                 110

Leu Glu Asn Asn Trp Asn Tyr Gly Gly Trp Phe Asp Pro Trp Val Leu
        115                 120                 125

Thr Gln Pro Pro Ser Val Ser Val Ala Pro Gly Gln Thr Ala Arg Ile
    130                 135                 140

Thr Cys Gly Gly Asn Asn Ile Gly Ser Lys Ser Val His Trp Tyr Gln
145                 150                 155                 160

Gln Lys Pro Gly Gln Ala Pro Val Leu Val Val Tyr Asp Asp Ser Asp
                165                 170                 175

Arg Pro Ser Gly Ile Pro Glu Arg Phe Ser Gly Ser Asn Ser Gly Asn
            180                 185                 190

Thr Ala Thr Leu Thr Ile Ser Arg Val Glu Ala Gly Asp Glu Ala Asp
        195                 200                 205

Tyr Tyr Cys Gln Val Trp Asp Ser Ser Ser Asp His Trp Val Phe Gly
    210                 215                 220

Gly Gly Thr Lys Leu Thr Val Leu Cys Gln Val Trp Asp Ser Ser Ser
225                 230                 235                 240

Asp His Trp Val Phe
                245
```

<210> SEQ ID NO 799
<211> LENGTH: 247
<212> TYPE: PRT
<213> ORGANISM: Mus musculus

<400> SEQUENCE: 799

```
Arg Gly Asn Leu Leu Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asp Tyr Gly Gly Trp Phe
                85                  90                  95
```

```
Asp Pro Trp Gly Gln Gly Thr Leu Val Thr Val Ser Ser Cys Ala Arg
            100                 105                 110

Leu Glu Asn Asn Trp Asp Tyr Gly Gly Trp Phe Asp Pro Trp Ser Tyr
        115                 120                 125

Val Leu Thr Gln Pro Pro Ser Val Ser Val Ala Pro Gly Gln Thr Ala
    130                 135                 140

Arg Ile Thr Cys Gly Gly Asn Asn Ile Gly Ser Lys Ser Val His Trp
145                 150                 155                 160

Tyr Gln Gln Lys Pro Gly Gln Ala Pro Val Leu Val Val Tyr Asp Asp
                165                 170                 175

Ser Asp Arg Pro Ser Gly Ile Pro Glu Arg Phe Ser Gly Ser Asn Ser
            180                 185                 190

Gly Asn Thr Ala Thr Leu Thr Ile Ser Arg Val Glu Ala Gly Asp Glu
        195                 200                 205

Ala Asp Tyr Tyr Cys Gln Val Trp Asp Ser Ser Ser Asp His Trp Val
    210                 215                 220

Phe Gly Gly Gly Thr Lys Leu Thr Val Leu Cys Gln Val Trp Asp Ser
225                 230                 235                 240

Ser Ser Asp His Trp Val Phe
                245


<210> SEQ ID NO 800
<211> LENGTH: 245
<212> TYPE: PRT
<213> ORGANISM: Mus musculus

<400> SEQUENCE: 800

Pro Gly Glu Ser Leu Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Leu Glu Asn Asn Trp Asn Tyr Gly Gly Trp Phe
                85                  90                  95

Asp Pro Trp Gly Gln Gly Thr Leu Val Thr Val Ser Ser Cys Ala Arg
            100                 105                 110

Leu Glu Asn Asn Trp Asn Tyr Gly Gly Trp Phe Asp Pro Trp Val Leu
        115                 120                 125

Thr Gln Pro Pro Ser Val Ser Val Ala Pro Gly Gln Thr Ala Arg Ile
    130                 135                 140

Thr Cys Gly Gly Asn Asn Ile Gly Ser Lys Ser Val His Trp Tyr Gln
145                 150                 155                 160

Gln Lys Pro Gly Gln Ala Pro Val Leu Val Val Tyr Asp Asp Ser Asp
                165                 170                 175

Arg Pro Ser Gly Ile Pro Glu Arg Phe Ser Gly Ser Asn Ser Gly Asn
            180                 185                 190

Thr Ala Thr Leu Thr Ile Ser Arg Val Glu Ala Gly Asp Glu Ala Asp
        195                 200                 205

Tyr Tyr Cys Gln Val Trp Asp Ser Ser Ser Asp His Trp Val Phe Gly
    210                 215                 220
```

Gly Gly Thr Lys Leu Thr Val Leu Cys Gln Val Trp Asp Ser Ser Ser
225 230 235 240

Asp His Trp Val Phe
245

<210> SEQ ID NO 801
<211> LENGTH: 236
<212> TYPE: PRT
<213> ORGANISM: Mus musculus

<400> SEQUENCE: 801

Pro Gly Ala Ser Val Lys Val Ser Cys Lys Ala Ser Gly Gly Thr Phe
1 5 10 15

Ser Ser Tyr Ala Ile Ser Trp Val Arg Gln Ala Pro Gly Gln Gly Leu
20 25 30

Glu Trp Met Gly Gly Ile Ile Pro Ile Phe Gly Thr Ala Asn Tyr Ala
35 40 45

Gln Lys Phe Gln Gly Arg Val Thr Ile Thr Ala Asp Glu Ser Thr Ser
50 55 60

Thr Ala Tyr Met Glu Leu Ser Ser Leu Arg Ser Glu Asp Thr Ala Val
65 70 75 80

Tyr Tyr Cys Ala Arg Asp Tyr Tyr Tyr Tyr Gly Met Asp Val Trp Gly
85 90 95

Gln Gly Thr Thr Val Thr Val Ser Ser Cys Ala Arg Asp Tyr Tyr Tyr
100 105 110

Tyr Gly Met Asp Val Trp Asp Ile Arg Met Thr Gln Ser Pro Ser Ser
115 120 125

Leu Ser Ala Ser Val Gly Asp Arg Val Thr Ile Thr Cys Arg Ala Ser
130 135 140

Gln Ser Ile Ser Arg Tyr Val Asn Trp Tyr Gln Gln Lys Pro Gly Lys
145 150 155 160

Ala Pro Asn Leu Leu Ile Tyr Gly Ala Ser Asn Leu Glu Ser Gly Val
165 170 175

Pro Ser Arg Phe Ser Gly Ser Gly Ser Gly Thr Asp Phe Thr Leu Thr
180 185 190

Asn Ser Ser Leu Gln Pro Glu Asp Phe Ala Ser Tyr Tyr Cys Gln Gln
195 200 205

Thr Tyr Asn Asp Pro Pro Thr Phe Gly Gly Gly Thr Arg Met Glu Ile
210 215 220

Lys Cys Gln Gln Thr Tyr Asn Asp Pro Pro Thr Phe
225 230 235

<210> SEQ ID NO 802
<211> LENGTH: 238
<212> TYPE: PRT
<213> ORGANISM: Mus musculus

<400> SEQUENCE: 802

Pro Gly Ser Ser Val Lys Val Ser Cys Lys Ala Ser Gly Gly Thr Phe
1 5 10 15

Ser Ser Tyr Ala Ile Ser Trp Val Arg Gln Ala Pro Gly Gln Gly Leu
20 25 30

Glu Trp Met Gly Gly Ile Ile Pro Ile Phe Gly Thr Ala Asn Tyr Ala
35 40 45

Gln Lys Phe Gln Gly Arg Val Thr Ile Thr Ala Asp Glu Ser Thr Ser
50 55 60

```
Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Val Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Ser Tyr Leu Asn Trp Tyr Gln Gln Lys Pro
145                 150                 155                 160

Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Pro Lys Val
    210                 215                 220

Glu Ile Lys Cys Gln Gln Ser Tyr Ser Thr Pro Pro Thr Phe
225                 230                 235


<210> SEQ ID NO 803
<211> LENGTH: 241
<212> TYPE: PRT
<213> ORGANISM: Mus musculus

<400> SEQUENCE: 803

Pro Gly Ala Ser Val Lys Val Ser Cys Lys Ala Ser Gly Tyr Thr Phe
1               5                   10                  15

Thr Ser Tyr Gly Ile Ser Trp Val Arg Gln Ala Pro Gly Gln Gly Leu
            20                  25                  30

Glu Trp Met Gly Trp Ile Ser Ala Tyr Asn Gly Asn Thr Asn Tyr Ala
        35                  40                  45

Gln Lys Leu Gln Gly Arg Val Thr Met Thr Thr Asp Thr Ser Thr Ser
    50                  55                  60

Thr Ala Tyr Met Glu Leu Arg Ser Leu Arg Ser Asp Asp Thr Ala Val
65                  70                  75                  80

Tyr Tyr Cys Ala Arg Asp Ile Gly Tyr Tyr Tyr Gly Met Asp Val Trp
                85                  90                  95

Gly Gln Gly Thr Thr Val Thr Val Ser Ser Cys Ala Arg Asp Ile Gly
            100                 105                 110

Tyr Tyr Tyr Gly Met Asp Val Trp Ser Ser Glu Leu Thr Gln Asp Pro
        115                 120                 125

Ala Val Ser Val Ala Leu Gly Gln Thr Val Arg Ile Thr Cys Gln Gly
    130                 135                 140

Asp Ser Leu Arg Ser Tyr Tyr Ala Ser Trp Tyr Gln Gln Glu Pro Gly
145                 150                 155                 160

Gln Ala Pro Val Leu Val Ile Tyr Gly Lys Asn Asn Arg Pro Ser Gly
                165                 170                 175

Ile Ser Asp Arg Phe Ser Gly Ser Ser Ser Gly Asn Thr Ala Ser Leu
            180                 185                 190

Thr Ile Thr Gly Ala Gln Ala Glu Asp Glu Ala Asp Tyr Tyr Cys Asn
```

```
        195                 200                 205

Ser Arg Asp Ser Ser Gly Asn His Val Val Phe Gly Gly Gly Thr Arg
    210                 215                 220

Leu Thr Val Leu Cys Asn Ser Arg Asp Ser Ser Gly Asn His Val Val
225                 230                 235                 240

Phe


<210> SEQ ID NO 804
<211> LENGTH: 238
<212> TYPE: PRT
<213> ORGANISM: Mus musculus

<400> SEQUENCE: 804

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Gln Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Asn Tyr Leu Asn Trp Tyr Gln Gln Lys Pro
145                 150                 155                 160

Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Thr Lys Leu
    210                 215                 220

Glu Thr Lys Cys Gln Gln Ser Tyr Ser Thr Pro Pro Thr Phe
225                 230                 235


<210> SEQ ID NO 805
<211> LENGTH: 238
<212> TYPE: PRT
<213> ORGANISM: Mus musculus

<400> SEQUENCE: 805

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45
```

```
Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Val Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Ser Tyr Leu Asn Trp Tyr Gln Gln Lys Pro
145                 150                 155                 160

Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Thr Lys Val
    210                 215                 220

Glu Leu Lys Cys Gln Gln Ser Tyr Ser Thr Pro Pro Thr Phe
225                 230                 235


<210> SEQ ID NO 806
<211> LENGTH: 238
<212> TYPE: PRT
<213> ORGANISM: Mus musculus

<400> SEQUENCE: 806

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Gln Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ser Asn Tyr Leu Asn Trp Tyr Gln Gln Lys Pro
145                 150                 155                 160

Gly Lys Ala Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
```

```
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Pro Lys Leu
    210                 215                 220

Glu Ile Lys Cys Gln Gln Ser Tyr Ser Thr Pro Pro Thr Phe
225                 230                 235


<210> SEQ ID NO 807
<211> LENGTH: 234
<212> TYPE: PRT
<213> ORGANISM: Mus musculus

<400> SEQUENCE: 807

Ser Gly Glu Ser Leu Lys Ile Ser Cys Lys Gly Ser Gly Tyr Ser Phe
1               5                   10                  15

Ser Thr Tyr Trp Ile Gly Trp Val Arg Gln Met Pro Gly Lys Gly Leu
            20                  25                  30

Glu Trp Met Gly Leu Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Val Gly Asp Gly Tyr Ser Leu Asp Tyr Trp Gly
                85                  90                  95

Gln Gly Thr Leu Val Thr Val Ser Ser Cys Ala Arg Val Gly Asp Gly
            100                 105                 110

Tyr Ser Leu Asp Tyr Trp Ser Val Leu Thr Gln Pro Pro Ser Val Ser
        115                 120                 125

Val Ser Pro Gly Gln Thr Ala Ser Ile Thr Cys Ser Gly His Lys Leu
    130                 135                 140

Gly Glu Arg Phe Ala Tyr Trp Tyr Gln Gln Lys Pro Gly Gln Ser Pro
145                 150                 155                 160

Val Leu Val Ile Asn Gln Tyr Ile Arg Arg Pro Ser Gly Ile Pro Glu
                165                 170                 175

Arg Phe Ser Gly Ser Asn Ser Gly Ser Thr Ala Thr Leu Thr Ile Ser
            180                 185                 190

Gly Thr Gln Ala Met Asp Glu Ala Asp Tyr Tyr Cys Gln Thr Trp Asp
        195                 200                 205

Gly Ser Ile Val Val Phe Gly Gly Gly Thr Lys Leu Thr Val Leu Cys
    210                 215                 220

Gln Thr Trp Asp Gly Ser Ile Val Val Phe
225                 230


<210> SEQ ID NO 808
<211> LENGTH: 238
<212> TYPE: PRT
<213> ORGANISM: Mus musculus

<400> SEQUENCE: 808

Pro Gly Arg Ser Leu Arg Leu Ser Cys Ala Ala Ser Gly Phe Thr Phe
1               5                   10                  15

Ser Ser Tyr Gly Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
```

```
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Lys Ala Ile Thr Ser Ile Glu Pro Tyr Trp Gly Gln
                85                  90                  95

Gly Thr Leu Val Thr Val Ser Ser Cys Ala Lys Ala Ile Thr Ser Ile
            100                 105                 110

Glu Pro Tyr Trp Gln Thr Val Val Thr Gln Glu Pro Ser Phe Ser Val
        115                 120                 125

Ser Pro Gly Gly Thr Val Thr Leu Thr Cys Gly Leu Ser Ser Gly Ser
    130                 135                 140

Val Ser Thr Ser Tyr Tyr Pro Ser Trp Tyr Gln Gln Thr Pro Gly Gln
145                 150                 155                 160

Ala Pro Arg Thr Leu Ile Tyr Asn Thr Asp Thr Arg Ser Ser Arg Val
                165                 170                 175

Pro Asp Arg Phe Ser Gly Ser Ile Val Gly Asn Lys Ala Ala Leu Thr
            180                 185                 190

Ile Thr Gly Ala Gln Ala Asp Asp Glu Ser Asp Tyr Tyr Cys Val Leu
        195                 200                 205

Tyr Met Gly Ser Gly Ile Trp Val Phe Gly Gly Gly Thr Lys Leu Thr
    210                 215                 220

Val Leu Cys Val Leu Tyr Met Gly Ser Gly Ile Trp Val Phe
225                 230                 235


<210> SEQ ID NO 809
<211> LENGTH: 241
<212> TYPE: PRT
<213> ORGANISM: Mus musculus

<400> SEQUENCE: 809

Ser Gly Glu Ser Leu Lys Ile Ser Cys Lys Gly Ser Gly Tyr Ser Phe
1               5                   10                  15

Ser Thr Tyr Trp Ile Gly Trp Val Arg Gln Met Pro Gly Lys Gly Leu
            20                  25                  30

Glu Trp Met Gly Leu Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Val Gly Asp Gly Tyr Ser Leu Asp Tyr Trp Gly
                85                  90                  95

Gln Gly Thr Leu Val Thr Val Ser Ser Cys Ala Arg Val Gly Asp Gly
            100                 105                 110

Tyr Ser Leu Asp Tyr Trp Gln Pro Val Leu Thr Gln Pro Pro Ser Ala
        115                 120                 125

Ser Gly Thr Pro Gly Gln Arg Val Thr Ile Ser Cys Ser Gly Gly Ser
    130                 135                 140

Ser Asn Ile Gly Arg Asn Tyr Val Tyr Trp Tyr Gln Gln Leu Pro Gly
145                 150                 155                 160

Thr Ala Pro Asn Leu Leu Ile Ser Arg Asn His Gln Arg Pro Ser Gly
                165                 170                 175
```

Val Pro Asp Arg Phe Ser Gly Ser Arg Ser Asp Thr Ser Ala Ser Leu
180 185 190

Ala Ile Ser Gly Leu Arg Ser Glu Asp Glu Ala Asp Tyr Tyr Cys Ala
195 200 205

Thr Trp Asp Asp Ala Leu Ser Gly Trp Val Phe Gly Gly Gly Thr Lys
210 215 220

Leu Thr Val Leu Cys Ala Thr Trp Asp Asp Ala Leu Ser Gly Trp Val
225 230 235 240

Phe

<210> SEQ ID NO 810
<211> LENGTH: 238
<212> TYPE: PRT
<213> ORGANISM: Mus musculus

<400> SEQUENCE: 810

Pro Gly Ser Ser Val Lys Val Ser Cys Lys Ala Ser Gly Gly Thr Phe
1 5 10 15

Ser Ser Tyr Ala Ile Ser Trp Val Arg Gln Ala Pro Gly Gln Gly Leu
20 25 30

Glu Trp Met Gly Gly Ile Ile Pro Ile Phe Gly Thr Ala Asn Tyr Ala
35 40 45

Gln Lys Phe Gln Gly Arg Val Thr Ile Thr Ala Asp Glu Ser Thr Ser
50 55 60

Thr Ala Tyr Met Glu Leu Ser Ser Leu Arg Ser Glu Asp Thr Ala Val
65 70 75 80

Tyr Tyr Cys Ala Arg Glu Met Tyr Tyr Tyr Tyr Gly Met Asp Val Trp
85 90 95

Gly Gln Gly Thr Thr Val Thr Val Ser Ser Cys Ala Arg Glu Met Tyr
100 105 110

Tyr Tyr Tyr Gly Met Asp Val Trp Asp Ile Val Met Thr Gln Ser Pro
115 120 125

Ser Ser Leu Ser Ala Ser Val Gly Asp Arg Val Thr Ile Thr Cys Arg
130 135 140

Ala Ser Gln Ser Ile Ser Ser Tyr Leu Asn Trp Tyr Gln Gln Lys Pro
145 150 155 160

Gly Lys Ala Pro Lys Leu Leu Ile Tyr Ala Ala Ser Ser Leu Gln Ser
165 170 175

Gly Val Pro Ser Arg Phe Ser Gly Ser Gly Ser Gly Thr Asp Phe Thr
180 185 190

Leu Thr Ile Ser Ser Leu Gln Pro Glu Asp Phe Ala Thr Tyr Tyr Cys
195 200 205

Gln Gln Ser Tyr Ser Thr Pro Pro Thr Phe Gly Gln Gly Thr Lys Val
210 215 220

Glu Thr Lys Cys Gln Gln Ser Tyr Ser Thr Pro Pro Thr Phe
225 230 235

<210> SEQ ID NO 811
<211> LENGTH: 240
<212> TYPE: PRT
<213> ORGANISM: Mus musculus

<400> SEQUENCE: 811

Pro Gly Arg Ser Leu Arg Leu Ser Cys Ala Ala Ser Gly Phe Ala Phe
1 5 10 15

Ser Ser Tyr Gly Met His Trp Val Arg Gln Ala Pro Gly Lys Gly Leu

```
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Lys Gly Gln Gly Asp Gly Met Asp Val Trp Gly Gln
                85                  90                  95

Gly Thr Thr Val Thr Val Ser Ser Cys Ala Lys Gly Gln Gly Asp Gly
            100                 105                 110

Met Asp Val Trp Gln Ser Ala Leu Thr Gln Pro Pro Ser Ala Ser Gly
        115                 120                 125

Ser Pro Gly Gln Ser Val Thr Ile Ser Cys Thr Gly Thr Ser Ser Asp
    130                 135                 140

Val Gly Gly Tyr Asn Tyr Val Ser Trp Tyr Gln Gln His Pro Gly Lys
145                 150                 155                 160

Ala Pro Lys Leu Met Leu Tyr Gly Val Ser Asn Arg Pro Ser Gly Ile
                165                 170                 175

Ser Ser Arg Phe Ser Gly Ser Lys Ser Gly Asn Thr Ala Ser Leu Thr
            180                 185                 190

Ile Ser Gly Leu Gln Ala Glu Asp Glu Ala Asp Tyr Tyr Cys Ser Ser
        195                 200                 205

Tyr Thr Ser Ser Ser Thr Leu Val Val Phe Gly Gly Gly Thr Lys Leu
    210                 215                 220

Thr Val Leu Cys Ser Ser Tyr Thr Ser Ser Ser Thr Leu Val Val Phe
225                 230                 235                 240


<210> SEQ ID NO 812
<211> LENGTH: 231
<212> TYPE: PRT
<213> ORGANISM: Mus musculus

<400> SEQUENCE: 812

Pro Gly Glu Ser Leu Gln Ile Ser Cys Lys Gly Ser Gly Tyr Lys Phe
1               5                   10                  15

Ala Asn Tyr Trp Ile Gly Trp Val Arg Gln Met Pro Gly Lys Gly Leu
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Arg Leu Gly Trp Gly Met Asp Val Trp Gly Gln Gly
                85                  90                  95

Thr Thr Val Thr Val Ser Ser Cys Ala Arg Leu Gly Trp Gly Met Asp
            100                 105                 110

Val Trp Asp Ile Val Met Thr Gln Ser Pro Ser Ser Leu Ser Ala Ser
        115                 120                 125

Val Gly Asp Arg Val Thr Ile Thr Cys Arg Ala Ser Gln Ser Ile Ser
    130                 135                 140

Ser Tyr Leu Asn Trp Tyr Gln Gln Lys Pro Gly Lys Ala Pro Asn Leu
145                 150                 155                 160
```

```
Ile Tyr Ala Ala Ser Ser Leu Arg Ser Gly Val Pro Ser Arg Phe Ser
                165                 170                 175

Gly Ser Gly Ser Gly Thr Asp Phe Thr Leu Thr Ile Ser Ser Leu Gln
            180                 185                 190

Pro Glu Asp Phe Ala Thr Tyr Tyr Cys Gln Gln Ser Tyr Ser Thr Pro
        195                 200                 205

Trp Thr Phe Gly Gln Gly Thr Lys Val Glu Ile Lys Cys Gln Gln Ser
    210                 215                 220

Tyr Ser Thr Pro Trp Thr Phe
225                 230
```

<210> SEQ ID NO 813
<211> LENGTH: 244
<212> TYPE: PRT
<213> ORGANISM: Mus musculus

<400> SEQUENCE: 813

```
Pro Gly Ala Ser Val Lys Val Ser Cys Lys Ala Ser Gly Tyr Thr Phe
1               5                   10                  15

Lys Asn Phe Gly Ile Ser Trp Val Arg Arg Ala Pro Gly Gln Gly Pro
            20                  25                  30

Glu Trp Met Gly Trp Ile Ser Gly Arg Lys Gly Asn Thr Ile Tyr Ala
        35                  40                  45

Gln Lys Phe Gln Gly Arg Val Thr Met Thr Thr Asp Thr Ser Thr Thr
    50                  55                  60

Thr Ala Tyr Met Glu Leu Arg Ser Leu Arg Ser Asp Asp Thr Ala Val
65                  70                  75                  80

Tyr Tyr Cys Ala Arg Val Trp Gly Asp Thr Thr Leu Gly Tyr Gly Met
                85                  90                  95

Asp Val Trp Gly Gln Gly Thr Thr Val Thr Val Ser Ser Cys Ala Arg
            100                 105                 110

Val Trp Gly Asp Thr Thr Leu Gly Tyr Gly Met Asp Val Trp Asp Ile
        115                 120                 125

Gln Met Thr Gln Ser Pro Ser Ser Leu Ser Ala Ser Val Gly Asp Arg
    130                 135                 140

Val Thr Ile Thr Cys Gln Ala Ser Gln Asp Ile Ser Asn Tyr Leu Asn
145                 150                 155                 160

Trp Tyr Gln Gln Lys Pro Gly Lys Ala Pro Lys Leu Leu Ile Tyr Asp
                165                 170                 175

Ala Ser Asn Leu Glu Thr Gly Val Pro Ser Arg Phe Ser Gly Ser Gly
            180                 185                 190

Ser Gly Thr Asp Phe Thr Phe Thr Ile Ser Ser Leu Gln Pro Glu Asp
        195                 200                 205

Ile Ala Thr Tyr Tyr Cys Gln Gln Tyr Asp Asn Leu Pro Leu Thr Phe
    210                 215                 220

Gly Gly Gly Thr Lys Val Glu Ile Lys Cys Gln Gln Tyr Asp Asn Leu
225                 230                 235                 240

Pro Leu Thr Phe
```

<210> SEQ ID NO 814
<211> LENGTH: 238
<212> TYPE: PRT
<213> ORGANISM: Mus musculus

<400> SEQUENCE: 814

```
Pro Gly Gly Ser Leu Arg Leu Ser Cys Ala Ala Ser Gly Phe Thr Phe
```

```
1               5                   10                  15

Ser Ser Tyr Glu Met Asn Trp Val Arg Gln Ala Pro Gly Lys Gly Leu
            20                  25                  30

Glu Trp Val Ser Tyr Ile Ser Ser Ser Gly Ser Thr Ile Tyr Tyr Ala
        35                  40                  45

Asp Ser Val Lys Gly Arg Phe Thr Ile Ser Arg Asp Asn Ala Lys Asn
    50                  55                  60

Ser Leu Tyr Leu Gln Met Asn Ser Leu Arg Ala Glu Asp Thr Ala Val
65                  70                  75                  80

Tyr Tyr Cys Ala Arg Arg Arg Gly Gly Gly Phe Asp Tyr Trp Gly Gln
                85                  90                  95

Gly Thr Leu Val Thr Val Ser Ser Cys Ala Arg Arg Arg Gly Gly Gly
            100                 105                 110

Phe Asp Tyr Trp Gln Ser Ala Leu Thr Gln Pro Ala Ser Val Ser Gly
        115                 120                 125

Ser Pro Gly Gln Ser Ile Thr Ile Ser Cys Thr Gly Thr Ser Ser Asp
    130                 135                 140

Val Gly Gly Tyr Asn Tyr Val Ser Trp Tyr Gln Gln His Pro Gly Lys
145                 150                 155                 160

Ala Pro Lys Leu Met Ile Tyr Asp Val Ser Asn Arg Pro Ser Gly Val
                165                 170                 175

Ser Asn Arg Phe Ser Gly Ser Lys Ser Gly Asn Thr Ala Ser Leu Thr
            180                 185                 190

Ile Ser Gly Leu Gln Ala Glu Asp Glu Ala Asp Tyr Tyr Cys Ser Ser
        195                 200                 205

Tyr Thr Ser Ser Ser Thr Trp Val Phe Gly Gly Gly Thr Lys Leu Thr
    210                 215                 220

Val Leu Cys Ser Ser Tyr Thr Ser Ser Ser Thr Trp Val Phe
225                 230                 235


<210> SEQ ID NO 815
<211> LENGTH: 244
<212> TYPE: PRT
<213> ORGANISM: Mus musculus

<400> SEQUENCE: 815

Pro Gly Glu Ser Leu Lys Ile Ser Cys Lys Gly Ser Gly Tyr Ser Phe
1               5                   10                  15

Thr Ser Tyr Trp Ile Gly Trp Val Arg Gln Met Pro Gly Lys Gly Leu
            20                  25                  30

Glu Trp Met Gly Ile Ile Tyr Pro Gly Asp Ser Asp Thr Arg Tyr Ser
        35                  40                  45

Pro Ser Phe Gln Gly Gln Val Thr Ile Ser Ala Asp Lys Ser Ile Ser
    50                  55                  60

Thr Ala Tyr Leu Gln Trp Ser Ser Leu Lys Ala Ser Asp Thr Ala Met
65                  70                  75                  80

Tyr Tyr Cys Ala Ile Pro Trp Asp Ala Glu Leu Gly Asn Tyr Gly Met
                85                  90                  95

Asp Val Trp Gly Gln Gly Thr Thr Val Thr Val Ser Ser Cys Ala Ile
            100                 105                 110

Pro Trp Asp Ala Glu Leu Gly Asn Tyr Gly Met Asp Val Trp Asp Ile
        115                 120                 125

Gln Met Thr Gln Ser Pro Ser Ser Leu Ser Ala Ser Val Gly Asp Arg
    130                 135                 140
```

```
Val Thr Ile Thr Cys Arg Ala Ser Gln Ser Ile Ser Ser Tyr Leu Asn
145                 150                 155                 160

Trp Tyr Gln Gln Lys Pro Gly Lys Ala Pro Lys Leu Leu Ile Tyr Ala
                165                 170                 175

Ala Ser Ser Leu Gln Ser Gly Val Pro Ser Arg Phe Ser Gly Ser Gly
            180                 185                 190

Ser Gly Thr Asp Phe Thr Leu Thr Ile Ser Ser Leu Gln Pro Glu Asp
        195                 200                 205

Phe Ala Thr Tyr Tyr Cys Leu Gln Asp Tyr Asn Tyr Pro Pro Ala Phe
    210                 215                 220

Gly Gln Gly Thr Lys Val Glu Ile Lys Cys Leu Gln Asp Tyr Asn Tyr
225                 230                 235                 240

Pro Pro Ala Phe


<210> SEQ ID NO 816
<211> LENGTH: 231
<212> TYPE: PRT
<213> ORGANISM: Mus musculus

<400> SEQUENCE: 816

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Lys Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Gly Arg Trp Ser Gly Leu Gly Asp Tyr Trp Gly
                85                  90                  95

Gln Gly Thr Leu Val Thr Val Ser Ser Cys Ala Arg Gly Arg Trp Ser
            100                 105                 110

Gly Leu Gly Asp Tyr Trp Met Thr Gln Ser Pro Ser Ser Leu Ser Ala
        115                 120                 125

Ser Val Gly Asp Arg Val Thr Ile Thr Cys Gln Ala Ser Glu Asp Ile
    130                 135                 140

Arg Met Tyr Leu Gly Trp Tyr Gln Gln Lys Ala Gly Arg Ala Pro Lys
145                 150                 155                 160

Leu Leu Ile Phe Glu Gly Ser Ser Leu Glu Pro Gly Val Pro Ser Arg
                165                 170                 175

Phe Ser Gly Ser Gly Ser Gly Thr His Phe Thr Phe Thr Ile Ser Ser
            180                 185                 190

Leu Gln Pro Asp Asp Phe Ala Thr Tyr Tyr Cys Gln Gln Tyr Tyr Asp
        195                 200                 205

Asp Pro Gln Phe Gly Gly Gly Thr Lys Val Val Leu Lys Cys Gln Gln
    210                 215                 220

Tyr Tyr Asp Asp Pro Gln Phe
225                 230


<210> SEQ ID NO 817
<211> LENGTH: 236
<212> TYPE: PRT
<213> ORGANISM: Mus musculus
```

<400> SEQUENCE: 817

Pro Ser Gly Thr Leu Ser Leu Thr Cys Ala Val Ser Gly Gly Ser Ile
1               5                   10                  15

Ser Ser Ser Asn Trp Trp Ser Trp Val Arg Gln Pro Pro Gly Lys Gly
            20                  25                  30

Leu Glu Trp Ile Gly Glu Ile Tyr His Ser Gly Ser Thr Asn Tyr Asn
        35                  40                  45

Pro Ser Leu Lys Ser Arg Val Thr Ile Ser Val Asp Lys Ser Lys Asn
    50                  55                  60

Gln Phe Ser Leu Lys Leu Ser Ser Val Thr Ala Ala Asp Thr Ala Val
65                  70                  75                  80

Tyr Tyr Cys Ala Arg Ala Arg Gly Gly Arg Tyr Phe Asp Tyr Trp Gly
                85                  90                  95

Gln Gly Thr Leu Val Thr Val Ser Ser Cys Ala Arg Ala Arg Gly Gly
            100                 105                 110

Arg Tyr Phe Asp Tyr Trp Asp Ile Val Leu Thr Gln Ser Pro Ser Phe
        115                 120                 125

Leu Ser Ala Ser Val Gly Asp Arg Val Thr Ile Thr Cys Arg Ala Ser
    130                 135                 140

Gln Gly Ile Ser Thr Tyr Leu Ala Trp Tyr Gln Gln Lys Pro Gly Thr
145                 150                 155                 160

Ala Pro Lys Val Leu Met Tyr Ala Ala Ser Thr Leu His Ser Gly Val
                165                 170                 175

Pro Ser Arg Phe Ser Gly Ser Gly Ser Gly Thr Glu Phe Thr Leu Thr
            180                 185                 190

Ile Ser Ser Leu Gln Pro Glu Asp Phe Ala Ile Tyr Tyr Cys Gln Gln
        195                 200                 205

Leu Asn Gly Tyr Pro Thr Thr Phe Gly Gly Gly Thr Arg Val Glu Ile
    210                 215                 220

Lys Cys Gln Gln Leu Asn Gly Tyr Pro Thr Thr Phe
225                 230                 235

<210> SEQ ID NO 818
<211> LENGTH: 238
<212> TYPE: PRT
<213> ORGANISM: Mus musculus

<400> SEQUENCE: 818

Pro Gly Arg Ser Leu Arg Leu Ser Cys Ala Ala Ser Gly Phe Thr Phe
1               5                   10                  15

Ser Ser Tyr Gly Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Lys Gly Gln Gly Asp Gly Met Asp Val Trp Gly Gln
                85                  90                  95

Gly Thr Thr Val Thr Val Ser Ser Cys Ala Lys Gly Gln Gly Asp Gly
            100                 105                 110

Met Asp Val Trp Tyr Glu Leu Thr Gln Pro Pro Ser Ala Ser Gly Thr
        115                 120                 125

```
Pro Gly Gln Arg Val Thr Ile Ser Cys Ser Gly Ser Ser Ser Asn Val
    130                 135                 140

Gly Ser Arg Thr Val Ser Trp Phe Gln Gln Leu Pro Gly Thr Ala Pro
145                 150                 155                 160

Lys Leu Leu Ile Tyr Ser Asn Asn Leu Arg Pro Ser Gly Val Pro Asp
                165                 170                 175

Arg Phe Ser Gly Ser Lys Ser Gly Thr Ser Ala Ser Leu Ala Ile Ser
            180                 185                 190

Gly Leu Gln Ser Glu Asp Glu Ala Asp Tyr Tyr Cys Ala Ala Trp Asp
        195                 200                 205

Asp Ser Leu Ile Gly His Val Phe Gly Thr Gly Thr Lys Val Thr Val
    210                 215                 220

Val Cys Ala Ala Trp Asp Asp Ser Leu Ile Gly His Val Phe
225                 230                 235


<210> SEQ ID NO 819
<211> LENGTH: 249
<212> TYPE: PRT
<213> ORGANISM: Mus musculus

<400> SEQUENCE: 819

Pro Gly Gly Ser Leu Arg Leu Ser Cys Ala Ala Ser Gly Phe Thr Phe
1               5                   10                  15

Ser Ser Tyr Ser Met Asn Trp Val Arg Gln Ala Pro Gly Lys Gly Leu
            20                  25                  30

Glu Trp Val Ser Ser Ile Ser Ser Ser Ser Ser Tyr Ile Tyr Tyr Ala
        35                  40                  45

Asp Ser Val Lys Gly Arg Phe Thr Ile Ser Arg Asp Asn Ala Lys Asn
    50                  55                  60

Ser Leu Tyr Leu Gln Met Asn Ser Leu Arg Ala Glu Asp Thr Ala Val
65                  70                  75                  80

Tyr Tyr Cys Ala Arg Asp Gln Leu Ala Ala Arg Arg Gly Tyr Tyr Tyr
                85                  90                  95

Gly Met Asp Val Trp Gly Gln Gly Thr Thr Val Thr Val Ser Ser Cys
            100                 105                 110

Ala Arg Asp Gln Leu Ala Ala Arg Arg Gly Tyr Tyr Tyr Gly Met Asp
        115                 120                 125

Val Trp Val Leu Thr Gln Pro Pro Ser Val Ser Val Ala Pro Gly Gln
    130                 135                 140

Thr Ala Thr Ile Ala Cys Gly Gly Asn Asn Ile Gly Thr Lys Ser Val
145                 150                 155                 160

His Trp Tyr Gln Gln Lys Pro Gly Gln Ala Pro Val Leu Val Val Tyr
                165                 170                 175

Asp Asp Ser Asp Arg Pro Ser Gly Ile Pro Glu Arg Phe Ser Gly Ser
            180                 185                 190

Asn Ser Gly Asn Thr Ala Thr Leu Thr Ile Ser Arg Val Glu Ala Gly
        195                 200                 205

Asp Glu Ala Asp Tyr Tyr Cys Gln Val Trp Asp Ser Ser Ser Asp His
    210                 215                 220

Val Val Phe Gly Gly Gly Thr Lys Leu Thr Val Leu Cys Gln Val Trp
225                 230                 235                 240

Asp Ser Ser Ser Asp His Val Val Phe
                245


<210> SEQ ID NO 820
```

<211> LENGTH: 241
<212> TYPE: PRT
<213> ORGANISM: Mus musculus

<400> SEQUENCE: 820

Pro Gly Arg Ser Leu Arg Leu Ser Cys Ala Ala Ser Gly Phe Thr Phe
1 5 10 15

Ser Ser Tyr Gly Met His Trp Val Arg Gln Ala Pro Gly Lys Gly Leu
20 25 30

Glu Trp Val Ala Val Ile Ser Tyr Asp Gly Ser Asn Lys Tyr Tyr Ala
35 40 45

Asp Ser Val Lys Gly Arg Phe Thr Ile Ser Arg Asp Asn Ser Lys Asn
50 55 60

Thr Leu Tyr Leu Gln Met Asn Ser Leu Arg Ala Glu Asp Thr Ala Val
65 70 75 80

Tyr Tyr Cys Ala Lys Gly Asp Val Asn Tyr Gly Met Asp Val Trp Gly
85 90 95

Gln Gly Thr Thr Val Thr Val Ser Ser Cys Ala Lys Gly Asp Val Asn
100 105 110

Tyr Gly Met Asp Val Trp Ser Tyr Val Leu Thr Gln Pro Pro Ser Val
115 120 125

Ser Val Ala Pro Gly Gln Thr Ala Arg Ile Ser Cys Gly Gly Ser Asn
130 135 140

Ile Gly Ser Lys Thr Val Asn Trp Tyr Arg Lys Lys Ala Gly Gln Ala
145 150 155 160

Pro Val Leu Val Val Tyr Asp Gly Arg Asp Arg Pro Ser Gly Ile Pro
165 170 175

Glu Arg Phe Ser Gly Ser Asn Ser Gly Asn Ala Ala Thr Leu Ile Ile
180 185 190

Ser Arg Val Glu Val Gly Asp Glu Ala Asp Tyr Tyr Cys Gln Val Trp
195 200 205

Asp Thr Ser Gly Asp Leu His Trp Ala Phe Gly Gly Gly Thr Lys Leu
210 215 220

Thr Val Leu Cys Gln Val Trp Asp Thr Ser Gly Asp Leu His Trp Ala
225 230 235 240

Phe

<210> SEQ ID NO 821
<211> LENGTH: 256
<212> TYPE: PRT
<213> ORGANISM: Mus musculus

<400> SEQUENCE: 821

Pro Ser Gly Thr Leu Ser Leu Thr Cys Ala Val Ser Gly Gly Ser Ile
1 5 10 15

Ser Ser Ser Asn Trp Trp Ser Trp Val Arg Gln Pro Pro Gly Lys Gly
20 25 30

Leu Glu Trp Ile Gly Glu Ile Tyr His Ser Gly Ser Thr Asn Tyr Asn
35 40 45

Pro Ser Leu Lys Ser Arg Val Thr Ile Ser Val Asp Lys Ser Lys Asn
50 55 60

Gln Phe Ser Leu Lys Leu Ser Ser Val Thr Ala Ala Asp Thr Ala Val
65 70 75 80

Tyr Tyr Cys Ala Arg Asp Phe Tyr Tyr Gly Ser Gly Ser Tyr Pro Asn
85 90 95

```
Gly Tyr Tyr Tyr Gly Met Asp Val Trp Gly Gln Gly Thr Thr Val Thr
            100                 105                 110

Val Ser Ser Cys Ala Arg Asp Phe Tyr Tyr Gly Ser Gly Ser Tyr Pro
        115                 120                 125

Asn Gly Tyr Tyr Tyr Gly Met Asp Val Trp Asp Ile Val Met Thr Gln
    130                 135                 140

Ser Pro Ser Ser Leu Ser Ala Ser Leu Gly Asp Arg Val Thr Ile Thr
145                 150                 155                 160

Cys Arg Ala Ser Gln Ser Ile Asn Ser Tyr Leu Asn Trp Tyr Gln Gln
                165                 170                 175

Lys Pro Gly Lys Ala Pro Arg Leu Leu Ile Tyr Thr Ala Ser Thr Leu
            180                 185                 190

Gln Ser Gly Val Pro Ser Arg Phe Ser Gly Ser Gly Ala Gly Thr Asp
        195                 200                 205

Phe Thr Leu Thr Ile Ser Ser Leu Gln Pro Glu Asp Val Ala Thr Tyr
    210                 215                 220

Tyr Cys Gln Gln Ser Tyr Thr Thr Pro Leu Thr Phe Gly Gly Gly Thr
225                 230                 235                 240

Lys Met Glu Ile Lys Cys Gln Gln Ser Tyr Thr Thr Pro Leu Thr Phe
                245                 250                 255


<210> SEQ ID NO 822
<211> LENGTH: 241
<212> TYPE: PRT
<213> ORGANISM: Mus musculus

<400> SEQUENCE: 822

Pro Gly Arg Ser Leu Arg Leu Ser Cys Ala Ala Ser Gly Phe Thr Phe
1               5                   10                  15

Ser Ser Tyr Gly Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Lys Gly Asp Val Asn Tyr Gly Met Asp Val Trp Gly
                85                  90                  95

Gln Gly Thr Thr Val Thr Val Ser Ser Cys Ala Lys Gly Asp Val Asn
            100                 105                 110

Tyr Gly Met Asp Val Trp Ser Tyr Val Leu Thr Gln Pro Pro Ser Val
        115                 120                 125

Ser Val Ala Pro Gly Lys Thr Ala Arg Ile Thr Cys Gly Gly Asn Asn
    130                 135                 140

Ile Gly Ser Lys Ser Val His Trp Tyr Gln Gln Lys Pro Gly Gln Ala
145                 150                 155                 160

Pro Val Leu Val Val Tyr Asp Asp Thr Asp Arg Pro Ser Gly Ile Pro
                165                 170                 175

Glu Arg Phe Ser Gly Ser Asn Ser Gly Asn Thr Ala Thr Leu Thr Ile
            180                 185                 190

Ser Arg Val Glu Ala Gly Asp Glu Ala Asp Tyr Tyr Cys Gln Val Trp
        195                 200                 205

Asp Ser Ser Ser Asp Leu Leu Trp Val Phe Gly Gly Gly Thr Lys Leu
    210                 215                 220
```

```
Ala Val Leu Cys Gln Val Trp Asp Ser Ser Ser Asp Leu Leu Trp Val
225                 230                 235                 240

Phe


<210> SEQ ID NO 823
<211> LENGTH: 251
<212> TYPE: PRT
<213> ORGANISM: Mus musculus

<400> SEQUENCE: 823

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Asp Phe Asn Pro Phe Ser Ile Thr Ile Phe Glu
                85                  90                  95

Met Asp Val Trp Gly Gln Gly Thr Thr Val Thr Val Ser Ser Cys Ala
            100                 105                 110

Arg Asp Phe Asn Pro Phe Ser Ile Thr Ile Phe Glu Met Asp Val Trp
        115                 120                 125

Gln Ser Val Leu Thr Gln Pro Pro Ser Val Ser Ala Ala Pro Gly Gln
    130                 135                 140

Lys Val Thr Ile Ser Cys Ser Gly Ser Ser Ser Asn Ile Gly Asn Asn
145                 150                 155                 160

Tyr Val Ser Trp Tyr Gln Gln Leu Pro Gly Thr Ala Pro Lys Leu Leu
                165                 170                 175

Ile Tyr Asp Asn Asn Lys Arg Pro Ser Gly Ile Pro Asp Arg Phe Ser
            180                 185                 190

Gly Ser Lys Ser Gly Thr Ser Ala Thr Leu Gly Ile Thr Gly Leu Gln
        195                 200                 205

Thr Gly Asp Glu Ala Asp Tyr Tyr Cys Gly Thr Trp Asp Ser Ser Leu
    210                 215                 220

Ser Ala Leu Val Phe Gly Gly Gly Thr Lys Leu Thr Val Leu Cys Gly
225                 230                 235                 240

Thr Trp Asp Ser Ser Leu Ser Ala Leu Val Phe
                245                 250


<210> SEQ ID NO 824
<211> LENGTH: 240
<212> TYPE: PRT
<213> ORGANISM: Mus musculus

<400> SEQUENCE: 824

Pro Gly Arg Ser Leu Arg Leu Ser Cys Ala Ala Ser Gly Phe Thr Phe
1               5                   10                  15

Ser Ser Tyr Gly Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45
```

```
Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Lys Gly Asp Val Asn Tyr Gly Met Asp Val Trp Gly
                85                  90                  95

Gln Gly Thr Thr Val Thr Val Ser Ser Cys Ala Lys Gly Asp Val Asn
            100                 105                 110

Tyr Gly Met Asp Val Trp Ser Tyr Val Leu Thr Gln Pro Pro Ser Val
        115                 120                 125

Ser Val Ala Pro Gly Gln Thr Ala Arg Ile Ser Cys Gly Gly Ser Asn
    130                 135                 140

Ile Gly Ser Lys Thr Val Asn Trp Tyr Arg Lys Lys Ala Gly Gln Ala
145                 150                 155                 160

Pro Val Leu Val Val Tyr Asp Gly Arg Asp Arg Pro Ser Gly Ile Pro
                165                 170                 175

Glu Arg Phe Ser Gly Ser Asn Ser Gly Asn Ala Ala Thr Leu Ile Ile
            180                 185                 190

Ser Arg Val Glu Val Gly Asp Glu Ala Asp Tyr Tyr Cys Gln Val Trp
        195                 200                 205

Asp Thr Ser Gly Asp Leu His Trp Ala Phe Gly Gly Arg Thr Lys Leu
    210                 215                 220

Thr Arg Cys Gln Val Trp Asp Thr Ser Gly Asp Leu His Trp Ala Phe
225                 230                 235                 240


<210> SEQ ID NO 825
<211> LENGTH: 240
<212> TYPE: PRT
<213> ORGANISM: Mus musculus

<400> SEQUENCE: 825

Pro Gly Arg Ser Leu Arg Leu Ser Cys Ala Ala Ser Gly Phe Thr Phe
1               5                   10                  15

Ser Ser Tyr Gly Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Lys Gly Asp Val Asn Tyr Gly Met Asp Val Trp Gly
                85                  90                  95

Gln Gly Thr Thr Val Thr Val Ser Ser Cys Ala Lys Gly Asp Val Asn
            100                 105                 110

Tyr Gly Met Asp Val Trp Ser Tyr Val Leu Thr Gln Pro Pro Ser Val
        115                 120                 125

Ser Val Ala Pro Gly Gln Thr Ala Arg Ile Ser Cys Gly Gly Ser Asn
    130                 135                 140

Ile Gly Ser Lys Thr Val Asn Trp Tyr Arg Lys Lys Ala Gly Gln Ala
145                 150                 155                 160

Pro Val Leu Val Val Tyr Asp Gly Arg Asp Arg Pro Ser Gly Ile Pro
                165                 170                 175

Glu Arg Phe Ser Gly Ser Asn Ser Gly Asn Ala Ala Thr Leu Ile Ile
            180                 185                 190
```

Ser Arg Val Glu Val Gly Glu Gly Gly Gln Tyr Leu Gln Val Trp Asp
        195                 200                 205

Thr Ser Gly Asp Leu His Trp Ala Phe Gly Gly Gly Thr Lys Leu Thr
    210                 215                 220

Val Leu Leu Gln Val Trp Asp Thr Ser Gly Asp Leu His Trp Ala Phe
225                 230                 235                 240

<210> SEQ ID NO 826
<211> LENGTH: 241
<212> TYPE: PRT
<213> ORGANISM: Mus musculus

<400> SEQUENCE: 826

Pro Gly Arg Ser Leu Arg Leu Ser Cys Ala Ala Ser Gly Phe Thr Phe
1               5                   10                  15

Ser Ser Tyr Gly Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Asn Leu Ala Met Gly Gln Tyr Phe Asp Tyr Trp Gly
                85                  90                  95

Gln Gly Thr Leu Val Thr Val Ser Ser Cys Ala Asn Leu Ala Met Gly
            100                 105                 110

Gln Tyr Phe Asp Tyr Trp Gln Ala Val Leu Thr Gln Pro Pro Ser Ala
        115                 120                 125

Ser Gly Thr Pro Gly Gln Arg Val Thr Ile Ser Cys Ser Gly Ser Ser
    130                 135                 140

Ser Asn Ile Gly Ser Asn Thr Val Asn Trp Tyr Gln Gln Leu Pro Gly
145                 150                 155                 160

Thr Ala Pro Lys Leu Leu Ile Tyr Ser Asn Asn Gln Arg Pro Ser Gly
                165                 170                 175

Val Pro Asp Arg Phe Ser Gly Ser Lys Ser Gly Thr Ser Ala Ser Leu
            180                 185                 190

Ala Ile Ser Gly Leu Gln Ser Glu Asp Glu Ala Asp Tyr Tyr Cys Ala
        195                 200                 205

Ala Trp Asp Asp Ser Leu Asn Gly Pro Val Phe Gly Gly Gly Thr Lys
    210                 215                 220

Leu Thr Val Leu Cys Ala Ala Trp Asp Asp Ser Leu Asn Gly Pro Val
225                 230                 235                 240

Phe

<210> SEQ ID NO 827
<211> LENGTH: 238
<212> TYPE: PRT
<213> ORGANISM: Mus musculus

<400> SEQUENCE: 827

Pro Gly Ser Ser Val Lys Val Ser Cys Lys Ala Ser Gly Gly Thr Phe
1               5                   10                  15

Ser Ser Tyr Ala Ile Ser Trp Val Arg Gln Ala Pro Gly Gln Gly Leu
            20                  25                  30

```
Glu Trp Met Gly Gly Ile Ile Pro Ile Phe Gly Thr Ala Asn Tyr Ala
        35                  40                  45

Gln Lys Phe Gln Gly Arg Val Thr Ile Thr Ala Asp Glu Ser Thr Ser
    50                  55                  60

Thr Ala Tyr Met Glu Leu Ser Ser Leu Arg Ser Glu Asp Thr Ala Val
65                  70                  75                  80

Tyr Tyr Cys Ala Arg Glu Met Tyr Tyr Tyr Tyr Gly Met Asp Val Trp
                85                  90                  95

Gly Gln Gly Thr Thr Val Thr Val Ser Ser Cys Ala Arg Glu Met Tyr
            100                 105                 110

Tyr Tyr Tyr Gly Met Asp Val Trp Asp Ile Val Met Thr Gln Ser Pro
        115                 120                 125

Ser Ser Leu Ser Ala Ser Val Gly Asp Arg Val Thr Ile Thr Cys Arg
    130                 135                 140

Ala Ser Gln Ser Ile Ile Thr Tyr Leu Asn Trp Tyr Gln Gln Lys Pro
145                 150                 155                 160

Gly Lys Val Pro Lys Leu Leu Ile Tyr Ala Ala Ser Ser Leu Gln Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Gln Ser Tyr Ser Thr Pro Pro Thr Phe Gly Gln Gly Thr Lys Leu
    210                 215                 220

Glu Ile Lys Cys Gln Gln Ser Tyr Ser Thr Pro Pro Thr Phe
225                 230                 235


<210> SEQ ID NO 828
<211> LENGTH: 241
<212> TYPE: PRT
<213> ORGANISM: Mus musculus

<400> SEQUENCE: 828

Pro Gly Gly Ser Leu Arg Phe Ser Cys Ala Ala Ser Gly Phe Thr Phe
1               5                   10                  15

Ser Ser Tyr Gly Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Asn Leu Ala Met Gly Gln Tyr Phe Asp Tyr Trp Gly
                85                  90                  95

Gln Gly Thr Leu Val Thr Val Ser Ser Cys Ala Asn Leu Ala Met Gly
            100                 105                 110

Gln Tyr Phe Asp Tyr Trp Gln Ala Val Leu Thr Gln Pro Pro Ser Ala
        115                 120                 125

Ser Gly Thr Pro Gly Gln Arg Val Thr Ile Ser Cys Ser Gly Ser Ser
    130                 135                 140

Ser Asn Ile Gly Ser Asn Thr Val Asn Trp Tyr Gln Gln Leu Pro Gly
145                 150                 155                 160

Thr Ala Pro Lys Leu Leu Ile Tyr Ser Asn Asn Gln Arg Pro Ser Gly
                165                 170                 175
```

Val Pro Asp Arg Phe Ser Gly Ser Lys Ser Gly Thr Ser Ala Ser Leu
180 185 190

Ala Ile Ser Gly Leu Gln Ser Glu Asp Glu Ala Asp Tyr Tyr Cys Ala
195 200 205

Ala Trp Asp Asp Ser Leu Asn Gly Pro Val Phe Gly Gly Gly Thr Lys
210 215 220

Leu Thr Val Leu Cys Ala Ala Trp Asp Asp Ser Leu Asn Gly Pro Val
225 230 235 240

Phe

<210> SEQ ID NO 829
<211> LENGTH: 249
<212> TYPE: PRT
<213> ORGANISM: Mus musculus

<400> SEQUENCE: 829

Pro Gly Arg Ser Leu Arg Leu Ser Cys Ala Ala Ser Gly Phe Thr Phe
1 5 10 15

Ser Ser Tyr Ala Met His Trp Val Arg Gln Ala Pro Gly Lys Gly Leu
20 25 30

Glu Trp Val Ala Val Ile Ser Tyr Asp Gly Ser Asn Lys Tyr Tyr Ala
35 40 45

Asp Ser Val Lys Gly Arg Phe Thr Ile Ser Arg Asp Asn Ser Lys Asn
50 55 60

Thr Leu Tyr Leu Gln Met Asn Ser Leu Arg Ala Glu Asp Thr Ala Val
65 70 75 80

Tyr Tyr Cys Ala Arg Asp Leu Gly Glu Ala Lys Ser Ser Ser Pro His
85 90 95

Glu Pro Asp Tyr Trp Gly Gln Gly Thr Leu Val Thr Val Ser Ser Cys
100 105 110

Ala Arg Asp Leu Gly Glu Ala Lys Ser Ser Ser Pro His Glu Pro Asp
115 120 125

Tyr Trp Leu Thr Gln Ser Pro Leu Ser Leu Ser Val Thr Pro Gly Gln
130 135 140

Pro Ala Ser Ile Ser Cys Lys Ser Ser Gln Ser Leu Leu His Ser Asp
145 150 155 160

Gly Lys Thr Tyr Leu Asp Trp Tyr Leu Gln Lys Pro Gly Gln Pro Pro
165 170 175

Gln Leu Leu Ile Tyr Glu Val Ser Asn Arg Phe Ser Gly Val Pro Asp
180 185 190

Arg Phe Ser Gly Ser Gly Ser Gly Thr Asp Phe Thr Leu Lys Ile Ser
195 200 205

Arg Val Glu Ala Glu Asp Val Gly Ile Tyr Tyr Cys Met Gln Thr Lys
210 215 220

Gln Leu Pro Leu Thr Phe Gly Gly Gly Pro Lys Leu Glu Ile Cys Met
225 230 235 240

Gln Thr Lys Gln Leu Pro Leu Thr Phe
245

<210> SEQ ID NO 830
<211> LENGTH: 249
<212> TYPE: PRT
<213> ORGANISM: Mus musculus

<400> SEQUENCE: 830

```
Pro Gly Arg Ser Leu Arg Leu Ser Cys Ala Ala Ser Gly Phe Thr Phe
1               5                   10                  15

Ser Ser Tyr Ala Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Arg Asp Leu Gly Glu Ala Lys Ser Ser Ser Pro His
                85                  90                  95

Glu Pro Asp Tyr Trp Gly Gln Gly Thr Leu Val Thr Val Ser Ser Cys
            100                 105                 110

Ala Arg Asp Leu Gly Glu Ala Lys Ser Ser Ser Pro His Glu Pro Asp
        115                 120                 125

Tyr Trp Leu Thr Gln Ser Pro Leu Ser Leu Ser Val Thr Pro Gly Gln
    130                 135                 140

Pro Ala Ser Ile Ser Cys Lys Ser Ser Gln Ser Leu Leu His Ser Asp
145                 150                 155                 160

Gly Lys Thr Tyr Leu Asp Trp Tyr Leu Gln Lys Pro Gly Gln Pro Pro
                165                 170                 175

Gln Leu Leu Ile Tyr Glu Val Ser Asn Arg Phe Ser Gly Val Pro Asp
            180                 185                 190

Arg Phe Ser Gly Ser Gly Ser Gly Thr Asp Phe Thr Leu Lys Ile Ser
        195                 200                 205

Arg Val Glu Ala Glu Asp Val Gly Ile Tyr Tyr Cys Met Gln Thr Lys
    210                 215                 220

Gln Leu Pro Leu Thr Phe Gly Gly Gly Thr Lys Leu Glu Ile Cys Met
225                 230                 235                 240

Gln Thr Lys Gln Leu Pro Leu Thr Phe
                245


<210> SEQ ID NO 831
<211> LENGTH: 241
<212> TYPE: PRT
<213> ORGANISM: Mus musculus

<400> SEQUENCE: 831

Leu Gly Arg Ser Leu Arg Leu Ser Cys Ala Ala Ser Gly Phe Thr Phe
1               5                   10                  15

Ser Ser Tyr Gly Met His Trp Val Arg Gln Ala Pro Gly Lys Gly Leu
            20                  25                  30

Glu Trp Val Ala Val Ile Ser Tyr Asp Gly Ser Asn Lys Tyr Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Lys Gly Asp Val Asn Tyr Gly Met Asp Val Trp Gly
                85                  90                  95

Gln Gly Thr Thr Val Thr Val Ser Ser Cys Ala Lys Gly Asp Val Asn
            100                 105                 110

Tyr Gly Met Asp Val Trp Ser Tyr Val Leu Thr Gln Pro Pro Ser Val
        115                 120                 125
```

```
Ser Val Ala Pro Gly Gln Thr Ala Arg Ile Ser Cys Gly Gly Ser Asn
    130                 135                 140

Ile Gly Ser Lys Thr Val Asn Trp Tyr Arg Lys Lys Ala Gly Gln Ala
145                 150                 155                 160

Pro Val Leu Val Val Tyr Asp Gly Arg Asp Arg Pro Ser Gly Ile Pro
                165                 170                 175

Glu Arg Phe Ser Gly Ser Asn Ser Gly Asn Ala Ala Thr Leu Ile Ile
            180                 185                 190

Ser Arg Val Glu Val Gly Asp Glu Ala Asp Tyr Tyr Cys Gln Val Trp
        195                 200                 205

Asp Thr Ser Gly Asp Leu His Trp Ala Phe Gly Gly Gly Thr Lys Leu
    210                 215                 220

Thr Val Leu Cys Gln Val Trp Asp Thr Ser Gly Asp Leu His Trp Ala
225                 230                 235                 240

Phe


<210> SEQ ID NO 832
<211> LENGTH: 237
<212> TYPE: PRT
<213> ORGANISM: Mus musculus

<400> SEQUENCE: 832

Pro Ser Glu Thr Leu Ser Leu Thr Cys Thr Val Ser Gly Asp Ser Ile
1               5                   10                  15

Ser Ser Ser Ser Tyr Tyr Trp Ser Trp Ile Arg Gln Pro Pro Gly Lys
            20                  25                  30

Gly Leu Glu Trp Ile Gly Glu Ile Asn His Ser Gly Ser Thr Asn Tyr
        35                  40                  45

Asn Pro Ser Leu Lys Ser Arg Val Thr Ile Ser Val Asp Thr Ser Lys
    50                  55                  60

Asn Gln Phe Ser Leu Lys Leu Ser Ser Val Thr Ala Ala Asp Thr Ala
65                  70                  75                  80

Val Tyr Tyr Cys Ala Arg Asp Gln Glu Met Tyr Tyr Phe Asp Tyr Trp
                85                  90                  95

Gly Gln Gly Thr Leu Val Thr Val Ser Ser Cys Ala Arg Asp Gln Glu
            100                 105                 110

Met Tyr Tyr Phe Asp Tyr Trp Asp Ile Gln Met Thr Gln Ser Pro Ser
        115                 120                 125

Ser Val Ser Ala Ser Val Gly Asp Arg Val Thr Ile Thr Cys Arg Ala
    130                 135                 140

Ser Gln Gly Ile Ser Ser Trp Leu Ala Trp Tyr Gln Gln Lys Pro Gly
145                 150                 155                 160

Lys Ala Pro Lys Leu Leu Ile Tyr Ala Ala Ser Ser Leu Gln Ser Gly
                165                 170                 175

Val Pro Ser Arg Phe Ser Gly Ser Gly Ser Gly Thr Asp Phe Thr Leu
            180                 185                 190

Thr Ile Ser Ser Leu Gln Pro Glu Asp Phe Ala Thr Tyr Tyr Cys Gln
        195                 200                 205

Gln Ala Asn Ser Phe Pro Pro Thr Phe Gly Pro Gly Thr Lys Val Asp
    210                 215                 220

Ile Lys Cys Gln Gln Ala Asn Ser Phe Pro Pro Thr Phe
225                 230                 235


<210> SEQ ID NO 833
```

<211> LENGTH: 239
<212> TYPE: PRT
<213> ORGANISM: Mus musculus

<400> SEQUENCE: 833

Pro Ser Gly Thr Leu Ser Leu Thr Cys Asp Val Ser Gly Gly Ser Ile
1 5 10 15

Ser Arg Ser Asn Trp Trp Ile Trp Val Arg Gln Pro Pro Gly Lys Gly
20 25 30

Leu Glu Trp Ile Gly Glu Ile Tyr His Thr Gly Ser Thr Asn Tyr Asn
35 40 45

Pro Ser Leu Lys Arg Arg Val Thr Ile Ser Val Asp Lys Ser Lys Asn
50 55 60

Gln Phe Ser Leu Asn Leu Ser Ser Val Thr Ala Ala Asp Thr Ala Val
65 70 75 80

Tyr Tyr Cys Ala Arg Gly Lys Gly Ser Tyr Ala Phe Asp Ile Trp Gly
85 90 95

Leu Gly Thr Met Val Thr Val Ser Ser Cys Ala Arg Gly Lys Gly Ser
100 105 110

Tyr Ala Phe Asp Ile Trp Val Leu Thr Gln Pro His Ser Val Ser Glu
115 120 125

Ser Pro Gly Lys Thr Val Thr Ile Ser Cys Thr Gly Ser Gly Gly Asn
130 135 140

Ile Ala Arg Asn Tyr Val Gln Trp Tyr Gln His Arg Pro Gly Arg Ala
145 150 155 160

Pro Ser Thr Val Ile Tyr Glu Asp Asp Arg Arg Pro Ser Gly Val Pro
165 170 175

Asp Arg Phe Ser Gly Ser Thr Asp Ile Ser Ser Asn Ser Ala Ser Leu
180 185 190

Thr Ile Ser Gly Leu Lys Thr Glu Asp Glu Ala Asp Tyr Tyr Cys Gln
195 200 205

Ser Tyr Asp Gly Asn Asn His Met Val Phe Gly Gly Gly Thr Arg Val
210 215 220

Thr Val Leu Cys Gln Ser Tyr Asp Gly Asn Asn His Met Val Phe
225 230 235

<210> SEQ ID NO 834
<211> LENGTH: 242
<212> TYPE: PRT
<213> ORGANISM: Mus musculus

<400> SEQUENCE: 834

Pro Gly Arg Ser Leu Arg Leu Ser Cys Ala Ala Ser Gly Phe Thr Phe
1 5 10 15

Ser Ser Tyr Gly Met His Trp Val Arg Gln Ala Pro Gly Lys Gly Leu
20 25 30

Glu Trp Val Ala Val Ile Ser Tyr Asp Gly Asn Asn Lys Tyr Tyr Thr
35 40 45

Asp Ser Val Lys Gly Arg Phe Thr Ile Ser Arg Asp Asn Ser Lys Asn
50 55 60

Thr Val Tyr Leu Gln Met Asn Ser Leu Arg Ala Glu Asp Thr Ala Val
65 70 75 80

Tyr Tyr Cys Ala Lys Gly Tyr Ser Ser Ser Pro Gly Asp Tyr Trp Gly
85 90 95

Gln Gly Thr Leu Val Thr Val Ser Ser Cys Ala Lys Gly Tyr Ser Ser
100 105 110

```
Ser Pro Gly Asp Tyr Trp Gln Ser Ala Leu Thr Gln Pro Ala Ser Val
        115                 120                 125

Ser Gly Ser Pro Gly Gln Ser Ile Thr Ile Ser Cys Thr Gly Thr Ser
    130                 135                 140

Ser Asp Val Gly Ala Tyr Asn Tyr Val Ser Trp Tyr Gln Gln Tyr Pro
145                 150                 155                 160

Gly Lys Ala Pro Lys Leu Met Ile Tyr Asp Val Ser Asn Arg Pro Ser
                165                 170                 175

Gly Val Ser Asp Arg Phe Ser Gly Ser Lys Ser Gly Asn Thr Ala Ser
            180                 185                 190

Leu Thr Ile Ser Gly Leu Gln Ala Glu Asp Glu Ala Asp Tyr Tyr Cys
        195                 200                 205

Ser Ser Tyr Thr Ser Ser Ser Thr Leu Trp Val Phe Gly Gly Gly Thr
    210                 215                 220

Lys Leu Thr Ala Leu Cys Ser Ser Tyr Thr Ser Ser Ser Thr Leu Trp
225                 230                 235                 240

Val Phe


<210> SEQ ID NO 835
<211> LENGTH: 239
<212> TYPE: PRT
<213> ORGANISM: Mus musculus

<400> SEQUENCE: 835

Pro Ser Gly Asp Leu Ser Leu Thr Cys Asp Val Ser Gly Gly Ser Ile
1               5                   10                  15

Ser Arg Ser Asn Trp Trp Ile Trp Val Arg Gln Pro Pro Gly Lys Gly
            20                  25                  30

Leu Glu Trp Ile Gly Glu Ile Tyr His Thr Gly Ser Thr Asn Tyr Asn
        35                  40                  45

Pro Ser Leu Lys Arg Arg Val Thr Ile Ser Val Asp Lys Ser Lys Asn
    50                  55                  60

Gln Phe Ser Leu Asn Leu Ser Ser Val Thr Ala Ala Asp Thr Ala Val
65                  70                  75                  80

Tyr Tyr Cys Ala Arg Gly Lys Gly Ser Tyr Ala Phe Asp Ile Trp Gly
                85                  90                  95

Leu Gly Thr Met Val Thr Val Ser Ser Cys Ala Arg Gly Lys Gly Ser
            100                 105                 110

Tyr Ala Phe Asp Ile Trp Val Leu Thr Gln Pro His Ser Val Ser Glu
        115                 120                 125

Ser Pro Gly Lys Thr Val Thr Ile Ser Cys Thr Gly Ser Gly Gly Asn
    130                 135                 140

Ile Ala Arg Asn Tyr Val Gln Trp Tyr Gln His Arg Pro Gly Arg Ala
145                 150                 155                 160

Pro Ser Thr Val Ile Tyr Glu Asp Asp Arg Arg Pro Ser Gly Val Pro
                165                 170                 175

Asp Arg Phe Ser Gly Ser Thr Asp Ile Ser Ser Asn Ser Ala Ser Leu
            180                 185                 190

Thr Ile Ser Gly Leu Lys Thr Glu Asp Glu Ala Asp Tyr Tyr Cys Gln
        195                 200                 205

Ser Tyr Asp Gly Asn Asn His Met Val Phe Gly Gly Thr Arg Val
    210                 215                 220

Thr Val Leu Cys Gln Ser Tyr Asp Gly Asn Asn His Met Val Phe
225                 230                 235
```

<210> SEQ ID NO 836
<211> LENGTH: 226
<212> TYPE: PRT
<213> ORGANISM: Mus musculus

<400> SEQUENCE: 836

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Met Tyr Tyr Tyr Tyr Gly Met Asp Val Trp Gly Gln Gly
            100                 105                 110

Thr Thr Val Thr Val Ser Ser Asp Ile Gln Met Thr Gln Ser Pro Ser
        115                 120                 125

Ser Leu Ser Ala Ser Val Gly Asp Arg Val Thr Ile Thr Cys Arg Ala
    130                 135                 140

Ser Gln Ser Ile Ser Ser Tyr Leu Asn Trp Tyr Gln Gln Lys Pro Gly
145                 150                 155                 160

Lys Ala Pro Lys Leu Leu Ile Tyr Ala Ala Ser Ser Leu Gln Ser Gly
                165                 170                 175

Val Pro Ser Arg Phe Ser Gly Ser Gly Ser Gly Thr Asp Phe Thr Leu
            180                 185                 190

Thr Ile Ser Ser Leu Gln Pro Glu Asp Phe Ala Thr Tyr Tyr Cys Gln
        195                 200                 205

Gln Ser Tyr Ser Thr Pro Pro Ala Phe Gly Gln Gly Thr Lys Leu Glu
    210                 215                 220

Ile Lys
225

<210> SEQ ID NO 837
<211> LENGTH: 231
<212> TYPE: PRT
<213> ORGANISM: Mus musculus

<400> SEQUENCE: 837

Gln Val Gln Leu Gln Glu Ser Gly Pro Gly Leu Val Lys Pro Ser Gly
1               5                   10                  15

Thr Leu Ser Leu Thr Cys Thr Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

```
Ala Arg Gly Val Ile Ala Ala Ala Gly Thr Tyr Phe Asp Tyr Trp Gly
            100                 105                 110

Gln Gly Thr Leu Val Thr Val Ser Ser Gln Ala Val Leu Thr Gln Pro
        115                 120                 125

Pro Ser Ala Ser Gly Thr Pro Gly Gln Arg Val Thr Ile Ser Cys Ser
    130                 135                 140

Gly Ser Arg Pro Asn Val Ala Ser Asn Ser Val Asn Trp Tyr Gln Gln
145                 150                 155                 160

Phe Pro Gly Thr Ala Pro Arg Leu Leu Ile Tyr Ser Asp Asn Gln Arg
                165                 170                 175

Pro Ser Gly Val Pro Asp Arg Phe Ser Gly Ser Lys Ser Gly Thr Ser
            180                 185                 190

Ala Ser Leu Ala Ile Ser Gly Leu Gln Phe Glu Asp Glu Ala Asp Tyr
        195                 200                 205

Tyr Cys Glu Thr Trp Asp Asp Ser Leu Arg Gly Val Val Phe Gly Gly
    210                 215                 220

Gly Thr Lys Val Thr Val Leu
225                 230


<210> SEQ ID NO 838
<211> LENGTH: 230
<212> TYPE: PRT
<213> ORGANISM: Mus musculus

<400> SEQUENCE: 838

Gln Leu Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Arg Thr His Tyr Tyr Tyr Gly Met Asp Ile Trp Gly Gln
            100                 105                 110

Gly Thr Thr Val Thr Val Ser Ser Gln Ser Val Leu Thr Gln Pro Pro
        115                 120                 125

Ser Thr Ser Gly Thr Pro Gly Gln Arg Val Thr Ile Ser Cys Ser Gly
    130                 135                 140

Ser Ser Ser Asn Ile Gly Ser Asn Thr Val Asn Trp Tyr His Gln Leu
145                 150                 155                 160

Pro Gly Thr Ala Pro Arg Leu Leu Ile Tyr Ser Asn Asn Gln Arg Pro
                165                 170                 175

Ser Gly Val Pro Asp Arg Phe Ser Gly Ser Lys Ser Gly Thr Ser Ala
            180                 185                 190

Ser Leu Ala Leu Ser Gly Leu Gln Ser Glu Asp Glu Gly Asp Tyr Tyr
        195                 200                 205

Cys Ala Ala Trp Asp Asp Ser Leu Asn Gly Tyr Val Phe Gly Thr Gly
    210                 215                 220

Thr Lys Val Thr Val Leu
```

225 230

<210> SEQ ID NO 839
<211> LENGTH: 230
<212> TYPE: PRT
<213> ORGANISM: Mus musculus

<400> SEQUENCE: 839

Glu Val Arg Leu Gly Gln Ser Gly Pro Glu Leu Lys Asn Pro Gly Asp
1 5 10 15

Phe Arg Lys Ile Ser Cys Lys Gly Ser Gly Tyr Ser Phe Thr Ser Tyr
20 25 30

Trp Ile Gly Trp Val Arg Gln Met Pro Gly Lys Gly Leu Glu Trp Met
35 40 45

Gly Ile Ile Tyr Pro Gly Asp Ser Asp Thr Arg Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Leu Glu Asn Asn Trp Asp Tyr Gly Gly Trp Phe Asp Pro Trp
100 105 110

Gly Gln Gly Thr Leu Val Thr Val Ser Ser Ser Tyr Val Leu Thr Gln
115 120 125

Pro Pro Ser Val Ser Val Ala Pro Gly Gln Thr Ala Arg Ile Thr Cys
130 135 140

Gly Gly Asn Asn Ile Gly Ser Lys Ser Val His Trp Tyr Gln Gln Lys
145 150 155 160

Pro Gly Gln Ala Pro Val Leu Val Val Tyr Asp Asp Ser Asp Arg Pro
165 170 175

Ser Gly Ile Pro Glu Arg Phe Ser Gly Ser Asn Ser Gly Asn Thr Ala
180 185 190

Thr Leu Thr Ile Ser Arg Val Glu Ala Gly Asp Glu Ala Asp Tyr Tyr
195 200 205

Cys Gln Val Trp Asp Ser Ser Ser Asp His Trp Val Phe Gly Gly Gly
210 215 220

Thr Lys Leu Thr Val Leu
225 230

<210> SEQ ID NO 840
<211> LENGTH: 244
<212> TYPE: PRT
<213> ORGANISM: Mus musculus

<400> SEQUENCE: 840

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys

```
                85                  90                  95

Ala Arg Asp Gly Ala Gly Asn Tyr Asp Ile Leu Thr Gly Asp Arg Ser
            100                 105                 110

Glu Asp Tyr Tyr Tyr Tyr Tyr Gly Met Asp Val Trp Gly Gln Gly Thr
        115                 120                 125

Thr Val Thr Val Ser Ser Ser Tyr Glu Leu Thr Gln Pro Pro Ser Ala
    130                 135                 140

Ser Gly Ala Pro Gly Gln Arg Val Ser Ile Ser Cys Ser Gly Gly Tyr
145                 150                 155                 160

Ser Asn Ile Gly Ser Asn Thr Val Asn Trp Tyr Gln Gln Leu Pro Gly
                165                 170                 175

Ala Ala Pro Lys Phe Leu Ile Tyr Ser Asp Asn Gln Arg Pro Ser Gly
            180                 185                 190

Val Pro Asp Arg Phe Ser Gly Ser Lys Ser Gly Thr Ser Ala Ser Leu
        195                 200                 205

Ala Ile Ser Gly Leu Gln Ser Glu Asp Glu Ala Asp Tyr Tyr Cys Ala
    210                 215                 220

Thr Trp Asp Asp Ser Leu Asn Gly Pro Val Phe Gly Gly Gly Thr Lys
225                 230                 235                 240

Leu Thr Val Leu


<210> SEQ ID NO 841
<211> LENGTH: 226
<212> TYPE: PRT
<213> ORGANISM: Mus musculus

<400> SEQUENCE: 841

Gln Val Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Gly Tyr Tyr Tyr Gly Met Asp Val Trp Gly Gln Gly
            100                 105                 110

Thr Thr Val Thr Val Ser Ser Asp Ile Val Met Thr Gln Thr Pro Ser
        115                 120                 125

Ser Leu Ser Ala Ser Val Gly Asp Arg Val Ala Ile Thr Cys Gln Ala
    130                 135                 140

Ser Arg Asn Ile Trp Ser Tyr Val Asn Trp Tyr Gln Gln Lys Pro Gly
145                 150                 155                 160

Glu Ala Pro Arg Leu Leu Ile Tyr Gly Ala Ser Thr Leu Gln Arg Gly
                165                 170                 175

Val Pro Ser Arg Phe Ser Gly Ser Gly Ser Gly Thr Gly Phe Thr Leu
            180                 185                 190

Thr Ile Asn Ser Leu Gln Pro Glu Asp Phe Ala Thr Tyr Phe Cys Gln
        195                 200                 205

Gln Ser His Ser Thr Pro Ile Thr Phe Gly Gly Gly Thr Arg Val Asp
```

```
    210                 215                 220

Ile Lys
225


<210> SEQ ID NO 842
<211> LENGTH: 229
<212> TYPE: PRT
<213> ORGANISM: Mus musculus

<400> SEQUENCE: 842

Gln Leu Gln Leu Gln Glu Ser Gly Pro Gly Leu Val Asn Leu Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Ser Ser Gly Pro Tyr Gly Met Asp Val Trp Gly
            100                 105                 110

Gln Gly Thr Thr Val Thr Val Ser Ser Gln Ser Val Leu Thr Gln Pro
        115                 120                 125

Pro Ser Val Ser Val Ala Pro Gly Gln Thr Ala Arg Val Thr Cys Gly
    130                 135                 140

Gly Ser Asn Ile Gly Ser Gln Ser Val His Trp Tyr Gln Gln Lys Pro
145                 150                 155                 160

Gly Gln Ala Pro Val Leu Val Val Tyr Asp Asp Tyr Asp Arg Pro Ser
                165                 170                 175

Gly Ile Pro Glu Arg Phe Ser Gly Ser Asn Ser Gly Asn Thr Ala Thr
            180                 185                 190

Leu Thr Ile Thr Arg Val Asp Ala Gly Asp Glu Ala Asp Tyr Tyr Cys
        195                 200                 205

Gln Ile Trp Asp Ser Ser Ser Ala His Val Val Phe Gly Gly Gly Thr
    210                 215                 220

Lys Leu Thr Val Leu
225


<210> SEQ ID NO 843
<211> LENGTH: 231
<212> TYPE: PRT
<213> ORGANISM: Mus musculus

<400> SEQUENCE: 843

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
```

```
65                  70                  75                  80

Leu Lys Leu Ser Ser Val Thr Ala Ala Asp Thr Ala Val Tyr Tyr Cys
                85                  90                  95

Ala Arg Val Asn Tyr Gly Asp Tyr Asp Trp Tyr Phe Asp Leu Trp Gly
            100                 105                 110

Arg Gly Thr Leu Val Thr Val Ser Ser Gln Pro Val Leu Thr Gln Pro
        115                 120                 125

Pro Ser Ala Ser Gly Thr Pro Gly Gln Arg Val Thr Ile Ser Cys Ser
    130                 135                 140

Gly Ser Ser Ser Asn Ile Gly Ser Asn Phe Val Thr Trp Tyr Gln Gln
145                 150                 155                 160

Leu Pro Gly Thr Ala Pro Lys Leu Leu Ile Tyr Ser Asn Asn Gln Arg
                165                 170                 175

Pro Ser Gly Val Ser Asp Arg Phe Ser Ala Ser Lys Ser Gly Thr Ser
            180                 185                 190

Ala Ser Leu Ala Ile Ser Arg Leu Gln Ser Gln Asp Glu Ala Glu Tyr
        195                 200                 205

Tyr Cys Ala Ala Trp Asp Asp Ser Leu Arg Ser Tyr Val Phe Gly Ser
    210                 215                 220

Gly Thr Lys Val Thr Val Val
225                 230


<210> SEQ ID NO 844
<211> LENGTH: 229
<212> TYPE: PRT
<213> ORGANISM: Mus musculus

<400> SEQUENCE: 844

Gln Val Gln Leu Gly Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Pro Leu Arg Tyr Tyr Tyr Tyr Tyr Gly Met Asp Val Trp
            100                 105                 110

Gly Gln Gly Thr Thr Val Thr Val Ser Ser Asp Ile Gln Met Thr Gln
        115                 120                 125

Ser Pro Ser Ser Leu Ser Ala Ser Val Gly Asp Arg Val Thr Ile Thr
    130                 135                 140

Cys Arg Ala Ser Gln Ser Ile Ser Ser Tyr Leu Asn Trp Tyr Gln Gln
145                 150                 155                 160

Lys Pro Gly Lys Ala Pro Lys Leu Leu Ile Tyr Ala Ala Ser Ser Leu
                165                 170                 175

Gln Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
        195                 200                 205
```

-continued

```
Tyr Cys Gln Gln Ser Tyr Ser Thr Pro Trp Thr Phe Gly Gln Gly Thr
    210                 215                 220

Lys Val Glu Ile Lys
225


<210> SEQ ID NO 845
<211> LENGTH: 165
<212> TYPE: PRT
<213> ORGANISM: Mus musculus

<400> SEQUENCE: 845

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Ser Ser Ser His Ser Ser Trp Asp Asn Gln Cys Gln Cys Thr Ser Ser
    50                  55                  60

Ala Thr Arg Ser Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly
                165


<210> SEQ ID NO 846
<211> LENGTH: 6
<212> TYPE: PRT
<213> ORGANISM: Artificial Sequence
<220> FEATURE:
<223> OTHER INFORMATION: linker
<220> FEATURE:
<221> NAME/KEY: SITE
<222> LOCATION: (6)..(6)
<223> OTHER INFORMATION: Biotin moiety is attached

<400> SEQUENCE: 846

Gly Ser Gly Ser Gly Lys
1               5
```

ENGINEERED CD25 POLYPEPTIDES AND USES THEREOF

CROSS-REFERENCE TO RELATED APPLICATIONS

This application is a continuation of International Application No. PCT/US2019/061567, filed Nov. 14, 2019, which claims the priority benefit of U.S. Provisional Application No. 62/902,334, filed Sep. 18, 2019; and U.S. Provisional Application No. 62/767,431, filed Nov. 14, 2018, the entire contents of which are hereby incorporated by reference in their entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: RBYC_024_01US_SeqList_ST25.txt, date recorded: Aug. 2, 2021, file size ~393 kilobytes).

BACKGROUND

The CD25 protein is the alpha chain of the interleukin-2 (IL-2) receptor and is a transmembrane protein present on regulatory T cells, and activated T cells. In a normal state, regulatory T cells constitutively express CD25 and act to suppress the expansion of effector T cells. Regulatory T cells maintain the healthy state and inhibit effector T cells from reacting against self antigens or over-reacting to foreign antigens. In a normal, protective immune response, effector T cells multiply after contact with foreign antigen and overcome inhibition by regulatory T cells. In case of proliferative diseases, however, cancer cells may disable the healthy immune response by increasing the amount of regulatory T cells and thereby limiting the generation of effector T cells against them. Thus, there is interest in therapeutics for to alter the proliferation of CD25-expressing regulatory T cells, for example to dampen the immune system for use in cancer therapies. These therapeutics may include CD25-targeting antibodies.

CD25-targeting antibodies can be produced by immunization of animals using CD25 immunogens, however, current methods of developing CD25 immunogens often lead to unpredictable, undesirable characteristics, such as antibody promiscuity or low cross-reactivity across species.

Thus, what is needed in the art are new engineered polypeptides having structural and/or dynamic similarity to CD25 or portions thereof, for example engineered polypeptides designed to mimic epitopes outside the IL-2 binding site.

SUMMARY

In one aspect, the disclosure provides an engineered polypeptide, wherein the engineered polypeptide shares at least 46% structural and/or dynamic identity to a CD25 reference target, wherein the CD25 reference target is a portion of a CD25 selected from CD25 residues 55-63, 13-20:127-132, 5-17, 5-11:156-163, 77-89, 147-157, 11-14, or 44-56.

In embodiments, the engineered polypeptide shares at least 60% structural and/or dynamic identity to the CD25 reference target. In embodiments, the engineered polypeptide shares at least 80% structural and/or dynamic identity to the CD25 reference target. In embodiments, the engineered polypeptide shares at least 80% sequence identity to an amino-acid sequence selected from SEQ ID NOS: 1-16. In embodiments, the engineered polypeptide shares at least 46% structural and/or dynamic identity to a CD25 reference target, wherein the CD25 reference target is a portion of CD25 selected from CD25 residues 55-63, 13-20:127-132, 5-17, 5-11:156-163, 77-89, 147-157, 11-14, or 44-56. In embodiments, the engineered polypeptide shares at least 80% structural and/or dynamic identity to the CD25 reference target. In embodiments, the structural and/or dynamic identity to the CD25 reference target is determined using the structure of CD25 deposited at PDB ID NO: 2ERJ, chain A. In embodiments, the engineered polypeptide comprises an N-terminal modification or a C-terminal modification, optionally an N-terminal Biotin-$PEG_2$- or a C-terminal-GSGSGK-Biotin (SEQ ID NO: 846).

In embodiments, between 10% to 98% of the amino acids of the engineered polypeptide meet one or more CD25 reference target-derived constraints. In embodiments, the amino acids that meet the one or more CD25 reference target-derived constraints have less than 8.0 Å backbone root-mean-square deviation (RSMD) structural homology with the CD25 reference target. In embodiments, the amino acids that meet the one or more CD25 reference target-derived constraints have a van der Waals surface area overlap with the reference of between 30 $Å^2$ to 3000 $Å^2$. In embodiments, the CD25 reference target-derived constraints are independently selected from the group consisting of: atomic distances; atomic fluctuations; atomic energies; chemical descriptors; solvent exposures; amino acid sequence similarity; bioinformatic descriptors; non-covalent bonding propensity; phi angles; psi angles; van der Waals radii; secondary structure propensity; amino acid adjacency; and amino acid contact.

In embodiments, the engineered polypeptide shares 46%-96% RMSIP or more structural similarity to the reference target across the amino acids of the polypeptide that meet the one or more reference target-derived constraints.

In another aspect, the disclosure provides a CD25-specific antibody comprising an antigen-binding domain that specifically binds a CD25 epitope selected from CD25 residues 55-63, 13-20:127-132, 5-17, 5-11:156-163, 77-89, 147-157, 11-14, or 44-56. In embodiments, the antibody competes for binding of CD25 with an epitope-specific reference binding agent, wherein the epitope-specific binding agent is IL-2, daclizumab, basioliximab, and/or 7G7B6. In embodiments, the antibody does not compete with an off-target reference binding agent, wherein the off0target binding agent is IL-2, daclizumab, basioliximab, and/or 7G7B6. In embodiments, the antibody has a $k_{off}$ of less than $10^{-2}$/s, less than $10^{-3}$/s, or less than $10^{-4}$/s, wherein the $k_{off}$ is measured using biolayer interferometry with soluble human CD25. In embodiments, the antibody has a $k_{off}$ of between $10^{-2}$/s $10^{-5}$/s, wherein the $k_{off}$ is measured using biolayer interferometry with soluble human CD25. In embodiments, the antibody has a $K_D$ less than 100 nM, less than 25 nM, or less than 5 nM, wherein the $K_D$ is measured using biolayer interferometry with soluble human CD25. In embodiments, the antibody has a $K_D$ between 100 nM and 1 nM, wherein the $K_D$ is measured using biolayer interferometry with soluble human CD25.

In embodiments, the antibody specifically binds cells expressing CD25. In embodiments, the antibody binds cells expressing CD25 with a mean fluorescence intensity (MFI) of at least $10^4$ or at least $10^5$. In embodiments, the antibody binds cells expressing CD25 with a mean fluorescence intensity (MFI) of between $10^4$ and 106. In embodiments, the antibody does not bind CD25(−) cells. In embodiments, the antibody binds CD25(−) cells with a mean fluorescence intensity (MFI) of less than 10'. In embodiments, the antibody comprises the six CDRs of any one of Combinations 1-126 of Table 7D.

In embodiments, the antibody comprising six complementarity determining regions (CDRs) for any one of YU390-B12, YU397-F01, YU397-D01, YU398-A11, YU404-H01, YU400-B07, YU400-D09, YU401-B01, YU401-G07, YU404-C02, YU403-G07, YU403-G05, YU391-B12, YU400-A03, YU400-D02, YU392-A09, YU392-B11, YU392-B12, YU392-E05, YU392-E06, YU392-G08, YU389-A03, YU392-G09, YU392-G12, YU392-H02, YU392-H04, YU402-F01, YU389-B111, YU394-D08, or YU390-A11, as provided in Table 3A and Table 3B.

In embodiments, the antibody comprises a heavy chain variable region and a light chain variable region that each share at least 90%, 95%, 99%, or 100% sequence identity with the heavy chain variable region and the light chain variable region of YU390-B12, YU397-F01, YU397-D01, YU398-A11, YU404-H01, YU400-B07, YU400-D09, YU401-B01, YU401-G07, YU404-C02, YU403-G07, YU403-G05, YU391-B12, YU400-A03, YU400-D02, YU392-A09, YU392-B11, YU392-B12, YU392-E05, YU392-E06, YU392-G08, YU389-A03, YU392-G09, YU392-G12, YU392-H02, YU392-H04, YU402-F01, YU389-B11, YU394-D08, or YU390-All, as provided in Table 5. In embodiments, the antibody is a full-length immunoglobulin G monoclonal antibody. In embodiments, the antibody comprises single chain variable fragment (scFv) that share at least 90%, 95%, 99%, or 100% sequence identity with the scFv sequence of YU390-B12, YU397-F01, YU397-D01, YU398-A11, YU404-H01, YU400-B07, YU400-D09, YU401-B01, YU401-G07, YU404-C02, YU403-G07, YU403-G05, YU391-B12, YU400-A03, YU400-D02, YU392-A09, YU392-B11, YU392-B12, YU392-E05, YU392-E06, YU392-G08, YU389-A03, YU392-G09, YU392-G12, YU392-H02, YU392-H04, YU402-F01, YU389-B11, YU394-D08, or YU390-A11, as provided in Table 5.

In embodiments, the antibody is a human antibody. In embodiments, the antibody is a humanized antibody. In embodiments, the antibody is a chimeric antibody. In embodiments, the antibody comprises a mouse variable domain and a human constant domain. In embodiments, the antibody also binds cynomologous monkey CD25.

In another aspect, the disclosure provides a pharmaceutical composition comprising any antibody of disclosure and optionally a pharmaceutically acceptable excipient. In another aspect, the disclosure provides a method of treating a subject in need of treatment comprising administering to the subject a therapeutically effective amount of any antibody or pharmaceutical composition of the disclosure. In embodiments, the subject suffers from a cancer. In embodiments, the subject suffers from an autoimmune disease or disorder.

In another aspect, the disclosure provides a method of depleting the number of regulatory T cells in a subject comprising administering to the subject a therapeutically effective amount of any antibody or pharmaceutical composition of the disclosure. In embodiments, the subject suffers from a cancer. In embodiments, the subject suffers from an autoimmune disease or disorder.

In another aspect, the disclosure provides a kit comprising the antibodies of any antibody or pharmaceutical composition of the disclosure.

In some aspects, provided herein is an engineered immunogen having at least 60% sequence similarity to a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11. In some embodiments, the engineered immunogen has at least 80% similarity to the sequence. In other embodiments, the engineered immunogen has at least 90% similarity to the sequence. In certain embodiments, the engineered immunogen shares at least one characteristic with CD25. In still further embodiments, the engineered immunogen binds to an antibody of CD25. In some embodiments, the engineered immunogen has higher binding affinity to an antibody of CD25 at pH below 7.0, compared to binding affinity at pH between about 7.3 and about 7.5. In some embodiments, the engineered immunogen has higher binding affinity to an antibody of CD25 at pH between about 6.4 and about 6.6, compared to binding affinity at pH between about 7.3 and about 7.5.

In yet other embodiments, provided herein is a method of producing an antibody, comprising immunizing an animal with an engineered immunogen having at least 60% sequence similarity to a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11; and producing an antibody. In some embodiments of the method, the antibody is an antibody to CD25. In certain embodiments, the antibody exhibits higher binding affinity for CD25 at pH below 7.0, compared to binding affinity at pH between about 7.3 and about 7.5. In still further embodiments, the antibody exhibits higher binding affinity for CD25 at pH between about 6.4 and about 6.6, compared to binding affinity at pH between about 7.3 and about 7.5. In some embodiments, the antibody does not block binding of CD25 to IL-2. In other embodiments, the antibody does block binding of CD25 to IL-2. In some embodiments, the antibody does not block binding of CD25 to IL-2. In some embodiments, the antibody prevents heterotrimerization of IL-2R-alpha, IL-2R-beta, and IL-2R-gamma. In certain embodiments, the antibody is capable of binding to both the cis orientation and the trans orientation of CD25.

DESCRIPTION OF THE FIGURES

The present application can be understood by reference to the following description taking in conjunction with the accompanying figures.

FIG. 3A shows the extraction of spatially-associated topological information about an interface of interest in a reference, and use thereof in defining a topological constraint for use in selecting an engineered polypeptide. FIG. 3B provides a schematic detailing the in silico screen step, demonstrating how mismatched candidates are discarded while candidates that match the topology are retained. FIG. 3C presents the top 12 selected engineered polypeptide candidates identified.

FIGS. 4A-4B provide a second set of schematics demonstrating the selection of a different group of engineered polypeptides based on a different set of reference parameters, using the methods described herein. FIG. 4A shows extraction of spatially-associated topological information and construction of a topology matrix. FIG. 4B provides a list of top 8 engineered polypeptide candidates selected by in silico comparing candidates to the topological constraints.

FIG. 14A shows bind to CD25(+) cells. FIG. 14B shows binding to control CD25(−) cells.

DETAILED DESCRIPTION

Figure 1:
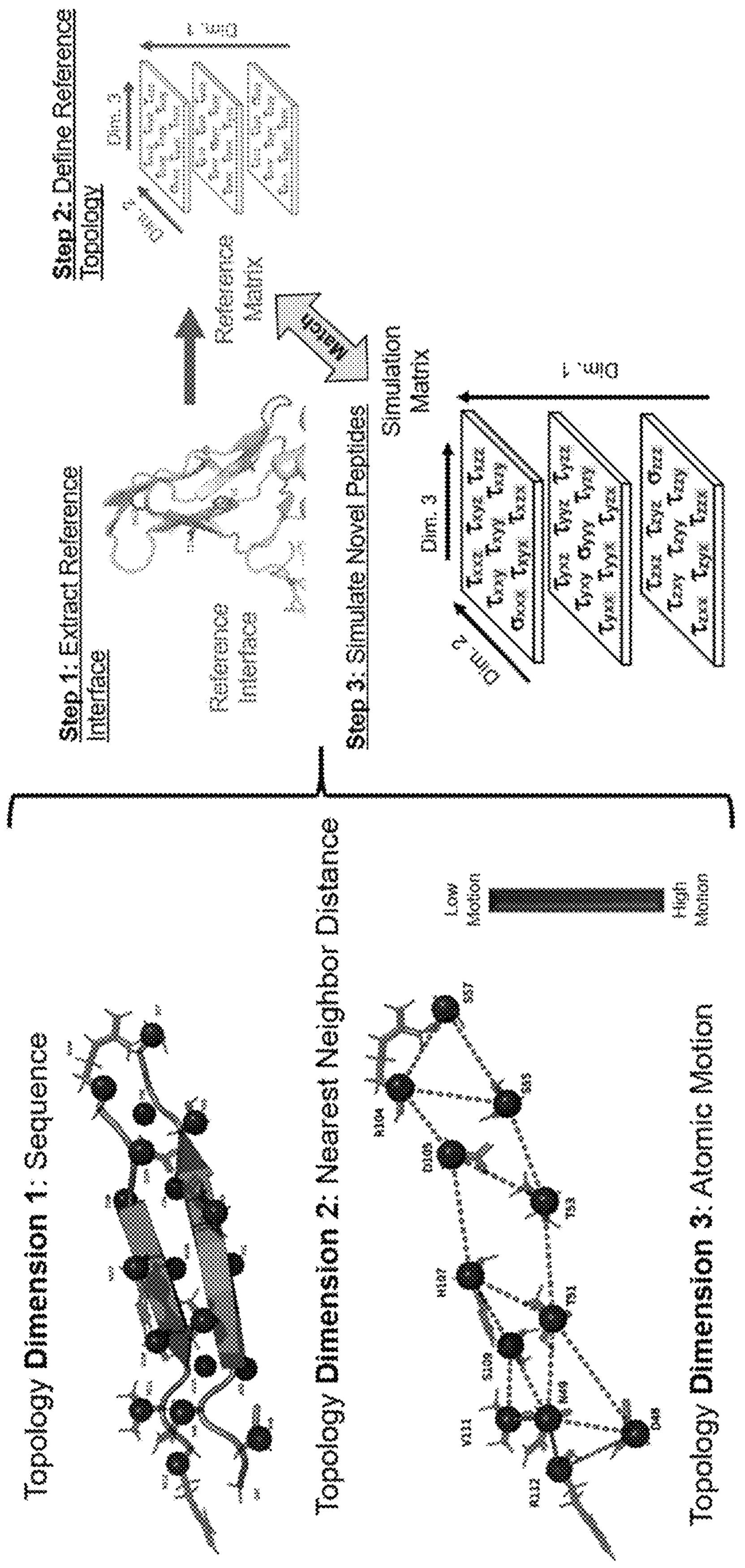
FIG. 1 provides a schematic demonstrating construction of an exemplary combination of three spatially-associated topological constraints, for use in selecting an engineered polypeptide as described herein.
Figure 2:
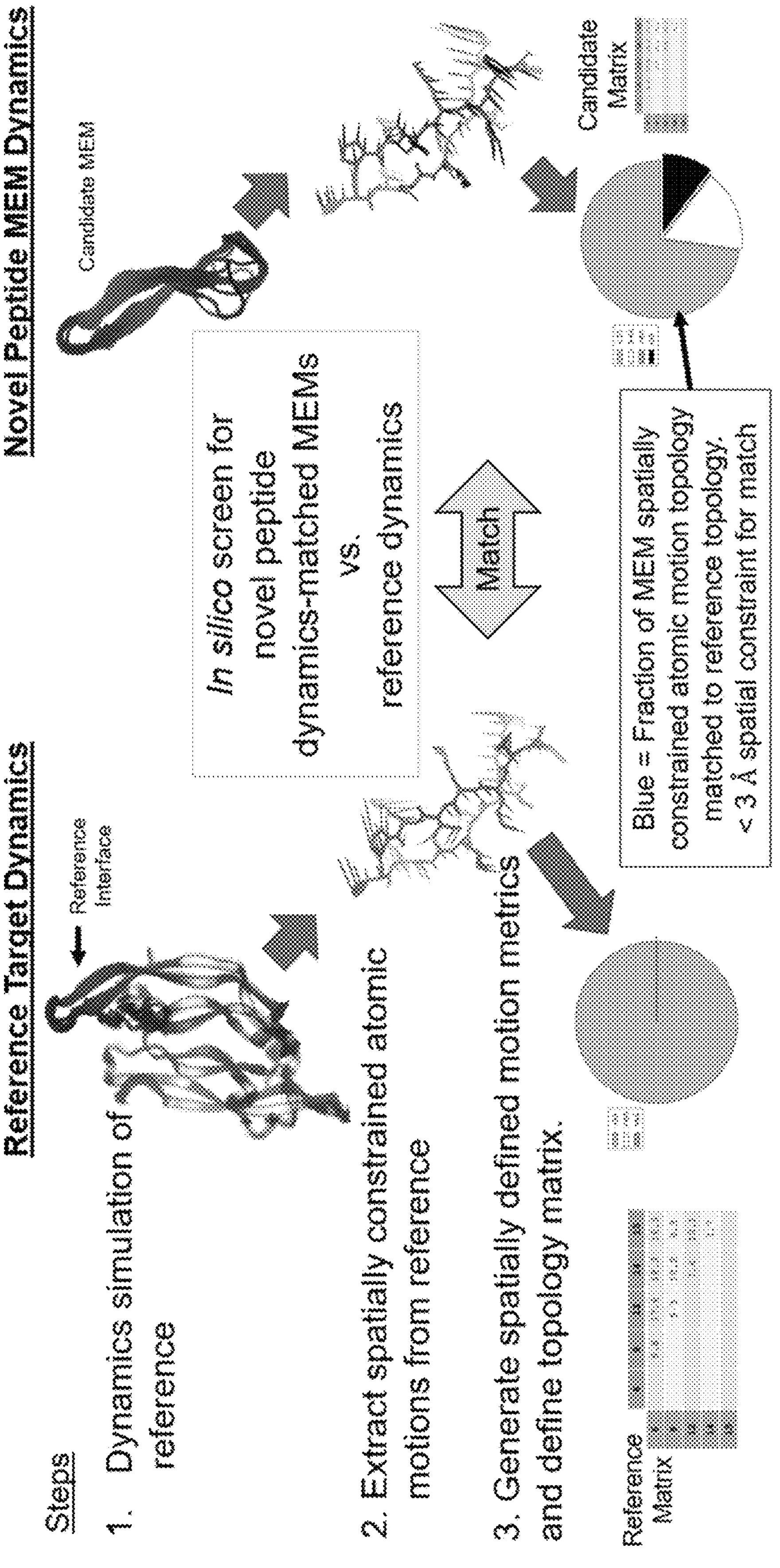
FIG. 2 provides a schematic of the steps involved in some exemplary methods of determining the reference-derived spatially-associated topological constraints and their use in selecting an engineered polypeptide. The engineered polypeptides are herein referred to as meso-scale molecules, MEMs, or meso-scale peptides.
Figure 3A:
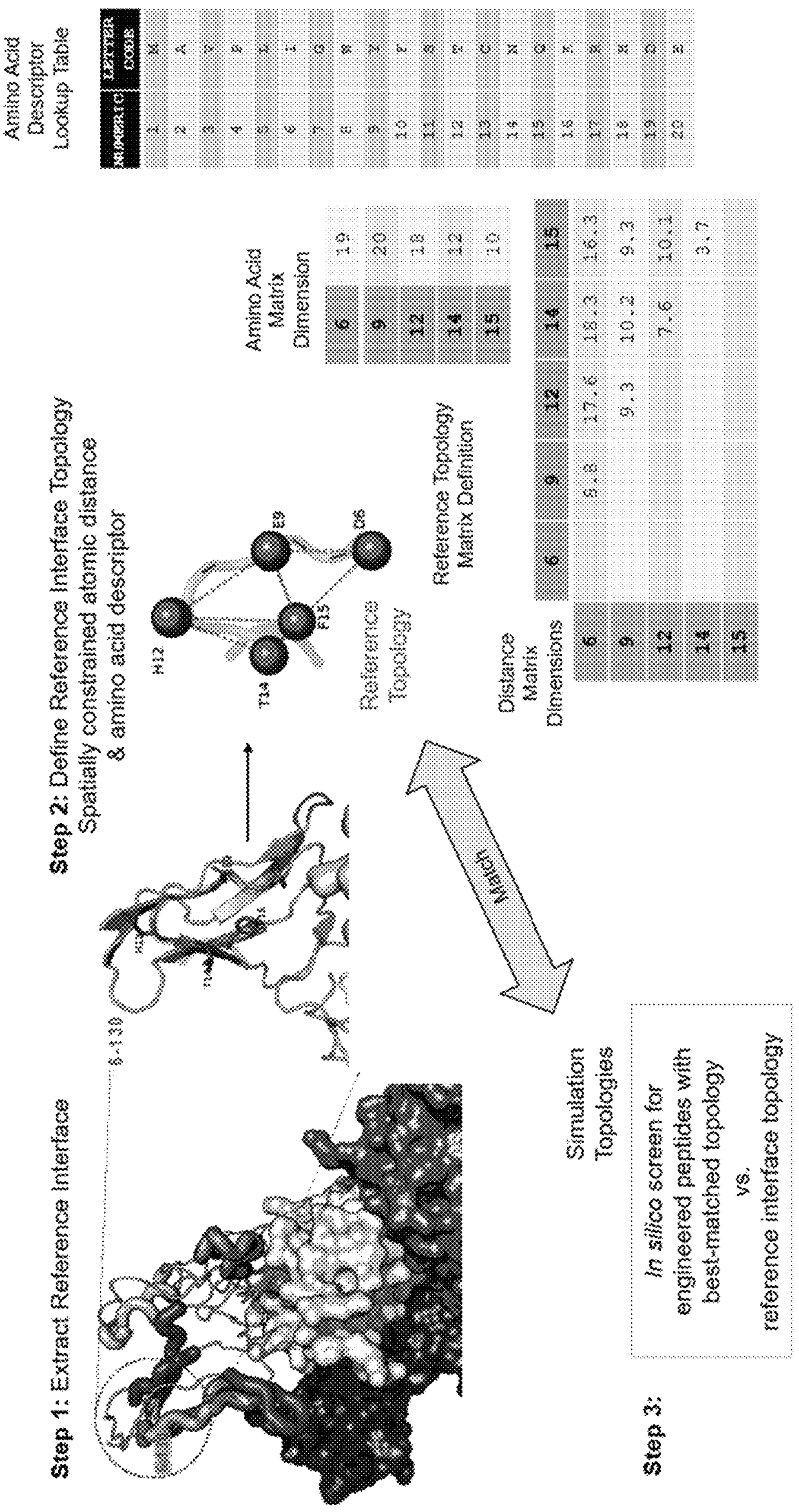
FIGS. 3A-3C provide schematics demonstrating the selection of a group of engineered polypeptides using the methods described herein.
Figure 3B:
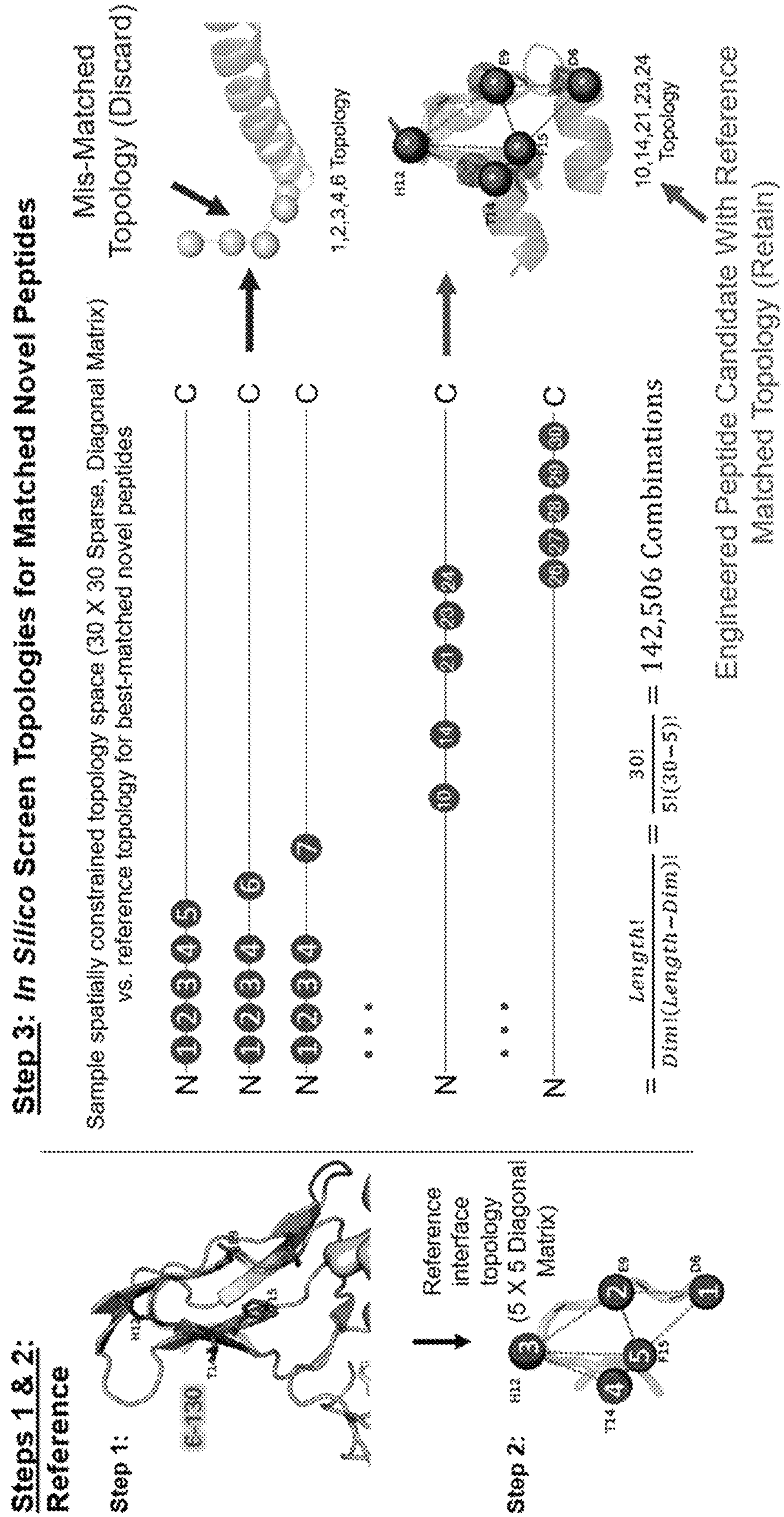
Figure 3C:
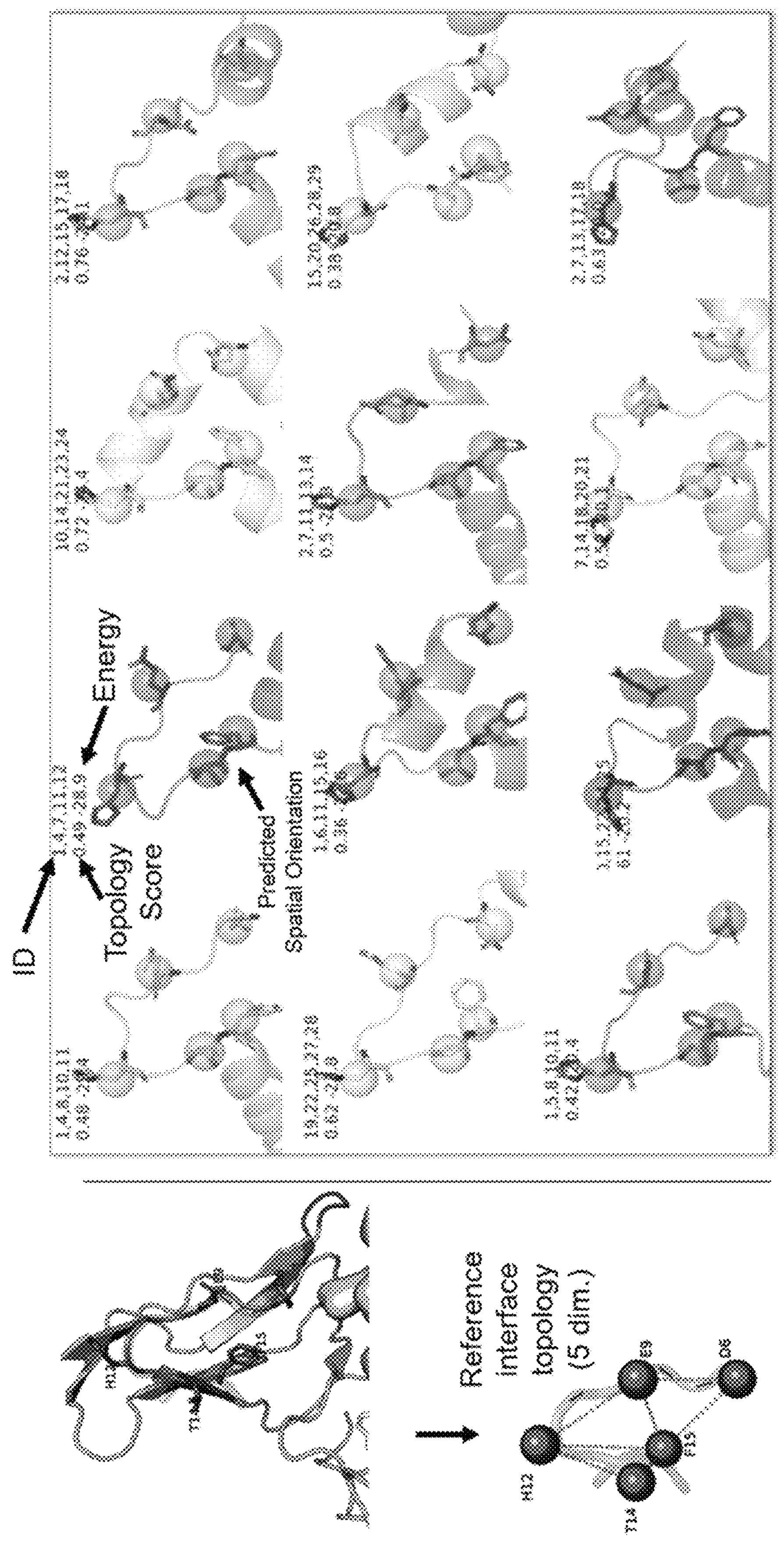
Figure 4B:
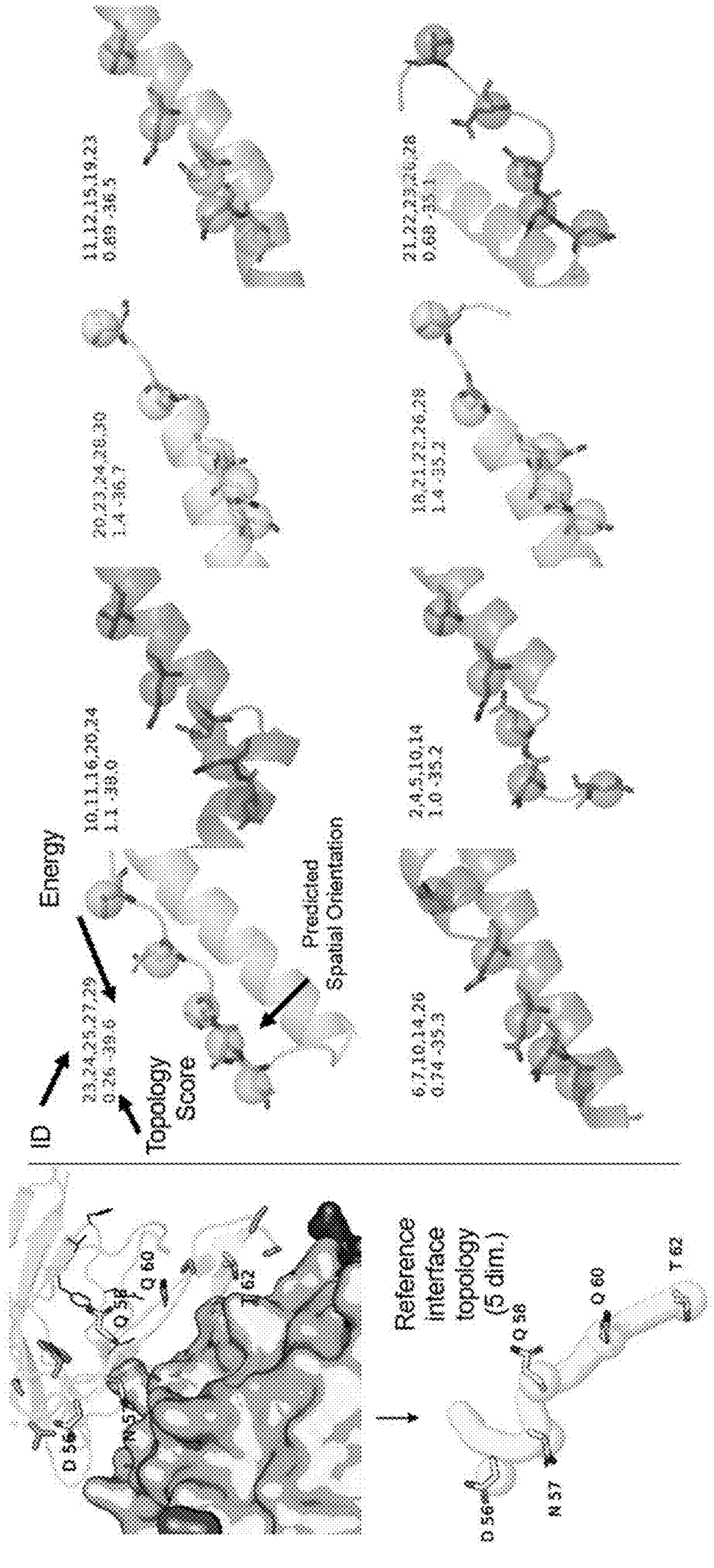

Provided herein are engineered polypeptides that share structural and/or dynamic identity with a portion of reference CD25 target. Epitopes of interest include but are not limited to the eight epitopes shown in FIG. 6. In some embodiments, the selected epitope is non-overlapping with the binding site (epitope) for IL-2, daclizumab, and/or basiliximab. In some embodiments, the epitope overlaps the epitope for 7G7B6. In some embodiments, the selected epitope is selected from 55-63, 12-20:127-132 (a discontinuous epitope), 5-17, 5-11:156-163 (a discontinuous epitope), 77-89, 147-157, 11-14, or 44-56. In some embodiments, the engineered polypeptides are conformationally stable and represent CD25 epitopes that are involved in interactions with antibodies that bind specifically to CD25. In some embodiments, the engineered polypeptides represent a surface portion of CD25 that is not known to interact with antibodies that bind specifically to CD25. Such engineered polypeptides may be used, for example, to select and/or produce antibodies that bind specifically to CD25.

I. Engineered Polypeptides.

In some embodiments, the engineered polypeptide provided herein shares at least 4600 structural and/or dynamic identity to a CD25 reference target, wherein the CD25 reference target is a portion of CD25 selected from those listed in the table below. As generally provided herein, the % structural/dynamic identity is the root mean square inner product (RMSIP) identity (as provided herein above)×10000. In some embodiments, the structural identity refers to sequence identity.

| Reference Target No. | CD25 Residues | Sequence |
|---|---|---|
| 1 | 55-63 | SWDNQCQCT (SEQ ID NO: 22) |
| 2 | 13-20:127-132 | ATFKAMA (SEQ ID NO: 23):MVYYQC (SEQ ID NO: 24) |
| 3 | 5-17 | DDPPEIPHATFKA (SEQ ID NO: 25) |
| 4 | 5-11:156-163 | DDPPEIP (SEQ ID NO: 26):RWTQPQLI (SEQ ID NO: 27) |
| 5 | 77-89 | QPEEQKERKTTEM (SEQ ID NO: 28) |
| 6 | 147-157 | VCKMTHGKTRW (SEQ ID NO: 29) |
| 7 | 11-14 | IPHA (SEQ ID NO: 30) |
| 8 | 44-56 | YMLCTGSSSHSSW (SEQ ID NO: 31) |

In some embodiments, the engineered polypeptide provided herein 8000 sequence identity to an amino-acid sequence selected from:

(SEQ ID NO: 1)
CDCQAQWTPGMRAPGYDPYCLNC (SEQ ID NO: 2)
MVYCQPDCTAKCMHGCDRDTMKECCDRLK (SEQ ID NO: 3)
DDCPEVPHATFKGPGQKWEGPGGGDCSK (SEQ ID NO: 4)
DDCIEVPGPAECAERACRAQEERQRQPQCI (SEQ ID NO: 5)
AEEEKIKIEQKERKTTIKLAKEAK (SEQ ID NO: 6)
CHLQIMTHGKIIYVPC (SEQ ID NO: 7)
DDGDRCAKEHEIPHATGEECQKRDKS (SEQ ID NO: 8)
CKQLVIYFTGNSSHSSVFYIYYDC (SEQ ID NO: 9)
GSGDEDCKKFQSDDNWENYTSTRHLTFCDEKRS (SEQ ID NO: 10)
GSGNEEIEKKIKDCTGNSSHSSWEEALECALKK

-continued (SEQ ID NO: 11)
GSGDERIERLIKECTGNSSHSSWEEALECALRR (SEQ ID NO: 12)
GSGSHPCAYWRWVIKMTHGKTRWVLELVFCYRD (SEQ ID NO: 13)
GSGKCEEEAKKIASKMTHGKTREEEAEEYLKKC (SEQ ID NO: 14)
GSGDDESEKRTTERDTRKCTKAKANDNQCQPTE (SEQ ID NO: 15)
GSGSSEWDKWVEEWYKKMCTEAKKNDNQCQPTK (SEQ ID NO: 16)
GSGQCTVWVFRNGDKILYIYEDCDNDNQHQQTL In some embodiments, the polypeptide shares at least 60%, at least 70%, at least 75%, at least 80%, at least 85%, at least 90%, or at least 95% structural and/or dynamic identity to the CD25 reference target. In some embodiments, polypeptide shares at least 60%, at least 70%, at least 75%, at least 80%, at least 85%, at least 90%, or at least 95% sequence identity to the CD25 reference target.

In some embodiments, the engineered polypeptide is designed to mimic a selected CD25 epitope. For example, in some embodiments, the polypeptide comprises a meso-scale engineered molecule, e.g. a meso-scale engineered polypeptide. Provided herein are methods of selecting meso-scale engineered polypeptides, and compositions comprising and methods of using said engineered polypeptides. For example, provided herein are methods of using engineered polypeptides in in vitro selection of antibodies.

The engineered polypeptides of the present disclosure are between 1 kDa and 10 kDa, referred to herein as "meso-scale". Engineered polypeptides of this size may, in some embodiments, have certain advantages, such as protein-like functionality, a large theoretical space from which to select candidates, cell permeability, and/or structural and dynamical variability. The terms meso-scale peptides and meso-scale polypeptides are used interchangeably herein, and the term meso-scale molecules (MEM) is intended to cover these.

The methods provided herein comprise identifying a plurality of spatially-associated topological constraints, some of which may be derived from a CD25 reference target, constructing a combination of said constraints, comparing candidate peptides with said combination, and selecting a candidate that has constraints which overlap with the combination. By using spatially-associated topological constraints, different aspects of an engineered polypeptide can be included in the combination depending on the intended use, or desired function, or another desired characteristic. Further, not all constraints must, in some embodiments, be derived from a CD25 reference target. Through such methods, in some embodiments the selected engineered polypeptides are not simply variations of a CD25 reference target (such as might be obtained through peptide mutagenesis or progressive modification of a single reference), but rather may have a different overall structure than the reference peptide, while still retaining desired functional characteristics and/or key substructures.

Further provided herein are methods of using said engineered polypeptides, which include methods of programmable in vitro selection using one or more engineered polypeptides. Such selection may be used, for example, in the identification of antibodies.

These methods and engineered polypeptides are described in greater detail below.

II. Methods of Selecting Engineered Polypeptides

In some aspects, provided herein are methods of selecting an engineered polypeptide, comprising:

identifying one or more topological characteristics of a CD25 reference target;

designing spatially-associated constraints for each topological characteristic to produce a combination of CD25 reference target-derived constraints;

comparing spatially-associated topological characteristics of candidate peptides with the combination derived from the CD25 reference target; and selecting a candidate peptide with spatially-associated topological characteristics that overlap with the combination of constraints derived from the CD25 reference target.

In some embodiments, one or more additional spatially-associated topological constraints that are not derived from the CD25 reference target are included in the combination.

a. Spatially-Associated Topological Constraints

The engineered polypeptides described herein are selected based on how closely they match a combination of spatially-associated topological constraints. This combination may also be described using the mathematical concept of a "tensor". In such a combination (or tensor), each constraint is independently described in three dimensional space (e.g., spatially-associated), and the combination of these constraints in three dimensional space provides, for example, a representational "map" of different desired characteristics and their desired level (if applicable) relative to location. This map is not, in some embodiments, based on a linear or otherwise pre-determined amino acid backbone, and therefore can allow for flexibility in the structures that could fulfill the desired combination, as described. For example, in some embodiments, the "map" includes a spatial area wherein the prescribed constraint limitations could be adequately met by two adjacent amino acids—in some embodiments, these amino acids could be directly bonded (e.g., two contiguous amino acids) while in other embodiments, the amino acids are not directly bonded to each other but could be brought together in space by the folding of the peptide (e.g., are not contiguous amino acids). The separate constraints themselves are also not necessarily based on structure, but could include, for example, chemical descriptors and/or functional descriptors. In some embodiments, constraints include structural descriptors, such as a desired secondary structure or amino acid residue. In certain embodiments, each constraint is independently selected.

For example, FIG. 1 is a schematic demonstrating the construction of a representative combination of spatially-associated topological constraints. The three constraints in FIG. 1 are sequence, nearest neighbor distance, and atomic motion, with nearest neighbor distance and atomic motion combined into one graphic. As shown, some constraints are mapped independent of the location of the backbone (e.g., atomic motion of certain side chains), therefore allowing for a much greater variety of structural configurations to be tried, compared to just varying one or more positions on a reference scaffold. The three different constraints and their spatial descriptions are combined into a matrix (e.g., tensor), and then a series of candidate peptides can be compared with this combination to identify new engineered polypeptides which meet the desired criteria. In some embodiments, one or more additional non-reference derived constraints is also included in the combination. Comparison of candidate peptides with a defined combination may be done, for example, using in silico methods to evaluate the constraints of each candidate peptide against the desired combination, and rate how well candidates match. Said candidates which have the desired level of overlap with the prescribed combination may then be synthesized using standard peptide synthetic methods known to one of skill in the art, and evaluated.

In some embodiments, the combination of constraints comprises at least 3, at least 4, at least 5, at least 6, at least 7, at least 8, at least 9, at least 10, at least 11, at least 12, between 3 to 12, between 3 to 10, between 3 to 8, between 3 to 6, or 3, or 4, or 5, or 6 independently selected spatially-associated topological constraints. One or more of the constraints is derived from a CD25 reference target. In some embodiments, each of the constraints is derived from the CD25 reference target. In other embodiments, at least one constraint is derived from the CD25 reference target, and the remaining constraints are not derived from the reference target. For example, in some embodiments, between 1 and 9 constraints, between 1 and 7 constraints, between 1 and 5 constraints, or between 1 and 3 constraints are derived from the CD25 reference target, and between 1 and 9 constraints, between 1 and 7 constraints, between 1 and 5 constraints, or between 1 and 3 constraints are not derived from the CD25 reference target.

Once the combination of constraints has been constructed, a series of candidate peptides is compared to said combination to identify one or more new engineered polypeptides which meet the desired criteria. In some embodiments, at least 5, at least 10, at least 15, at least 20, at least 25, at least 30, at least 40, at least 50, at least 60, at least 70, at least 80, at least 90, at least 100, at least 125, at least 150, at least 175, at least 200, or at least 250 or more candidate peptides are compared to the combination to identify one or more new engineered polypeptides which meet the desired criteria. In some embodiments, more than 250 candidate peptides, more than 300 candidate peptides, more than 400 candidate peptides, more than 500 candidate peptides, more than 600 candidate peptides, or more than 750 candidate peptides are compared, for example. In some embodiments, topological characteristic simulations are used to evaluate the topological characteristic overlap, if any, of a candidate peptide compared to the combination of constraints. In some embodiments, one or more candidate peptides are also compared to the CD25 reference target, and overlap, if any, of candidate peptide topological characteristics with CD25 reference target topological characteristics is evaluated. In some embodiments, the engineered polypeptide is identified from a computational sample of more than 5, more than 10, more than 20, more than 30, more than 40, more than 50, more than 60, more than 70, more than 80, more than 90, or more than 100 distinct peptide and topological characteristic simulations and an engineered polypeptide is selected, wherein the selected engineered polypeptide has the highest topological characteristic overlap compared the CD25 reference target, out of the total sampled population.

The spatially-associated topological constraints used to construct the desired combination (e.g., the desired tensor) may each be independently selected from a wide group of possible characteristics. These may include, for example, constraints describing structural, dynamical, chemical, or functional characteristics, or any combinations thereof.

Structural constraints may include, for example, atomic distance, amino acid sequence similarity, solvent exposure, phi angle, psi angle, secondary structure, or amino acid contact, or any combinations thereof.

Dynamical constraints may include, for example, atomic fluctuation, atomic energy, van der Waals radii, amino acid adjacency, or non-covalent bonding propensity. Atomic energy may include, for example, pairwise attractive energy between two atoms, pairwise repulsive energy between two atoms, atom-level solvation energy, pairwise charged attraction energy between two atoms, pairwise hydrogen bonding attraction energy between two atoms, or non-covalent bonding energy, or any combinations thereof.

Chemical characteristics may include, for example, chemical descriptors. Such chemical descriptors may include, for example, hydrophobicity, polarity, atomic volume, atomic radius, net charge, log P, HPLC retention, van der Waals radii, charge patterns, or H-bonding patterns, or any combinations thereof.

Functional characteristics may include, for example, bioinformatic descriptors, biological responses, or biological functions. Bioinformatic descriptors may include, for example, BLOSUM similarity, pKa, zScale, Cruciani Properties, Kidera Factors, VHSE-scale, ProtFP, MS-WHIM scores, T-scale, ST-scale, Transmembrane tendency, protein buried area, helix propensity, sheet propensity, coil propensity, turn propensity, immunogenic propensity, antibody epitope occurrence, and/or protein interface occurrence, or any combinations thereof.

In some embodiments, designing the constraints incorporates information about per-residue energy, per-residue interaction, per-residue fluctuation, per-residue atomic distance, per-residue chemical descriptor, per-residue solvent exposure, per-residue amino acid sequence similarity, per-residue bioinformatic descriptor, per-residue non-covalent bonding propensity, per-residue phi/psi angles, per-residue van der Waals radii, per-residue secondary structure propensity, per-residue amino acid adjacency, or per-residue amino acid contact. In some embodiments, these characteristics are used for a subset of the total residues in the CD25 reference target, or a subset of the total residues of the total combination of constraints, or a combination thereof. In some embodiments, one or more different characteristics are used for one or more different residues. That is, in some embodiments, one or more characteristics are used for a subset of residues, and at least one different characteristic is used for a different subset of residues. In some embodiments, one or more of said characteristics used to design one or more constraints is determined by computer simulation. Suitable computer simulation methods may include, for example, molecular dynamics simulations, Monte Carlo simulations, coarse-grained simulations, Gaussian network models, machine learning, or any combinations thereof.

In some embodiments multiple constraints are selected from one category. For example, in some embodiments, the combination comprises two or more constraints that are independently a type of biological response. In some embodiments, two or more constraints are independently a type of secondary structure. In certain embodiments, two or more constraints are independently a type of chemical descriptor. In other embodiments, the combination comprises no overlapping categories of constraints.

In some embodiments, one or more constraints is independently associated with a biological response or biological function. In some embodiments, said constraint is a spatially defined atom(s)-level constraint, or spatially defined shape/area/volume-level constraint (such as a characteristic shape/area/volume that can be satisfied by several different atomic compositions), or a spatially defined dynamic-level constraint (such as a characteristic dynamic or set of dynamics that can be satisfied by several different atomic compositions).

In some embodiments, one or more constraints is derived from a protein structure or peptide structure associated with a biological function or biological response. For example, in some embodiments, one or more constraints is derived from an extracellular domain, such as a G protein-coupled receptor (GPCR) extracellular domain, or an ion channel extracellular domain. In some embodiments, one or more constraints is derived from a protein-protein interface junction. In some embodiments, one or more constraints is derived from a protein-peptide interface junction, such as MHC-peptide or GPCR-peptide interfaces. In certain embodiments, the atoms or amino acids constrained to such a protein or peptide structure are atoms or amino acids associated with a biological function or biological response. In some embodiments, the atoms or amino acids in the engineered polypeptide constrained to such a protein or peptide structure are atoms or amino acids derived from a CD25 reference target. In some embodiments, one or more constraints is derived from a polymorphic region of a CD25 reference target (e.g., a region subject to allelic variation between individuals).

In some embodiments, the one or more atoms associated with a biological function or biological response are selected from the group consisting of carbon, oxygen, nitrogen, hydrogen, sulfur, phosphorus, sodium, potassium, zinc, manganese, magnesium, copper, iron, molybdenum, and nickel. In certain embodiments, the atoms are selected from the group consisting of oxygen, nitrogen, sulfur, and hydrogen.

In some embodiments, wherein one of the constraints is one or more amino acids associated with a biological function or biological response, and/or the engineered polypeptide comprises one or more amino acids associated with a biological function or biological response, the one or more amino acids are independently selected from the group consisting of the 20 proteinogenic naturally occurring amino acids, non-proteinogenic naturally occurring amino acids, and non-natural amino acids. In some embodiments, the non-natural amino acids are chemically synthesized. In certain embodiments, the one or more amino acids are selected from the 20 proteinogenic naturally occurring amino acids. In other embodiments, the one or more amino acids are selected from the non-proteinogenic naturally occurring amino acids. In still further embodiments, the one or more amino acids are selected from non-natural amino acids. In still further embodiments, the one or more amino acids are selected from a combination of 20 proteinogenic naturally occurring amino acids, non-proteinogenic naturally occurring amino acids, and non-natural amino acids.

While the combination of constraints used to select an engineered polypeptide as described herein comprises at least one constraint derived from a CD25 reference target, in some embodiments one or more constraints of the combination are not derived from a CD25 reference target. Thus, in certain embodiments, the selected engineered polypeptide comprises one or more characteristics that are not shared with the CD25 reference target.

In some embodiments, one or more constraints derived from the CD25 reference target and used in the combination describes the inverse of the characteristic as observed in the CD25 reference target. Thus, for example, a CD25 reference target may have a certain pattern of positive charge, a constraint related to charge is derived from said CD25 reference target, and the derived constraint describes a similar pattern but of neutral charge, or of negative charge. Thus, in some embodiments one or more inverse constraints are derived from the CD25 reference target and included in the combination. Such inverse constraints may be useful, for example, in selecting engineered polypeptides as control molecules for certain assays or panning methods, or as negative selection molecules in the programmable in vitro selection methods described herein.

In some embodiments, the combination of spatially-defined topological constraints comprises one or more non-reference derived topological constraints. In some embodiments, the one or more non-reference derived topological constraints enforces or stabilizes one or more secondary structural elements, enforces atomic fluctuations, alters peptide total hydrophobicity, alters peptide solubility, alters peptide total charge, enables detection in a labeled or label-free assay, enables detection in an in vitro assay, enables detection in an in vivo assay, enables capture from a complex mixture, enables enzymatic processing, enables cell membrane permeability, enables binding to a secondary target, or alters immunogenicity. In certain embodiments, the one or more non-reference derived topological constraints constrains one or more atoms or amino acids in the combination of constraints (or subsequently selected peptide) that were derived from the CD25 reference target. For example, in some embodiments, the combination of constraints includes a secondary structure that was derived from the CD25 reference target, and the combination of constraints also comprises a constraint that stabilizes the secondary structural element (e.g., through additional hydrogen bonding, or hydrophobic interactions, or side chain stacking, or a salt bridge, or a disulfide bond), wherein the stabilizing constraint is not present in the CD25 reference target. In another example, in some embodiments the combination of constraints (or subsequently selected peptide) comprises one or more atoms or amino acids that was derived from the CD25 reference target, and the combination of constraints also includes a constraint that enforces atomic fluctuations in at least a portion of the atoms or amino acids derived from the target reference, wherein the constraint is not present in the target reference. In some embodiments, one or more non-reference derived constraints is an inverse constraint. For example, in some embodiments, two combinations of constraints are constructed to select engineered polypeptides with inverse characteristics. In some such embodiments, a first combination of constraints will comprise one or more constraints derived from the CD25 reference target, and one or more constraints not derived from the CD25 reference target; and a second combination of constraints will comprise the same one or more constraints derived from the CD25 reference target, and the inverse of one or more of non-CD25 reference target constraints of the first combination.

b. CD25 Reference Target

Any suitable CD25 reference target may be used to derive one or more spatially-associated topological constraints for use in the methods provided herein. In some embodiments, the CD25 reference target is a full-length native protein. In other embodiments, the CD25 reference target is a portion of a full-length native protein. In still further embodiments, the CD25 reference target is a non-native protein, or portion thereof.

In some embodiments, a CD25 reference target is selected from:

| Reference Target No. | CD25 Residues | Sequence |
|---|---|---|
| 1 | 55-63 | SWDNQCQCT (SEQ ID NO: 22) |

-continued

| Reference Target No. | CD25 Residues | Sequence |
|---|---|---|
| 2 | 13-20:127-132 | ATFKAMA (SEQ ID NO: 23):MVYYQC (SEQ ID NO: 24) |
| 3 | 5-17 | DDPPEIPHATFKA (SEQ ID NO: 25) |
| 4 | 5-11:156-163 | DDPPEIP (SEQ ID NO: 26):RWTQPQLI (SEQ ID NO: 27) |
| 5 | 77-89 | QPEEQKERKTTEM (SEQ ID NO: 28) |
| 6 | 147-157 | VCKMTHGKTRW (SEQ ID NO: 29) |
| 7 | 11-14 | IPHA (SEQ ID NO: 30) |
| 8 | 44-56 | YMLCTGSSSHSSW (SEQ ID NO: 31) |

For example, in some embodiments, the CD25 reference target is a portion of CD25, such as an epitope or a predicted epitope. In some embodiments, the methods provided herein may be used to select one or more engineered polypeptides that are immunogens, and which may be used to raise one or more antibodies that specifically bind to the protein from which the target reference is derived. In still further embodiments, the methods provided herein may be used to select one or more engineered polypeptides which in turn may be used to select one or more binding partners of a protein of interest, such as an antibody, a Fab-displaying phage, or an scFv-displaying phage.

c. Comparison of Constraints

In some embodiments, the one or more constraints (e.g., reference-derived or non-reference derived) are determined by molecular simulation (e.g. molecular dynamics), or laboratory measurement (e.g. NMR), or a combination thereof. Once the constraints have been derived and combined, engineered polypeptide candidates are, in some embodiments, generated using a computational protein design (e.g., Rosetta). In some embodiments, other methods of sampling peptide space are used. Dynamics simulations may then be carried out on the candidate engineered polypeptides to obtain the parameters of constraints that have been selected. A covariance matrix of atomic fluctuations is generated for the CD25 reference target, covariance matrices are generated for the residues in each of the candidate engineered polypeptides, and these covariance matrices are compared to determine overlap. Principal component analysis is performed to compute the eigenvectors and eigenvalues for each covariance matrix—one covariance matrix for the CD25 reference target and one covariance for each of the candidate engineered polypeptides—and those eigenvectors with the largest eigenvalues are retained.

The eigenvectors describe the most, second-most, third-most, N-most dominant motion observed in a set of simulated molecular structures. Without wishing to be bound by any theory, if a candidate engineered polypeptide moves like the CD25 reference target, its eigenvectors will be similar to the eigenvectors of the CD25 reference target. The similarity of eigenvectors corresponds to their components (a 3D vector centered on each CA atom) being aligned, pointing in the same direction.

In some embodiments, this similarity between candidate engineered polypeptide and CD25 reference target eigenvectors is computed using the inner product of two eigenvectors. The inner product value is 0 if two eigenvectors are 90 degrees to each other or 1 if the two eigenvectors point precisely in the same direction. Without wishing to be bound by theory, since the ordering of eigenvectors is based on their eigenvalues, and eigenvalues may not necessarily be the same between two different molecules due to the stochastic nature by which molecular dynamics (MD) simulations sample the underlying energy landscape of those different molecules, the inner product between multiple, differentially ranked eigenvectors is, in some embodiments, needed (e.g. eigenvector 1 of the engineered polypeptide by eigenvector 2, 3, 4, etc. of the CD25 reference target). In addition, molecular motions are complex and may involve more than one (or more than a few) dominant/principal modes of motion. Thus, in some embodiments, the inner product between all pairs of eigenvectors in a candidate engineered polypeptide and the CD25 reference target are computed. This results in a matrix of inner products the dimensions of which are determined by the number of eigenvectors analyzed. For example, for 10 eigenvectors, the matrix of inner products is 10 by 10. This matrix of inner products can be distilled into a single value by computing the root mean-square value of the 100 (if 10 by 10) inner products. This is the root mean square inner product (RMSIP). From this comparison, one or more candidate engineered polypeptides that have similarity with the defined combination of constraints are selected.

d. Additional Steps

In some embodiments, selection of one or more engineered polypeptides comprises one or more additional steps. For example, in some embodiments an engineered polypeptide candidate is selected based on similarity to the defined combination of spatially-associated topological constraints, as described herein, and then undergoes one or more analyses to determine one or more additional characteristics, and one or more structural adjustments to impart or enforce said desired characteristics. For example, in some embodiments, the selected candidate is analyzed, such as through molecule dynamics simulations, to determine overall stability of the molecule and/or propensity for a particular folded structure. In some embodiments, one or more modifications are made to the engineered polypeptide to impart or reinforce a desired level of stability, or a desired propensity for a desired folded structure. Such modifications may include, for example, the installation of one or more cross-links (such as a disulfide bond), salt bridges, hydrogen bonding interactions, or hydrophobic interactions, or any combinations thereof.

The methods provided herein may further comprise assaying one or more selected engineered polypeptides for one or more desired characteristics, such as desired binding interactions or activity. Any suitable assay may be used, as appropriate to measure the desired characteristic.

In other aspects, provided herein are engineered polypeptides, such as engineered polypeptides selected through the methods described herein. In some embodiments, the engineered polypeptide has a molecular mass between 1 kDa and 10 kDa, and comprises up to 50 amino acids. In certain embodiments, the engineered polypeptide has a molecular mass between 2 kDa and 10 kDa, between 2 kDa and 10 kDa, between 3 kDa and 10 kDa, between 4 kDa and 10 kDa, between 5 kDa and 10 kDa, between 6 kDa and 10 kDa, between 7 kDa and 10 kDa, between 8 kDa and 10 kDa, between 9 kDa and 10 kDa, between 1 kDa and 9 kDa, between 1 kDa and 8 kDa, between 1 kDa and 7 kDa, between 1 kDa and 6 kDa, between 1 kDa and 5 kDa, between 1 kDa and 4 kDa, between 1 kDa and 3 kDa, or between 1 kDa and 2 kDa. In certain embodiments, the engineered polypeptide comprises up to 45 amino acids, up to 40 amino acids, up to 35 amino acids, up to 30 amino acids, up to 25 amino acids, up to 20 amino acids, at least 5 amino acids, at least 10 amino acids, at least 15 amino acids, at least 20 amino acids, at least 25 amino acids, at least 30 amino acids, at least 35 amino acids, or at least 40 amino acids.

In certain embodiments, the engineered polypeptide comprises a combination of spatially-associated topological constraints, wherein one or more of the constraints is a CD25 reference target-derived constraint. Any constraints described herein may be used in the combination, in some embodiments. In still further embodiments, between 10% to 98% of the amino acids of the engineered polypeptide meet the one or more CD25 reference target-derived constraints (e.g., if the engineered polypeptide comprises 50 amino acids, between 5 to 49 amino acids meet the one or more CD25 reference target-derived constraints). In some embodiments, between 20% to 98%, between 30% to 98%, between 40% to 98%, between 50% to 98%, between 60% to 98%, between 70% to 98%, between 80% to 98%, between 90% to 98%, between 10% to 90%, between 10% to 80%, between 10% to 70%, between 10% to 60%, between 10% to 50%, between 10% to 40%, between 10% to 30%, or between 10% to 20% of the amino acids of the engineered polypeptide meet the one or more CD25 reference target-derived constraints. In still further embodiments, the one or more amino acids that meet the one or more CD25 reference target-derived constraints have less than 8.0 Å, less than 7.5 Å, less than 7.0 Å, less than 6.5 Å, less than 6.0 Å, less than 5.5 Å, or less than 5.0 Å backbone root-mean-square deviation (RSMD) structural homology with the CD25 reference target. In some embodiments, the engineered polypeptide has a molecular mass of between 1 kDa and 10 kDa; comprises up to 50 amino acids; a combination of spatially-associated topological constraints, wherein one or more of the constraints is a CD25 reference target-derived constraint; between 10% to 98% of the amino acids of the engineered polypeptide meet the one or more CD25 reference target-derived constraints; and the amino acids that meet the one or more CD25 reference target-derived constraints have less than 8.0 Å backbone root-mean-square deviation (RSMD) structural homology with the CD25 reference target.

In some embodiments, the amino acids of the engineered polypeptide that meet the one or more CD25 reference target-derived constraints have between 10% and 90% sequence homology, between 20% and 90% sequence homology, between 30% and 90% sequence homology, between 40% and 90% sequence homology, between 50% and 90% sequence homology, between 60% and 90% sequence homology, between 70% and 90% sequence homology, or between 80% and 90% sequence homology with the CD25 reference target. In some embodiments, the amino acids that meet the one or more CD25 reference target-derived constraints have a van der Waals surface area overlap with the reference of between 30 $Å^2$ to 3000 $Å^2$, or between 100 $Å^2$ to 3000 $Å^2$, or between 250 $Å^2$ to 3000 $Å^2$, or between 500 $Å^2$ to 3000 $Å^2$, or between 750 $Å^2$ to 3000 $Å^2$, or between 1000 $Å^2$ to 3000 $Å^2$, or between 1250 $Å^2$ to 3000 $Å^2$, or between 1500 $Å^2$ to 3000 $Å^2$, or between 1750 $Å^2$ to 3000 $Å^2$, or between 2000 $Å^2$ to 3000 $Å^2$, or between 2250 $Å^2$ to 3000 $Å^2$, or between 2500 $Å^2$ to 3000 $Å^2$, or between 2750 $Å^2$ to 3000 $Å^2$.

The combination of constraints that the engineered polypeptide meets may comprise two or more, three or more, four or more, five or more, six or more, or seven or more CD25 reference target-derived constraints. The combination may comprise one or more constraints not derived from the CD25 reference target, as described elsewhere in the present disclosure. These reference-derived constraints, and non-reference derived constraints if present, may independently be any of the constraints described herein, such as any of the structural, dynamical, chemical, or functional characteristics described herein, or any combinations thereof.

In some embodiments, the engineered polypeptide comprises at least one structural difference when compared to the CD25 reference target. Such structural differences may include, for example, a difference in the sequence, number of amino acid residues, total number of atoms, total hydrophilicity, total hydrophobicity, total positive charge, total negative charge, one or more secondary structures, shape factor, Zernike descriptors, van der Waals surface, structure graph nodes and edges, volumetric surface, electrostatic potential surface, hydrophobic potential surface, local diameter, local surface features, skeleton model, charge density, hydrophilic density, surface to volume ratio, amphiphilicity density, or surface roughness, or any combinations thereof. In some embodiments, the difference in one or more characteristics (such as one or more characteristics described herein) is at least 10%, at least 20%, at least 30%, at least 40%, at least 50%, at least 60%, at least 70%, at least 80%, at least 90%, at least 100%, or greater than 100% when compared to the characteristic in the CD25 reference target, as applicable to the type of characteristic. For example, in some embodiments the difference is the total number of atoms, and the engineered polypeptide has at least 10%, at least 20%, or at least 30% more atoms than the CD25 reference target, or at least 10%, at least 20%, or at least 30% fewer atoms than the CD25 reference target. In some embodiments, the difference is in total positive charge, and the total positive charge of the engineered polypeptide is at least 10%, at least 20%, at least 30%, at least 40%, or at least 50% larger (e.g., more positive) than the CD25 reference target, while in other embodiments the total positive charge of the engineered polypeptide is at least 10%, at least 20%, at least 30%, at least 40%, or at least 50% smaller (e.g., less positive) than the CD25 reference target.

In some embodiments, the combination of spatially-defined topological constraints includes one or more secondary structural elements not present in the CD25 reference target. Thus, in some embodiments, the engineered polypeptide comprises one or more secondary structural elements that are not present in the CD25 reference target. In some embodiments, the combination and/or engineered polypeptide comprises one secondary structural element, two secondary structural elements, three secondary structural elements, four secondary structural elements, or more than four secondary structural elements not found in the CD25 reference target. In some embodiments, each secondary structural element is independently selected form the group consisting of helices, sheets, loops, turns, and coils. In some embodiments, each secondary structural element not present in the CD25 reference target is independently an α-helix, β-bridge, β-strand, $3_{10}$ helix, π-helix, turn, loop, or coil.

In certain embodiments, the CD25 reference target comprises one or more atoms associated with a biological response or a biological function (such as one described herein); the engineered polypeptide comprises one or more atoms associated with a biological response or a biological function (such as one described herein); and the atomic fluctuations of said atoms in the engineered polypeptide overlap with the atomic fluctuations of said atoms in the CD25 reference target. Thus, for example, in some embodiments the atoms themselves are different atoms, but their atomic fluctuations overlap. In other embodiments, the atoms are the same atoms, and their atomic fluctuations overlap. In still further embodiments, the atoms are independently the same or different. In some embodiments, the overlap is a root mean square inner product (RMSIP) greater than 0.25. In some embodiments, the overlap is a RMSIP greater than 0.3, greater than 0.35, greater than 0.4, greater than 0.45, greater than 0.5, greater than 0.55, greater than 0.6, greater than 0.65, greater than 0.7, greater than 0.75, greater than 0.8, greater than 0.85, greater than 0.9, or greater than 0.95. In certain embodiments, the RMSIP is calculated by:

$$RMSIP = \left(\frac{1}{10}\sum_{i=1}^{10}\sum_{j=1}^{10}(\eta_i \cdot v_j)^2\right)^{1/2},$$

where n is the eigenvector of the engineered polypeptide topological constraints, and v is the eigenvector of the CD25 reference target topological constraints.

In some embodiments, the engineered polypeptide comprises atoms or amino acids (or combination thereof) associated with a biological response or biological function, and at least a portion of said atoms or amino acids or combination is derived from a CD25 reference target, and certain constraints of the set of atoms or amino acids in the engineered polypeptide and the set in the CD25 reference target can be described by a matrix. In some embodiments, the matrix is an L×L matrix. In other embodiments, the matrix is an S×S×M matrix. In still further embodiments, the matrix is an L×2 phi/psi angle matrix For example in some embodiments, the atomic fluctuations of the atoms or amino acids in the engineered polypeptide that are associated with a biological response or biological function are described by an L×L matrix; a portion of said atoms or amino acids are derived from the CD25 reference target; and the atomic fluctuations in the CD25 reference target of said portion are described by an L×L matrix. In some embodiments, the adjacency of each set (related to amino acid location) is described by corresponding L×L matrices. In certain embodiments, the mean percentage error (MPE) across all matrix elements (i, j) of the engineered polypeptide L×L atomic fluctuation or adjacency matrix is less than or equal to 75% relative to the corresponding (i, j) elements in the CD25 reference target atomic fluctuation or adjacency matrix, for the fraction of the engineered polypeptide derived from the CD25 reference target. In some embodiments, the MPE is less than 70%, less than 65%, less than 60%, less than 55%, less than 50%, less than 45%, or less than 40% relative to the corresponding elements in the CD25 reference target matrix, for the fraction of the engineered polypeptide derived from the CD25 reference target. In some embodiments, wherein the matrices represent atomic fluctuations, L is the number of amino acid positions and the (i, j) value in the atomic fluctuation matrix element is the sum of intra-molecular atomic fluctuations for the $i^{th}$ and $j^{th}$ amino acid respectively if the (i, j) atomic distance is less than or equal to 7 Å, or zero if the (i, j) atomic distance is greater than 7 Å or if (i, j) is on the diagonal. Alternatively, in some embodiments the atomic distance can serve as a weighting factor for the atomic fluctuation matrix element (i, j) instead of a 0 or 1 multiplier. In certain embodiments, the $i^{th}$ and $j^{th}$ atomic fluctuations and distances can be determined by molecular simulation (e.g. molecular dynamics) and/or laboratory measurement (e.g. NMR). In other embodiments, wherein the matrices represent adjacency, L is the number of amino acid positions and the value in adjacency matrix element (i, j) is the intra-molecular atomic distance between the $i^{th}$ and $j^{th}$ amino acid respectively if the atomic distance is less than or equal to 7 Å, or zero if the atomic distance is greater than 7 Å or if (i, j) is on the diagonal. Alternatively, in some embodiments the atomic distance can serve as a weighting factor for the adjacency matrix element (i, j) instead of a 0 or 1 multiplier. In certain embodiments, the $i^{th}$ and $j^{th}$ atomic distances could be determined by molecular simulation (e.g. molecular dynamics) and/or laboratory measurement (e.g. NMR).

In certain embodiments, the atoms or amino acids associated with a response or function in the engineered polypeptide have a topological constraint chemical descriptor vector and a mean percentage error (MPE) less than 75% relative to the reference described by the same chemical descriptor, for the fraction of the engineered polypeptide derived from the CD25 reference target, wherein each $i^{th}$ element in the chemical descriptor vector corresponds to an amino acid position index. In some embodiments, the MPE is less than 70%, less than 65%, less than 60%, less than 55%, less than 50%, less than 45%, or less than 40% relative to the reference described by the same chemical descriptor, for the fraction of the engineered polypeptide derived from the CD25 reference target.

In still further embodiments, the matrix is an L×2 phi/psi angel matrix, and the atoms or amino acids associated with a response or function in the engineered polypeptide have an MPE less than 75% with respect to the reference phi/psi angles matrix in the fraction of the engineered polypeptide derived from the reference target, wherein L is the number of amino acid positions and phi, psi values are in dimensions (L,1) and (L,2) respectively. In some embodiments, the MPE is less than 70%, less than 65%, less than 60%, less than 55%, less than 50%, less than 45%, or less than 40% with respect to the reference phi/psi angles matrix in the fraction of the engineered polypeptide derived from the reference target. In some embodiments, the phi/psi values are determined by molecular simulation (e.g. molecular dynamics), knowledge-based structure prediction, or laboratory measurement (e.g. NMR).

In some embodiments, the matrix is an S×S×M secondary structural element interaction matrix, and the atoms or amino acids associated with a response or function in the engineered polypeptide have less than 75% mean percentage error (MPE) relative to the reference secondary structural element relationship matrix, in the fraction of the engineered polypeptide derived from the reference target, where S is the number of secondary structural elements and M is the number of interaction descriptors. In some embodiments, the MPE is less than 70%, less than 65%, less than 60%, less than 55%, less than 50%, less than 45%, or less than 40% relative to the reference secondary structural element relationship matrix, in the fraction of the engineered polypeptide derived from the reference target. Interaction descriptors may include, for example, hydrogen bonding, hydrophobic packing, van der Waals interaction, ionic interaction, covalent bridge, chirality, orientation, or distance, or any combinations thereof. In the secondary structural element interaction matrix index, (i, j, m)=$m^{th}$ interaction descriptor value between the $i^{th}$ and $j^{th}$ secondary structural elements.

Mean Percentage Error (MPE) for different matrices as described herein may be calculated by:

$$\text{Mean Percentage Error } (MPE) = \frac{100\%}{n}\sum_{n}^{1}\frac{|ref_n - eng_n|}{ref_n},$$

where n is the topological constraint vector or matrix position index for the engineered polypeptide ($eng_n$) and the corresponding reference ($ref_n$), summed up to vector or matrix position n.

In some embodiments, the engineered polypeptide has an MPE of less than 75% compared to the CD25 reference target. In certain embodiments, the engineered polypeptide has an MPE of less than 70%, less than 65%, less than 60%, less than 55%, less than 50%, less than 45%, or less than 40% compared to the CD25 reference target. In some embodiments, the MPE is determined by Total Topological Constraint Distance (TCD), topological clustering coefficient (TCC), Euclidean distance, power distance, Soergel distance, Canberra distance, Sorensen distance, Jaccard distance, Mahalanobis distance, Hamming distance, Quantitative Estimate of Likeness (QEL), or Chain Topology Parameter (CTP).

e. Secondary Structural Element

In some embodiments, at least a portion of the engineered polypeptide is topologically constrained to one or more secondary structural elements. In some embodiments, the atoms or amino acids associated with a biological response or biological function in the engineered polypeptide are topologically constrained to one or more secondary structural elements. In some embodiments, the secondary structural element is independently a sheet, helix, turn, loop, or coil. In some embodiments, the secondary structural element is independently an α-helix, β-bridge, β-strand, $3_{10}$ helix, π-helix, turn, loop, or coil. In certain embodiments, one or more of the secondary structural elements to which at least a portion of the engineered polypeptide is topologically constrained is present in the CD25 reference target. In some embodiments, at least a portion of the engineered polypeptide is topologically constrained to a combination of secondary structural elements, wherein each element is independently selected from the group consisting of sheet, helix, turn, loop, and coil. In still further embodiments, each element is independently selected from the group consisting of an α-helix, β-bridge, β-strand, $3_{10}$ helix, π-helix, turn, loop, and coil.

In some embodiments, the secondary structural element is a parallel or anti-parallel sheet. In some embodiments, a sheet secondary structure comprises greater than or equal to 2 residues. In some embodiments, a sheet secondary structure comprises less than or equal to 50 residues. In still further embodiments, a sheet secondary structure comprises between 2 and 50 residues. Sheets can be parallel or anti-parallel. In some embodiments, a parallel sheet secondary structure may be described as having two strands i, j in a parallel (N-termini of i and j strands opposing orientation), and a pattern of hydrogen bonding of residues i:j. In some embodiments, an anti-parallel sheet secondary structure may also be described as having two strands i, j in an anti-parallel (N-termini of i and j strands same orientation), and a pattern of hydrogen bonding of residues i:j−1, i:j+1. In certain embodiments, the orientation and hydrogen bonding of strands can be determined by knowledge-based or molecular dynamics simulation and/or laboratory measurement.

In some embodiments, the secondary structural element is a helix. Helices may be right or left handed. In some embodiments, the helix has a residue per turn (residues/turn) value of between 2.5 and 6.0, and a pitch between 3.0 Å and 9.0 Å. In some embodiments, the residues/turn and pitch are determined by knowledge-based or molecular dynamics simulation and/or laboratory measurement.

In some embodiments, the secondary structural element is a turn. In some embodiments, a turn comprises between 2 to 7 residues, and 1 or more inter-residue hydrogen bonds. In some embodiments, the turn comprises 2, 3, or 4 inter-residue hydrogen bonds. In certain embodiments, the turn is determined by knowledge-based or molecular dynamics simulation and/or laboratory measurement.

In still further embodiments, the secondary structural element is a coil. In certain embodiments, the coil comprises between 2 to 20 residues and zero predicted inter-residue hydrogen bonds. In some embodiments, these coil parameters are determined by knowledge-based or molecular dynamics simulation and/or laboratory measurement.

In still further embodiments, the engineered polypeptide comprises one or more atoms or amino acids derived from the CD25 reference target, wherein said atoms or amino acids have a secondary structure. In some embodiments, these atoms or amino acids are associated with a biological response or biological function. In some embodiments, the secondary structure motif vector of the atoms or amino acids in the engineered polypeptide has a cosine similarity greater than 0.25 relative to the CD25 reference target secondary structure motif vector for the fraction of the engineered polypeptide derived from the CD25 reference target, wherein the length of the vector is the number of secondary structure motifs and the value at the $i^{th}$ vector position defines the identity of the secondary structure motif (e.g. helix, sheet) derived from a lookup table. In some embodiments, each motif comprises two or more amino acids. In certain embodiments, motifs include, for example, α-helix, β-bridge, β-strand, $3_{10}$ helix, π-helix, turn, and loop. In some embodiments, the cosine similarity is greater than 0.3, greater than 0.35, greater than 0.4, greater than 0.45, or greater than 0.5 relative to the CD25 reference target secondary structure motif vector for the fraction of the engineered polypeptide derived from the CD25 reference target. Cosine similarity may be calculated by:

$$\text{Cosine Similarity} = \frac{\sum_{i=1}^{n} A_i B_i}{\sqrt{\sum_{i=1}^{n} A_i^2}\sqrt{\sum_{i=1}^{n} B_i^2}}$$

wherein A is the peptide vector of secondary structure motif identifiers, B is the reference vector of secondary structure motif identifiers, n is the length of the secondary structure motif vector, and i is the $i^{th}$ secondary structure motif.

In some embodiments, one or more atoms or amino acids of the engineered polypeptide which are derived from the CD25 reference target can be compared to the corresponding CD25 reference target atoms or amino acids using a total topological constraint distance (TCD). In some embodiments, the total TCD of said engineered polypeptide atoms or amino acids derived from the CD25 reference target is +/−75% relative to the TCD distance of the corresponding atoms in the CD25 reference target, wherein two intra-molecule topological constraints are interacting if their pairwise distance is less than or equal to 7 Å. In some embodiments, the atoms or amino acids in the engineered polypeptide being compared are associated with a biological function or biological response. The $i^{th}$, $j^{th}$ pairwise distance of two atoms or amino acids can, in some embodiments, be determined by molecular simulation (e.g. molecular dynamics) and/or laboratory measurement (e.g. NMR). An exemplary equation for calculating total topological constraint distance (TCD) is:

$$\frac{1}{L^2}\sum_{i<j}^{i=1:L}|S_{ij}|\Delta_{ij},$$

where i, j are the intra-molecular position indices for amino acids (i, j), $S_{ij}$ is the difference between constraints S(i) and S(j), Δ(i,j)=1 if amino acids (i, j) are within the 7 Å interaction threshold, and L is the number of amino acid positions in the peptide or the corresponding CD25 reference target. Alternatively, in some embodiments, Δ(i,j) can serve as a weighting factor for the $S_{ij}$ difference instead of a 0 or 1 multiplier.

In some embodiments, one or more atoms or amino acids of the engineered polypeptide which are derived from the CD25 reference target can be compared to the corresponding CD25 reference target atoms or amino acids using a chain topology parameter (CTP). In some embodiments, the CTP of said engineered polypeptide atoms or amino acids is +/−50% relative to the CTP of the corresponding atoms or amino acids in the CD25 reference target, wherein intra-chain topological interaction is a pairwise distance less than or equal to 7 Å. In some embodiments, the atoms or amino acids in the engineered polypeptide being compared are associated with a biological function or biological response. In some embodiments, $i^{th}$, $j^{th}$ pairwise distance can be determined by molecular simulation (e.g. molecular dynamics) and/or laboratory measurement (e.g. NMR). An exemplary equation for evaluating CTP is:

$$\text{Chain Topology Parameter } (CTP) = \frac{1}{L\cdot N}\sum_{i<j}^{i=1:L} S_{ij}^2\Delta_{ij},$$

where i, j are the position indices for amino acids (i, j), $S_{ij}$ is the difference between topological constraints S(i) and S(j), Δ(i,j)=1 if amino acids (i, j) are within the 7 Å chain topological interaction threshold, L is the number of amino acid positions in the peptide or the corresponding CD25 reference target, and N is the total number of intra-chain contacts that meet the 7 Å topological interaction threshold in the engineered polypeptide or CD25 reference target. Alternatively, in some embodiments Δ(i,j) can serve as a weighting factor for the $S_{ij}$ difference instead of a 0 or 1 multiplier.

In some embodiments, one or more atoms or amino acids of the engineered polypeptide which are derived from the CD25 reference target can be compared to the corresponding CD25 reference target atoms or amino acids using a quantitative estimate of likeness (QEL). In some embodiments, the QEL of said engineered polypeptide atoms or amino acids is +/−50% relative to the QEL of the corresponding atoms or amino acids in the CD25 reference target. In some embodiments, the atoms or amino acids in the engineered polypeptide being compared are associated with a biological function or biological response. An exemplary equation for determining QEL is:

$$\text{Quantitative Estimate of Likeness } (QEL) = \exp\left(\frac{1}{n}\sum_{i=1}^{n}\ln di\right),$$

wherein di is a topological constraint for the $i^{th}$ amino acid or atom position, or a composition function (e.g. linear regression function) that combines multiple topological constraints for the $i^{th}$ amino acid or atom position, and n is the number of amino acid or atom positions in the peptide or the CD25 reference target.

In some embodiments, one or more atoms or amino acids of the engineered polypeptide which are derived from the CD25 reference target can be compared to the corresponding CD25 reference target atoms or amino acids using a topological clustering coefficient (TCC) vector and a mean percentage error (MPE). In some embodiments, the TCC vector and MPE is less than 75% relative to the TCC of the corresponding atoms or amino acids in the CD25 reference target, wherein each element (i) of the vector is a topological clustering coefficient for the $i^{th}$ amino acid position, intra-molecule clusters are defined by an interacting edge distance less than or equal to 7 Å, and two edges: i–j, j–1 from the $i^{th}$ amino acid position. In some embodiments, the atoms or amino acids in the engineered polypeptide being compared are associated with a biological function or biological response. In some embodiments, the $i^{th}$, $j^{th}$ and $1^{th}$ edge distance can be determined by molecular simulation (e.g. molecular dynamics) and/or laboratory measurement (e.g. NMR). An exemplary equation for evaluating the topological clustering coefficient for the $i^{th}$ position is:

$$\text{Topological Clustering Coefficient for the } i^{th} \text{ position } (TCC_i) = \frac{^{i=1:L}S_{ijl}\Delta_{ij}\Delta_{il}\Delta_{jl}}{N_c(N_c-1)/2},$$

wherein Δ(i,j)=1, Δ(i,1)=1, Δ(j,1)=1 if intra-molecular amino acid positions: (i, j), (i, 1), (j, 1) are within the 7 Å interacting edge threshold respectively, Sip is the combination (e.g. sum) of topological constraints for the $i^{th}$, $j^{th}$ and $1^{th}$ amino acid, L is the number of amino acid positions in the peptide vector or corresponding CD25 reference target vector, No is the number of intra-molecular interacting amino acid positions for the $i^{th}$ amino acid, meeting the 7 Å edge threshold and two edges: i–j, j–1 from the $i^{th}$ amino acid. Alternatively, in some embodiments, Δ(i,j), Δ(i,1) and Δ(j,1) can serve as weighting factors for the clustering coefficient vector element (i) instead of a 0 or 1 multiplier.

In still further embodiments, one or more atoms or amino acids of the engineered polypeptide which are derived from the CD25 reference target can be compared to the corresponding CD25 reference target atoms or amino acids using an L×M topological constraint matrix and mean percentage error (MPE) of: Euclidean distance, power distance, Soergel distance, Canberra distance, Sorensen distance, Jaccard distance, Mahalanobis distance, or Hamming distance across all M-dimensions. The L×M matrix element (1, m) contains the $m^{th}$ constraint value for the $1^{th}$ amino acid position, wherein L is the number of amino acid positions and M is the number of distinct topological constraints. In some embodiments, the MPE of the engineered polypeptide L×M matrix is less than 75% relative to the matrix of the corresponding CD25 reference target atoms or amino acids. In some embodiments, the MPE is less than 70%, less than 65%, less than 60%, less than 55%, less than 50%, or less than 45%. In some embodiments, the atoms or amino acids in the engineered polypeptide being compared are associated with a biological function or biological response.

III. Programmable In Vitro Selection

In other aspects, further provided herein are methods of using the engineered polypeptides described herein in selecting binding partners using a series of programmed selection steps, wherein at least one selection step includes evaluating the interactions of a pool of potential binding partners with an engineered polypeptide.

Figure 5:
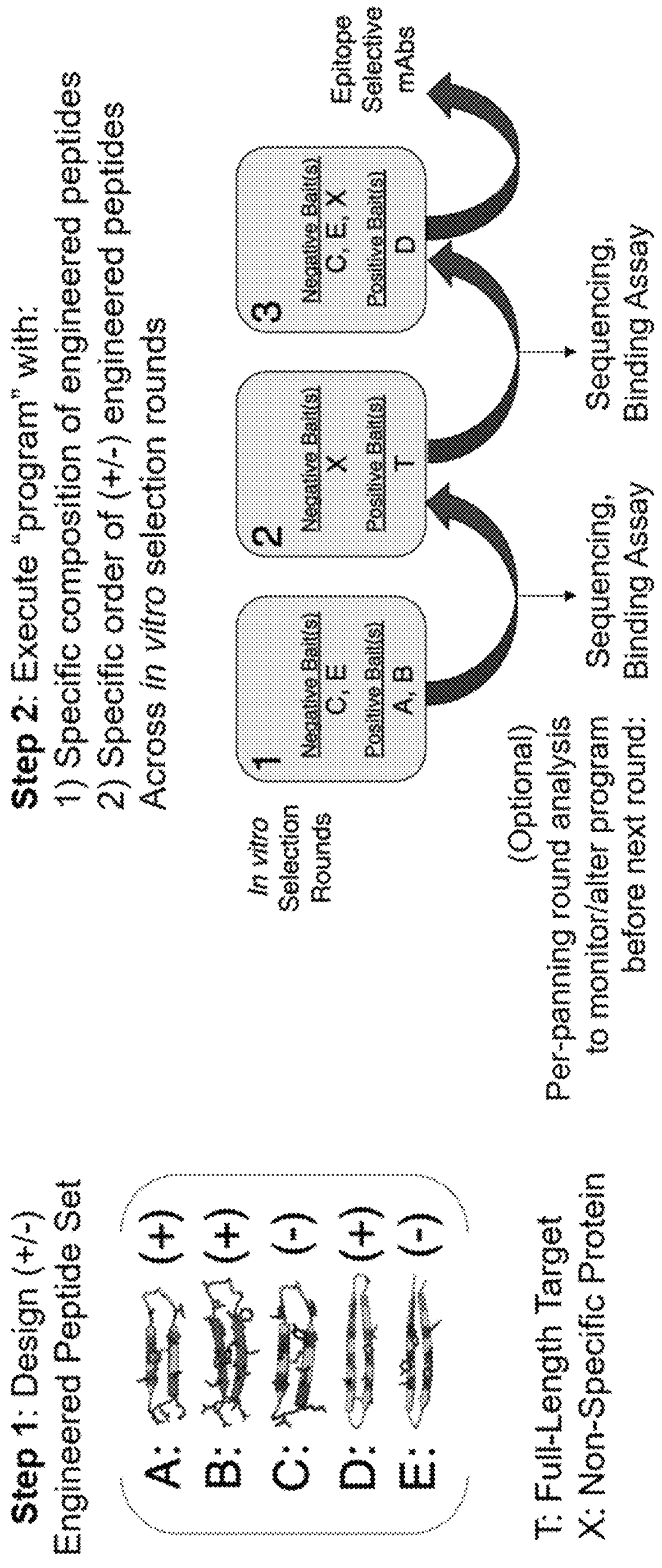
FIG. 5 is a schematic providing an overview of the design of an exemplary programmable in vitro selection using engineered polypeptides as described herein, and also using native proteins as positive (T) or negative (X) selection molecules.

In some embodiments, provided herein are methods of steering the selection of a binding molecule using two or more selection molecules. In some embodiments, the methods include subjecting a pool of candidate binding molecules to at least one round of selection, wherein each round comprises at least one negative selection step wherein at least a portion of the pool is screened against a negative selection molecule, and at least one positive selection step wherein at least a portion of the pool is screened against a positive selection molecule. In some embodiments the method comprises at least two rounds, at least three rounds, at least four rounds, at least five rounds, at least six rounds, at least seven rounds, at least eight rounds, at least nine rounds, at least ten rounds, or more, wherein each round independently comprises at least one negative selection step and at least one positive selection step. In some embodiments, each round independently comprises more than one negative selection step, or more than one positive selection step, or a combination thereof. FIG. 5 provides an exemplary schematic detailing three rounds of selection, wherein the first and third round comprise more than one negative selection step, and the first round further comprises more than one positive selection round. As shown in the scheme, two negative selection molecules ("baits") are used in the first round, and three negative selection molecules are used in the third round. In addition, two positive selection molecules are used in the first round.

In some embodiments wherein the method comprises more than one round, each negative and positive selection molecule is independently chosen. In other embodiments, the same negative selection molecule, or the same positive selection molecule, or a combination thereof, may be used in more than one round. For example, in FIG. 5, the same negative selection molecules used in round 1 are used again in round 3, with an additional third negative selection molecule also included in round 3. The order of negative and positive selection steps may be, in certain embodiments, independently chosen within each round of selection. Thus, for example, in some embodiments, the method comprises one or more rounds of selection, wherein each round comprises first a negative selection step, and then a positive selection step. In other embodiments, the method comprises one or more rounds of selection, wherein each round comprises first a positive selection step, and then a negative selection step. In still further embodiments, the method comprises one or more rounds of selection, wherein each round independently comprise a negative selection step and a positive selection step, wherein in each round the negative selection step is independently before the positive selection step or after the positive selection step.

Such methods of selection use positive (+) and negative (−) steps to steer the library of candidate binding molecules towards and away from certain desired characteristics, such as binding specificity or binding affinity. By using multiple steps with both positive and negative selection molecules, the pool of candidates can be directed in a stepwise manner to select for characteristics that are desirable and against characteristics that are undesirable. Further, in some embodiments the order of each step within each round, and the order of the rounds relative to each other can direct the selection in different directions. Thus, for example, in some embodiments a method comprising one round with (+) selection followed by (−) selection will result in a different final pool of candidates than if (−) selection is first, followed by (+) selection. Extrapolating this out to methods comprising multiple rounds, the order of selection steps may result in a different final pool of selected candidates even if the same positive and negative selection molecules are used overall.

In some embodiments a selection molecule is used that has in inverse characteristic of another selection molecule. This may be useful, for example, to ensure that the candidate binding partners identified using the positive selection molecule (or excluded because of a negative selection molecule) were identified (or excluded) because of a desired trait (or undesired trait), not because of a separate, unrelated binding interaction. To remove binding partners that are binding through unrelated interactions, an inverse selection molecule can be used that has similar or the same structure and characteristics as the selection molecule, except for the residues/structures conveying the desired trait (or undesired trait). For example, if interaction with a particular charge pattern in a positive selection molecule is desired, an inverse negative selection molecule may be used that has replaced the residues providing that charge pattern with uncharged residues, and/or residues of the opposite charge. Thus, for certain selection molecules, multiple different corresponding inverse selection molecules may be possible.

In the selection methods provided herein, at least one of the selection molecules is an engineered polypeptide as described herein. In some embodiments, more than one engineered polypeptide is used. In some embodiments, each engineered polypeptide is independently a positive or negative selection molecule. In certain embodiments, each selection molecule used in the one or more rounds of selection is independently an engineered polypeptide. In other embodiments, at least one molecule that is not an engineered polypeptide is used as a selection molecule. Such selection molecules that are not engineered polypeptides may comprise, for example, a naturally-occurring polypeptide, or a portion thereof. In other embodiments, one or more selection molecules that are not engineered polypeptides may comprise, for example, a non-naturally occurring polypeptide or portion thereof. For example, in some embodiments one or more selection molecules (e.g., positive selection molecule or negative selection molecule) is an immunogen, an antibody, cell-surface receptor, or a transmembrane protein, or a signaling protein, or a multiprotein complex, or a peptide-protein complex, or any portions thereof, or any combinations thereof. In some embodiments, one or more selection molecules is CD25 or a portion of any of CD25.

The positive and negative characteristics being selected for or against in each step may be selected from a variety of traits, and may be tailored depending on the desired features of the final one or more binding molecules obtained. Such desired features may depend, for example, on the intended use of the one or more binding molecules. For example, in some embodiments the methods provided herein are used to screen antibody candidates for one or more positive characteristics such as high specificity, and against one or more negative characteristics such as cross-reactivity. It should be understood that what is considered a positive characteristic in one context might be a negative characteristic in another context, and vice versa. Thus, a positive selection molecule in one series of selection rounds may, in some embodiments, be a negative selection molecule in a different series of selection rounds, or in selecting a different type of binding molecule, or in selecting the same type of binding molecule but for a different purpose.

In some embodiments, each selection characteristic is independently selected from the group consisting of amino acid sequence, polypeptide secondary structure, molecular dynamics, chemical features, biological function, immunogenicity, CD25 reference target(s) multi-specificity, cross-species CD25 reference target reactivity, selectivity of desired CD25 reference target(s) over undesired reference target(s), selectivity of reference target(s) within a sequence and/or structurally homologous family, selectivity of reference target(s) with similar protein function, selectivity of distinct desired reference target(s) from a larger family of undesired targets with high sequence and/or structurally homology, selectivity for distinct reference target alleles or mutations, selectivity for distinct reference target residue level chemical modifications, selectivity for cell type, selectivity for tissue type, selectivity for tissue environment, tolerance to reference target(s) structural diversity, tolerance to reference target(s) sequence diversity, and tolerance to reference target(s) dynamics diversity. In some embodiments, each selection characteristic is a different type of selection characteristic. In other embodiments, two or more selection characteristics are different characteristics but of the same type. For example, in some embodiments, two or more selection characteristics are polypeptide secondary structure, wherein one is a positive selection for a desired polypeptide secondary structure and one is a negative selection for an undesired polypeptide secondary structure. In some embodiments, two or more selection characteristics are selectivity for cell type, wherein a positive selection characteristic is selectivity for a specific desired cell type, and a negative selection characteristic is selectivity for a specific undesired cell type. In some embodiments, two or more, three or more, four or more, five or more, or six or more selection characteristics are of the same type.

In some embodiments, the selection characteristic is binding to an engineered polypeptide of the disclosure. For example, the engineered polypeptides shown in FIG. 7, Table 1, Table 8, and Table 9 may be used to select for antibodies (or other binding agents) that specifically bind to the epitopes shown in FIG. 6 and Table 7. Illustrative selection strategies are provided in Table 10.

In yet another aspect, provided herein is a composition comprising two or more selection steering polypeptides, wherein each polypeptide is independently a positive selection molecule comprising one or more positive steering characteristics, or a negative selection molecule comprising one or more negative steering characteristics. Such characteristics may, in some embodiments, be selected from the group consisting of amino acid sequence, polypeptide secondary structure, molecular dynamics, chemical features, biological function, immunogenicity, reference target(s) multi-specificity, cross-species reference target reactivity, selectivity of desired reference target(s) over undesired reference target(s), selectivity of reference target(s) within a sequence and/or structurally homologous family, selectivity of reference target(s) with similar protein function, selectivity of distinct desired reference target(s) from a larger family of undesired targets with high sequence and/or structurally homology, selectivity for distinct reference target alleles or mutations, selectivity for distinct reference target residue level chemical modifications, selectivity for cell type, selectivity for tissue type, selectivity for tissue environment, tolerance to reference target(s) structural diversity, tolerance to reference target(s) sequence diversity, and tolerance to reference target(s) dynamics diversity.

Thus, in further aspects, provided herein is a method of screening a library of binding molecules with a selection steering composition as described herein, wherein each round of selection comprises: a negative selection step of screening at least a portion of the pool against a negative selection molecule; and a positive selection step of screening at least a portion of the pool for a positive selection molecule; wherein the order of selection steps within each round, and the order of rounds, result in the selection of a different subset of the pool than an alternative order.

In some embodiments, the binding partners being evaluated using the composition of selection steering polypeptides as described herein, or the methods of screening as described herein, are a phage library, for example a Fab-containing phage library; or a cell library, for example a B-cell library or a T-cell library.

In some embodiments of the methods of screening provided herein, the methods comprise two or more, three or more, four or more, five or more, six or more, or seven or more rounds of selection. In some embodiments, wherein there is more than one round, each round comprises a different set of selection molecules. In other embodiments, wherein there is more than one round, at least two rounds comprise the same negative selection molecule, the same positive selection molecule, or both.

In some embodiments of the screening methods, the method comprises analyzing the subset of the pool prior to proceeding to the next round of selection. In certain embodiments, each subset pool analysis is independently selected from the group consisting of peptide/protein biosensor binding, peptide/protein ELISA, peptide library binding, cell extract binding, cell surface binding, cell activity assay, cell proliferation assay, cell death assay, enzyme activity assay, gene expression profile, protein modification assay, Western blot, and immunohistochemistry. In some embodiments, gene expression profile comprises full sequence repertoire analysis of the subset pool, such as next-generation sequencing. In some embodiments, statistical and/or informatic scoring, or machine learning training is used to evaluate one or more subsets of the pool in one or more selection rounds.

In some embodiments, the identity and/or order of positive and/or negative selection molecules for a subsequent round is determined by analyzing a subset pool from one selection round. In some embodiments, statistical and/or informatic scoring, or machine learning training, is used to evaluate one or more subsets of the pool in one or more selection rounds to determine the identity and/or order of the positive and/or negative selection molecules for a subsequent round (such as the next round, or a round further along in the program).

In still further embodiments, the methods of selection include modifying a subset pool obtained from a selection round before proceeding to the next selection round. Such modifications may include, for example, genetic mutation of the subset pool, genetic depletion of the subset pool (e.g., selecting a subset of the subset pool to move forward in selection), genetic enrichment of the subset pool (e.g., increasing the size of the pool), chemical modification of at least a portion of the subset pool, or enzymatic modification of at least a portion of the subset pool, or any combinations thereof. In some embodiments, statistical and/or informatic scoring, or machine learning training is used to evaluate a subset pool and determine the one or more modifications to make prior to moving the modified subset pool forward in selection. In certain embodiments, such statistical and/or informatic scoring, or machine learning training, is also used to determine the identity and/or order of positive and/or negative selection molecules for a subsequent round of selection.

Any suitable assay may be used to evaluate the binding of a pool of binding partners with the selection molecules in each step. In some embodiments, binding is directly evaluated, for example by directly detecting a label on the binding partner. Such labels may include, for example, fluorescent labels, such as a fluorophore or a fluorescent protein. In other embodiments, binding is indirectly evaluated, for example using a sandwich assay. In a sandwich assay, a binding partner binds to the selection molecule, and then a secondary labeled reagent is added to label the bound binding partner. This secondary labeled reagent is then detected. Examples of sandwich assay components include His-tagged-binding partner detected with an anti-His-tag antibody or His-tag-specific fluorescent probe; a biotin-labeled binding partner detected with labeled streptavidin or labeled avidin; or an unlabeled binding partner detected with an anti-binding-partner antibody.

In some embodiments, the binding partners being selected in each step are identified based on the binding signal, or dose-response, using any number of available detection methods. These detection methods may include, for example, imaging, fluorescence-activated cell sorting (FACS), mass spectrometry, or biosensors. In some embodiments, a hit threshold is defined (for example the median signal), and any with signal above that signal is flagged as a putative hit motif.

IV. Use of Engineered polypeptides to Produce Antibodies

The engineered polypeptides provided herein, and identified by the methods provided herein, may be used, for example, to produce one or more antibodies. In some embodiments, the antibody is a monoclonal or polyclonal antibody. Thus, in some embodiments, provided herein is an antibody produced by immunizing an animal with an immunogen, wherein the immunogen is an engineered polypeptide as provided herein. In some embodiments, the animal is a human, a rabbit, a mouse, a hamster, a monkey, etc. In certain embodiments, the monkey is a cynomolgus monkey, a macaque monkey, or a rhesus macaque monkey. Immunizing the animal with an engineered polypeptide can comprise, for example, administering at least one dose of a composition comprising the peptide and optionally an adjuvant to the animal. In some embodiments, generating the antibody from an animal comprises isolating a B cell which expresses the antibody. Some embodiments further comprise fusing the B cell with a myeloma cell to create a hybridoma which expresses the antibody. In some embodiments, the antibody generated using the engineered polypeptide can cross react with a human and a monkey, for example a cynomolgus monkey.

a. Characteristics of the Engineered Polypeptide

The engineered polypeptides provided herein have one or more characteristics in common with CD25. In some embodiments, they exhibit at least one characteristic of the surface of CD25, for example the functional interface surface that binds with a binding partner of CD25. In some embodiments, the binding partner is an antibody that binds specifically to CD25. In some embodiments, the engineered polypeptide exhibits at least one characteristic of a portion of the surface of CD25 that is not known to interact to an antibody to CD25.

In some embodiments of certain types of characteristics, the engineered polypeptide presents a mimic of a functional interface of CD25 (such as a binding surface), but the characteristic shared by the engineered polypeptide may be best described as being shared with CD25 as a whole. For example, one characteristic that is shared may be binding between a binding partner of CD25 and CD25, wherein the binding occurs with a functional binding interface of CD25, but the structure and orientation of the functional binding interface is supported by the rest of the CD25 protein.

Such shared characteristics may include, for example, structural metrics, or functional metrics, or combinations thereof. The at least one shared characteristic may include, for example, one or more structural similarities, similarity of conformational entropy, one or more chemical descriptor similarities, one or more functional binding similarities, or one or more phenotypic similarities, or any combinations thereof. In certain embodiments, the engineered polypeptide shares one or more of these characteristics with at least a portion of the surface of CD25, such as a functional interface, for example a binding surface.

In some embodiments, the engineered polypeptide has structural similarity to CD25 (or a portion of the surface of CD25, such as a binding surface), and this structural similarity is evaluated by backbone root-mean-square deviation (RMSD) or side-chain RMSD. RMSD evaluates the average distance between atoms, and can be applied to three-dimensional structures to compare how similar two separate structures are in three-dimensional space. In some embodiments, the RMSD of the backbone, or amino acid side chains, or both, between the engineered polypeptide and CD25 (or a functional interface of CD25) is lower than the RMSD between CD25 (or a functional interface of CD25) and a different molecule. In some embodiments, it is a portion of CD25 (or a portion of a functional interface of CD25) that is compared with the engineered polypeptide. The RMSD may be evaluated, for example, using the experimentally measured structure or the simulated structure of the engineered polypeptide; and the experimentally measured structure or the simulated structure of CD25 (or a functional interface thereof). In some embodiments, a engineered polypeptide is considered structurally similar to CD25 if the backbone of the engineered polypeptide has an average RMSD less than or equal to 6.0 Å relative to the backbone of an x-ray structure of CD25.

In some embodiments, the engineered polypeptide has similar conformational entropy to CD25 (or a portion of the surface of CD25, such as a binding surface), and this conformational entropy is evaluated, for example, using the experimentally measured structure or the simulated structure of the engineered polypeptide, and the experimentally measured structure or the molecular dynamics simulated motion of CD25 (or portion thereof). In such simulations, in some embodiments the experimentally measured structure or the molecular dynamics simulated motion of CD25 (or portion thereof, such as a portion of the binding surface) is used. In certain embodiments, the conformational entropy of the engineered polypeptide is considered similar to that of CD25 (or portion thereof) if an engineered polypeptide molecular dynamics ensemble run under standard physiological conditions has all states with all non-hydrogen atomic position RMSDs≤6.0 Å relative to a known x-ray crystal structure of CD25 (or portion thereof).

In still other embodiments, the engineered polypeptide has one or more chemical descriptors similar to CD25 (or a portion thereof, such as the binding surface). In other embodiments, the engineered polypeptide has one or more chemical descriptors complementary to a binding partner of CD25 (e.g., an antibody to CD25). Such chemical descriptors (which may be similar or complementary) may include, for example, hydrophobicity patterns, H-bonding patterns, atomic volume/radii, charge patterns, or atomic occupancy patterns, or any combinations thereof. These chemical descriptors may, in some embodiments, be evaluated using the experimentally measured structure or the simulated structure of the engineered polypeptide, and the experimentally measured structure or the simulated structure of CD25 (or a portion thereof, such as the binding surface).

In still other embodiments, the engineered polypeptide has similar functional binding as CD25. For example, in some embodiments the engineered polypeptide has binding to a CD25 binding partner, or fragment thereof. In some embodiments, the binding partner is a fragment of the native binding partner, or is a modified native binding partner. Such modifications may include, for example, a fusion protein comprising at least a fragment of the native binding partner; labeling with a chromophore; labeling with a fluorophore; labeling with biotin; or labeling with a His-tag. In some embodiments, the engineered polypeptide has binding with a binding partner of CD25 that is within about two orders of magnitude, or within about one order of magnitude, of the binding of CD25 with a binding partner. In some embodiments, the similarity of binding is evaluated by comparing the binding constant ($K_d$), or the inhibitory constant ($K_i$), or the binding on-rate, or the binding off-rate, or the binding affinity of the binding pairs, or the Gibbs free energy of binding (AG). In some embodiments, the binding partner is an antibody to CD25.

In some embodiments, the binding constant ($K_d$) of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the $K_d$ of CD25 with the binding partner. In other embodiments, the inhibitory constant ($K_i$) of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the $K_i$ of CD25 and the binding partner. In still further embodiments, the binding on-rate of the engineered polypeptide with a CD25 binding partner is similar to the binding on-rate of CD25 and the binding partner. In some embodiments, the binding on-rate of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the on-rate of CD25 and the binding partner. In other embodiments, the binding off-rate of the engineered polypeptide with a CD25 binding partner is similar to the binding off-rate of CD25 and the binding partner. In some embodiments, the binding off-rate of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the off-rate of CD25 and the binding partner. In still further embodiments, the binding affinity of the engineered polypeptide with a CD25 binding partner is similar to the binding affinity of CD25 and the binding partner. In some embodiments, the binding affinity of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the binding affinity of CD25 and the binding partner. In some embodiments, the Gibbs free energy of binding of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the Gibbs free energy of binding of CD25 and the binding partner. In some embodiments, the CD25 binding partner is an antibody of CD25.

In yet other embodiments, the engineered polypeptide shares sequence similarity with CD25, or a portion thereof (such as a binding surface of CD25). The similarity may be compared to the continuous amino acid sequence of CD25 (or portion thereof), or to a discontinuous sequence of CD25 (or portion thereof). For example, in certain embodiments, a binding surface of CD25 is formed by discontinuous amino acid sequences, and the engineered polypeptide has sequence similarity with at least a portion of the discontinuous sequences that form the surface. In other embodiments, the engineered polypeptide has sequence similarity with at least a portion of a continuous amino acid sequence that forms a binding surface of CD25. In some embodiments, the binding surface of CD25 comprises an epitope that binds to an antibody to CD25.

In some embodiments, the engineered polypeptide has a sequence that is at least 40% identical, at least 45% identical, at least 50% identical, at least 55% identical, at least 60% identical, at least 65% identical, at least 70% identical, at least 75% identical, at least 80% identical, at least 85% identical, or at least 90% identical, to a portion of the continuous sequence of CD25, for example a continuous sequence that forms a binding surface of CD25. In certain embodiments, the engineered polypeptide has a sequence that is at least 40% identical, at least 45% identical, at least 50% identical, at least 55% identical, at least 60% identical, at least 65% identical, at least 70% identical, at least 75% identical, at least 80% identical, at least 85% identical, or at least 90% identical, to a portion of the discontinuous sequence of CD25, for example the discontinuous sequence that forms a binding surface of CD25. In certain embodiments, the engineered polypeptide has a sequence that is at least 40% identical, at least 45% identical, at least 50% identical, at least 55% identical, at least 60% identical, at least 65% identical, at least 70% identical, at least 75% identical, at least 80% identical, at least 85% identical, or at least 90% identical, to a contiguous portion of a binding surface of CD25. In still further embodiments, the engineered polypeptide has a sequence that is at least 40% identical, at least 45% identical, at least 50% identical, at least 55% identical, at least 60% identical, at least 65% identical, at least 70% identical, at least 75% identical, at least 80% identical, at least 85% identical, or at least 90% identical, to two or more discontiguous portions of a binding surface of CD25. In some embodiments, the engineered polypeptide has a sequence at least partly identical (as described herein) with a binding surface of CD25, wherein the binding surface comprises an epitope that binds to one or more antibodies to CD25.

In certain embodiments, sequence similarity of the engineered polypeptide and CD25 (or portion thereof) is evaluated using the peptide portion(s) of the engineered polypeptide, not including a linker, if present. In certain embodiments, one or more linking moieties are considered as well, for example if the engineered polypeptide comprises one or more linkers that comprise an amino acid.

b. Engineered Polypeptide

In some embodiments, the engineered polypeptide comprises more than one peptide, for example at least two peptides, or at least three peptides, or greater. In some embodiments, the engineered polypeptide comprises between 1 and 10 peptides, between 1 and 8 peptides, between 1 and 6 peptides, between 1 and 4 peptides, between 2 and 10 peptides, between 2 and 8 peptides, between 2 and 6 peptides, or between 2 and 4 peptides.

In some embodiments, the engineered polypeptide comprises between 2 to 100 amino acids, for example, between 2 to 80 amino acids, between 2 to 70 amino acids, between 2 to 60 amino acids, between 2 to 50 amino acids, between 2 to 40 amino acids, between 2 to 30 amino acids, between 2 to 25 amino acids, between 2 to 20 amino acids, between 2 to 15 amino acids, between 5 to 30 amino acids, between 5 to 25 amino acids, between 5 to 20 amino acids, between 5 to 15 amino acids, or between 9 and 15 amino acids.

In certain embodiments, the engineered polypeptide comprises greater than one peptide, for example at least two peptides, or at least three peptides, or at least four peptides, or greater, and each peptide independently comprises between 1 to 100 amino acids, or between 2 to 100 amino acids, for example, between 2 to 80 amino acids, between 2 to 70 amino acids, between 2 to 60 amino acids, between 2 to 50 amino acids, between 2 to 40 amino acids, between 2 to 30 amino acids, between 2 to 25 amino acids, between 2 to 20 amino acids, between 2 to 15 amino acids, between 5 to 30 amino acids, between 5 to 25 amino acids, between 5 to 20 amino acids, between 5 to 15 amino acids, or between 9 and 15 amino acids.

In some embodiments, the engineered polypeptide comprises only naturally occurring amino acids. In other embodiments, the engineered polypeptide comprises non-natural amino acids, for example a combination of naturally occurring and non-natural amino acids.

In some embodiments, wherein the engineered polypeptide comprises two or greater peptides, each peptide independently exhibits at least one characteristic of CD25, or a portion thereof (such as a binding surface). In some embodiments, each peptide independently exhibits 1 to 10, 1 to 9, 1 to 8, 1 to 7, 1, to 6, 1 to 5, 1 to 4, 1 to 3, or 1, or 2 characteristics of CD25, or a portion thereof. In some embodiments, the characteristics are shared with a portion of CD25 that interacts with an antibody of CD25.

In some embodiments, the engineered polypeptide has at least one characteristic that is complementary to a binding partner of CD25, for example an antibody of CD25.

In some embodiments, a peptide of the engineered polypeptide shares one or more structural similarities with CD25, or a portion thereof. The structural similarity may be, in some embodiments, evaluated by backbone RMSD or side-chain RMSD. For example, in certain embodiments, the RMSD of the backbone, or amino acid side chains, or both, between a peptide of the engineered polypeptide and CD25 (or a portion thereof) is lower than the RMSD between CD25 (or portion thereof) and a different molecule (such as a different peptide). In some embodiments, a portion of CD25 is compared with the peptide, for example a portion of the surface of CD25, such as a surface that interacts with an antibody to CD25. RMSD of structural similarity may be evaluated, for example, using the experimentally measured structure or the simulated structure of the peptide and the experimentally measured structure or the simulated structure of CD25 or portion thereof. In some embodiments, a peptide of the engineered polypeptide is considered structurally similar to CD25 (or portion thereof) if the backbone of the peptide has an average RMSD less than or equal to 6.0 Å relative to the backbone of a known x-ray structure of CD25, or the portion thereof.

In some embodiments, the engineered polypeptide has similar conformational entropy to CD25 or a portion thereof. In some embodiments, the experimentally measured structure or the molecular dynamics simulated motion of the peptide is used to compare the conformation entropy with the experimentally measured structure or the simulated structure of CD25, or a portion thereof. The conformational entropy is considered similar, in some embodiments, if a peptide molecular dynamics ensemble run under standard physiological conditions has all states with all non-hydrogen atomic portions RMSDs≤6.0 Å relative to a known x-ray crystal structure of CD25, or portion thereof. In some embodiments, a portion of CD25 is compared with the peptide, for example a surface portion of CD25 that interacts with an antibody of CD25.

In further embodiments, the similarity between a peptide of the engineered polypeptide and CD25 (or portion thereof) may be one or more chemical descriptors. In some embodiments, the peptide has one or more chemical descriptors in common with CD25 (or a portion thereof), or one or more chemical descriptors that is complementary to a binding partner of CD25 (for example, an antibody to CD25). Chemical descriptors may include, for example, hydrophobicity patterns, H-bonding patterns, atomic volume/radii, charge patterns, or atomic occupancy patterns, or any combinations thereof. In some embodiments, a peptide of the engineered polypeptide has one or more hydrophobicity patterns, H-bonding patterns, atomic volume/radii, charge patterns, or atomic occupancy patterns, or any combinations thereof, similar those in CD25 or a portion thereof, or which is complementary to a binding partner of CD25 (such as an antibody to CD25). In some embodiments, the similarity is having the same chemical descriptor in common, such as one or more of the same hydrophobicity patterns, H-bonding patterns, atomic volume/radii, charge patterns, or atomic occupancy patterns. Complementary chemical descriptors includes, for example, a peptide with a positive charge pattern that complements the negative charge pattern of a binding partner of CD25, such as an antibody to CD25. These chemical descriptors may, in some embodiments, be evaluated using an experimentally measured structure or a simulated structure of the peptide, and an experimentally measured structure or a simulated structure of CD25, or the CD25 binding partner (e.g., for complementary evaluation).

For example, in some embodiments, the engineered polypeptide binds binding partner of CD25 that is similar to the binding of CD25 with the binding partner (for example, IL-2). In some embodiments, the binding partner is the native binding partner, a fragment of a native binding partner, or a modified native binding partner or fragment thereof, or an antibody that binds specifically to CD25. In some embodiments, the binding partner binds under certain circumstances but not others. In some embodiments, the binding partner binds under pathological conditions, or binds under non-pathological conditions. The binding partner may be, for example, constitutively expressed, or the product of a facultative gene, or comprise a protein or a fragment thereof. In certain embodiments, the binding partner is a fragment of a native binding partner, or is a modified native binding partner. Modifications may include, in some embodiments, a fusion protein comprising at least a fragment of the native binding partner; labeling with a chromophore; labeling with a fluorophore; labeling with biotin; or labeling with a His-tag.

In some embodiments, the engineered polypeptide has binding with a binding partner of CD25 that is within about two orders of magnitude, or within about one order of magnitude, of the binding of CD25 with the binding partner. In some embodiments, the similarity of binding is evaluated by comparing the binding constant ($K_d$), or the inhibitory constant ($K_i$), or the binding on-rate, or the binding off-rate, or the binding affinity of the binding pairs, or the Gibbs free energy of binding ($\Delta G$). In some embodiments, the binding partner is an antibody to CD25.

In some embodiments, the binding constant ($K_d$) of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the $K_d$ of CD25 with the binding partner. In other embodiments, the inhibitory constant ($K_i$) of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the $K_i$ of CD25 and the binding partner. In still further embodiments, the binding on-rate of the engineered polypeptide with a CD25 binding partner is similar to the binding on-rate of CD25 and the binding partner. In some embodiments, the binding on-rate of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the on-rate of CD25 and the binding partner. In other embodiments, the binding off-rate of the engineered polypeptide with a CD25 binding partner is similar to the binding off-rate of CD25 and the binding partner. In some embodiments, the binding off-rate of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the off-rate of CD25 and the binding partner. In still further embodiments, the binding affinity of the engineered polypeptide with a CD25 binding partner is similar to the binding affinity of CD25 and the binding partner. In some embodiments, the binding affinity of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the binding affinity of CD25 and the binding partner. In some embodiments, the Gibbs free energy of binding of the engineered polypeptide with a CD25 binding partner is within 1000-fold, within 800-fold, within 600-fold, within 400-fold, within 200-fold, within 100-fold, within 90-fold, within 80-fold, within 70-fold, within 60-fold, within 50-fold, within 40-fold, within 30-fold, within 20-fold, within 10-fold, within 8-fold, within 6-fold, within 4-fold, within 2-fold, within 1.5-fold, within 1.2-fold, or about the same as the Gibbs free energy of binding of CD25 and the binding partner. In some embodiments, the CD25 binding partner is an antibody of CD25.

In some embodiments, the engineered polypeptide has sequence similarity with CD25, or a portion thereof. In some embodiments, the engineered polypeptide has sequence similarity with a portion of the surface of CD25 that binds to an antibody of CD25. In certain embodiments, the sequence similarity is compared to the continuous amino acid sequence of CD25. In other embodiments, the sequence similarity is compared to a discontinuous sequence of CD25. For example, in certain embodiments, a binding surface of folded CD25 is formed by discontinuous amino acid sequences, and the engineered polypeptide has sequence similarity with at least a portion of the discontinuous sequences that form the surface. In some embodiments, the engineered polypeptide has sequence similarity with at least a portion of a continuous amino acid sequence that forms a binding surface of CD25. In some embodiments, the engineered polypeptide has a sequence that is at least 50% identical, at least 55% identical, at least 60% identical, at least 65% identical, at least 70% identical, at least 75% identical, at least 80% identical, at least 85% identical, at least 90% identical, at least 95% identical, or at least 99% identical to at least a portion of a continuous sequence of CD25, such as a continuous sequence that forms a binding surface. In certain embodiments, the engineered polypeptide has a sequence that is at least 40% identical, at least 45% identical, at least 50% identical, at least 55% identical, at least 60% identical, at least 65% identical, at least 70% identical, at least 75% identical, at least 80% identical, at least 85% identical, or at least 90% identical, to at least a portion of the discontinuous sequence of CD25, for example the discontinuous sequence that forms a binding surface. In certain embodiments, the engineered polypeptide has a sequence that is at least 40% identical, at least 45% identical, at least 50% identical, at least 55% identical, at least 60% identical, at least 65% identical, at least 70% identical, at least 75% identical, at least 80% identical, at least 85% identical, or at least 90% identical, to a contiguous portion of CD25. In still further embodiments, the engineered polypeptide has a sequence that is at least 40% identical, at least 45% identical, at least 50% identical, at least 55% identical, at least 60% identical, at least 65% identical, at least 70% identical, at least 75% identical, at least 80% identical, at least 85% identical, or at least 90% identical, to two or more discontiguous portions of CD25. In some embodiments, for engineered polypeptides that comprise at least two peptides, two or more peptides of the engineered immunogen independently share sequence similarity with CD25, such as with a binding surface of CD25. In some embodiments, the portion of CD25 that shares sequence similarity with the engineered polypeptide is a surface that binds to an antibody to CD25.

c. Linking Moiety

The engineered polypeptides provided herein optionally comprise a linking moiety. When present, the linking moiety may be, for example, independently a cross-link or a linker.

In some embodiments, the engineered polypeptide comprises N number of peptides, and N−1 number of linking moieties; or N number of peptides, and N−1 number of linking moieties; or N number of peptides, and N number of linking moieties; or N number of peptides, and N+1 number of linking moieties; or N number of peptides, and N+2 number of linking moieties; or N number of peptides, and N−2 number of linking moieties, wherein N is 3 or larger.

In some embodiments, the engineered polypeptide comprises at least one linking moiety, at least two linking moieties, at least three linking moieties, at least four linking moieties, at least five linking moieties, at least six linking moieties, between one to six linking moieties, between one to five linking moieties, between one to four linking moieties, between one to three linking moieties, one linking moiety, or two linking moieties. In some embodiments, each linking moiety is independently a cross-link or a linker. In certain embodiments, each linking moiety is a cross-link. In other embodiments, each linking moiety is a linker. In still further embodiments, at least one linking moiety is a cross-link, and the remaining linking moieties are independently cross-links or a linkers. In other embodiments, at least one linking moiety is a linker, and the remaining linking moieties are independently cross-links or a linkers.

A cross-link includes, for example, a covalent bond between the side chain of one amino acid and a moiety of another amino acid. The amino acids may be independently natural or non-natural amino acids. In some embodiments, cross-links include a covalent bond between the side chains of two amino acids, or between the side chain of one amino acid and the amine or carboxyl group of another amino acid. A cross-link may form within one peptide or between two separate peptides. In some embodiments, the engineered polypeptides provided herein comprise mixture of both intra-peptide and inter-peptide cross-links. In some embodiments, the cross-link is a disulfide bond between two thiol groups of amino acid side chains, such as a disulfide bond between two cysteines. In some embodiments, the cross-link is an amide bond between an amine group and a carboxylic acid group of two amino acids, wherein at least one of the amine and the carboxylic acid group is located on a side chain of an amino acid (e.g., the amide bond is not a backbone amide bond). In some embodiments, the cross-link is an amide bond formed between diaminopimelic acid and aspartic acid. In some embodiments, an amide cross-link is a lactam. In some embodiments, the cross-link is an oxime. In some embodiments, the cross-link is a hydrazone. In some embodiments, a cross-link comprises a covalent bond between a side chain of an amino acid and a moiety of another amino acid, wherein one or both of the side chain and the moiety are modified to form the covalent bond. Such modifications may include, for example, oxidation, reduction, reaction with a catalyst to form an intermediate, or other modifications known to one of skill in the art.

A linker includes, for example, a molecule that is covalently bonded to at least two sites of a peptide, or between at least two peptides. A linker may bond to two sites within one peptide or between two separate peptides, or a combination of both. For example, a linker that comprises at more than two peptide-attachment sites may form both intra-peptide and inter-peptide bonds. In engineered polypeptides comprising at least two peptides and at least one linker, the peptides and linker may be connected in a variety of different configurations. For example, an engineered polypeptide may have peptide-linker-peptide-etc. pattern, ending with a peptide. In some embodiments, an engineered polypeptide comprises a linker that forms a branching point, for example a linker that is independently attached to three peptides. In some embodiments, an engineered polypeptide comprises a linker with three peptide-attachment sites, wherein the linker is only attached to two peptides.

In some embodiments, a linker comprises one or more amino acids. Amino acids that form part of a linker may, in some embodiments, be identified separately from the the engineered polypeptide. In certain embodiments, the linker is a region that separates and presents peptides of the engineered polypeptide in a structural, chemical, and/or dynamical manner that reflects the structure and/or function of a functional interface of the interface protein. In still further embodiments, the linker does not have a function on its own when not connected to the peptides of engineered polypeptide, for example does not exhibit binding to a binding partner of CD25. In some embodiments, each linker independently comprises at least one, at least two, at least three, at least four, at least five, at least six, or more amino acids. In some embodiments, each linker independently comprises one amino acid, two amino acids, three amino acids, four amino acids, five amino acids, or six amino acids. Amino acids that form part of a linker may be, in some embodiments, naturally occurring amino acids or non-naturally occurring amino acids. Each linker may, in some embodiments, independently comprise one or more alpha-amino acids, one or more beta-amino acids, or one or more gamma-amino acids, or any combinations thereof. In certain embodiments, a linker independently comprises a cyclic beta residue. Cyclic beta residues may include, for example, APC or ACPC. In still further embodiments, a linker may comprise one or more glycine residues, one or more serine residues, or one or more proline residues. In some embodiments, a linker has an amino acid sequence selected from the group consisting of AP, GP, GSG (SEQ ID NO: 32), (GGGGS)n (SEQ ID NO: 33), (GSG)n (SEQ ID NO: 34), GGGSGGGGS (SEQ ID NO: 35), GGGGSGGGS (SEQ ID NO: 36), (PGSG)n (SEQ ID NO: 37), and PGSGSG (SEQ ID NO: 38), wherein n is an integer between 1 and 10. In some embodiments, the engineered polypeptide comprises at least one linker, wherein each linker does not comprise amino acids, or wherein each linker does not comprise natural amino acids, or wherein each linker comprises at least one non-natural amino acid.

In some embodiments, a linker comprises a polymer. In some embodiments, the polymer is polyethylene glycol (PEG). A linker comprising PEG may comprise, for example, at least 3 PEG monomer units, at least 4 PEG monomer units, at least 5 PEG monomer units, at least 6 PEG monomer units, at least 7 PEG monomer units, at least 8 PEG monomer units, at least 9 PEG monomer units, at least 10 PEG monomer units, at least 11 PEG monomer units, at least 12 PEG monomer units, or greater than 12 PEG monomer units. In some embodiments of a linker comprising PEG, the PEG comprises between 3 to 12 monomer units, between 3 to 6 monomer units, between 6 to 12 monomer units, or between 4 to 8 monomer units. In some embodiments, the engineered polypeptide comprises at least one linker comprising PEG3 (comprising 3 monomer units), PEG6, or PEG12. In some embodiments, at least one linker is independently PEG3, PEG6, or PEG12. In further embodiments, the linker comprises a multi-arm PEG. For example, in certain embodiments, at least one linker independently comprises a 4-arm PEG, or an 8-arm PEG. In certain embodiments, each arm independently comprises between 3 to 12 monomer units, or between 3 to 6 monomer units, or between 6 to 12 monomer units, or between 4 to 8 monomer units. In certain embodiments, each arm of the multi-arm PEG comprises the same number of monomer units, for example a 4- or 8-arm PEG wherein each arm comprises 3 monomer units, 6 monomer units, or 12 monomer units.

In other embodiments, a linker comprises a dendrimer. Dendrimers include, for example, molecules with a tree-like branching architecture, comprising a symmetric core from which molecular moieties radially extend, with branch points forming new layers in the molecule. Each new branch point introduces a new, larger layer, and these radial extensions often terminate in functional groups at the exterior terminal surface of the dendrimer. Thus, increasing the number of branch points in turn amplifies the possible number of terminal functional groups at the surface.

In some embodiments, at least one linker comprises a small molecule that is not an amino acid or polymer. In some embodiments, at least one linker comprises a benzodiazepine. In some embodiments, the linker comprises a moiety that is the product of a sulfhydryl-maleimide reaction, which may be a pyrrolidine dione moiety (for example a pyrrolidine-2,5-dione moiety). In some embodiments, the linker comprises an amidine moiety. In some embodiments, the linker comprises a thioether moiety.

In some embodiments, at least one linker comprises trans-pyrrolidine-3,4-dicarboxamide.

In some embodiments, wherein the engineered polypeptide comprises at least two linkers (e.g., in embodiments wherein the engineered polypeptide comprises at least two linking moieties wherein each linking moiety is independently a linker or a cross-link, or wherein each linking moiety is independently a linker), each linker is independently any of the linkers described herein. For example, in some embodiments, each linker is independently a linker comprising one or more amino acids, a linker comprising a polymer, a linker comprising a dendrimer, or a linker comprising a small molecule that is not an amino acid or polymer.

The one or more linking moieties of the engineered polypeptide may impart a particular structural or functional characteristic of interest, or a combination thereof. For example, in some embodiments a linking moiety is present in the engineered polypeptide to impart a structural characteristic, or a functional characteristic, or a combination thereof. Such structural characteristics may include, for example, increased structural flexibility, decreased structural flexibility, a directional feature, increased length, or decreased length. Directional features that may be of interest may include, for example, a structural turn, or maintaining a linear structure. Functional characteristics may include, for example, enhanced solubility, one or more protonation sites, one or more proteolytic sites, one or more enzymatic modification sites, one or more oxidation sites, a label, or a capture handle. In some embodiments, a linker comprises one or more functional characteristics, or one or more structural characteristics, or a combinations thereof.

In some embodiments, one or more linkers independently introduce a structural "turn" into the engineered polypeptide. Examples of such linker include Gly-Pro, Ala-Pro, and trans-pyrrolidine-3,4-dicarboxamide. In some embodiments, one or more linkers present in the engineered polypeptide increases structural flexibility of the engineered polypeptide, compared to the linker not being present, or the selection of a different linker. For example, a linker that is longer and/or less sterically hindered than another linker may, in some embodiments, result in the molecule having greater structural flexibility than if the linker were not present, or if another linker were used instead. In other embodiments, one or more linking moieties independently decreases structural flexibility in the engineered polypeptide, such as including a linker that is shorter and/or more sterically hindered than another linker, or a cross-link at a location or of a type that reduces flexibility of one or more peptides. The presence of a cross-link at a particular location between certain peptides, or between certain amino acid side chains, may result in the molecule having less structural flexibility than if the cross-link was at a different location or between different side chains (e.g., a disulfide or an amide cross-link), or if the cross-link were not present.

d. Additional Components

In some embodiments, the engineered polypeptides provided herein comprise one or more additional components. For example, in some embodiments, the engineered polypeptide comprises one or more moieties that attach the engineered polypeptide to a solid surface, such as a bead or flat surface. In some embodiments, the attachment moieties comprise a polymer (such as PEG), or biotin, or a combination thereof. In some embodiments, attaching the engineered polypeptide to a solid surface may, for example, enable assessment of one or more characteristics of the engineered polypeptide, such as assessment of binding with a binding partner of CD25 (for example, an antibody to CD25).

e. Sequence Similarity

In some embodiments, the engineered polypeptide provided herein has one of the sequences listed in Table 1:

TABLE 1

| SEQ ID NO | Sequence |
|---|---|
| SEQ ID NO: 1 | CDCQAQWTPGMRAPGYDPYCLNC |
| SEQ ID NO: 2 | MVYCQPDCTAKCMHGCDRDTMKECCDRLK |
| SEQ ID NO: 3 | DDCPEVPHATFKGPGQKWEGPGGGDCSK |
| SEQ ID NO: 4 | DDCIEVPGPAECAERACRAQEERQRQPQCI |
| SEQ ID NO: 5 | AEEEKIKIEQKERKTTIKLAKEAK |
| SEQ ID NO: 6 | CHLQIMTHGKIIYVPC |
| SEQ ID NO: 7 | DDGDRCAKEHEIPHATGEECQKRDKS |
| SEQ ID NO: 8 | CKQLVIYFTGNSSHSSVFYIYYDC |
| SEQ ID NO: 9 | GSGDEDCKKFQSDDNWENYTSTRHLTFCDEKRS |
| SEQ ID NO: 10 | GSGNEEIEKKIKDCTGNSSHSSWEEALECALKK |

TABLE 1-continued

| SEQ ID NO | Sequence |
|---|---|
| SEQ ID NO: 11 | GSGDERIERLIKECTGNSSHSSWEEALECALRR |
| SEQ ID NO: 12 | GSGSHPCAYWRWVIKMTHGKTRWVLELVFCYRD |
| SEQ ID NO: 13 | GSGKCEEEAKKIASKMTHGKTREEEAEEYLKKC |
| SEQ ID NO: 14 | GSGDDESEKRTTERDTRKCTKAKANDNQCQPTE |
| SEQ ID NO: 15 | GSGSSEWDKWVEEWYKKMCTEAKKNDNQCQPTK |
| SEQ ID NO: 16 | GSGQCRVWVFRNGDKILYIYEDCDNDNQHQQTL |

In some embodiments, the engineered polypeptide has at least 6000 sequence similarity with any one of SEQ ID NOS: 1-21. In some embodiments, the engineered polypeptide has at least 7000 sequence similarity with any one of SEQ ID NOS: 1-21. In some embodiments, the engineered polypeptide has at least 8000 sequence similarity with any one of SEQ ID NOS: 1-21. In some embodiments, the engineered polypeptide has at least 90% sequence similarity with any one of SEQ TD NOS: 1-21. In some embodiments, the engineered polypeptide has at least 9500 sequence similarity with any one of SEQ ID NOS: 1-21. In some embodiments, the engineered polypeptide comprises any one of SEQ TD NOS: 1-21. In certain embodiments, the engineered polypeptide has any one of SEQ ID NOS: 1-21.

In some embodiments, the engineered polypeptide comprises any one of SEQ ID NOS: 1-21; and is modified at the N terminus, or the C terminus, or both. For example, in some embodiments the C terminus or the N terminus is covalently bonded to another molecule. In still further embodiments, the engineered polypeptide comprises any one of SEQ ID NOS: 1-21; and one or more amino acids at the N terminus or the C terminus, or both.

In some embodiments, the N-terminal molecule is a biotin-$PEG_2$:

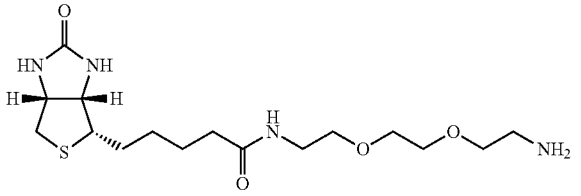 [SMILES: NCCOCCOCCNC(=O)CCCC[C@@H]1SC[C@@H]2NC(=O)N[C@@H]21]

In some embodiments, the C-terminal molecule is a linker followed by biotin (e.g. a -GSGSGK-Biotin (SEQ ID NO: 846)). Other linkers suitable for attaching biotin to the C-terminus of the engineered polypeptide include GSG (SEQ ID NO: 32), GSS (SEQ ID NO: 39), GGS (SEQ ID NO: 40), GGSGGS (SEQ ID NO: 41), GSSGSS (SEQ ID NO: 42), GSGK (SEQ ID NO: 43), GSSK (SEQ ID NO: 44), GGSK (SEQ ID NO: 45), GGSGGSK (SEQ ID NO: 46), GSSGSSK (SEQ ID NO: 47), and the like.

V. Methods of Selecting an Engineered polypeptide

Further provided herein are methods of selecting an engineered polypeptide as described herein. Such methods may include, for example, using an iterative optimization of engineered polypeptide structural characteristics.

In some embodiments, one or more sections of CD25 are identified as the target interface. In some embodiments, at least a portion of the identified section(s) binds to an antibody of CD25. Thus, for example, in some embodiments a portion of CD25 that is an epitope for one or more antibodies is identified as the target interface. In other embodiments, a section of CD25 is identified as the target interface that does not bind to an antibody, or for which it is unknown if antibody binding occurs. In certain embodiments, the crystal structure for at least a portion of CD25 is unknown, and the initial selection of a target interface includes molecular dynamics simulations of CD25 and CD25 binding. In some embodiments, one or more initial input sequences are obtained from the identified section or sections, wherein each sequence is independently continuous or discontinuous. In developing an engineered polypeptide candidate, at least some of the interface residues of each sequence are retained, and one or more linking moieties are incorporated into the sequence to provide desired structural and dynamic characteristics. In some embodiments, one or more non-interface residues are added to the sequence, or one or more residues in the input sequence are replaced with one or more non-interface residues, to achieve desired structural and dynamic characteristics relative to the cognate target structure and dynamics. In some embodiments, these non-interface residues are not from the target interface of CD25, or do not share one or more characteristics with the target interface of CD25, or share fewer characteristics and/or share characteristics less strongly with the target interface of CD25 than the retained interface residues. These intermediate, non-interface residues may, in some embodiments, form part or all of an amino acid linker.

Next, in some embodiments the initial design (or multiple designs) is produced and the molecular dynamics simulated to determine flexibility and overall stability of the design. If this initial design does not meet RMSD requirements, it may undergo iterative optimization of one or more linking moieties (such as one or more cross-links, or intermediate linker residues) using computational mutagenesis, in some embodiments. During this optimization, in some embodiments the interface residues are fixed while one or more of the linking moieties is changed, or removed, or added. The iterative optimization may be repeated until the engineered polypeptide RMSD interface residue positions relative to the target interface and structural order metric meet certain requirements (for example, ≤6.0 Å and ≥0.25, respectively, wherein structural order is on a 0-1 normalized scale, where 1=perfect structural stability).

In some embodiments, the intermediate structural stability residue regions can range from 1-50 amino acids in length. In certain embodiments, these intermediate structural stability residue regions are linkers, for example amino acid linkers. In some embodiments, the relatively small size of an engineered polypeptide produced by certain embodiments of the methods provided herein (compared, for example, to approaches that graft an interface onto a large structurally stabilizing scaffold) may enable chemical synthesis of the molecule, in contrast to a larger molecule that may require an in vitro expression system. Furthermore, in some embodiments the methods provided herein enable the incorporation of non-natural amino acids into intermediate positions or the interface positions, which may allow for fine control of interface engineering with novel moieties and properties such as post-translational modifications, solubility, cell-permeability, enzyme reactivity, pH sensitivity, oxidation sensitivity, etc. In still further embodiments, an engineered polypeptide may be selected with a higher likelihood of species cross-reactivity or disease-related mutation reactivity in selected antibodies when the engineered polypeptide is used as an immunogen or epitope-bait.

In some embodiments, the optimized molecule is the engineered polypeptide provided herein. In other embodiments, the optimized molecule is a candidate engineered polypeptide that may undergo further evaluation, further adjustment, or be used to generate a peptide library or a candidate engineered polypeptide library, or any combinations thereof. In certain embodiments, the method further includes using the engineered polypeptide candidate to generate a peptide library, or an engineered polypeptide candidate library, and then contacting the library with a binding partner of CD25 (such as an antibody to CD25). The peptide library may include, for example, peptides which are smaller than and share at least some sequence similarity with the engineered polypeptide candidate, and in which certain residues are optionally replaced with other residues. An engineered polypeptide candidate library may include, for example, variations of the engineered polypeptide candidate.

In some embodiments, the peptides of the peptide library comprise between 2 to 15 amino acids, between 5 to 15 amino acids, between 10 to 15 amino acids, between 2 to 10 amino acids, or between 5 to 10 amino acids. In some embodiments, the total number of amino acids in each peptide of the library includes both the interface amino acids and structural amino acids, which may include, for example, linker amino acids. The engineered polypeptide candidate library may be prepared by, for example, varying one or more amino acids or linking moieties in the candidates to make new library members. The engineered polypeptide candidates in the engineered polypeptide candidate library, in some embodiments, independently comprise between 5 to 40 amino acids, between 10 to 35 amino acids, between 15 to 35 amino acids, or between 20 to 30 amino acids. In some embodiments, the total number of amino acids in each engineered polypeptide candidate of the candidate library can, in some embodiments, include both the interface amino acids and structural amino acids, which may include, for example, linker amino acids. The peptide library and the engineered polypeptide candidate library can, in some embodiments, independently comprise between 5,000 and 100,000 members, between 5,000 and 80,000 members, between 5,000 and 60,000 members, between 5,000 and 40,000 members, between 5,000 and 30,000 members, between 10,000 and 25,000 members, between 15,000 and 20,000 members, or about 17,000 members (e.g., distinct peptides or distinct engineered polypeptide candidates). In some embodiments, multiple separate libraries are produced and evaluated. In certain embodiments, the library members do not comprise certain cross-links. For example, in some embodiments, a library is evaluated wherein the library members do not have disulfide cross-links.

In some embodiments, to produce candidates for a candidate library, one or more linking moieties is added or removed, or location changed, in the design of the original engineered polypeptide candidate. For example, in some embodiments, a disulfide cross-link is removed, or is added, or the location of which is moved. In other embodiments, a lactam cross-link is removed, or is added, or the location of which is moved. In some embodiments, one or more amino acid residues is replaced. The binding of a CD25 binding partner to the peptide library, or engineered polypeptide candidate library, or both (if present), can provide additional information that may be used to further refine the design of the engineered polypeptide, or to select an engineered polypeptide. Additional information from screening these libraries may, for example, be used to make changes to the engineered polypeptide, for example to increase binding affinity with a binding partner of CD25. The engineered polypeptide candidate library can, in some embodiments, provide additional information regarding the effect of certain linker moieties on binding interactions (including presence or location of such moieties), such as cross-links including disulfide bonds and lactams. The peptide or engineered polypeptide candidate libraries, or both, may in some embodiments be used to identify common motifs (e.g., amino acid patterns or linking moieties, or combinations thereof) that may increase binding affinity or binding specificity for a binding partner of CD25, or provide other desired characteristics. Evaluating the binding of the cognate binding partner with the members of the peptide or the engineered polypeptide candidate libraries, or both, can provide additional structural and functional information, which may be used to further refine the engineered polypeptide design or to select an engineered polypeptide candidate.

a. Selection by Binding Under Variable pH

In some embodiments, an engineered polypeptide is selected based, at least in part, on structural flexibility at physiological pH compared to structural flexibility at a lower pH. For example, CD25 may be overexpressed on tumor cells, and therefore binding of an antibody to CD25 with greater affinity in a tumor microenvironment may be desired in some embodiments. Therefore, in some embodiments, it may be desirable to select an engineered polypeptide that is more rigid at lower pH, or in which one or more amino acids have a particular orientation at lower pH, or has greater binding affinity or binding selectivity at lower pH, compared to the same engineered polypeptide at physiological pH. In many cancerous tumors, the growth rate of cancerous cells can outpace the oxygen supply available in portions of the tumor, resulting in a hypoxic microenvironment within the tumor. The level of oxygen in tissues can affect the pH of the tissue environment, and hypoxic levels can lead to decreased pH (including, for example, by the buildup of acidic metabolites from anaerobic glycolysis). Thus, in some embodiments, selecting an engineered polypeptide that has greater binding at low pH (e.g., has desirable structural characteristics that lead to binding interactions), but has reduced binding at physiological pH (e.g., has decreased, fewer, or no desirable structural characteristics that lead to binding interactions), can, in some embodiments, result in an engineered polypeptide that can produce an antibody with greater binding to the desired target in a tumor, compared to binding not in a tumor. Physiological pH is typically between about 7.35 and about 7.45, for example about 7.4. The pH of a tumor microenvironment may be, for example, less than about 7.45, less than about 7.45, between about 7.45 and about 6.0, between about 7.0 and about 6.0, between about 6.8 and about 6.2, between about 6.7 and about 6.3, about 6.4, about 6.5, about 6.6, about 6.7, about 6.8, about 6.9 or about 7.0. In some embodiments, an engineered polypeptide can be evaluated at different pHs using computational methods, for example molecular dynamics simulations. In other embodiments, an engineered polypeptide is selected based on differential pH characteristics using an in vitro method. Suitable in vitro methods may include, for example, phage panning at different pHs. For example, an antibody phage display library can be used to pan one or more engineered polypeptides at physiological pH, and phage that bind at that pH can be discarded. Then, a second round of panning can be carried out at a lower pH, and phage that bind to the one or more engineered polypeptides at the lower pH can be selected. In some embodiments, engineered polypeptides which bind to no phage at a lower pH, or which bind to phage with similar affinity at both low and physiological pH, may be less desirable for use in generating an antibody that targets tumor cells.

b. Inverse Peptide Evaluation

In still further embodiments, selecting an engineered polypeptide may include comparing the binding of the engineered polypeptide to binding of an inverse engineered polypeptide. An inverse engineered polypeptide may be based on the engineered polypeptide, but replacing one or more of the interface-interacting amino acid residues (e.g., based on the surface of CD25) with an amino acid that exhibits an inverse characteristic. For example, an amino acid with a large, sterically bulky, hydrophobic side chain may be replaced with an amino acid that has a smaller side chain, or hydrophilic side chain, or a side chain that is both smaller and hydrophilic. In some embodiments, an amino acid with a hydrogen bond-donating side chain may be replaced with an amino acid that has a hydrogen bond-accepting side chain, or with a an amino acid that has a side chain that does not hydrogen bond. Binding characteristics that may be compared using the engineered polypeptide and the inverse engineered polypeptide may include, in some embodiments, specificity and/or affinity. Comparing the binding characteristics of a engineered polypeptide with the binding characteristics of an inverse engineered polypeptide may, in some embodiments, help select engineered polypeptides in which the interface-interacting amino acids drive the binding interactions, rather than characteristics of a linking moiety such as a linker. Engineered polypeptides in which binding is driven by a linking moiety such as a linker may be less desirable in some embodiments as they may exhibit off-target binding, or other undesirable binding characteristics.

In further embodiments, the method further comprises modifying the selected engineered polypeptides.

c. Binding Evaluation

As described herein, in some embodiments, the method of selecting an engineered polypeptide provided herein comprises evaluating the binding of an engineered polypeptide candidate to a protein or fragment thereof, for example a binding partner of CD25 (such as an antibody to CD25). For example, in some embodiments, an engineered polypeptide candidate library or peptide library is screened for binding to a binding partner of CD25.

Binding of a protein or fragment thereof (e.g., a binding partner of CD25) with one or more peptides or engineered polypeptide candidates (such as a member of a library) may be evaluated in various ways. In some embodiments, binding is directly evaluated, for example by directly detecting a label on the protein or fragment thereof. Such labels may include, for example, fluorescent labels, such as a fluorophore or a fluorescent protein. In other embodiments, binding is indirectly evaluated, for example using a sandwich assay. In a sandwich assay, a peptide or engineered polypeptide candidate (such as a member of a library) binds to a binding partner, and then a secondary labeled reagent is added to label the bound binding partner. This secondary labeled reagent is then detected. Examples of sandwich assay components include His-tagged-binding partner detected with an anti-His-tag antibody or His-tag-specific fluorescent probe; a biotin-labeled binding partner detected with labeled streptavidin or labeled avidin; or an unlabeled binding partner detected with an anti-binding-partner antibody.

In some embodiments, peptides or engineered polypeptide candidates of interest are identified based on the binding signal, or dose-response, using any number of available detection methods. These detection methods may include, for example, imaging, fluorescence-activated cell sorting (FACS), mass spectrometry, or biosensors. In some embodiments, a hit threshold is defined (for example the median signal), and any with signal above that signal is flagged as a putative hit motif.

For the development of the combinatorial library, peptides identified from the peptide library based on binding with the protein or fragment thereof may, in some embodiments, be further clustered into distinct groups using sequence or structural information, or a combinations thereof. This grouping may be done, for example, using generally available sequence alignment, chemical descriptors, structural prediction, and entropy prediction informatics tools (e.g. MUSCLE, CLUSTALW, PSIPRED, AMBER, Hydropathy Calculator, and Isoelectric Point Calculator) and clustering algorithms (e.g., K-Means, Gibbs, and Hierarchical). Clusters of motifs (e.g., structural or functional motifs) present in peptide hits can be identified from this analysis. Individual peptide motif hits can also be identified. Using these motif clusters and individual motifs, in some embodiments, design rules can be formulated that define one or more of sequence, structure, and chemical characteristics of the motifs that appear to drive the protein interactions at the target interface. In some embodiments, the structure of the target interface is not necessary for identification of these interface motif design rules. Rather, the design rules can, in some embodiments, be derived from analysis of peptides identified from screening the peptide library.

In some embodiments, the binding assay has a sensitivity dynamic range of about $10^5$. Thus, in some embodiments, an engineered polypeptide candidate is identified as of interest if it has a binding event with a CD25 binding partner that is within a $10^5$ signal bracket of the native CD25:binding partner signal. The type of signal may be different depending on what type of assay is being used, or how it is being evaluated. For example, in some embodiments, the signal is response units in a sensorgram, fluorescence signal in an image-based readout, or enzymatic readout in an enzyme-based assay. The signal for binding events may be measured relative to CD25:binding partner signal.

In some embodiments, the engineered polypeptide candidate is modified prior to evaluating binding. For example, in some embodiments, biotin, PEG, or another attachment moiety, or combination thereof, is bonded to the C terminus or the N terminus of the peptide to enable it to be used with a binding evaluation system. For example, in some embodiments biotin-PEG12- is covalently attached to the N-terminus of the engineered polypeptide. In other embodiments, the engineered polypeptide candidate is modified at the C terminus with -GSGSGK-PEG4-biotin (SEQ ID NO: 48). In certain embodiments, such a biotin-modified engineered polypeptide candidate is then bound to a streptavidin bead through the biotin moiety, and the bead-supported immunogen is evaluated for binding to a binding partner of CD25.

VI. Use of Engineered Polypeptides and CD25 Antibodies

The engineered polypeptides provided herein, and identified by the methods provided herein, may be used, for example, to produce one or more antibodies that bind specifically to CD25. In some embodiments, the antibody is a monoclonal or polyclonal antibody.

The term “antibody,” as used herein, refers to a protein, or polypeptide sequences derived from an immunoglobulin molecule, which specifically binds to an antigen. Antibodies can be intact immunoglobulins of polyclonal or monoclonal origin, or fragments thereof and can be derived from natural or from recombinant sources.

The terms "antibody fragment" or "antibody binding domain" refer to at least one portion of an antibody, or recombinant variants thereof, that contains the antigen binding domain, i.e., an antigenic determining variable region of an intact antibody, that is sufficient to confer recognition and specific binding of the antibody fragment to a target, such as an antigen and its defined epitope. Examples of antibody fragments include, but are not limited to, Fab, Fab', F(ab')2, and Fv fragments, single-chain (sc)Fv ("scFv") antibody fragments, linear antibodies, single domain antibodies (abbreviated "sdAb") (either VL or VH), camelid VHH domains, and multi-specific antibodies formed from antibody fragments.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived.

"Heavy chain variable region" or "VH" (or, in the case of single domain antibodies, e.g., nanobodies, "VHH") with regard to an antibody refers to the fragment of the heavy chain that contains three CDRs interposed between flanking stretches known as framework regions, these framework regions are generally more highly conserved than the CDRs and form a scaffold to support the CDRs.

Unless specified, as used herein a scFv may have the VL and VH variable regions in either order, e.g., with respect to the N-terminal and C-terminal ends of the polypeptide, the scFv may comprise VL-linker-VH or may comprise VH-linker-VL.

The term "antibody light chain," refers to the smaller of the two types of polypeptide chains present in antibody molecules in their naturally occurring conformations. Kappa ("K").

Thus, in some embodiments, provided herein is an antibody produced by immunizing an animal with an immunogen, wherein the immunogen is an engineered polypeptide as provided herein. In some embodiments, the animal is a human, a rabbit, a mouse, a hamster, a monkey, etc. In certain embodiments, the monkey is a cynomolgus monkey, a macaque monkey, or a rhesus macaque monkey. Immunizing the animal with an engineered polypeptide can comprise, for example, administering at least one dose of a composition comprising the immunogen and optionally an adjuvant to the animal. In some embodiments, generating the antibody from an animal comprises isolating a B cell which expresses the antibody. Some embodiments further comprise fusing the B cell with a myeloma cell to create a hybridoma which expresses the antibody. In some embodiments, the antibody generated using the engineered polypeptide can cross react with a human and a monkey, for example a cynomolgus monkey.

In certain embodiments, the method of generating an antibody further comprises determining one or more epitopes for the antibody. In some embodiments, the method comprises screening the antibody for binding to two or more epitopes, for example by contacting an epitope library with the antibody, and evaluating binding of the antibody to epitopes of the library. In certain embodiments, an antibody that binds to two or more epitopes is discarded. In some embodiments, the engineered polypeptide mimics one epitope of CD25. In other embodiments, the engineered polypeptide mimics two or more epitopes of CD25. In certain embodiments, screening an antibody for binding to two or more epitopes, wherein the engineered polypeptide mimics two or more epitopes of the CD25, comprises contacting an epitope library with the antibody, and evaluating binding of the antibody to epitopes of the library, and discarding one or more antibodies that binds to two or more epitopes, wherein the epitopes are not those mimicked by the engineered polypeptide.

In some embodiments, the antibody produced using an engineered polypeptide as provided herein binds specifically to CD25. In certain embodiments, the antibody does not block binding of IL-2 with CD25 when the antibody is bound to CD25.

In some embodiments, the antibody is a non IL-2-blocking antibody (a non IL-2 blocker)—that is, the binding of the antibody to CD25 does not disrupt or prevent binding of the IL-2 ligand to CD25 (the IL-2 alpha chain), and does not affect IL-2 mediated signal transduction, e.g. signaling through the IL-2/JAK3/STAT-5 signaling pathway. In some embodiments, the antibody does not disrupt the binding of IL-2 ligand to CD25 (IL-2 alpha chain), and binds to a different epitope than where the 7G7B6 antibody binds. In some embodiments, the antibody does not disrupt the binding of the IL-2 ligand to CD25 (IL-2 alpha chain), but does disrupt the trimerization of the beta, gamma, and alpha (CD25) chains of the IL-2 receptor.

In some embodiments, the antibody is an IL-2 blocking antibody, e.g., the antibody disrupts or prevents binding of the IL-2 ligand to the alpha, beta, and/or gamma chains of the receptor, and decreases or inhibits IL-2 mediated signal transduction. In certain embodiments, the antibody disrupts or prevents binding of the IL-2 ligand to CD25. In some embodiments, the antibody disrupts or prevents the binding of the IL-2 ligand to CD25, and binds to a different epitope than to which either daclizumab or baciliximab bind.

In some embodiments, the CD25 antibody is a partially blocking antibody, and partially, but not completely, disrupts binding of the IL-2 ligand to the alpha, beta, and/or gamma chains of the IL-2 receptor (CD25), and/or partially, but not completely decreases IL-2 mediated signal transduction.

In some embodiments, the antibody disrupts or prevents heterotrimerization of the alpha, beta, and gamma IL-2 chains. In some embodiments, the antibody does not block binding of the IL-2 ligand with CD25, but does disrupt or prevent heterotrimerization of the alpha, beta, and gamma IL-2R chains. In certain embodiments, the antibody selectively binds to Treg cells. In other embodiments, the antibody selectively binds to Teff cells.

In still further embodiments, whether an antibody produced using an engineered polypeptide as provided herein blocks binding of CD25 with IL-2 is evaluated. In some embodiments, an antibody that does not block CD25 binding with IL-2 is selected. In other embodiments, an antibody that does block binding of CD25 with IL-2 is selected. Such blocking or non-blocking may be evaluated, for example, by coupling CD25 to a biosensor tip, and evaluating binding by the antibody in the presence and absence IL-2. In some embodiments, the an antibody is expressed with a 6×His tag that can be used with Ni-NTA in flow cytometry to evaluate binding of the antibody, and blocking or non-blocking of IL-2 binding to CD25. In certain embodiments, the binding of the antibody is evaluated at physiological pH (e.g., between about pH 7.3 and about pH 7.5, or about pH 7.4), and also at the pH of a tumor microenvironment (e.g., between about pH 6.4 and about pH 6.6, or about pH 6.5). In certain embodiments, the blocking/non-blocking activity is compared to the binding of an IL-2 blocker antibody (for example, daclizumab or basiliximab). In certain embodiments, the blocking/non-blocking activity is compared to the binding of an IL-2 non-blocker antibody (for example, antibody 7G7B6). In certain embodiments, the blocking/non-blocking activity is compared to both an IL-2 blocking antibody and an IL-2 non-blocking antibody.

In some embodiments, the antibody is an agonist antibody to CD25. In other embodiments, the antibody is an antagonist antibody to CD25.

In some embodiments, the antibody binds to CD25 in the trans orientation. In other embodiments the antibody binds to CD25 in the cis orientation. In still further embodiments, the antibody is capable of binding to CD25 in either the cis or the trans configuration.

The antibody clone of origin can be identified by the ID shown, e.g. the Clone ID in Table 2. For example, the antibody may comprise the heavy chain complementary determining regions of antibody clone "YU389-A01" as presented in row 1 of Table 2.

In some embodiments, the antibody has a CDR-H1, CDR-H2, CDR-H3, CDR-L1, CDR-L2, and CDR-L3, each independently selected from those disclosed in Table 2.

TABLE 2

| Clone ID | Heavy Chain CDR 1 | Heavy Chain CDR 2 | Heavy Chain CDR 3 | Light Chain CDR 1 | Light Chain CDR 2 | Light Chain CDR 3 |
|---|---|---|---|---|---|---|
| YU389-A01 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| YU389-A02 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| YU389-A03 | GGSISSGGYY (SEQ ID NO: 283) | IYYSGST (SEQ ID NO: 384) | ARGNLWSGYYF (SEQ ID NO: 111) | SSNIGNNF (SEQ ID NO: 650) | DST (SEQ ID NO: 191) | GSWDTNLSGYV (SEQ ID NO: 289) |
| YU389-A05 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| YU389-A07 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| YU389-B11 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| YU389-D07 | GGTFSSYA (SEQ ID NO: 286) | IIPIFGTA (SEQ ID NO: 326) | AREMYYYYGMDV (SEQ ID NO: 103) | QSISNY (SEQ ID NO: 563) | AAS (SEQ ID NO: 49) | QQSYSTPPT (SEQ ID NO: 534) |
| YU390-A11 | GFTFSSYG (SEQ ID NO: 275) | ISYDGSNK (SEQ ID NO: 362) | AKELLEGAFDI (SEQ ID NO: 64) | NIETKS (SEQ ID NO: 455) | DDD (SEQ ID NO: 158) | QVWDSSSGHREV (SEQ ID NO: 613) |
| YU390-A12 | GYTFTSYY (SEQ ID NO: 313) | INPSGGST (SEQ ID NO: 339) | ARDRVTMVRGALAY (SEQ ID NO: 97) | KLGDKY (SEQ ID NO: 404) | KDN (SEQ ID NO: 386) | QAWDSSTYV (SEQ ID NO: 473) |
| YU390-B12 | GFTFSSYG (SEQ ID NO: 275) | ISYDGSNK (SEQ ID NO: 362) | AKELLEGAFDI (SEQ ID NO: 64) | NIETKS (SEQ ID NO: 455) | DDD (SEQ ID NO: 158) | QVWDSSSGHREV (SEQ ID NO: 613) |
| YU390-C03 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| YU390-C11 | GYTFTSYG (SEQ ID NO: 312) | ISAYNGNT (SEQ ID NO: 346) | ARERSYYGMDV (SEQ ID NO: 105) | QSVSNY (SEQ ID NO: 574) | GAS (SEQ ID NO: 260) | QQYNHWPPL (SEQ ID NO: 544) |

TABLE 2-continued

| Clone ID | Heavy Chain CDR 1 | Heavy Chain CDR 2 | Heavy Chain CDR 3 | Light Chain CDR 1 | Light Chain CDR 2 | Light Chain CDR 3 |
|---|---|---|---|---|---|---|
| YU390-D01 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| YU390-D03 | GGTFSSYA (SEQ ID NO: 286) | IMPIFDTA (SEQ ID NO: 332) | ASWSERIGYQYGLDV (SEQ ID NO: 145) | QTISQW (SEQ ID NO: 582) | KAS (SEQ ID NO: 385) | QQYSGDSMYT (SEQ ID NO: 553) |
| YU390-D05 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| YU390-D11 | GYTFTSYG (SEQ ID NO: 312) | ISAYNGNT (SEQ ID NO: 346) | ARERSYYGMDV (SEQ ID NO: 105) | QSVSNY (SEQ ID NO: 574) | GAS (SEQ ID NO: 260) | QQYNHWPPL (SEQ ID NO: 544) |
| YU390-G03 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| YU390-H11 | GYTFTSYG (SEQ ID NO: 312) | ISAYNGNT (SEQ ID NO: 346) | ARERSYYGMDV (SEQ ID NO: 105) | QSVSNY (SEQ ID NO: 574) | GAS (SEQ ID NO: 260) | QQYNHWPPL (SEQ ID NO: 544) |
| YU392-A05 | GYTFTSYY (SEQ ID NO: 313) | INPSGGST (SEQ ID NO: 339) | ARDILGLDY (SEQ ID NO: 81) | SSNIGSNY (SEQ ID NO: 655) | RNN (SEQ ID NO: 635) | AAWDDSLSGVV (SEQ ID NO: 56) |
| YU392-A07 | GYTFTDYY (SEQ ID NO: 306) | VDPEDGET (SEQ ID NO: 693) | ATEDTAMGGIDY (SEQ ID NO: 146) | SSNIGSNY (SEQ ID NO: 655) | SNN (SEQ ID NO: 644) | AAWDDSLNGVV (SEQ ID NO: 53) |
| YU392-A09 | GYTFTDYY (SEQ ID NO: 306) | VDPEDGET (SEQ ID NO: 693) | ATEGRYGMDV (SEQ ID NO: 147) | NFNIGNNL (SEQ ID NO: 453) | AND (SEQ ID NO: 69) | ATWDDSLSGVV (SEQ ID NO: 151) |
| YU392-B11 | GYTFTDYY (SEQ ID NO: 306) | VDPEDGET (SEQ ID NO: 693) | AVEGGRAPGTYYYDSSGLAY (SEQ ID NO: 153) | SSNIGSNY (SEQ ID NO: 655) | SNN (SEQ ID NO: 644) | ATWDDSLSGVV (SEQ ID NO: 151) |
| YU393-A01 | GGSISSGGYS (SEQ ID NO: 282) | IYHSGST (SEQ ID NO: 365) | ARAGYYYGMDV (SEQ ID NO: 71) | RNIWSY (SEQ ID NO: 634) | GAS (SEQ ID NO: 260) | QQSHSTPIT (SEQ ID NO: 526) |
| YU393-A02 | GGTFSSYA (SEQ ID NO: 286) | IIPIFGTA (SEQ ID NO: 326) | ARDLGTMVRGVIEPYYFDY (SEQ ID NO: 85) | QSISSW (SEQ ID NO: 566) | DAF (SEQ ID NO: 156) | QQYNSYSRT (SEQ ID NO: 551) |
| YU393-A03 | GGSISSSNW (SEQ ID NO: 284) | IYHSGST (SEQ ID NO: 365) | ARGVRGTGFDP (SEQ ID NO: 118) | QSVSSR (SEQ ID NO: 576) | GAS (SEQ ID NO: 260) | QQYTNWPQT (SEQ ID NO: 554) |
| YU393-A04 | GYTFTSYG (SEQ ID NO: 312) | ISAYNGNT (SEQ ID NO: 346) | ARDRNGYFQH (SEQ ID NO: 94) | QTISGL (SEQ ID NO: 581) | GAS (SEQ ID NO: 260) | LQYDRYSGA (SEQ ID NO: 426) |
| YU393-A08 | GFTFSSYG (SEQ ID NO: 275) | ISYDGSNK (SEQ ID NO: 362) | AKDLLGELSFFDY (SEQ ID NO: 61) | DIESEM (SEQ ID NO: 163) | DDS (SEQ ID NO: 159) | QVWHTTNDHVL (SEQ ID NO: 615) |

TABLE 2-continued

| Clone ID | Heavy Chain CDR 1 | Heavy Chain CDR 2 | Heavy Chain CDR 3 | Light Chain CDR 1 | Light Chain CDR 2 | Light Chain CDR 3 |
|---|---|---|---|---|---|---|
| YU393-A09 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU393-A11 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU393-B02 | GGTFSSYA (SEQ ID NO: 286) | IIPIFGTA (SEQ ID NO: 326) | ARDRSYYGMDV (SEQ ID NO: 96) | QSIGNY (SEQ ID NO: 558) | AAT (SEQ ID NO: 50) | QQSKQIP YT (SEQ ID NO: 528) |
| YU393-B03 | GGTFSSYA (SEQ ID NO: 286) | IIPIFGTA (SEQ ID NO: 326) | ARDKGYYGMDV (SEQ ID NO: 83) | QGISSW (SEQ ID NO: 489) | AVS (SEQ ID NO: 154) | QQSYSLP LT (SEQ ID NO: 531) |
| YU393-B04 | GGTFSSYA (SEQ ID NO: 286) | IIPIFGTA (SEQ ID NO: 326) | ARDRSYYGMDV (SEQ ID NO: 96) | QSIGNY (SEQ ID NO: 558) | AAT (SEQ ID NO: 50) | QQSKQIP YT (SEQ ID NO: 528) |
| YU393-B05 | GFTFSNYG (SEQ ID NO: 271) | ISHDGHVK (SEQ ID NO: 349) | AKEISPRSSVGWPL DY (SEQ ID NO: 63) | QSVS STY (SEQ ID NO: 577) | GAS (SEQ ID NO: 260) | QQFDISG GLI (SEQ ID NO: 518) |
| YU393-B06 | GFTFSSSA (SEQ ID NO: 272) | ISYDGSNK (SEQ ID NO: 362) | ARDFWSGYNELGG MDV (SEQ ID NO: 76) | QDISNY (SEQ ID NO: 485) | DAS (SEQ ID NO: 157) | QQYDNL PLT (SEQ ID NO: 542) |
| YU393-B07 | GFTFSSYW (SEQ ID NO: 277) | IKQDGSEK (SEQ ID NO: 328) | ARTWFGEFFDY (SEQ ID NO: 134) | NIESES (SEQ ID NO: 454) | DDS (SEQ ID NO: 159) | QVWDSS SDHTVA (SEQ ID NO: 609) |
| YU393-B08 | GYTFTSYG (SEQ ID NO: 312) | ISAYNGNT (SEQ ID NO: 346) | ARVIGGWFDP (SEQ ID NO: 136) | SSDVGAY NY (SEQ ID NO: 647) | GVS (SEQ ID NO: 295) | SSYTTTD TFV (SEQ ID NO: 665) |
| YU393-C02 | GFIFSRHA (SEQ ID NO: 264) | ISYDGSNK (SEQ ID NO: 362) | ARGRLAYGDIEGF DY (SEQ ID NO: 112) | QDINNY (SEQ ID NO: 482) | DAS (SEQ ID NO: 157) | QQYDNL PYT (SEQ ID NO: 543) |
| YU393-C03 | GYTFNNYG (SEQ ID NO: 302) | ISVYNGDI (SEQ ID NO: 359) | ARDILRGESSILDH (SEQ ID NO: 82) | QGISNS (SEQ ID NO: 488) | AAS (SEQ ID NO: 49) | QQYYSTP PH (SEQ ID NO: 556) |
| YU393-C05 | GGTFSSYA (SEQ ID NO: 286) | IIPIFGTA (SEQ ID NO: 326) | ARDRYYYGMDV (SEQ ID NO: 98) | QSISSY (SEQ ID NO: 567) | AAS (SEQ ID NO: 49) | QQSYSTP LT (SEQ ID NO: 532) |
| YU393-C07 | GFTFSSYA (SEQ ID NO: 273) | ISYDGSNK (SEQ ID NO: 362) | ARDLLGSGYDIIDY (SEQ ID NO: 86) | NIGSKS (SEQ ID NO: 456) | DDS (SEQ ID NO: 159) | QVWDSS SDHVV (SEQ ID NO: 610) |
| YU393-C08 | GYTFTSYG (SEQ ID NO: 312) | ISAYNGNT (SEQ ID NO: 346) | ARVWGKNGDFDY (SEQ ID NO: 142) | SSNIGNNY (SEQ ID NO: 651) | DNN (SEQ ID NO: 190) | GTWDSS LSAYV (SEQ ID NO: 294) |
| YU393-D03 | GYTFTTYA (SEQ ID NO: 314) | INTNTGDP (SEQ ID NO: 344) | ARDRFHYGMDV (SEQ ID NO: 90) | EGIRTS (SEQ ID NO: 218) | GAS (SEQ ID NO: 260) | QQTHTW PWT (SEQ ID NO: 538) |

TABLE 2-continued

| Clone ID | Heavy Chain CDR 1 | Heavy Chain CDR 2 | Heavy Chain CDR 3 | Light Chain CDR 1 | Light Chain CDR 2 | Light Chain CDR 3 |
|---|---|---|---|---|---|---|
| YU393-D04 | GYTFTSYG (SEQ ID NO: 312) | ISAYNGNT (SEQ ID NO: 346) | ARDRGDY (SEQ ID NO: 92) | QGTSSW (SEQ ID NO: 491) | AAS (SEQ ID NO: 49) | QQANSFP LT (SEQ ID NO: 514) |
| YU393-D05 | GFTFNNAW (SEQ ID NO: 267) | IKSKTDGG TT (SEQ ID NO: 330) | TTEGVELLSFGGAP FDY (SEQ ID NO: 683) | QSISSY (SEQ ID NO: 567) | AAS (SEQ ID NO: 49) | QQSYSTP YT (SEQ ID NO: 536) |
| YU393-D07 | GFTFSSYE (SEQ ID NO: 274) | ISSSGSTI (SEQ ID NO: 351) | ARRRGGGFDY (SEQ ID NO: 132) | SSDVGGY NY (SEQ ID NO: 649) | DVS (SEQ ID NO: 201) | SSYTSSS TYV (SEQ ID NO: 664) |
| YU393-E04 | GFTFSSYW (SEQ ID NO: 277) | IKQDGSEK (SEQ ID NO: 328) | AREKGSWFDP (SEQ ID NO: 102) | QSVSNNY (SEQ ID NO: 573) | GAS (SEQ ID NO: 260) | QRYGSSP R (SEQ ID NO: 557) |
| YU393-E05 | GGTFSSYA (SEQ ID NO: 286) | IIPIFGTA (SEQ ID NO: 326) | ARDKGYYGMDV (SEQ ID NO: 83) | QGINSY (SEQ ID NO: 487) | AAS (SEQ ID NO: 49) | QQVHSFP FT (SEQ ID NO: 541) |
| YU393-E07 | GFTFSSYG (SEQ ID NO: 275) | ISSRGSTI (SEQ ID NO: 350) | ARDRGDRVGGLVF DY (SEQ ID NO: 91) | NIGSKS (SEQ ID NO: 456) | DDS (SEQ ID NO: 159) | QVWDSS SDHVV (SEQ ID NO: 610) |
| YU393-F03 | GYSFTTYW (SEQ ID NO: 300) | IYPGDSDT (SEQ ID NO: 377) | ARQVAGGLDY (SEQ ID NO: 131) | QAVRID (SEQ ID NO: 472) | GAS (SEQ ID NO: 260) | LQHNTFP YT (SEQ ID NO: 423) |
| YU393-F04 | GYTFTSYG (SEQ ID NO: 312) | ISAYNGNT (SEQ ID NO: 346) | ARDRGYYGMDV (SEQ ID NO: 93) | QSISRY (SEQ ID NO: 564) | AAS (SEQ ID NO: 49) | QQSHSTP LT (SEQ ID NO: 527) |
| YU393-F06 | GYSFTSYW (SEQ ID NO: 299) | IYPGDSDT (SEQ ID NO: 377) | FRFGEGFDY (SEQ ID NO: 259) | QSIGYW (SEQ ID NO: 559) | RAS (SEQ ID NO: 619) | QQYNSY PFT (SEQ ID NO: 548) |
| YU393-F07 | GYSFTTYW (SEQ ID NO: 300) | IYPGDSDT (SEQ ID NO: 377) | ARQVAGGLDY (SEQ ID NO: 131) | SSNVGSN Y (SEQ ID NO: 656) | RNN (SEQ ID NO: 635) | AAWDDS LSGVV (SEQ ID NO: 56) |
| YU393-G01 | GYSFNTYW (SEQ ID NO: 297) | IYPSDSDT (SEQ ID NO: 383) | ARDGGYYFDD (SEQ ID NO: 79) | QSVSSTY (SEQ ID NO: 577) | GTS (SEQ ID NO: 291) | QQYNSSP LMYT (SEQ ID NO: 547) |
| YU393-G03 | GGTFSSYA (SEQ ID NO: 286) | IIPIFGTA (SEQ ID NO: 326) | ARDKGYYGMDV (SEQ ID NO: 83) | QSIKNY (SEQ ID NO: 561) | AAS (SEQ ID NO: 49) | QQTYSTP LT (SEQ ID NO: 540) |
| YU393-G04 | GYTFTSYG (SEQ ID NO: 312) | ISAYNGNT (SEQ ID NO: 346) | ARDFRMDV (SEQ ID NO: 75) | QDIKRR (SEQ ID NO: 480) | DAS (SEQ ID NO: 157) | QQANTFP QT (SEQ ID NO: 516) |
| YU393-G07 | GFTFRRYW (SEQ ID NO: 268) | IKQDGSEK (SEQ ID NO: 328) | ARDAYAYGLDV (SEQ ID NO: 73) | SGSIASSY (SEQ ID NO: 640) | EDN (SEQ ID NO: 216) | QSYDGSS VV (SEQ ID NO: 579) |

TABLE 2-continued

| Clone ID | Heavy Chain CDR 1 | Heavy Chain CDR 2 | Heavy Chain CDR 3 | Light Chain CDR 1 | Light Chain CDR 2 | Light Chain CDR 3 |
|---|---|---|---|---|---|---|
| YU393-G08 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU393-G11 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU393-G12 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU393-H03 | GGSISSSN W (SEQ ID NO: 284) | IYHSGST (SEQ ID NO: 365) | ARDLMNYGMDV (SEQ ID NO: 87) | QSISSY (SEQ ID NO: 567) | AAS (SEQ ID NO: 49) | QQSYSTP PT (SEQ ID NO: 534) |
| YU393-H07 | GFTFSSYA (SEQ ID NO: 273) | ISYDGSNK (SEQ ID NO: 362) | ARDLLGSGYDIIDY (SEQ ID NO: 86) | NIGSKS (SEQ ID NO: 456) | DDS (SEQ ID NO: 159) | QVWDSS SDHVV (SEQ ID NO: 610) |
| YU393-H09 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU394-A01 | GFTFSSYW (SEQ ID NO: 277) | IKQDGSEK (SEQ ID NO: 328) | AREYDYGDYVFDY (SEQ ID NO: 107) | NSNVGNN Y (SEQ ID NO: 465) | DND (SEQ ID NO: 188) | GSWEAR ESVFV (SEQ ID NO: 290) |
| YU394-A02 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU394-A07 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU394-A09 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTP PT (SEQ ID NO: 534) |
| YU394-C01 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU394-E02 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU394-H01 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU394-H03 | GYSFTSYW (SEQ ID NO: 299) | IYPGDSDT (SEQ ID NO: 377) | ARLENNWNYGGW FDP (SEQ ID NO: 128) | NIGSKS (SEQ ID NO: 456) | DDS (SEQ ID NO: 159) | QVWDSS SDHWV (SEQ ID NO: 611) |

TABLE 2-continued

| Clone ID | Heavy Chain CDR 1 | Heavy Chain CDR 2 | Heavy Chain CDR 3 | Light Chain CDR 1 | Light Chain CDR 2 | Light Chain CDR 3 |
|---|---|---|---|---|---|---|
| YU394-H04 | GYSFTSYW (SEQ ID NO: 299) | IYPGDSDT (SEQ ID NO: 377) | ARLENNWDYGGW FDP (SEQ ID NO: 127) | NIGSKS (SEQ ID NO: 456) | DDS (SEQ ID NO: 159) | QVWDSS SDHWV (SEQ ID NO: 611) |
| YU394-H05 | GYSFTSYW (SEQ ID NO: 299) | IYPGDSDT (SEQ ID NO: 377) | ARLENNWNYGGW FDP (SEQ ID NO: 128) | NIGSKS (SEQ ID NO: 456) | DDS (SEQ ID NO: 159) | QVWDSS SDHWV (SEQ ID NO: 611) |
| YU394-H07 | GGTFSSYA (SEQ ID NO: 286) | IIPIFGTA (SEQ ID NO: 326) | ARDYYYYGMDV (SEQ ID NO: 101) | QSISRY (SEQ ID NO: 564) | GAS (SEQ ID NO: 260) | QQTYND PPT (SEQ ID NO: 539) |
| YU395-A02 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTP PT (SEQ ID NO: 534) |
| YU395-B12 | GYTFTSYG (SEQ ID NO: 312) | ISAYNGNT (SEQ ID NO: 346) | ARDIGYYYGMDV (SEQ ID NO: 80) | SLRSYY (SEQ ID NO: 643) | GKN (SEQ ID NO: 287) | NSRDSSG NHVV (SEQ ID NO: 466) |
| YU395-C06 | GGTFSSYA (SEQ ID NO: 286) | IIPIFGTA (SEQ ID NO: 326) | AREMYYYYGMDV (SEQ ID NO: 103) | QSISNY (SEQ ID NO: 563) | AAS (SEQ ID NO: 49) | QQSYSTP PT (SEQ ID NO: 534) |
| YU395-C08 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTP PT (SEQ ID NO: 534) |
| YU395-D05 | GGTFSSYA (SEQ ID NO: 286) | IIPIFGTA (SEQ ID NO: 326) | AREMYYYYGMDV (SEQ ID NO: 103) | QSISNY (SEQ ID NO: 563) | AAS (SEQ ID NO: 49) | QQSYSTP PT (SEQ ID NO: 534) |
| YU396-B12 | GYSFSTYW (SEQ ID NO: 298) | IYPGDSDT (SEQ ID NO: 377) | ARVGDGYSLDY (SEQ ID NO: 135) | KLGERF (SEQ ID NO: 405) | QYI (SEQ ID NO: 616) | QTWDGSI VV (SEQ ID NO: 583) |
| YU396-C03 | GFTFSSYG (SEQ ID NO: 275) | ISYDGSNK (SEQ ID NO: 362) | AKAITSIEPY (SEQ ID NO: 60) | SGSVSTSY Y (SEQ ID NO: 641) | NTD (SEQ ID NO: 467) | VLYMGS GIWV (SEQ ID NO: 694) |
| YU396-C12 | GYSFSTYW (SEQ ID NO: 298) | IYPGDSDT (SEQ ID NO: 377) | ARVGDGYSLDY (SEQ ID NO: 135) | SSNIGRNY (SEQ ID NO: 652) | RNH (SEQ ID NO: 633) | ATWDDA LSGWV (SEQ ID NO: 149) |
| YU396-G10 | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTP PT (SEQ ID NO: 534) |
| YU396-H12 | GFAFSSYG (SEQ ID NO: 262) | ISYDGSNK (SEQ ID NO: 362) | AKGQGDGMDV (SEQ ID NO: 66) | SSDVGGY NY (SEQ ID NO: 649) | GVS (SEQ ID NO: 295) | SSYTSSS TLVV (SEQ ID NO: 660) |
| YU397-A01 | GYKFANY W (SEQ ID NO: 296) | IYPGDSDT (SEQ ID NO: 377) | ARLGWGMDV (SEQ ID NO: 129) | QSISSY (SEQ ID NO: 567) | AAS (SEQ ID NO: 49) | QQSYSTP WT (SEQ ID NO: 535) |
| YU397-A02 | GYTFKNFG (SEQ ID NO: 301) | ISGRKGNT (SEQ ID NO: 347) | ARVWGDTTLGYG MDV (SEQ ID NO: 141) | QDISNY (SEQ ID NO: 485) | DAS (SEQ ID NO: 157) | QQYDNL PLT (SEQ ID NO: 542) |

TABLE 2-continued

| Clone ID | Heavy Chain CDR 1 | Heavy Chain CDR 2 | Heavy Chain CDR 3 | Light Chain CDR 1 | Light Chain CDR 2 | Light Chain CDR 3 |
|---|---|---|---|---|---|---|
| YU397-A03 | GFTFSSYE (SEQ ID NO: 274) | ISSSGSTI (SEQ ID NO: 351) | ARRRGGGFDY SEQ ID NO: 132) | SSDVGGY NY (SEQ ID NO: 649) | DVS (SEQ ID NO: 201) | SSYTSSS TWV (SEQ ID NO: 663) |
| YU397-B01 | GYSFTSYW (SEQ ID NO: 299) | IYPGDSDT (SEQ ID NO: 377) | AIPWDAELGNYGM DV (SEQ ID NO: 59) | QSISSY (SEQ ID NO: 567) | AAS (SEQ ID NO: 49) | LQDYNY PPA (SEQ ID NO: 422) |
| YU397-B02 | GGTFSSYA (SEQ ID NO: 286) | IIPIFGTA (SEQ ID NO: 326) | ARGRWSGLGDY (SEQ ID NO: 113) | EDIRMY (SEQ ID NO: 215) | EGS (SEQ ID NO: 219) | QQYYDD PQ (SEQ ID NO: 555) |
| YU397-D01 | GGSISSSN W (SEQ ID NO: 284) | IYHSGST (SEQ ID NO: 365) | ARARGGRYFDY (SEQ ID NO: 72) | QGISTY (SEQ ID NO: 490) | AAS (SEQ ID NO: 49) | QQLNGY PTT (SEQ ID NO: 525) |
| YU398-A11 | GFTFSSYG (SEQ ID NO: 275) | ISYDGSNK (SEQ ID NO: 362) | AKGQGDGMDV (SEQ ID NO: 66) | SSNVGSRT (SEQ ID NO: 657) | SNN (SEQ ID NO: 644) | AAWDDS LIGHV (SEQ ID NO: 51) |
| YU398-E10 | GFTFSSYS (SEQ ID NO: 276) | ISSSSSYI (SEQ ID NO: 352) | ARDQLAARRGYYY GMDV (SEQ ID NO: 89) | NIGTKS (SEQ ID NO: 459) | DDS (SEQ ID NO: 159) | QVWDSS SDHVV (SEQ ID NO: 610) |
| YU400-A05 | GFTFSSYG (SEQ ID NO: 275) | ISYDGSNK (SEQ ID NO: 362) | AKGDVNYGMDV (SEQ ID NO: 65) | NIGSKT (SEQ ID NO: 457) | DGR (SEQ ID NO: 162) | QVWDTS GDLHWA (SEQ ID NO: 614) |
| YU400-A12 | GGSISSSN W (SEQ ID NO: 284) | IYHSGST (SEQ ID NO: 365) | ARDFYYGSGSYPN GYYYGMDV (SEQ ID NO: 77) | QSINSY (SEQ ID NO: 562) | TAS (SEQ ID NO: 667) | QQSYTTP LT (SEQ ID NO: 537) |
| YU400-B07 | GFTFSSYG (SEQ ID NO: 275) | ISYDGSNK (SEQ ID NO: 362) | AKGDVNYGMDV (SEQ ID NO: 65) | NIGSKS (SEQ ID NO: 456) | DDT (SEQ ID NO: 160) | QVWDSS SDLLWV (SEQ ID NO: 612) |
| YU400-D09 | GGTFSSYA (SEQ ID NO: 286) | IIPIFGTA (SEQ ID NO: 326) | ARDFNPFSITIFEMD V (SEQ ID NO: 74) | SSNIGNNY (SEQ ID NO: 651) | DNN (SEQ ID NO: 190) | GTWDSS LSALV (SEQ ID NO: 292) |
| YU400-F07 | GFTFSSYG (SEQ ID NO: 275) | ISYDGSNK (SEQ ID NO: 362) | AKGDVNYGMDV (SEQ ID NO: 65) | NIGSKT (SEQ ID NO: 457) | DGR (SEQ ID NO: 162) | QVWDTS GDLHWA (SEQ ID NO: 614) |
| YU400-H08 | GFTFSSYG (SEQ ID NO: 275) | ISYDGSNK (SEQ ID NO: 362) | AKGDVNYGMDV (SEQ ID NO: 65) | NIGSKT (SEQ ID NO: 457) | DGR (SEQ ID NO: 162) | QVWDTS GDLHWA (SEQ ID NO: 614) |
| YU401-A11 | GFTFSSYG (SEQ ID NO: 275) | ISYDGSNK (SEQ ID NO: 362) | ANLAMGQYFDY (SEQ ID NO: 70) | SSNIGSNT (SEQ ID NO: 654) | SNN (SEQ ID NO: 644) | AAWDDS LNGPV (SEQ ID NO: 52) |
| YU401-B01 | GGTFSSYA (SEQ ID NO: 286) | IIPIFGTA (SEQ ID NO: 326) | AREMYYYYGMDV (SEQ ID NO: 103) | QSIITY (SEQ ID NO: 560) | AAS (SEQ ID NO: 49) | QQSYSTP PT (SEQ ID NO: 534) |
| YU401-D11 | GFTFSSYG (SEQ ID NO: 275) | ISYDGSNK (SEQ ID NO: 362) | ANLAMGQYFDY (SEQ ID NO: 70) | SSNIGSNT (SEQ ID NO: 654) | SNN (SEQ ID NO: 644) | AAWDDS LNGPV (SEQ ID NO: 52) |

TABLE 2-continued

| Clone ID | Heavy Chain CDR 1 | Heavy Chain CDR 2 | Heavy Chain CDR 3 | Light Chain CDR 1 | Light Chain CDR 2 | Light Chain CDR 3 |
|---|---|---|---|---|---|---|
| YU401-E11 | GFTFSSYA (SEQ ID NO: 273) | ISYDGSNK (SEQ ID NO: 362) | ARDLGEAKSSSPHE PDY (SEQ ID NO: 84) | QSLLHSD GKTY (SEQ ID NO: 570) | EVS (SEQ ID NO: 237) | MQTKQL PLT (SEQ ID NO: 443) |
| YU401-F11 | GFTFSSYA (SEQ ID NO: 273) | ISYDGSNK (SEQ ID NO: 362) | ARDLGEAKSSSPHE PDY (SEQ ID NO: 84) | QSLLHSD GKTY (SEQ ID NO: 570) | EVS (SEQ ID NO: 237) | MQTKQL PLT (SEQ ID NO: 443) |
| YU401-G07 | GFTFSSYG (SEQ ID NO: 275) | ISYDGSNK (SEQ ID NO: 362) | AKGDVNYGMDV (SEQ ID NO: 65) | NIGSKT (SEQ ID NO: 457) | DGR (SEQ ID NO: 162) | QVWDTS GDLHWA (SEQ ID NO: 614) |
| YU402-A02 | GDSISSSSY Y (SEQ ID NO: 261) | INHSGST (SEQ ID NO: 333) | ARDQEMYYFDY (SEQ ID NO: 88) | QGISSW (SEQ ID NO: 489) | AAS (SEQ ID NO: 49) | QQANSFP PT (SEQ ID NO: 515) |
| YU402-A11 | GGSISRSN W (SEQ ID NO: 281) | IYHTGST (SEQ ID NO: 366) | ARGKGSYAFDI (SEQ ID NO: 110) | GGNIARN Y (SEQ ID NO: 279) | EDD (SEQ ID NO: 214) | QSYDGN NHMV (SEQ ID NO: 578) |
| YU402-D10 | GFTFSSYG (SEQ ID NO: 275) | ISYDGNNK (SEQ ID NO: 360) | AKGYSSSPGDY (SEQ ID NO: 67) | SSDVGAY NY (SEQ ID NO: 647) | DVS (SEQ ID NO: 201) | SSYTSSS TLWV (SEQ ID NO: 661) |
| YU403-G05 | GGSISRSN W (SEQ ID NO: 281) | IYHTGST (SEQ ID NO: 366) | ARGKGSYAFDI (SEQ ID NO: 110) | GGNIARN Y (SEQ ID NO: 279) | EDD (SEQ ID NO: 214) | QSYDGN NHMV (SEQ ID NO: 578) |

In some embodiments, the CDR-H1 is selected from: GGTFSSYA (SEQ ID NO: 286), GGSISSGGYY (SEQ ID NO: 283), GFTFSSYG (SEQ ID NO: 275), GYTFTSYY (SEQ ID NO: 313), GYTFTSYG (SEQ ID NO: 312), GYTFTDYY (SEQ ID NO: 306), GGSISSGGYS (SEQ ID NO: 282), GGSISSSNW (SEQ ID NO: 284), GYSFTSYW (SEQ ID NO: 299), GFTFSNYG (SEQ ID NO: 271), GFTFSSSA (SEQ ID NO: 272), GFTFSSYW (SEQ ID NO: 277), GFIFSRHA (SEQ ID NO: 264), GYTFNNYG (SEQ ID NO: 302), GFTFSSYA (SEQ ID NO: 273), GYTFTTYA (SEQ ID NO: 314), GFTFNNAW (SEQ ID NO: 267), GFTFSSYE (SEQ ID NO: 274), GYSFTTYW (SEQ ID NO: 300), GYSFNTYW (SEQ ID NO: 297), GFTFRRYW (SEQ ID NO: 268), GYSFSTYW (SEQ ID NO: 298), GFAFSSYG (SEQ ID NO: 262), GYKFANYW (SEQ ID NO: 296), GYTFKNFG (SEQ ID NO: 301), GFTFSSYS (SEQ ID NO: 276), GDSISSSSYY (SEQ ID NO: 261), and GGSISRSNW (SEQ ID NO: 281);

In some embodiments, the CDR-H2 is selected from: IIPIFGTA (SEQ ID NO: 326), IIPIFGTA (SEQ ID NO: 326), IYYSGST (SEQ ID NO: 384), ISYDGSNK (SEQ ID NO: 362), INPSGGST (SEQ ID NO: 339), ISAYNGNT (SEQ ID NO: 346), IMPIFDTA (SEQ ID NO: 332), VDPEDGET (SEQ ID NO: 693), IYHSGST (SEQ ID NO: 365), IYPGDSDT (SEQ ID NO: 377), ISHDGHVK (SEQ ID NO: 349), IKQDGSEK (SEQ ID NO: 328), ISVYNGDI (SEQ ID NO: 359), INTNTGDP (SEQ ID NO: 344), IKSKTDGGTT (SEQ ID NO: 330), ISSSGSTI (SEQ ID NO: 351), ISSRGSTI (SEQ ID NO: 350), IYPSDSDT (SEQ ID NO: 383), ISGRKGNT (SEQ ID NO: 347), ISSSSSYI (SEQ ID NO: 352), INHSGST (SEQ ID NO: 333), IYHTGST (SEQ ID NO: 366), and ISYDGNNK (SEQ ID NO: 360);

In some embodiments, the CDR-H3 is selected from: AREMYYYYGMDV (SEQ ID NO: 103), ARE-MYYYYGMDV (SEQ ID NO: 103), ARGNLWSGYYF (SEQ ID NO: 111), AKELLEGAFDI (SEQ ID NO: 64), ARDRVTMVRGALAY (SEQ ID NO: 97), ARERSYYGMDV (SEQ ID NO: 105), ASWSERI-GYQYGLDV (SEQ ID NO: 145), ARDILGLDY (SEQ ID NO: 81), ATEDTAMGGIDY (SEQ ID NO: 146), ATEGRYGMDV (SEQ ID NO: 147), AVEG-GRAPGTYYYDSSGLAY (SEQ ID NO: 153), ARAGYYYGMDV (SEQ ID NO: 71), ARDLGTMVRGVIEPYYFDY (SEQ ID NO: 85), ARGVRGTGFDP (SEQ ID NO: 118), ARDRNGYFQH (SEQ ID NO: 94), AKDLLGELSFFDY (SEQ ID NO: 61), ARLENNWDYGGWFDP (SEQ ID NO: 127), ARDRSYYGMDV (SEQ ID NO: 96), ARDKGYYGMDV (SEQ ID NO: 83), AKEISPRSSVGWPLDY (SEQ ID NO: 63), ARDFWSGYNELGGMDV (SEQ ID NO: 76), ARTWFGEFFDY (SEQ ID NO: 134), ARVIGGWFDP (SEQ ID NO: 136), ARGRLAYGDTEGFDY (SEQ ID NO: 112), ARDILRGESSILDH (SEQ ID NO: 82), ARDRYYYGMDV (SEQ ID NO: 98), ARDLLGSGYDI-IDY (SEQ ID NO: 86), ARVWGKNGDFDY (SEQ ID NO: 142), ARDRFHYGMDV (SEQ ID NO: 90), ARDRGDY (SEQ ID NO: 92), TTEGVELLSFGGAPFDY (SEQ ID NO: 683), ARRRGGGFDY (SEQ ID NO: 132), AREKGSWFDP (SEQ ID NO: 102), ARDRGDRVGGLVFDY (SEQ ID NO: 91), ARQVAGGLDY (SEQ ID NO: 131), ARDR-GYYGMDV (SEQ ID NO: 93), FRFGEGFDY (SEQ ID NO: 259), ARDGGYYFDD (SEQ ID NO: 79), ARD-FRMDV (SEQ ID NO: 75), ARDAYAYGLDV (SEQ ID NO: 73), ARDLMNYGMDV (SEQ ID NO: 87), AREY- DYGDYVFDY (SEQ ID NO: 107), ARLENNWNYGGWFDP (SEQ ID NO: 128), ARDYYYYGMDV (SEQ ID NO: 101), ARDIGYYYGMDV (SEQ ID NO: 80), ARVGDGYSLDY (SEQ ID NO: 135), AKAITSIEPY (SEQ ID NO: 60), AKGQGDGMDV (SEQ ID NO: 66), ARLGWGMDV (SEQ ID NO: 129), ARVWGDTTLGYGMDV (SEQ ID NO: 141), AIPWDAELGNYGMDV (SEQ ID NO: 59), ARGRWSGLGDY (SEQ ID NO: 113), ARARGGRYFDY (SEQ ID NO: 72), ARDQLAARRGYYYGMDV (SEQ ID NO: 89), AKGDVNYGMDV (SEQ ID NO: 65), ARDFYYGSGSYPNGYYYGMDV (SEQ ID NO: 77), ARDFNPFSITIFEMDV (SEQ ID NO: 74), ANLAMGQYFDY (SEQ ID NO: 70), ARDLGEAKSSSPHEPDY (SEQ ID NO: 84), ARDQEMYYFDY (SEQ ID NO: 88), ARGKGSYAFDI (SEQ ID NO: 110), and AKGYSSSPGDY (SEQ ID NO: 67);

In some embodiments, the CDR-L1 is selected from: QSISSY (SEQ ID NO: 567), QSISSY (SEQ ID NO: 567), SSNIGNNF (SEQ ID NO: 650), QSISNY (SEQ ID NO: 563), NIETKS (SEQ ID NO: 455), KLGDKY (SEQ ID NO: 404), QSVSNY (SEQ ID NO: 574), QTISQW (SEQ ID NO: 582), SSNIGSNY (SEQ ID NO: 655), NFNIGNNL (SEQ ID NO: 453), RNIWSY (SEQ ID NO: 634), QSISSW (SEQ ID NO: 566), QSVSSR (SEQ ID NO: 576), QTISGL (SEQ ID NO: 581), DIESEM (SEQ ID NO: 163), NIGSKS (SEQ ID NO: 456), QSIGNY (SEQ ID NO: 558), QGISSW (SEQ ID NO: 489), QSVSSTY (SEQ ID NO: 577), QDISNY (SEQ ID NO: 485), NIESES (SEQ ID NO: 454), SSDVGAYNY (SEQ ID NO: 647), QDINNY (SEQ ID NO: 482), QGISNS (SEQ ID NO: 488), SSNIGNNY (SEQ ID NO: 651), EGIRTS (SEQ ID NO: 218), QGTSSW (SEQ ID NO: 491), SSDVGGYNY (SEQ ID NO: 649), QSVSNNY (SEQ ID NO: 573), QGINSY (SEQ ID NO: 487), QAVRID (SEQ ID NO: 472), QSISRY (SEQ ID NO: 564), QSIGYW (SEQ ID NO: 559), SSNVGSNY (SEQ ID NO: 656), QSIKNY (SEQ ID NO: 561), QDIKRR (SEQ ID NO: 480), SGSIASSY (SEQ ID NO: 640), NSNVGNNY (SEQ ID NO: 465), SLRSYY (SEQ ID NO: 643), KLGERF (SEQ ID NO: 405), SGSVSTSYY (SEQ ID NO: 641), SSNIGRNY (SEQ ID NO: 652), EDIRMY (SEQ ID NO: 215), QGISTY (SEQ ID NO: 490), SSNVGSRT (SEQ ID NO: 657), NIGTKS (SEQ ID NO: 459), NIGSKT (SEQ ID NO: 457), QSINSY (SEQ ID NO: 562), SSNIGSNT (SEQ ID NO: 654), QSIITY (SEQ ID NO: 560), QSLLHSDGKTY (SEQ ID NO: 570), and GGNIARNY (SEQ ID NO: 279).

In some embodiments, the CDR-L2 is selected from: AAS (SEQ ID NO: 49), AAS (SEQ ID NO: 49), DST (SEQ ID NO: 191), DDD (SEQ ID NO: 158), KDN (SEQ ID NO: 386), GAS (SEQ ID NO: 260), KAS (SEQ ID NO: 385), RNN (SEQ ID NO: 635), SNN (SEQ ID NO: 644), AND (SEQ ID NO: 69), DAF (SEQ ID NO: 156), DDS (SEQ ID NO: 159), AAT (SEQ ID NO: 50), AVS (SEQ ID NO: 154), DAS (SEQ ID NO: 157), GVS (SEQ ID NO: 295), DNN (SEQ ID NO: 190), DVS (SEQ ID NO: 201), RAS (SEQ ID NO: 619), GTS (SEQ ID NO: 291), EDN (SEQ ID NO: 216), DND (SEQ ID NO: 188), GKN (SEQ ID NO: 287), QYI (SEQ ID NO: 616), NTD (SEQ ID NO: 467), RNH (SEQ ID NO: 633), EGS (SEQ ID NO: 219), DGR (SEQ ID NO: 162), TAS (SEQ ID NO: 667), DDT (SEQ ID NO: 160), EVS (SEQ ID NO: 237), and EDD (SEQ ID NO: 214).

In some embodiments, the CDR-L3 is selected from: QQSYSTPPT (SEQ ID NO: 534), QQSYSTPPT (SEQ ID NO: 534), GSWDTNLSGYV (SEQ ID NO: 289), QVWDSSSGHREV (SEQ ID NO: 613), QAWDSSTYV (SEQ ID NO: 473), QQYNHWPPL (SEQ ID NO: 544), QQYSGDSMYT (SEQ ID NO: 553), AAWDDSLSGVV (SEQ ID NO: 56), AAWDDSLNGVV (SEQ ID NO: 53), ATWDDSLSGVV (SEQ ID NO: 151), QQSHSTPIT (SEQ ID NO: 526), QQYNSYSRT (SEQ ID NO: 551), QQYTNWPQT (SEQ ID NO: 554), LQYDRYSGA (SEQ ID NO: 426), QVWHTTNDHVL (SEQ ID NO: 615), QVWDSSSDHWV (SEQ ID NO: 611), QQSKQIPYT (SEQ ID NO: 528), QQSYSLPLT (SEQ ID NO: 531), QQFDISGGLI (SEQ ID NO: 518), QQYDNLPLT (SEQ ID NO: 542), QVWDSSSDHTVA (SEQ ID NO: 609), SSYTTTDTFV (SEQ ID NO: 665), QQYDNLPYT (SEQ ID NO: 543), QQYYSTPPH (SEQ ID NO: 556), QQSYSTPLT (SEQ ID NO: 532), QVWDSSSDHVV (SEQ ID NO: 610), GTWDSSLSAYV (SEQ ID NO: 294), QQTHTWPWT (SEQ ID NO: 538), QQANSFPLT (SEQ ID NO: 514), QQSYSTPYT (SEQ ID NO: 536), SSYTSSSTYV (SEQ ID NO: 664), QRYGSSPR (SEQ ID NO: 557), QQVHSFPFT (SEQ ID NO: 541), LQHNTFPYT (SEQ ID NO: 423), QQSHSTPLT (SEQ ID NO: 527), QQYNSYPFT (SEQ ID NO: 548), QQYNSSPLMYT (SEQ ID NO: 547), QQTYSTPLT (SEQ ID NO: 540), QQANTFPQT (SEQ ID NO: 516), QSYDGSSVV (SEQ ID NO: 579), GSWEARESVFV (SEQ ID NO: 290), QQTYNDPPT (SEQ ID NO: 539), NSRDSSGNHVV (SEQ ID NO: 466), QTWDGSIVV (SEQ ID NO: 583), VLYMGSGIWV (SEQ ID NO: 694), ATWDDALSGWV (SEQ ID NO: 149), SSYTSSSTLVV (SEQ ID NO: 660), QQSYSTPWT (SEQ ID NO: 535), SSYTSSSTWV (SEQ ID NO: 663), LQDYNYPPA (SEQ ID NO: 422), QQYYDDPQ (SEQ ID NO: 555), QQLNGYPTT (SEQ ID NO: 525), AAWDDSLIGHV (SEQ ID NO: 51), QVWDTSGDLHWA (SEQ ID NO: 614), QQSYTTPLT (SEQ ID NO: 537), QVWDSSSDLLWV (SEQ ID NO: 612), GTWDSSLSALV (SEQ ID NO: 292), AAWDDSLNGPV (SEQ ID NO: 52), MQTKQLPLT (SEQ ID NO: 443), QQANSFPPT (SEQ ID NO: 515), QSYDGNNHMV (SEQ ID NO: 578), and SSYTSSSTLWV (SEQ ID NO: 661).

In some embodiments, the antibody has a CDR-H1, CDR-H2, CDR-H3, CDR-L1, CDR-L2, and CDR-L3, each independently selected from those disclosed in Table 3 Å and Table 3B. It is possible to combine the CDRs from different antibodies in any combination to generate new antibodies. Gene synthesis and high-throughput screening technologies enable the skilled person to test all combinations of six CDRs without undue experimentation.

TABLE 3A

| VH_CDR1 | VH_CDR2 | VH_CDR3 |
|---|---|---|
| GGTFSSYA (SEQ ID NO: 286) | IIPIFGTA (SEQ ID NO: 326) | AREMYYYYGMDV (SEQ ID NO: 103) |
| GGTFSSYA (SEQ ID NO: 286) | IIPIFGTA (SEQ ID NO: 326) | AREMYYYYGMDV (SEQ ID NO: 103) |
| GGSISSGGYY (SEQ ID NO: 283) | IYYSGST (SEQ ID NO: 384) | ARGNLWSGYYF (SEQ ID NO: 111) |

TABLE 3A-continued

| VH_CDR1 | VH_CDR2 | VH_CDR3 |
|---|---|---|
| GGTFSSYA (SEQ ID NO: 286) | IIPIFGTA (SEQ ID NO: 326) | AREMYYYYGMDV (SEQ ID NO: 103) |
| GGTFSSYA (SEQ ID NO: 286) | IIPIFGTA (SEQ ID NO: 326) | AREMYYYYGMDV (SEQ ID NO: 103) |
| GGTFSSYA (SEQ ID NO: 286) | IIPIFGTA (SEQ ID NO: 326) | AREMYYYYGMDV (SEQ ID NO: 103) |
| GGTFSSYA (SEQ ID NO: 286) | IIPIFGTA (SEQ ID NO: 326) | AREMYYYYGMDV (SEQ ID NO: 103) |
| GFTFSSYG (SEQ ID NO: 275) | ISYDGSNK (SEQ ID NO: 362) | AKELLEGAFDI (SEQ ID NO: 64) |
| GYTFTSYY (SEQ ID NO: 313) | INPSGGST (SEQ ID NO: 339) | ARDRVTMVRGALAY (SEQ ID NO: 97) |
| GFTFSSYG (SEQ ID NO: 275) | ISYDGSNK (SEQ ID NO: 362) | AKELLEGAFDI (SEQ ID NO: 64) |
| GGTFSSYA (SEQ ID NO: 286) | IIPIFGTA (SEQ ID NO: 326) | AREMYYYYGMDV (SEQ ID NO: 103) |
| GYTFTSYG (SEQ ID NO: 312) | ISAYNGNT (SEQ ID NO: 346) | ARERSYYGMDV (SEQ ID NO: 105) |
| GGTFSSYA (SEQ ID NO: 286) | IIPIFGTA (SEQ ID NO: 326) | AREMYYYYGMDV (SEQ ID NO: 103) |
| GGTFSSYA (SEQ ID NO: 286) | IMPIFDTA (SEQ ID NO: 332) | ASWSERIGYQYGLDV (SEQ ID NO: 145) |
| GGTFSSYA (SEQ ID NO: 286) | IIPIFGTA (SEQ ID NO: 326) | AREMYYYYGMDV (SEQ ID NO: 103) |
| GYTFTSYG (SEQ ID NO: 312) | ISAYNGNT (SEQ ID NO: 346) | ARERSYYGMDV (SEQ ID NO: 105) |
| GGTFSSYA (SEQ ID NO: 286) | IIPIFGTA (SEQ ID NO: 326) | AREMYYYYGMDV (SEQ ID NO: 103) |
| GYTFTSYG (SEQ ID NO: 312) | ISAYNGNT (SEQ ID NO: 346) | ARERSYYGMDV (SEQ ID NO: 105) |
| GGTFSSYA (SEQ ID NO: 286) | IIPIFGTA (SEQ ID NO: 326) | AREMYYYYGMDV (SEQ ID NO: 103) |
| GGTFSSYA (SEQ ID NO: 286) | IIPIFGTA (SEQ ID NO: 326) | AREMYYYYGMDV (SEQ ID NO: 103) |
| GYTFTSYY (SEQ ID NO: 313) | INPSGGST (SEQ ID NO: 339) | ARDILGLDY (SEQ ID NO: 81) |
| GYSFTSYW (SEQ ID NO: 299) | IYPGDSDT (SEQ ID NO: 377) | ARLENNWDYGGWFDP (SEQ ID NO: 127) |
| GYTFTDYY (SEQ ID NO: 306) | VDPEDGET (SEQ ID NO: 693) | ATEDTAMGGIDY (SEQ ID NO: 146) |
| GYTFTDYY (SEQ ID NO: 306) | VDPEDGET (SEQ ID NO: 693) | ATEGRYGMDV (SEQ ID NO: 147) |
| GYTFTDYY (SEQ ID NO: 306) | VDPEDGET (SEQ ID NO: 693) | AVEGGRAPGTYYYDSSGLAY (SEQ ID NO: 153) |
| GGTFSSYA (SEQ ID NO: 286) | IIPIFGTA (SEQ ID NO: 326) | AREMYYYYGMDV (SEQ ID NO: 103) |
| GGSISSSNW (SEQ ID NO: 284) | IYHSGST (SEQ ID NO: 365) | ARGVIAAAGTYFDY (SEQ ID NO: 116) |
| GGSISSSNW (SEQ ID NO: 284) | IYHSGST (SEQ ID NO: 365) | ARERTHYYYGMDI (SEQ ID NO: 106) |
| GYSFTSYW (SEQ ID NO: 299) | IYPGDSDT (SEQ ID NO: 377) | ARLENNWDYGGWFDP (SEQ ID NO: 127) |

TABLE 3A-continued

| VH_CDR1 | VH_CDR2 | VH_CDR3 |
|---|---|---|
| GGTFSSYA (SEQ ID NO: 286) | IIPIFGTA (SEQ ID NO: 326) | ARDGAGNYDILTGDRSEDYYYYYGMDV (SEQ ID NO: 78) |
| GGSISSGGYS (SEQ ID NO: 282) | IYHSGST (SEQ ID NO: 365) | ARAGYYYGMDV (SEQ ID NO: 71) |
| GGSISSGGYY (SEQ ID NO: 283) | IYYSGST (SEQ ID NO: 384) | ARDSSSGPYGMDV (SEQ ID NO: 100) |
| GGSISSSNW (SEQ ID NO: 284) | IYHSGST (SEQ ID NO: 365) | ARVNYGDYDWYFDL (SEQ ID NO: 137) |
| GGTFSSYA (SEQ ID NO: 286) | IIPIFGTA (SEQ ID NO: 326) | ARDLGTMVRGVIEPYYFDY (SEQ ID NO: 85) |
| GGSISSSNW (SEQ ID NO: 284) | IYHSGST (SEQ ID NO: 365) | ARGVRGTGFDP (SEQ ID NO: 118) |
| GYTFTSYG (SEQ ID NO: 312) | ISAYNGNT (SEQ ID NO: 346) | ARDRNGYFQH (SEQ ID NO: 94) |
| GFTFSSYG (SEQ ID NO: 275) | ISYDGSNK (SEQ ID NO: 362) | AKDLLGELSFFDY (SEQ ID NO: 61) |
| GYSFTSYW (SEQ ID NO: 299) | IYPGDSDT (SEQ ID NO: 377) | ARLENNWDYGGWFDP (SEQ ID NO: 127) |
| GGTFSSYA (SEQ ID NO: 286) | IIPIFGTA (SEQ ID NO: 326) | ARDRSYYGMDV (SEQ ID NO: 96) |
| GGTFSSYA (SEQ ID NO: 286) | IIPIFGTA (SEQ ID NO: 326) | ARDKGYYGMDV (SEQ ID NO: 83) |
| GGTFSSYA (SEQ ID NO: 286) | IIPIFGTA (SEQ ID NO: 326) | ARDRSYYGMDV (SEQ ID NO: 96) |
| GFTFSNYG (SEQ ID NO: 271) | ISHDGHVK (SEQ ID NO: 349) | AKEISPRSSVGWPLDY (SEQ ID NO: 63) |
| GFTFSSSA (SEQ ID NO: 272) | ISYDGSNK (SEQ ID NO: 362) | ARDFWSGYNELGGMDV (SEQ ID NO: 76) |
| GFTFSSYW (SEQ ID NO: 277) | IKQDGSEK (SEQ ID NO: 328) | ARTWFGEFFDY (SEQ ID NO: 134) |
| GYTFTSYG (SEQ ID NO: 312) | ISAYNGNT (SEQ ID NO: 346) | ARVIGGWFDP (SEQ ID NO: 136) |
| GFIFSRHA (SEQ ID NO: 264) | ISYDGSNK (SEQ ID NO: 362) | ARGRLAYGDTEGFDY (SEQ ID NO: 112) |
| GYTFNNYG (SEQ ID NO: 302) | ISVYNGDI (SEQ ID NO: 359) | ARDILRGESSILDH (SEQ ID NO: 82) |
| GGTFSSYA (SEQ ID NO: 286) | IIPIFGTA (SEQ ID NO: 326) | ARDRYYYGMDV (SEQ ID NO: 98) |
| GFTFSSYA (SEQ ID NO: 273) | ISYDGSNK (SEQ ID NO: 362) | ARDLLGSGYDIIDY (SEQ ID NO: 86) |
| GYTFTSYG (SEQ ID NO: 312) | ISAYNGNT (SEQ ID NO: 346) | ARVWGKNGDFDY (SEQ ID NO: 142) |
| GYTFTTYA (SEQ ID NO: 314) | INTNTGDP (SEQ ID NO: 344) | ARDRFHYGMDV (SEQ ID NO: 90) |
| GYTFTSYG (SEQ ID NO: 312) | ISAYNGNT (SEQ ID NO: 346) | ARDRGDY (SEQ ID NO: 92) |
| GFTFNNAW (SEQ ID NO: 267) | IKSKTDGGTT (SEQ ID NO: 330) | TTEGVELLSFGGAPFDY (SEQ ID NO: 683) |
| GFTFSSYE (SEQ ID NO: 274) | ISSSGSTI (SEQ ID NO: 351) | ARRRGGGFDY (SEQ ID NO: 132) |
| GFTFSSYW (SEQ ID NO: 277) | IKQDGSEK (SEQ ID NO: 328) | AREKGSWFDP (SEQ ID NO: 102) |

TABLE 3A-continued

| VH_CDR1 | VH_CDR2 | VH_CDR3 |
|---|---|---|
| GGTFSSYA (SEQ ID NO: 286) | IIPIFGTA (SEQ ID NO: 326) | ARDKGYYGMDV (SEQ ID NO: 83) |
| GFTFSSYG (SEQ ID NO: 275) | ISSRGSTI (SEQ ID NO: 350) | ARDRGDRVGGLVFDY (SEQ ID NO: 91) |
| GYSFTTYW (SEQ ID NO: 300) | IYPGDSDT (SEQ ID NO: 377) | ARQVAGGLDY (SEQ ID NO: 131) |
| GYTFTSYG (SEQ ID NO: 312) | ISAYNGNT (SEQ ID NO: 346) | ARDRGYYGMDV (SEQ ID NO: 93) |
| GYSFTSYW (SEQ ID NO: 299) | IYPGDSDT (SEQ ID NO: 377) | FRFGEGFDY (SEQ ID NO: 259) |
| GYSFTTYW (SEQ ID NO: 300) | IYPGDSDT (SEQ ID NO: 377) | ARQVAGGLDY (SEQ ID NO: 131) |
| GYSFNTYW (SEQ ID NO: 297) | IYPSDSDT (SEQ ID NO: 383) | ARDGGYYFDD (SEQ ID NO: 79) |
| GGTFSSYA (SEQ ID NO: 286) | IIPIFGTA (SEQ ID NO: 326) | ARDKGYYGMDV (SEQ ID NO: 83) |
| GYTFTSYG (SEQ ID NO: 312) | ISAYNGNT (SEQ ID NO: 346) | ARDFRMDV (SEQ ID NO: 75) |
| GFTFRRYW (SEQ ID NO: 268) | IKQDGSEK (SEQ ID NO: 328) | ARDAYAYGLDV (SEQ ID NO: 73) |
| GYSFTSYW (SEQ ID NO: 299) | IYPGDSDT (SEQ ID NO: 377) | ARLENNWDYGGWFDP (SEQ ID NO: 127) |
| GYSFTSYW (SEQ ID NO: 299) | IYPGDSDT (SEQ ID NO: 377) | ARLENNWDYGGWFDP (SEQ ID NO: 127) |
| GYSFTSYW (SEQ ID NO: 299) | IYPGDSDT (SEQ ID NO: 377) | ARLENNWDYGGWFDP (SEQ ID NO: 127) |
| GGSISSSNW (SEQ ID NO: 284) | IYHSGST (SEQ ID NO: 365) | ARDLMNYGMDV (SEQ ID NO: 87) |
| GFTFSSYA (SEQ ID NO: 273) | ISYDGSNK (SEQ ID NO: 362) | ARDLLGSGYDIIDY (SEQ ID NO: 86) |
| GYSFTSYW (SEQ ID NO: 299) | IYPGDSDT (SEQ ID NO: 377) | ARLENNWDYGGWFDP (SEQ ID NO: 127) |
| GFTFSSYW (SEQ ID NO: 277) | IKQDGSEK (SEQ ID NO: 328) | AREYDYGDYVFDY (SEQ ID NO: 107) |
| GYSFTSYW (SEQ ID NO: 299) | IYPGDSDT (SEQ ID NO: 377) | ARLENNWDYGGWFDP (SEQ ID NO: 127) |
| GYSFTSYW (SEQ ID NO: 299) | IYPGDSDT (SEQ ID NO: 377) | ARLENNWDYGGWFDP (SEQ ID NO: 127) |
| GYTFTGYY (SEQ ID NO: 307) | INPNSGDT (SEQ ID NO: 336) | AILEYSSSGAEYFQH (SEQ ID NO: 58) |
| GGTFSSYA (SEQ ID NO: 286) | IIPIFGTA (SEQ ID NO: 326) | AREMYYYYGMDV (SEQ ID NO: 103) |
| GYSFTSYW (SEQ ID NO: 299) | IYPGDSDT (SEQ ID NO: 377) | ARLENNWDYGGWFDP (SEQ ID NO: 127) |
| GYTFTTYA (SEQ ID NO: 314) | ISAYNGNT (SEQ ID NO: 346) | ARGGLGGDDAFDI (SEQ ID NO: 108) |
| GGTFSSYA (SEQ ID NO: 286) | ISAYNGNT (SEQ ID NO: 346) | AREPLRYYYYYGMDV (SEQ ID NO: 104) |
| GYSFTSYW (SEQ ID NO: 299) | IYPGDSDT (SEQ ID NO: 377) | ARLENNWDYGGWFDP (SEQ ID NO: 127) |
| GYSFTSYW (SEQ ID NO: 299) | IYPGDSDT (SEQ ID NO: 377) | ARLENNWDYGGWFDP (SEQ ID NO: 127) |

TABLE 3A-continued

| VH_CDR1 | VH_CDR2 | VH_CDR3 |
|---|---|---|
| GYSFTSYW (SEQ ID NO: 299) | IYPGDSDT (SEQ ID NO: 377) | ARLENNWNYGGWFDP (SEQ ID NO: 128) |
| GYSFTSYW (SEQ ID NO: 299) | IYPGDSDT (SEQ ID NO: 377) | ARLENNWDYGGWFDP (SEQ ID NO: 127) |
| GYSFTSYW (SEQ ID NO: 299) | IYPGDSDT (SEQ ID NO: 377) | ARLENNWNYGGWFDP (SEQ ID NO: 128) |
| GGTFSSYA (SEQ ID NO: 286) | IIPIFGTA (SEQ ID NO: 326) | ARDYYYYGMDV (SEQ ID NO: 101) |
| GGTFSSYA (SEQ ID NO: 286) | IIPIFGTA (SEQ ID NO: 326) | AREMYYYYGMDV (SEQ ID NO: 103) |
| GGSISSSSYY (SEQ ID NO: 285) | IYYSGST (SEQ ID NO: 384) | ARLSRYYYYGMDV (SEQ ID NO: 130) |
| GYTFTSYG (SEQ ID NO: 312) | ISAYNGNT (SEQ ID NO: 346) | ARDIGYYYGMDV (SEQ ID NO: 80) |
| GGTFSSYA (SEQ ID NO: 286) | IIPIFGTA (SEQ ID NO: 326) | AREMYYYYGMDV (SEQ ID NO: 103) |
| GGTFSSYA (SEQ ID NO: 286) | IIPIFGTA (SEQ ID NO: 326) | AREMYYYYGMDV (SEQ ID NO: 103) |
| GGTFSSYA (SEQ ID NO: 286) | IIPIFGTA (SEQ ID NO: 326) | AREMYYYYGMDV (SEQ ID NO: 103) |
| GFTFSNAW (SEQ ID NO: 270) | IKSKNDGGTT (SEQ ID NO: 329) | TTAPSLMDV (SEQ ID NO: 682) |
| GYSFSTYW (SEQ ID NO: 298) | IYPGDSDT (SEQ ID NO: 377) | ARVGDGYSLDY (SEQ ID NO: 135) |
| GFTFSSYG (SEQ ID NO: 275) | ISYDGSNK (SEQ ID NO: 362) | AKAITSIEPY (SEQ ID NO: 60) |
| GYSFSTYW (SEQ ID NO: 298) | IYPGDSDT (SEQ ID NO: 377) | ARVGDGYSLDY (SEQ ID NO: 135) |
| GGTFSSYA (SEQ ID NO: 286) | IIPIFGTA (SEQ ID NO: 326) | AREMYYYYGMDV (SEQ ID NO: 103) |
| GFTFSSYA (SEQ ID NO: 273) | ISGSGGST (SEQ ID NO: 348) | AKNPYSNYVYWFDP (SEQ ID NO: 68) |
| GFAFSSYG (SEQ ID NO: 262) | ISYDGSNK (SEQ ID NO: 362) | AKGQGDGMDV (SEQ ID NO: 66) |
| GYKFANYW (SEQ ID NO: 296) | IYPGDSDT (SEQ ID NO: 377) | ARLGWGMDV (SEQ ID NO: 129) |
| GYTFKNFG (SEQ ID NO: 301) | ISGRKGNT (SEQ ID NO: 347) | ARVWGDTTLGYGMDV (SEQ ID NO: 141) |
| GFTFSSYE (SEQ ID NO: 274) | ISSSGSTI (SEQ ID NO: 351) | ARRRGGGFDY (SEQ ID NO: 132) |
| GYSFTSYW (SEQ ID NO: 299) | IYPGDSDT (SEQ ID NO: 377) | AIPWDAELGNYGMDV (SEQ ID NO: 59) |
| GGTFSSYA (SEQ ID NO: 286) | IIPIFGTA (SEQ ID NO: 326) | ARGRWSGLGDY (SEQ ID NO: 113) |
| GGSISSSNW (SEQ ID NO: 284) | IYHSGST (SEQ ID NO: 365) | ARARGGRYFDY (SEQ ID NO: 72) |
| GFTFSSYG (SEQ ID NO: 275) | ISYDGSNK (SEQ ID NO: 362) | AKGQGDGMDV (SEQ ID NO: 66) |
| GFTFSSYS (SEQ ID NO: 276) | ISSSSSYI (SEQ ID NO: 352) | ARDQLAARRGYYYGMDV (SEQ ID NO: 89) |
| GFDFNWYG (SEQ ID NO: 263) | IWYDGSNE (SEQ ID NO: 363) | ARDRRGSGWYEYFDY (SEQ ID NO: 95) |

TABLE 3A-continued

| VH_CDR1 | VH_CDR2 | VH_CDR3 |
|---|---|---|
| GFTFSSYG (SEQ ID NO: 275) | ISYDGSNK (SEQ ID NO: 362) | AKGDVNYGMDV (SEQ ID NO: 65) |
| GFTFSSYG (SEQ ID NO: 275) | ISYDGSDK (SEQ ID NO: 361) | AKDLSGLPIIDY (SEQ ID NO: 62) |
| GGSISSSNW (SEQ ID NO: 284) | IYHSGST (SEQ ID NO: 365) | ARDFYYGSGSYPNGYYYGMDV (SEQ ID NO: 77) |
| GFTFSSYG (SEQ ID NO: 275) | ISYDGSNK (SEQ ID NO: 362) | AKGDVNYGMDV (SEQ ID NO: 65) |
| GGTFSSYA (SEQ ID NO: 286) | IIPIFGTA (SEQ ID NO: 326) | ARDFNPFSITIFEMDV (SEQ ID NO: 74) |
| GFTFSSYG (SEQ ID NO: 275) | ISYDGSNK (SEQ ID NO: 362) | AKGDVNYGMDV (SEQ ID NO: 65) |
| GFTFSSYG (SEQ ID NO: 275) | ISYDGSNK (SEQ ID NO: 362) | AKGDVNYGMDV (SEQ ID NO: 65) |
| GFTFSSYG (SEQ ID NO: 275) | ISYDGSNK (SEQ ID NO: 362) | ANLAMGQYFDY (SEQ ID NO: 70) |
| GGTFSSYA (SEQ ID NO: 286) | IIPIFGTA (SEQ ID NO: 326) | AREMYYYYGMDV (SEQ ID NO: 103) |
| GFTFGDYA (SEQ ID NO: 266) | INTDGSIT (SEQ ID NO: 343) | ARDSHTVYYGSGSQDY (SEQ ID NO: 99) |
| GFTFSSYG (SEQ ID NO: 275) | ISYDGSNK (SEQ ID NO: 362) | ANLAMGQYFDY (SEQ ID NO: 70) |
| GFTFSSYA (SEQ ID NO: 273) | ISYDGSNK (SEQ ID NO: 362) | ARDLGEAKSSSPHEPDY (SEQ ID NO: 84) |
| GFTFSSYA (SEQ ID NO: 273) | ISYDGSNK (SEQ ID NO: 362) | ARDLGEAKSSSPHEPDY (SEQ ID NO: 84) |
| GFTFSSYG (SEQ ID NO: 275) | ISYDGSNK (SEQ ID NO: 362) | AKGDVNYGMDV (SEQ ID NO: 65) |
| GDSISSSSYY (SEQ ID NO: 261) | INHSGST (SEQ ID NO: 333) | ARDQEMYYFDY (SEQ ID NO: 88) |
| GGSISRSNW (SEQ ID NO: 281) | IYHTGST (SEQ ID NO: 366) | ARGKGSYAFDI (SEQ ID NO: 110) |
| GFTFSSYG (SEQ ID NO: 275) | ISYDGSDK (SEQ ID NO: 361) | AKDLSGLPIIDY (SEQ ID NO: 62) |
| GFTFSSYG (SEQ ID NO: 275) | ISYDGNNK (SEQ ID NO: 360) | AKGYSSSPGDY (SEQ ID NO: 67) |
| GGSISRSNW (SEQ ID NO: 281) | IYHTGST (SEQ ID NO: 366) | ARGKGSYAFDI (SEQ ID NO: 110) |

TABLE 3B

| VL_CDR1 | VL_CDR2 | VL_CDR3 |
|---|---|---|
| QSISSY (SEQ ID NO: 567) | AAS (SEQ ID NO: 49) | QQSYSTPPT (SEQ ID NO: 534) |
| QSISSY (SEQ ID NO: 567) | AAS (SEQ ID NO: 49) | QQSYSTPPT (SEQ ID NO: 534) |
| SSNIGNNF (SEQ ID NO: 650) | DST (SEQ ID NO: 191) | GSWDTNLSGYV (SEQ ID NO: 289) |
| QSISSY (SEQ ID NO: 567) | AAS (SEQ ID NO: 49) | QQSYSTPPT (SEQ ID NO: 534) |
| QSISSY (SEQ ID NO: 567) | AAS (SEQ ID NO: 49) | QQSYSTPPT (SEQ ID NO: 534) |
| QSISSY (SEQ ID NO: 567) | AAS (SEQ ID NO: 49) | QQSYSTPPT (SEQ ID NO: 534) |
| QSISNY (SEQ ID NO: 563) | AAS (SEQ ID NO: 49) | QQSYSTPPT (SEQ ID NO: 534) |

TABLE 3B-continued

| VL_CDR1 | VL_CDR2 | VL_CDR3 |
|---|---|---|
| NIETKS (SEQ ID NO: 455) | DDD (SEQ ID NO: 158) | QVWDSSSGHREV(SEQ ID NO: 613) |
| KLGDKY (SEQ ID NO: 404) | KDN (SEQ ID NO: 386) | QAWDSSTYV (SEQ ID NO: 473) |
| NIETKS (SEQ ID NO: 455) | DDD (SEQ ID NO: 158) | QVWDSSSGHREV (SEQ ID NO: 613) |
| QSISSY (SEQ ID NO: 567) | AAS (SEQ ID NO: 49) | QQSYSTPPT (SEQ ID NO: 534) |
| QSVSNY (SEQ ID NO: 574) | GAS (SEQ ID NO: 260) | QQYNHWPPL (SEQ ID NO: 544) |
| QSISSY (SEQ ID NO: 567) | AAS (SEQ ID NO: 49) | QQSYSTPPT (SEQ ID NO: 534) |
| QTISQW (SEQ ID NO: 582) | KAS (SEQ ID NO: 385) | QQYSGDSMYT (SEQ ID NO: 553) |
| QSISSY (SEQ ID NO: 567) | AAS (SEQ ID NO: 49) | QQSYSTPPT (SEQ ID NO: 534) |
| QSVSNY (SEQ ID NO: 574) | GAS (SEQ ID NO: 260) | QQYNHWPPL (SEQ ID NO: 544) |
| QSISSY (SEQ ID NO: 567) | AAS (SEQ ID NO: 49) | QQSYSTPPT (SEQ ID NO: 534) |
| QSVSNY (SEQ ID NO: 574) | GAS (SEQ ID NO: 260) | QQYNHWPPL (SEQ ID NO: 544) |
| QSISSY (SEQ ID NO: 567) | AAS (SEQ ID NO: 49) | QQSYSTPPA (SEQ ID NO: 533) |
| QSISSY (SEQ ID NO: 567) | AAS (SEQ ID NO: 49) | QQSYSTPPA (SEQ ID NO: 533) |
| SSNIGSNY (SEQ ID NO: 655) | RNN (SEQ ID NO: 635) | AAWDDSLSGVV (SEQ ID NO: 56) |
| NIGSKS (SEQ ID NO: 456) | DDS (SEQ ID NO: 159) | QVWDSSSDHWV (SEQ ID NO: 611) |
| SSNIGSNY (SEQ ID NO: 655) | SNN (SEQ ID NO: 644) | AAWDDSLNGVV (SEQ ID NO: 53) |
| NFNIGNNL (SEQ ID NO: 453) | AND (SEQ ID NO: 69) | ATWDDSLSGVV (SEQ ID NO: 151) |
| SSNIGSNY (SEQ ID NO: 655) | SNN (SEQ ID NO: 644) | ATWDDSLSGVV (SEQ ID NO: 151) |
| QSISNY (SEQ ID NO: 563) | AAS (SEQ ID NO: 49) | QQSYSTPPT (SEQ ID NO: 534) |
| RPNVASNS (SEQ ID NO: 636) | SDN (SEQ ID NO: 638) | ETWDDSLRGVV (SEQ ID NO: 227) |
| SSNIGSNT (SEQ ID NO: 654) | SNN (SEQ ID NO: 644) | AAWDDSLNGYV (SEQ ID NO: 54) |
| NIGSKS (SEQ ID NO: 456) | DDS (SEQ ID NO: 159) | QVWDSSSDHWV (SEQ ID NO: 611) |
| YSNIGSNT (SEQ ID NO: 726) | SDN (SEQ ID NO: 638) | ATWDDSLNGPV (SEQ ID NO: 150) |
| RNIWSY (SEQ ID NO: 634) | GAS (SEQ ID NO: 260) | QQSHSTPIT (SEQ ID NO: 526) |
| NIGSQS (SEQ ID NO: 458) | DDY (SEQ ID NO: 161) | QIWDSSSAHVV (SEQ ID NO: 510) |
| SSNIGSNF (SEQ ID NO: 653) | SNN (SEQ ID NO: 644) | AAWDDSLRSYV (SEQ ID NO: 55) |
| QSISSW (SEQ ID NO: 566) | DAF (SEQ ID NO: 156) | QQYNSYSRT (SEQ ID NO: 551) |
| QSVSSR (SEQ ID NO: 576) | GAS (SEQ ID NO: 260) | QQYTNWPQT (SEQ ID NO: 554) |
| QTISGL (SEQ ID NO: 581) | GAS (SEQ ID NO: 260) | LQYDRYSGA (SEQ ID NO: 426) |
| DIESEM (SEQ ID NO: 163) | DDS (SEQ ID NO: 159) | QVWHTTNDHVL (SEQ ID NO: 615) |
| NIGSKS (SEQ ID NO: 456) | DDS (SEQ ID NO: 159) | QVWDSSSDHWV (SEQ ID NO: 611) |
| QSIGNY (SEQ ID NO: 558) | AAT (SEQ ID NO: 50) | QQSKQIPYT (SEQ ID NO: 528) |
| QGISSW (SEQ ID NO: 489) | AVS (SEQ ID NO: 154) | QQSYSLPLT (SEQ ID NO: 531) |
| QSIGNY (SEQ ID NO: 558) | AAT (SEQ ID NO: 50) | QQSKQIPYT (SEQ ID NO: 528) |
| QSVSSTY (SEQ ID NO: 577) | GAS (SEQ ID NO: 260) | QQFDISGGLI (SEQ ID NO: 518) |
| QDISNY (SEQ ID NO: 485) | DAS (SEQ ID NO: 157) | QQYDNLPLT (SEQ ID NO: 542) |
| NIESES (SEQ ID NO: 454) | DDS (SEQ ID NO: 159) | QVWDSSSDHTVA (SEQ ID NO: 609) |
| SSDVGAYNY (SEQ ID NO: 647) | GVS (SEQ ID NO: 295) | SSYTTTDTFV (SEQ ID NO: 665) |
| QDINNY (SEQ ID NO: 482) | DAS (SEQ ID NO: 157) | QQYDNLPYT (SEQ ID NO: 543) |

TABLE 3B-continued

| VL_CDR1 | VL_CDR2 | VL_CDR3 |
|---|---|---|
| QGISNS (SEQ ID NO: 488) | AAS (SEQ ID NO: 49) | QQYYSTPPH (SEQ ID NO: 556) |
| QSISSY (SEQ ID NO: 567) | AAS (SEQ ID NO: 49) | QQSYSTPLT (SEQ ID NO: 532) |
| NIGSKS (SEQ ID NO: 456) | DDS (SEQ ID NO: 159) | QVWDSSSDHVV (SEQ ID NO: 610) |
| SSNIGNNY (SEQ ID NO: 651) | DNN (SEQ ID NO: 190) | GTWDSSLSAYV (SEQ ID NO: 294) |
| EGIRTS (SEQ ID NO: 218) | GAS (SEQ ID NO: 260) | QQTHTWPWT (SEQ ID NO: 538) |
| QGTSSW (SEQ ID NO: 491) | AAS (SEQ ID NO: 49) | QQANSFPLT (SEQ ID NO: 514) |
| QSISSY (SEQ ID NO: 567) | AAS (SEQ ID NO: 49) | QQSYSTPYT (SEQ ID NO: 536) |
| SSDVGGYNY (SEQ ID NO: 649) | DVS (SEQ ID NO: 201) | SSYTSSSTYV (SEQ ID NO: 664) |
| QSVSNNY (SEQ ID NO: 573) | GAS (SEQ ID NO: 260) | QRYGSSPR (SEQ ID NO: 557) |
| QGINSY (SEQ ID NO: 487) | AAS (SEQ ID NO: 49) | QQVHSFPFT (SEQ ID NO: 541) |
| NIGSKS (SEQ ID NO: 456) | DDS (SEQ ID NO: 159) | QVWDSSSDHVV (SEQ ID NO: 610) |
| QAVRID (SEQ ID NO: 472) | GAS (SEQ ID NO: 260) | LQHNTFPYT (SEQ ID NO: 423) |
| QSISRY (SEQ ID NO: 564) | AAS (SEQ ID NO: 49) | QQSHSTPLT (SEQ ID NO: 527) |
| QSIGYW (SEQ ID NO: 559) | RAS (SEQ ID NO: 619) | QQYNSYPFT (SEQ ID NO: 548) |
| SSNVGSNY (SEQ ID NO: 656) | RNN (SEQ ID NO: 635) | AAWDDSLSGVV (SEQ ID NO: 56) |
| QSVSSTY (SEQ ID NO: 577) | GTS (SEQ ID NO: 291) | QQYNSSPLMYT (SEQ ID NO: 547) |
| QSIKNY (SEQ ID NO: 561) | AAS (SEQ ID NO: 49) | QQTYSTPLT (SEQ ID NO: 540) |
| QDIKRR (SEQ ID NO: 480) | DAS (SEQ ID NO: 157) | QQANTFPQT (SEQ ID NO: 516) |
| SGSIASSY (SEQ ID NO: 640) | EDN (SEQ ID NO: 216) | QSYDGSSVV (SEQ ID NO: 579) |
| NIGSKS (SEQ ID NO: 456) | DDS (SEQ ID NO: 159) | QVWDSSSDHWV (SEQ ID NO: 611) |
| NIGSKS (SEQ ID NO: 456) | DDS (SEQ ID NO: 159) | QVWDSSSDHWV (SEQ ID NO: 611) |
| NIGSKS (SEQ ID NO: 456) | DDS (SEQ ID NO: 159) | QVWDSSSDHWV (SEQ ID NO: 611) |
| QSISSY (SEQ ID NO: 567) | AAS (SEQ ID NO: 49) | QQSYSTPPT (SEQ ID NO: 534) |
| NIGSKS (SEQ ID NO: 456) | DDS (SEQ ID NO: 159) | QVWDSSSDHVV (SEQ ID NO: 610) |
| NIGSKS (SEQ ID NO: 456) | DDS (SEQ ID NO: 159) | QVWDSSSDHWV (SEQ ID NO: 611) |
| NSNVGNNY (SEQ ID NO: 465) | DND (SEQ ID NO: 188) | GSWEARESVFV (SEQ ID NO: 290) |
| NIGSKS (SEQ ID NO: 456) | DDS (SEQ ID NO: 159) | QVWDSSSDHWV (SEQ ID NO: 611) |
| NIGSKS (SEQ ID NO: 456) | DDS (SEQ ID NO: 159) | QVWDSSSDHWV (SEQ ID NO: 611) |
| QSVSSN (SEQ ID NO: 575) | AAS (SEQ ID NO: 49) | QQYNNWWT (SEQ ID NO: 545) |
| QSISSY (SEQ ID NO: 567) | AAS (SEQ ID NO: 49) | QQSYSTPPT (SEQ ID NO: 534) |
| NIGSKS (SEQ ID NO: 456) | DDS (SEQ ID NO: 159) | QVWDSSSDHWV (SEQ ID NO: 611) |
| QSISSH (SEQ ID NO: 565) | AAS (SEQ ID NO: 49) | QQSYSTPPT (SEQ ID NO: 534) |
| QSISSY (SEQ ID NO: 567) | AAS (SEQ ID NO: 49) | QQSYSTPWT (SEQ ID NO: 535) |
| NIGSKS (SEQ ID NO: 456) | DDS (SEQ ID NO: 159) | QVWDSSSDHWV (SEQ ID NO: 611) |
| NIGSKS (SEQ ID NO: 456) | DDS (SEQ ID NO: 159) | QVWDSSSDHWV (SEQ ID NO: 611) |
| NIGSKS (SEQ ID NO: 456) | DDS (SEQ ID NO: 159) | QVWDSSSDHWV (SEQ ID NO: 611) |
| NIGSKS (SEQ ID NO: 456) | DDS (SEQ ID NO: 159) | QVWDSSSDHWV (SEQ ID NO: 611) |
| NIGSKS (SEQ ID NO: 456) | DDS (SEQ ID NO: 159) | QVWDSSSDHWV (SEQ ID NO: 611) |
| QSISRY (SEQ ID NO: 564) | GAS (SEQ ID NO: 260) | QQTYNDPPT (SEQ ID NO: 539) |

TABLE 3B-continued

| VL_CDR1 | VL_CDR2 | VL_CDR3 |
|---|---|---|
| QSISSY (SEQ ID NO: 567) | AAS (SEQ ID NO: 49) | QQSYSTPPT (SEQ ID NO: 534) |
| SSNIGNNY (SEQ ID NO: 651) | DNN (SEQ ID NO: 190) | GTWDSSLSAWV (SEQ ID NO: 293) |
| SLRSYY (SEQ ID NO: 643) | GKN (SEQ ID NO: 287) | NSRDSSGNHVV (SEQ ID NO: 466) |
| QSISNY (SEQ ID NO: 563) | AAS (SEQ ID NO: 49) | QQSYSTPPT (SEQ ID NO: 534) |
| QSISSY (SEQ ID NO: 567) | AAS (SEQ ID NO: 49) | QQSYSTPPT (SEQ ID NO: 534) |
| QSISNY (SEQ ID NO: 563) | AAS (SEQ ID NO: 49) | QQSYSTPPT (SEQ ID NO: 534) |
| NIGSKS (SEQ ID NO: 456) | DDS (SEQ ID NO: 159) | QVWDSSSDHPVV (SEQ ID NO: 608) |
| KLGERF (SEQ ID NO: 405) | QYI (SEQ ID NO: 616) | QTWDGSIVV (SEQ ID NO: 583) |
| SGSVSTSYY (SEQ ID NO: 641) | NTD (SEQ ID NO: 467) | VLYMGSGIWV (SEQ ID NO: 694) |
| SSNIGRNY (SEQ ID NO: 652) | RNH (SEQ ID NO: 633) | ATWDDALSGWV (SEQ ID NO: 149) |
| QSISSY (SEQ ID NO: 567) | AAS (SEQ ID NO: 49) | QQSYSTPPT (SEQ ID NO: 534) |
| SGRIASNY (SEQ ID NO: 639) | QDD (SEQ ID NO: 479) | QSYDSTTLV (SEQ ID NO: 580) |
| SSDVGGYNY (SEQ ID NO: 649) | GVS (SEQ ID NO: 295) | SSYTSSSTLVV (SEQ ID NO: 660) |
| QSISSY (SEQ ID NO: 567) | AAS (SEQ ID NO: 49) | QQSYSTPWT (SEQ ID NO: 535) |
| QDISNY (SEQ ID NO: 485) | DAS (SEQ ID NO: 157) | QQYDNLPLT (SEQ ID NO: 542) |
| SSDVGGYNY (SEQ ID NO: 649) | DVS (SEQ ID NO: 201) | SSYTSSSTWV (SEQ ID NO: 663) |
| QSISSY (SEQ ID NO: 567) | AAS (SEQ ID NO: 49) | LQDYNYPPA (SEQ ID NO: 422) |
| EDIRMY (SEQ ID NO: 215) | EGS (SEQ ID NO: 219) | QQYYDDPQ (SEQ ID NO: 555) |
| QGISTY (SEQ ID NO: 490) | AAS (SEQ ID NO: 49) | QQLNGYPTT (SEQ ID NO: 525) |
| SSNVGSRT (SEQ ID NO: 657) | SNN (SEQ ID NO: 644) | AAWDDSLIGHV (SEQ ID NO: 51) |
| NIGTKS (SEQ ID NO: 459) | DDS (SEQ ID NO: 159) | QVWDSSSDHVV (SEQ ID NO: 610) |
| SSDVGGYNY (SEQ ID NO: 649) | EVS (SEQ ID NO: 237) | SSYTSSSTPV (SEQ ID NO: 662) |
| NIGSKT (SEQ ID NO: 457) | DGR (SEQ ID NO: 162) | QVWDTSGDLHWA (SEQ ID NO: 614) |
| SSDVGGYNY (SEQ ID NO: 649) | EVS (SEQ ID NO: 237) | SSYTSSSTLV (SEQ ID NO: 659) |
| QSINSY (SEQ ID NO: 562) | TAS (SEQ ID NO: 667) | QQSYTTPLT (SEQ ID NO: 537) |
| NIGSKS (SEQ ID NO: 456) | DDT (SEQ ID NO: 160) | QVWDSSSDLLWV (SEQ ID NO: 612) |
| SSNIGNNY (SEQ ID NO: 651) | DNN (SEQ ID NO: 190) | GTWDSSLSALV (SEQ ID NO: 292) |
| NIGSKT (SEQ ID NO: 457) | DGR (SEQ ID NO: 162) | QVWDTSGDLHWA (SEQ ID NO: 614) |
| NIGSKT (SEQ ID NO: 457) | DGR (SEQ ID NO: 162) | QVWDTSGDLHWA (SEQ ID NO: 614) |
| SSNIGSNT (SEQ ID NO: 654) | SNN (SEQ ID NO: 644) | AAWDDSLNGPV (SEQ ID NO: 52) |
| QSIITY (SEQ ID NO: 560) | AAS (SEQ ID NO: 49) | QQSYSTPPT (SEQ ID NO: 534) |
| SSDVGGYNY (SEQ ID NO: 649) | EVS (SEQ ID NO: 237) | SSYTSSSTLV (SEQ ID NO: 659) |
| SSNIGSNT (SEQ ID NO: 654) | SNN (SEQ ID NO: 644) | AAWDDSLNGPV (SEQ ID NO: 52) |
| QSLLHSDGKTY (SEQ ID NO: 570) | EVS (SEQ ID NO: 237) | MQTKQLPLT (SEQ ID NO: 443) |
| QSLLHSDGKTY (SEQ ID NO: 570) | EVS (SEQ ID NO: 237) | MQTKQLPLT (SEQ ID NO: 443) |
| NIGSKT (SEQ ID NO: 457) | DGR (SEQ ID NO: 162) | QVWDTSGDLHWA (SEQ ID NO: 614) |
| QGISSW (SEQ ID NO: 489) | AAS (SEQ ID NO: 49) | QQANSFPPT (SEQ ID NO: 515) |
| GGNIARNY (SEQ ID NO: 279) | EDD (SEQ ID NO: 214) | QSYDGNNHMV (SEQ ID NO: 578) |
| SSDVGGYNF (SEQ ID NO: 648) | EVS (SEQ ID NO: 237) | SSYTKNNSVV (SEQ ID NO: 658) |

TABLE 3B-continued

| VL_CDR1 | VL_CDR2 | VL_CDR3 |
|---|---|---|
| SSDVGAYNY (SEQ ID NO: 647) | DVS (SEQ ID NO: 201) | SSYTSSSTLWV (SEQ ID NO: 661) |
| GGNIARNY (SEQ ID NO: 279) | EDD (SEQ ID NO: 214) | QSYDGNNHMV (SEQ ID NO: 578) |

In some embodiments, the antibody has the six CDRs of any one of the combinations provided in Table 4.

TABLE 4

| Combination # | VH_CDR1 | VH_CDR2 | VH_CDR3 | VL_CDR1 | VL_CDR2 | VL_CDR3 |
|---|---|---|---|---|---|---|
| 1. | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| 2. | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| 3. | GGSISSGGYY (SEQ ID NO: 283) | IYYSGST (SEQ ID NO: 384) | ARGNLWSGYYF (SEQ ID NO: 111) | SSNIGNNF (SEQ ID NO: 650) | DST (SEQ ID NO: 191) | GSWDTNLSGYV (SEQ ID NO: 289) |
| 4. | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| 5. | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| 6. | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| 7. | GGTFSSYA (SEQ ID NO: 286) | IIPIFGTA (SEQ ID NO: 326) | AREMYYYYGMDV (SEQ ID NO: 103) | QSISNY (SEQ ID NO: 563) | AAS (SEQ ID NO: 49) | QQSYSTPPT (SEQ ID NO: 534) |
| 8. | GFTFSSYG (SEQ ID NO: 275) | ISYDGSNK (SEQ ID NO: 362) | AKELLEGAFDI (SEQ ID NO: 64) | NIETKS (SEQ ID NO: 455) | DDD (SEQ ID NO: 158) | QVWDSSSGHREV (SEQ ID NO: 613) |
| 9. | GYTFTSYY (SEQ ID NO: 313) | INPSGGST (SEQ ID NO: 339) | ARDRVTMVRGALAY (SEQ ID NO: 97) | KLGDKY (SEQ ID NO: 404) | KDN (SEQ ID NO: 386) | QAWDSSTYV (SEQ ID NO: 473) |
| 10. | GFTFSSYG (SEQ ID NO: 275) | ISYDGSNK (SEQ ID NO: 362) | AKELLEGAFDI (SEQ ID NO: 64) | NIETKS (SEQ ID NO: 455) | DDD (SEQ ID NO: 158) | QVWDSSSGHREV (SEQ ID NO: 613) |
| 11. | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| 12. | GYTFTSYG (SEQ ID NO: 312) | ISAYNGNT (SEQ ID NO: 346) | ARERSYYGMDV (SEQ ID NO: 105) | QSVSNY (SEQ ID NO: 574) | GAS (SEQ ID NO: 260) | QQYNHWPPL (SEQ ID NO: 544) |

TABLE 4-continued

| Combination # | VH_CDR1 | VH_CDR2 | VH_CDR3 | VL_CDR1 | VL_CDR2 | VL_CDR3 |
|---|---|---|---|---|---|---|
| 13. | GGTFSSYA (SEQ ID NO: 286) | IIPIFGTA (SEQ ID NO: 326) | AREMYYY YGMDV (SEQ ID NO: 103) | QSISSY (SEQ ID NO: 567) | AAS (SEQ ID NO: 49) | QQSYSTPP T (SEQ ID NO: 534) |
| 14. | GGTFSSYA (SEQ ID NO: 286) | IMPIFDTA (SEQ ID NO: 332) | ASWSERIG YQYGLDV (SEQ ID NO: 145) | QTISQW (SEQ ID NO: 582) | KAS (SEQ ID NO: 385) | QQYSGDS MYT (SEQ ID NO: 553) |
| 15. | GGTFSSYA (SEQ ID NO: 286) | IIPIFGTA (SEQ ID NO: 326) | AREMYYY YGMDV (SEQ ID NO: 103) | QSISSY (SEQ ID NO: 567) | AAS (SEQ ID NO: 49) | QQSYSTPP T (SEQ ID NO: 534) |
| 16. | GYTFTSYG (SEQ ID NO: 312) | ISAYNGNT (SEQ ID NO: 346) | ARERSYYG MDV (SEQ ID NO: 105) | QSVSNY (SEQ ID NO: 574) | GAS (SEQ ID NO: 260) | QQYNHWP PL (SEQ ID NO: 544) |
| 17. | GGTFSSYA (SEQ ID NO: 286) | IIPIFGTA (SEQ ID NO: 326) | AREMYYY YGMDV (SEQ ID NO: 103) | QSISSY (SEQ ID NO: 567) | AAS (SEQ ID NO: 49) | QQSYSTPP T (SEQ ID NO: 534) |
| 18. | GYTFTSYG (SEQ ID NO: 312) | ISAYNGNT (SEQ ID NO: 346) | ARERSYYG MDV (SEQ ID NO: 105) | QSVSNY (SEQ ID NO: 574) | GAS (SEQ ID NO: 260) | QQYNHWP PL (SEQ ID NO: 544) |
| 19. | GGTFSSYA (SEQ ID NO: 286) | IIPIFGTA (SEQ ID NO: 326) | AREMYYY YGMDV (SEQ ID NO: 103) | QSISSY (SEQ ID NO: 567) | AAS (SEQ ID NO: 49) | QQSYSTPP A (SEQ ID NO: 533) |
| 20. | GGTFSSYA (SEQ ID NO: 286) | IIPIFGTA (SEQ ID NO: 326) | AREMYYY YGMDV (SEQ ID NO: 103) | QSISSY (SEQ ID NO: 567) | AAS (SEQ ID NO: 49) | QQSYSTPP A (SEQ ID NO: 533) |
| 21. | GYTFTSYY (SEQ ID NO: 313) | INPSGGST (SEQ ID NO: 339) | ARDILGLD Y (SEQ ID NO: 81) | SSNIGSNY (SEQ ID NO: 655) | RNN (SEQ ID NO: 635) | AAWDDSL SGVV (SEQ ID NO: 56) |
| 22. | GYSFTSYW (SEQ ID NO: 299) | IYPGDSDT (SEQ ID NO: 377) | ARLENNW DYGGWFD P (SEQ ID NO: 127) | NIGSKS (SEQ ID NO: 456) | DDS (SEQ ID NO: 159) | QVWDSSS DHWV (SEQ ID NO: 611) |
| 23. | GYTFTDYY (SEQ ID NO: 306) | VDPEDGET (SEQ ID NO: 693) | ATEDTAM GGIDY (SEQ ID NO: 146) | SSNIGSNY (SEQ ID NO: 655) | SNN (SEQ ID NO: 644) | AAWDDSL NGVV (SEQ ID NO: 53) |
| 24. | GYTFTDYY (SEQ ID NO: 306) | VDPEDGET (SEQ ID NO: 693) | ATEGRYG MDV (SEQ ID NO: 147) | NFNIGNNL (SEQ ID NO: 453) | AND (SEQ ID NO: 69) | ATWDDSLS GVV (SEQ ID NO: 151) |
| 25. | GYTFTDYY (SEQ ID NO: 306) | VDPEDGET (SEQ ID NO: 693) | AVEGGRAP GTYYYDSS GLAY (SEQ ID NO: 153) | SSNIGSNY (SEQ ID NO: 655) | SNN (SEQ ID NO: 644) | ATWDDSLS GVV (SEQ ID NO: 151) |
| 26. | GGTFSSYA (SEQ ID NO: 286) | IIPIFGTA (SEQ ID NO: 326) | AREMYYY YGMDV (SEQ ID NO: 103) | QSISNY (SEQ ID NO: 563) | AAS (SEQ ID NO: 49) | QQSYSTPP T (SEQ ID NO: 534) |
| 27. | GGSISSSNW (SEQ ID NO: 284) | IYHSGST (SEQ ID NO: 365) | ARGVIAAA GTYFDY (SEQ ID NO: 116) | RPNVASNS (SEQ ID NO: 636) | SDN (SEQ ID NO: 638) | ETWDDSLR GVV (SEQ ID NO: 227) |
| 28. | GGSISSSNW (SEQ ID NO: 284) | IYHSGST (SEQ ID NO: 365) | ARERTHYY YGMDI (SEQ ID NO: 106) | SSNIGSNT (SEQ ID NO: 654) | SNN (SEQ ID NO: 644) | AAWDDSL NGYV (SEQ ID NO: 54) |

TABLE 4-continued

| Combination # | VH_CDR1 | VH_CDR2 | VH_CDR3 | VL_CDR1 | VL_CDR2 | VL_CDR3 |
|---|---|---|---|---|---|---|
| 29. | GYSFTSYW (SEQ ID NO: 299) | IYPGDSDT (SEQ ID NO: 377) | ARLENNW DYGGWFD P (SEQ ID NO: 127) | NIGSKS (SEQ ID NO: 456) | DDS (SEQ ID NO: 159) | QVWDSSS DHWV (SEQ ID NO: 611) |
| 30. | GGTFSSYA (SEQ ID NO: 286) | IIPIFGTA (SEQ ID NO: 326) | ARDGAGN YDILTGDR SEDYYYY YGMDV (SEQ ID NO: 78) | YSNIGSNT (SEQ ID NO: 726) | SDN (SEQ ID NO: 638) | ATWDDSL NGPV (SEQ ID NO: 150) |
| 31. | GGSISSGGY S (SEQ ID NO: 282) | IYHSGST (SEQ ID NO: 365) | ARAGYYY GMDV (SEQ ID NO: 71) | RNIWSY (SEQ ID NO: 634) | GAS (SEQ ID NO: 260) | QQSHSTPIT (SEQ ID NO: 526) |
| 32. | GGSISSGGY Y (SEQ ID NO: 283) | IYYSGST (SEQ ID NO: 384) | ARDSSSGP YGMDV (SEQ ID NO: 100) | NIGSQS (SEQ ID NO: 458) | DDY (SEQ ID NO: 161) | QIWDSSSA HVV (SEQ ID NO: 510) |
| 33. | GGSISSSNW (SEQ ID NO: 284) | IYHSGST (SEQ ID NO: 365) | ARVNYGD YDWYFDL (SEQ ID NO: 137) | SSNIGSNF (SEQ ID NO: 653) | SNN (SEQ ID NO: 644) | AAWDDSL RSYV (SEQ ID NO: 55) |
| 34. | GGTFSSYA (SEQ ID NO: 286) | IIPIFGTA (SEQ ID NO: 326) | ARDLGTM VRGVIEPY YFDY (SEQ ID NO: 85) | QSISSW (SEQ ID NO: 566) | DAF (SEQ ID NO: 156) | QQYNSYSR T (SEQ ID NO: 551) |
| 35. | GGSISSSNW (SEQ ID NO: 284) | IYHSGST (SEQ ID NO: 365) | ARGVRGT GFDP (SEQ ID NO: 118) | QSVSSR (SEQ ID NO: 576) | GAS (SEQ ID NO: 260) | QQYTNWP QT (SEQ ID NO: 554) |
| 36. | GYTFTSYG (SEQ ID NO: 312) | ISAYNGNT (SEQ ID NO: 346) | ARDRNGY FQH (SEQ ID NO: 94) | QTISGL (SEQ ID NO: 581) | GAS (SEQ ID NO: 260) | LQYDRYSG A (SEQ ID NO: 426) |
| 37. | GFTFSSYG (SEQ ID NO: 275) | ISYDGSNK (SEQ ID NO: 362) | AKDLLGEL SFFDY (SEQ ID NO: 61) | DIESEM (SEQ ID NO: 163) | DDS (SEQ ID NO: 159) | QVWHTTN DHVL (SEQ ID NO: 615) |
| 38. | GYSFTSYW (SEQ ID NO: 299) | IYPGDSDT (SEQ ID NO: 377) | ARLENNW DYGGWFD P (SEQ ID NO: 127) | NIGSKS (SEQ ID NO: 456) | DDS (SEQ ID NO: 159) | QVWDSSS DHWV (SEQ ID NO: 611) |
| 39. | GGTFSSYA (SEQ ID NO: 286) | IIPIFGTA (SEQ ID NO: 326) | ARDRSYY GMDV (SEQ ID NO: 96) | QSIGNY (SEQ ID NO: 558) | AAT (SEQ ID NO: 50) | QQSKQIPY T (SEQ ID NO: 528) |
| 40. | GGTFSSYA (SEQ ID NO: 286) | IIPIFGTA (SEQ ID NO: 326) | ARDKGYY GMDV (SEQ ID NO: 83) | QGISSW (SEQ ID NO: 489) | AVS (SEQ ID NO: 154) | QQSYSLPL T (SEQ ID NO: 531) |
| 41. | GGTFSSYA (SEQ ID NO: 286) | IIPIFGTA (SEQ ID NO: 326) | ARDRSYY GMDV (SEQ ID NO: 96) | QSIGNY (SEQ ID NO: 558) | AAT (SEQ ID NO: 50) | QQSKQIPY T (SEQ ID NO: 528) |
| 42. | GFTFSNYG (SEQ ID NO: 271) | ISHDGHVK (SEQ ID NO: 349) | AKEISPRSS VGWPLDY (SEQ ID NO: 63) | QSVSSTY (SEQ ID NO: 577) | GAS (SEQ ID NO: 260) | QQFDISGG LI (SEQ ID NO: 518) |
| 43. | GFTFSSSA (SEQ ID NO: 272) | ISYDGSNK (SEQ ID NO: 362) | ARDFWSG YNELGGM DV (SEQ ID NO: 76) | QDISNY (SEQ ID NO: 485) | DAS (SEQ ID NO: 157) | QQYDNLPL T (SEQ ID NO: 542) |

TABLE 4-continued

| Combination # | VH_CDR1 | VH_CDR2 | VH_CDR3 | VL_CDR1 | VL_CDR2 | VL_CDR3 |
|---|---|---|---|---|---|---|
| 44. | GFTFSSYW (SEQ ID NO: 277) | IKQDGSEK (SEQ ID NO: 328) | ARTWFGEF FDY (SEQ ID NO: 134) | NIESES (SEQ ID NO: 454) | DDS (SEQ ID NO: 159) | QVWDSSS DHTVA (SEQ ID NO: 609) |
| 45. | GYTFTSYG (SEQ ID NO: 312) | ISAYNGNT (SEQ ID NO: 346) | ARVIGGWF DP (SEQ ID NO: 136) | SSDVGAY NY (SEQ ID NO: 647) | GVS (SEQ ID NO: 295) | SSYTTTDT FV (SEQ ID NO: 665) |
| 46. | GFIFSRHA (SEQ ID NO: 264) | ISYDGSNK (SEQ ID NO: 362) | ARGRLAY GDTEGFDY (SEQ ID NO: 112) | QDINNY (SEQ ID NO: 482) | DAS (SEQ ID NO: 157) | QQYDNLP YT (SEQ ID NO: 543) |
| 47. | GYTFNNYG (SEQ ID NO: 302) | ISVYNGDI (SEQ ID NO: 359) | ARDILRGE SSILDH (SEQ ID NO: 82) | QGISNS (SEQ ID NO: 488) | AAS (SEQ ID NO: 49) | QQYYSTPP H (SEQ ID NO: 556) |
| 48. | GGTFSSYA (SEQ ID NO: 286) | IIPIFGTA (SEQ ID NO: 326) | ARDRYYY GMDV (SEQ ID NO: 98) | QSISSY (SEQ ID NO: 567) | AAS (SEQ ID NO: 49) | QQSYSTPL T (SEQ ID NO: 532) |
| 49. | GFTFSSYA (SEQ ID NO: 273) | ISYDGSNK (SEQ ID NO: 362) | ARDLLGSG YDIIDY (SEQ ID NO: 86) | NIGSKS (SEQ ID NO: 456) | DDS (SEQ ID NO: 159) | QVWDSSS DHVV (SEQ ID NO: 610) |
| 50. | GYTFTSYG (SEQ ID NO: 312) | ISAYNGNT (SEQ ID NO: 346) | ARVWGKN GDFDY (SEQ ID NO: 142) | SSNIGNNY (SEQ ID NO: 651) | DNN (SEQ ID NO: 190) | GTWDSSLS AYV (SEQ ID NO: 294) |
| 51. | GYTFTTYA (SEQ ID NO: 314) | INTNTGDP (SEQ ID NO: 344) | ARDRFHY GMDV (SEQ ID NO: 90) | EGIRTS (SEQ ID NO: 218) | GAS (SEQ ID NO: 260) | QQTHTWP WT (SEQ ID NO: 538) |
| 52. | GYTFTSYG (SEQ ID NO: 312) | ISAYNGNT (SEQ ID NO: 346) | ARDRGDY (SEQ ID NO: 92) | QGTSSW (SEQ ID NO: 491) | AAS (SEQ ID NO: 49) | QQANSFPL T (SEQ ID NO: 514) |
| 53. | GFTFNNAW (SEQ ID NO: 267) | IKSKTDGG TT (SEQ ID NO: 330) | TTEGVELL SFGGAPFD Y (SEQ ID NO: 683) | QSISSY (SEQ ID NO: 567) | AAS (SEQ ID NO: 49) | QQSYSTPY T (SEQ ID NO: 536) |
| 54. | GFTFSSYE (SEQ ID NO: 274) | ISSSGSTI (SEQ ID NO: 351) | ARRRGGGF DY (SEQ ID NO: 132) | SSDVGGY NY (SEQ ID NO: 649) | DVS (SEQ ID NO: 201) | SSYTSSSTY V (SEQ ID NO: 664) |
| 55. | GFTFSSYW (SEQ ID NO: 277) | IKQDGSEK (SEQ ID NO: 328) | AREKGSW FDP (SEQ ID NO: 102) | QSVSNNY (SEQ ID NO: 573) | GAS (SEQ ID NO: 260) | QRYGSSPR (SEQ ID NO: 557) |
| 56. | GGTFSSYA (SEQ ID NO: 286) | IIPIFGTA (SEQ ID NO: 326) | ARDKGYY GMDV (SEQ ID NO: 83) | QGINSY (SEQ ID NO: 487) | AAS (SEQ ID NO: 49) | QQVHSFPF T (SEQ ID NO: 541) |
| 57. | GFTFSSYG (SEQ ID NO: 275) | ISSRGSTI (SEQ ID NO: 350) | ARDRGDR VGGLVFD Y (SEQ ID NO: 91) | NIGSKS (SEQ ID NO: 456) | DDS (SEQ ID NO: 159) | QVWDSSS DHVV (SEQ ID NO: 610) |
| 58. | GYSFTTYW (SEQ ID NO: 300) | IYPGDSDT (SEQ ID NO: 377) | ARQVAGG LDY (SEQ ID NO: 131) | QAVRID (SEQ ID NO: 472) | GAS (SEQ ID NO: 260) | LQHNTFPY T (SEQ ID NO: 423) |
| 59. | GYTFTSYG (SEQ ID NO: 312) | ISAYNGNT (SEQ ID NO: 346) | ARDRGYY GMDV (SEQ ID NO: 93) | QSISRY (SEQ ID NO: 564) | AAS (SEQ ID NO: 49) | QQSHSTPL T (SEQ ID NO: 527) |

TABLE 4-continued

| Combination # | VH_CDR1 | VH_CDR2 | VH_CDR3 | VL_CDR1 | VL_CDR2 | VL_CDR3 |
|---|---|---|---|---|---|---|
| 60. | GYSFTSYW (SEQ ID NO: 299) | IYPGDSDT (SEQ ID NO: 377) | FRFGEGFD Y (SEQ ID NO: 259) | QSIGYW (SEQ ID NO: 559) | RAS (SEQ ID NO: 619) | QQYNSYPF T (SEQ ID NO: 548) |
| 61. | GYSFTTYW (SEQ ID NO: 300) | IYPGDSDT (SEQ ID NO: 377) | ARQVAGG LDY (SEQ ID NO: 131) | SSNVGSNY (SEQ ID NO: 656) | RNN (SEQ ID NO: 635) | AAWDDSL SGVV (SEQ ID NO: 56) |
| 62. | GYSFNTYW (SEQ ID NO: 297) | IYPSDSDT (SEQ ID NO: 383) | ARDGGYY FDD (SEQ ID NO: 79) | QSVSSTY (SEQ ID NO: 577) | GTS (SEQ ID NO: 291) | QQYNSSPL MYT (SEQ ID NO: 547) |
| 63. | GGTFSSYA (SEQ ID NO: 286) | IIPIFGTA (SEQ ID NO: 326) | ARDKGYY GMDV (SEQ ID NO: 83) | QSIKNY (SEQ ID NO: 561) | AAS (SEQ ID NO: 49) | QQTYSTPL T (SEQ ID NO: 540) |
| 64. | GYTFTSYG (SEQ ID NO: 312) | ISAYNGNT (SEQ ID NO: 346) | ARDFRMD V (SEQ ID NO: 75) | QDIKRR (SEQ ID NO: 480) | DAS (SEQ ID NO: 157) | QQANTFPQ T (SEQ ID NO: 516) |
| 65. | GFTFRRYW (SEQ ID NO: 268) | IKQDGSEK (SEQ ID NO: 328) | ARDAYAY GLDV (SEQ ID NO: 73) | SGSIASSY (SEQ ID NO: 640) | EDN (SEQ ID NO: 216) | QSYDGSSV V (SEQ ID NO: 579) |
| 66. | GYSFTSYW (SEQ ID NO: 299) | IYPGDSDT (SEQ ID NO: 377) | ARLENNW DYGGWFD P (SEQ ID NO: 127) | NIGSKS (SEQ ID NO: 456) | DDS (SEQ ID NO: 159) | QVWDSSS DHWV (SEQ ID NO: 611) |
| 67. | GYSFTSYW (SEQ ID NO: 299) | IYPGDSDT (SEQ ID NO: 377) | ARLENNW DYGGWFD P (SEQ ID NO: 127) | NIGSKS (SEQ ID NO: 456) | DDS (SEQ ID NO: 159) | QVWDSSS DHWV (SEQ ID NO: 611) |
| 68. | GYSFTSYW (SEQ ID NO: 299) | IYPGDSDT (SEQ ID NO: 377) | ARLENNW DYGGWFD P (SEQ ID NO: 127) | NIGSKS (SEQ ID NO: 456) | DDS (SEQ ID NO: 159) | QVWDSSS DHWV (SEQ ID NO: 611) |
| 69. | GGSISSSNW (SEQ ID NO: 284) | IYHSGST (SEQ ID NO: 365) | ARDLMNY GMDV (SEQ ID NO: 87) | QSISSY (SEQ ID NO: 567) | AAS (SEQ ID NO: 49) | QQSYSTPP T (SEQ ID NO: 534) |
| 70. | GFTFSSYA (SEQ ID NO: 273) | ISYDGSNK (SEQ ID NO: 362) | ARDLLGSG YDIIDY (SEQ ID NO: 86) | NIGSKS (SEQ ID NO: 456) | DDS (SEQ ID NO: 159) | QVWDSSS DHVV (SEQ ID NO: 610) |
| 71. | GYSFTSYW SEQ ID NO: 299) | IYPGDSDT (SEQ ID NO: 377) | ARLENNW DYGGWFD P (SEQ ID NO: 127) | NIGSKS (SEQ ID NO: 456) | DDS (SEQ ID NO: 159) | QVWDSSS DHWV (SEQ ID NO: 611) |
| 72. | GFTFSSYW (SEQ ID NO: 277) | IKQDGSEK (SEQ ID NO: 328) | AREYDYG DYVFDY (SEQ ID NO: 107) | NSNVGNN Y (SEQ ID NO: 465) | DND (SEQ ID NO: 188) | GSWEARES VFV (SEQ ID NO: 290) |
| 73. | GYSFTSYW (SEQ ID NO: 299) | IYPGDSDT (SEQ ID NO: 377) | ARLENNW DYGGWFD P (SEQ ID NO: 127) | NIGSKS (SEQ ID NO: 456) | DDS (SEQ ID NO: 159) | QVWDSSS DHWV (SEQ ID NO: 611) |
| 74. | GYSFTSYW (SEQ ID NO: 299) | IYPGDSDT (SEQ ID NO: 377) | ARLENNW DYGGWFD P (SEQ ID NO: 127) | NIGSKS (SEQ ID NO: 456) | DDS (SEQ ID NO: 159) | QVWDSSS DHWV (SEQ ID NO: 611) |
| 75. | GYTFTGYY (SEQ ID NO: 307) | INPNSGDT (SEQ ID NO: 336) | AILEYSSSG AEYFQH (SEQ ID NO: 58) | QSVSSN (SEQ ID NO: 575) | AAS (SEQ ID NO: 49) | QQYNNW WT (SEQ ID NO: 545) |

TABLE 4-continued

| Combination # | VH_CDR1 | VH_CDR2 | VH_CDR3 | VL_CDR1 | VL_CDR2 | VL_CDR3 |
|---|---|---|---|---|---|---|
| 76. | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| 77. | GYSFTSYW (SEQ ID NO: 299) | IYPGDSDT (SEQ ID NO: 377) | ARLENNWDYGGWFDP (SEQ ID NO: 127) | NIGSKS (SEQ ID NO: 456) | DDS (SEQ ID NO: 159) | QVWDSSSDHWV (SEQ ID NO: 611) |
| 78. | GYTFTTYA (SEQ ID NO: 314) | ISAYNGNT (SEQ ID NO: 346) | ARGGLGGDDAFDI (SEQ ID NO: 108) | QSISSH (SEQ ID NO: 565) | AAS (SEQ ID NO: 49) | QQSYSTPPT (SEQ ID NO: 534) |
| 79. | GGTFSSYA (SEQ ID NO: 286) | ISAYNGNT (SEQ ID NO: 346) | AREPLRYYYYYGMDV (SEQ ID NO: 104) | QSISSY (SEQ ID NO: 567) | AAS (SEQ ID NO: 49) | QQSYSTPWT (SEQ ID NO: 535) |
| 80. | GYSFTSYW (SEQ ID NO: 299) | IYPGDSDT (SEQ ID NO: 377) | ARLENNWDYGGWFDP (SEQ ID NO: 127) | NIGSKS (SEQ ID NO: 456) | DDS (SEQ ID NO: 159) | QVWDSSSDHWV (SEQ ID NO: 611) |
| 81. | GYSFTSYW (SEQ ID NO: 299) | IYPGDSDT (SEQ ID NO: 377) | ARLENNWDYGGWFDP (SEQ ID NO: 127) | NIGSKS (SEQ ID NO: 456) | DDS (SEQ ID NO: 159) | QVWDSSSDHWV (SEQ ID NO: 611) |
| 82. | GYSFTSYW (SEQ ID NO: 299) | IYPGDSDT (SEQ ID NO: 377) | ARLENNWNYGGWFDP (SEQ ID NO: 128) | NIGSKS (SEQ ID NO: 456) | DDS (SEQ ID NO: 159) | QVWDSSSDHWV (SEQ ID NO: 611) |
| 83. | GYSFTSYW (SEQ ID NO: 299) | IYPGDSDT (SEQ ID NO: 377) | ARLENNWDYGGWFDP (SEQ ID NO: 127) | NIGSKS (SEQ ID NO: 456) | DDS (SEQ ID NO: 159) | QVWDSSSDHWV (SEQ ID NO: 611) |
| 84. | GYSFTSYW (SEQ ID NO: 299) | IYPGDSDT (SEQ ID NO: 377) | ARLENNWNYGGWFDP (SEQ ID NO: 128) | NIGSKS (SEQ ID NO: 456) | DDS (SEQ ID NO: 159) | QVWDSSSDHWV (SEQ ID NO: 611) |
| 85. | GGTFSSYA (SEQ ID NO: 286) | IIPIFGTA (SEQ ID NO: 326) | ARDYYYYGMDV (SEQ ID NO: 101) | QSISRY (SEQ ID NO: 564) | GAS (SEQ ID NO: 260) | QQTYNDPPT (SEQ ID NO: 539) |
| 86. | GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| 87. | GGSISSSSYY (SEQ ID NO: 285) | IYYSGST (SEQ ID NO: 384) | ARLSRYYYYGMDV (SEQ ID NO: 130) | SSNIGNNY (SEQ ID NO: 651) | DNN (SEQ ID NO: 190) | GTWDSSLSAWV (SEQ ID NO: 293) |
| 88. | GYTFTSYG (SEQ ID NO: 312) | ISAYNGNT (SEQ ID NO: 346) | ARDIGYYYGMDV (SEQ ID NO: 80) | SLRSYY (SEQ ID NO: 643) | GKN (SEQ ID NO: 287) | NSRDSSGNHVV (SEQ ID NO: 466) |
| 89. | GGTFSSYA (SEQ ID NO: 286) | IIPIFGTA (SEQ ID NO: 326) | AREMYYYYGMDV (SEQ ID NO: 103) | QSISNY (SEQ ID NO: 563) | AAS (SEQ ID NO: 49) | QQSYSTPPT (SEQ ID NO: 534) |

TABLE 4-continued

| Combi-nation # | VH_CDR1 | VH_CDR2 | VH_CDR3 | VL_CDR1 | VL_CDR2 | VL_CDR3 |
|---|---|---|---|---|---|---|
| 90. | GGTFSSYA (SEQ ID NO: 286) | IIPIFGTA (SEQ ID NO: 326) | AREMYYY YGMDV (SEQ ID NO: 103) | QSISSY (SEQ ID NO: 567) | AAS (SEQ ID NO: 49) | QQSYSTPP T (SEQ ID NO: 534) |
| 91. | GGTFSSYA (SEQ ID NO: 286) | IIPIFGTA (SEQ ID NO: 326) | AREMYYY YGMDV (SEQ ID NO: 103) | QSISNY (SEQ ID NO: 563) | AAS (SEQ ID NO: 49) | QQSYSTPP T (SEQ ID NO: 534) |
| 92. | GFTFSNAW (SEQ ID NO: 270) | IKSKNDGG TT (SEQ ID NO: 329) | TTAPSLMD V (SEQ ID NO: 682) | NIGSKS (SEQ ID NO: 456) | DDS (SEQ ID NO: 159) | QVWDSSS DHPVV (SEQ ID NO: 608) |
| 93. | GYSFSTYW (SEQ ID NO: 298) | IYPGDSDT (SEQ ID NO: 377) | ARVGDGY SLDY (SEQ ID NO: 135) | KLGERF (SEQ ID NO: 405) | QYI (SEQ ID NO: 616) | QTWDGSIV V (SEQ ID NO: 583) |
| 94. | GFTFSSYG (SEQ ID NO: 275) | ISYDGSNK (SEQ ID NO: 362) | AKAITSIEP Y (SEQ ID NO: 60) | SGSVSTSY Y (SEQ ID NO: 641) | NTD (SEQ ID NO: 467) | VLYMGSGI WV (SEQ ID NO: 694) |
| 95. | GYSFSTYW (SEQ ID NO: 298) | IYPGDSDT (SEQ ID NO: 377) | ARVGDGY SLDY (SEQ ID NO: 135) | SSNIGRNY (SEQ ID NO: 652) | RNH (SEQ ID NO: 633) | ATWDDAL SGWV (SEQ ID NO: 149) |
| 96. | GGTFSSYA (SEQ ID NO: 286) | IIPIFGTA (SEQ ID NO: 326) | AREMYYY YGMDV (SEQ ID NO: 103) | QSISSY (SEQ ID NO: 567) | AAS (SEQ ID NO: 49) | QQSYSTPP T (SEQ ID NO: 534) |
| 97. | GFTFSSYA (SEQ ID NO: 273) | ISGSGGST (SEQ ID NO: 348) | AKNPYSNY VYWFDP (SEQ ID NO: 68) | SGRIASNY (SEQ ID NO: 639) | QDD (SEQ ID NO: 479) | QSYDSTTL V (SEQ ID NO: 580) |
| 98. | GFAFSSYG (SEQ ID NO: 262) | ISYDGSNK (SEQ ID NO: 362) | AKGQGDG MDV (SEQ ID NO: 66) | SSDVGGY NY (SEQ ID NO: 649) | GVS (SEQ ID NO: 295) | SSYTSSSTL VV (SEQ ID NO: 660) |
| 99. | GYKFANYW (SEQ ID NO: 296) | IYPGDSDT (SEQ ID NO: 377) | ARLGWGM DV (SEQ ID ID NO: 49) | QSISSY (SEQ ID NO: 567) | AAS (SEQ NO: 129) | QQSYSTPW T (SEQ ID NO: 535) |
| 100. | GYTFKNFG (SEQ ID NO: 301) | ISGRKGNT (SEQ ID NO: 347) | ARVWGDT TLGYGMD V (SEQ ID NO: 141) | QDISNY (SEQ ID NO: 485) | DAS (SEQ ID NO: 157) | QQYDNLPL T (SEQ ID NO: 542) |
| 101. | GFTFSSYE (SEQ ID NO: 274) | ISSSGSTI (SEQ ID NO: 351) | ARRRGGGF DY (SEQ ID NO: 132) | SSDVGGY NY (SEQ ID NO: 649) | DVS (SEQ ID NO: 201) | SSYTSSST WV (SEQ ID NO: 663) |
| 102. | GYSFTSYW (SEQ ID NO: 299) | IYPGDSDT (SEQ ID NO: 377) | AIPWDAEL GNYGMDV (SEQ ID NO: 59) | QSISSY (SEQ ID NO: 567) | AAS (SEQ ID NO: 49) | LQDYNYPP A (SEQ ID NO: 422) |
| 103. | GGTFSSYA (SEQ ID NO: 286) | IIPIFGTA (SEQ ID NO: 326) | ARGRWSG LGDY (SEQ ID NO: 113) | EDIRMY (SEQ ID NO: 215) | EGS (SEQ ID NO: 219) | QQYYDDP Q (SEQ ID NO: 555) |
| 104. | GGSISSSNW (SEQ ID NO: 284) | IYHSGST (SEQ ID NO: 365) | ARARGGR YFDY (SEQ ID NO: 72) | QGISTY (SEQ ID NO: 490) | AAS (SEQ ID NO: 49) | QQLNGYPT T (SEQ ID NO: 525) |
| 105. | GFTFSSYG (SEQ ID NO: 275) | ISYDGSNK (SEQ ID NO: 362) | AKGQGDG MDV (SEQ ID NO: 66) | SSNVGSRT (SEQ ID NO: 657) | SNN (SEQ ID NO: 644) | AAWDDSLI GHV (SEQ ID NO: 51) |
| 106. | GFTFSSYS (SEQ ID NO: 276) | ISSSSSYI (SEQ ID NO: 352) | ARDQLAA RRGYYYG MDV (SEQ ID NO: 89) | NIGTKS (SEQ ID NO: 459) | DDS (SEQ ID NO: 159) | QVWDSSS DHVV (SEQ ID NO: 610) |

TABLE 4-continued

| Combination # | VH_CDR1 | VH_CDR2 | VH_CDR3 | VL_CDR1 | VL_CDR2 | VL_CDR3 |
|---|---|---|---|---|---|---|
| 107. | GFDFNWYG (SEQ ID NO: 263) | IWYDGSNE (SEQ ID NO: 363) | ARDRRGSG WYEYFDY (SEQ ID NO: 95) | SSDVGGY NY (SEQ ID NO: 649) | EVS (SEQ ID NO: 237) | SSYTSSSTP V (SEQ ID NO: 662) |
| 108. | GFTFSSYG (SEQ ID NO: 275) | ISYDGSNK (SEQ ID NO: 362) | AKGDVNY GMDV (SEQ ID NO: 65) | NIGSKT SEQ ID NO: 457) | DGR (SEQ ID NO: 162) | QVWDTSG DLHWA (SEQ ID NO: 614) |
| 109. | GFTFSSYG (SEQ ID NO: 275) | ISYDGSDK (SEQ ID NO: 361) | AKDLSGLP IIDY (SEQ ID NO: 62) | SSDVGGY NY (SEQ ID NO: 649) | EVS (SEQ ID NO: 237) | SSYTSSSTL V (SEQ ID NO: 659) |
| 110. | GGSISSSNW (SEQ ID NO: 284) | IYHSGST (SEQ ID NO: 365) | ARDFYYGS GSYPNGYY YGMDV (SEQ ID NO: 77) | QSINSY (SEQ ID NO: 562) | TAS (SEQ ID NO: 667) | QQSYTTPL T (SEQ ID NO: 537) |
| 111. | GFTFSSYG (SEQ ID NO: 275) | ISYDGSNK (SEQ ID NO: 362) | AKGDVNY GMDV (SEQ ID NO: 65) | NIGSKS (SEQ ID NO: 456) | DDT (SEQ ID NO: 160) | QVWDSSS DLLWV (SEQ ID NO: 612) |
| 112. | GGTFSSYA (SEQ ID NO: 286) | IIPIFGTA (SEQ ID NO: 326) | ARDFNPFSI TIFEMDV (SEQ ID NO: 74) | SSNIGNNY (SEQ ID NO: 651) | DNN (SEQ ID NO: 190) | GTWDSSLS ALV (SEQ ID NO: 292) |
| 113. | GFTFSSYG (SEQ ID NO: 275) | ISYDGSNK (SEQ ID NO: 362) | AKGDVNY GMDV (SEQ ID NO: 65) | NIGSKT SEQ ID NO: 457) | DGR (SEQ ID NO: 162) | QVWDTSG DLHWA (SEQ ID NO: 614) |
| 114. | GFTFSSYG (SEQ ID NO: 275) | ISYDGSNK (SEQ ID NO: 362) | AKGDVNY GMDV (SEQ ID NO: 65) | NIGSKT (SEQ ID NO: 457) | DGR (SEQ ID NO: 162) | QVWDTSG DLHWA (SEQ ID NO: 614) |
| 115. | GFTFSSYG (SEQ ID NO: 275) | ISYDGSNK (SEQ ID NO: 362) | ANLAMGQ YFDY (SEQ ID NO: 70) | SSNIGSNT (SEQ ID NO: 654) | SNN (SEQ ID NO: 644) | AAWDDSL NGPV (SEQ ID NO: 52) |
| 116. | GGTFSSYA (SEQ ID NO: 286) | IIPIFGTA (SEQ ID NO: 326) | AREMYYY YGMDV (SEQ ID NO: 103) | QSIITY (SEQ ID NO: 560) | AAS (SEQ ID NO: 49) | QQSYSTPP T (SEQ ID NO: 534) |
| 117. | GFTFGDYA (SEQ ID NO: 266) | INTDGSIT (SEQ ID NO: 343) | ARDSHTVY YGSGSQDY (SEQ ID NO: 99) | SSDVGGY NY (SEQ ID NO: 649) | EVS (SEQ ID NO: 237) | SSYTSSSTL V (SEQ ID NO: 659) |
| 118. | GFTFSSYG (SEQ ID NO: 275) | ISYDGSNK (SEQ ID NO: 362) | ANLAMGQ YFDY (SEQ ID NO: 70) | SSNIGSNT (SEQ ID NO: 654) | SNN (SEQ ID NO: 644) | AAWDDSL NGPV (SEQ ID NO: 52) |
| 119. | GFTFSSYA (SEQ ID NO: 273) | ISYDGSNK (SEQ ID NO: 362) | ARDLGEA KSSSPHEP DY (SEQ ID NO: 84) | QSLLHSDG KTY (SEQ ID NO: 570) | EVS (SEQ ID NO: 237) | MQTKQLPL T (SEQ ID NO: 443) |
| 120. | GFTFSSYA (SEQ ID NO: 273) | ISYDGSNK (SEQ ID NO: 362) | ARDLGEA KSSSPHEP DY (SEQ ID NO: 84) | QSLLHSDG KTY (SEQ ID NO: 570) | EVS (SEQ ID NO: 237) | MQTKQLPL T (SEQ ID NO: 443) |
| 121. | GFTFSSYG (SEQ ID NO: 275) | ISYDGSNK (SEQ ID NO: 362) | AKGDVNY GMDV (SEQ ID NO: 65) | NIGSKT (SEQ ID NO: 457) | DGR (SEQ ID NO: 162) | QVWDTSG DLHWA (SEQ ID NO: 614) |
| 122. | GDSISSSSYY (SEQ ID NO: 261) | INHSGST (SEQ ID NO: 333) | ARDQEMY YFDY (SEQ ID NO: 88) | QGISSW (SEQ ID NO: 489) | AAS (SEQ ID NO: 49) | QQANSFPP T (SEQ ID NO: 515) |

TABLE 4-continued

| Combination # | VH_CDR1 | VH_CDR2 | VH_CDR3 | VL_CDR1 | VL_CDR2 | VL_CDR3 |
|---|---|---|---|---|---|---|
| 123. | GGSISRSNW (SEQ ID NO: 281) | IYHTGST (SEQ ID NO: 366) | ARGKGSY AFDI (SEQ ID NO: 110) | GGNIARNY (SEQ ID NO: 279) | EDD (SEQ ID NO: 214) | QSYDGNN HMV (SEQ ID NO: 578) |
| 124. | GFTFSSYG (SEQ ID NO: 275) | ISYDGSDK (SEQ ID NO: 361) | AKDLSGLP IIDY (SEQ ID NO: 62) | SSDVGGY NF (SEQ ID NO: 648) | EVS (SEQ ID NO: 237) | SSYTKNNS VV (SEQ ID NO: 658) |
| 125. | GFTFSSYG (SEQ ID NO: 275) | ISYDGNNK (SEQ ID NO: 360) | AKGYSSSP GDY (SEQ ID NO: 67) | SSDVGAY NY (SEQ ID NO: 647) | DVS (SEQ ID NO: 201) | SSYTSSSTL WV (SEQ ID NO: 661) |
| 126. | GGSISRSNW (SEQ ID NO: 281) | IYHTGST (SEQ ID NO: 366) | ARGKGSY AFDI (SEQ ID NO: 110) | GGNIARNY (SEQ ID NO: 279) | EDD (SEQ ID NO: 214) | QSYDGNN HMV (SEQ ID NO: 578) |

In some embodiments, the antibody is an scFv selected from Table 5, or any antibody having an antigen-binding domain derived from the scFv's in Table 5. In embodiments, the full length heavy chain and light chain variable regions are extracted from the scFv sequences in Table 5 and used to generate soluble Fab fragments, monoclonal antibodies, bispecific antibodies, or any other type of antibody known in the art. Where an scFv in Table 5 is a VH:VL scFv, it is possible to reverse the order of the heavy and light chains to generate a VL:VH scFv. Where an scFv in Table 5 is a VL: VH scFv, it is possible to reverse the order of the heavy and light chains to generate a VH: VL scFv.

TABLE 5

| Clone ID | scFv sequence |
|---|---|
| YU389-A01 | PGSSVKVSCKASGGTFSSYAISWVRQAPGQGLEWMGGIIPIFGTANYAQKFQGRVTITADESTSTAYMELSSLRSEDTAVYYCAREMYYYYGMDVWGQGTTVTVSSCAREMYYYYGMDVWDIQMTQSPSSLSASVGDRVTITCRASQSISSYLNWYQQKPGKAPKLLIYAASSLQSGVPSRFSGSGSGTDFTLTISSLQPEDFATYYCQQSYSTPPTFGQGTKVEIKCQQSYSTPPTF (SEQ ID NO: 728) |
| YU389-A02 | PGSSVKVSCKASGGTFSSYAISWVRQAPGQGLEWMGGIIPIFGTANYAQKFQGRVTITADESTSTAYMELSSLRSEDTAVYYCAREMYYYYGMDVWGQGTTVTVSSCAREMYYYYGMDVWEIVMTQSPSSLSASVGDRVTITCRASQSISSYLNWYQQKPGKAPKLLTYAASSLQSGVPSRFSGSGSGTDFTLTISSLQPEDFATYYCQQSYSTPPTFGPGTKVDIKCQQSYSTPPTF (SEQ ID NO: 729) |
| YU389-A03 | PSQTLSLTCTVSGGSISSGGYYWSWIRQHPGKGLEWIGYIYYSGSTYYNPSLKSRVTISVDTSKNQFSLKLSSVTAADTAVYYCARGNLWSGYYFWGQGTLVTVSSCARGNLWSGYYFWQSVLTQPPSVSAAPGQKVTISCSGSSSNIGNNFVSWYQQVPGTAPKLLTYDSTKRPAGIPDRFSGSKSGTSATLEIAGLQTGDEADYYCGSWDTNLSGYVFGTGTKVTVLCGSWDTNLSGYVF (SEQ ID NO: 730) |
| YU389-A04 | PGSSVKVSCKASGGTFSSYAISWVRQAPGQGLEWMGGIIPIFGTANYAQKFQGRVTITADESTSTAYMELSSLRSEDTAVYYCAREMYYYYGMDVWGQGTTVTVSSCAREMYYYYGMDVWDIQMTQSPSSLSASVGDRVTITCRASQSISSYLNWYQQKPGKAPKLLIYAASSLQSGVPSRFSGSGSGTDFTLTISSLQPEDFATYYCQQSYSTPPTFGQGTKVEIKCQQSYSTPPTF (SEQ ID NO: 731) |
| YU389-A05 | PGSSVKVSCKASGGTFSSYAISWVRQAPGQGLEWMGGIIPIFGTANYAQKFQGRVTITADESTSTAYMELSSLRSEDTAVYYCAREMYYYYGMDVWGQGTTVTVSSCAREMYYYYGMDVWDIQMTQSPSSLSASVGDRVTITCRASQSISSYLNWYQQKPGKAPKLLIYAASSLQSGVPSRFSGSGSGTDFTLTISSLQPEDFATYYCQQSYSTPPTFGQGTKVETNCQQSYSTPPTF (SEQ ID NO: 732) |
| YU389-A07 | PGSSVKVSCKASGGTFSSYAISWVRQAPGQGLEWMGGIIPIFGTANYAQKFQGRVTITADESTSTAYMELSSLRSEDTAVYYCAREMYYYYGMDVWGQGTTVTVSSCAREMYYYYGMDVWDIQMTQSPSSLSASVGDRVTITCRASQSISSYLNWYQQKPGKAPKLLIYAASSLQSGVPSRFSGSGSGTDFTLTISSLQPEDFATYYCQQSYSTPPTFGQGTKVETKCQQSYSTPPTF (SEQ ID NO: 733) |

TABLE 5-continued

| Clone ID | scFv sequence |
|---|---|
| YU389-B11 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWEIVMTQSPSSLSASVGDRVTITCR ASQSISSYLNWYQQKPGKAPKLLIYAASSLQSGVPSRFSGSGSGTDFTLT ISSLQPEDFATYYCQQSYSTPPTFGQGTKLEIKCQQSYSTPPTF (SEQ ID NO: 734) |
| YU389-D07 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWDIQMTQSPSSLSASVGDRVTITC RASQSISNYLNWYQQKPGKAPKLLIYAASSLQSGVPSRFSGSGSGTDFT LTISSLQPEDFATYYCQQSYSTPPTFGQGTKLEIKCQQSYSTPPTF (SEQ ID NO: 735) |
| YU390-A11 | PGRSLRLSCAASGFTFSSYGMHWVRQAPGKGLEWVAVISYDGSNKYY ADSVKGRFTISRDNSKNTLYLQMNSLRAEDTAVYYCAKELLEGAFDIW GQGTMVTVSSCAKELLEGAFDIWSYVLTQPPSLSVAPGQTARITCGGD NIETKSVHWYQQRPGQAPVLVVYDDDDRPSGIPERFSGSNSGNTATLTI SRVEAGDEADYYCQVWDSSSGHREVFGGRTKPALLCQVWDSSSGHRE VF (SEQ ID NO: 736) |
| YU390-A12 | PGASVKVSCKASGYTFTSYYMHWVRQAPGQGLEWMGIINPSGGSTSY AQKFQGRVTMTRDTSTSTVYMELSSLRSEDTAVYYCARDRVTMVRGA LAYWGQGTLVTVSSCARDRVTMVRGALAYWSYELTQPPSVSVSPGHT ATITCSGEKLGDKYVYWYQQKPGQSPLLVMYKDNKRPSATPERFSGSN SGDTATLTIRGTQAMDEADYYCQAWDSSTYVFGSGTKVTVLCQAWDS STYVF (SEQ ID NO: 737) |
| YU390-B12 | PGRSLRLSCAASGFTFSSYGMHWVRQAPGKGLEWVAVISYDGSNKYY ADSVKGRFTISRDNSKNTLYLQMNSLRAEDTAVYYCAKELLEGAFDIW GQGTMVTVSSCAKELLEGAFDIWSYVLTQPPSLSVAPGQTARITCGGD NIETKSVHWYQQRPGQAPVLVVYDDDDRPSGIPERFSGSNSGNTATLTI SRVEAGDEADYYCQVWDSSSGHREVFGGGTKLTVLCQVWDSSSGHRE VF (SEQ ID NO: 738) |
| YU390-C03 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWDIQMTQSPSSLSASVGDRVTITC RASQSISSYLNWYQQKPGKAPKLLIYAASSLQSGVPSRFSGSGSGTDFTL TISSLQPEDFATYYCQQSYSTPPTFGQGPKVEIKCQQSYSTPPTF (SEQ ID NO: 739) |
| YU390-C11 | PGASAKVSCKASGYTFTSYGISWVRQAPGQGLEWMGWISAYNGNTNY AQKLQGRVTMTTDTSTSTAYMELRSLRSDDTAVYYCARERSYYGMDV WGQGTTVTVSSCARERSYYGMDVWTQSPATLSVSPGESATLSCRASQS VSNYLAWYQQKPGQAPRLLIYGASTRATGIPARFSGSGSGTEFTLTISSL QSEDFAVYYCQQYNHWPPLFGGGTKVETKCQQYNHWPPLF (SEQ ID NO: 740) |
| YU390-D01 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWDIQMTQSPSSLSASVGDRVTITC RASQSISSYLNWYQQKPGKAPKLLIYAASSLQSGVPSRFSGSGSGTDFTL TISSLQPEDFATYYCQQSYSTPPTFGQGPKVELKCQQSYSTPPTF (SEQ ID NO: 741) |
| YU390-D03 | PGSSVKVSCKVSGGTFSSYAISWVRQAPGQGLEWMGGIMPIFDTAEYA QKFQGRVTITADESTSTAYMELSTLRSEDTAVYYCASWSERIGYQYGL DVWGQGTTVTVSSCASWSERIGYQYGLDVWDIRMTQSPSTLSASVGD RVSITCRASQTISQWLAWFHQKPGKAPKWYKASRLESGVSSRFSGSGS GTEFTLTITSLQPDDIGTYYCQQYSGDSMYTFGQGTRLEIRCQQYSGDS MYTF (SEQ ID NO: 742) |
| YU390-D05 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWDIQMTQSPSSLSASVGDRVTITC RASQSISSYLNWYQQKPGKAPKLLIYAASSLQSGVPSRFSGSGSGTDFTL TISSLQPEDFATYYCQQSYSTPPTFGQGTKVETCQQSYSTPPTF (SEQ ID NO: 743) |
| YU390-D11 | PGASAKVSCKASGYTFTSYGISWVRQAPGQGLEWMGWISAYNGNTNY AQKLQGRVTMTTDTSTSTAYMELRSLRSDDTAVYYCARERSYYGMDV WGQGTTVTVSSCARERSYYGMDVWTQSPATLSVSPGESATLSCRASQS VSNYLAWYQQKPGQAPRLLIYGASTRATGIPARFSGSGSGTEFTLTISSL QSEDFAVYYCQQYNHWPPLFGGGTKVEIKCQQYNHWPPLF (SEQ ID NO: 744) |

TABLE 5-continued

| Clone ID | scFv sequence |
|---|---|
| YU390-G03 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWDIQMTQSPSSLSASVGDRVTITC RASQSISSYLNWYQQKPGKAPKLLIYAASSLQSGVPSRFSGSGSGTDFTL TISSLQPEDFATYYCQQSYSTPPTFGQGTKVELKCQQSYSTPPTF (SEQ ID NO: 745) |
| YU390-H11 | PGASAKVSCKASGYTFTSYGISWVRQAPGQGLEWMGWISAYNGNTNY AQKLQGRVTMTTDTSTSTAYMELRSLRSDDTAVYYCARERSYYGMDV WGQGTTVTVSSCARERSYYGMDVWTQSPATLSVSPGESATLSCRASQS VSNYLAWYQQKPGQAPRLLIYGASTRATGIPARFSGSGSGTEFTLTISSL QSEDFAVYYCQQYNHWPPLFGGGNGGEIKCQQYNHWPPLF (SEQ ID NO: 746) |
| YU392-A05 | PGASVKVSCKASGYTFTSYYMHWVRQAPGQGLEWMGIINPSGGSTSY AQKFQGRVTMTRDTSTSTVYMELSSLRSEDTAVYYCARDILGLDYWG QGTLVTVSSCARDILGLDYWQPGLTQPPSASETPGQRVTISCSGSSSNIG SNYVYWYQQLPGTAPKLLIYRNNQRPSGVPGRFSGSKSGTSASLAISGL RSEDEADYYCAAWDDSLSGVVFGGGTKLTVCAAWDDSLSGVVF (SEQ ID NO: 747) |
| YU392-A07 | PGATVKISCKVSGYTFTDYYMHWVQQAPGKGLEWMGLVDPEDGETIY AEKFQGRVTITADTSTDTAYMELSSLRSEDTAVYYCATEDTAMGGIDY WGQGTLVTVSSCATEDTAMGGIDYWQPVLTQSPSASGTPGQRVTISCS GSSSNIGSNYVYWYQQLPGTAPKLLIYSNNQRPSGVPDRFSGSKSGTSA SLAISGLQSEDEADYYCAAWDDSLNGVVFGGGTKLTVLCAAWDDSLN GVVF (SEQ ID NO: 748) |
| YU392-A09 | PGATVKISCKVSGYTFTDYYMHWVQQAPGKGLEWMGLVDPEDGETIY AEKFQGRVTITADTSTDTAYMELSSLRSEDTAVYYCATEGRYGMDVW GQGTTVTVSSCATEGRYGMDVWQAVLTQPPSVSGTPGQRVTISCSGNN FNIGNNLVYWYQQLPGTAPKLLIYANDERPSGVPDRFSGSKSGTSASLA ISGLRSEDDADYYCATWDDSLSGVVFGGGTKLTALCATWDDSLSGVV F (SEQ ID NO: 749) |
| YU392-B11 | PGATVKISCKVSGYTFTDYYMHWVQQAPGKGLEWMGLVDPEDGETIY AEKFQGRVTITADTSTDTAYMELSSLRSEDTAVYYCAVEGGRAPGTYY YDSSGLAYWGQGTLVTVSSCAVEGGRAPGTYYYDSSGLAYWQAGLT QPPSASGTPGQRVTISCSGSSSNIGSNYVYWYQQLPGTAPKLLIYSNNQR PSGVPDRFSGSKSGTSASLAISGLRSEDEADYYCATWDDSLSGVVFGGG TKLTVLCATWDDSLSGVVF (SEQ ID NO: 750) |
| YU393-A01 | PSQTLSLTCAVSGGSISSGGYSWSWIRQPPGKGLEWIGYIYHSGSTYYNP SLKSRVTISVDRSKNQFSLKLSSVTAADTAVYYCARAGYYYGMDVWG QGTTVTVSSCARAGYYYGMDVWDIVMTQTPSSLSASVGDRVAITCQA SRNIWSYVNWYQQKPGEAPRLLIYGASTLQRGVPSRFSGSGSGTGFTLT INSLQPEDFATYFCQQSHSTPITFGGGTRVDIKCQQSHSTPITF (SEQ ID NO: 751) |
| YU393-A02 | PGSSVKVSCKASGGTFSSYAISWVRQAPGQGLEWMGGIIPIFGTANYAQ KFQGRVTITADKSTSTAYMELSSLRSDDTAVYYCARDLGTMVRGVIEP YYFDYWGQGTLVTVSSCARDLGTMVRGVIEPYYFDYWDIQMTQSPST LSASVGDRVTITCRASQSISSWLAWYQQKPGKAPKLLIYDAFSLESGVP SRFSGSGSGTEFTLTISSLQPDDFATYYCQQYNSYSRTFGQGTKVEIKCQ QYNSYSRTF (SEQ ID NO: 752) |
| YU393-A03 | PSGTLSLTCAVSGGSISSSNWWSWVRQPPGKGLEWIGEIYHSGSTNYNP SLKSRVTISVDKSKNQFSLKLSSVTAADTAVYYCARGVRGTGFDPWGQ GTLVTVSSCARGVRGTGFDPWTQSPGTLSVSPGERATLSCRASQSVSSR LAWYQQKPGQAPRLLIYGASTRATGIPARFSGSGSGTEFTLTISSLQSED FAVYFCQQYTNWPQTFGQGTKVEIKCQQYTNWPQTF (SEQ ID NO: 753) |
| YU393-A04 | PGASVKVSCKASGYTFTSYGISWVRQAPGQGLEWMGWISAYNGNTNY AQKLQGRVTMTTDTSTSTAYMELRSLRSDDTAVYYCARDRNGYFQH WGQGTLVTVSSCARDRNGYFQHWDIVMTQTPSTLSASVGDRVTITCRA SQTISGLLAWYQQKPGKAPNLLIYGASNSQSGVPSRFTGSGSGTEFTLTI TNLQPDDFATYYCLQYDRYSGAFGQGTKLEIKCLQYDRYSGAF (SEQ ID NO: 754) |
| YU393-A08 | PGRSLRLSCAASGFTFSSYGMHWVRQAPGKGLEWVAVISYDGSNKYY ADSVKGRFTISRDNSKNTLYLQMNSLRAEDTAVYYCAKDLLGELSFFD YWGQGTLVTVSSCAKDLLGELSFFDYWSVLTQPPSVSVAPGQTARIPC GGDDIESEMVHWYQQKPGQAPVLVVYDDSVRPSGIPERFSGSNSGNTA TLIISGVEAGDEAAYYCQVWHTTNDHVLFGGGTNLTVLCQVWHTTND HVLF (SEQ ID NO: 755) |

TABLE 5-continued

| Clone ID | scFv sequence |
|---|---|
| YU393-A09 | PGDLWKISCKGSGYSFTSYWIGWVRQMPGKGLEWMGIIYPGDSDTRYSPSFQGQVTISADKSISTAYLQWSSLKASDTAMYYCARLENNWDYGGWFDPWGQGTLVTVSSCARLENNWDYGGWFDPWSYVLTQPPSVSVAPGQTARITCGGNNIGSKSVHWYQQKPGQAPVLVVYDDSDRPSGIPERFSGSNSGNTATLTISRVEAGDEADYYCQVWDSSSDHWVFGGGTKLTVLCQVWDSSSDHWVF (SEQ ID NO: 756) |
| YU393-A11 | PGESLKISCKGSGYSFTSYWIGWVRQMPGKGLEWMGIIYPGDSDTRYSPSFQGQVTISADKSISTAYLQWSSLKASDTAMYYCARLENNWDYGGWFDPWGQGTLVTVSSCARLENNWDYGGWFDPWSYVLTQPPSVSVAPGQTARITCGGNNIGSKSVHWYQQKPGQAPVLVVYDDSDRPSGIPERFSGSNSGNTATLTISRVEAGDEADYYCQVWDSSSDHWVFGGGTKLTVLCQVWDSSSDHWVF (SEQ ID NO: 757) |
| YU393-B02 | PGSSVKVSCKASGGTFSSYAISWVRQAPGQGLEWMGGIIPIFGTANYAQKFQGRVTITADKSTSTAYMELSSLRSEDTAVYYCARDRSYYGMDVWGQGTTVTVSSCARDRSYYGMDVWDIRLTQSPSSLSASVGDRVTITCRASQSIGNYLNWYQQRLGEAPKVLIYAATRLQRGVPSRFSASASGTDFTLTISSLQPEDFTTYYCQQSKQIPYTFGQGTKLQIKCQQSKQIPYTF (SEQ ID NO: 758) |
| YU393-B03 | PGSSVKVSCKASGGTFSSYAISWVRQAPGQGLEWMGGIIPIFGTANYAQKFQGRVTITADKSTSTAYMELSSLRSEDTAVYYCARDKGYYGMDVWGQGTTVTVSSCARDKGYYGMDVWDIQMTQSPSSVSASVGDRVTITCRASQGISSWLAWYQQKPGKAPKLLIYAVSSLQSGVPSRFSGSGSGTDFTLTISSLQPEDFATYYCQQSYSLPLTFGGGTEVLIKCQQSYSLPLTF (SEQ ID NO: 759) |
| YU393-B04 | PGSSVKVSCKASGGTFSSYAISWVRQAPGQGLEWMGGIIPIFGTANYAQKFQGRVTITADESTSTAYMELSSLRSEDTAVYYCARDRSYYGMDVWGQGTTVTVSSCARDRSYYGMDVWDIQMTQSPSSLSASVGDRVTITCRASQSIGNYLNWYQQRLGEAPKVLIYAATRLQRGVPSRFSAGASGTDFTLTISSLQPEDFTTYYCQQSKQIPYTFGQGTKLQIKCQQSKQIPYTF (SEQ ID NO: 760) |
| YU393-B05 | PGRSLRLSCAASGFTFSNYGMHWVRQAPGKGLEWVAVISHDGHVKWHGDSVKGRFTISRDNSKNTLYLQLDSLRTEDTAVYYCAKEISPRSSVGWPLDYWGQGTLVTVSSCAKEISPRSSVGWPLDYWTQSPGTLSLSPGERATLSCRADQSVSSTYLAWYQQRPGQAPRLLIYGASNRATGIPDRFSGSGSGSDFTLTISRLEPEDFAVYYCQQFDISGGLIFGPGTKVDIKCQQFDISGGLIF (SEQ ID NO: 761) |
| YU393-B06 | PGRSLRLSCAASGFTFSSSAMHWVRQAPGKGLEWVAVISYDGSNKYYADSVKGRFTISRDKAKNSLYLQMNSLRAEDTAVYYCARDFWSGYNELGGMDVWGQGTTVTVSSCARDFWSGYNELGGMDVWEIVMTQSPSSLSASVGDRVTITCQASQDISNYLNWYQQKPGKAPKLLIYDASNLETGVPSRFSGSGSGTDFTFTISSLQPEDIATYYCQQYDNLPLTFGGGTKVEIKCQQYDNLPLTF (SEQ ID NO: 762) |
| YU393-B07 | PGGSLRLSCAASGFTFSSYWMSWVRQAPGKGLEWVANIKQDGSEKYYVDSVKGRFTISRDNAKNSLYLQMNSLRAEDTAVYYCARTWFGEFFDYWGQGTLVTVSSCARTWFGEFFDYWSVLTQPPSVSVAPGQTARVTCGGNNIESESVHWYQQKPGQAPVLVVYDDSARPSGIPERFSGSNSGNTATLTISRVEAGDEADYYCQVWDSSSDHTVAFGGGTKLAVLCQVWDSSSDHTVAF (SEQ ID NO: 763) |
| YU393-B08 | PGASVKVSCKASGYTFTSYGISWVRQAPGQGLEWMGWISAYNGNTNYAQKLQGRVTMTTDTSTSTAYMELRSLRSDDTAVYYCARVIGGWFDPWGQGTLVTVSSCARVIGGWFDPWQSALTQPASVSGSPGQSITISCTGTSSDVGAYNYVSWYQQQPGKAPELMIYGVSHRPSRVSNRFSGSKSGNTASLTISGLQTEDEADYYCSSYTTTDTFVLGSGTKVTVLCSSYTTTDTFVL (SEQ ID NO: 764) |
| YU393-C02 | PGRSLRLSCAASGFIFSRHAMHWVRQAPDKGLEWVAVISYDGSNKYYADSVKGRFTISRDNPKNTLYLQMNSLRAEDTAVYYCARGRLAYGDTEGFDYWGQGTLVTVSSCARGRLAYGDTEGFDYWDIVMTQSPSSLSASVGDRVTITCQASQDINNYLSWFQHKPGKAPKLLIYDASDLETGVPSRFSGSGSGPEFSFTITNLQPEDVATYYCQQYDNLPYTFGQGTKVEIRCQQYDNLPYTF (SEQ ID NO: 765) |
| YU393-C03 | PGASVKVSCKASGYTFNNYGLAWVRQAPGQGLEWMGWISVYNGDINYAQKFQGRVTMTTDRATRTAYMELRSLISDDTAVYYCARDILRGESSILDHWGQGTLVTVSCARDILRGESSILDHWDIVMTQSPSSLSASVGDRVTITCRASQGISNSLAWYQQKPGKAPKLLLYAASRLESGVPSRFSGSGSGTDYTLTISSLQPEDFATYYCQQYYSTPPHFGGGTKVEIKCQQYYSTPPHF (SEQ ID NO: 766) |

TABLE 5-continued

| Clone ID | scFv sequence |
|---|---|
| YU393-C05 | PGSSVKVSCKASGGTFSSYAISWVRQAPGQGLEWMGGIIPIFGTANYAQ KFQGRVTITADESTSTAYMELSSLRSDDTAVYYCARDRYYYGMDVWG QGTTVTVSSCARDRYYYGMDVWAIRMTQSPSSLSASVGDRVTITCRAS QSISSYLNWYQQKPGKAPKLLIYAASSLQSGVPSRFSGSGSGTDFTLTIS SLQPEDFATYYCQQSYSTPLTFGGGTKVEIKCQQSYSTPLTF (SEQ ID NO: 767) |
| YU393-C07 | PGRSLRLSCAASGFTFSSYAMEIWVRQAPGKGLEWVAVISYDGSNKYY ADSVKGRFTISRDNSKNTLYLQMNSLRAEDTAVYYCARDLLGSGYDII DYWGQGTLVTVSSCARDLLGSGYDIIDYWSYVLTQPPSVSVAPGQTAR ITCGGNNIGSKSVHWYQQKPGQAPVLVVYDDSDRPSGIPERFSGSNSGN TATLTISRVEAGDEADYYCQVWDSSSDHVVFGGGTKLTVLCQVWDSS SDHVVF (SEQ ID NO: 768) |
| YU393-C08 | PGASVKVSCKASGYTFTSYGISWVRQAPGQGLEWMGWISAYNGNTNY AQKLQGRVTMTTDTSTSTAYMELRSLRSDDTAVYYCARVWGKNGDF DYWGQGTLVTVSSCARVWGKNGDFDYWQSVLTQPPSVSAAPGQKVTI SCSGSSSNIGNNYVSWYQQLPGTAPKWYDNNKRPSGIPDRFSGSKSGT SATLGITGLQTGDEADYYCGTWDSSLSAYVFGTGTKVTVLCGTWDSSL SAYVF (SEQ ID NO: 769) |
| YU393-D03 | PGASVKVSCKASGYTFTTYAMNWVRQAPGQGLEWMGGINTNTGDPT YAQGSTGRFVFSSDTSVSTAYLQISSLKPEDTAVYYCARDRFHYGMDV WGQGTTVTVSSCARDRFHYGMDVWTQSPDTLSVSPGDGATLSCRASE GIRTSVAWYQQRPGQAPRLLIYGASTRAAGVPARFSGSGSGTEFTLTISS LQSDDFAVYYCQQTHTWPWTFGQGTKAEIKCQQTHTWPWTF (SEQ ID NO: 770) |
| YU393-D04 | PGASVKVSCKASGYTFTSYGISWVRQAPGQGLEWMGWISAYNGNTNY AQKLQGRVTMTTDTSTSTAYMELRSLRSDDTAVYYCARDRGDYWGQ GTLVTVSSCARDRGDYWDIQMTQSPSSVSASVGDRVTITCRASQGTSS WLAWYQQKPGKAPKLLIYAASSLQSGVPSRFSGSGSGTDFTLTISSLQP EDFATYYCQQANSFPLTFGGGTKVEIKCQQANSFPLTF (SEQ ID NO: 771) |
| YU393-D05 | PGGSLRLSCAASGFTFNNAWMSWVRQAPGKGLEWVGRIKSKTDGGTT DYGAPVKGRFTISRDDSKNTLYLQMNSLKTEDTAVYYCTTEGVELLSF GGAPFDYWGQGTLVTVSSCTTEGVELLSFGGAPFDYWDIQMTQSPSSL SASVGDRVTITCRASQSISSYLNWYQQKPGKAPKLLIYAASSLQSGVPS RFSGSGSGTDFTLTISSLQPEDFATYYCQQSYSTPYTFGQGTKLEIKCQQ SYSTPYTF (SEQ ID NO: 772) |
| YU393-D07 | PGGSLRLSCAASGFTFSSYEMNWVRQAPGKGLEWVSYISSSGSTIYYAD SVKGRFTISRDNAKNSLYLQMNSLRAEDTAVYYCARRRGGGFDYWGQ GTLVTVSSCARRRGGGFDYWQSALTQPASVSGSPGQSITISCTGTSSDV GGYNYVSWYQQHPGKAPKLMIYDVSNRPSGVSNRFSGSKSGNTASLTI SGLQAEDEADYYCSSYTSSSTYVFGTGTKVTVLCSSYTSSSTYVF (SEQ ID NO: 773) |
| YU393-E04 | PGGSLRLSCAASGFTFSSYWMSWVRQAPGKGLEWVANIKQDGSEKYY VDSVGGRFTISRDNAKNSLYLQMNSLRAEDTAVYYCAREKGSWFDPW GQGTLVTVSSCAREKGSWFDPWTQSPGTLSLSPGERATLSCRASQSVSN NYLAWYQQKPGQAPRLLIYGASSRATGIPDRFSGNGSGTDFTLTISRLEP EDFAVYYCQRYGSSPRFGGGTKVEIKCQRYGSSPRF (SEQ ID NO: 774) |
| YU393-E05 | PGSSVKVSCKASGGTFSSYAISWVRQAPGQGLEWMGGIIPIFGTANYAQ KFQGRVTITADKSTSTAYMELSSLRSEDTAVYYCARDKGYYGMDVWG QGTTVTVS SCARDKGYYGMDVWMTQSPSFLSASVGDRVTITCRASQGI NSYLVWYKQKPGKAPDLLIYAASTLQSGVPSRFSGSGSGTDFTLTISSLQ PEDFATYYCQQVHSFPFTFGPGTKVEIKCQQVHSFPFTF (SEQ ID NO: 775) |
| YU393-E07 | PGGSLRLSCAASGFTFSSYGINWVRQAPGKGLEWVSYISSRGSTILYADS VKGRFTISRDNARNSVHLQMNSLRDEDTAVYYCARDRGDRVGGLVFD YWGQGSLVTVSSCARDRGDRVGGLVFDYWVLTQPPSVSVAPGQTARI TCGGNNIGSKSVHWYQQKPGQAPVLVVYDDSDRPSGIPERFSGSNSGN TATLTISRVEAGDEADYYCQVWDSSSDHVVFGGGTKLTVLCQVWDSS SDHVVF (SEQ ID NO: 776) |
| YU393-F03 | PGESLKISCKGSGYSFTTYWIAWVRQMPGKGLEWMGIIYPGDSDTTYSP SFQGQVTISADKSITTTYLQWSSLKASDTAMYYCARQVAGGLDYWGQ GTLVTVSSCARQVAGGLDYWDIVLTQSPSSLSASVGDRVTITCRASQAV RIDLSWYQQKPGKAPERLIFGASGLQRGVPSRFSGSGSGTEFTLTISSLQP EDFATYYCLQHNTFPYTFGQGTKLEIKCLQHNTFPYTF (SEQ ID NO: 777) |
| YU393-F04 | PGASVKVSCKASGYTFTSYGISWVRQAPGQGLEWMGWISAYNGNTNY AQKLQGRVTMTTDTSTSTAYMELRSLRSDDTAVYYCARDRGYYGMD |

TABLE 5-continued

| Clone ID | scFv sequence |
|---|---|
| | VWGQGTTVTVSSCARDRGYYGMDVWDIQMTQSPSSLSASVGDRVTIT CRASQSISRYLNWYQQKPGKDPKLLIYAASSLQSGVPSRFSGSGSGTDF TLTISSLQPEDFATYYCQQSHSTPLTFGGGTKVEIKCQQSHSTPLTF (SEQ ID NO: 778) |
| YU393-F06 | PGESLKISCKGSGYSFTSYWIGWVRQMPGKGLEWMGIIYPGDSDTRYSP SFQGQVTISADKSISTAYLQWSSLKASDTAMYYCFRFGEGFDYWGQGT LVTVSSCFRFGEGFDYWMTQSPSTLSASVGDRVTITCRASQSIGYWLA WYQQRPGRAPKLLMYRASNLKSGVPSRFSGSGSGTEFTLTISSLQPDDF ATYYCQQYNSYPFTFGPGTKVDIKCQQYNSYPFTF (SEQ ID NO: 779) |
| YU393-F07 | PGESLKISCKGSGYSFTTYWIAWVRQMPGKGLEWMGIIYPGDSDTTYSP SFQGQVTISADKSITTTYLQWSSLKASDTAMYYCARQVAGGLDYWGQ GTLVTVSSCARQVAGGLDYWQSVLTQPPSASGTPGQRVTISCSGSSSNV GSNYVSWYQQLPGTAPKLLIQRNNRRPSGVPDRFSGSKSGTSASLAISG LRSEDEADYYCAAWDDSLSGVVFGGGTKLTVLCAAWDDSLSGVVF (SEQ ID NO: 780) |
| YU393-G01 | PGESLKISCKSSGYSFNTYWIGWVRQMPGKGLEWMGIIYPSDSDTRYSP SFQGQVTISADKSINTAYLQWSSLKASDSAMYYCARDGGYYFDDWGQ GTLVTVSSCARDGGYYFDDWTQSPGTLSLSPGERATLSCRASQSVSSTY LAWYQQKPGQAPRLLIYGTSRRATGIPDRFSGSGSGTDFTLTISRLEPED FAVYYCQQYNSSPLMYTFGQGTRLEIKCQQYNSSPLMYTF (SEQ ID NO: 781) |
| YU393-G03 | PGSSVKVSCKASGGTFSSYAISWVRQAPGQGLEWMGGIIPIFGTANYAQ KFQGRVTITADKSTSTAYMELSSLRSEDTAVYYCARDKGYYGMDVWG QGTTVTVSPCARDKGYYGMDVWDIVMTQSPSSLSASIGDRVTITCRAS QSIKNYLNWYQQKPGKAPKLLIYAASSLQNGVPSRFSGSGSGTDFTVTI SSLQPEDFAIYYCQQTYSTPLTFGGGTNVEIKCQQTYSTPLTF (SEQ ID NO: 782) |
| YU393-G04 | PGSSVKVSCKASGYTFTSYGISWVRQAPGQGLEWMGWISAYNGNTNY AQKLQGRVTMTTDTSTSTAYMELRGLRSDDTAVYYCARDFRMDVWG QGTTVTVSSCARDFRMDVWDIRLTQSPSSVASSVGDSVTVTCRASQDIK RRLAWYLQKPGQAPKLLIFDASRLHTGVPSRFSGSGSGTDFTLIINSLQP EDFGTYYCQQANTFPQTFGQGTKVEIKCQQANTFPQTF (SEQ ID NO: 783) |
| YU393-G07 | PGGSLRLSCAASGFTFRRYWMTWVRQAPGKGLEWVANIKQDGSEKYY VDSVKGRFAVSRDNANNSLYLRMNSLRAEDTAVYYCARDAYAYGLD VWGQGTAVTVSSCARDAYAYGLDVWVLTQPHSVSESPGKTVTISCTGS SGSIASSYVHWYQQRPGRVPTPVIYEDNQRPSGVPDRFSGSIDSSSNSAS LTISGLKTEDEADYYCQSYDGSSVVFGGGTKLTVLCQSYDGSSVVF (SEQ ID NO: 784) |
| YU393-G08 | PGDLRKISCKGSGYSFTSYWIGWVRQMPGKGLEWMGIIYPGDSDTRYS PSFQGQVTISADKSISTAYLQWSSLKASDTAMYYCARLENNWDYGGW FDPWGQGTLVTVSSCARLENNWDYGGWFDPWSYVLTQPPSVSVAPGQ TARITCGGNNIGSKSVHWYQQKPGQAPVLVVYDDSDRPSGIPERFSGSN SGNTATLTISRVEAGDEADYYCQVWDSSSDHWVFGGGTKLTVLCQVW DSSSDHWVF (SEQ ID NO: 785) |
| YU393-G11 | PGNLWKISCKGSGYSFTSYWIGWVRQMPGKGLEWMGIIYPGDSDTRYS PSFQGQVTISADKSISTAYLQWSSLKASDTAMYYCARLENNWDYGGW FDPWGQGTLVTVSSCARLENNWDYGGWFDPWSYVLTQPPSVSVAPGQ TARITCGGNNIGSKSVHWYQQKPGQAPVLVVYDDSDRPSGIPERFSGSN SGNTATLTISRVEAGDEADYYCQVWDSSSDHWVFGGGTKLTVLCQVW DSSSDHWVF (SEQ ID NO: 786) |
| YU393-G12 | PGNLLKISCKGSGYSFTSYWIGWVRQMPGKGLEWMGIIYPGDSDTRYS PSFQGQVTISADKSISTAYLQWSSLKASDTAMYYCARLENNWDYGGW FDPWGQGTLVTVSSCARLENNWDYGGWFDPWSYVLTQPPSVSVAPGQ TARITCGGNNIGSKSVHWYQQKPGQAPVLVVYDDSDRPSGIPERFSGSN SGNTATLTISRVEAGDEADYYCQVWDSSSDHWVFGGGTKLTVLCQVW DSSSDHWVF (SEQ ID NO: 787) |
| YU393-H03 | PSGTLSLTCAVSGGSISSSNWWSWVRQPPGKGLEWIGEIYHSGSTNYNP SLKSRVTISVDKSKNQFSLKLSSVTAADTAVYYCARDLMNYGMDVWG QGTTVTVSSCARDLMNYGMDVWMTQSPSSLSASVGDRVTITCRASQSI SSYLNWYQQKPGKAPKLLIYAASSLQSGVPSRFSGSGSGTDFTLTISSLQ PEDFATYYCQQSYSTPPTFGQGTKVEIKCQQSYSTPPTF (SEQ ID NO: 788) |
| YU393-H07 | PGRSLRLSCAASGFTFSSYAMEIWVRQAPGKGLEWVAVISYDGSNKYY ADSVKGRFTISRDSSKNTLYLQMNSLRAEDTAVYYCARDLLGSGYDIID YWGQGTLVTVSSCARDLLGSGYDIIDYWVLTQSPSVSVAPGKTARITC GGNNIGSKSVHWYQQKPGQAPVLVVYDDSDRPSGIPERFSGSN SGNTA |

TABLE 5-continued

| Clone ID | scFv sequence |
|---|---|
| | TLTISRVEAGDEADYYCQVWDSSSDHVVFGGGTKLTVLCQVWDSSSD HVVF (SEQ ID NO: 789) |
| YU393-H09 | PGDL*KISCKGSGYSFTSYWIGWVRQMPGKGLEWMGIIYPGDSDTRYSP SFQGQVTISADKSISTAYLQWSSLKASDTAMYYCARLENNWDYGGWF DPWGQGTLVTVSSCARLENNWDYGGWFDPWSYVLTQPPSVSVAPGQT ARITCGGNNIGSKSVHWYQQKPGQAPVLVVYDDSDRPSGIPERFSGSNS GNTATLTISRVEAGDEADYYCQVWDSSSDHWVFGGGTKLTVLCQVW DSSSDHWVF (SEQ ID NO: 790) |
| YU394-A01 | PGGSLRLSCAASGFTFSSYWMSWVRQAPGKGLEWVANIKQDGSEKYY VDSVKGRFTISRDNAKNSLYLQMNSLRAEDTAVYYCAREYDYGDYVF DYWGQGTLVTVSSCAREYDYGDYVFDYWYELTQPPSMSATPGQKVTI TCSGSNSNVGNNYVSWYQQVPGTAPKWYDNDRRPSGIPDRFSGAKS GTSATLGITGLQTGDEADYYCGSWEARESVFVFGGGTKLTVCGSWEAR ESVFVF (SEQ ID NO: 791) |
| YU394-A02 | PGDLLKISCKGSGYSFTSYWIGWVRQMPGKGLEWMGHYPGDSDTRYS PSFQGQVTISADKSISTAYLQWSSLKASDTAMYYCARLENNWDYGGW FDPWGQGTLVTVSSCARLENNWDYGGWFDPWSYVLTQPPSVSVAPGQ TARITCGGNNIGSKSVHWYQQKPGQAPVLVVYDDSDRPSGIPERFSGSN SGNTATLTISRVEAGDEADYYCQVWDSSSDHWVFGGGTKLTVLCQVW DSSSDHWVF (SEQ ID NO: 792) |
| YU394-A07 | RGDLLKISCKGSGYSFTSYWIGWVRQMPGKGLEWMGIIYPGDSDTRYS PSFQGQVTISADKSISTAYLQWSSLKASDTAMYYCARLENNWDYGGW FDPWGQGTLVTVSSCARLENNWDYGGWFDPWSYVLTQPPSVSVAPGQ TARITCGGNNIGSKSVHWYQQKPGQAPVLVVYDDSDRPSGIPERFSGSN SGNTATLTISRVEAGDEADYYCQVWDSSSDHWVFGGGTKLTVLCQVW DSSSDHWVF (SEQ ID NO: 793) |
| YU394-A09 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWDIVMTQSPSSLSASVGDRVTITC RASQSISSYLNWYQQKPGKAPKLLIYAASSLQSGVPSRFSGSGSGTDFTL TISSLQPEDFATYYCQQSYSTPPTFGQGTKVEIKCQQSYSTPPTF (SEQ ID NO: 794) |
| YU394-C01 | PGDPLKISCKGSGYSFTSYWIGWVRQMPGKGLEWMGIIYPGDSDTRYS PSFQGQVTISADKSISTAYLQWSSLKASDTAMYYCARLENNWDYGGW FDPWGQGTLVTVSSCARLENNWDYGGWFDPWSYVLTQPPSVSVAPGQ TARITCGGNNIGSKSVHWYQQKPGQAPVLVVYDDSDRPSGIPERFSGSN SGNTATLTISRVEAGDEADYYCQVWDSSSDHWVFGGGTKLTVLCQVW DSSSDHWVF (SEQ ID NO: 795) |
| YU394-E02 | PGDFLKISCKGSGYSFTSYWIGWVRQMPGKGLEWMGIIYPGDSDTRYS PSFQGQVTISADKSISTAYLQWSSLKASDTAMYYCARLENNWDYGGW FDPWGQGTLVTVSSCARLENNWDYGGWFDPWSYVLTQPPSVSVAPGQ TARITCGGNNIGSKSVHWYQQKPGQAPVLVVYDDSDRPSGIPERFSGSN SGNTATLTISRVEAGDEADYYCQVWDSSSDHWVFGGGTKLTVLCQVW DSSSDHWVF (SEQ ID NO: 796) |
| YU394-H01 | PGEFRKISCKGSGYSFTSYWIGWVRQMPGKGLEWMGIIYPGDSDTRYSP SFQGQVTISADKSISTAYLQWSSLKASDTAMYYCARLENNWDYGGWF DPWGQGTLVTVSSCARLENNWDYGGWFDPWSYVLTQPPSVSVAPGQT ARITCGGNNIGSKSVHWYQQKPGQAPVLVVYDDSDRPSGIPERFSGSNS GNTATLTISRVEAGDEADYYCQVWDSSSDHWVFGGGTKLTVLCQVW DSSSDHWVF (SEQ ID NO: 797) |
| YU394-H03 | RGDLLKISCKGSGYSFTSYWIGWVRQMPGKGLEWMGIIYPGDSDTRYS PSFQGQVTISADKSISTAYLQWSSLKASDTAMYYCARLENNWNYGGW FDPWGQGTLVTVSSCARLENNWNYGGWFDPWVLTQPPSVSVAPGQTA RITCGGNNIGSKSVHWYQQKPGQAPVLVVYDDSDRPSGIPERFSGSNSG NTATLTISRVEAGDEADYYCQVWDSSSDHWVFGGGTKLTVLCQVWDS SSDHWVF (SEQ ID NO: 798) |
| YU394-H04 | RGNLLKISCKGSGYSFTSYWIGWVRQMPGKGLEWMGIIYPGDSDTRYS PSFQGQVTISADKSISTAYLQWSSLKASDTAMYYCARLENNWDYGGW FDPWGQGTLVTVSSCARLENNWDYGGWFDPWSYVLTQPPSVSVAPGQ TARITCGGNNIGSKSVHWYQQKPGQAPVLVVYDDSDRPSGIPERFSGSN SGNTATLTISRVEAGDEADYYCQVWDSSSDHWVFGGGTKLTVLCQVW DSSSDHWVF (SEQ ID NO: 799) |

TABLE 5-continued

| Clone ID | scFv sequence |
|---|---|
| YU394-H05 | PGESLKISCKGSGYSFTSYWIGWVRQMPGKGLEWMGIIYPGDSDTRYSP SFQGQVTISADKSISTAYLQWSSLKASDTAMYYCARLENNWNYGGWF DPWGQGTLVTVSSCARLENNWNYGGWFDPWVLTQPPSVSVAPGQTA RITCGGNNIGSKSVHWYQQKPGQAPVLVVYDDSDRPSGIPERFSGSNSG NTATLTISRVEAGDEADYYCQVWDSSSDHWVFGGGTKLTVLCQVWDS SSDHWVF (SEQ ID NO: 800) |
| YU394-H07 | PGASVKVSCKASGGTFSSYAISWVRQAPGQGLEWMGGIIPIFGTANYAQ KFQGRVTITADESTSTAYMELSSLRSEDTAVYYCARDYYYYGMDVWG QGTTVTVSSCARDYYYYGMDVWDIRMTQSPSSLSASVGDRVTITCRAS QSISRYVNWYQQKPGKAPNLLIYGASNLESGVPSRFSGSGSGTDFTLTN SSLQPEDFASYYCQQTYNDPPTFGGGTRMEIKCQQTYNDPPTF (SEQ ID NO: 801) |
| YU395-A02 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWDIVMTQSPSSLSASVGDRVTITC RASQSISSYLNWYQQKPGKAPKLLIYAASSLQSGVPSRFSGSGSGTDFTL TISSLQPEDFATYYCQQSYSTPPTFGQGPKVEIKCQQSYSTPPTF (SEQ ID NO: 802) |
| YU395-B12 | PGASVKVSCKASGYTFTSYGISWVRQAPGQGLEWMGWISAYNGNTNY AQKLQGRVTMTTDTSTSTAYMELRSLRSDDTAVYYCARDIGYYYGMD VWGQGTTVTVSSCARDIGYYYGMDVWSSELTQDPAVSVALGQTVRIT CQGDSLRSYYASWYQQEPGQAPVLVIYGKNNRPSGISDRFSGSSSGNTA SLTITGAQAEDEADYYCNSRDSSGNHVVFGGGTRLTVLCNSRDSSGNH VVF (SEQ ID NO: 803) |
| YU395-C06 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWDIQMTQSPSSLSASVGDRVTITC RASQSISNYLNWYQQKPGKAPKLLIYAASSLQSGVPSRFSGSGSGTDFT LTISSLQPEDFATYYCQQSYSTPPTFGQGTKLETKCQQSYSTPPTF (SEQ ID NO: 804) |
| YU395-C08 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWDIVMTQSPSSLSASVGDRVTITC RASQSISSYLNWYQQKPGKAPKLLIYAASSLQSGVPSRFSGSGSGTDFTL TISSLQPEDFATYYCQQSYSTPPTFGQGTKVELKCQQSYSTPPTF (SEQ ID NO: 805) |
| YU395-D05 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWDIQMTQSPSSLSASVGDRVTITC RASQSISNYLNWYQQKPGKAPKLLIYAASSLQSGVPSRFSGSGSGTDFT LTISSLQPEDFATYYCQQSYSTPPTFGQGPKLEIKCQQSYSTPPTF (SEQ ID NO: 806) |
| YU396-B12 | SGESLKISCKGSGYSFSTYWIGWVRQMPGKGLEWMGLIYPGDSDTRYS PSFQGQVTISADKSISTAYLQWSSLKASDTAMYYCARVGDGYSLDYWG QGTLVTVSSCARVGDGYSLDYWSVLTQPPSVSVSPGQTASITCSGHKLG ERFAYWYQQKPGQSPVLVINQYIRRPSGIPERFSGSNSGSTATLTISGTQ AMDEADYYCQTWDGSIVVFGGGTKLTVLCQTWDGSIVVF (SEQ ID NO: 807) |
| YU396-C03 | PGRSLRLSCAASGFTFSSYGMHWVRQAPGKGLEWVAVISYDGSNKYY ADSVKGRFTISRDNSKNTLYLQMNSLRAEDTAVYYCAKAITSIEPYWG QGTLVTVSSCAKAITSIEPYWQTVVTQEPSFSVSPGGTVTLTCGLSSGSV STSYYPSWYQQTPGQAPRTLIYNTDTRSSRVPDRFSGSIVGNKAALTITG AQADDESDYYCVLYMGSGIWVFGGGTKLTVLCVLYMGSGIWVF (SEQ ID NO: 808) |
| YU396-C12 | SGESLKISCKGSGYSFSTYWIGWVRQMPGKGLEWMGLIYPGDSDTRYS PSFQGQVTISADKSISTAYLQWSSLKASDTAMYYCARVGDGYSLDYWG QGTLVTVSSCARVGDGYSLDYWQPVLTQPPSASGTPGQRVTISCSGGSS NIGRNYVYWYQQLPGTAPNLLISRNHQRPSGVPDRFSGSRSDTSASLAIS GLRSEDEADYYCATWDDALSGWVFGGGTKLTVLCATWDDALSGWVF (SEQ ID NO: 809) |
| YU396-G10 | PGSSVKVSCKASGGTFSSYAISWVRQAPGQGLEWMGGIIPIFGTANYAQ KFQGRVTITADESTSTAYMELSSLRSEDTAVYYCAREMYYYYGMDVW GQGTTVTVSSCAREMYYYYGMDVWDIVMTQSPSSLSASVGDRVTITC RASQSISSYLNWYQQKPGKAPKLLIYAASSLQSGVPSRFSGSGSGTDFTL TISSLQPEDFATYYCQQSYSTPPTFGQGTKVETKCQQSYSTPPTF (SEQ ID NO: 810) |

TABLE 5-continued

| Clone ID | scFv sequence |
|---|---|
| YU396-H12 | PGRSLRLSCAASGFAFSSYGMHWVRQAPGKGLEWVAVISYDGSNKYY ADSVKGRFTISRDNSKNTLYLQMNSLRAEDTAVYYCAKGQGDGMDV WGQGTTVTVSSCAKGQGDGMDVWQSALTQPPSASGSPGQSVTISCTGT SSDVGGYNYVSWYQQHPGKAPKLMLYGVSNRPSGISSRFSGSKSGNTA SLTISGLQAEDEADYYCSSYTSSSTLVVFGGGTKLTVLCSSYTSSSTLVV F (SEQ ID NO: 811) |
| YU397-A01 | PGESLQISCKGSGYKFANYWIGWVRQMPGKGLEWMGIIYPGDSDTRYS PSFQGQVTISADKSISTAYLQWSSLKASDTAMYYCARLGWGMDVWGQ GTTVTVSSCARLGWGMDVWDIVMTQSPSSLSASVGDRVTITCRASQSIS SYLNWYQQKPGKAPNLIYAASSLRSGVPSRFSGSGSGTDFTLTISSLQPE DFATYYCQQSYSTPWTFGQGTKVEIKCQQSYSTPWTF (SEQ ID NO: 812) |
| YU397-A02 | PGASVKVSCKASGYTFKNFGISWVRRAPGQGPEWMGWISGRKGNTIY AQKFQGRVTMTTDTSTTTAYMELRSLRSDDTAVYYCARVWGDTTLGY GMDVWGQGTTVTVSSCARVWGDTTLGYGMDVWDIQMTQSPSSLSAS VGDRVTITCQASQDISNYLNWYQQKPGKAPKWYDASNLETGVPSRFS GSGSGTDFTFTISSLQPEDIATYYCQQYDNLPLTFGGGTKVEIKCQQYD NLPLTF (SEQ ID NO: 813) |
| YU397-A03 | PGGSLRLSCAASGFTFSSYEMNWVRQAPGKGLEWVSYISSSGSTIYYAD SVKGRFTISRDNAKNSLYLQMNSLRAEDTAVYYCARRGGGFDYWGQ GTLVTVSSCARRRGGGFDYWQSALTQPASVSGSPGQSITISCTGTSSDV GGYNYVSWYQQHPGKAPKLMIYDVSNRPSGVSNRFSGSKSGNTASLTI SGLQAEDEADYYCSSYTSSSTWVFGGGTKLTVLCSSYTSSSTWVF (SEQ ID NO: 814) |
| YU397-B01 | PGESLKISCKGSGYSFTSYWIGWVRQMPGKGLEWMGIIYPGDSDTRYSP SFQGQVTISADKSISTAYLQWSSLKASDTAMYYCAIPWDAELGNYGMD VWGQGTTVTVSSCAIPWDAELGNYGMDVWDIQMTQSPSSLSASVGDR VTITCRASQSISSYLNWYQQKPGKAPKLLIYAASSLQSGVPSRFSGSGSG TDFTLTISSLQPEDFATYYCLQDYNYPPAFGQGTKVEIKCLQDYNYPPA F (SEQ ID NO: 815) |
| YU397-B02 | PGSSVKVSCKASGGTFSSYAISWVRQAPGQGLEWMGGIIPIFGTANYAQ KFQGRVTITADKSTSTAYMELSSLRSEDTAVYYCARGRWSGLGDYWG QGTLVTVSSCARGRWSGLGDYWMTQSPSSLSASVGDRVTITCQASEDI RMYLGWYQQKAGRAPKLLIFEGSSLEPGVPSRFSGSGSGTHFTFTISSLQ PDDFATYYCQQYYDDPQFGGGTKVVLKCQQYYDDPQF (SEQ ID NO: 816) |
| YU397-D01 | PSGTLSLTCAVSGGSISSSNWWSWVRQPPGKGLEWIGEIYHSGSTNYNP SLKSRVTISVDKSKNQFSLKLSSVTAADTAVYYCARARGGRYFDYWGQ GTLVTVSSCARARGGRYFDYWDIVLTQSPSFLSASVGDRVTITCRASQG ISTYLAWYQQKPGTAPKVLMYAASTLHSGVPSRFSGSGSGTEFTLTISSL QPEDFAIYYCQQLNGYPTTFGGGTRVEIKCQQLNGYPTTF (SEQ ID NO: 817) |
| YU398-A11 | PGRSLRLSCAASGFTFSSYGMEIWVRQAPGKGLEWVAVISYDGSNKYY ADSVKGRFTISRDNSKNTLYLQMNSLRAEDTAVYYCAKGQGDGMDV WGQGTTVTVSSCAKGQGDGMDVWYELTQPPSASGTPGQRVTISCSGSS SNVGSRTVSWFQQLPGTAPKLLIYSNNLRPSGVPDRFSGSKSGTSASLAI SGLQSEDEADYYCAAWDDSLIGHVFGTGTKVTVVCAAWDDSLIGHVF (SEQ ID NO: 818) |
| YU398-E10 | PGGSLRLSCAASGFTFSSYSMNWVRQAPGKGLEWVSSISSSSSYIYYAD SVKGRFTISRDNAKNSLYLQMNSLRAEDTAVYYCARDQLAARRGYYY GMDVWGQGTTVTVSSCARDQLAARRGYYYGMDVWVLTQPPSVSVAP GQTATIACGGNNIGTKSVHWYQQKPGQAPVLVVYDDSDRPSGIPERFS GSNSGNTATLTISRVEAGDEADYYCQVWDSSSDHVVFGGGTKLTVLCQ VWDSSSDHVVF (SEQ ID NO: 819) |
| YU400-A05 | PGRSLRLSCAASGFTFSSYGMEIWVRQAPGKGLEWVAVISYDGSNKYY ADSVKGRFTISRDNSKNTLYLQMNSLRAEDTAVYYCAKGDVNYGMDV WGQGTTVTVSSCAKGDVNYGMDVWSYVLTQPPSVSVAPGQTARISCG GSNIGSKTVNWYRKKAGQAPVLVVYDGRDRPSGIPERFSGSNSGNAAT LIISRVEVGDEADYYCQVWDTSGDLHWAFGGGTKLTVLCQVWDTSGD LHWAF (SEQ ID NO: 820) |
| YU400-A12 | PSGTLSLTCAVSGGSISSSNWWSWVRQPPGKGLEWIGEIYHSGSTNYNP SLKSRVTISVDKSKNQFSLKLSSVTAADTAVYYCARDFYYGSGSYPNG YYYGMDVWGQGTTVTVSSCARDFYYGSGSYPNGYYYGMDVWDIVM TQSPSSLSASLGDRVTITCRASQSINSYLNWYQQKPGKAPRLLIYTASTL QSGVPSRFSGSGAGTDFTLTISSLQPEDVATYYCQQSYTTPLTFGGGTK MEIKCQQSYTTPLTF (SEQ ID NO: 821) |

TABLE 5-continued

| Clone ID | scFv sequence |
|---|---|
| YU400-B07 | PGRSLRLSCAASGFTFSSYGMHWVRQAPGKGLEWVAVISYDGSNKYY<br>ADSVKGRFTISRDNSKNTLYLQMNSLRAEDTAVYYCAKGDVNYGMDV<br>WGQGTTVTVSSCAKGDVNYGMDVWSYVLTQPPSVSVAPGKTARITCG<br>GNNIGSKSVHWYQQKPGQAPVLVVYDDTDRPSGIPERFSGSNSGNTAT<br>LTISRVEAGDEADYYCQVWDSSSDLLWVFGGGTKLAVLCQVWDSSSD<br>LLWVF (SEQ ID NO: 822) |
| YU400-D09 | PGSSVKVSCKASGGTFSSYAISWVRQAPGQGLEWMGGIIPIFGTANYAQ<br>KFQGRVTITADESTSTAYMELSSLRSEDTAVYYCARDFNPFSITIFEMDV<br>WGQGTTVTVSSCARDFNPFSITIFEMDVWQSVLTQPPSVSAAPGQKVTI<br>SCSGSSSNIGNNYVSWYQQLPGTAPKWYDNNKRPSGIPDRFSGSKSGT<br>SATLGITGLQTGDEADYYCGTWDSSLSALVFGGGTKLTVLCGTWDSSL<br>SALVF (SEQ ID NO: 823) |
| YU400-F07 | PGRSLRLSCAASGFTFSSYGMHWVRQAPGKGLEWVAVISYDGSNKYY<br>ADSVKGRFTISRDNSKNTLYLQMNSLRAEDTAVYYCAKGDVNYGMDV<br>WGQGTTVTVSSCAKGDVNYGMDVWSYVLTQPPSVSVAPGQTARISCG<br>GSNIGSKTVNWYRKKAGQAPVLVVYDGRDRPSGIPERFSGSNSGNAAT<br>LIISRVEVGDEADYYCQVWDTSGDLHWAFGGRTKLTRCQVWDTSGDL<br>HWAF (SEQ ID NO: 824) |
| YU400-H08 | PGRSLRLSCAASGFTFSSYGMHWVRQAPGKGLEWVAVISYDGSNKYY<br>ADSVKGRFTISRDNSKNTLYLQMNSLRAEDTAVYYCAKGDVNYGMDV<br>WGQGTTVTVSSCAKGDVNYGMDVWSYVLTQPPSVSVAPGQTARISCG<br>GSNIGSKTVNWYRKKAGQAPVLVVYDGRDRPSGIPERFSGSNSGNAAT<br>LIISRVEVGEGGQY*LQVWDTSGDLHWAFGGGTKLTVLLQVWDTSGD<br>LHWAF (SEQ ID NO: 825) |
| YU401-A11 | PGRSLRLSCAASGFTFSSYGMHWVRQAPGKGLEWVAVISYDGSNKYY<br>ADSVKGRFTISRDNSKNTLYLQMNSLRAEDTAVYYCANLAMGQYFDY<br>WGQGTLVTVSSCANLAMGQYFDYWQAVLTQPPSASGTPGQRVTISCS<br>GSSSNIGSNTVNWYQQLPGTAPKLLIYSNNQRPSGVPDRFSGSKSGTSA<br>SLAISGLQSEDEADYYCAAWDDSLNGPVFGGGTKLTVLCAAWDDSLN<br>GPVF (SEQ ID NO: 826) |
| YU401-B01 | PGSSVKVSCKASGGTFSSYAISWVRQAPGQGLEWMGGIIPIFGTANYAQ<br>KFQGRVTITADESTSTAYMELSSLRSEDTAVYYCAREMYYYYGMDVW<br>GQGTTVTVSSCAREMYYYYGMDVWDIVMTQSPSSLSASVGDRVTITC<br>RASQSIITYLNWYQQKPGKVPKLLIYAASSLQSGVPSRFSGSGSGTDFTL<br>TISSLQPEDFATYYCQQSYSTPPTFGQGTKLEIKCQQSYSTPPTF (SEQ ID<br>NO: 827) |
| YU401-D11 | PGGSLRFSCAASGFTFSSYGMHWVRQAPGKGLEWVAVISYDGSNKYY<br>ADSVKGRFTISRDNSKNTLYLQMNSLRAEDTAVYYCANLAMGQYFDY<br>WGQGTLVTVSSCANLAMGQYFDYWQAVLTQPPSASGTPGQRVTISCS<br>GSSSNIGSNTVNWYQQLPGTAPKLLIYSNNQRPSGVPDRFSGSKSGTSA<br>SLAISGLQSEDEADYYCAAWDDSLNGPVFGGGTKLTVLCAAWDDSLN<br>GPVF (SEQ ID NO: 828) |
| YU401-E11 | PGRSLRLSCAASGFTFSSYAMHWVRQAPGKGLEWVAVISYDGSNKYY<br>ADSVKGRFTISRDNSKNTLYLQMNSLRAEDTAVYYCARDLGEAKSSSP<br>HEPDYWGQGTLVTVSSCARDLGEAKSSSPHEPDYWLTQSPLSLSVTPG<br>QPASISCKSSQSLLHSDGKTYLDWYLQKPGQPPQLLIYEVSNRFSGVPD<br>RFSGSGSGTDFTLKISRVEAEDVGIYYCMQTKQLPLTFGGGPKLEICMQ<br>TKQLPLTF (SEQ ID NO: 829) |
| YU401-F11 | PGRSLRLSCAASGFTFSSYAMHWVRQAPGKGLEWVAVISYDGSNKYY<br>ADS VKGRFTISRDNSKNTLYLQMNSLRAEDTAVYYCARDLGEAKSSSP<br>HEPDYWGQGTLVTVSSCARDLGEAKSSSPHEPDYWLTQSPLSLSVTPG<br>QPASISCKSSQSLLHSDGKTYLDWYLQKPGQPPQLLIYEVSNRFSGVPD<br>RFSGSGSGTDFTLKISRVEAEDVGIYYCMQTKQLPLTFGGGTKLEICMQ<br>TKQLPLTF (SEQ ID NO: 830) |
| YU401-G07 | LGRSLRLSCAASGFTFSSYGMHWVRQAPGKGLEWVAVISYDGSNKYY<br>ADSVKGRFTISRDNSKNTLYLQMNSLRAEDTAVYYCAKGDVNYGMDV<br>WGQGTTVTVSSCAKGDVNYGMDVWSYVLTQPPSVSVAPGQTARISCG<br>GSNIGSKTVNWYRKKAGQAPVLVVYDGRDRPSGIPERFSGSNSGNAAT<br>LIISRVEVGDEADYYCQVWDTSGDLHWAFGGGTKLTVLCQVWDTSGD<br>LHWAF (SEQ ID NO: 831) |
| YU402-A02 | PSETLSLTCTVSGDSISSSSYYWSWIRQPPGKGLEWIGEINHSGSTNYNPS<br>LKSRVTISVDTSKNQFSLKLSSVTAADTAVYYCARDQEMYYFDYWGQ<br>GTLVTVSSCARDQEMYYFDYWDIQMTQSPSSVSASVGDRVTITCRASQ<br>GISSWLAWYQQKPGKAPKLLIYAASSLQSGVPSRFSGSGSGTDFTLTISS<br>LQPEDFATYYCQQANSFPPTFGPGTKVDIKCQQANSFPPTF (SEQ ID NO:<br>832) |

TABLE 5-continued

| Clone ID | scFv sequence |
|---|---|
| YU402-A11 | PSGTLSLTCDVSGGSISRSNWWIWVRQPPGKGLEWIGEIYHTGSTNYNP SLKRRVTISVDKSKNQFSLNLSSVTAADTAVYYCARGKGSYAFDIWGL GTMVTVSSCARGKGSYAFDIWVLTQPHSVSESPGKTVTISCTGSGGNIA RNYVQWYQHRPGRAPSTVIYEDDRRPSGVPDRFSGSTDISSNSASLTISG LKTEDEADYYCQSYDGNNHMVFGGGTRVTVLCQSYDGNNHMVF (SEQ ID NO: 833) |
| YU402-D10 | PGRSLRLSCAASGFTFSSYGMEIWVRQAPGKGLEWVAVISYDGNNKYY TDSVKGRFTISRDNSKNTVYLQMNSLRAEDTAVYYCAKGYSSSPGDY WGQGTLVTVSSCAKGYSSSPGDYWQSALTQPASVSGSPGQSITISCTGT SSDVGAYNYVSWYQQYPGKAPKLMIYDVSNRPSGVSDRFSGSKSGNT ASLTISGLQAEDEADYYCSSYTSSSTLWVFGGGTKLTALCSSYTSSSTL WVF (SEQ ID NO: 834) |
| YU403-G05 | PSGDLSLTCDVSGGSISRSNWWIWVRQPPGKGLEWIGEIYHTGSTNYNP SLKRRVTISVDKSKNQFSLNLSSVTAADTAVYYCARGKGSYAFDIWGL GTMVTVSSCARGKGSYAFDIWVLTQPHSVSESPGKTVTISCTGSGGNIA RNYVQWYQHRPGRAPSTVIYEDDRRPSGVPDRFSGSTDISSNSASLTISG LKTEDEADYYCQSYDGNNHMVFGGGTRVTVLCQSYDGNNHMVF (SEQ ID NO: 835) |
| YU391-B12 | QMQLVQSGAEVKKPGSSVKVSCKASGGTFSSYAISWVRQAPGQGLEW MGGIIPIFGTANYAQKFQGRVTITADESTSTAYMELSSLRSEDTAVYYC AREMYYYYGMDVWGQGTTVTVSSDIQMTQSPSSLSASVGDRVTITCR ASQSISSYLNWYQQKPGKAPKLLIYAASSLQSGVPSRFSGSGSGTDFTLT ISSLQPEDFATYYCQQSYSTPPAFGQGTKLEIK (SEQ ID NO: 836) |
| YU392-E05 | QVQLQESGPGLVKPSGTLSLTCTVSGGSISSSNWWSWVRQPPGKGLEW IGEIYHSGSTNYNPSLKSRVTISVDKSKNQFSLKLSSVTAADTAVYYCAR GVIAAAGTYFDYWGQGTLVTVSSQAVLTQPPSASGTPGQRVTISCSGSR PNVASNSVNWYQQFPGTAPRLLIYSDNQRPSGVPDRFSGSKSGTSASLA ISGLQFEDEADYYCETWDDSLRGVVFGGGTKVTVL (SEQ ID NO: 837) |
| YU392-E06 | QLQLQESGPGLVKPSGTLSLTCAVSGGSISSSNWWSWVRQPPGKGLEW IGEIYHSGSTNYNPSLKSRVTISVDKSKNQFSLKLSSVTAADTAVYYCAR ERTHYYYGMDIWGQGTTVTVSSQSVLTQPPSTSGTPGQRVTISCSGSSS NIGSNTVNWYHQLPGTAPRLLIYSNNQRPSGVPDRFSGSKSGTSASLAL SGLQSEDEGDYYCAAWDDSLNGYVFGTGTKVTVL (SEQ ID NO: 838) |
| YU392-G08 | EVRLGQSGPELKNPGDFRKISCKGSGYSFTSYWIGWVRQMPGKGLEW MGIIYPGDSDTRYSPSFQGQVTISADKSISTAYLQWSSLKASDTAMYYC ARLENNWDYGGWFDPWGQGTLVTVSSSYVLTQPPSVSVAPGQTARIT CGGNNIGSKSVHWYQQKPGQAPVLVVYDDSDRPSGIPERFSGSNSGNT ATLTISRVEAGDEADYYCQVWDSSSDHWVFGGGTKLTVL (SEQ ID NO: 839) |
| YU392-G09 | QVQLVQSGAEVKKPGSSVKVSCKASGGTFSSYAISWVRQAPGQGLEW MGGIIPIFGTANYAQKFQGRVTITADESTSTAYMELSSLRSEDTAVYYC ARDGAGNYDILTGDRSEDYYYYYGMDVWGQGTTVTVSSSYELTQPPS ASGAPGQRVSISCSGGYSNIGSNTVNWYQQLPGAAPKFLIYSDNQRPSG VPDRFSGSKSGTSASLAISGLQSEDEADYYCATWDDSLNGPVFGGGTK LTVL (SEQ ID NO: 840) |
| YU392-G12 | QVQLQESGSGLVKPSQTLSLTCAVSGGSISSGGYSWSWIRQPPGKGLEW IGYIYHSGSTYYNPSLKSRVTISVDRSKNQFSLKLSSVTAADTAVYYCA RAGYYYGMDVWGQGTTVTVSSDIVMTQTPSSLSASVGDRVAITCQAS RNIWSYVNWYQQKPGEAPRLLIYGASTLQRGVPSRFSGSGSGTGFTLTI NSLQPEDFATYFCQQSHSTPITFGGGTRVDIK (SEQ ID NO: 841) |
| YU392-H02 | QLQLQESGPGLVNLSQTLSLTCTVSGGSISSGGYYWSWIRQHPGKGLE WIGYIYYSGSTYYNPSLKSRVTISVDTSKNQFSLKLSSVTAADTAVYYC ARDSSSGPYGMDVWGQGTTVTVSSQSVLTQPPSVSVAPGQTARVTCG GSNIGSQSVHWYQQKPGQAPVLVVYDDYDRPSGIPERFSGSNSGNTAT LTITRVDAGDEADYYCQIWDSSSAHVVFGGGTKLTVL (SEQ ID NO: 842) |
| YU392-H04 | QVQLQESGPGLVKPSGTLSLTCAVSGGSISSSNWWSWVRQPPGKGLEW IGEIYHSGSTNYNPSLKSRVTISVDKSKNQFSLKLSSVTAADTAVYYCAR VNYGDYDWYFDLWGRGTLVTVSSQPVLTQPPSASGTPGQRVTISCSGS SSNIGSNFVTWYQQLPGTAPKWYSNNQRPSGVSDRFSASKSGTSASLA ISRLQSQDEAEYYCAAWDDSLRSYVFGSGTKVTVV (SEQ ID NO: 843) |
| YU394-D08 | QVQLGESGAEVKKPGSSVKVSCKASGGTFSSYAISWVRQAPGQGLEW MGWISAYNGNTNYAQKLQGRVTMTTDTSTSTAYMELRSLRSDDTAVY YCAREPLRYYYYYGMDVWGQGTTVTVSSDIQMTQSPSSLSASVGDRV TITCRASQSISSYLNWYQQKPGKAPKLLIYAASSLQSGVPSRFSGSGSGT DFTLTISSLQPEDFATYYCQQSYSTPWTFGQGTKVEIK (SEQ ID NO: 844) |

In some embodiments, the antibody has a CDR-H1, CDR-H2, CDR-H3, CDR-L1, CDR-L2, and CDR-L3, each independently selected from those disclosed in Table 14 Å and Table 14B. In some embodiments, the antibody has a CDR-H1, CDR-H2, CDR-H3, CDR-L1, CDR-L2, and CDR-L3, each independently selected from any one clone listed in Table 14A and Table 14B. In some embodiments, the antibody has a CDR-H1, CDR-H2, CDR-H3, CDR-L1, CDR-L2, and CDR-L3, each independently selected from those disclosed, in groups, in Table 15A and Table 15B. The disclosure provides antibodies having CDRs from individual clones or from matching any one CDR with any other five CDRs. The antibodies identified in Table 14 Å and Table 14B are derived from mouse phage-display library. Known methods may be used to convert these CDRs into humanized or chimeric antibodies.

VII. Use of CD25 Antibodies

In some embodiments, the CD25 antibodies provided herein are useful for therapeutics, e.g. for use in proliferative diseases or disorders such as cancer or for use in autoimmune diseases.

Accordingly provided herein are methods of treating a cancer comprising administering to a subject in need thereof a therapeutically effective amount of a therapeutic CD25 antibody. In some embodiments, the cancer is a primary cancer. In some embodiments, the cancer is a metastatic cancer. In some embodiments, the cancer involves a solid tumor; in other embodiments, the cancer involves a liquid tumor, e.g. a blood based cancer. In exemplary embodiments, the CD25 antibody is a non-IL-2 blocking antibody.

Accordingly provided herein are methods of treating an autoimmune-related disease or disorder comprising administering to a subject in need thereof a therapeutically effective amount of a therapeutic CD25 antibody. In exemplary embodiments, the CD25 antibody is an non IL-2 blocking antibody.

As used herein, a subject refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Subjects may be male or female.

The administration of any of the therapeutic CD25 antibodies provided herein may be administered in combination with other known drugs/treatments (e.g. small molecule drugs, or biologics. The administration may be sequential or concurrent.

In vivo administration of the therapeutic CD25 antibodies described herein may be carried out intravenously, intratumorally, intracranially, intralesionally (e.g. intralesional injection, direct contact diffusion), intracavitary (intraperitoneal, intralpleural, intrauterine, intrarectal), intraperitoneally, intramuscularly, subcutaneously, topically, orally, transdermally, by implantation, by inhalation, intrathecally, intraventricularly, or intranasally. In an exemplary embodiment, the route of administration is by intravenous injection.

A therapeutically effective amount of the therapeutic antibody generally will be administered. The appropriate dosage of the therapeutic antibody may be determined based on the severity of the disease, the clinical condition of the subject, the subject's clinical history and response to the treatment, and the discretion of the attending physician.

VIII. Diagnostic Uses

The CD25 antibodies provided herein may be used for diagnostic and detection purposes. Depending on the application, the CD25 antibody may be detected and quantified in vivo or in vitro.

The CD25 antibodies provided herein are amendable for use in a variety of immunoassays. These immunoassays include, but are not limited to enzyme-linked immunosorbent assay (ELISA), Western blot, radioimmunoassay (RIA), flow cytometry, a radioimmunoassay, an immunofluorescence assay, spectrophotometry, radiography, electrophoresis, high performance liquid chromatography (HPLC), or thin layer chromatography (TLC).

The CD25 antibodies provided herein may be comprise a detectable label, for example detectable by spectroscopic, photochemical, biochemical, immunochemical, fluorescent, electrical, optical or chemical methods. Useful labels in the present invention include, but are not limited to fluorescent dyes, radiolabels, enzymes, colorimetric lables, avidin or biotin.

In some embodiments, the CD25 antibody is radiolabeled with an isotope, useful for imaging by nuclear medicine equipment (SPECT, PET, or scintigraphy).

VIII. Pharmaceutical Compositions

The disclosure provides compositions comprising therapeutic CD25 antibodies, In some embodiments the composition is sterile. The pharmaceutical compositions generally comprise an effective amount of the therapeutic antibody in a pharmaceutically acceptable excipient.

IX. Kits and Articles of Manufacture

The disclosure also provides for kits comprising any of the CD25 antibodies described herein, e.g. for either therapeutic or diagnostic uses. In some embodiments, the kits further contain a component selected from any of secondary antibodies, reagents for immunohistochemistry analysis, pharmaceutically acceptable excipient and instruction manual and any combination thereof. In some embodiments, the kit comprises any one or more of the therapeutic compositions described herein, with one or more pharmaceutically acceptable excipients.

The present application also provides articles of manufacture comprising any one of the therapeutic or diagnostic compositions or kits described herein. Examples of an article of manufacture include vials (e.g. sealed vials).

The description provided herein sets forth numerous exemplary configurations, methods, parameters, and the like. It should be recognized, however, that such description is not intended as a limitation on the scope of the present disclosure, but is instead provided as a description of exemplary embodiments.

EXAMPLES

The following Examples are merely illustrative and are not meant to limit any aspects of the present disclosure in any way.

Example 1: Development of Engineered Immunogens Sharing Characteristics of CD25

A crystal structure of CD25 was obtained. A number of the crystal structures available for CD25 are missing a mobile loop section of the protein. Molecular dynamics simulations were performed to gain a greater understanding of this mobile loop, and binding interactions of CD25 with IL-2.

Figure 34A:
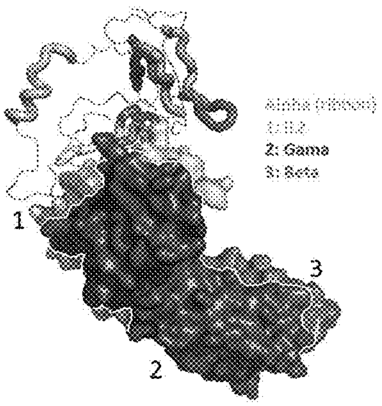
FIG. 34A is a model of IL-2 binding with the IL-2R complex, showing the CD25 section (ribbon), IL-2 (1), IL-2R-gamma (2), and IL-2R-beta (3).
Figure 34B:
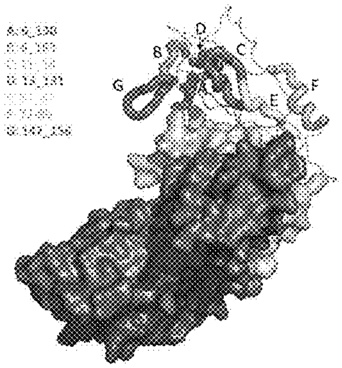
FIG. 34B is another view of IL-2 binding with the IL-2R complex, listing areas of CD25 that were used as inputs to develop different selected exemplary engineered immunogens.
Figure 34C:
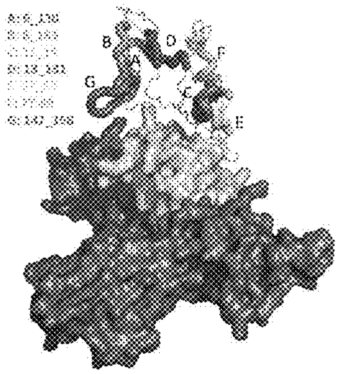
FIG. 34C is another view of IL-2 binding with the IL-2R complex listing areas of CD25 that were used as inputs to develop different selected exemplary engineered immunogens.

Different sections of CD25 were selected as inputs for developing an engineered immunogen. Some of these areas are shown in FIG. 34B and FIG. 34C. These inputs were used with the ROSETTA program to improve to the overall desirable structural and dynamic properties of the interfacial residues. This process made changes to the structural (non-interface) parts of the segment to stabilize and recapitulate the structure, conformation, dynamics and other properties of the interface residues in-context of the native CD25 from which they were derived. The stability and flexibility of the segment under development was also analyzed, and the sequence adjusted if needed to change these parameters. For example, the N or the C terminus can be extended by the addition of one or more amino acids to add desired properties. The effect of cross-linking on the engineered immunogen candidates was also evaluated, using disulfide bonds bonds forming between the side chains of different amino acid residues. At each stage of design engineering—amino acid addition, crosslinking, and structural residue optimization—the native scoring and energy functions of the ROSETTA program were used to quantitatively evaluate each of the many design candidates. Those candidates possessing the best ROSETTA energies are carried forward to subsequent stages of design, and ultimately forward to evaluation and validation by molecular dynamics simulation. In addition to evaluating these parameters at physiological pH (e.g., around pH 7.4), parameters were also evaluated in some instances at tumor microenvironment pH (e.g., around pH 6.5).

Figure 32:
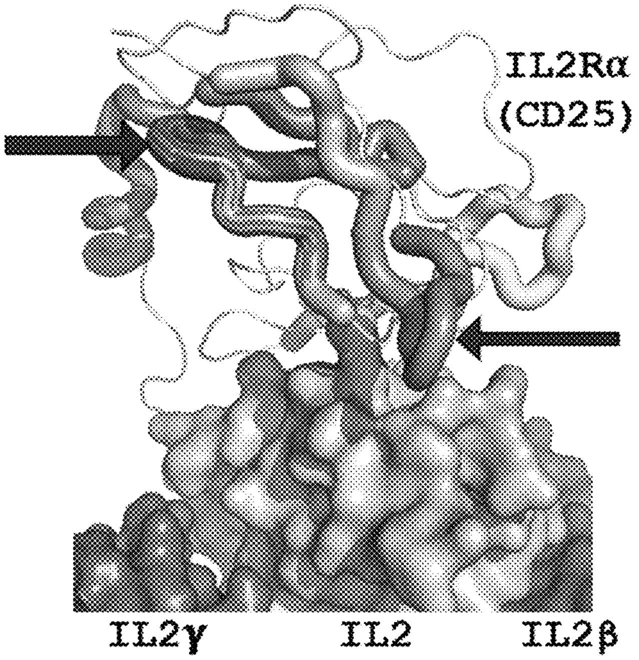
FIG. 32 presents a model of CD25 (ribbon) binding with IL-2 ligand (space-filling), IL-2R-gamma, and IL-2R-beta. The left and right arrows indicate selected sections of CD25 that were used to develop engineered immunogens that mimic CD25.
Figure 33A:
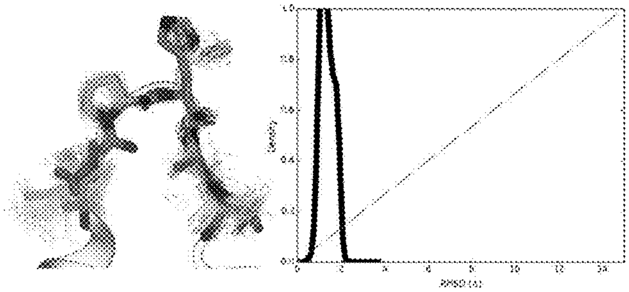
FIG. 33A is an exemplary graph of molecule stability vs. root mean square deviation (RMSD) evaluation at physiological pH for an engineered immunogen developed using as an initial input the section of CD25 indicated with the left arrow in FIG. 32.
Figure 33B:
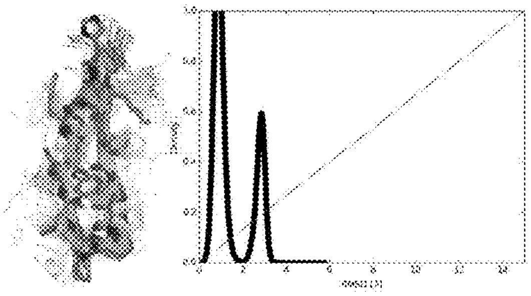
FIG. 33B is an exemplary graph of molecule stability vs. root mean square deviation (RMSD) evaluation at physiological pH for an engineered immunogen developed using as an initial input the section of CD25 indicated with the right arrow in FIG. 32.
Figure 33C:
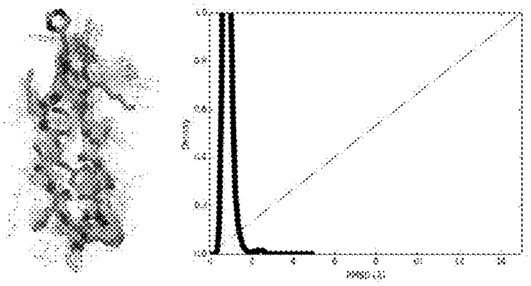
FIG. 33C is an exemplary graph of molecule stability vs. root mean square deviation (RMSD) evaluation at tumor microenvironment pH (lower pH) for the engineered immunogen in FIG. 2B (developed using as an initial input the section of CD25 indicated with the right arrow in FIG. 32).

Quantitative metrics for ranking the different designs using molecular dynamics (MD) simulation included similarity to CD25, evaluated through RMSD; and structural flexibility of the candidates. FIG. 33A and FIG. 33B show exemplary comparisons of stability vs. RMSD at physiological pH for exemplary engineered immunogens developed using the input sections indicated in FIG. 32 (left arrow for FIG. 33A, right arrow for FIG. 33B). FIG. 33C is an exemplary comparison of stability vs. RMSD at tumor microenvironment pH for the exemplary immunogen of FIG. 33B. A representative scoring algorithm is presented below.

$$\text{Score}_{similarity+flexibility} = \frac{\Sigma(\alpha_i f_i)}{f_0},\ \alpha_i = \begin{cases} 0, & rmsd_i > k_{max}(\text{Å}) \\ 1, & rmsd_i \le k_{max}(\text{Å}) \end{cases}$$

$f_i$ = Fraction of ensemble $k_{max}$ = Similarity cutoff

Structural similarity was calculated using root mean square deviation (RMSD) between the atomic coordinates of each peptide conformation in the MD ensemble and the reference structure after RMS alignment to the reference structure. The RMSD was computed using the computationally designed engineered immunogen candidate structure as the reference structure or by using the experimentally characterized (e.g., X-ray crystal structure) structure as the reference. In these simulations, the functional interface residues of the candidate (in some simulations) and all residues including the structural residues of the candidate (in other simulations) were compared to the reference.

The ensemble of conformations sampled by MD were clustered into groups (clusters) structurally similar to each other based on RMSD. Disorder was evaluated as the fraction of the conformations in the MD ensemble that could not be grouped into a cluster of similar conformations due to structural dissimilarity (e.g., high RMSD) to all other conformations in the ensemble. Thus, an engineered immunogen candidate with more disorder than an alternative candidate was more flexible. Order was evaluated as the fraction of the conformations in the MD ensemble that were grouped into a cluster of similar conformations (low RMSD). An engineered immunogen candidate with more order than an alternate candidate was less flexible when a higher fraction of its ensemble of conformations fell into fewer clusters than the alternate candidate.

The clusters populated by an engineered immunogen candidate were compared with a reference structure using RMSD. If the RMSD of a cluster was below a threshold value of 4 Angstroms, the cluster was considered ordered (e.g., low flexibility) and similar to the reference (structural similarity). An engineered immunogen candidate with a high fraction of its ensemble meeting this criterion of low flexibility and high structural similarity is predicted to be more active than an alternate candidate with a low fraction of its ensemble meeting this criterion of low flexibility and high structural similarity.

This quantitative analysis was combined with qualitative analysis of the MD trajectories regarding biophysical, biological and physical-chemical interactions, and used to select given immunogen candidates to evaluate in vitro. Table 6 below lists eleven engineered immunogens prepared as described above.

TABLE 6

Engineered Immunogens

| Label | Sequence | Cross-Link | SEQ ID |
|---|---|---|---|
| 13_131_CYN | TVYPQPDATAKCVHGCDPREYTKAVEDAK | C12-C16 | 17 |
| 11_14_CYN | DWGDDCKKKHEITHATGDYCEKLDKS | C6-C20 | 18 |
| 6_163_CYN | DDCIKVTGPAECAERACRAQEERQRQPQCI | C3-C17 | 19 |
| 57_63 | CDCQAQWTPGMRAPGYDPYCLNCGS | C1-C23, C3-C20 | 20 |
| 13_131 | MVYCQPDCTAKCMHGCDRDTMKECCDRLK | C12-C16, C8-C25, C4-C24 | 2 |
| 6_130 | DDCPEVPHATFKGPGQKWEGPGGGDCSK | C3-C26 | 3 |
| 6_163 | DDCIEVPGPAECAERACRAQEERQRQPQCI | C3-C17, C12-C29 | 4 |
| 77_89 | AEEEKIKIEQKERKTTIKLAKEAK | none | 5 |
| 147_156 | CHLQIMTHGKIIYVPCGS | C1-C23 | 21 |

TABLE 6-continued

| Engineered Immunogens | | | |
|---|---|---|---|
| Label | Sequence | Cross-Link | SEQ ID |
| 11_14 | DDGDRCAKEHEIPHATGEECQKRDKS | C6-C23 | 7 |
| 44_56 | CKQLVIYFTGNSSHSSVFYIYYDC | C1-C24 | 8 |

Example 2: Evaluation of Engineered Immunogens In Vitro

The binding of the engineered immunogens prepared in Example 1 are evaluated using an antibody to CD25. The engineered immunogens are modified on the C-terminus with a -GSGSGK-biotin group (SEQ ID NO: 846), and then bound separately to a streptavidin-coated biosensor tip. Buffer containing the CD25 antibody is flowed over the tip during an association phase of 300 seconds, and then the flowed solution is switched to buffer without the CD25 antibody and the dissociation from the biosensor tip will be measured. A control is also run where the tip does not have any engineered immunogen or protein initially bound, to evaluate any background binding of the CD25 antibody to the tip. A second control is performed where full length CD25 is biotinylated and bound to the biosensor tip, to demonstrate the binding level of the CD25 antibody to full length CD25. The data obtained from these biosensor experiments is used to qualitatively rank binding of the engineered immunogens.

Example 3: Evaluation of Engineered Immunogens with Phage Panning

Engineered immunogens provided herein are evaluated using phage panning techniques.

Mouse HuCD25 immunized phage libraries are transformed by electroporation in TG1 and phage propagated with the addition of CM13 using standard Phage Display protocols. TG1 cultures secreting phage are PEG precipitated with PEG/NaCl after incubation on ice for one hour. Exemplary libraries that may be used include 7807, 7808, 7809, and 7810.

Tumor microenvironment (TME) pH subtractive selections: Phage panning is carried out physiological pH and TME pH. To deplete antibodies that bind with high affinity to full-length CD25 at physiological pH, subtractive panning is first carried out by counter-selection of 3×10^11 pfu phage (1000-fold representation of a 3×10^8) at pH 7.4 by absorption for 1 hour on ELISA plates coated with 10 ug/ml full-length CD25 (400 nM) in PBST pH 7.4. Resulting phage supernatant is collected and pH is adjusted to pH 6.5 with PBST. Subsequent phage panning selections are carried out at pH 6.5.

Panning selections are pre-cleared with 25 microliters streptavidin Dynabeads with no antigen after a one hour incubation. Phage are then added to new pre-blocked Eppendorf LoBind tube. Biotinylated engineered immunogens (such as those described in Example 1) are added at 100 nM concentration (in some cases, additional 500 mMNaCl was added to reduce non-specific binding of immunogen to phage) for 40 min to one hour. Samples are then incubated with 25 microliters streptavidin beads or streptavidin coated plates at RT for one hour. Samples are pelleted and washed using magnet/magnetic beads or with plates, washed 7-10 times with PBST. Tubes are changed twice to remove residual phage.

To elute phage, 50-800 μL glycine pH 2.2 is added to the beads and plates, respectively, and incubated for no more than ten minutes, then neutralized with high pH Tris 9.0. Eluted phage is added to 1-5 ml TG1 freshly grown (OD600~0.5), and incubated for 20-30 minutes.

Fractional log dilution series are plated, and the remainder transferred to 25 ml 2×YT. 1 ml glycerol stock is saved for a subsequent panning round, and helper phage/IPTG added at OD600~0.5.

The selection against the engineered immunogen at pH 6.5 with counter-selection at pH 7.4 is carried out once more. The periplasmic extracts are subsequently evaluated using phage ELISA and octet screening.

To ensure that fab phage also bind full-length CD25 in addition to the engineered immunogen, a final selection with full-length CD25 can optionally be carried out, with full-length CD25 in place of the engineered immunogen (2 rounds selection against engineered immunogen, then 1 round selection against full length CD25).

To carry out selection with full-length CD25, after pre-clearing the panning selections with 25 microliters streptavidin Dynabeads, and adding phage to new pre-blocked Eppendorf LoBind tubes, biotinylated full-length CD25 is added at 100 nm concentration for one hour. The samples are then incubated with 25 microliters streptavidin beads at RT for one hour. Pelleting, washing, and elution steps are followed as described above.

Example 4: Phage ELISA Protocol and Biosensor/Octet Screening

ELISA Extract Preparation: Phage ELISA and periplasmic extract preparation for Fab Octet screening are conducted.

The CD25 antigen is diluted, added to the ELISA plate wells, and incubated. Following the incubation, wells are washed twice with PBS, then blocked by adding BSA followed by incubation for 2 hours at 25° C. Phage are diluted two-fold in 1×PBST 1.0% BSA, pH 6.5, 50 microliters are added per and incubated for 5 minutes at room temperature. The blocking solution is shaken out of the wells, and 50 μL of the dilute phage preparation is added to each well, and incubated for 1 hour at room temperature. The ELISA plate wells are washed 3-5 times with 200 microliters PBST pH 6.5. HRP-conjugated anti-M13 antibodies are diluted (Abcam, ab50370) 1:5000 with 1×PBST 1.0% BSA pH 6.5. 50 microliters of diluted secondary antibody conjugate is added to each well, and incubated for 1 hour at room temperature. ELISA plate wells are washed 3-5 times with 200 microliters PBST pH 6.5. The ECL Lumo substrate is prepared (e.g. Supersignal ELISA Pico Chemiluminescent Substrate) as described, into a 1:1 mixture. 50 microliters substrate solution is added to each well, incubated at room temperature for 5 to 60 minutes before reading.

Colonies are inoculated in 0.03-4 ml 2×YT 0.2% Glucose with 0.1 ml overnight culture (1 ml cultures in 96-well plate or 4 ml cultures in 14-ml falcon tubes). They are incubated at 250-700 rpm at 37° C. until the OD600~0.5-1.0. Cultures are induced with 50-400 μL 0.025-0.1M IPTG. In some cases, the temperature is reduced to 30° C. with shaking at 250 rpm. They are then incubated overnight. 1-4 ml cultures are harvested by pelleting 3400 rcf for 10-15 minutes. The supernatant is discarded. Cultures are resuspended with 50-75 μL PPB buffer (30 mM Tris-HCl, pH 8.0, 1 mM EDTA, 20% Sucrose) with 1× Halt Protease Inhibitor and incubated on a rocking platform for 15 minutes at room temperature or 4° C. for 10 min. Then, cultures are resuspended with 150-225 μL of cold ddH20 with 1× Halt Protease Inhibitor and incubated on a rocking platform for one hour at room temperature or 4° C. for 1-2 hours. The lysate suspension was spun at 15000 rcf for 10-15 min at 4° C. Supernatant is collected and diluted.

Fab Expression and Purification Protocol: Cell cultures are inoculated, grown up overnight, and then induced with 50 μL of 25 mM-1M IPTG. The temperature was reduced to 30° C. and rpm to 150. Incubation was done overnight. 50 ml cultures or plates were harvested by pelleting 3400 rcf for 15 minutes. The supernatant was discarded. Cell pellets from 50 mL cultures were placed in a −80° C. freezer for 1 hour, while cultures grown in plates had 75 μL of PPB added with 1× Halt protease inhibitor, EDTA-free (Thermo Fisher Scientific) and vortexed. Plates are shaken at 4° C. for 10 minutes at 1000 rpm. The volume of 225 uL of cold water with 1× Halt protease inhibitor, EDTA-free (Thermo Fisher Scientific) is added to each well. Samples were mixed and shaken at 4° C. for 1-2 hours at max speed i.e. 1000 rpm. Plates are spun at 3500 rpm for 10 mins at 4° C. The supernatant (PPE) is transferred to fresh plates and stored at −20° C. Cell pellets from the 50 mL cultures are removed from the freezer and 5 ml PBS, 10 mM Imidazole is added with 2.5 mg/ml lysozyme and 1× Halt protease inhibitor, EDTA-free (Thermo Fisher Scientific). After pellets are thawed at room temperature for 30 minutes and lysates were centrifuged for 15 minutes at 3400 rcf The supernatant is removed and pellet discarded. 500 μL Ni-NTA resin was added (pre-washed and pelleted) or a Ni-NTA spin column was used for Fab purification. Incubate with cleared lysate for 30 min-1 hr. This was spun at 1500 rcf. These were washed 5 times with 1 ml PBS, 10 mM Imidazole. Buffer was discarded after each spin. 1 ml PBS, 200 mM Imidazole were added and mixed, incubated for 30 minutes and spun at 1500 rcf for 15 minutes. The eluted protein was stored at 4° C. or 20° C. after determining protein concentration. Zeba columns were used for desalting/buffer exchange.

OctetBiosensor Screening: For Octet Koff rate screening in raw supernatants, 50 μL of lysate is used in 384-well Pall ForteBio Octet plates. Data is collected on an Octet RED 384 (MD ForteBio). Briefly, Human CD25 is coupled to AR2G tips (1 ug/ml). For data collection, baseline is assessed in PBST 1% BSA buffer for 60 seconds. Tips are then moved to 50 μL lysate and association measured for 300 seconds. Finally, tips are moved to PBST 1% BSA buffer. Tips are then regenerated with 200 mM Tris-Glycine, pH 2.5 and neutralized with PBST, 1% BSA. For data analysis, double referencing (no CD25 on tip as well as blank reference well) is performed on Octet HT 11.0 software for reference subtraction.

Example 5: Evaluation of Antibodies Generated from Immunogens

Antibodies are produced by immunizing mice with the engineered immunogens described herein. These antibodies are evaluated for cross-reactivity, cross-blocking, affinity, and off-rate estimation.

Protocol for cross-reactivity determination by Biosensor (Octet Red 384, Pall Forte Bio): This protocol is used to determine the ability of individual test clones (anti-human CD25 mouse monoclonals) to bind the target (antigen) from human, cynomologous monkey, and mouse species. The target proteins are either covalently coupled via primary amines to dextran coated sensor tips or by affinity capturing the 6×-His tagged target proteins on anti-6×-His monoclonal antibody coated sensor tip. The monoclonal supernatants, in solution, are made to bind to the antigen on the biosensor tip. The net binding signal is the binding signal with the subtraction of corresponding signal with blank media or buffer binding to blank or antigen coated tips. A signal >3× background binding is considered as real binding event.

Protocol for cross-blocking by Biosensor: This method is to determine if the individual test clones (anti-human CD25 mouse monoclonals) are able to cross-block control antibodies. Cross-blocking may indicate that the test clones recognize an epitope that overlaps with the corresponding epitopes of the control antibodies. Additionally, this might imply that the test antibodies could have similar functional properties as the control antibodies. For this protocol, the control antibodies are covalently coupled via primary amines to dextran coated sensor tips. The target antigens, in solution, are made to bind to the control antibodies. Following this step, the test antibody, in solution, is made to bind to the antigen in a sandwich format. If the test antibody can bind to the antigen, it indicates that it does not cross-block the control antibody, while a non-binding may be interpreted as an ability to cross-block the control antibody.

Protocol for affinity determination by Biosensor: This method is used to determine the affinities of the individual test clones with antigens, when the concentration of the test antibodies is known. A capture molecule, such as Protein G or anti-mouse IgG-monoclonal or anti-human IgG-monoclonal is coated on the biosensor tip. Test clones are captured on the capture molecule coated surface. To these test clones, antigens in solution are made to associate and dissociate for time periods ranging from 60 to 600 seconds for association phase and 60 to 1800 seconds for dissociation phase. The result data (or 'sensograms') are then fit using either a 1:1 Langmuir model or 2:1 heterogeneous model. The former assumes that the interacting pairs are homogenous if a 2:1 model for fitting the data results in a better fit, it indicates that the clones require further sub-cloning due to inherent heterogeneity. The data curve fits provide the dissociation constant as a ratio of the on and off-rate constants Protocol for off-rate estimation by Biosensor: This method is used to estimate the dissociation rate constant of test clones when the concentration of antibodies is not known or if the test clones require further subcloning. A capture molecule, such as Protein G or anti-mouse IgG-monoclonal or anti-human IgG-monoclonal is coated on the biosensor tip. Test clones are captured on the capture molecule coated surface. To these test clones, antigens in solution are made to associate and dissociate for time periods ranging from 60 to 600 seconds for association phase and 60 to 1800 seconds for dissociation phase. The result data (or 'sensograms') are then fit using either a 1:1 Langmuir model or 2:1 heterogeneous model. The former assumes that the interacting pairs are homogenous if a 2:1 model for fitting the data results in a better fit, it indicates that the clones require further sub-cloning due to inherent heterogeneity. The data is fit only for the off-rate constant and not the on-rate (or association) rate constant. This provides the estimates of off-rate constant, which can be used to rank-order the test clones.

Example 6: Selection of Engineered Polypeptides Using a CD25 Portion as the Reference Target The sequence and three dimensional (3D) structure of CD25 was retrieved from the protein databank (PDB) (PDB ID NO: 2ERJ, chain Δ):

(SEQ ID NO: 845)
ELCDDDPPEIPHATFKAMAYKEGTMLNCECKRGFRRIKSGSLYMLCTGSS

SHSSWDNQCQCTSSATRSTTKQVTPQPEEQKERKTTEMQSPMQPVDQASL

PGHCREPPPWENEATERIYHFVVGQMVYYQCVQGYRALHRGPAESVCKMT

HGKTRWTQPQLICTG

Figure 6:
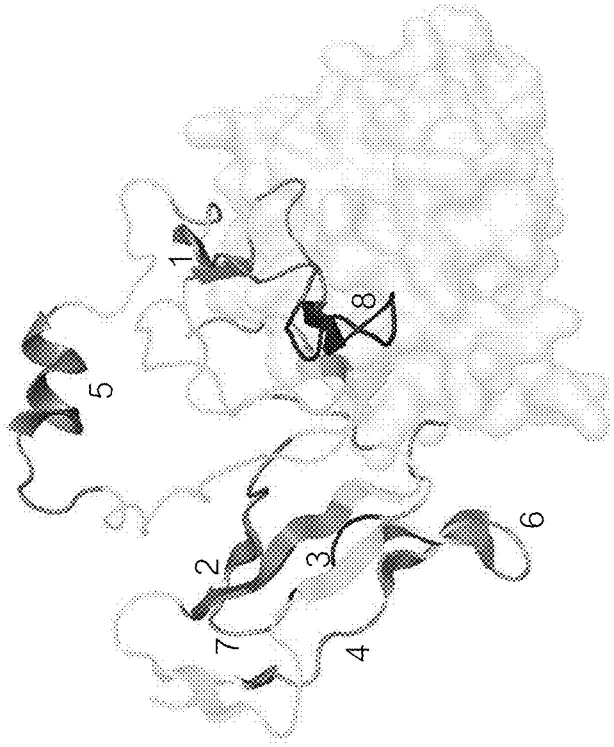
FIG. 6 shows a diagram of eight epitopes on CD25 outside the IL-2 interface targeted for generation of the engineered polypeptides of the disclosure.

As shown in FIG. 6, a putative therapeutic epitopes of CD25 were identified as reference targets for engineered polypeptide selection. Residues positions with respect to SEQ ID NO: 1) and epitope sequences are provided in Table 7.

TABLE 7

| Epitope # | Epitope ID | Epitope Positions | Epitope Sequence |
|---|---|---|---|
| 1 | _55-63_ | 55-63 | SWDNQCQCT (SEQ ID NO: 22) |
| 2 | _13-20_127-132_ | 13-20:127-132 | ATFKAMA (SEQ ID NO: 23) . . . MVYYQC (SEQ ID NO: 24) |
| 3 | _6-17_ | 5-17 | DDPPEIPHATFKA (SEQ ID NO: 25) |
| 4 | _5-11_156-163_ | 5-11:156-163 | DDPPEIP (SEQ ID NO: 26) . . . RWTQPQLI (SEQ ID NO: 27) |
| 5 | _77-89_ | 77-89 | QPEEQKERKTTEM (SEQ ID NO: 28) |
| 6 | _147-157_ | 147-157 | VCKMTHGKTRW (SEQ ID NO: 29) |
| 7 | _11-14_ | 11-14 | IPHA (SEQ ID NO: 30) |
| 8 | _44-56_ | 44-56 | YMLCTGSSSHSSW (SEQ ID NO: 31) |

Atomic distance and amino acid descriptor topology were determined. The atomic distance and amino acid descriptor topology of the reference target were obtained using dynamic simulations, and a covariance matrix of atomic fluctuations was generated for the epitope in the reference target. Next, different engineered polypeptide candidates were generated using computational protein design (e.g., Rosetta), dynamics simulations performed on the candidates, and the atomic distance and amino acid descriptor topologies determined. A covariance matrix of atomic fluctuations was generated for the reference target epitope, and for the residues in the candidates corresponding to the residues in the epitope of the reference target.

Principal component analysis was performed to compute the eigenvectors and eigenvalues for each covariance matrix—one covariance matrix for each reference target and one covariance for each of the candidates—and only those eigenvectors with the largest eigenvalues are retained. Eigenvectors describe the most, second-most, third-most, N-most dominant motion observed in a set of simulated molecular structures. If a candidate moves like the reference epitope, its eigenvectors will be similar to the eigenvectors of the reference target (epitope). The similarity of eigenvectors corresponds to their components (a 3D vector centered on each CA atom) being aligned—pointing in the same direction. This similarity between candidates and reference target eigenvectors was computed using the inner product of two eigenvectors. The inner product value was 0 if two eigenvectors are 90 degrees to each other or 1 if the two eigenvectors point precisely in the same direction.

Since the ordering of eigenvectors is based on their eigenvalues, and eigenvalues may not necessarily be the same between two different molecules due to the stochastic nature by which molecular dynamics simulations sample the underlying energy landscape of those different molecules, the inner product between multiple, differentially ranked eigenvectors was needed (e.g., eigenvector 1 of the candidate by eigenvector 2, 3, 4, etc. of the reference target). In addition, without wishing to be bound by any theory, molecular motions are complex and may involve more than one (or more than a few) dominant/principal modes of motion.

To solve these two challenges, the inner product between all pairs of eigenvectors in the candidates and the reference target were computed. This resulted in a matrix of inner products the dimensions of which were determined by the number of eigenvectors analyzed—for 10 eigenvectors, the matrix of inner products is 10 by 10. This matrix of inner products was distilled into a single value by computing the root mean-square value of the inner products. This is the root mean square inner product (RMSIP).

Principal component analysis (PCA) reduces the 3 L×3 L dimensional coordinate covariance matrices (L being number of atoms) into sets of eigenvectors, Φ (reference target) and Ψ (MEM), and eigenvalues, Λ. The set Φ contains N eigenvectors $\varphi_i$ for the reference target and the set Ψ contains N eigenvectors $\psi_j$ for the MEM, where eigenvectors are ordered in their respective sets by their associated eigenvalues. The eigenvector with the largest eigenvalue accounts for the largest fraction of total coordinate covariation. The inner product of each $\varphi_i$ and $\psi_j$ eigenvector is computed to compare the similarity of motion between the reference target and the MEM. The root mean square of all inner product combinations of $\varphi_i$ and $\psi_j$ eigenvectors renders the total similarity of motion of the engineered polypeptide candidate (MEM) to the reference target (RMSIP).

Figure 7:
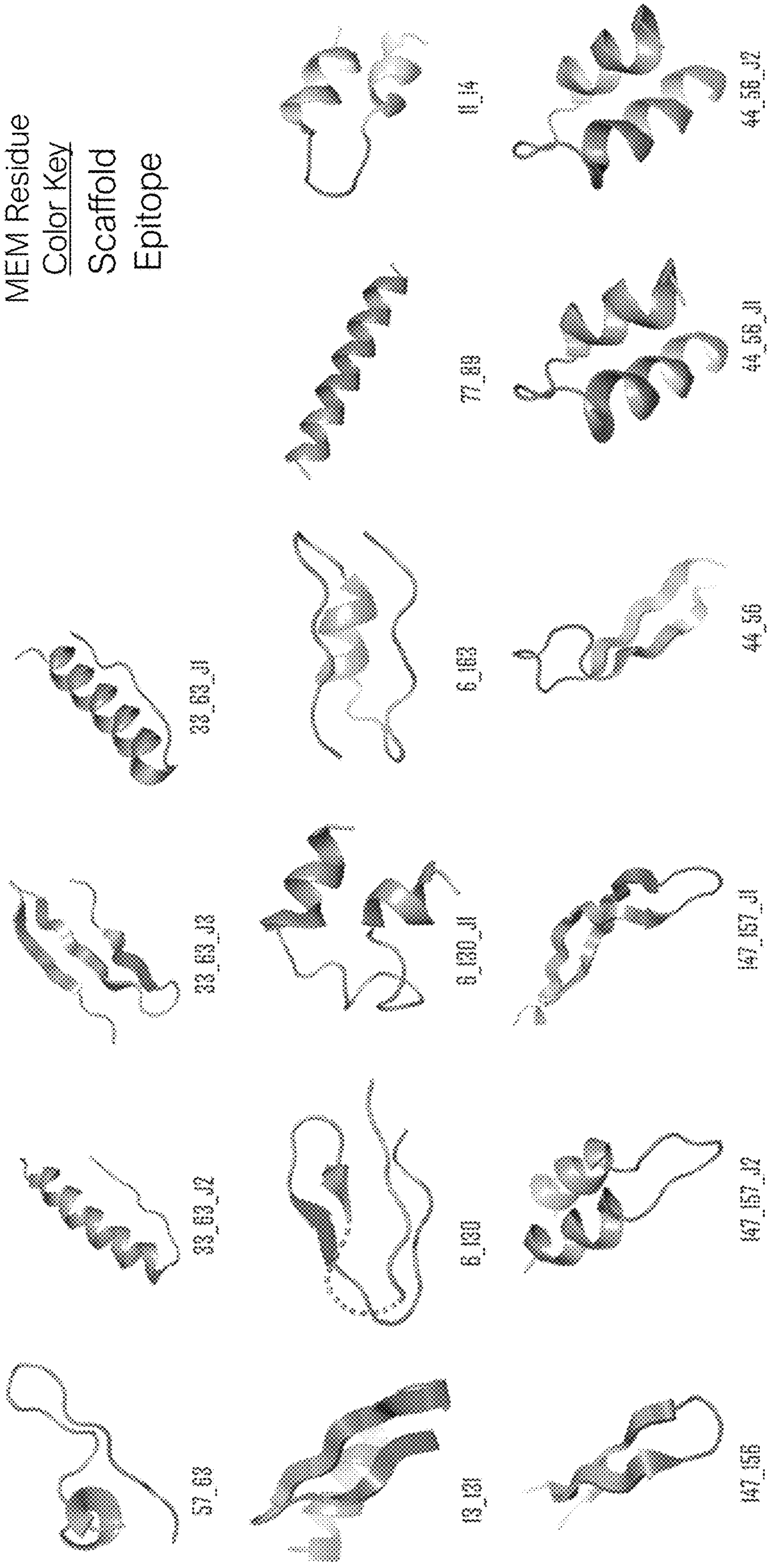
FIG. 7 shows 16 engineered polypeptides designed to mimic eight epitopes outside the IL-2 interface on CD25. In each diagram the CD25 target epitope residues are shown in gold. Scaffold residues designed to support these epitope residues are shown in gray.
Figure 8:
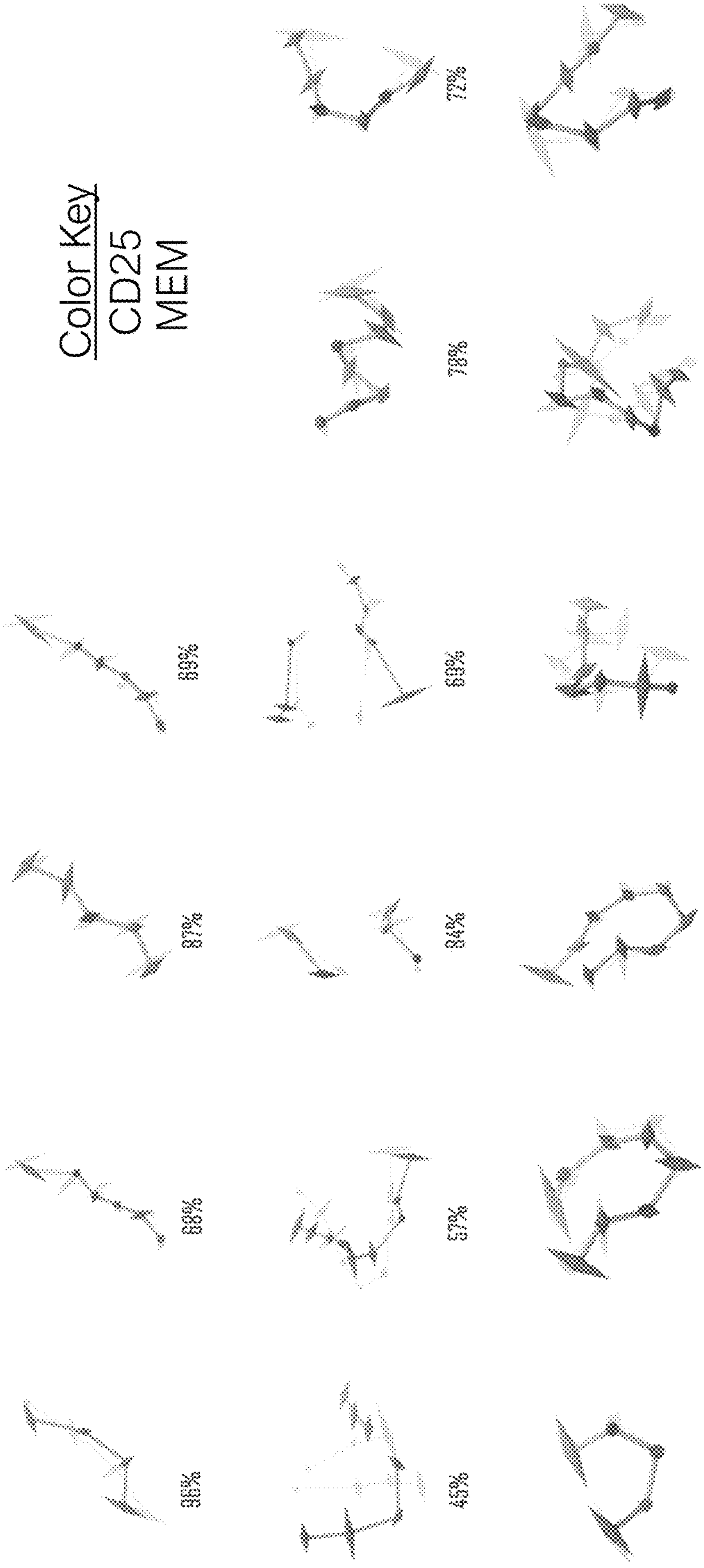
FIG. 8 shows diagrams of computationally determined deviation of the engineered polypeptide from target epitope. The engineered polypeptides show similarity in structure and dynamics to the target epitope (46% to 96% RMSIP).

As shown in FIG. 7, in each engineered polypeptide, epitope residues (gold) and position in the in 3D space by addition of scaffold residues (grey) selected by this computational design procedure. Residues positions with respect to PDB ID NO: 2ERJ, chain A, and epitope sequences are provided in Table 8 and Table 9. Crosslink positions refer to the expected occurrence of intracellular disulfide bond formation in each MEM sequence.

TABLE 8

| MEM ID | N-Terminal Linker | MEM Sequence (N→C) | C-Terminal Linker | Crosslink Positions | Epitope # |
|---|---|---|---|---|---|
| 57_63 | — | CDCQAQWTPGMR APGYDPYCLNC (SEQ ID NO: 1) | GSGSGK-Biotin (SEQ ID NO: 846) | C1-C23, C3-C20 | 1 |
| 13_131 | — | MVYCQPDCTAKC MHGCDRDTMKEC CDRLK (SEQ ID NO: 2) | GSGSGK-Biotin (SEQ ID NO: 846) | C12-C16, C8-C25, C4-C24 | 2 |
| 6_130 | — | DDCPEVPHATFKG PGQKWEGPGGGD CSK (SEQ ID NO: 3) | GSGSGK-Biotin (SEQ ID NO: 846) | C3-C26 | 3 |
| 6_163 | — | DDCIEVPGPAECA ERACRAQEERQRQ PQCI (SEQ ID NO: 4) | GSGSGK-Biotin (SEQ ID NO: 846) | C3-C17, C12-C29 | 4 |
| 77_89 | — | AEEEKIKIEQKERK TTIKLAKEAK (SEQ ID NO: 5) | GSGSGK-Biotin (SEQ ID NO: 846) | none | 5 |
| 147_156 | — | CHLQIMTHGKIIYV PC (SEQ ID NO: 6) | GSGSGK-Biotin (SEQ ID NO: 846) | C1-C23 | 6 |
| 11_14 | — | DDGDRCAKEHEIP HATGEECQKRDKS (SEQ ID NO: 7) | GSGSGK-Biotin (SEQ ID NO: 846) | C6-C20 | 7 |
| 44_56 | — | CKQLVIYFTGNSS HSSVFYIYYDC (SEQ ID NO: 8) | GSGSGK-Biotin (SEQ ID NO: 846) | C1-C24 | 8 |
| 6_130_J1 | Biotin-PEG2 | GSGDEDCKKFQSD DNWENYTSTRHLT FCDEKRS (SEQ ID NO: 9) | — | C7-C28 | 3 |
| 44_56_J1 | Biotin-PEG2 | GSGNEEIEKKIKDC TGNSSHSSWEEAL ECALKK (SEQ ID NO: 10) | — | C14-C29 | 8 |
| 44_56_J2 | Biotin-PEG2 | GSGDERIERLIKEC TGNSSHSSWEEAL ECALRR (SEQ ID NO: 11) | — | C14-C29 | 8 |
| 147_157_J1 | Biotin-PEG2 | GSGSHPCAYWRW VIKMTHGKTRWV LELVFCYRD (SEQ ID NO: 12) | — | C7-C30 | 6 |
| 147_157_J2 | Biotin-PEG2 | GSGKCEEEAKKIA SKMTHGKTREEEA EEYLKKC (SEQ ID NO: 13) | — | C5-C33 | 6 |

TABLE 8-continued

| MEM ID | N-Terminal Linker | MEM Sequence (N→C) | C-Terminal Linker | Crosslink Positions | Epitope # |
|---|---|---|---|---|---|
| 33_63_J1 | Biotin-PEG2 | GSGDDESEKRTTERDTRKCTKAKANDNQCQPTE (SEQ ID NO: 14) | — | C19-C29 | 1 |
| 33_63_J2 | Biotin-PEG2 | GSGSSEWDKWVEEWYKKMCTEAKKNDNQCQPTK (SEQ ID NO: 15) | — | C19-C29 | 1 |
| 33_63_J3 | Biotin-PEG2 | GSGQCRVWVFRNGDKILYIYEDCDNDNQHQQTL (SEQ ID NO: 16) | — | C5-C22 | 1 |

*Biotin-PEG2 = Biotin-Poly-ethyleneglycol(2)

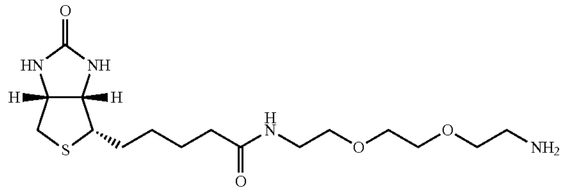 [SMILES: NCCOCCOCCNC(=O)CCCC[C@@H]1SC[C@@H]2NC(=O)N[C@@H]21]

TABLE 9

| MEM ID | Epitope # | CD25 Interface Residues (bold and underline: **X**) MEM Scaffold Residues (plain text: X) |
|---|---|---|
| 57_63 | 1 | C**D**C**Q**A**QWT**PGMRAPGYDPYCLNC (SEQ ID NO: 1) |
| 13_131 | 2 | **MVY**C**Q**PDC**T**A**K**C**M**HGCDRDTMKECCDRLK (SEQ ID NO: 2) |
| 6_130 | 3 | **DD**C**PE**V**PHATFK**GPGQKWEGPGGGDCSK (SEQ ID NO: 3) |
| 6_163 | 4 | **DD**CI**E**V**P**GPAECAERACRAQEE**R**QR**QPQ**C**I (SEQ ID NO: 4)** |
| 77_89 | 5 | AE**EE**KI**K**IE**QKERKTT**IKLAKEAK (SEQ ID NO: 5) |
| 147_156 | 6 | CHLQI**MTHGK**IIYVPC (SEQ ID NO: 6) |
| 11_14 | 7 | DDGDRCAKEH**EIPHAT**GEECQKRDKS (SEQ ID NO: 7) |
| 44_56 | 8 | CKQLVIYF**TGNSS**HSSVFYIYYDC (SEQ ID NO: 8) |
| 6_130_J1 | 3 | GSGDEDCKKFQSD**D**NW**E**NYTSTR**H**L**TF**CDEKRS (SEQ ID NO: 9) |
| 44_56_J1 | 8 | GSGNEEIEKKIKDC**TGNSSHSSW**EEALECALKK (SEQ ID NO: 10) |
| 44_56_J2 | 8 | GSGDERIERLIKEC**TGNSSHSSW**EEALECALRR (SEQ ID NO: 11) |
| 147_157_J1 | 6 | GSGSHPCAYWRWVI**KMTHGKTRW**VLELVFCYRD (SEQ ID NO: 12) |
| 147_157_J2 | 6 | GSGKCEEEAKKIAS**KMTHGKTR**EEEAEEYLKKC (SEQ ID NO: 13) |
| 33_63_J1 | 1 | GSGDDESEKRTTERDTRKCTKAKAN**DNQCQ**P**T**E (SEQ ID NO: 14) |
| 33_63_J2 | 1 | GSGSSEWDKWVEEWYKKMCTEAKKN**DNQCQ**P**T**K (SEQ ID NO: 15) |
| 33_63_J3 | 1 | GSGQCRVWVFRNGDKILYIYEDCDN**DNQ**H**Q**Q**T**L (SEQ ID NO: 16) |

Example 7: Selection of Antibodies Using MEM Programmed In Vitro Selection

Thirty-two different panning strategies (S1-S32) were devised, each comprising three rounds, of positive selection (Table 10). Each program used at least one engineered polypeptide as a selection molecule. A conventional selection was also included using conventional methods (CD25 as the positive target). Bovine serum albumin (BSA) was used a negative target selecting against non-specific binding.

The panning protocol began with a human naïve scFv library, and panning was performed in solution, with the selection molecules bound to biotin (but still in solution). For each round, the starting pool was combined with the negative selection molecule (BSA) first in solution, and then a streptavidin-coated substrate (e.g., magnetic beads) was applied to the mixture to bind the negative selection molecules. Thus, any phage in the pool that was bound to the negative selection molecule was also bound to the streptavidin-coated support. The remaining solution was removed, and this flow through was then taken on to the positive selection step. The flow through was combined with positive selection molecule (antigen 1), allowed to bind, and then a streptavidin-coated solid substrate applied to the mixture. In this step, the bound phage were retained while the remaining unbound phage were removed. Then the bound phage were eluted. *E. coli* were transfected with the eluted phage using a 30 minute cultivation, the transfected cells were split for next-generation sequencing and DNA isolation for analysis, and then the phage amplified for use in the subsequent panning round. For each panning program, in each round negative selection was performed first, and positive selection second.

TABLE 10

| Strategy | Round 1 Antigen | Round 2 Antigen | Round 3 Antigen |
|---|---|---|---|
| S1 | 57_63 | CD25 | 57_63 |
| S2 | 57_63 | CD25 | CD25 |
| S3 | 13_131 | CD25 | 13_131 |
| S4 | 13_131 | CD25 | CD25 |
| S5 | 6_130 | CD25 | 6_130 |
| S6 | 6_130 | CD25 | CD25 |
| S7 | 6_163 | CD25 | 6_163 |
| S8 | 6_163 | CD25 | CD25 |
| S9 | 77_89 | CD25 | 77_89 |
| S10 | 77_89 | CD25 | CD25 |
| S11 | 147_156 | CD25 | 147_156 |
| S12 | 147_156 | CD25 | CD25 |
| S13 | 11_14 | CD25 | 11_14 |
| S14 | 11_14 | CD25 | CD25 |
| S15 | 44_56 | CD25 | 44_56 |
| S16 | 44_56 | CD25 | CD25 |
| S17 | 6_130_J1 | CD25 | 6_130_J1 |
| S18 | 6_130_J1 | CD25 | CD25 |
| S19 | 44_56_J1 | CD25 | 44_56_J1 |
| S20 | 44_56_J1 | CD25 | CD25 |
| S21 | 44_56_J2 | CD25 | 44_56_J2 |
| S22 | 44_56_J2 | CD25 | CD25 |
| S23 | 147_157_J1 | CD25 | 147_157_J1 |
| S24 | 147_157_J1 | CD25 | CD25 |
| S25 | 147_157_J2 | CD25 | 147_157_J2 |
| S26 | 147_157_J2 | CD25 | CD25 |
| S27 | 33_63_J1 | CD25 | 33_63_J1 |
| S28 | 33_63_J1 | CD25 | CD25 |
| S29 | 33_63_J2 | CD25 | 33_63_J2 |
| S30 | 33_63_J2 | CD25 | CD25 |
| S31 | 33_63_J3 | CD25 | 33_63_J3 |
| S32 | 33_63_J3 | CD25 | CD25 |
| S33 | CD25 | CD25 | CD25 |

Figure 9:
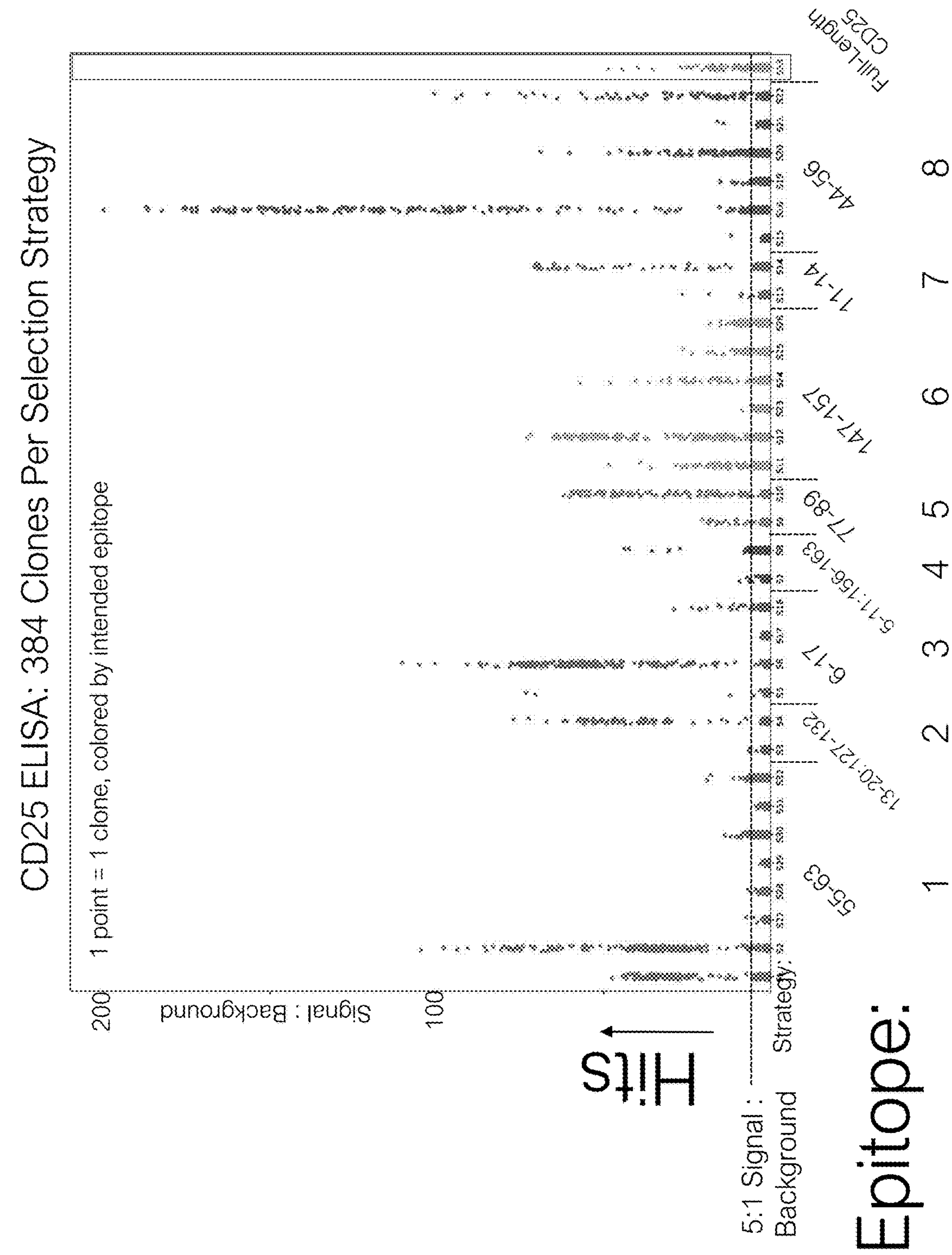
FIG. 9 show ELISA analysis for 384 anti-CD25 scFv clones per in vitro selection strategy. Eight CD25 epitopes were targeted with 32 programmed selection strategies. The figures show the ELISA analysis of individual scFv's from each selection strategy. Each scFv was tested by ELISA against full-length CD25. Selection strategies S1-S32 are ordered by epitope number 1-8, corresponding to the epitope shown in FIG. 6.
Figure 10:
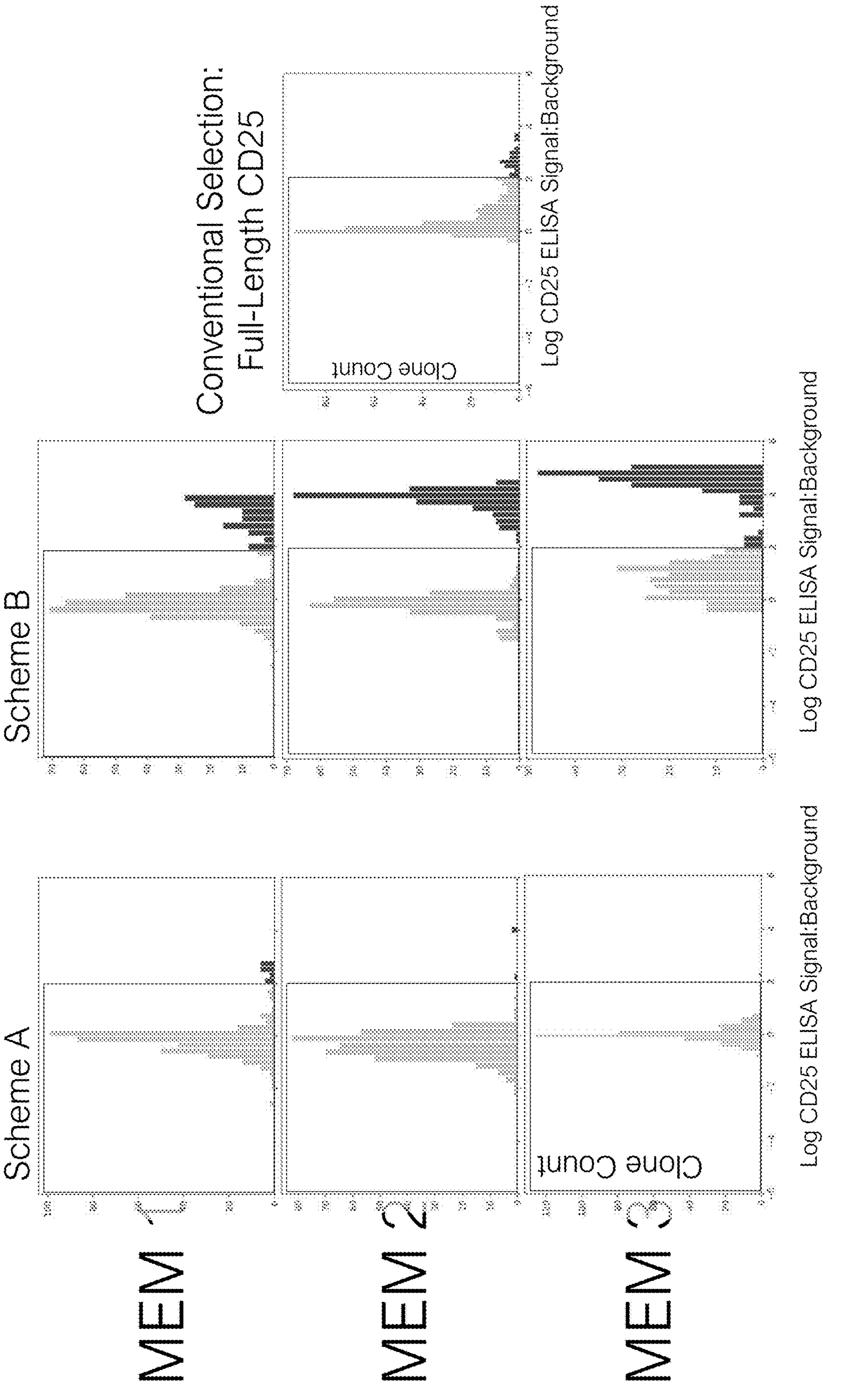
FIG. 10 shows that MEM-programmed selection schemes enrich distinct high affinity clonal subsets. Histograms for two different selection strategies (Scheme A and Scheme B) for each of three MEM polypeptides are shown. The schemes in the right panel resulted in higher numbers of high-affinity clones. Panning with full-length CD25 results in comparatively few high-affinity clones.

Primary ELISA Screen and Hit Selection 384 clones for each strategy were selected for ELISA response analysis to full-length CD25 after three rounds of panning (FIG. 9). Data are shown with the sorted strategies ordered by epitope (FIG. 6). At least one strategy for each epitope yielded clones capable of binding to CD25. It was observed that different strategies using the same engineered polypeptides enrich distinct high-affinity clonal subsets (FIG. 10, black bars). As shown in Table 11, most iVEM-programmed selection strategies produced anti-CD25 hits more productively than conventional full-length panning.

TABLE 11

| Strategy | CD25 Epitope | Anti-Hu CD25% Hit Rate |
|---|---|---|
| S16 | 8 | 65.0 |
| S2 | 1 | 59.0 |
| S12 | 6 | 51.0 |
| S6 | 4 | 46.0 |
| S10 | 5 | 30.0 |
| S33 | Full-length CD25 | 19.0 |
| S4 | 3 | 17.0 |
| S14 | 7 | 16.0 |

Of the hits 1475 were selected for further characterization because they met one of two criteria in ELISA: 1)>10:1 signal to noise (s/n) in full-length CD25 ELISA; or 2)>3:1 s/n in MEM ELISA and >5:1 s/n in CD25 ELISA.

Confirmatory Testing by Biolayer Interferometry

The affinity of the different scFv antibodies were evaluated on a ForteBio® Octet RED384™ biolayer interferometry instrument, using a single-cycle kinetics assay design. His-tagged scFv's were immobilized on anti-his biosensor (Fortebio® HIS1K). Full-length CD25 analyte was washed over the sensor tip and the binding of the molecules in the analyte to the scFv's recorded. Each assay was run in duplicate. Controls were also run, using just a buffer (to control for sensor drift) and a separate control of purified polyclonal IgG isotype antibodies from human serum (to control for non-specific IgG binding).

Figure 11:
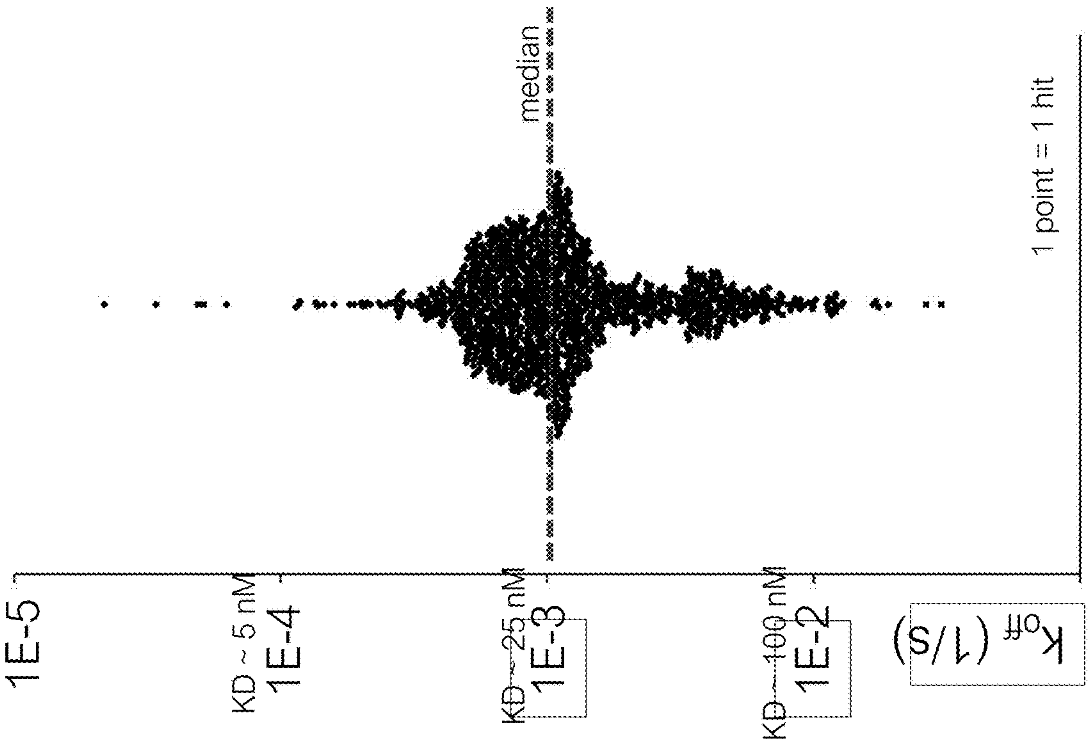
FIG. 11 shows data from biolayer interferometry for 1433 anti-CD25 scFv's identified by phage display panning. The y-axis plots $k_{off}$(1/s) for each clone. Median observed $k_{on}$ was $1.35\times10^5$ (1/Ms). $K_D$ estimates assume $k_{on}$ of $4.5\times10^4$ (1/Ms). 1433 out of 1475 tested screening hits (97%) are confirm to bind CD25. The plot depicts the off-rate distribution for the 1433 confirmed hits.
Figure 12:
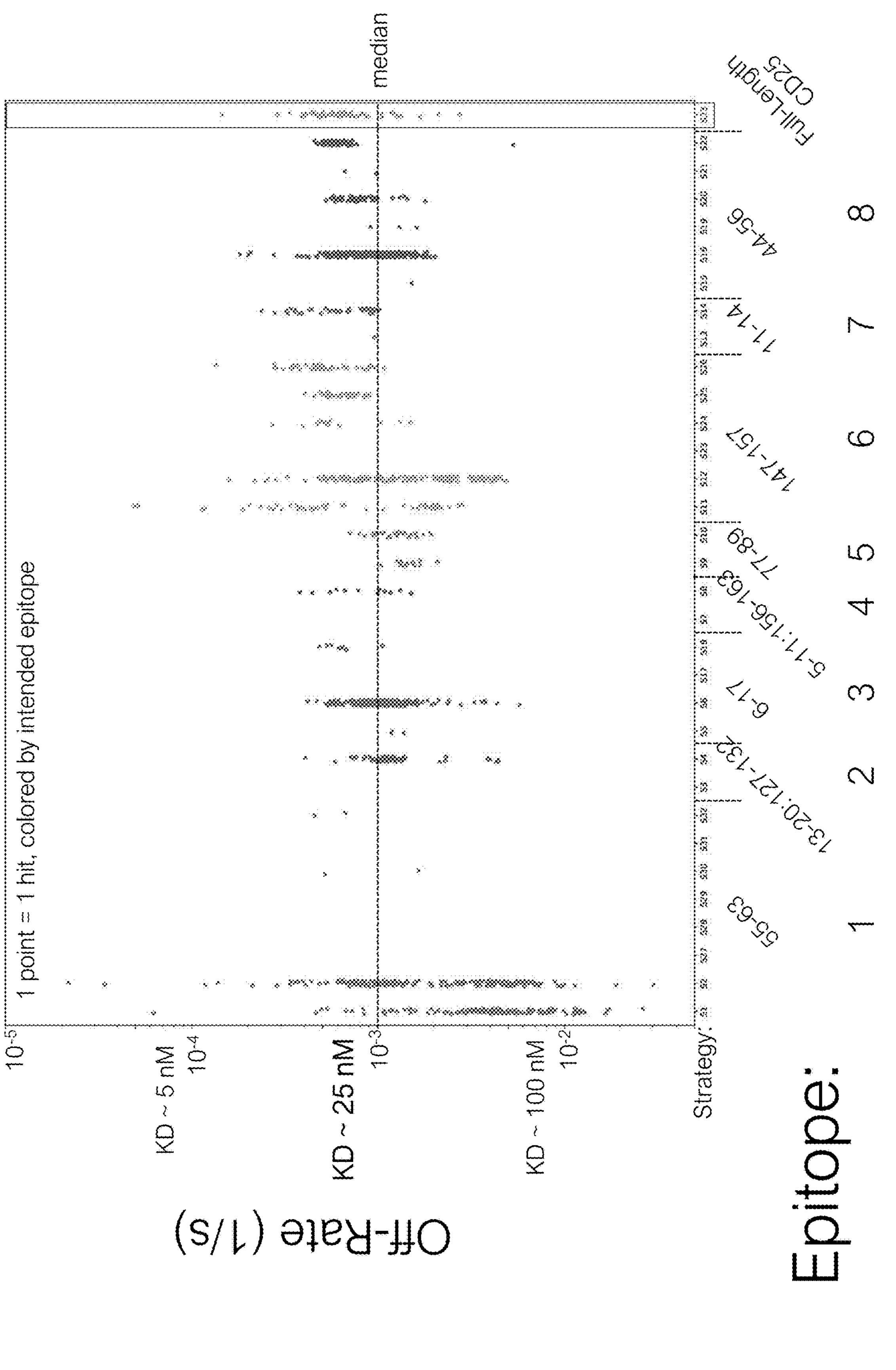
FIG. 12 shows data from biolayer interferometry for anti-CD25 scFv's identified by phage display panning. Hits are identified by panning strategy used. Data is shown for only those hits with $k_{off}$ of less than $10^{-3}$/s.

As shown in FIG. 11, biolayer interferometry of 1475 anti-CD25 scFv's identified by phage display panning. Shows that 1433 hits (97%) are confirm to bind CD25. The observed $K_D$ range of the hits was 10-200 nM, with a median $K_D$ of 28.5 nM. As shown in FIG. 11, most screening strategies generated scFv with high affinity for CD25. Only scFv's having $k_{off}$ less than $10^{-3}$/s are shown. Approximate $K_D$ values are given on the y-axis. As shown in FIG. 12, most of the panning strategies resulted in at least one hit that has $k_{off}$ of less than $10^{-3}$/s.

Confirmatory Testing by Flow Cytometry

Figure 13:
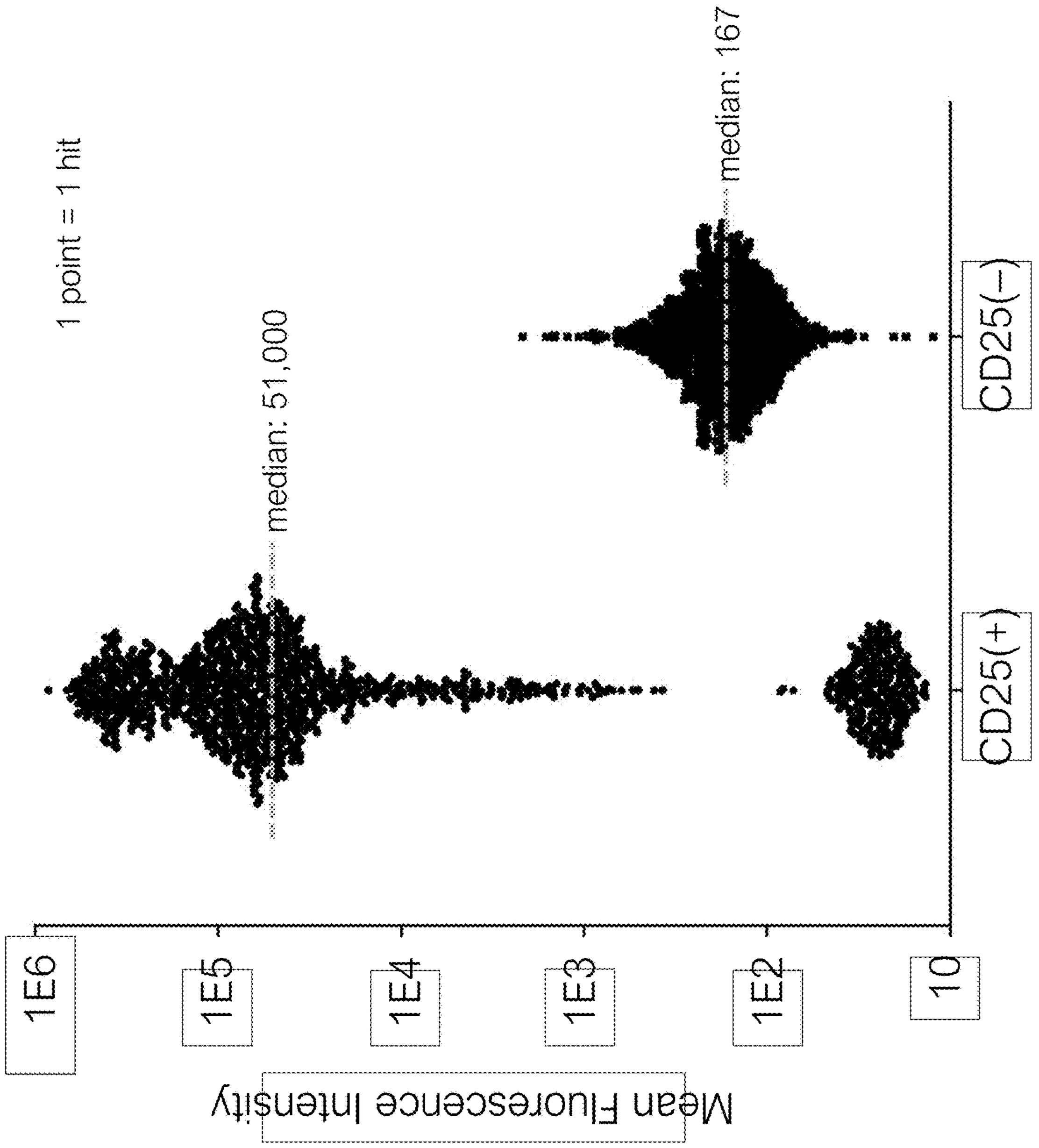
FIG. 13 shows data from flow cytometry for anti-CD25 scFv's identified by phage display panning. The CD25 specificity the different scFv antibodies were evaluated on flow cytometer using cells that express CD25 [CD25(+)] or do not express CD25 [CD25(−)].
Figure 14A:
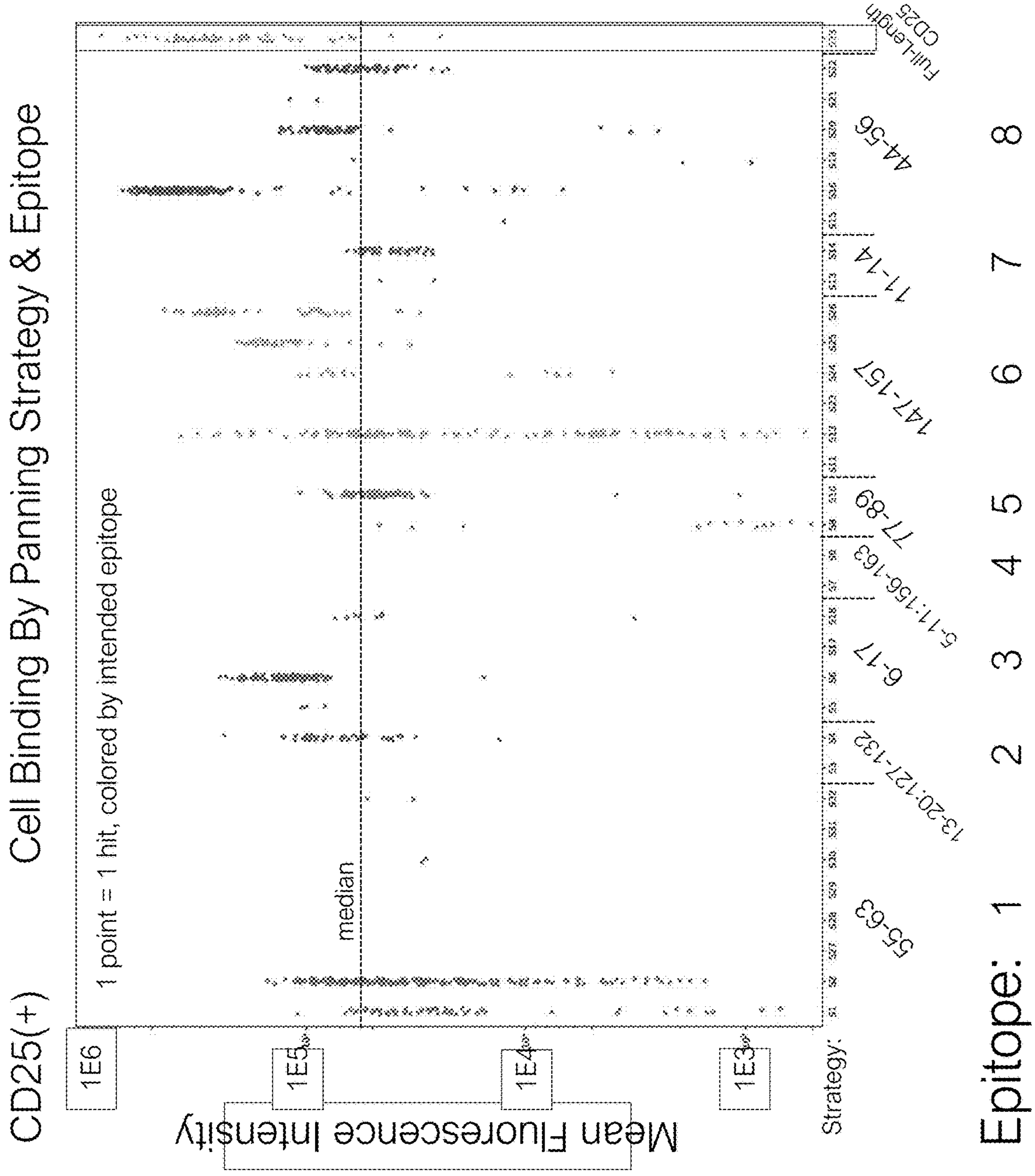
FIG. 14A-14B show data from flow cytometry for anti-CD25 scFv's identified by phage display panning. Hits are identified by panning strategy used.
Figure 14B:
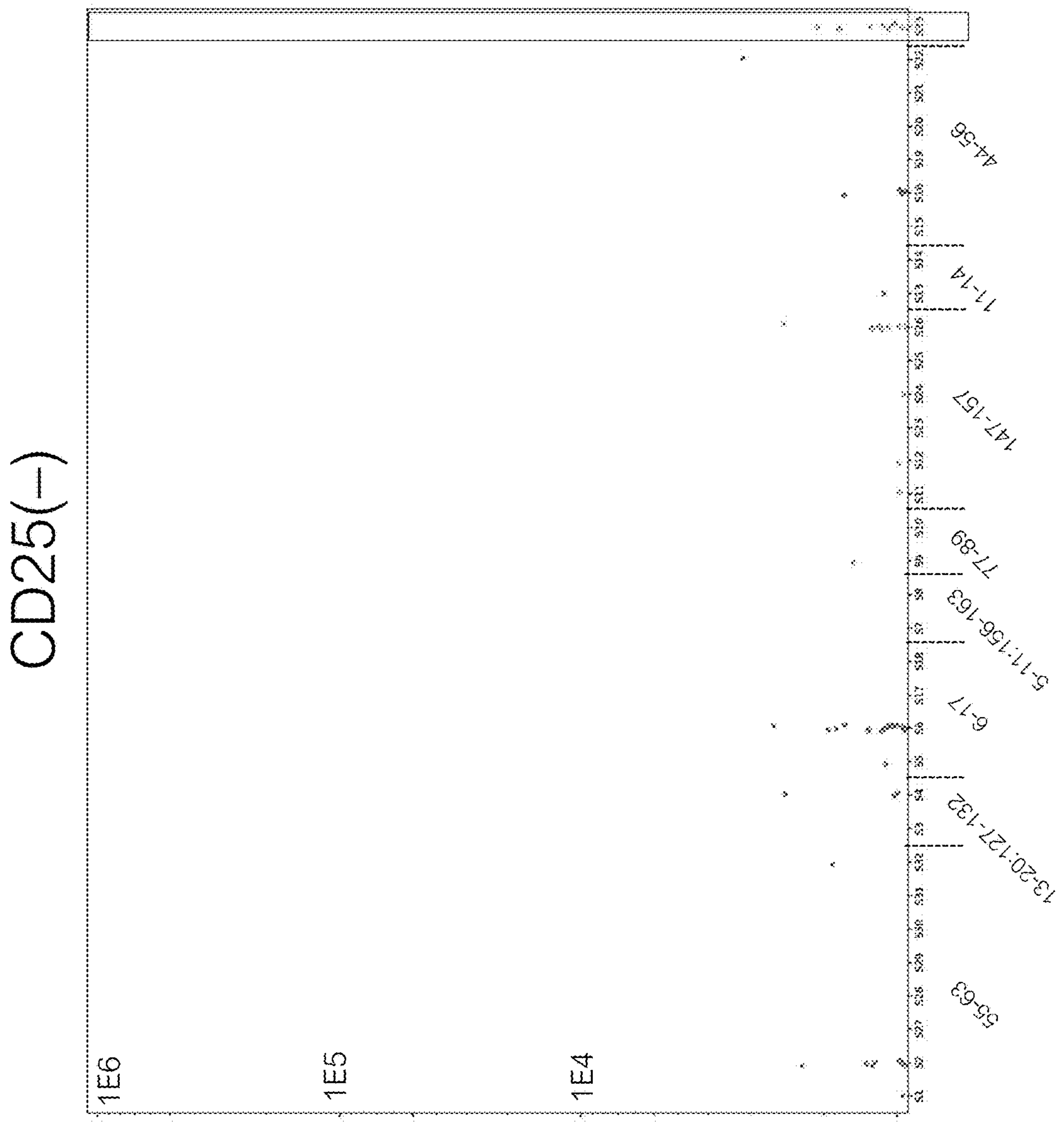

The CD25 specificity the different scFv antibodies were evaluated on flow cytometer using cells that express CD25 [CD25(+)] or do not express CD25 [CD25(−)]. As shown in FIG. 13, of 1248 scFv hits analyzed in this assay, 1160 (93%) bind specifically to CD25(+) cells.

Sequence Analysis of Hits

Figure 15:
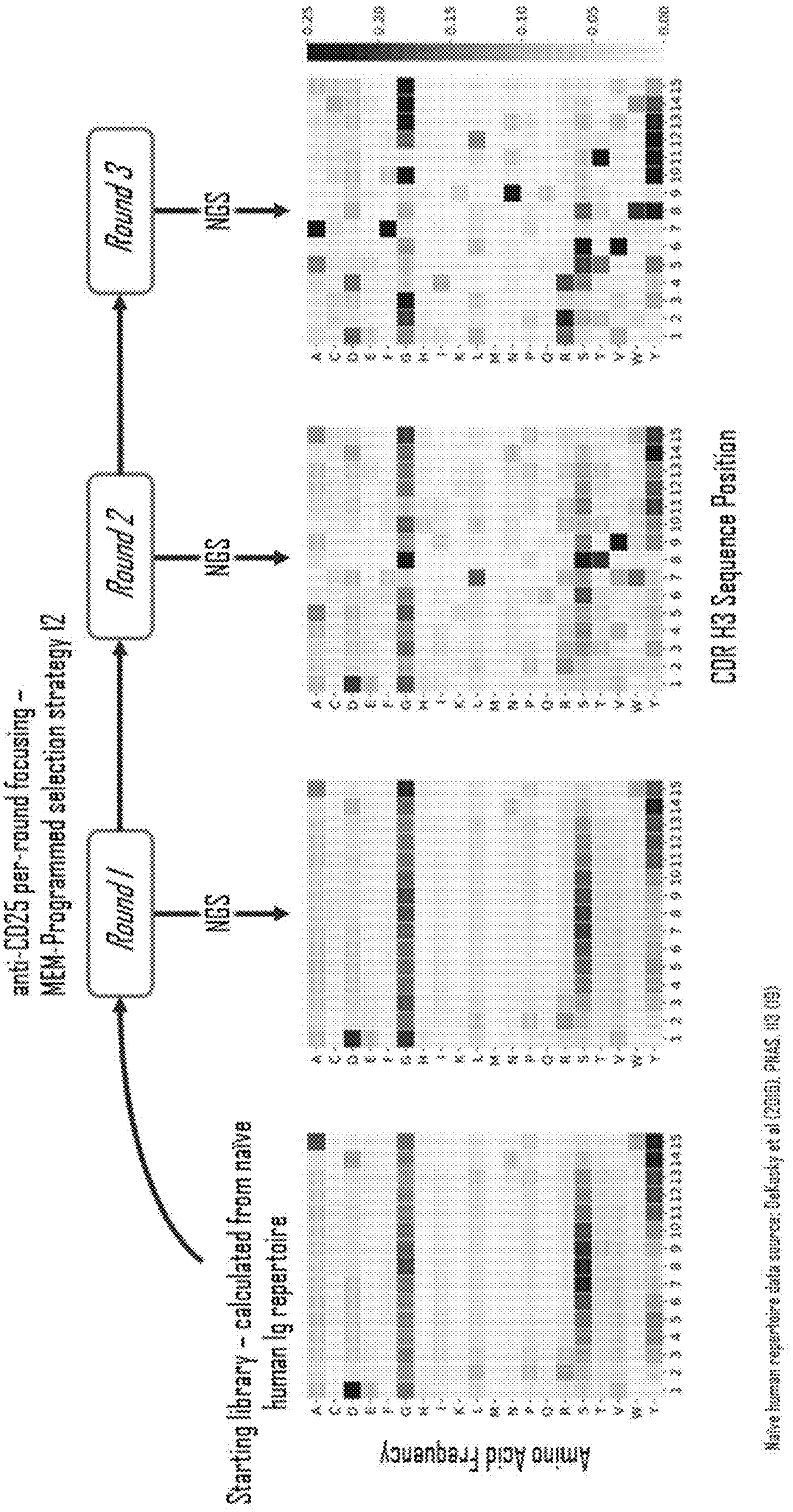
FIG. 15 show amino acid residue enrichment at each CDR H3 position in a representative enrichment strategy (S12).
Figure 16:
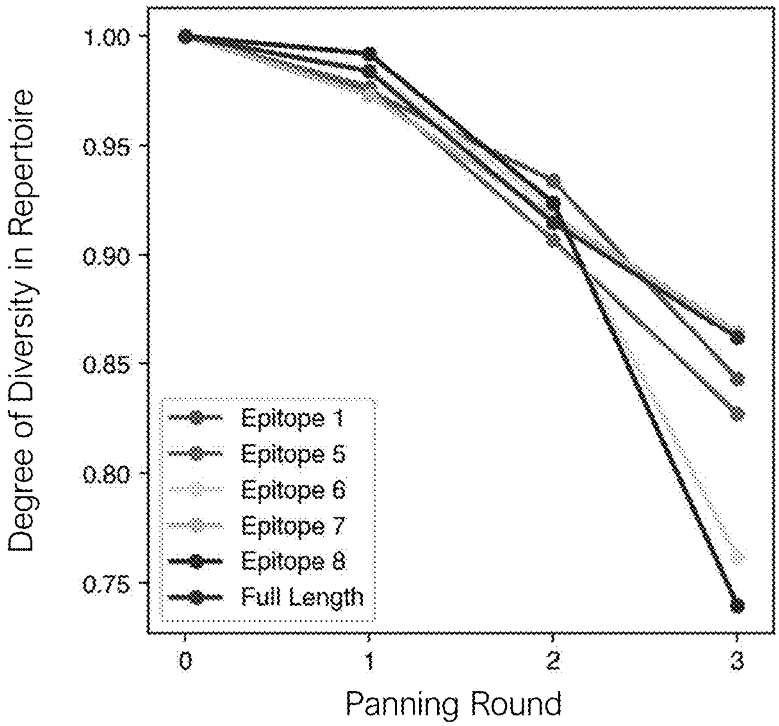
FIG. 16 shows a graph of sequence diversity during each round of MEM- or CD25-steered in vitro selection.
Figure 17:
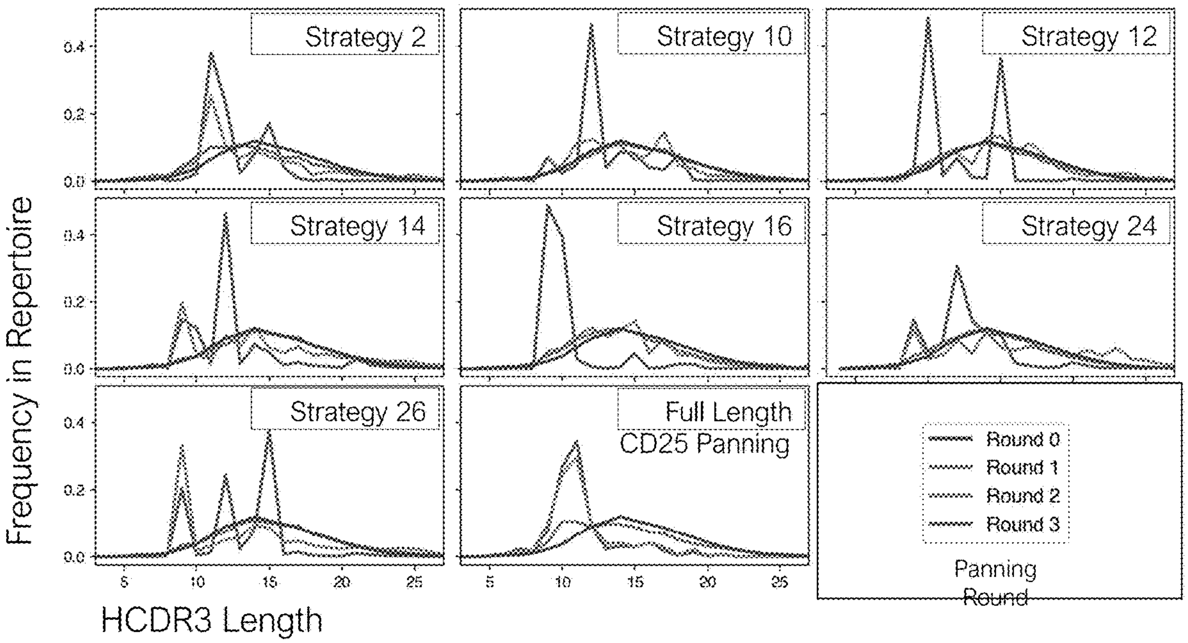
FIG. 17 shows a graph of CDR length during each round of MEM- or CD25-steered in vitro selection.

Next generation sequencing was performed on each round of panned phage. As shown in FIG. 15, MEM-steered panning focuses CDR diversity of antibody libraries in a strategy-dependent manner. Each round of selection decreased repertoire diversity (FIG. 16) and focused CDR length to preferred lengths for each MEM (FIG. 17).

Individual scFv's were sequenced using Sanger sequencing methods. Complete protein sequences for each scFv are provided in Table 5. Immunoglobulin gene usage and complementarity determining regions are provided in Table 12 and Table 2, respectively.

TABLE 12

| Clone ID | VH Germline | DH Germline | JH Germline | VL Germline | VJ Germline |
|---|---|---|---|---|---|
| YU389-A01 | IGHV1-69*01 | IGHD2-8*01 | IGHJ6*01 | IGKV1-39*01 | IGKJ1*01 |
| YU389-A02 | IGHV1-69*12 | IGHD2-8*01 | IGHJ6*01 | IGKV1-39*01 | IGKJ3*01 |
| YU389-A03 | IGHV4-31*03 | IGHD3-3*01 | IGHJ5*02 | IGLV1-51*01 | IGLJ1*01 |
| YU389-A05 | IGHV1-69*12 | IGHD2-8*01 | IGHJ6*01 | IGKV1-39*01 | IGKJ1*01 |
| YU389-A07 | IGHV1-69*01 | IGHD2-8*01 | IGHJ6*01 | IGKV1-39*01 | IGKJ1*01 |
| YU389-B11 | IGHV1-69*12 | IGHD2-8*01 | IGHJ6*01 | IGKV1-39*01 | IGKJ2*02 |
| YU389-D07 | IGHV1-69*01 | IGHD2-8*01 | IGHJ6*01 | IGKV1-39*01 | IGKJ2*02 |
| YU390-A11 | IGHV3-30*18 | IGHD6-19*01 | IGHJ3*02 | IGLV3-21*02 | IGLJ3*01 |
| YU390-A12 | IGHV1-46*01 | IGHD3-10*01 | IGHJ4*02 | IGLV3-1*01 | IGLJ1*01 |
| YU390-B12 | IGHV3-30*18 | IGHD6-19*01 | IGHJ3*02 | IGLV3-21*02 | IGLJ3*01 |
| YU390-C03 | IGHV1-69*12 | IGHD2-8*01 | IGHJ6*01 | IGKV1-39*01 | IGKJ1*01 |
| YU390-C11 | IGHV1-18*01 | IGHD2-15*01 | IGHJ6*01 | IGKV3-15*01 | IGKJ4*01 |
| YU390-D01 | IGHV1-69*01 | IGHD2-8*01 | IGHJ6*01 | IGKV1-39*01 | IGKJ1*01 |
| YU390-D03 | IGHV1-69*01 | IGHD3-22*01 | IGHJ6*01 | IGKV1-5*03 | IGKJ2*01 |
| YU390-D05 | IGHV1-69*12 | IGHD2-8*01 | IGHJ6*01 | IGKV1-39*01 | IGKJ1*01 |
| YU390-D11 | IGHV1-18*01 | IGHD2-15*01 | IGHJ6*01 | IGKV3-15*01 | IGKJ4*01 |
| YU390-G03 | IGHV1-69*12 | IGHD2-8*01 | IGHJ6*01 | IGKV1-39*01 | IGKJ1*01 |
| YU390-H11 | IGHV1-18*01 | IGHD2-15*01 | IGHJ6*01 | IGKV3-15*01 | IGKJ4*01 |
| YU392-A05 | IGHV1-46*01 | IGHD1-26*01 | IGHJ4*02 | IGLV1-47*01 | IGLJ3*01 |
| YU392-A07 | IGHV1-69-2*01 | IGHD5-5*01 | IGHJ4*02 | IGLV1-44*01 | IGLJ3*01 |
| YU392-A09 | IGHV1-69-2*01 | IGHD2-15*01 | IGHJ6*01 | IGLV1-47*01 | IGLJ3*01 |
| YU392-B11 | IGHV1-69-2*01 | IGHD3-22*01 | IGHJ4*02 | IGLV1-47*02 | IGLJ3*01 |
| YU393-A01 | IGHV4-30-2*01 | IGHD3-10*01 | IGHJ6*01 | IGKV1-39*01 | IGKJ4*01 |
| YU393-A02 | IGHV1-69*14 | IGHD3-10*01 | IGHJ4*02 | IGKV1-5*01 | IGKJ1*01 |
| YU393-A03 | IGHV4-4*02 | IGHD3-10*01 | IGHJ5*02 | IGKV3-15*01 | IGKJ1*01 |
| YU393-A04 | IGHV1-18*01 | IGHD1-1*01 | IGHJ1*01 | IGKV1-5*03 | IGKJ1*01 |
| YU393-A08 | IGHV3-30*18 | IGHD3-16*02 | IGHJ4*02 | IGLV3-21*02 | IGLJ3*01 |
| YU393-A09 | IGHV5-51*03 | IGHD1-7*01 | IGHJ5*02 | IGLV3-21*02 | IGLJ3*02 |
| YU393-A11 | IGHV5-51*01 | IGHD1-7*01 | IGHJ5*02 | IGLV3-21*02 | IGLJ3*02 |
| YU393-B02 | IGHV1-69*14 | IGHD2-2*01 | IGHJ6*01 | IGKV1-39*01 | IGKJ2*01 |
| YU393-B03 | IGHV1-69*14 | IGHD2-8*01 | IGHJ6*01 | IGKV1-12*01 | IGKJ4*01 |
| YU393-B04 | IGHV1-69*01 | IGHD2-2*01 | IGHJ6*01 | IGKV1-39*01 | IGKJ2*01 |
| YU393-B05 | IGHV3-30*18 | IGHD6-19*01 | IGHJ4*02 | IGKV3-20*01 | IGKJ3*01 |
| YU393-B06 | IGHV3-30-3*01 | IGHD3-3*01 | IGHJ6*01 | IGKV1-33*01 | IGKJ4*01 |
| YU393-B07 | IGHV3-7*01 | IGHD3-10*01 | IGHJ4*02 | IGLV3-21*02 | IGLJ3*01 |
| YU393-B08 | IGHV1-18*01 | IGHD3-22*01 | IGHJ5*02 | IGLV2-14*01 | IGLJ1*01 |
| YU393-C02 | IGHV3-30-3*01 | IGHD4-17*01 | IGHJ4*02 | IGKV1-33*01 | IGKJ2*01 |
| YU393-C03 | IGHV1-18*01 | IGHD3-10*02 | IGHJ4*02 | IGKV1-NL1*01 | IGKJ4*01 |
| YU393-C05 | IGHV1-69*12 | IGHD3-10*01 | IGHJ6*01 | IGKV1-39*01 | IGKJ4*01 |
| YU393-C07 | IGHV3-30-3*01 | IGHD5-12*01 | IGHJ4*02 | IGLV3-21*02 | IGLJ3*01 |
| YU393-C08 | IGHV1-18*04 | IGHD2-8*01 | IGHJ4*02 | IGLV1-51*01 | IGLJ1*01 |
| YU393-D03 | IGHV7-4-1*02 | IGHD2-21*01 | IGHJ6*01 | IGKV3-15*01 | IGKJ1*01 |
| YU393-D04 | IGHV1-18*04 | IGHD1-26*01 | IGHJ4*02 | IGKV1-12*01 | IGKJ4*01 |
| YU393-D05 | IGHV3-15*01 | IGHD3-10*01 | IGHJ4*02 | IGKV1-39*01 | IGKJ2*01 |
| YU393-D07 | IGHV3-48*03 | IGHD2-15*01 | IGHJ4*02 | IGLV2-14*01 | IGLJ1*01 |
| YU393-E04 | IGHV3-7*01 | IGHD3-10*01 | IGHJ5*02 | IGKV3-20*01 | IGKJ4*01 |
| YU393-E05 | IGHV1-69*06 | IGHD2-8*01 | IGHJ6*01 | IGKV1-9*01 | IGKJ3*01 |
| YU393-E07 | IGHV3-48*02 | IGHD5-12*01 | IGHJ4*02 | IGLV3-21*02 | IGLJ3*01 |
| YU393-F03 | IGHV5-51*03 | IGHD6-19*01 | IGHJ4*02 | IGKV1-17*01 | IGKJ2*01 |
| YU393-F04 | IGHV1-18*04 | IGHD3-10*01 | IGHJ6*01 | IGKV1-39*01 | IGKJ4*01 |
| YU393-F06 | IGHV5-51*01 | IGHD3-16*01 | IGHJ4*02 | IGKV1-5*03 | IGKJ3*01 |
| YU393-F07 | IGHV5-51*03 | IGHD6-19*01 | IGHJ4*02 | IGLV1-47*01 | IGLJ3*01 |
| YU393-G01 | IGHV5-51*01 | IGHD2-8*02 | IGHJ4*02 | IGKV3-20*01 | IGKJ2*01 |
| YU393-G03 | IGHV1-69*06 | IGHD2-8*01 | IGHJ6*01 | IGKV1-39*01 | IGKJ4*01 |
| YU393-G04 | IGHV1-18*01 | IGHD3-3*01 | IGHJ6*01 | IGKV1-12*01 | IGKJ1*01 |
| YU393-G07 | IGHV3-7*01 | IGHD2-8*02 | IGHJ6*01 | IGLV6-57*02 | IGLJ3*01 |
| YU393-G08 | IGHV5-51*03 | IGHD1-7*01 | IGHJ5*02 | IGLV3-21*02 | IGLJ3*02 |
| YU393-G11 | IGHV5-51*01 | IGHD1-7*01 | IGHJ5*02 | IGLV3-21*02 | IGLJ3*02 |
| YU393-G12 | IGHV5-51*03 | IGHD1-7*01 | IGHJ5*02 | IGLV3-21*02 | IGLJ3*02 |
| YU393-H03 | IGHV4-4*02 | IGHD2-8*01 | IGHJ6*01 | IGKV1-39*01 | IGKJ1*01 |
| YU393-H07 | IGHV3-30-3*01 | IGHD5-12*01 | IGHJ4*02 | IGLV3-21*03 | IGLJ3*01 |
| YU393-H09 | IGHV5-51*03 | IGHD1-7*01 | IGHJ5*02 | IGLV3-21*02 | IGLJ3*02 |
| YU394-A01 | IGHV3-7*01 | IGHD4-17*01 | IGHJ4*02 | IGLV1-51*01 | IGLJ3*02 |
| YU394-A02 | IGHV5-51*03 | IGHD1-7*01 | IGHJ5*02 | IGLV3-21*02 | IGLJ3*02 |
| YU394-A07 | IGHV5-51*03 | IGHD1-7*01 | IGHJ5*02 | IGLV3-21*02 | IGLJ3*02 |
| YU394-A09 | IGHV1-69*01 | IGHD2-8*01 | IGHJ6*01 | IGKV1-39*01 | IGKJ1*01 |
| YU394-C01 | IGHV5-51*03 | IGHD1-7*01 | IGHJ5*02 | IGLV3-21*02 | IGLJ3*02 |
| YU394-E02 | IGHV5-51*03 | IGHD1-7*01 | IGHJ5*02 | IGLV3-21*02 | IGLJ3*02 |
| YU394-H01 | IGHV5-51*03 | IGHD1-7*01 | IGHJ5*02 | IGLV3-21*02 | IGLJ3*02 |
| YU394-H03 | IGHV5-51*03 | IGHD1-7*01 | IGHJ5*02 | IGLV3-21*02 | IGLJ3*02 |
| YU394-H04 | IGHV5-51*03 | IGHD1-7*01 | IGHJ5*02 | IGLV3-21*02 | IGLJ3*02 |
| YU394-H05 | IGHV5-51*03 | IGHD1-7*01 | IGHJ5*02 | IGLV3-21*02 | IGLJ3*02 |
| YU394-H07 | IGHV1-69*13 | IGHJ6*01 | IGKV1-39*01 | IGKJ4*01 | |
| YU395-A02 | IGHV1-69*01 | IGHD2-8*01 | IGHJ6*01 | IGKV1-39*01 | IGKJ1*01 |
| YU395-B12 | IGHV1-18*01 | IGHD3-16*02 | IGHJ6*01 | IGLV3-19*01 | IGLJ3*01 |
| YU395-C06 | IGHV1-69*01 | IGHD2-8*01 | IGHJ6*01 | IGKV1-39*01 | IGKJ2*02 |
| YU395-C08 | IGHV1-69*01 | IGHD2-8*01 | IGHJ6*01 | IGKV1-39*01 | IGKJ1*01 |

TABLE 12-continued

| Clone ID | VH Germline | DH Germline | JH Germline | VL Germline | VJ Germline |
|---|---|---|---|---|---|
| YU395-D05 | IGHV1-69*01 | IGHD2-8*01 | IGHJ6*01 | IGKV1-39*01 | IGKJ2*02 |
| YU396-B12 | IGHV5-51*01 | IGHD2-21*01 | IGHJ4*02 | IGLV3-1*01 | IGLJ3*01 |
| YU396-C03 | IGHV3-30*18 | IGHD3-9*01 | IGHJ4*02 | IGLV8-61*01 | IGLJ3*02 |
| YU396-C12 | IGHV5-51*01 | IGHD2-21*01 | IGHJ4*02 | IGLV1-47*01 | IGLJ3*02 |
| YU396-G10 | IGHV1-69*12 | IGHD2-8*01 | IGHJ6*01 | IGKV1-39*01 | IGKJ1*01 |
| YU396-H12 | IGHV3-30*18 | IGHD3-9*01 | IGHJ6*01 | IGLV2-14*01 | IGLJ3*01 |
| YU397-A01 | IGHV5-51*03 | IGHD6-19*01 | IGHJ6*01 | IGKV1-39*01 | IGKJ1*01 |
| YU397-A02 | IGHV1-18*01 | IGHD3-3*01 | IGHJ6*01 | IGKV1-33*01 | IGKJ4*02 |
| YU397-A03 | IGHV3-48*03 | IGHD2-15*01 | IGHJ4*02 | IGLV2-14*01 | IGLJ3*02 |
| YU397-B01 | IGHV5-51*03 | IGHD3-10*01 | IGHJ6*01 | IGKV1-39*01 | IGKJ1*01 |
| YU397-B02 | IGHV1-69*14 | IGHD2-2*01 | IGHJ4*02 | IGKV1-33*01 | IGKJ4*01 |
| YU397-D01 | IGHV4-4*02 | IGHD2-15*01 | IGHJ4*02 | IGKV1-9*01 | IGKJ4*01 |
| YU398-A11 | IGHV3-30*18 | IGHD3-9*01 | IGHJ6*01 | IGLV1-44*01 | IGLJ1*01 |
| YU398-E10 | IGHV3-21*01 | IGHD6-6*01 | IGHJ6*01 | IGLV3-21*02 | IGLJ3*01 |
| YU400-A05 | IGHV3-30*18 | IGHD3-10*01 | IGHJ6*01 | IGLV3-21*02 | IGLJ3*02 |
| YU400-A12 | IGHV4-4*02 | IGHD3-10*01 | IGHJ6*01 | IGKV1-39*01 | IGKJ4*01 |
| YU400-B07 | IGHV3-30*18 | IGHD3-10*01 | IGHJ6*01 | IGLV3-21*03 | IGLJ3*02 |
| YU400-D09 | IGHV1-69*01 | IGHD3-3*01 | IGHJ6*01 | IGLV1-51*01 | IGLJ3*01 |
| YU400-F07 | IGHV3-30*18 | IGHD3-10*01 | IGHJ6*01 | IGLV3-21*02 | IGLJ3*02 |
| YU400-H08 | IGHV3-30*18 | IGHD3-10*01 | IGHJ6*01 | IGLV3-21*02 | IGLJ3*02 |
| YU401-A11 | IGHV3-30*18 | IGHD3-16*01 | IGHJ4*02 | IGLV1-44*01 | IGLJ3*01 |
| YU401-B01 | IGHV1-69*01 | IGHD2-8*01 | IGHJ6*01 | IGKV1-39*01 | IGKJ2*02 |
| YU401-D11 | IGHV3-30*18 | IGHD3-16*01 | IGHJ4*02 | IGLV1-44*01 | IGLJ3*01 |
| YU401-E11 | IGHV3-30*01 | IGHD6-6*01 | IGHJ4*02 | IGKV2D-29*01 | IGKJ4*01 |
| YU401-F11 | IGHV3-30*01 | IGHD6-6*01 | IGHJ4*02 | IGKV2D-29*01 | IGKJ4*01 |
| YU401-G07 | IGHV3-30*18 | IGHD3-10*01 | IGHJ6*01 | IGLV3-21*02 | IGLJ3*02 |
| YU402-A02 | IGHV4-39*07 | IGHD6-13*01 | IGHJ4*02 | IGKV1-12*01 | IGKJ3*01 |
| YU402-A11 | IGHV4-4*02 | IGHD2-8*01 | IGHJ3*02 | IGLV6-57*02 | IGLJ3*01 |
| YU402-D10 | IGHV3-30*18 | IGHD6-6*01 | IGHJ4*02 | IGLV2-14*01 | IGLJ3*02 |
| YU403-G05 | IGHV4-4*02 | IGHD2-8*01 | IGHJ3*02 | IGLV6-57*02 | IGLJ3*01 |

Analysis of the CDRs and germline usages suggest that the 1475 scFv's sequenced represent at least 126 distinct clones. The set includes 40 different VH+JH frameworks choices, and 35 VL+JL framework choices. Unique CDR sequences include:

| | |
|---|---|
| CDR-H1 | GGTFSSYA , GGSISSGGYY (SEQ ID NO: 283), GFTFSSYG (SEQ ID NO: 275), GYTFTSYY (SEQ ID NO: 313), GYTFTSYG (SEQ ID NO: 312), GYTFTDYY (SEQ ID NO: 306), GGSISSGGYS (SEQ ID NO: 282), GGSISSSNW (SEQ ID NO: 284), GYSFTSYW , GFTFSNYG (SEQ ID NO: 271), GFTFSSSA (SEQ ID NO: 272), GFTFSSYW (SEQ ID NO: 277), GFIFSRHA (SEQ ID NO: 264), GYTFNNYG (SEQ ID NO: 302), GFTFSSYA (SEQ ID NO: 273), GYTFTTYA (SEQ ID NO: 314), GFTFNNAW (SEQ ID NO: 267), GFTFSSYE (SEQ ID NO: 274), GYSFTTYW (SEQ ID NO: 300), GYSFNTYW (SEQ ID NO: 297), GFTFRRYW (SEQ ID NO: 268), GYSFSTYW (SEQ ID NO: 298), GFAFSSYG (SEQ ID NO: 262), GYKFANYW (SEQ ID NO: 296), GYTFKNFG (SEQ ID NO: 301), GFTFSSYS (SEQ ID NO: 276), GDSISSSSYY (SEQ ID NO: 261), and GGSISRSNW (SEQ ID NO: 281) |
| CDR-H2 | IIPIFGTA (SEQ ID NO: 326), IIPIFGTA (SEQ ID NO: 326), IYYSGST (SEQ ID NO: 384), ISYDGSNK (SEQ ID NO: 362), INPSGGST (SEQ ID NO: 339), ISAYNGNT , IMPIFDTA (SEQ ID NO: 332), VDPEDGET (SEQ ID NO: 693), IYHSGST (SEQ ID NO: 365), IYPGDSDT (SEQ ID NO: 377), ISHDGHVK (SEQ ID NO: 349), IKQDGSEK (SEQ ID NO: 328), ISVYNGDI (SEQ ID NO: 359), INTNTGDP (SEQ ID NO: 344), IKSKTDGGTT (SEQ ID NO: 330), ISSSGSTI (SEQ ID NO: 351), ISSRGSTI (SEQ ID NO: 350), IYPSDSDT (SEQ ID NO: 383), ISGRKGNT (SEQ ID NO: 347), ISSSSSYI (SEQ ID NO: 352), INHSGST (SEQ ID NO: 333), IYHTGST (SEQ ID NO: 366), and ISYDGNNK (SEQ ID NO: 360) |
| CDR-H3 | AREMYYYYGMDV (SEQ ID NO: 103), AREMYYYYGMDV (SEQ ID NO: 103), ARGNLWSGYYF (SEQ ID NO: 111), AKELLEGAFDI (SEQ ID NO: 64), ARDRVTMVRGALAY (SEQ ID NO: 97), ARERSYYGMDV (SEQ ID NO: 105), ASWSERIGYQYGLDV (SEQ ID NO: 145), ARDILGLDY (SEQ ID NO: 81), ATEDTAMGGIDY (SEQ ID NO: 146), ATEGRYGMDV (SEQ ID NO: 147), AVEGGRAPGTYYYDSSGLAY (SEQ ID NO: 153), ARAGYYYGMDV (SEQ ID NO: 71), ARDLGTMVRGVIEPYYFDY (SEQ ID NO: 85), ARGVRGTGFDP (SEQ ID NO: 118), ARDRNGYFQH (SEQ ID NO: 94), AKDLLGELSFFDY (SEQ ID NO: 61), ARLENNWDYGGWFDP , ARDRSYYGMDV (SEQ ID NO: 96), ARDKGYYGMDV (SEQ ID NO: 83), AKEISPRSSVGWPLDY (SEQ ID NO: 63), ARDFWSGYNELGGMDV (SEQ ID NO: 76), ARTWFGEFFDY (SEQ ID NO: 134), ARVIGGWFDP (SEQ ID NO: 136), ARGRLAYGDTEGFDY (SEQ ID NO: 112), ARDILRGESSILDH (SEQ ID NO: 82), ARDRYYYGMDV (SEQ ID NO: |

-continued

| | |
|---|---|
| | 98), ARDLLGSGYDIIDY (SEQ ID NO: 86), ARVWGKNGDFDY (SEQ ID NO: 142), ARDRFHYGMDV (SEQ ID NO: 90), ARDRGDY (SEQ ID NO: 92), TTEGVELLSFGGAPFDY (SEQ ID NO: 683), ARRRGGGFDY (SEQ ID NO: 132), AREKGSWFDP (SEQ ID NO: 102), ARDRGDRVGGLVFDY (SEQ ID NO: 91), ARQVAGGLDY (SEQ ID NO: 131), ARDRGYYGMDV (SEQ ID NO: 93), FRFGEGFDY (SEQ ID NO: 259), ARDGGYYFDD (SEQ ID NO: 79), ARDFRMDV (SEQ ID NO: 75), ARDAYAYGLDV (SEQ ID NO: 73), ARDLMNYGMDV (SEQ ID NO: 87), AREYDYGDYVFDY (SEQ ID NO: 107), ARLENNWNYGGWFDP (SEQ ID NO: 128), ARDYYYYGMDV (SEQ ID NO: 101), ARDIGYYYGMDV (SEQ ID NO: 80), ARVGDGYSLDY (SEQ ID NO: 135), AKAITSIEPY (SEQ ID NO: 60), AKGQGDGMDV (SEQ ID NO: 66), ARLGWGMDV (SEQ ID NO: 129), ARVWGDTTLGYGMDV (SEQ ID NO: 141), AIPWDAELGNYGMDV (SEQ ID NO: 59), ARGRWSGLGDY (SEQ ID NO: 113), ARARGGRYFDY (SEQ ID NO: 72), ARDQLAARRGYYYGMDV (SEQ ID NO: 89), AKGDVNYGMDV (SEQ ID NO: 65), ARDFYYGSGSYPNGYYYGMDV (SEQ ID NO: 77), ARDFNPFSITIFEMDV (SEQ ID NO: 74), ANLAMGQYFDY (SEQ ID NO: 70), ARDLGEAKSSSPHEPDY (SEQ ID NO: 84), ARDQEMYYFDY (SEQ ID NO: 88), ARGKGSYAFDI (SEQ ID NO: 110), and AKGYSSSPGDY (SEQ ID NO: 67) |
| CDR-L1 | QSISSY (SEQ ID NO: 567), QSISSY (SEQ ID NO: 567), SSNIGNNF (SEQ ID NO: 650), QSISNY (SEQ ID NO: 563), NIETKS (SEQ ID NO: 455), KLGDKY (SEQ ID NO: 404), QSVSNY (SEQ ID NO: 574), QTISQW (SEQ ID NO: 582), SSNIGSNY (SEQ ID NO: 655), NFNIGNNL (SEQ ID NO: 453), RNIWSY (SEQ ID NO: 634), QSISSW (SEQ ID NO: 566), QSVSSR (SEQ ID NO: 576), QTISGL (SEQ ID NO: 581), DIESEM (SEQ ID NO: 163), NIGSKS (SEQ ID NO: 456), QSIGNY (SEQ ID NO: 558), QGISSW (SEQ ID NO: 489), QSVSSTY (SEQ ID NO: 577), QDISNY (SEQ ID NO: 485), NIESES (SEQ ID NO: 454), SSDVGAYNY (SEQ ID NO: 647), QDINNY (SEQ ID NO: 482), QGISNS (SEQ ID NO: 488), SSNIGNNY (SEQ ID NO: 651), EGIRTS (SEQ ID NO: 218), QGTSSW (SEQ ID NO: 491), SSDVGGYNY (SEQ ID NO: 649), QSVSNNY (SEQ ID NO: 573), QGINSY (SEQ ID NO: 487), QAVRID (SEQ ID NO: 472), QSISRY (SEQ ID NO: 564), QSIGYW (SEQ ID NO: 559), SSNVGSNY (SEQ ID NO: 656), QSIKNY (SEQ ID NO: 561), QDIKRR (SEQ ID NO: 480), SGSIASSY (SEQ ID NO: 640), NSNVGNNY (SEQ ID NO: 465), SLRSYY (SEQ ID NO: 643), KLGERF (SEQ ID NO: 405), SGSVSTSYY (SEQ ID NO: 641), SSNIGRNY (SEQ ID NO: 652), EDIRMY (SEQ ID NO: 215), QGISTY (SEQ ID NO: 490), SSNVGSRT (SEQ ID NO: 657), NIGTKS (SEQ ID NO: 459), NIGSKT (SEQ ID NO: 457), QSINSY (SEQ ID NO: 562), SSNIGSNT (SEQ ID NO: 654), QSIITY (SEQ ID NO: 560), QSLLHSDGKTY (SEQ ID NO: 570), and GGNIARNY (SEQ ID NO: 279) |
| CDR-L2 | AAS (SEQ ID NO: 49), AAS (SEQ ID NO: 49), DST (SEQ ID NO: 191), DDD (SEQ ID NO: 158), KDN (SEQ ID NO: 386), GAS (SEQ ID NO: 260), KAS (SEQ ID NO: 385), RNN (SEQ ID NO: 635), SNN (SEQ ID NO: 644), AND, DAF (SEQ ID NO: 156), DDS (SEQ ID NO: 159), AAT (SEQ ID NO: 50), AVS (SEQ ID NO: 154), DAS (SEQ ID NO: 157), GVS (SEQ ID NO: 295), DNN (SEQ ID NO: 190), DVS (SEQ ID NO: 201), RAS (SEQ ID NO: 619), GTS (SEQ ID NO: 291), EDN (SEQ ID NO: 216), DND (SEQ ID NO: 188), GKN (SEQ ID NO: 287), QYI (SEQ ID NO: 616), NTD (SEQ ID NO: 467), RNH (SEQ ID NO: 633), EGS (SEQ ID NO: 219), DGR (SEQ ID NO: 162), TAS (SEQ ID NO: 667), DDT (SEQ ID NO: 160), EVS (SEQ ID NO: 237), and EDD (SEQ ID NO: 214) |
| CDR-L3 | QQSYSTPPT (SEQ ID NO: 534), QQSYSTPPT (SEQ ID NO: 534), GSWDTNLSGYV (SEQ ID NO: 289), QVWDSSSGHREV (SEQ ID NO: 613), QAWDSSTYV (SEQ ID NO: 473), QQYNHWPPL (SEQ ID NO: 544), QQYSGDSMYT (SEQ ID NO: 553), AAWDDSLSGVV (SEQ ID NO: 56), AAWDDSLNGVV (SEQ ID NO: 53), ATWDDSLSGVV (SEQ ID NO: 151), QQSHSTPIT (SEQ ID NO: 526), QQYNSYSRT (SEQ ID NO: 551), QQYTNWPQT (SEQ ID NO: 554), LQYDRYSGA (SEQ ID NO: 426), QVWHTTNDHVL (SEQ ID NO: 615), QVWDSSSDHWV (SEQ ID NO: 611), QQSKQIPYT (SEQ ID NO: 528), QQSYSLPLT (SEQ ID NO: 531), QQFDISGGLI (SEQ ID NO: 518), QQYDNLPLT (SEQ ID NO: 542), QVWDSSSDHTVA (SEQ ID NO: 609), SSYTTTDTFV (SEQ ID NO: 665), QQYDNLPYT (SEQ ID NO: 543), QQYYSTPPH (SEQ ID NO: 556), QQSYSTPLT (SEQ ID NO: 532), QVWDSSSDHVV (SEQ ID NO: 610), GTWDSSLSAYV (SEQ ID NO: 294), QQTHTWPWT (SEQ ID NO: 538), QQANSFPLT (SEQ ID NO: 514), QQSYSTPYT (SEQ ID NO: 536), SSYTSSSTYV (SEQ ID NO: 664), QRYGSSPR (SEQ ID NO: 557), QQVHSFPFT (SEQ ID NO: 541), LQHNTFPYT (SEQ ID NO: 423), QQSHSTPLT (SEQ ID NO: 527), QQYNSYPFT (SEQ ID NO: 548), QQYNSSPLMYT (SEQ ID NO: 547), QQTYSTPLT (SEQ ID NO: 540), QQANTFPQT (SEQ ID NO: 516), QSYDGSSVV (SEQ ID NO: 579), GSWEARESVFV (SEQ ID NO: 290), QQTYNDPPT (SEQ ID NO: 539), NSRDSSGNHVV (SEQ ID NO: 466), QTWDGSIVV (SEQ ID NO: 583), VLYMGSGIWV (SEQ ID NO: 694), ATWDDALSGWV (SEQ ID NO: 149), SSYTSSSTLVV (SEQ ID NO: 660), QQSYSTPWT (SEQ ID NO: 535), SSYTSSSTWV (SEQ ID NO: 663), LQDYNYPPA (SEQ ID NO: 422), QQYYDDPQ (SEQ ID NO: 555), QQLNGYPTT (SEQ ID NO: 525), AAWDDSLIGHV (SEQ ID NO: 51), QVWDTSGDLHWA (SEQ ID NO: 614), |

-continued

| |
|---|
| QQSYTTPLT (SEQ ID NO: 537), QVWDSSSDLLWV (SEQ ID NO: 612), GTWDSSLSALV (SEQ ID NO: 292), AAWDDSLNGPV (SEQ ID NO: 52), MQTKQLPLT (SEQ ID NO: 443), QQANSFPPT (SEQ ID NO: 515), QSYDGNNHMV (SEQ ID NO: 578), and SSYTSSSTLWV (SEQ ID NO: 661) |

Sequence analysis applied to scFv's directed to individual target epitopes identifies common CDR usage patterns within each set of antibody:

For CD25 epitope 1 (55-63), CDRs used include:

| CDR-H1 | CDR-H2 | CDR-H3 | CDR-L1 | CDR-L2 | CDR-L3 |
|---|---|---|---|---|---|
| GFTFSSYG (SEQ ID NO: 275) | ISYDGSNK (SEQ ID NO: 362) | AKGDVNYGMDV (SEQ ID NO: 65) | NIGSKS (SEQ ID NO: 456) | DDT (SEQ ID NO: 160) | QVWDSSSDLLWV (SEQ ID NO: 612) |
| | | | NIGSKT (SEQ ID NO: 457) | DGR (SEQ ID NO: 162) | QVWDTSGDLHWA (SEQ ID NO: 614) |
| | ISYDGNNK (SEQ ID NO: 360) | AKGYSSSPGDY (SEQ ID NO: 67) | SSDVGAYNY (SEQ ID NO: 647) | DVS (SEQ ID NO: 201) | SSYTSSSTLWV (SEQ ID NO: 661) |
| GGTFSSYA (SEQ ID NO: 286) | IIPIFGTA (SEQ ID NO: 326) | ARDFNPFSITIFEMDV (SEQ ID NO: 74) | SSNIGNNY (SEQ ID NO: 651) | DNN (SEQ ID NO: 190) | GTWDSSLSALV (SEQ ID NO: 292) |
| GGSISSSNW (SEQ ID NO: 284) | IYHSGST (SEQ ID NO: 365) | ARDFYYGSGSYPNGYYYGMDV (SEQ ID NO: 77) | QSINSY (SEQ ID NO: 562) | TAS (SEQ ID NO: 667) | QQSYTTPLT (SEQ ID NO: 537) |
| GYSFNTYW (SEQ ID NO: 297) | IYPSDSDT (SEQ ID NO: 383) | ARDGGYYFDD (SEQ ID NO: 79) | QSVSSTY (SEQ ID NO: 577) | GTS (SEQ ID NO: 291) | QQYNSSPLMYT (SEQ ID NO: 547) |
| GGTFSSYA (SEQ ID NO: 286) | IIPIFGTA (SEQ ID NO: 326) | ARDYYYYGMDV (SEQ ID NO: 101) | QSISRY (SEQ ID NO: 564) | GAS (SEQ ID NO: 260) | QQTYNDPPT (SEQ ID NO: 539) |
| | | AREMYYYYGMDV (SEQ ID NO: 103) | QSISSY (SEQ ID NO: 567) | AAS (SEQ ID NO: 49) | QQSYSTPPT (SEQ ID NO: 534) |
| | | | QSISNY (SEQ ID NO: 563) | | |
| | | | QSIITY (SEQ ID NO: 560) | | |
| | | | QSISSY (SEQ ID NO: 567) | | |
| GGSISRSNW (SEQ ID NO: 281) | IYHTGST (SEQ ID NO: 366) | ARGKGSYAFDI (SEQ ID NO: 110) | GGNIARNY (SEQ ID NO: 279) | EDD (SEQ ID NO: 214) | QSYDGNNHMV (SEQ ID NO: 578) |

For CD25 epitope 2 (13-20:127-132), CDRs used include:

| CDR-HI | CDR-H2 | CDR-H3 | CDR-L1 | CDR-L2 | CDR-L3 |
|---|---|---|---|---|---|
| GFTFSSYG (SEQ ID NO: 275) | ISYDGSNK (SEQ ID NO: 362) | ANLAMGQYFDY (SEQ ID NO: 70) | SSNIGSNT (SEQ ID NO: 654) | SNN (SEQ ID NO: 644) | AAWDDSLNGPV (SEQ ID NO: 52) |
| GFTFSSYA (SEQ ID NO: 273) | | ARDLGEAKSSSPHEPDY (SEQ ID NO: 84) | QSLLHSDGKTY (SEQ ID NO: 570) | EVS (SEQ ID NO: 237) | MQTKQLPLT (SEQ ID NO: 443) |
| GDSISSSSYY (SEQ ID NO: 261) | INHSGST (SEQ ID NO: 333) | ARDQEMYYFDY (SEQ ID NO: 88) | QGISSW (SEQ ID NO: 489) | AAS (SEQ ID NO: 49) | QQANSFPPT (SEQ ID NO: 515) |
| GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |

For CD25 epitope 3 (5-17), CDRs used include:

| CDR-HI | CDR-H2 | CDR-H3 | CDR-L1 | CDR-L2 | CDR-L3 |
|---|---|---|---|---|---|
| GFTFSSYG (SEQ ID NO: 275) | ISYDGSNK (SEQ ID NO: 362) | AKAITSIEPY (SEQ ID NO: 60) | SGSVSTSYY (SEQ ID NO: 641) | NTD (SEQ ID NO: 467) | VLYMGSGIWV (SEQ ID NO: 694) |
| GFTFSSYG (SEQ ID NO: 275) | ISYDGSNK (SEQ ID NO: 362) | AKELLEGAFDI (SEQ ID NO: 64) | NIETKS (SEQ ID NO: 455) | DDD (SEQ ID NO: 158) | QVWDSSSGHREV (SEQ ID NO: 613) |
| GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| | | | QSISNY (SEQ ID NO: 563) | | |

For CD25 epitope 4 (5-11:156-163), CDRs used include:

| CDR-HI | CDR-H2 | CDR-H3 | CDR-L1 | CDR-L2 | CDR-L3 |
|---|---|---|---|---|---|
| GGTFSSYA (SEQ ID NO: 286) | IIPIFGTA (SEQ ID NO: 326) | AREMYYYYGMDV (SEQ ID NO: 103) | QSISNY (SEQ ID NO: 563) | AAS (SEQ ID NO: 49) | QQSYSTPPT (SEQ ID NO: 534) |
| GYTFTSYG (SEQ ID NO: 312) | ISAYNGNT (SEQ ID NO: 346) | ARERSYYGMDV (SEQ ID NO: 105) | QSVSNY (SEQ ID NO: 574) | GAS (SEQ ID NO: 260) | QQYNHWPPL (SEQ ID NO: 544) |

For CD25 epitope 5 (77-89), CDRs used include:

| CDR-HI | CDR-H2 | CDR-H3 | CDR-L1 | CDR-L2 | CDR-L3 |
|---|---|---|---|---|---|
| GFTFSSYG (SEQ ID NO: 275) | ISYDGSNK (SEQ ID NO: 362) | AKELLEGAFDI (SEQ ID NO: 64) | NIETKS (SEQ ID NO: 455) | DDD (SEQ ID NO: 158) | QVWDSSSGHREV (SEQ ID NO: 613) |
| GYTFTSYY (SEQ ID NO: 313) | INPSGGST (SEQ ID NO: 339) | ARDRVTMVRGALAY (SEQ ID NO: 97) | KLGDKY (SEQ ID NO: 404) | KDN (SEQ ID NO: 386) | QAWDSSTYV (SEQ ID NO: 473) |

For CD25 epitope 6 (147-157), CDRs used include:

| CDR-H1 | CDR-H2 | CDR-H3 | CDR-L1 | CDR-L2 | CDR-L3 |
|---|---|---|---|---|---|
| GFTFSSYG (SEQ ID NO: 275) | ISYDGSNK (SEQ ID NO: 362) | AKGQGDGMDV (SEQ ID NO: 66) | SSNVGSRT (SEQ ID NO: 657) | SNN (SEQ ID NO: 644) | AAWDDSLIGHV (SEQ ID NO: 51) |
| GGSISSGGYS (SEQ ID NO: 282) | IYHSGST (SEQ ID NO: 365) | ARAGYYYGMDV (SEQ ID NO: 71) | RNIWSY (SEQ ID NO: 634) | GAS (SEQ ID NO: 260) | QQSHSTPIT (SEQ ID NO: 526) |
| GYTFTSYG (SEQ ID NO: 312) | ISAYNGNT (SEQ ID NO: 346) | ARDIGYYYGMDV (SEQ ID NO: 80) | SLRSYY (SEQ ID NO: 643) | GKN (SEQ ID NO: 287) | NSRDSSGNHVV (SEQ ID NO: 466) |
| GYTFTSYY (SEQ ID NO: 313) | INPSGGST (SEQ ID NO: 339) | ARDILGLDY (SEQ ID NO: 81) | SSNIGSNY (SEQ ID NO: 655) | RNN (SEQ ID NO: 635) | AAWDDSLSGVV (SEQ ID NO: 56) |
| GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| | | | QSISNY (SEQ ID NO: 563) | | |
| GFTFSSYW (SEQ ID NO: 277) | IKQDGSEK (SEQ ID NO: 328) | AREYDYGDYVFDY (SEQ ID NO: 107) | NSNVGNNY (SEQ ID NO: 465) | DND (SEQ ID NO: 188) | GSWEARESVFV (SEQ ID NO: 290) |
| GYSFTSYW (SEQ ID NO: 299) | IYPGDSDT (SEQ ID NO: 377) | ARLENNWDYGGWFDP (SEQ ID NO: 127) | NIGSKS (SEQ ID NO: 456) | DDS (SEQ ID NO: 159) | QVWDSSSDHWV (SEQ ID NO: 611) |
| | IYPGDSDT (SEQ ID NO: 377) | | | | |
| GYTFTDYY (SEQ ID NO: 306) | VDPEDGET (SEQ ID NO: 693) | ATEDTAMGGIDY (SEQ ID NO: 146) | SSNIGSNY (SEQ ID NO: 655) | SNN (SEQ ID NO: 644) | AAWDDSLNGVV (SEQ ID NO: 53) |
| | | ATEGRYGMDV (SEQ ID NO: 147) | NFNIGNNL (SEQ ID NO: 453) | AND (SEQ ID NO: 69) | ATWDDSLSGVV (SEQ ID NO: 151) |
| | | AVEGGRAPGTYYYDSSGLAY (SEQ ID NO: 153) | SSNIGSNY (SEQ ID NO: 655) | SNN (SEQ ID NO: 644) | |

For CD25 epitope 7 (11-14), CDRs used include:

| CDR-HI | CDR-H2 | CDR-H3 | CDR-L1 | CDR-L2 | CDR-L3 |
|---|---|---|---|---|---|
| GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |

For CD25 epitope 8 (44-56), CDRs used include:

| CDR-H1 | CDR-H2 | CDR-H3 | CDR-L1 | CDR-L2 | CDR-L3 |
|---|---|---|---|---|---|
| GYSFTSYW (SEQ ID NO: 299) | IYPGDSDT (SEQ ID NO: 377) | AIPWDAELGNYGMDV (SEQ ID NO: 59) | QSISSY (SEQ ID NO: 567) | AAS (SEQ ID NO: 49) | LQDYNYPPA (SEQ ID NO: 422) |
| GFAFSSYG (SEQ ID NO: 262) | ISYDGSNK (SEQ ID NO: 362) | AKGQGDGMDV (SEQ ID NO: 66) | SSDVGGYNY (SEQ ID NO: 649) | GVS (SEQ ID NO: 295) | SSYTSSSTLVV (SEQ ID NO: 660) |
| GGSISSSNW (SEQ ID NO: 284) | IYHSGST (SEQ ID NO: 365) | ARARGGRYFDY (SEQ ID NO: 72) | QGISTY (SEQ ID NO: 490) | AAS (SEQ ID NO: 49) | QQLNGYPTT (SEQ ID NO: 525) |
| GGTFSSYA (SEQ ID NO: 286) | IIPIFGTA (SEQ ID NO: 326) | AREMYYYYGMDV (SEQ ID NO: 103) | QSISSY (SEQ ID NO: 567) | AAS (SEQ ID NO: 49) | QQSYSTPPT (SEQ ID NO: 534) |
| | | | QSISNY (SEQ ID NO: 563) | | |
| | | ARGRWSGLGDY (SEQ ID NO: 113) | EDIRMY (SEQ ID NO: 215) | EGS SEQ ID NO: 219) | QQYYDDPQ (SEQ ID NO: 555) |
| GYKFANYW (SEQ ID NO: 296) | IYPGDSDT (SEQ ID NO: 377) | ARLGWGMDV (SEQ ID NO: 129) | QSISSY (SEQ ID NO: 567) | AAS (SEQ ID NO: 49) | QQSYSTPWT (SEQ ID NO: 535) |
| GFTFSSYE (SEQ ID NO: 274) | ISSSGSTI (SEQ ID NO: 351) | ARRRGGGFDY (SEQ ID NO: 132) | SSDVGGYNY (SEQ ID NO: 649) | DVS (SEQ ID NO: 201) | SSYTSSSTWV (SEQ ID NO: 663) |
| GYSFSTYW (SEQ ID NO: 298) | IYPGDSDT (SEQ ID NO: 377) | ARVGDGYSLDY (SEQ ID NO: 135) | SSNIGRNY (SEQ ID NO: 652) | RNH (SEQ ID NO: 633) | ATWDDALSGWV (SEQ ID NO: 149) |
| | | | KLGERF (SEQ ID NO: 405) | QYI (SEQ ID NO: 616) | QTWDGSIVV (SEQ ID NO: 583) |
| GYTFKNFG (SEQ ID NO: 301) | ISGRKGNT (SEQ ID NO: 347) | ARVWGDTTLGYGMDV (SEQ ID NO: 141) | QDISNY (SEQ ID NO: 485) | DAS (SEQ ID NO: 157) | QQYDNLPLT (SEQ ID NO: 542) |
| GFTFSSYG (SEQ ID NO: 275) | ISYDGSNK (SEQ ID NO: 362) | AKDLLGELSFFDY (SEQ ID NO: 61) | DIESEM (SEQ ID NO: 163) | DDS (SEQ ID NO: 159) | QVWHTTNDHVL (SEQ ID NO: 615) |
| GFTFSNYG (SEQ ID NO: 271) | ISHDGHVK (SEQ ID NO: 349) | AKEISPRSSVGWPLDY (SEQ ID NO: 63) | QSVSSTY (SEQ ID NO: 577) | GAS (SEQ ID NO: 260) | QQFDISGGLI (SEQ ID NO: 518) |
| GFTFRRYW (SEQ ID NO: 268) | IKQDGSEK (SEQ ID NO: 328) | ARDAYAYGLDV (SEQ ID NO: 73) | SGSIASSY (SEQ ID NO: 640) | EDN (SEQ ID NO: 216) | QSYDGSSVV (SEQ ID NO: 579) |
| GYTFTSYG (SEQ ID NO: 312) | ISAYNGNT (SEQ ID NO: 346) | ARDFRMDV (SEQ ID NO: 75) | QDIKRR (SEQ ID NO: 480) | DAS (SEQ ID NO: 157) | QQANTFPQT (SEQ ID NO: 516) |

-continued

| CDR-H1 | CDR-H2 | CDR-H3 | CDR-L1 | CDR-L2 | CDR-L3 |
|---|---|---|---|---|---|
| GFTFSSSA (SEQ ID NO: 272) | ISYDGSNK (SEQ ID NO: 362) | ARDFWSGYNELGGMDV (SEQ ID NO: 76) | QDISNY (SEQ ID NO: 485) | | QQYDNLPLT (SEQ ID NO: 542) |
| GYTFNNYG (SEQ ID NO: 302) | ISVYNGDI (SEQ ID NO: 359) | ARDILRGESSILDH (SEQ ID NO: 82) | QGISNS (SEQ ID NO: 488) | AAS (SEQ ID NO: 49) | QQYYSTPPH (SEQ ID NO: 556) |
| GGTFSSYA (SEQ ID NO: 286) | IIPIFGTA (SEQ ID NO: 326) | ARDKGYYGMDV (SEQ ID NO: 83) | QSIKNY (SEQ ID NO: 561) | | QQTYSTPLT (SEQ ID NO: 540) |
| | | | QGINSY (SEQ ID NO: 487) | | QQVHSFPFT (SEQ ID NO: 541) |
| | | | QGISSW (SEQ ID NO: 489) | AVS (SEQ ID NO: 154) | QQSYSLPLT (SEQ ID NO: 531) |
| | | ARDLGTMVRGVIEPYYFDY (SEQ ID NO: 85) | QSISSW (SEQ ID NO: 566) | DAF (SEQ ID NO: 156) | QQYNSYSRT (SEQ ID NO: 551) |
| GFTFSSYA (SEQ ID NO: 273) | ISYDGSNK (SEQ ID NO: 362) | ARDLLGSGYDIIDY (SEQ ID NO: 86) | NIGSKS (SEQ ID NO: 456) | DDS (SEQ ID NO: 159) | QVWDSSSDHVV (SEQ ID NO: 610) |
| GGSISSSNW (SEQ ID NO: 284) | IYHSGST (SEQ ID NO: 365) | ARDLMNYGMDV (SEQ ID NO: 87) | QSISSY (SEQ ID NO: 567) | AAS (SEQ ID NO: 49) | QQSYSTPPT (SEQ ID NO: 534) |
| GFTFSSYS (SEQ ID NO: 276) | ISSSSSYI (SEQ ID NO: 352) | ARDQLAARRGYYYGMDV (SEQ ID NO: 89) | NIGTKS (SEQ ID NO: 459) | DDS (SEQ ID NO: 159) | QVWDSSSDHVV (SEQ ID NO: 610) |
| GYTFTTYA (SEQ ID NO: 314) | INTNIGDP (SEQ ID NO: 344) | ARDRFHYGMDV (SEQ ID NO: 90) | EGIRTS (SEQ ID NO: 218) | GAS (SEQ ID NO: 260) | QQTHTWPWT (SEQ ID NO: 538) |
| GFTFSSYG (SEQ ID NO: 275) | ISSRGSTI (SEQ ID NO: 350) | ARDRGDRVGGLVFDY (SEQ ID NO: 91) | NIGSKS (SEQ ID NO: 456) | DDS (SEQ ID NO: 159) | QVWDSSSDHVV (SEQ ID NO: 610) |
| GYTFTSYG (SEQ ID NO: 312) | ISAYNGNT (SEQ ID NO: 346) | ARDRGDY (SEQ ID NO: 92) | QGTSSW (SEQ ID NO: 491) | AAS (SEQ ID NO: 49) | QQANSFPLT (SEQ ID NO: 514) |
| | | ARDRGYYGMDV (SEQ ID NO: 93) | QSISRY (SEQ ID NO: 564) | | QQSHSTPLT (SEQ ID NO: 527) |
| | | ARDRNGYFQH (SEQ ID NO: 94) | QTISGL (SEQ ID NO: 581) | GAS (SEQ ID NO: 260) | LQYDRYSGA (SEQ ID NO: 426) |
| GGTFSSYA (SEQ ID NO: 286) | IIPIFGTA (SEQ ID NO: 326) | ARDRSYYGMDV (SEQ ID NO: 96) | QSIGNY (SEQ ID NO: 558) | AAT (SEQ ID NO: 50) | QQSKQIPYT (SEQ ID NO: 528) |
| | | ARDRYYYGMDV (SEQ ID NO: 98) | QSISSY (SEQ ID NO: 567) | AAS (SEQ ID NO: 49) | QQSYSTPLT (SEQ ID NO: 532) |

-continued

| CDR-H1 | CDR-H2 | CDR-H3 | CDR-L1 | CDR-L2 | CDR-L3 |
|---|---|---|---|---|---|
| GFTFSSYW (SEQ ID NO: 277) | IKQDGSEK (SEQ ID NO: 328) | AREKGSWFDP (SEQ ID NO: 102) | QSVSNNY (SEQ ID NO: 573) | GAS (SEQ ID NO: 260) | QRYGSSPR (SEQ ID NO: 557) |
| GFIFSRHA (SEQ ID NO: 264) | ISYDGSNK (SEQ ID NO: 362) | ARGRLAYGDTEGFDY (SEQ ID NO: 112) | QDINNY (SEQ ID NO: 482) | DAS (SEQ ID NO: 157) | QQYDNLPYT (SEQ ID NO: 543) |
| GGSISSSNW (SEQ ID NO: 284) | IYHSGST (SEQ ID NO: 365) | ARGVRGTGFDP (SEQ ID NO: 118) | QSVSSR (SEQ ID NO: 576) | GAS (SEQ ID NO: 260) | QQYTNWPQT (SEQ ID NO: 554) |
| GYSFTTYW (SEQ ID NO: 300) | IYPGDSDT (SEQ ID NO: 377) | ARQVAGGLDY (SEQ ID NO: 131) | SSNVGSNY (SEQ ID NO: 656) | RNN (SEQ ID NO: 635) | AAWDDSLSGVV (SEQ ID NO: 56) |
| | | | QAVRID (SEQ ID NO: 472) | GAS (SEQ ID NO: 260) | LQHNTFPYT (SEQ ID NO: 423) |
| GFTFSSYE (SEQ ID NO: 274) | ISSSGSTI (SEQ ID NO: 351) | ARRRGGGFDY (SEQ ID NO: 132) | SSDVGGYNY (SEQ ID NO: 649) | DVS (SEQ ID NO: 201) | SSYTSSSTYV (SEQ ID NO: 664) |
| GFTFSSYW (SEQ ID NO: 277) | IKQDGSEK (SEQ ID NO: 328) | ARTWFGEFFDY (SEQ ID NO: 134) | NIESES (SEQ ID NO: 454) | DDS (SEQ ID NO: 159) | QVWDSSSDHTVA (SEQ ID NO: 609) |
| GYTFTSYG (SEQ ID NO: 312) | ISAYNGNT (SEQ ID NO: 346) | ARVIGGWFDP (SEQ ID NO: 136) | SSDVGAYNY (SEQ ID NO: 647) | GVS (SEQ ID NO: 295) | SSYTTTDTFV (SEQ ID NO: 665) |
| | | ARVWGKNGDFDY (SEQ ID NO: 142) | SSNIGNNY (SEQ ID NO: 651) | DNN (SEQ ID NO: 190) | GTWDSSLSAYV (SEQ ID NO: 294) |
| GYSFTSYW (SEQ ID NO: 299) | IYPGDSDT (SEQ ID NO: 377) | FRFGEGFDY (SEQ ID NO: 259) | QSIGYW (SEQ ID NO: 559) | RAS (SEQ ID NO: 619) | QQYNSYPFT (SEQ ID NO: 548) |
| GFTFNNAW (SEQ ID NO: 267) | IKSKIDGGIT (SEQ ID NO: 330) | TTEGVELLSFGGAPFDY (SEQ ID NO: 683) | QSISSY (SEQ ID NO: 567) | AAS (SEQ ID NO: 49) | QQSYSTPYT (SEQ ID NO: 536) |

Figure 18:
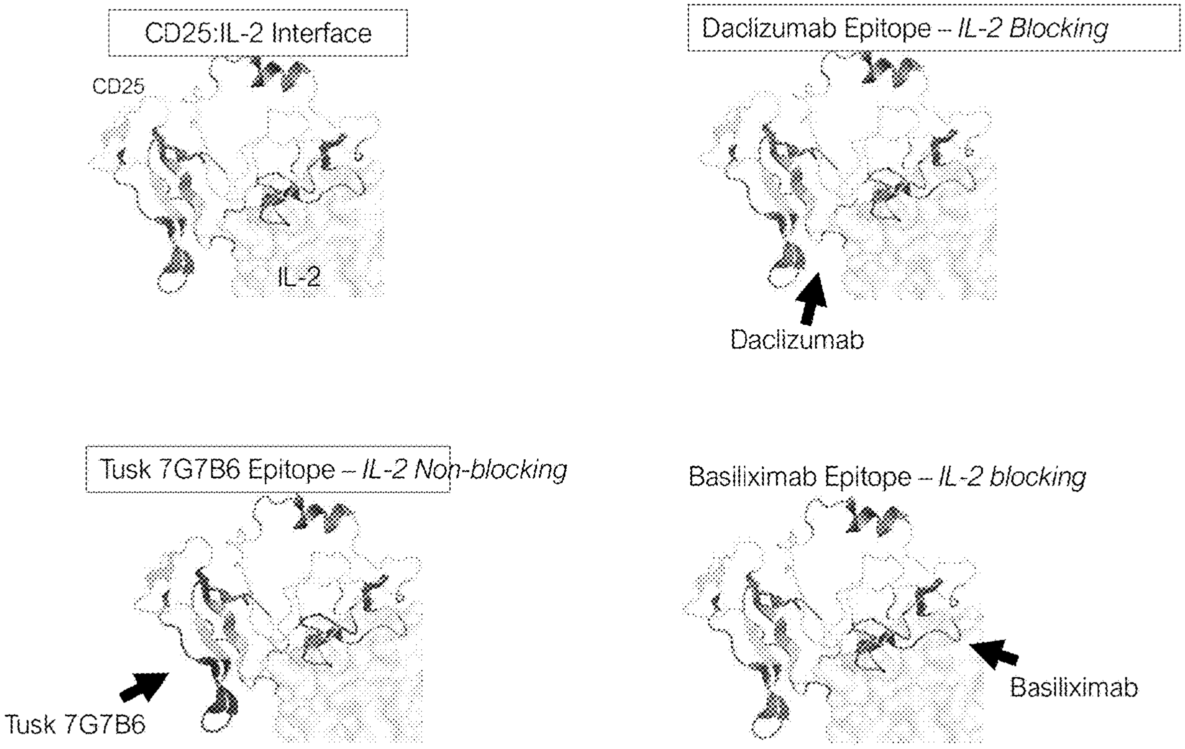
FIG. 18 shows ribbon diagrams of CD25 indicated the approximate binding sites for IL-2 and three antibodies (daclizumab, Tusk 7G7B6, and basiliximab) used in epitope resolution with a four-target competitive binding assay.

Example 8: Confirmation of Epitope Specificity by Competitive Binding 126 anti-CD25 clones were subjected to epitope resolution with a four-target competitive binding assay, as depicted in FIG. 18. The binding sites for IL-2, daclizumab, and basioliximab shown in the figure are based on X-ray crystallographic structure determination. The binding site for 7G7B6 is based on peptide mapping.

Cross-competition assays were performed in the classical sandwich format, involves immobilizing the first antibody onto the biosensor, followed by incubation with the antigen, and then the second sandwiching antibody. His-tagged scFv were expressed and purified in situ on the biosensor using His-tag capture from supernatant. Biosensor His-tag capture was normalized across scFv clones by monitoring the tip loading response to a consistent level across all scFv measurements. The scFv's were each individually captured to an anti-His biosensor (Fortebio HIS1K). A baseline measurement was taken in running buffer. Then CD25 was captured to the antibodies. Finally each of various competitive analytes were added, including IL-2, 7G7B6, Basiliximab, or Daclizumab. The competitive analyte can bind the captured CD25 only if competitive analyte's binding epitope does not overlap that of immobilized scFv.

Figure 19:
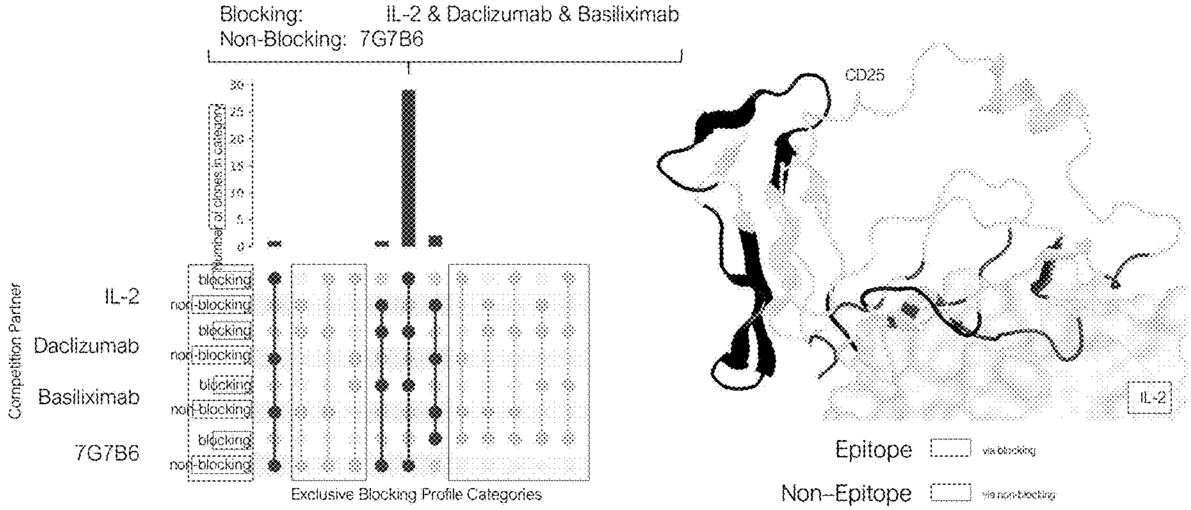
FIG. 19 shows that full-length CD25 panning clones are dominated by IL-2 interface epitope. Most clones are blocked by IL-2, daclizumab, and basioliximab, but not 7G7B6.

As shown in FIG. 19, the full-length CD25 panning clones are dominated by IL-2 interface epitope. Most clones are blocked by IL-2, daclizumab, and basioliximab, but not 7G7B6.

Figure 20:
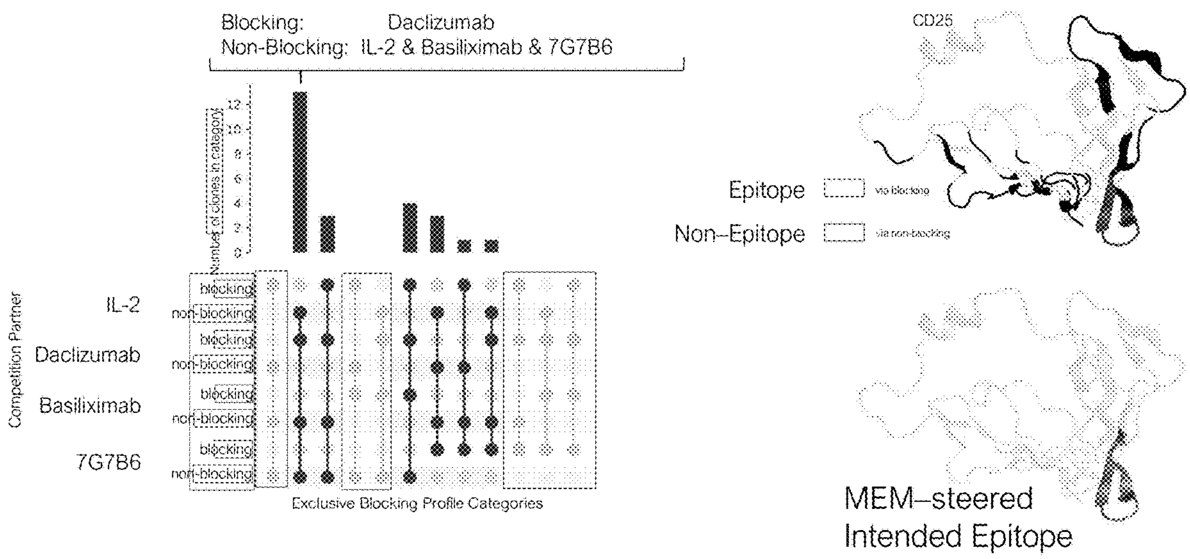
FIG. 20 shows that 147-157 epitope MEM-steered clones primarily bind at the intended epitope. Most clones are blocked by daclizumab but not by IL-2, basioliximab, or 7G7B6.

As shown in FIG. 20, the 147-157 epitope MEM-steered clones primarily bind at the intended epitope. Most clones are blocked by daclizumab but not by IL-2, basioliximab, or 7G7B6.

Figure 21:
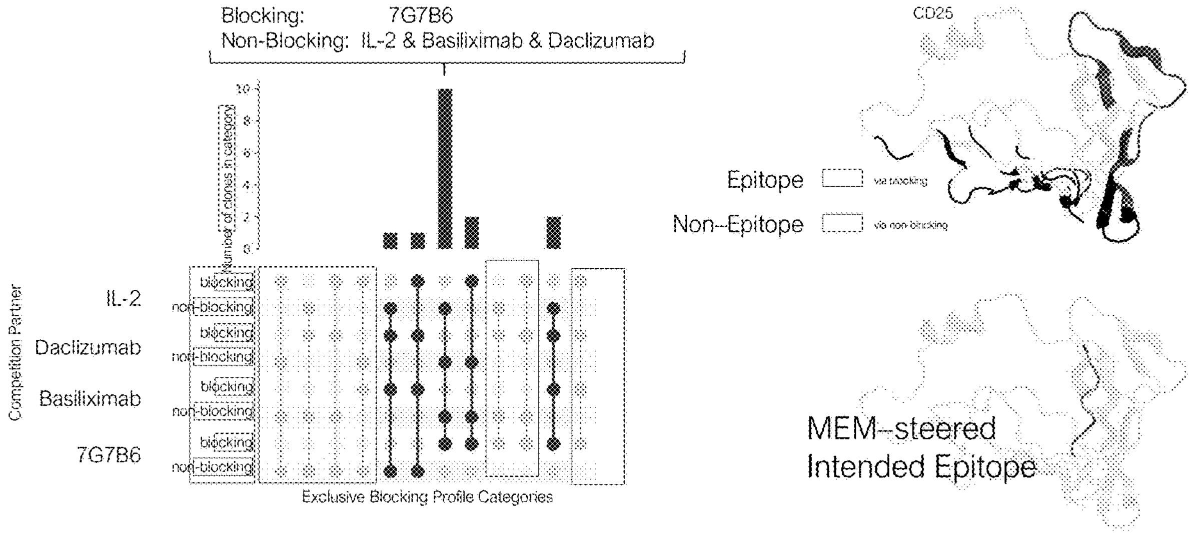
FIG. 21 shows that 6-17 epitope MEM-steered clones primarily bind at the intended epitope. Most clones are blocked by 7G7B6 but not by IL-2, daclizumab, or basioliximab.

As shown in FIG. 21, the 6-17 epitope MEM-steered clones primarily bind at the intended epitope. Most clones are blocked by 7G7B6 but not by IL-2, daclizumab, or basioliximab.

Figure 22:
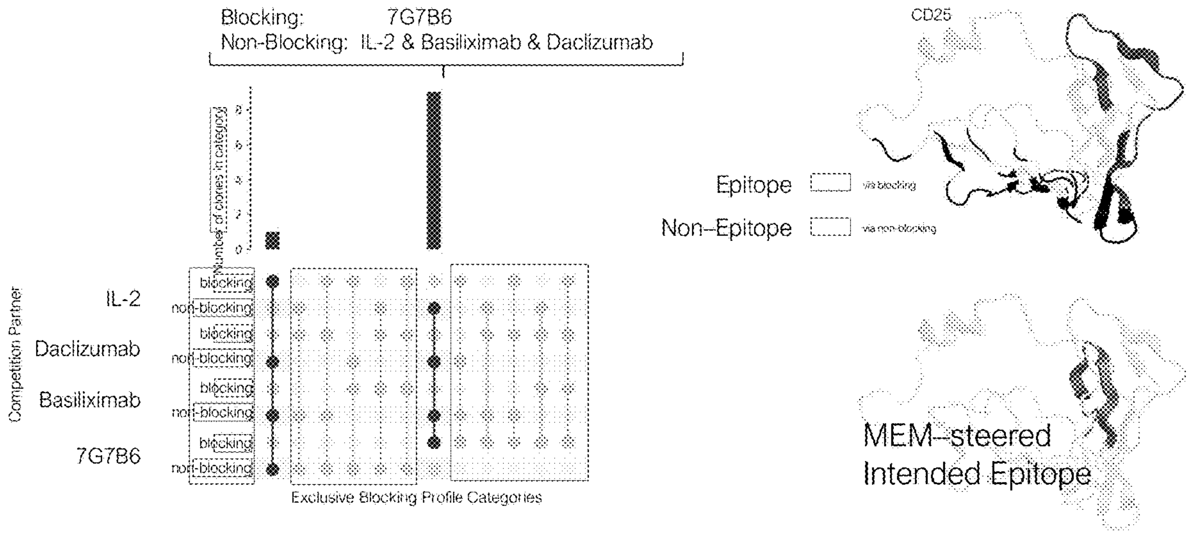
FIG. 22 shows that 13-20:127-132 epitope MEM-steered clones primarily bind at the intended epitope. Most clones are blocked by 7G7B6 but not by IL-2, daclizumab, or basioliximab.

As shown in FIG. 22, the 13-20:127-132 epitope MEM-steered clones primarily bind at the intended epitope. Most clones are blocked by 7G7B6 but not by IL-2, daclizumab, or basioliximab.

Figure 23:
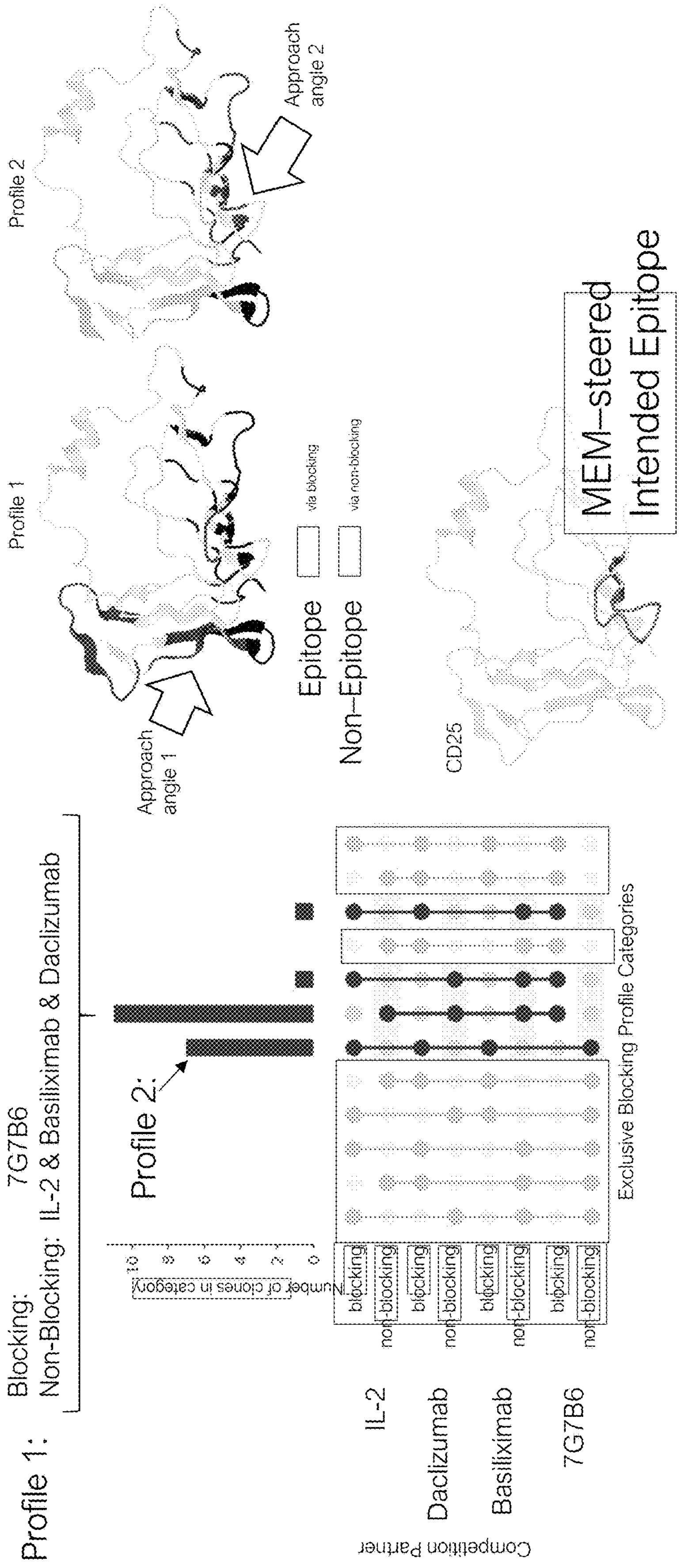
FIG. 23 shows that 44-56 epitope MEM-steered clones primarily bind at the intended epitope. The clones divided into two profiles. In profile 1, clones are blocked by 7G7B6 but not by IL-2, daclizumab, or basioliximab. In profile 2, clones are blocked by IL-2, daclizumab, and basioliximab, but not 7G7B6. These blocking profiles indicate binding to the intended epitope from different approach angles.

As shown in FIG. 23, the 44-56 epitope MEM-steered clones primarily bind at the intended epitope. The clones divided into two profiles. In profile 1, clones are blocked by 7G7B6 but not by IL-2, daclizumab, or basioliximab. In profile 2, clones are blocked by IL-2, daclizumab, and basioliximab, but not 7G7B6. These blocking profiles indicate binding to the intended epitope from different approach angles.

Figure 24:
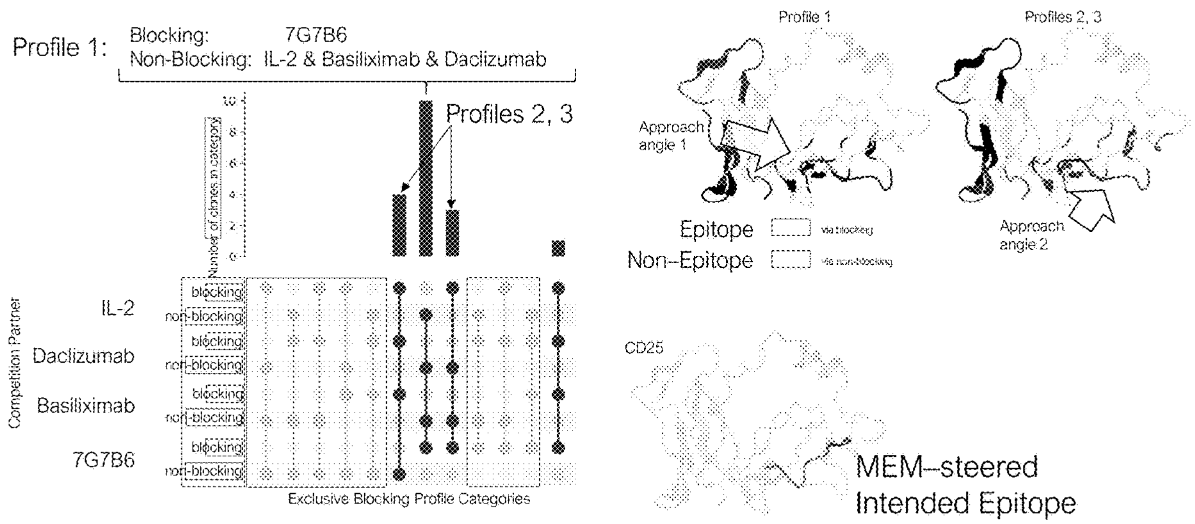
FIG. 24 shows that 55-63 epitope MEM-steered clones primarily bind at the intended epitope. The clones divided into three profiles. In profile 1, clones are blocked by 7G7B6 but not by IL-2, daclizumab, or basioliximab. In profile 2, clones are blocked by IL-2, daclizumab, and basioliximab, but not 7G7B6. These blocking profiles indicate binding to the intended epitope from different approach angles. In profile 3, clones are blocked by IL-2 and 7G7B6, but not daclizumab or basioliximab. These blocking profiles indicate binding to the intended epitope from different approach angles.

As shown in FIG. 24, the 55-63 epitope MEM-steered clones primarily bind at the intended epitope. The clones divided into three profiles. In profile 1, clones are blocked by 7G7B6 but not by IL-2, daclizumab, or basioliximab. In profile 2, clones are blocked by IL-2, daclizumab, and basioliximab, but not 7G7B6. These blocking profiles indicate binding to the intended epitope from different approach angles. In profile 3, clones are blocked by IL-2 and 7G7B6, but not daclizumab or basioliximab. These blocking profiles indicate binding to the intended epitope from different approach angles.

Example 9: Mapping of Functional Epitopes by Alanine Mutagenesis

Figure 25:
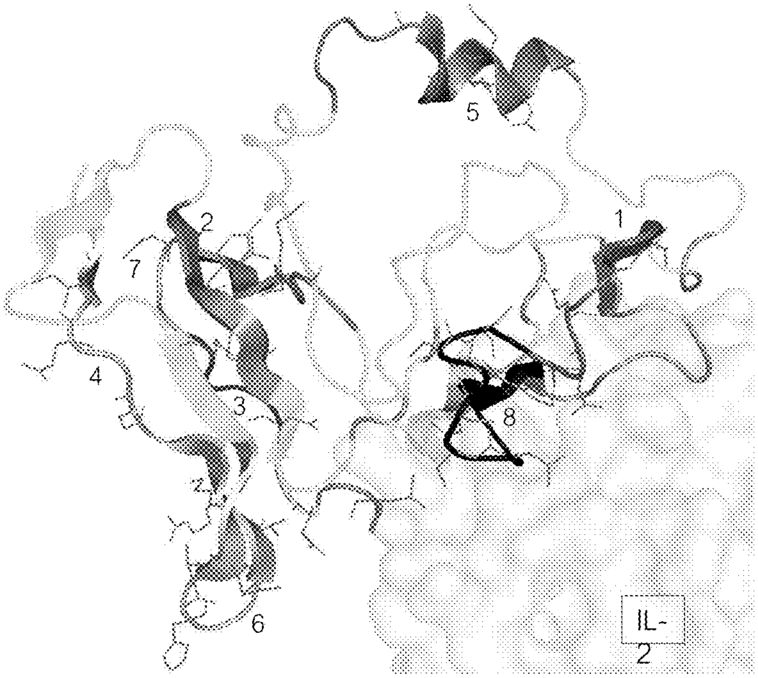
FIG. 25 shows alanine mutations designed to confirm or reject that MEM-steered clones bin the intended epitopes. The eight epitopes are indicated in color. Sites of residues mutated to alanine are shown by red sticks.
Figure 26:
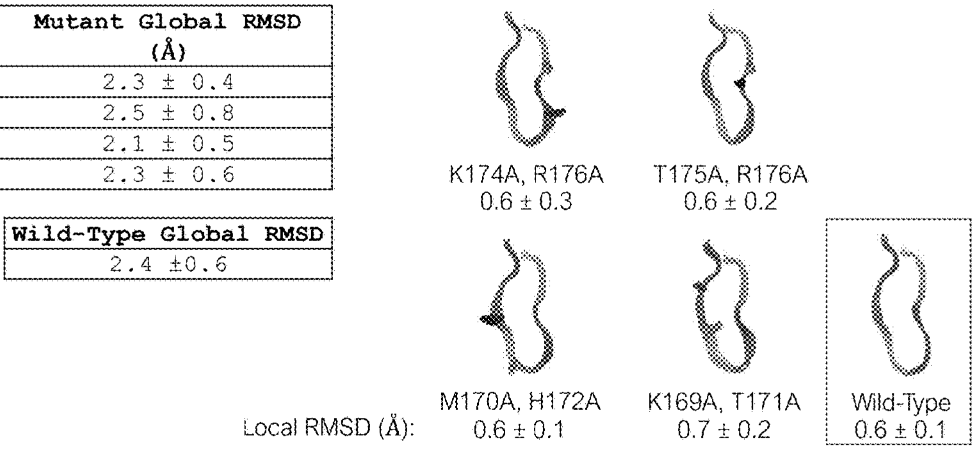
FIG. 26 shows alanine mutations in the 147-157 CD25 epitope do not impact global or local stability. For each mutant and wild-type: RMSD from 3 independent 100 ns MD simulations in explicit solvent for each of 8 different starting apo-CD25 configurations using the crystal structure as the reference.
Figure 27:
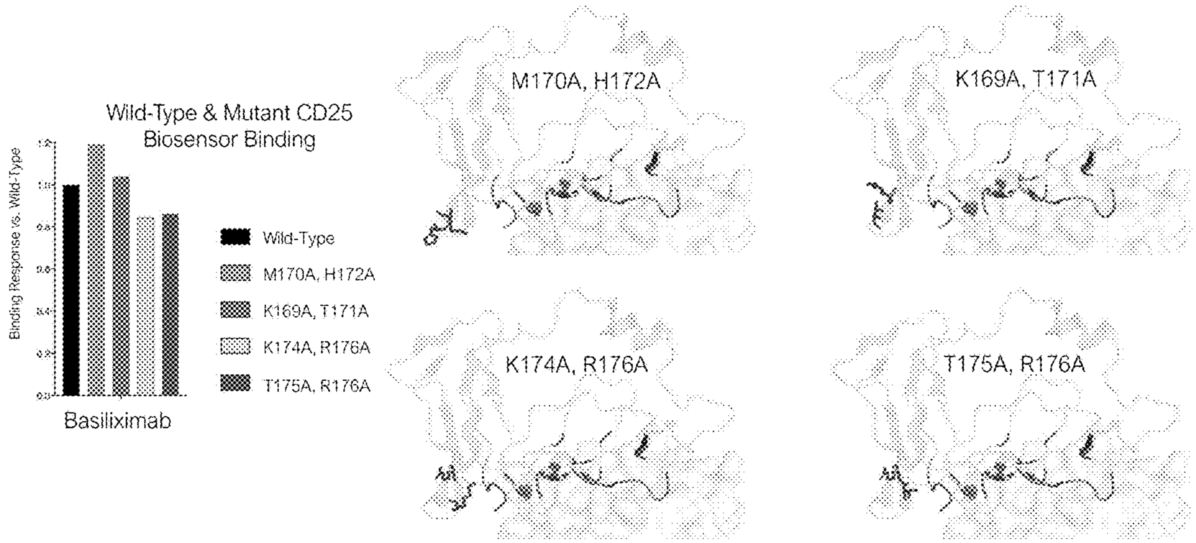
FIG. 27 shows reliability of Ala-mutant epitope mapping demonstrated with basiliximab control antibody. Ala mutant binding responses corroborate crystal structure of the basiliximab epitope. The basiliximab-CD25 epitope known from X-ray crystal structures is shown in orange.
Figure 28:
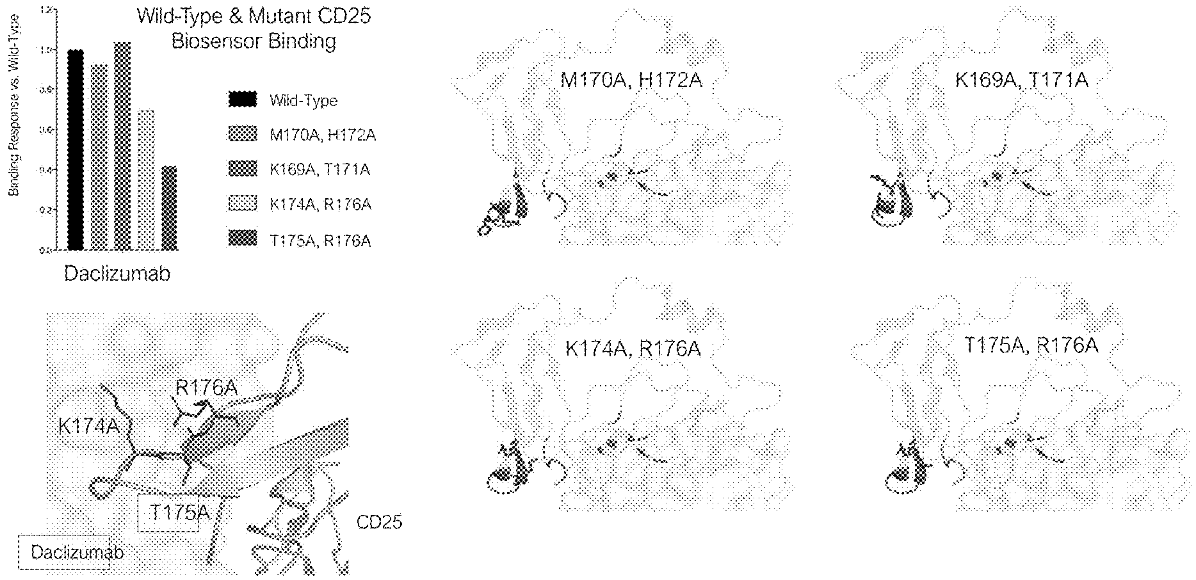
FIG. 28 shows reliability of Ala-mutant epitope mapping demonstrated with daclizumab control antibody. Ala mutant binding responses corroborate crystal structure of the daclizumab epitope. The daclizumab-CD25 epitope known from X-ray crystal structures is shown in orange. Inset at bottom left shows an epitope zoom, showing T175A impact on daclizumab binding.
Figure 29:
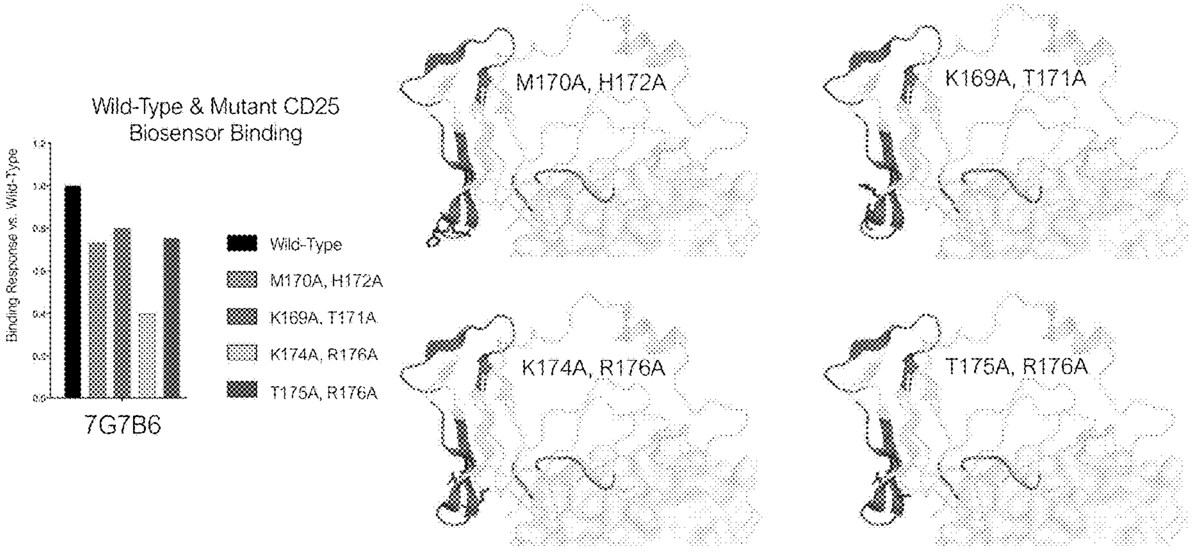
FIG. 29 shows reliability of Ala-mutant epitope mapping demonstrated with 7G7B6 control antibody. Ala mutant binding responses corroborate peptide mapping of the 7G7B6 epitope.
Figure 30:
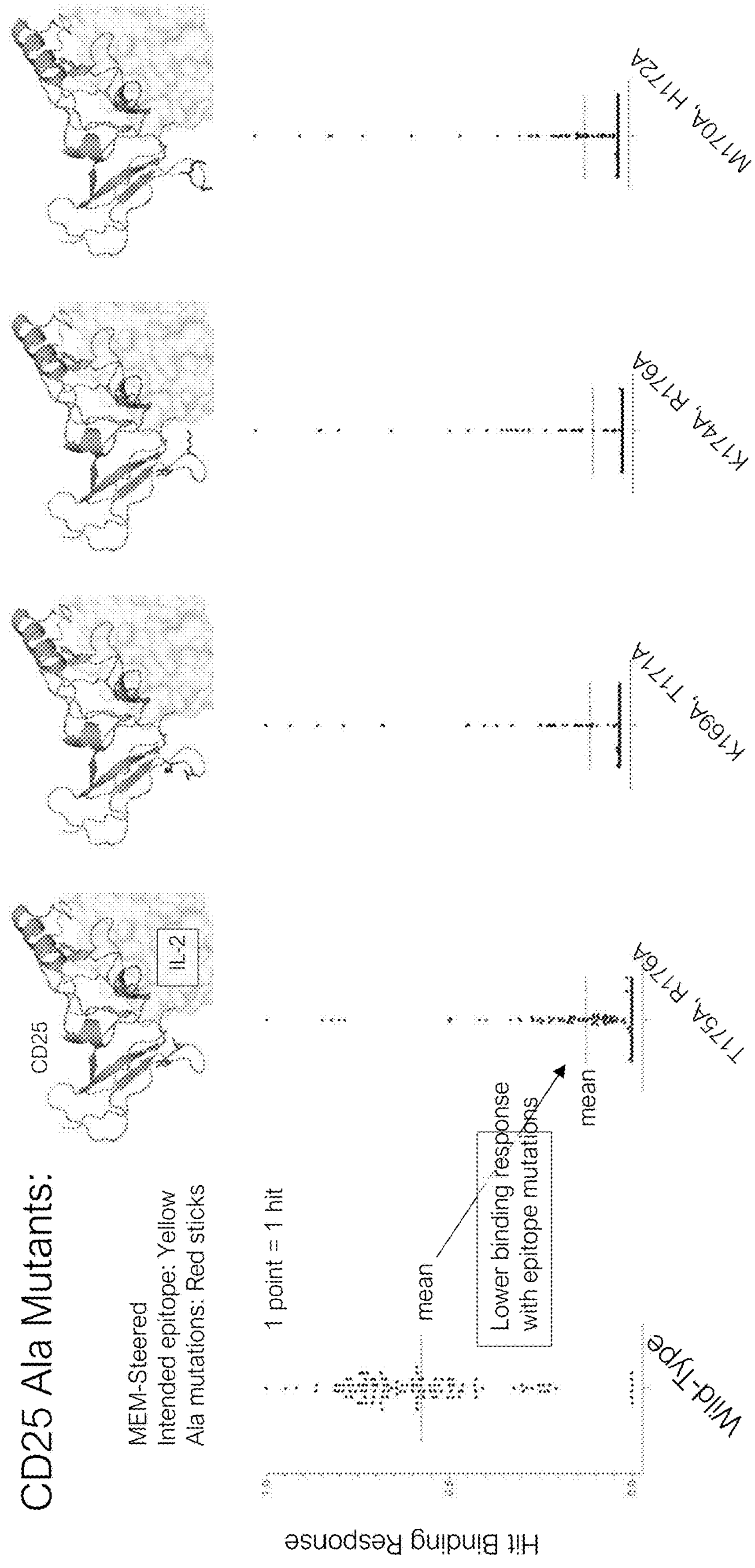
FIG. 30 shows epitope mapping of MEM-programmed selection hits for the 147-157 epitope. Most hits show ala mutation sensitivity in the intended epitope.

Alanine mutations were designed to confirm or reject that MEM-steered clones bin the intended epitopes (FIG. 25). Alanine mutagenesis was selected as an orthogonal method for binning antibodies because it operates on the functional epitope, rather than the structural epitope defined by competition assays. Various pairs of surface-accessible residues were selected for mutagenesis. Computational modeling is used to confirm that the alanine mutations selected for use in these assays do not impact global or local stability. For example, FIG. 26 shows results for modeling of alanine mutations within the 145-157 epitope. For each mutant and wild-type: RMSD from 3 independent 100 ns MD simulations in explicit solvent for each of 8 different starting apo-CD25 configurations using the crystal structure as the reference. As shown in FIGS. 27-29, alanine mutant versions of CD25 have the binding responses to basiliximab, daclizumab, and 7G7B6, respectively.

As intended, binding scFv hits from in vitro selection with the 147-157 epitope-targeted engineered polypeptides are consistent with specificity for the intended portion of CD25.

Figure 31:
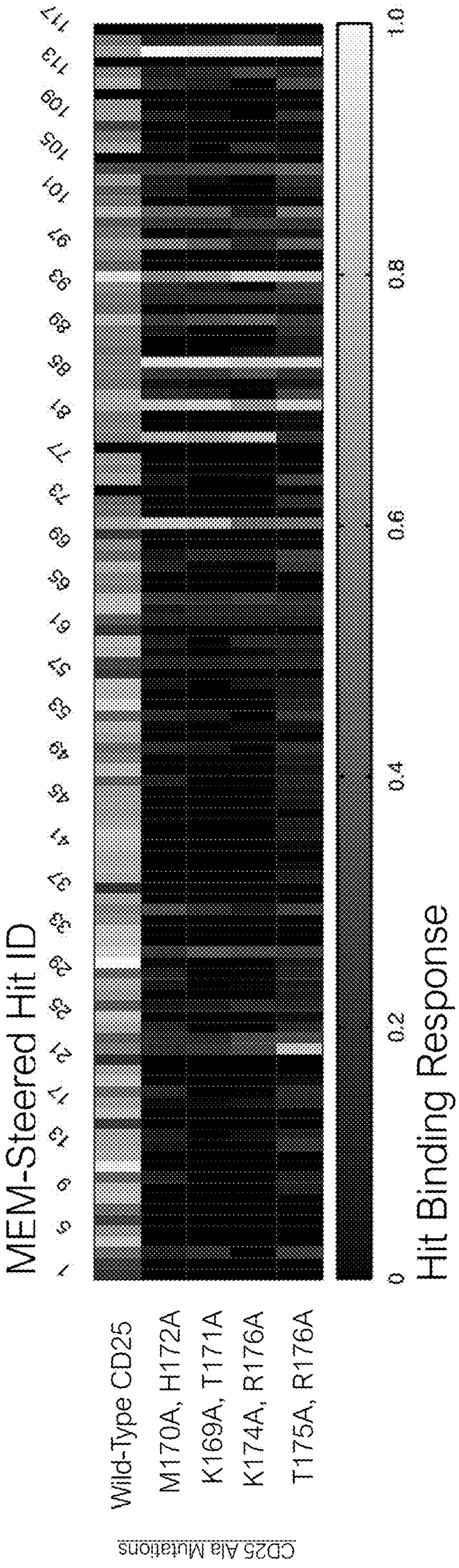
FIG. 31 shows sensitivity to alanine substitution of various MEM-steered antibodies hits. Functional epitope diversity is observed. MEM-steered hits have distinct in-epitope alanine substitution position sensitivity.

Each of 117 scFv's from the screening campaign were tested against four alanine mutations pairs (FIG. 31). Functional epitope diversity is observed. MEM-steered hits have distinct in-epitope alanine substitution position sensitivity.

Example 10: Confirmatory Testing of Antibodies in Immunoglobulin G (IgG1) Format Thirty antibodies were selected for additional testing as full-length immunoglobulins. The heavy and light chain sequences were cloned into human immunoglobulin G (IgG1) format and expressed and purified. Binding to CD25 was assessed by Octet® as shown in Table 13.

TABLE 13

Human IgG1 Clone Selection/Epitope Details and Biophysical Measurements

| Sample_ID | Biosensor Measured CD25 Affinity | Epitope | Selection R1_Antigen | Selection R2_Antigen | Selection R3_Antigen |
|---|---|---|---|---|---|
| YU390-B12 | 1.366E−08 | _77-89_ | 77_89 | CD25 | 77_89 |
| YU397-F01 | 7.053E−08 | _44-56_ | 44_56 | CD25 | CD25 |
| YU397-D01 | 3.857E−09 | _44-56_ | 44_56 | CD25 | CD25 |
| YU398-A11 | 1.209E−08 | _147-157_ | 147_156 | CD25 | CD25 |
| YU404-H01 | 5.179E−08 | _55-63_ | 57_63 | CD25 | CD25 |
| YU400-B07 | 5.775E−08 | _55-63_ | 57_63 | CD25 | 57_63 |
| YU400-D09 | 5.455E−08 | _55-63_ | 57_63 | CD25 | 57_63 |
| YU401-B01 | 7.038E−08 | _55-63_ | 57_63 | CD25 | CD25 |
| YU401-G07 | 1.535E−08 | _55-63_ | 57_63 | CD25 | 57_63 |
| YU404-C02 | 1.262E−08 | _55-63_ | 57_63 | CD25 | CD25 |
| YU403-G07 | 2.956E−08 | _55-63_ | 57_63 | CD25 | CD25 |
| YU403-G05 | 3.193E−08 | _55-63_ | 57_63 | CD25 | CD25 |
| YU391-B12 | 4.581E−08 | _77-89_ | 77_89 | CD25 | CD25 |
| YU400-A03 | 1.022E−08 | _147-157_ | 147_156 | CD25 | CD25 |
| YU400-D02 | 1.011E−08 | _147-157_ | 147_156 | CD25 | CD25 |
| YU392-A09 | 1.237E−08 | _147-157_ | 147_156 | CD25 | 147_156 |
| YU392-B11 | 6.558E−08 | _147-157_ | 147_156 | CD25 | 147_156 |
| YU392-B12 | 4.04E−08 | _147-157_ | 147_156 | CD25 | CD25 |
| YU392-E05 | 1.612E−08 | _147-157_ | 147_156 | CD25 | 147_156 |
| YU392-E06 | 8.301E−09 | _147-157_ | 147_156 | CD25 | 147_156 |
| YU392-G08 | 8.259E−09 | _147-157_ | 147_156 | CD25 | 147_156 |
| YU389-A03 | 9.546E−09 | _6-17_ | 6_130 | CD25 | CD25 |
| YU392-G09 | 2.019E−08 | _147-157_ | 147_156 | CD25 | 147_156 |

TABLE 13-continued

| Human IgG1 Clone Selection/Epitope Details and Biophysical Measurements | | | | | |
|---|---|---|---|---|---|
| Sample_ID | Biosensor Measured CD25 Affinity | Epitope | Selection R1_Antigen | Selection R2_Antigen | Selection R3_Antigen |
| YU392-G12 | 2.571E−08 | _147-157_ | 147_156 | CD25 | CD25 |
| YU392-H02 | 1.055E−08 | _77-89_ | 77_89 | CD25 | CD25 |
| YU392-H04 | 9.098E−09 | _147-157_ | 147_156 | CD25 | 147_156 |
| YU402-F01 | 6.303E−09 | _13-20_127-132_ | 13_131 | CD25 | CD25 |
| YU389-B11 | 1.418E−07 | _6-17_ | 6_130 | CD25 | CD25 |
| YU394-D08 | 4.432E−08 | _11-14_ | 11_14 | CD25 | 11_14 |
| YU390-A11 | 1.327E−08 | _6-17_ | 6_130 | CD25 | CD25 |

Example 11: Panning Biased Library of Mouse Antibody Sequences

A phage-display library was generated from the immunoglobulin genes of a mouse immunized with full-length CD25. This library, biased towards CD25-binding antibodies, was panned against the indicated engineered polypeptides, yielding the complementarity determining region sequences indicated in Table 14A and Table 14B.

TABLE 14A

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M1 | 33_63 | EVRLQQSGAELVRSGA SVKLSCTAS (SEQ ID NO: 236) | GFNIKD YY (SEQ ID NO: 265) | IHWVKQRPEQGL EWIGW (SEQ ID NO: 324) | IDPDNGE T (SEQ ID NO: 318) | EYAPKFQGKATMTADTSSNTAHLQ LSSLTSEDTAVYYC (SEQ ID NO: 239) | TVFWYGNNY AGFAY (SEQ ID NO: 684) | WGQGTLV TV (SEQ ID NO: 702) |
| M2 | 33_63 | EVRLQQSGAELVRSGA SVKLSCTAS (SEQ ID NO: 236) | GFNIKD YY (SEQ ID NO: 265) | IHWVKQRPEQGL EWIGW (SEQ ID NO: 324) | IDPDNGE T (SEQ ID NO: 318) | EYAPKFQGKATMTADTSSNTAHLQ LSSLTSEDTAVYYC (SEQ ID NO: 239) | TVFWYGNNY AGFAY (SEQ ID NO: 684) | WGQGTLV TV (SEQ ID NO: 702) |
| M3 | 44_56 | EVRLQQSGAELVRSGA SVKLSCTAS (SEQ ID NO: 236) | GFNIKD YY SEQ ID NO: 265) | IHWVKQRPEQGL EWIGW (SEQ ID NO: 324) | IDPDNGE T (SEQ ID NO: 318) | EYAPKFQGKATMTADTSSNTAHLQ LSSLTSEDTAVYYC (SEQ ID NO: 239) | TVFWYGNNY AGFAY (SEQ ID NO: 684) | WGQGTLV TV (SEQ ID NO: 702) |
| M4 | 44_56 | EVHLQQFGAELVRSGA SVKLSCTAS (SEQ ID NO: 228) | GFNIKD YY (SEQ ID NO: 265) | IHWVKQRPEQGL EWIGW (SEQ ID NO: 324) | IDPDNGE T (SEQ ID NO: 318) | EYAPKFQGKATMTADTSSNTAHLQ LSSLAPEDTAVYYC (SEQ ID NO: 238) | TVFWYGNNY AGFAY (SEQ ID NO: 684) | WGQGTPV TVSS (SEQ ID NO: 705) |
| M5 | 147_156 | QAYLQQSGAELVRSGA SVKLSCTAS (SEQ ID NO: 477) | GFNIKD YY (SEQ ID NO: 265) | IHWVKQRPEQGL EWIGW (SEQ ID NO: 324) | IDPDNGE T (SEQ ID NO: 318) | EYAPKFQGKATMTADTSSNTAHLQ LSSLTSEDTAVYYC (SEQ ID NO: 239) | TVFWYGNNY AGFAY (SEQ ID NO: 684) | WGQGTLV TV (SEQ ID NO: 702) |
| M6 | 44_56 | QAYLQQSGAELVRSGA SVKLSCTAS (SEQ ID NO: 477) | GFNIKD YY (SEQ ID NO: 265) | IHWVKQRPEQGL EWIGW (SEQ ID NO: 324) | IDPDNGE T (SEQ ID NO: 318) | EYAPKFQGKATMTADTSSNTAHLQ LSSLTSEDTAVYYC (SEQ ID NO: 239) | TVFWYGNNY AGFAY (SEQ ID NO: 684) | WGQGTPV TVSS (SEQ ID NO: 705) |
| M7 | 6_130 | QAYLQQSGAELVRSGA SVKLSCTAS (SEQ ID NO: 477) | GFNIKD YY (SEQ ID NO: 265) | IHWVKQRPEQGL EWIGW (SEQ ID NO: 324) | IDPDNGE T (SEQ ID NO: 318) | EYAPKFQGKATMTADTSSNTAHLQ LSSLTSEDTAVYYC (SEQ ID NO: 239) | TVFWYGNNY AGFAY (SEQ ID NO: 684) | WGQGTLV TVSS (SEQ ID NO: 704) |
| M8 | 6_163 | EVLLQQSGAELVRSGA SAKLSCTAS (SEQ ID NO: 233) | GFNIKD YY (SEQ ID NO: 265) | IHWVKQRPEQGL EWIGW (SEQ ID NO: 324) | IDPDNGE T (SEQ ID NO: 318) | EYAPKFQGKATMTADTSSNTAHLQ LSSLTSEDTAVYYC (SEQ ID NO: 239) | TVFWYGNNY AGFAY (SEQ ID NO: 684) | WGQGTLV TV (SEQ ID NO: 702) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M9 | 147_157 | EVRLQQSGAELVRSGA SVKLSCTAS (SEQ ID NO: 236) | GFNIKD YY (SEQ ID NO: 265) | IHWVKQRPEQGL EWIGW (SEQ ID NO: 324) | IDPDNGE TEYAP (SEQ ID NO: 319) | KFQGKATMTADTSSNTAHLQLSSL TSEDTAVYYC (SEQ ID NO: 403) | TVFWYGNNY AGFAY (SEQ ID NO: 684) | WGQGTPV TVSS (SEQ ID NO: 705) |
| M10 | 147_157 | QAYLQQSGAELVRSGA SVKLSCTAS (SEQ ID NO: 477) | GFNIKD YY (SEQ ID NO: 265) | IHWVKQRPEQGL EWIGW (SEQ ID NO: 324) | IDPDNGE TEYAP (SEQ ID NO: 319) | KFQGKATMTADTSSNTAHLQLSSL TSEDTAVYYC (SEQ ID NO: 403) | TVFWYGNNY AGFAY (SEQ ID NO: 684) | WGQGTLV TVSA (SEQ ID NO: 703) |
| M11 | 147_157 | EVRLQQSGAELVRSGA SVKLSCTAS (SEQ ID NO: 236) | GFNIKD YY (SEQ ID NO: 265) | IHWVKQRPEQGL EWIGW (SEQ ID NO: 324) | IDPDNGE TEYAP (SEQ ID NO: 319) | KFQGKATMTADTSSNTAHLQLSSL TSEDTAVYYC (SEQ ID NO: 403) | TVFWYGNNY AGFAY (SEQ ID NO: 684) | WGQGTLV TVSA (SEQ ID NO: 703) |
| M12 | 33_63 | EVRLQQSGAELVRSGA SVKLSCTAS (SEQ ID NO: 236) | GFNIKD YY (SEQ ID NO: 265) | IHWVKQRPEQGL EWIGW (SEQ ID NO: 324) | IDPDNGE TEYAP (SEQ ID NO: 319) | KFQGKATMTADTSSNTAHLQLSSL TSEDTAVYYC (SEQ ID NO: 403) | TVFWYGNNY AGFAY (SEQ ID NO: 684) | WGQGTLV TVSA (SEQ ID NO: 703) |
| M13 | 33_63 | EVRLQQSGAELVRSGA SVKLSCTAS (SEQ ID NO: 236) | GFNIKD YY (SEQ ID NO: 265) | IHWVKQRPEQGL EWIGW (SEQ ID NO: 324) | IDPDNGE TEYAP (SEQ ID NO: 319) | KFQGKATMTADTSSNTAHLQLSSL TSEDTAVYYC (SEQ ID NO: 403) | TVFWYGNNY AGFAY (SEQ ID NO: 684) | WGQGTLV TVSA (SEQ ID NO: 703) |
| M14 | 33_63 | EVRLQQSGAELVRSGA SVKLSCTAS (SEQ ID NO: 236) | GFNIKD YY (SEQ ID NO: 265) | IHWVKQRPEQGL EWIGW (SEQ ID NO: 324) | IDPDNGE TEYAP (SEQ ID NO: 319) | KFQGKATMTADTSSNTAHLQLSSL TSEDTAVYYC (SEQ ID NO: 403) | TVFWYGNNY AGFAY (SEQ ID NO: 684) | WGQGTPV TVSS (SEQ ID NO: 705) |
| M15 | 33_63 | EVRLQQSGAELVRSGA SVKLSCTAS (SEQ ID NO: 236) | GFNIKD YY (SEQ ID NO: 265) | IHWVKQRPEQGL EWIGW (SEQ ID NO: 324) | IDPDNGE TEYAP (SEQ ID NO: 319) | KFQGKATMTADTSSNTAHLQLSSL TSEDTAVYYC (SEQ ID NO: 403) | TVFWYGNNY AGFAY (SEQ ID NO: 684) | WGQGTLV TVSS (SEQ ID NO: 704) |
| M16 | 33_63 | QAYLQQSGAELVRSGA SVKLSCTAS (SEQ ID NO: 477) | GFNIKD YY (SEQ ID NO: 265) | IHWVKQRPEQGL EWIGW (SEQ ID NO: 324) | IDPDNGE TEYAP (SEQ ID NO: 319) | KFQGKATMTADTSSNTAHLQLSSL TSEDTAVYYC (SEQ ID NO: 403) | TVFWYGNNY AGFAY (SEQ ID NO: 684) | WGQGTLV TVSA (SEQ ID NO: 703) |
| M17 | 33_63 | QAYLQQSGAELVRSGA SVKLSCTAS (SEQ ID NO: 477) | GFNIKD YY (SEQ ID NO: 265) | IHWVKQRPEQGL EWIGW (SEQ ID NO: 324) | IDPDNGE TEYAP (SEQ ID NO: 319) | KFQGKATMTADTSSNTAHLQLSSL TSEDTAVYYC (SEQ ID NO: 403) | TVFWYGNNY AGFAY (SEQ ID NO: 684) | WGQGTLV TVSA (SEQ ID NO: 703) |
| M18 | 44_56 | QAYLQQSGAELVRSGA SVKLSCTAS (SEQ ID NO: 477) | GFNIKD YY (SEQ ID NO: 265) | IHWVKQRPEQGL EWIGW (SEQ ID NO: 324) | IDPDNGE TEYAP (SEQ ID NO: 319) | KFQGKATMTADTSSNTAHLQLSSL TSEDTAVYYC (SEQ ID NO: 403) | TVFWYGNNY AGFAY (SEQ ID NO: 684) | WGQGTLV TVSA (SEQ ID NO: 703) |
| M19 | 44_56 | EVHLQQSGAELVRSGA SVKLSCTAS (SEQ ID NO: 231) | GFNIKD YY (SEQ ID NO: 265) | IHWVKQRPEQGL EWIGW (SEQ ID NO: 324) | IDPDNGE TEYAP (SEQ ID NO: 319) | KFQGKATMTADTSSNTAHLQLSSL TSEDTAVYYC (SEQ ID NO: 403) | TVFWYGNNY AGFAY (SEQ ID NO: 684) | WGAGTSL TVSS (SEQ ID NO: 699) |
| M20 | 33_63 | QVQLQQPGAELVRPGA SVKLSCKAS (SEQ ID NO: 589) | GYSFTS YW (SEQ ID NO: 299) | MNWVKQRPGQGL EWIGI (SEQ ID NO: 442) | IHPSDSE TRLNQ (SEQ ID NO: 322) | KFKDKATLIVDKSSSTAYMQLSSP TSEDSAVYYC (SEQ ID NO: 390) | ARSRGIPFA Y (SEQ ID NO: 133) | WGQGTLV TVSA (SEQ ID NO: 703) |
| M21 | 33_63 | QVQLQQPGADLMKPGA SVKISCKAS (SEQ ID NO: 587) | GYTFSN YW (SEQ ID NO: 304) | IEWIKQRPGHGL EWVGE (SEQ ID NO: 321) | ILPGSGF TNYNE (SEQ ID NO: 331) | NFKGKATFTADISSNITYMQLSSL TSEDSAVYYC (SEQ ID NO: 452) | ARGGTSVVH FDY (SEQ ID NO: 109) | WGQGTSL TVSS (SEQ ID NO: 708) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M22 | 44_56 | EVRLQQSGADLMKPGA SVKISCKAS (SEQ ID NO: 235) | GYTFSN YW (SEQ ID NO: 304) | IEWIKQRPGHGL EWVGE (SEQ ID NO: 321) | ILPGSGF TNYNE (SEQ ID NO: 331) | NFKGKATFTADISSNITYMQLSSL TSEDSAVYYC (SEQ ID NO: 452) | ARGGTSVVH FDY (SEQ ID NO: 109) | WGQGTTV TVSS (SEQ ID NO: 713) |
| M23 | 44_56 | EVRLQQSGADLMKPGA SVKISCKAS (SEQ ID NO: 235) | GYTFSN YW (SEQ ID NO: 304) | IEWIKQRPGHGL EWIGE (SEQ ID NO: 320) | ILPGSGF TNYNE (SEQ ID NO: 331) | NFKGKATFTADISSNITYMQLSSL SSEDSAVYYC (SEQ ID NO: 451) | SRGGTSFVH FDY (SEQ ID NO: 646) | WGQGTTL TVSS (SEQ ID NO: 709) |
| M24 | 6_130 | QIQLQQPGAELAKPGA SVKMSCKAS (SEQ ID NO: 500) | GYTFTR YW (SEQ ID NO: 311) | MRWVKQRPGQDL EWIGY (SEQ ID NO: 446) | INPGSDY T (SEQ ID NO: 334) | DYNEKEKDKAILTADKSSSTAYMQ LSSLTSDDSAVYYC (SEQ ID NO: 213) | ARXGYFDY (SEQ ID NO: 143) | WGRGTTV TVSS (SEQ ID NO: 716) |
| M25 | 33_63 | QVQLQQSGAELAKPGA SVKMSCKAS (SEQ ID NO: 593) | GYTFNR FW (SEQ ID NO: 303) | IHWIRQRPGQSL EWIGY (SEQ ID NO: 323) | INPNSDY I (SEQ ID NO: 335) | EYNQMFEDRATLTADTSSSTAYIQ LSSLTSEDSAVYYC (SEQ ID NO: 245) | ARGTIIDY (SEQ ID NO: 114) | WGQGTTL TVSS (SEQ ID NO: 709) |
| M26 | 6_163 | QVQLQQSGAELAKPGA SVKMSCKAS (SEQ ID NO: 593) | GYTFNR FW (SEQ ID NO: 303) | IHWIRQRPGQSL EWIGY (SEQ ID NO: 323) | INPNSDY I (SEQ ID NO: 335) | EYNQMFEDRATLTADTSSSTAYIQ LSSLTSEDSAVYYC (SEQ ID NO: 245) | ARGTIIDY (SEQ ID NO: 114) | WGQGTTL TVSS (SEQ ID NO: 709) |
| M27 | 33_63 | QVQLQQSGAELAKPGA SVKMSCKAS (SEQ ID NO: 593) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M28 | 33_63 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M29 | 33_63 | QIQLQQPGAELAKPGA SVKMSCKAS (SEQ ID NO: 500) | GYTFTR YW (SEQ ID NO: 311) | MHWVKQRPGQDL EWIGY (SEQ ID NO: 432) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTV TVSS (SEQ ID NO: 713) |
| M30 | 33_63 | QIQLQQSGAELAKPGA SVKMSCKAS (SEQ ID NO: 503) | GYTFTR YW (SEQ ID NO: 311) | MHWVKQRPGQDL EWIGY (SEQ ID NO: 432) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTSL TVS S (SEQ ID NO: 708) |
| M31 | 44_56 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M32 | 44_56 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M33 | 44_56 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M34 | 44_56 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M35 | 44_56 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M36 | 44_56 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M37 | 44_56 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ NO: 242) ID NO: 337) | EYNQKFKDKATLTADKSSSTAYMQ LSSLTSDDSAVYYC (SEQ ID NO: 124) | ARHGYFDY (SEQ ID | WGQGTTL TVSS (SEQ ID NO: 709) |
| M38 | 44_56 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M39 | 44_56 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M40 | 44_56 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M41 | 44_56 | QVQLQQSGAELAKPGA SVKMSCKAS (SEQ ID NO: 593) | GYTFTR YW (SEQ ID NO: 311) | MHWVKQRPGQDL EWIGY (SEQ ID NO: 432) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M42 | 44_56 | QVQLQQSGAELAKPGA SVKMSCKAS (SEQ ID NO: 593) | GYTFTR YW (SEQ ID NO: 311) | MHWVKQRPGQDL EWIGY (SEQ ID NO: 432) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M43 | 44_56 | QIQLQQPGAELAKPGA SVKMSCKAS (SEQ ID NO: 500) | GYTFTR YW (SEQ ID NO: 311) | MHWVKQRPGQDL EWIGY (SEQ ID NO: 432) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTV TVSS (SEQ ID NO: 713) |
| M44 | 44_56 | QIQLQQSGAELAKPGA SVKMSCKAS (SEQ ID NO: 503) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M45 | 44_56 | QIQLQQPGAELAKPGA SVKMSCKAS (SEQ ID NO: 500) | GYTFTR YW (SEQ ID NO: 311) | MHWVKQRPGQDL EWIGY (SEQ ID NO: 432) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTV TVSS (SEQ ID NO: 713) |
| M46 | 44_56 | QVQLQQSGAELAKPGA SVKMSCKAS (SEQ ID NO: 593) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLASDDSAVYYC (SEQ ID NO: 241) | ARHGYFDY (SEQ ID NO: 124) | WGQGTTV TV (SEQ ID NO: 711) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M47 | 57_63 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M48 | 6_130 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M49 | 6_130 | QVQLQQPGAELAKPGA SVKMSCKAS (SEQ ID NO: 588) | GYTFTR YW (SEQ ID NO: 311) | MHWVKQRPGQDL EWIGY (SEQ ID NO: 432) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M50 | 6_130 | QVQLQQSGAELAKPGA SVKMSCKAS (SEQ ID NO: 593) | GYTFTR YW (SEQ ID NO: 311) | IHWVKQRPGQDL EWIGY (SEQ ID NO: 325) | INPRTDY T (SEQ ID NO: 337) | EYNQKFKDKATLTADKSSSTAYMQ LSSLASDDSAVYYC (SEQ ID NO: 241) | ARHGYFDY (SEQ ID NO: 124) | WGQGTTV TV (SEQ ID NO: 711) |
| M51 | 6_163 | QVQLQQSGAELAKPGA SVKMSCKAS (SEQ ID NO: 593) | GYTFTR YW (SEQ ID NO: 311) | MHWVKQRPGQDL EWIGY (SEQ ID NO: 432) | INPRTDY T (SEQ ID NO: 337) | EYNQKFKDKATLTADKSSSTAYMQ LSSLTSDDSAVYYC (SEQ ID NO: 242) | ARHGYFDY (SEQ ID NO: 124) | WGQGTTL TVSS (SEQ ID NO: 709) |
| M52 | 6_163 | QIQLQQSGAELAKPGA SVKMSCKAS (SEQ ID NO: 503) | GYTFTR YW (SEQ ID NO: 311) | MHWVKQRPGQDL EWIGY (SEQ ID NO: 432) | INPRTDY T (SEQ ID NO: 337) | EYNQKFEDRATLTADKSSSTAYMQ LSSLTSDDSAVYYC (SEQ ID NO: 240) | ARHGYFDY (SEQ ID NO: 124) | WGQGTTV TVSS (SEQ ID NO: 713) |
| M53 | 57_63 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY T (SEQ ID NO: 337) | EYNQKFKDKATLTANKSSSTAYMQ LSSLTSDDSAVYYC (SEQ ID NO: 243) | ARHXYFDY (SEQ ID NO: 125) | WGQGTTL TVSS (SEQ ID NO: 709) |
| M54 | 33_63 | QVQLQQSGAELAKPGA SVKMSCKAS (SEQ ID NO: 593) | GYTFTK YW (SEQ ID NO: 308) | MHWVKQRPGQDL EWIGY (SEQ ID NO: 432) | INPRTDY TEYNQ (SEQ ID NO: 338) | KFKDKATLTADKSSSTAYMQLSSL TSDDSAVYYC (SEQ ID NO: 389) | AIHGYFDY (SEQ ID NO: 57) | WGQGTTL TVSS (SEQ ID NO: 709) |
| M55 | 147_157 | QVQMKQSGAELAKPGA SVKMSCKAS (SEQ ID NO: 604) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTSL TVSS (SEQ ID NO: 708) |
| M56 | 147_157 | QVQLQQSGAELAKPGA SVKMSCKAS (SEQ ID NO: 593) | GYTFTR YW (SEQ ID NO: 311) | MHWVKQRPGQDL EWIGY (SEQ ID NO: 432) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTTL TVSS (SEQ ID NO: 709) |
| M57 | 147_157 | QVQLQQSGAELAKPGA SVKMSCKAS (SEQ ID NO: 593) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTTV TVSS (SEQ ID NO: 713) |
| M58 | 33_63 | QIQLKESGAELAKPGA SVKMSCKAS (SEQ ID NO: 499) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTTL TVSS (SEQ ID NO: 709) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M59 | 33_63 | QVQLQQSGAELAKPGA SVKMSCKAS (SEQ ID NO: 593) | GYTFTR YW (SEQ ID NO: 311) | MHWVKQRPGQDL EWIGY (SEQ ID NO: 432) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTTL TVSS (SEQ ID NO: 709) |
| M60 | 33_63 | QIQLQQPGAELAKPGA SVKMSCKAS (SEQ ID NO: 500) | GYTFTR YW (SEQ ID NO: 311) | MHWVKQRPGQDL EWIGY (SEQ ID NO: 432) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTTV TVSS (SEQ ID NO: 713) |
| M61 | 33_63 | QIQLQQSGAELAKPGA SVKMSCKAS (SEQ ID NO: 503) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTTL TVSS (SEQ ID NO: 709) |
| M62 | 33_63 | QVQLQQSGAELAKPGA SVKMSCKAS (SEQ ID NO: 593) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL ASDDSAVYYC (SEQ ID NO: 388) | ARHGYFDY (SEQ ID NO: 124) | WGQGTTV TVSA (SEQ ID NO: 712) |
| M63 | 33_63 | QIQLQQSGAELAKPGA SVKMSCKAS (SEQ ID NO: 503) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTSL TVSS (SEQ ID NO: 708) |
| M64 | 33_63 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTTL TVSS (SEQ ID NO: 709) |
| M65 | 33_63 | QIQLQQSGAELAKPGA SVKMSCKAS (SEQ ID NO: 503) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTSL TVSS (SEQ ID NO: 708) |
| M66 | 33_63 | QIQLQQPGAELAKPGA SVKMSCKAS (SEQ ID NO: 500) | GYTFTR YW (SEQ ID NO: 311) | MHWVKQRPGQDL EWIGY (SEQ ID NO: 432) | INPRTDY TEYNQ (SEQ ID NO: 338) | KFEDKATLTADKSSSTAYMQLSSL TSDDSAVYYC (SEQ ID NO: 387) | ARHGYFDY (SEQ ID NO: 124) | WGQGTTL TVSS (SEQ ID NO: 709) |
| M67 | 33_63 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTTL TVSS (SEQ ID NO: 709) |
| M68 | 33_63 | QIQLQQPGAELAKPGA SVKMSCKAS (SEQ ID NO: 500) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTTV TVSS (SEQ ID NO: 713) |
| M69 | 33_63 | QIQLQQSGAELAKPGA SVKMSCKAS (SEQ ID NO: 503) | GYTFTR YW (SEQ ID NO: 311) | MHWVKQRPGQDL EWIGY (SEQ ID NO: 432) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTSL TVSS (SEQ ID NO: 708) |
| M70 | 33_63 | QIQLQQSGAELAKPGA SVKMSCKAS (SEQ ID NO: 503) | GYTFTR YW (SEQ ID NO: 311) | MHWVKQRPGQDL EWIGY (SEQ ID NO: 432) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTSL TVSS (SEQ ID NO: 708) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M71 | 33_63 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTTL TVSS (SEQ ID NO: 709) |
| M72 | 33_63 | QIQLQQSGAELAKPGA SVKMSCKAS (SEQ ID NO: 503) | GYTFTR YW (SEQ ID NO: 311) | MHWVKQRPGQDL EWIGY (SEQ ID NO: 432) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTSL TVSS (SEQ ID NO: 708) |
| M73 | 44_56 | QVQLQQPGAELAKPGA SVKMSCKAS (SEQ ID NO: 588) | GYTFTR YW (SEQ ID NO: 311) | IHWVKQRPGQDL EWIGY (SEQ ID NO: 325) | INPRTDY TEYNQ (SEQ ID NO: 338) | KFKDKATLTADKSSSTAYMQLSSL TSDDSAVYYC (SEQ ID NO: 389) | ARHGYFDY (SEQ ID NO: 124) | WGQGTTL TVSS (SEQ ID NO: 709) |
| M74 | 44_56 | EVHLQQSGAELAKPGA SVKMSCKAS (SEQ ID NO: 229) | GYTFTR FW (SEQ ID NO: 310) | MHWVKQRPGQGL EWIGY (SEQ ID NO: 433) | INPSTDY I (SEQ ID NO: 340) | EYNQMFEDRATLTADKSSSTAYIQ LTSLTSEDSAVYYC (SEQ ID NO: 244) | ARGTIIDY (SEQ ID NO: 114) | WGQGTTL TVSS (SEQ ID NO: 709) |
| M75 | 6_163 | QVQLQQSGAELAKPGA SVKMSCKAS (SEQ ID NO: 593) | GYTFNR FW (SEQ ID NO: 303) | MHWVKQRPGQGL EWIGY (SEQ ID NO: 433) | INPSTGY I (SEQ ID NO: 341) | EHNQKFKDKATLTADKSSSTAYMQ LSSLTSEDSAVYYC (SEQ ID NO: 220) | ARGTVVDY (SEQ ID NO: 115) | WGQGTTL TVSS (SEQ ID NO: 709) |
| M76 | 147_157 | QVQLVETGGGLVQPGG SRGLSCEGS (SEQ ID NO: 603) | GFTFSG FW (SEQ ID NO: 269) | MSWVRQTPGKTL EWIGD (SEQ ID NO: 448) | INSDGSA INYAP (SEQ ID NO: 342) | SIKDRFTIFRDNDKSTLYLQMSNV RSEDTATYFC (SEQ ID NO: 642) | MRYDGYYWY FDV (SEQ ID NO: 447) | WGAGTTV TVSS (SEQ ID NO: 700) |
| M77 | 44_56 | QVQLQQSGAGLVRPGV SLKISCKGS (SEQ ID NO: 602) | GYTFTD YA (SEQ ID NO: 305) | MHWVRQTHAKSL KWIGV (SEQ ID NO: 440) | INTYSGD A (SEQ ID NO: 345) | IYNQKFKGKATMTVDKSSNTAYRE LAKLTSEDSAIYYC (SEQ ID NO: 370) | ARGVSFDY (SEQ ID NO: 119) | WGQGTTV TVYS (SEQ ID NO: 714) |
| M78 | 33_63 | QIQLQQSGAELVRPGV SLKISCKGS (SEQ ID NO: 506) | GYTFTD YA (SEQ ID NO: 305) | MHWVRQSHAKSL EWIGV (SEQ ID NO: 436) | INTYSGD A (SEQ ID NO: 345) | IYNQKFKGKATMTVDKSSSTAYLE LARLTSDDSAIYYC (SEQ ID NO: 371) | ARGVTFDY (SEQ ID NO: 122) | WGQGTSL TVSS (SEQ ID NO: 708) |
| M79 | 57_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | INTYSGD A (SEQ ID NO: 345) | IYNQKFKGKATMTVDKSSSTAYLE LARLTSDDSAIYYC (SEQ ID NO: 371) | ARGVTFDY (SEQ ID NO: 122) | WGQGTTV TVSS (SEQ ID NO: 713) |
| M80 | 44_56 | QVQLQQSGAELVRPGV SLKISCKGS (SEQ ID NO: 598) | GYTFTD YA (SEQ ID NO: 305) | MHWVRPSHAKSL EWIGV (SEQ ID NO: 435) | ISTYSGD A (SEQ ID NO: 353) | IYNQKFKGKATMTVDKSSSTAYLE LARLTSDDSAIYYC (SEQ ID NO: 371) | ARGVPFDY (SEQ ID NO: 117) | WAQSTIL TVSS (SEQ ID NO: 697) |
| M81 | 147_156 | QIQLQQSGAELVRPGV SLKISCKGS (SEQ ID NO: 506) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDI (SEQ ID NO: 120) | WGQGTSL TVSS (SEQ ID NO: 708) |
| M82 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDY (SEQ ID NO: 122) | WGQGTTL TVSS (SEQ ID NO: 709) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M83 | 33_63 | QVQLQQPGAELVRPGV SLKISCKGS (SEQ ID NO: 591) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDY (SEQ ID NO: 122) V NO: | WGQGTTV TVSS (SEQ ID 713) |
| M84 | 33_63 | QIQLQQPGAELVRPGV SLKISCKGS (SEQ ID NO: 502) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDNSAIYYC (SEQ ID NO: 373) | ARGVTFDY (SEQ ID NO: 122) | WGQGTTV TVSS (SEQ ID NO: 713) |
| M85 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDY (SEQ ID NO: 122) | WGQGTTV TVSS (SEQ ID NO: 713) |
| M86 | 33_63 | QIQLQQSGAELVRPGV SLKISCKGS (SEQ ID NO: 506) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVNKSSSTAYLE LARLTSDDSAIYYC (SEQ ID NO: 375) | ARGVTFDY (SEQ ID NO: 122) | WGQGTSL TVSS (SEQ ID NO: 708) |
| M87 | 33_63 | QVQLIQSGAELVRPGV SLKISCKGS (SEQ ID NO: 584) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDY (SEQ ID NO: 122) | WGQGTTV TVSS (SEQ ID NO: 713) |
| M88 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD A (SEQ ID NO: 353) | IYDQKFQGKATMTVDKSSSTAYLG LARLTSDDSAIYYC (SEQ ID NO: 364) | ARGVTFDY (SEQ ID NO: 122) | WGQGTTV TVSS (SEQ ID NO: 713) |
| M89 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDY (SEQ ID NO: 122) | WGQGTTV TVSS (SEQ ID NO: 713) |
| M90 | 33_63 | QVQLQQPGAELVRPGV SLKISCKGS (SEQ ID NO: 591) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDY (SEQ ID NO: 122) | WGQGTTV TVSS (SEQ ID NO: 713) |
| M91 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD A (SEQ ID NO: 353) | IYNQKFKDKATMTVDKSSSTAYLE LARLTSEDSAIYYC (SEQ ID NO: 367) | ARGVTFDY (SEQ ID NO: 122) | WGQGTTL TVSS (SEQ ID NO: 709) |
| M92 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDY (SEQ ID NO: 122) | WGQGTSL TVSS (SEQ ID NO: 708) |
| M93 | 33_63 | QIQLQQSGAELVRPGV SLKISCKGS (SEQ ID NO: 506) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDY (SEQ ID NO: 122) | WGQGTSL TVSS (SEQ ID NO: 708) |
| M94 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSEDSAIYYC (SEQ ID NO: 374) | ARGVTFDY (SEQ ID NO: 122) | WGQGTTL TVSS (SEQ ID NO: 709) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M95 | 44_56 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDA (SEQ ID NO: 353) | IYNQKFKGKATMTVDKSSSTAYLELARLTSDDSAIYYC (SEQ ID NO: 371) | ARGVTFDY (SEQ ID NO: 122) | WGQGTSLTVSS (SEQ ID NO: 708) |
| M96 | 44_56 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDA (SEQ ID NO: 353) | IYNQKFKGKATMTVDKSSSTAYLELARLTSDDSAIYYC (SEQ ID NO: 371) | ARGVTFDY (SEQ ID NO: 122) | WGQGTSLTVSS (SEQ ID NO: 708) |
| M97 | 44_56 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDA (SEQ ID NO: 353) | IYNQKFKGKATMTVDKSSSTAYLELARLTSEDSAIYYC (SEQ ID NO: 374) | ARGVTFDY (SEQ ID NO: 122) | WGQGTTLTVSS (SEQ ID NO: 709) |
| M98 | 147_156 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDA (SEQ ID NO: 353) | IYNQKFKGKATMTVDKSSSTAYLELARLTSDHSAIYYC (SEQ ID NO: 372) | ARGVTFDY (SEQ ID NO: 122) | WGQGTTVTVSS (SEQ ID NO: 713) |
| M99 | 147_156 | QIQLQQSGAELVRPGVSLKISCKGS (SEQ ID NO: 506) | GYTFTDYA (SEQ ID NO: 305) | MHWVRQSHAKSLEWIGV (SEQ ID NO: 436) | ISTYSGDA (SEQ ID NO: 353) | IYNQKFKGKATMTVDKSSSTAYLELARLTSDDSAIYYC (SEQ ID NO: 371) | ARGVTFDY (SEQ ID NO: 122) | WGQGTSLTVSS (SEQ ID NO: 708) |
| M100 | 147_156 | QVQLQQSGAELMRPGVSLKISCKGS (SEQ ID NO: 594) | GYTFTDYA (SEQ ID NO: 305) | MHWVRQSHAKSLEWIGV (SEQ ID NO: 436) | ISTYSGDA (SEQ ID NO: 353) | LYNQKFKGKATMTVDKSSSTAYLELARLTSDDSAIYYC (SEQ ID NO: 431) | ARGVTFDY (SEQ ID NO: 122) | WGQGTTLTVSS (SEQ ID NO: 709) |
| M101 | 44_56 | QVQLQQSGAELVRPGVSLKISCKGS (SEQ ID NO: 598) | GYTFTDYA (SEQ ID NO: 305) | MHWVRQSHAKSPEWIGV (SEQ ID NO: 439) | ISTYSGDA (SEQ ID NO: 353) | IYNQKFKGKATMTVDKSSSTAYLELARLTSDDSAIYYC (SEQ ID NO: 371) | ARGVTFDY (SEQ ID NO: 122) | WGQGTTLTVSS (SEQ ID NO: 709) |
| M102 | 57_63 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDA (SEQ ID NO: 353) | IYNQKFKGKATMTVDKSSSTAYLELARLTSDDSAIYYC (SEQ ID NO: 371) | ARGVTFDY (SEQ ID NO: 122) | WGQGTTVTVSS (SEQ ID NO: 713) |
| M103 | 57_63 | QVQMQQSGAELVRPGVSLKISCKGS (SEQ ID NO: 606) | GYTFTDYA (SEQ ID NO: 305) | MQWVRQSHAKSLEWIGV (SEQ ID NO: 445) | ISTYSGDA (SEQ ID NO: 353) | IYNQKFKSKATMTVDKSSSTAYLELARLTSEDSAIYYC (SEQ ID NO: 376) | ARGVTFDY (SEQ ID NO: 122) | WGQGTTVTVSS (SEQ ID NO: 713) |
| M104 | 6_130 | QVQLQQSGAGLVRPGVSLKISCKGS (SEQ ID NO: 602) | GYTFTDYA (SEQ ID NO: 305) | MHWVRQSHAKSLEWIGV (SEQ ID NO: 436) | ISTYSGDA (SEQ ID NO: 353) | IYNQKFKGKATMTVDKSSSTAYLELARLTSEDSAIYYC (SEQ ID NO: 374) | ARGVTFDY (SEQ ID NO: 122) | WGQGTTVTVSS (SEQ ID NO: 713) |
| M105 | 6_130 | QIQLQQSGAELVRPGVSLKISCKGS (SEQ ID NO: 506) | GYTFTDYA (SEQ ID NO: 305) | MHWVRQSHAKSLEWIGV (SEQ ID NO: 436) | ISTYSGDA (SEQ ID NO: 353) | IYNQKFKGKATMTVDKSSSTAYLELARLTSDDSAIYYC (SEQ ID NO: 371) | ARGVTFDY (SEQ ID NO: 122) | WGQGTSLTV (SEQ ID NO: 706) |
| M106 | 6_130 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDA (SEQ ID NO: 353) | IYNQKFKGKATMTVDKSSSTAYLELARLTSEDSAIYYC (SEQ ID NO: 374) | ARGVTFDY (SEQ ID NO: 122) | WGQGTTLTVSS (SEQ ID NO: 709) |
| M107 | 6_130 | QAYLQQSGAELVRPGVSLKISCKGS (SEQ ID NO: 475) | GYTFTDYA (SEQ ID NO: 305) | MHWVRQSHAKSLEWIGV (SEQ ID NO: 436) | ISTYSGDA (SEQ ID NO: 353) | IYNQKFKGKATMTVDKSSSTAYLELARLTSEDSAIYYC (SEQ ID NO: 374) | ARGVTFDY (SEQ ID NO: 122) | WGQGTTLTVSS (SEQ ID NO: 709) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M108 | 6_163 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDY (SEQ ID NO: 122) | WGQGTTV TVSS (SEQ ID NO: 713) |
| M109 | 77_89 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDY (SEQ ID NO: 122) | WGQGTTV TVSS (SEQ ID NO: 713) |
| M110 | 77_89 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSDDSAIYYC (SEQ ID NO: 371) | ARGVTFDY (SEQ ID NO: 122) | WGQGTTV TVSS (SEQ ID NO: 713) |
| M111 | 77_89 | QIQLQQSGAELVRPGV SLKISCKGS (SEQ ID NO: 506) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSSTAYLE LARLTSEDSAIYYC (SEQ ID NO: 374) | ARGVTFDY (SEQ ID NO: 122) | WGQGTTL TVSS (SEQ ID NO: 709) |
| M112 | 77_89 | QAYLQQSGAELVRPGV SLKISCKGS (SEQ ID NO: 475) | GYTFTD YA (SEQ ID NO: 305) | MHWVRQSHAKSL EWIGV (SEQ ID NO: 436) | ISTYSGD A (SEQ ID NO: 353) | LYNQKFKGKATMTVDKSSSTAYLE LARLTSDDSAIYYC (SEQ ID NO: 431) | ARGVTFDY (SEQ ID NO: 122) | WGQGTTL TVSS (SEQ ID NO: 709) |
| M113 | 77_89 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD A (SEQ ID NO: 353) | LYNQKFKGKATMTVDKSSSTAYLE LARLTSDDSAIYYC (SEQ ID NO: 431) | ARGVTFDY (SEQ ID NO: 122) | WGQGTTL TVSS (SEQ ID NO: 709) |
| M114 | 57_63 | QIQLQQPGAELVRPGV SLKISCKGS (SEQ ID NO: 502) | GYTFTD YA (SEQ ID NO: 305) | MHWVRQSHAKSL EWIVV (SEQ ID NO: 437) | ISTYSGD A (SEQ ID NO: 353) | IYNQKFKGKATMTVDKSSITAYLE LARLTSDDSAVYYC (SEQ ID NO: 368) | ARXVTFDY (SEQ ID NO: 144) | WGQGTTV TVSS (SEQ ID NO: 713) |
| M115 | 44_56 | QVQMQQSGAELVRPGV SLKISCKGS (SEQ ID NO: 606) | GYTFTD YA (SEQ ID NO: 305) | MQWVRQSHAKSL EWIGV (SEQ ID NO: 445) | ISTYSGD A (SEQ ID NO: 353) | IYNQKFKSKATMTVDKSSSTAYLE LARLTSEDSAIYYC (SEQ ID NO: 376) | ATGVTFDY (SEQ ID NO: 148) | WGQGTTV TVSS (SEQ ID NO: 713) |
| M116 | 57_63 | QIQLQQSGAELVRPGV SLKISCKGS (SEQ ID NO: 506) | GYTFTD YA (SEQ ID NO: 305) | MHWVRQSHAKSL EWIGV (SEQ ID NO: 436) | ISTYSGD A (SEQ ID NO: 353) | IYNQKFKGKATMTVDKSSNTAYLE LARLTSDDSAIYYC (SEQ ID NO: 369) | ATGVTFDY (SEQ ID NO: 148) | WGQGTIL TVSS (SEQ ID NO: 701) |
| M117 | 147_157 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M118 | 147_157 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | (SEQ ID NO: 398) | ARGVTFDY (SEQ ID NO: 122) | WGQGTTV TVSS (SEQ ID NO: 713) |
| M119 | 147_157 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M120 | 147_157 | EVQLQQSGAELVRPGVSLKISCKGS (SEQ ID NO: 234) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTLTVSS (SEQ ID NO: 709) |
| M121 | 147_157 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |
| M122 | 147_157 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSEDSAIYYC (SEQ ID NO: 399) | ARGVTFDY (SEQ ID NO: 122) | WGQGTTLTVSS (SEQ ID NO: 709) |
| M123 | 147_157 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDAIYNQ (SEQ ID NO: 354) | KFKDKATMTVDKSSSTAYLELARLTSEDSAIYYC (SEQ ID NO: 391) | ARGVTFDY (SEQ ID NO: 122) | WGQGTTLTVSS (SEQ ID NO: 709) |
| M124 | 147_157 | QIQLQQSGAELVRPGVSLKISCKGS (SEQ ID NO: 506) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTSLTVSA (SEQ ID NO: 707) |
| M125 | 147_157 | QVQLQQPGAELVRPGVSLKISCKGS (SEQ ID NO: 591) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |
| M126 | 147_157 | QVQLQQPGAELVRPGVSLKISCKGS (SEQ ID NO: 591) | GYTFTDYA (SEQ ID NO: 305) | MQWVRQSHAKSLEWIGV (SEQ ID NO: 445) | ISTYSGDAIYNQ (SEQ ID NO: 354) | KFKGKATMTVDKSSSTAYLELARLTSEDSAIYYC (SEQ ID NO: 399) | ARGVTFDY (SEQ ID NO: 122) | WGQGTTVTVSS (SEQ ID NO: 713) |
| M127 | 147_157 | QVQLQQPGAELVRPGVSLKISCKGS (SEQ ID NO: 591) | GYTFTDYA (SEQ ID NO: 305) | MQWVRQSHAKSLEWIGV (SEQ ID NO: 445) | ISTYSGDAIYNQ (SEQ ID NO: 354) | KFKGKATMTVDKSSSTAYLELARLTSEDSAIYYC (SEQ ID NO: 399) | ARGVTFDY (SEQ ID NO: 122) | WGQGTTVTVSS (SEQ ID NO: 713) |
| M128 | 147_157 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |
| M129 | 147_157 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |
| M130 | 147_157 | QVQLQQSGAELVRPGVSLKISCKGS (SEQ ID NO: 598) | GYTFTDYA (SEQ ID NO: 305) | MHWVRQSHAKSLKWIGV (SEQ ID NO: 438) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |
| M131 | 33_63 | QVQMKQSGAELVRPGVSLKISCKGS (SEQ ID NO: 605) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |
| M132 | 33_63 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M133 | 33_63 | QIQLQQSGAELVRPGV SLKISCKGS (SEQ ID NO: 506) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTSL TVSS (SEQ ID NO: 708) |
| M134 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M135 | 33_63 | QVQLQQSGAELVRPGV SLKISCKGS (SEQ ID NO: 598) | GYTFTD YA (SEQ ID NO: 305) | MHWVRQSHAKSP EWIGV (SEQ ID NO: 439) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTL TVSS (SEQ ID NO: 709) |
| M136 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M137 | 33_63 | QIQLQQSGAELVRPGV SLKISCKGS (SEQ ID NO: 506) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTSL TVSS (SEQ ID NO: 708) |
| M138 | 33_63 | QVQLQQPGAELVRPGV SLKISCKGS (SEQ ID NO: 591) | GYTFTD YA (SEQ ID NO: 305) | MHWVRQSHAKSL EWIG (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M139 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTL TVSS (SEQ ID NO: 709) |
| M140 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M141 | 33_63 | QIQLQQSGAELVRPGV SLKISCKGS (SEQ ID NO: 506) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSEDSAIYYC (SEQ ID NO: 399) | ARGVTFDY (SEQ ID NO: 122) | WGQGTSL TVSS (SEQ ID NO: 708) |
| M142 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTSL TVSS (SEQ ID NO: 708) |
| M143 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M144 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M145 | 33_63 | QAYLQQSGAELVRPGV SLKISCKGS (SEQ ID NO: 475) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSEDSAIYYC (SEQ ID NO: 399) | ARGVTFDY (SEQ ID NO: 122) | WGQGTTL TVSS (SEQ ID NO: 709) |
| M146 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSEDSAIYYC (SEQ ID NO: 399) | ARGVTFDY (SEQ ID NO: 122) | WGQGTTL TVSS (SEQ ID NO: 709) |
| M147 | 33_63 | QVQLKQSGAELVRPGV SLKISCKGS (SEQ ID NO: 585) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTSL TVSS (SEQ ID NO: 708) |
| M148 | 33_63 | QVQMKQSGAELVRPGV SLKISCKGS (SEQ ID NO: 605) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSEDSAIYYC (SEQ ID NO: 399) | ARGVTFDY (SEQ ID NO: 122) | WGQGTTL TVSS (SEQ ID NO: 709) |
| M149 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSEDSAIYYC (SEQ ID NO: 399) | ARGVTFDY (SEQ ID NO: 122) | WGQGTTL TVSS (SEQ ID NO: 709) |
| M150 | 33_63 | QAYLQQSGAELVRPGV SLKISCKGS (SEQ ID NO: 475) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSEDSAIYYC (SEQ ID NO: 399) | ARGVTFDY (SEQ ID NO: 122) | WGQGTTL TVSS (SEQ ID NO: 709) |
| M151 | 33_63 | QAYLQQSGAELVRPGV SLKISCKGS (SEQ ID NO: 475) | GYTFTD YA (SEQ ID NO: 305) | VQWVRQSHAKSL EWIGV (SEQ ID NO: 695) | ISTYSGD AIYNQ (SEQ ID NO: 354) | KFKGKATMTVDKSSSTAYLELARL TSEDSAIYYC (SEQ ID NO: 399) | ARGVTFDY (SEQ ID NO: 122) | WGQGTTL TVSS (SEQ ID NO: 709) |
| M152 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M153 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M154 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSEDSAIYYC (SEQ ID NO: 399) | ARGVTFDY (SEQ ID NO: 122) | WGQGTTL TVSS (SEQ ID NO: 709) |
| M155 | 44_56 | QVQLKQSGAELVRPGV SLKISCKGS (SEQ ID NO: 585) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTSL TVSS (SEQ ID NO: 708) |
| M156 | 44_56 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M157 | 44_56 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M158 | 44_56 | QVQMKQSGAELVRPGVSLKISCKGS (SEQ ID NO: 605) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |
| M159 | 44_56 | QVQMKQSGAELVRPGVSLKISCKGS (SEQ ID NO: 605) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |
| M160 | 44_56 | QVQMKQSGAELVRPGVSLKISCKGS (SEQ ID NO: 605) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |
| M161 | 44_56 | QAYLQQSGAELVRPGVSLKISCKGS (SEQ ID NO: 475) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSEDSAIYYC (SEQ ID NO: 399) | ARGVTFDY (SEQ ID NO: 122) | WGQGTTLTVSS (SEQ ID NO: 709) |
| M162 | 44_56 | QIQLQQSGAELVRPGVSLKISCKGS (SEQ ID NO: 506) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTSLTVSA (SEQ ID NO: 707) |
| M163 | 44_56 | QIQLQQPGAELVRPGVSLKISCKGS (SEQ ID NO: 502) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |
| M164 | 44_56 | QIQLQQPGAELVRPGVSLKISCKGS (SEQ ID NO: 502) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |
| M165 | 44_56 | QAYLQQSGAELVRPGVSLKISCKGS (SEQ ID NO: 475) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSEDSAIYYC (SEQ ID NO: 399) | ARGVTFDY (SEQ ID NO: 122) | WGQGTTLTVSS (SEQ ID NO: 709) |
| M166 | 44_56 | QVQMQQSGAELVRPGVSLKISCKGS (SEQ ID NO: 606) | GYTFTDYA (SEQ ID NO: 305) | MQWVRQSHAKSLEWIGV (SEQ ID NO: 445) | ISTYSGDAIYNQ (SEQ ID NO: 354) | KFKSKATMTVDKSSSTAYLELARLTSEDSAIYYC (SEQ ID NO: 402) | ARGVTFDY (SEQ ID NO: 122) | WGQGTTVTVSS (SEQ ID NO: 713) |
| M167 | 44_56 | QVQMQQSGAELVRPGVSLKISCKGS (SEQ ID NO: 606) | GYTFTDYA (SEQ ID NO: 305) | MQWVRQSHAKSLEWIGV (SEQ ID NO: 445) | ISTYSGDAIYNQ (SEQ ID NO: 354) | KFKSKATMTVDKSSSTAYLELARLTSEDSAIYYC (SEQ ID NO: 402) | ARGVTFDY (SEQ ID NO: 122) | WGQGTTVTVSS (SEQ ID NO: 713) |
| M168 | 44_56 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSEDSAIYYC (SEQ ID NO: 399) | ARGVTFDY (SEQ ID NO: 122) | WGQGTTLTVSS (SEQ ID NO: 709) |
| M169 | 44_56 | QVQLQQSGAELVRPGVSLKISCKGS (SEQ ID NO: 598) | GYTFTDYA (SEQ ID NO: 305) | MHWVRQSHAKSLEWIGV (SEQ ID NO: 436) | ISTYSGDAIYNQ (SEQ ID NO: 354) | KFKGKATMTVDKSSSTAYLELARLTSDDSAIYYC (SEQ ID NO: 398) | ARGVTFDY (SEQ ID NO: 122) | WGQGTTVTVSS (SEQ ID NO: 713) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M170 | 44_56 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M171 | 44_56 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M172 | 44_56 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD AIYNQ (SEQ ID NO: 354) | KFKGKATMTVDKSSSTAYLELARL TSDDSAIYYC (SEQ ID NO: 398) | ARGVTFDY (SEQ ID NO: 122) | WGQGTSL TVSS (SEQ ID NO: 708) |
| M173 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD ALYNQ (SEQ ID NO: 355) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M174 | 33_63 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD ALYNQ (SEQ ID NO: 355) | KFKGKATMTVDKSSSTAYLELARL TSDDSAIYYC (SEQ ID NO: 398) | ARGVTFDY (SEQ ID NO: 122) | WGQGTTV TVSS (SEQ ID NO: 713) |
| M175 | 33_63 | QIQLQQSGAELVRPGV SLKISCKGS (SEQ ID NO: 506) | GYTFTD YA (SEQ ID NO: 305) | MHWVRQSHAKSL EWIGV (SEQ ID NO: 436) | ISTYSGD ALYNQ (SEQ ID NO: 355) | KFKGKATMTVDKSSSTAYLELARL TSDDSAIYYC (SEQ ID NO: 398) | ARGVTFDY (SEQ ID NO: 122) | WGQGTTL TVSS (SEQ ID NO: 709) |
| M176 | 44_56 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD ALYNQ (SEQ ID NO: 355) | KFKGKATMTVDKSSSTAYLELARL TSEDSAIYYC (SEQ ID NO: 399) | ARGVTFDY (SEQ ID NO: 122) | WGQGTSL TVSS (SEQ ID NO: 708) |
| M177 | 44_56 | QVQLQQSGAELVRPGV SLKISCKGS (SEQ ID NO: 598) | GYTFTD YA (SEQ ID NO: 305) | MHWVRQSHAKSL EWIGV (SEQ ID NO: 436) | ISTYSGD ALYNQ (SEQ ID NO: 355) | KFKGKATMTVDKSSSTAYLELARL TSEDSAIYYC (SEQ ID NO: 399) | ARGVTFDY (SEQ ID NO: 122) | WGQGTSL TVSS (SEQ ID NO: 708) |
| M178 | 44_56 | QAYLQQSGAELVRPGV SLKISCKGS (SEQ ID NO: 475) | GYTFTD YA (SEQ ID NO: 305) | MHWVRQSHAKSL EWIGV (SEQ ID NO: 436) | ISTYSGD ALYNQ (SEQ ID NO: 355) | KFKGKATMTVDKSSSTAYLELARL TSDDSAIYYC (SEQ ID NO: 398) | ARGVTFDY (SEQ ID NO: 122) | WGQGTTL TVSS (SEQ ID NO: 709) |
| M179 | 44_56 | QAYLQQSGAELVRPGV SLKISCKGS (SEQ ID NO: 475) | GYTFTD YA (SEQ ID NO: 305) | MHWVRQSHAKSL EWIGV (SEQ ID NO: 436) | ISTYSGD ALYNQ (SEQ ID NO: 355) | KFKGKATMTVDKSSSTAYLELARL TSDDSAIYYC (SEQ ID NO: 398) | ARGVTFDY (SEQ ID NO: 122) | WGQGTTL TVSS (SEQ ID NO: 709) |
| M180 | 44_56 | QIQLQQSGAELVRPGV SLKISCKGS (SEQ ID NO: 506) | GYTFTD YA (SEQ ID NO: 305) | MHWVRQSHAKSL EWIGV (SEQ ID NO: 436) | ISTYSGD ALYNQ (SEQ ID NO: 355) | KFKGKATMTVDKSSXTAYLELARL TSDDSAIYYC (SEQ ID NO: 401) | AXGVTFDY (SEQ ID NO: 155) | WGQGTTL TVSS (SEQ ID NO: 709) |
| M181 | 33_63 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD V (SEQ ID NO: 356) | SYNQKFKGKATMTVDKSSSTAYME LARLTSEDSAIYYC (SEQ ID NO: 666) | ARGVTFDS (SEQ ID NO: 121) | WGQGTTL TVSS (SEQ ID NO: 709) |
| M182 | 33_63 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD V (SEQ ID NO: 356) | SYNQKFKGKATMTVDKSSSTAYME LARLTSEDSAIYYC (SEQ ID NO: 666) | ARGVTFDS (SEQ ID NO: 121) | WGQGTTV TVSS (SEQ ID NO: 713) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M183 | 33_63 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD V (SEQ ID NO: 356) | SYNQKFKGKATMTVDKSSSTAYME LARLTSEDSAIYYC (SEQ ID NO: 666) | ARGVTFDS (SEQ ID NO: 121) | WGQGTTV TVSS (SEQ ID NO: 713) |
| M184 | 33_63 | QAYLQQSGAEMVRPGV SVKISCKGS (SEQ ID NO: 478) | GYTFTD YA (SEQ ID NO: 305) | MHWVRQSHAKSL EWIGV (SEQ ID NO: 436) | ISTYSGD V (SEQ ID NO: 356) | SYNQKFKGKATMTVDKSSSTAYME LARLTSEDSAIYYC (SEQ ID NO: 666) | ARGVTFDS (SEQ ID NO: 121) | WGQGTTL TVSS (SEQ ID NO: 709) |
| M185 | 44_56 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD V (SEQ ID NO: 356) | SYNQKFKGKATMTVDKSSSTAYME LARLTSEDSAIYYC (SEQ ID NO: 666) | ARGVTFDS (SEQ ID NO: 121) | WGQGTTL TVSS (SEQ ID NO: 709) |
| M186 | 6_130 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD V (SEQ ID NO: 356) | SYNQKFKGKATMTVDKSSSTAYME LARLTSEDSAIYYC (SEQ ID NO: 666) | ARGVTFDS (SEQ ID NO: 121) | WGQGTSL TVSS (SEQ ID NO: 708) |
| M187 | 6_130 | QIQLQQSGAELVRPGV SVKISCKGS (SEQ ID NO: 507) | GYTFTD YA (SEQ ID NO: 305) | MHWVKQSHAKSL EWIGV (SEQ ID NO: 434) | ISTYSGD V (SEQ ID NO: 356) | SYNQKFKGKATMTVDKSSSTAYME LARLTSEDSAIYYC (SEQ ID NO: 666) | ARGVTFDS (SEQ ID NO: 121) | WGQGTTL TVSS (SEQ ID NO: 709) |
| M188 | 6_163 | QVQLQQPGAELVRPGV SVKISCKGS (SEQ ID NO: 592) | GYTFTD YA (SEQ ID NO: 305) | MHWVKQSHAKSL EWIGV (SEQ ID NO: 434) | ISTYSGD V (SEQ ID NO: 356) | SYNQKFKGKATMTVDKSSSTAYME LARLTSEDSAIYYC (SEQ ID NO: 666) | ARGVTFDS (SEQ ID NO: 121) | WGQGTTV TVSS (SEQ ID NO: 713) |
| M189 | 6_163 | EVHLQQSGAELVRPGV SVKISCKGS (SEQ ID NO: 230) | GYTFTD YA (SEQ ID NO: 305) | MHWVKQSHAKSL EWIGV (SEQ ID NO: 434) | ISTYSGD V (SEQ ID NO: 356) | SYNQKFKGKATMTVDKSSSTAYME LARLTSEDSAIYYC (SEQ ID NO: 666) | ARGVTFDS (SEQ ID NO: 121) | WGQGTTV TVSS (SEQ ID NO: 713) |
| M190 | 77_89 | QIQLQQSGAELVRPGV SVKISCKGS (SEQ ID NO: 507) | GYTFTD YA (SEQ ID NO: 305) | MHWVKQSHAKSL EWIGV (SEQ ID NO: 434) | ISTYSGD V (SEQ ID NO: 356) | SYNQKFKGKATMTVDKSSSTAYME LARLTSEDSAIYYC (SEQ ID NO: 666) | ARGVTFDS (SEQ ID NO: 121) | WGQGTSL TVSS (SEQ ID NO: 708) |
| M191 | 77_89 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD V (SEQ ID NO: 356) | SYNQKFKGKATMTVDKSSSTAYME LARLTSEDSAIYYC (SEQ ID NO: 666) | ARGVTFDS (SEQ ID NO: 121) | WGQGTTV TVSS (SEQ ID NO: 713) |
| M192 | 57_63 | QIQLQQSGAEMVRPGV SVKISCKGS (SEQ ID NO: 509) | GYTFTD YA (SEQ ID NO: 305) | MHWVRQSHAKSL EWIGV (SEQ ID NO: 436) | ISTYSGD V (SEQ ID NO: 356) | SYNQKFKGKATMTVDKSSSTAYME LARLTSEDSAIYYC (SEQ ID NO: 666) | ATXVTFDS (SEQ ID NO: 152) | WGQGTTL TVSS (SEQ ID NO: 709) |
| M193 | 147_157 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD VNYNQ (SEQ ID NO: 357) | KFKGKATMTVDKSSSTAYMELARL TSEDSAIYYC (SEQ ID NO: 400) | ARGVTFDS (SEQ ID NO: 121) | WGQGTSL TVSS (SEQ ID NO: 708) |
| M194 | 33_63 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) 357) | ISTYSGD VNYNQ (SEQ ID NO: 708) | KFKGKATMTVDKSSSTAYMELARL TSEDSAIYYC (SEQ ID NO: 400) | ARGVTFDS (SEQ ID NO: 121) | WGQGTSL TVSS (SEQ ID NO: |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M195 | 44_56 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD VNYNQ (SEQ ID NO: 357) | KFKGKATMTVDKSSSTAYMELARL TSEDSAIYYC (SEQ ID NO: 400) | ARGVTFDS (SEQ ID NO: 121) | WGQGTSL TVSS (SEQ ID NO: 708) |
| M196 | 44_56 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD VNYNQ (SEQ ID NO: 357) | KFKGKATMTVDKSSSTAYMELARL TSEDSAIYYC (SEQ ID NO: 400) | ARGVTFDS (SEQ ID NO: 121) | WGQGTSL TVSS (SEQ ID NO: 708) |
| M197 | 44_56 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD VNYNQ (SEQ ID NO: 357) | KFKGKATMTVDKSSSTAYMELARL TSEDSAIYYC (SEQ ID NO: 400) | ARGVTFDS (SEQ ID NO: 121) | WGQGTSL TVSS (SEQ ID NO: 708) |
| M198 | 147_157 | QAYLQQSGAELVRPGV SVKISCKGS (SEQ ID NO: 476) | GYTFTD YA (SEQ ID NO: 305) | MHWVKQSHAKSL EWIGV (SEQ ID NO: 434) | ISTYSGD VSYNQ (SEQ ID NO: 358) | KFKDKATMTVDKSSSTAYMELARL TSEDSAIYYC (SEQ ID NO: 392) | ARGVTFDS (SEQ ID NO: 121) | WGQGTTL TVSS (SEQ ID NO: 709) |
| M199 | 147_157 | QIQLQQSGAELVRPGV SVKISCKGS (SEQ ID NO: 507) | GYTFTD YA (SEQ ID NO: 305) | MHWVKQSHAKSL EWIGV (SEQ ID NO: 434) | ISTYSGD VSYNQ (SEQ ID NO: 358) | KFKGKATMTVDKSSSTAYMELARL TSEDSAIYYC (SEQ ID NO: 400) | ARGVTFDS (SEQ ID NO: 121) | WGQGTTV TVSS (SEQ ID NO: 713) |
| M200 | 33_63 | QVQLQQPGAELVRPGV SVKISCKGS (SEQ ID NO: 592) | GYTFTD YA (SEQ ID NO: 305) | MHWVKQSHAKSL EWIGV (SEQ ID NO: 434) | ISTYSGD VSYNQ (SEQ ID NO: 358) | KFKGKATMTVDKSSSTAYMELARL TSEDSAIYYC (SEQ ID NO: 400) | ARGVTFDS (SEQ ID NO: 121) | WGQGTTL TVSS (SEQ ID NO: 709) |
| M201 | 33_63 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD VSYNQ (SEQ ID NO: 358) | KFKGKATMTVDKSSSTAYMELARL TSEDSAIYYC (SEQ ID NO: 400) | ARGVTFDS (SEQ ID NO: 121) | WGQGTSL TVSS (SEQ ID NO: 708) |
| M202 | 33_63 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD VSYNQ (SEQ ID NO: 358) | KFKGKATMTVDKSSSTAYMELARL TSEDSAIYYC (SEQ ID NO: 400) | ARGVTFDS (SEQ ID NO: 121) | WGQGTTV TVSS (SEQ ID NO: 713) |
| M203 | 33_63 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD VSYNQ (SEQ ID NO: 358) | KFKGKATMTVDKSSSTAYMELARL TSEDSAIYYC (SEQ ID NO: 400) | ARGVTFDS (SEQ ID NO: 121) | WGQGTTL TXSS (SEQ ID NO: 710) |
| M204 | 33_63 | QVQLQQSGAELVRPGV SVKISCKGS (SEQ ID NO: 599) | GYTFTD YA (SEQ ID NO: 305) | MHWVKQSHAKSL EWIGV (SEQ ID NO: 434) | ISTYSGD VSYNQ (SEQ ID NO: 358) | KFKGKATMTVDKSSSTAYMELARL TSEDSAIYYC (SEQ ID NO: 400) | ARGVTFDS (SEQ ID NO: 121) | WGQGTTV TVSS (SEQ ID NO: 713) |
| M205 | 33_63 | QAYLQQSGAELVRPGV SVKISCKGS (SEQ ID NO: 476) | GYTFTD YA (SEQ ID NO: 305) | MHWVKQSHAKSL EWIGV (SEQ ID NO: 434) | ISTYSGD VSYNQ (SEQ ID NO: 358) | KFKGKATMTVDKSSSTAYMELARL TSEDSAIYYC (SEQ ID NO: 400) | ARGVTFDS (SEQ ID NO: 121) | WGQGTTV TVSS (SEQ ID NO: 713) |
| M206 | 33_63 | QVQMQQSGAELVRPGV SVKISCKGS (SEQ ID NO: 607) | GYTFTD YA (SEQ ID NO: 305) | MHWVKQSHAKSL EWIGV (SEQ ID NO: 434) | ISTYSGD VSYNQ (SEQ ID NO: 358) | KFKGKATMTVDKSSSTAYMELARL TSEDSAIYYC (SEQ ID NO: 400) | ARGVTFDS (SEQ ID NO: 121) | WGQGTTV TVSS (SEQ ID NO: 713) |
| M207 | 33_63 | QAYLQQSGAELVRPGV SVKISCKGS (SEQ ID NO: 476) | GYTFTD YA (SEQ ID NO: 305) | MHWVKQSHAKSL EWIGV (SEQ ID NO: 434) | ISTYSGD VSYNQ (SEQ ID NO: 358) | KFKGKATMTVDKSSSTAYMELARL TSEDSAIYYC (SEQ ID NO: 400) | ARGVTFDS (SEQ ID NO: 121) | WGQGTTL TVSS (SEQ ID NO: 709) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M208 | 33_63 | QIQLQQSGAELVRPGVSVKISCKGS (SEQ ID NO: 507) | GYTFTDYA (SEQ ID NO: 305) | MQWVKQSHAKSLEWIGV (SEQ ID NO: 444) | ISTYSGDVSYNQ (SEQ ID NO: 358) | KFKGKATMTVDKSSNTAYMELARLTSEDSAIYYC (SEQ ID NO: 397) | ARGVTFDS (SEQ ID NO: 121) | WGQGTTLTVSS (SEQ ID NO: 709) |
| M209 | 33_63 | QIQLQQSGAEMVRPGVSVKISCKGS (SEQ ID NO: 509) | GYTFTDYA (SEQ ID NO: 305) | MHWVRQSHAKSLEWIGV (SEQ ID NO: 436) | ISTYSGDVSYNQ (SEQ ID NO: 358) | KFKGKATMTVDKSSSTAYMELARLTSEDSAIYYC (SEQ ID NO: 400) | ARGVTFDS (SEQ ID NO: 121) | WGQGTTVTVSS (SEQ ID NO: 713) |
| M210 | 33_63 | QAYLQQSGAELVRPGVSVKISCKGS (SEQ ID NO: 476) | GYTFTDYA (SEQ ID NO: 305) | MHWVKQSHAKSLEWIGV (SEQ ID NO: 434) | ISTYSGDVSYNQ (SEQ ID NO: 358) | KFKGKATMTVDKSSSTAYMELARLTSEDSAIYYC (SEQ ID NO: 400) | ARGVTFDS (SEQ ID NO: 121) | WGQGTTLTVSS (SEQ ID NO: 709) |
| M211 | 33_63 | QVQLQQSGAEMVRPGVSVKISCKGS (SEQ ID NO: 601) | GYTFTDYA (SEQ ID NO: 305) | MHWVRQSHAKSLEWIGV (SEQ ID NO: 436) | ISTYSGDVSYNQ (SEQ ID NO: 358) | KFKGKATMTVDKSSSTAYMELARLTSEDSAIYYC (SEQ ID NO: 400) | ARGVTFDS (SEQ ID NO: 121) | WGQGTTVTVSS (SEQ ID NO: 713) |
| M212 | 33_63 | QAYLQQSGAEMVRPGVSVKISCKGS (SEQ ID NO: 478) | GYTFTDYA (SEQ ID NO: 305) | MHWVRQSHAKSLEWIGV (SEQ ID NO: 436) | ISTYSGDVSYNQ (SEQ ID NO: 358) | KFKGKATMTVDKSSSTAYMELARLTSEDSAIYYC (SEQ ID NO: 400) | ARGVTFDS (SEQ ID NO: 121) | WGQGTTVTVSS (SEQ ID NO: 713) |
| M213 | 44_56 | EVLLQQSGAELVRPGVSVKISCKGS (SEQ ID NO: 232) | GYTFTDYA (SEQ ID NO: 305) | MHWVKQSHAKSLEWIGV (SEQ ID NO: 434) | ISTYSGDVSYNQ (SEQ ID NO: 358) | KFKGKATMTVDKSSSTAYMELARLTSEDSAIYYC (SEQ ID NO: 400) | ARGVTFDS (SEQ ID NO: 121) | WGQGTTVTVSS (SEQ ID NO: 713) |
| M214 | 44_56 | QAYLQQSGAELVRPGVSVKISCKGS (SEQ ID NO: 476) | GYTFTDYA (SEQ ID NO: 305) | MHWVKQSHAKSLEWIGV (SEQ ID NO: 434) | ISTYSGDVSYNQ (SEQ ID NO: 358) | KFKGKATMTVDKSSSTAYMELARLTSEDSAIYYC (SEQ ID NO: 400) | ARGVTFDS (SEQ ID NO: 121) | WGQGTTVTVSS (SEQ ID NO: 713) |
| M215 | 44_56 | QAYLQQSGAELVRPGVSVKISCKGS (SEQ ID NO: 476) | GYTFTDYA (SEQ ID NO: 305) | MHWVKQSHAKSLEWIGV (SEQ ID NO: 434) | ISTYSGDVSYNQ (SEQ ID NO: 358) | KFKGKATMTVDKSSSTAYMELARLTSEDSAIYYC (SEQ ID NO: 400) | ARGVTFDS (SEQ ID NO: 121) | WGQGTTLTVSS (SEQ ID NO: 709) |
| M216 | 44_56 | QAYLQQSGAELVRPGVSVKISCKGS (SEQ ID NO: 476) | GYTFTDYA (SEQ ID NO: 305) | MHWVKQSHAKSLEWIGV (SEQ ID NO: 434) | ISTYSGDVSYNQ (SEQ ID NO: 358) | KFKGKATMTVDKSSSTAYMELARLTSEDSAIYYC (SEQ ID NO: 400) | ARGVTFDS (SEQ ID NO: 121) | WGQGTTLTVSS (SEQ ID NO: 709) |
| M217 | 44_56 | QVQLQQSGAELVRPGVSVKISCKGS (SEQ ID NO: 599) | GYTFTDYA (SEQ ID NO: 305) | MHWVKQSHAKSLEWIGV (SEQ ID NO: 434) | ISTYSGDVSYNQ (SEQ ID NO: 358) | KFKGKATMTVDKSSSTAYMELARLTSEDSAIYYC (SEQ ID NO: 400) | ARGVTFDS (SEQ ID NO: 121) | WGQGTTVTVSS (SEQ ID NO: 713) |
| M218 | 33_63 | QIQLQQSGAELVRPGVSVKISCKGS (SEQ ID NO: 507) | GYTFTDYA (SEQ ID NO: 305) | MHWVKQSHAKSLEWIGV (SEQ ID NO: 434) | ISTYSGDVSYNQ (SEQ ID NO: 358) | KFKGKATMTVDKSSSTAYMELARLTSEDSAIYYC (SEQ ID NO: 400) | ARGVTSDS (SEQ ID NO: 123) | WGQGTSLTVSS (SEQ ID NO: 708) |
| M219 | 6_163 | QVQLQQSGAEMVRPGTSVKISCKAS (SEQ ID NO: 600) | GYTFTKYW (SEQ ID NO: 308) | LGWVKQRPGHGLEWIGD (SEQ ID NO: 416) | IYPGGDYT (SEQ ID NO: 378) | NYNEKFKGKATLTADTSSSTAYMQLSSLTSEDSAVYFC (SEQ ID NO: 469) | ARVTPAS (SEQ ID NO: 139) | WGQGTTVTVSS (SEQ ID NO: 713) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M220 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGDY T (SEQ ID NO: 378) | NYNEKFKGKATLTADTSSSTAYMQ LSSLTSEDSAVYFC (SEQ ID NO: 469) | ARVTPSS (SEQ ID NO: 140) | WGQGTTL TVSS (SEQ ID NO: 709) |
| M221 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGDY T (SEQ ID NO: 378) | NYNEKFKGKATLTADTSSSTAYMQ LSSLTSEDSAVYFC (SEQ ID NO: 469) | ARVTPSS (SEQ ID NO: 140) | WGQGTTL TVSS (SEQ ID NO: 709) |
| M222 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGDY T (SEQ ID NO: 378) | NYNEKFKGKATLTADTSSSTAYMQ LSSLTSEDSAVYFC (SEQ ID NO: 469) | ARVTPSS (SEQ ID NO: 140) | WGQGTTL TVSS (SEQ ID NO: 709) |
| M223 | 44_56 | QIQLQQSGAEMVRPGT SVKISCKAS (SEQ ID NO: 508) | GYTFTK YW (SEQ ID NO: 308) | LGWVKQRPGHGL EWIGD (SEQ ID NO: 416) | IYPGGDY TNYNE (SEQ ID NO: 379) | KFKGKATLTADTSSSTAYMQLSSL TSEDSAVYFC (SEQ ID NO: 395) | ARVTPAS (SEQ ID NO: 139) | WGQGTSL TVSS (SEQ ID NO: 708) |
| M224 | 147_157 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGDY TNYNE (SEQ ID NO: 379) | KFKGKATLTADTSSSTAYMQLSSL TSEDSAAYFC (SEQ ID NO: 394) | ARVTPSS (SEQ ID NO: 140) | WGQGTTV TVSS (SEQ ID NO: 713) |
| M225 | 147_157 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGDY TNYNE (SEQ ID NO: 379) | KFKGKAILTADISSSTAYMQLSSL TSEDSAVYFC (SEQ ID NO: 395) | ARVTPSS (SEQ ID NO: 140) | WGQGTTL TVSS (SEQ ID NO: 709) |
| M226 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGDY TNYNE (SEQ ID NO: 379) | KFKGKAILTADISSSTAYMQLSSL TSEDSAVYFC (SEQ ID NO: 395) | ARVTPSS (SEQ ID NO: 140) | WGQGTTL TVSS (SEQ ID NO: 709) |
| M227 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGDY TNYNE (SEQ ID NO: 379) | KFKGKAILTADISSSTAYMQLSSL TSEDSAVYFC (SEQ ID NO: 395) | ARVTPSS (SEQ ID NO: 140) | WGQGTTL TVSS (SEQ ID NO: 709) |
| M228 | 44_56 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGDY TNYNE (SEQ ID NO: 379) | KFKGKAILTADISSSTAYMQLSSL TSEDSAVYFC (SEQ ID NO: 395) | ARVTPSS (SEQ ID NO: 140) | WGQGTTL TVSS (SEQ ID NO: 709) |
| M229 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY A (SEQ ID NO: 380) | NYNEKFKGKAILTADISSSTAYMQ LSSLTSEDSAVYFC (SEQ ID NO: 469) | ARVTPAS (SEQ ID NO: 139) | WGQGTTV TVSS (SEQ ID NO: 713) |
| M230 | 147_157 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTIL TVSS (SEQ ID NO: 701) |
| M231 | 147_157 | QVQLQQSGAELVRPGT SVKISCKAS (SEQ ID NO: 596) | GYTFTN YW (SEQ ID NO: 309) | LGWIKQRPGHGL EWIGD (SEQ ID NO: 414) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTL TVSS (SEQ ID NO: 709) |
| M232 | 33_63 | QIQLQQSGAELVRPGT SVKISCRAS (SEQ ID NO: 505) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTL TVSS (SEQ ID NO: 709) |

TABLE 14A-continued

| ID | Epitope | H FR1 AA | H CDR1 AA | H FR2 AA | H CDR2 AA | H FR3 AA | H CDR3 AA | H FR4 AA |
| --- | --- | --- | --- | --- | --- | --- | --- | --- |
| M233 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKATLTADTSSSTAYMQ LSSLTSEDSAVYFC (SEQ ID NO: 469) | ARVTPAS (SEQ ID NO: 139) | WGQGTSL TVSS (SEQ ID NO: 708) |
| M234 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFQGKATLTADTSSSTAYMQ LSSLTSEDSAVYFC (SEQ ID NO: 470) | ARVTPAS (SEQ ID NO: 139) | WGQGTPV TVSS (SEQ ID NO: 705) |
| M235 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKATLTADTSSSTAYMQ LSSLTSEDSAVYFC (SEQ ID NO: 469) | ARVTPAS (SEQ ID NO: 139) | WGQGTTL TVSS (SEQ ID NO: 709) |
| M236 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKATLTADTSSSTAYMQ LSSLTSEDSAVYFC (SEQ ID NO: 469) | ARVTPAS (SEQ ID NO: 139) | WGQGTTV TVSS (SEQ ID NO: 713) |
| M237 | 33_63 | QIQLQQSGAELVRPGT SVKISCKAS (SEQ ID NO: 504) | GYTFTN YW (SEQ ID NO: 309) | LGWVKQRPGHGL EWIGD (SEQ ID NO: 416) | IYPGGGY T (SEQ ID NO: 381) | NYNEKFKGKATLTADTSSSTAYMQ LSSLTSEDSAVYFC (SEQ ID NO: 469) | ARVTPAS (SEQ ID NO: 139) | WGQGTSL TVSS (SEQ ID NO: 708) |
| M238 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKATLTADTSSSTAYMQ LSSLTSEDSAVYFC (SEQ ID NO: 469) | ARVTPAS (SEQ ID NO: 139) | WGQGTTL TVSS (SEQ ID NO: 709) |
| M239 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKATLTADTSSSTAYMQ LSSLTSEDSAVYFC (SEQ ID NO: 469) | ARVTPAS (SEQ ID NO: 139) | WGQGTTL TVSS (SEQ ID NO: 709) |
| M240 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTV TVSS (SEQ ID NO: 713) |
| M241 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTSL TVSS (SEQ ID NO: 708) |
| M242 | 44_56 | QVQLQQSGAELVRPGT SVKISCKAS (SEQ ID NO: 596) | GYTFTN YW (SEQ ID NO: 309) | LGWIKQRPGHGL EWIGD (SEQ ID NO: 414) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTSL TVSS (SEQ ID NO: 708) |
| M243 | 44_56 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTV TVSS (SEQ ID NO: 713) |
| M244 | 6_130 | QIQLQQSGAELVRPGT SVKISCKAS (SEQ ID NO: 504) | GYTFTN YW (SEQ ID NO: 309) | LGWVKQRPGHGL EWIGD (SEQ ID NO: 416) | IYPGGGY T (SEQ ID NO: 381) | NYNEKERGKAILTADTSSSTAYMQ LSSLTSEDSAVYFC (SEQ ID NO: 471) | ARVTPAS (SEQ ID NO: 139) | WGQGTSL TVSS (SEQ ID NO: 708) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M245 | 6_130 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTV TVSS (SEQ ID NO: 713) |
| M246 | 6_163 | QIQLQQSGAELVRPGT SVKISCKAS (SEQ ID NO: 504) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTV TVSS (SEQ ID NO: 713) |
| M247 | 6_163 | QVQLQQPGAELVRPGT SVKISCKAS (SEQ ID NO: 590) | GYTFTN YW (SEQ ID NO: 309) | LGWVKQRPGHGL EWIGD (SEQ ID NO: 416) | IYPGGGY T (SEQ NO: 469) ID NO: 381) | NYNEKFKGKAILTADISSSTAYMQ LSSLTSEDSAVYFC (SEQ ID NO: 139) | ARVTPAS (SEQ ID | WGQGTSL TVSS (SEQ ID NO: 708) |
| M248 | 6_163 | QVQLQQSGAELVRPGT SVKISCKAS (SEQ ID NO: 596) | GYTFTN YW (SEQ ID NO: 309) | LGWIKQRPGHGL EWIGD (SEQ ID NO: 414) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTSL TVSS (SEQ ID NO: 708) |
| M249 | 6_163 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTL TVSS (SEQ ID NO: 709) |
| M250 | 6_163 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTV TVSS (SEQ ID NO: 713) |
| M251 | 77_89 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTL TVSS (SEQ ID NO: 709) |
| M252 | 77_89 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTL TVSS (SEQ ID NO: 709) |
| M253 | 77_89 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTL TVSS (SEQ ID NO: 709) |
| M254 | 77_89 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTL TVSS (SEQ ID NO: 709) |
| M255 | 77_89 | QIQLQQSGAELVRPGT SVKISCKAS (SEQ ID NO: 504) | GYTFTN YW (SEQ ID NO: 309) | LGWIKQRPGHGL EWIGD (SEQ ID NO: 414) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTV TVSS (SEQ ID NO: 713) |
| M256 | 77_89 | QIQLQQSGAELVRPGT SVKISCKAS (SEQ ID NO: 504) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTL TVSS (SEQ ID NO: 709) |
| M257 | 77_89 | QIQLQQSGAELVRPGT SVKISCKAS (SEQ ID NO: | GYTFTN YW 504) ID NO: 309) | LGWVKQRPGHGL EWIGD (SEQ (SEQ | IYPGGGY T (SEQ ID NO: 416) 381) | NYNEKFKGKAILTADISSSTAYMQ LSSLTSEDSAVYFC (SEQ ID ID NO: NO: 469) | ARVTPAS (SEQ ID NO: 139) | WGQGTSL TVSS (SEQ ID NO: 708) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M258 | 77_89 | QVQLQQSGAELVRPGT SVKISCKAS (SEQ ID NO: 596) | GYTFTN YW (SEQ ID NO: 309) | LGWIKQRPGHGL EWIGD (SEQ ID NO: 414) | IYPGGGY T (SEQ ID NO: 381) | NYNEKFKGKAILTADISSNTAYMQ LSSLTSEDSAVYFC (SEQ ID NO: 468) | ARVTPAS (SEQ ID NO: 139) | WGQGTSL TVSS (SEQ ID NO: 708) |
| M259 | 77_89 | QAYLQQSGAELVRPGT SVKISCKAS (SEQ ID NO: 474) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTSL TVSS (SEQ ID NO: 708) |
| M260 | 77_89 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY T (SEQ ID NO: 381) | NYNEKFKGKAILTADISSSTAYMQ LSSLTSEDSAVYFC (SEQ ID NO: 469) | ARVTPAS (SEQ ID NO: 139) | WGQGTTL TVSS (SEQ ID NO: 709) |
| M261 | 33_63 | QAYLQQSGAELVRPGT SVKISCKAS (SEQ ID NO: 474) | GYTFTN YW (SEQ ID NO: 309) | LGWVKQRPGHGL EWIGD (SEQ ID NO: 416) | IYPGGGY TNYNE (SEQ ID NO: 382) | KFKGKAILTADISSSTAYMQLSSL TSEDSAVYFC (SEQ ID NO: 395) | ARITPAS (SEQ ID NO: 126) | WGQGTSL TVSS (SEQ ID NO: 708) |
| M262 | 33_63 | QIQLQQPGAELVRPGT SVKISCKAS (SEQ ID NO: 501) | GYTFTN YW (SEQ ID NO: 309) | LGWVKQRPGHGL EWIGD (SEQ ID NO: 416) | IYPGGGY TNYNE (SEQ ID NO: 382) | KFKGKAILTADISSSTAYMQLNSL TSEDSAVYFC (SEQ ID NO: 393) | ARVSPAS (SEQ ID NO: 138) | WGQGTTL TVSS (SEQ ID NO: 709) |
| M263 | 147_157 | QVQLQQSGAELVRPGT SVKISCKAS(SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTV TVSS (SEQ ID NO: 713) |
| M264 | 147_157 | QIQLQQSGAELVRPGT SVKISCKAS (SEQ ID NO: 504) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTSL TVSS (SEQ ID NO: 708) |
| M265 | 147_157 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTV TVSS (SEQ ID NO: 713) |
| M266 | 147_157 | QVQLQPGAELVRPGTS VKISCKAS (SEQ ID NO: 586) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTV TVSS (SEQ ID NO: 713) |
| M267 | 147_157 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | EFKGKATLTADTSSSTAYMQLSSL TSEDSAVYFC (SEQ ID NO: 217) | ARVTPAS (SEQ ID NO: 139) | WGQGTTL TVSS (SEQ ID NO: 709) |
| M268 | 147_157 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTL TVSS (SEQ ID NO: 709) |
| M269 | 147_157 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTSL TVSS (SEQ ID NO: 708) |
| M270 | 147_157 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTSL TVSS (SEQ ID NO: 708) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M271 | 147_157 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTSL TVSS (SEQ ID NO: 708) |
| M272 | 147_157 | QIQLQQSGAELVRPGT SVKISCKAS (SEQ ID NO: 504) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTL TVSS (SEQ ID NO: 709) |
| M273 | 147_157 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTXL TVSS (SEQ ID NO: 715) |
| M274 | 147_157 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTV TVSS (SEQ ID NO: 713) |
| M275 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTSL TVSS (SEQ ID NO: 708) |
| M276 | 33_63 | QVQLQQPGAELVRPGT SVKISCKAS (SEQ ID NO: 590) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTL TVSS (SEQ ID NO: 709) |
| M277 | 33_63 | QVQLQQSGAELVRPGI SVKISCKAS (SEQ ID NO: 595) | GYTFTN YW (SEQ ID NO: 309) | LGWVKQRPGHGL EWIGD (SEQ ID NO: 416) | IYPGGGY TNYNE (SEQ ID NO: 382) | EFKGKATLTADTSSSTAYMQLSSL TSEDSAVYFC (SEQ ID NO: 217) | ARVTPAS (SEQ ID NO: 139) | WGQGTTL TVSS (SEQ ID NO: 709) |
| M278 | 33_63 | QIQLQQSGAELVRPGT SVKISCKAS (SEQ ID NO: 504) | GYTFTN YW (SEQ ID NO: 309) | LGWVKQGPGHGL EWIGD (SEQ ID NO: 415) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTV TVSS (SEQ ID NO: 713) |
| M279 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTV TVSS (SEQ ID NO: 713) |
| M280 | 33_63 | QVQLQQPGAELVRPGT SVKISCKAS (SEQ ID NO: 590) | GYTFTN YW (SEQ ID NO: 309) | LGWIKQRPGHGL EWIGD (SEQ ID NO: 414) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTL TVSS (SEQ ID NO: 709) |
| M281 | 33_63 | QVQLQQSGAELVRPGT SVKISCKAS (SEQ ID NO: 596) | GYTFTN YW (SEQ ID NO: 309) | LGWIKQRPGHGL EWIGD (SEQ ID NO: 414) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTSL TVSS (SEQ ID NO: 708) |
| M282 | 33_63 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTL TVSS (SEQ ID NO: 709) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M283 | 33_63 | QIQLQQSGAELVRPGTSVKISCKAS (SEQ ID NO: 504) | GYTFTNYW (SEQ ID NO: 309) | LGWVKQGPGHGLEWIGD (SEQ ID NO: 415) | IYPGGGYTNYNE (SEQ ID NO: 382) | KFKGKATLTADTSSSTAYMQLSSLTSEDSAVYFC (SEQ ID NO: 395) | ARVTPAS (SEQ ID NO: 139) | WGQGTTVTVSS (SEQ ID NO: 713) |
| M284 | 33_63 | QVQLQQSGAELVRPGTSVKISCKAS (SEQ ID NO: 596) | GYTFTNYW (SEQ ID NO: 309) | LGWVKQRPGHGLEWIGD (SEQ ID NO: 416) | IYPGGGYTNYNE (SEQ ID NO: 382) | KFKGKATLTADTSSSTAYMQLSSLTSEDSAVYFC (SEQ ID NO: 395) | ARVTPAS (SEQ ID NO: 139) | WGQGTTLTVSS (SEQ ID NO: 709) |
| M285 | 33_63 | QVQLQQPGAELVRPGTSVKISCKAS (SEQ ID NO: 590) | GYTFTNYW (SEQ ID NO: 309) | LGWVKQRPGHGLEWIGD (SEQ ID NO: 416) | IYPGGGYTNYNE (SEQ ID NO: 382) | KFKGKATLTADTSSSTAYMQLSSLTSEDSAVYFC (SEQ ID NO: 395) | ARVTPAS (SEQ ID NO: 139) | WGQGTTLTVSS (SEQ ID NO: 709) |
| M286 | 33_63 | QIQLQQSGAELVRPGTSVKISCKAS (SEQ ID NO: 504) | GYTFTNYW (SEQ ID NO: 309) | LGWVKQRPGHGLEWIGD (SEQ ID NO: 416) | IYPGGGYTNYNE (SEQ ID NO: 382) | KFKGKATLTADTSSSTAYMQLSSLTSEDSAVYFC (SEQ ID NO: 395) | ARVTPAS (SEQ ID NO: 139) | WGQGTSLTVSS (SEQ ID NO: 708) |
| M287 | 33_63 | QIQLQQSGAELVRPGTSVKISCKAS (SEQ ID NO: 504) | GYTFTNYW (SEQ ID NO: 309) | LGWVKQRPGHGLEWIGD (SEQ ID NO: 416) | IYPGGGYTNYNE (SEQ ID NO: 382) | KFKGKATLTADTSSSTAYMQLSSLTSEDSAVYFC (SEQ ID NO: 395) | ARVTPAS (SEQ ID NO: 139) | WGQGTSLTVSS (SEQ ID NO: 708) |
| M288 | 33_63 | QIQLQQSGAELVRPGTSVKISCKAS (SEQ ID NO: 504) | GYTFTNYW (SEQ ID NO: 309) | LGWVKQRPGHGLEWIGD (SEQ ID NO: 416) | IYPGGGYTNYNE (SEQ ID NO: 382) | KFKGKATLTADTSSSTAYMQLSSLTSEDSAVYFC (SEQ ID NO: 395) | ARVTPAS (SEQ ID NO: 139) | WGQGTSLTVSS (SEQ ID NO: 708) |
| M289 | 33_63 | QVQLQQSGAELVRPGTSVKISCKAS (SEQ ID NO: 596) | GYTFTNYW (SEQ ID NO: 309) | LGWVKQRPGHGLEWIGD (SEQ ID NO: 416) | IYPGGGYTNYNE (SEQ ID NO: 382) | EFKGKATLTADTSSSTAYMQLSSLTSEDSAVYFC (SEQ ID NO: 217) | ARVTPAS (SEQ ID NO: 139) | WGQGTTLTVSS (SEQ ID NO: 709) |
| M290 | 33_63 | QVQLQQSGAELVRPGTSVKISCKAS (SEQ ID NO: 596) | GYTFTNYW (SEQ ID NO: 309) | LGWIKQRPGHGLEWIGD (SEQ ID NO: 414) | IYPGGGYTNYNE (SEQ ID NO: 382) | KFKGKATLTADTSSSTAYMQLSSLTSEDSAVYFC (SEQ ID NO: 395) | ARVTPAS (SEQ ID NO: 139) | WGQGTSLTVSS (SEQ ID NO: 708) |
| M291 | 33_63 | QVQLQQSGAELVRPGTSVKISCKAS (SEQ ID NO: 596) | GYTFTNYW (SEQ ID NO: 309) | LGWIKQRPGHGLEWIGD (SEQ ID NO: 414) | IYPGGGYTNYNE (SEQ ID NO: 382) | KFKGKATLTADTSSSTAYMQLSSLTSEDSAVYFC (SEQ ID NO: 395) | ARVTPAS (SEQ ID NO: 139) | WGQGTSLTVSS (SEQ ID NO: 708) |
| M292 | 33_63 | QVQLQQSGAELVRPGTSVKISCKAS (SEQ ID NO: 596) | GYTFTNYW (SEQ ID NO: 309) | LGWVKQRPGHGLEWIGD (SEQ ID NO: 416) | IYPGGGYTNYNE (SEQ ID NO: 382) | KFKGKATLTADTSSSTAYMQLSSLTSEDSAVYFC (SEQ ID NO: 395) | ARVTPAS (SEQ ID NO: 139) | WGQGTTVTVSS (SEQ ID NO: 713) |
| M293 | 33_63 | QVQLQQSGAELVRPGTSVKISCKAS (SEQ ID NO: 596) | GYTFTNYW (SEQ ID NO: 309) | LGWIKQRPGHGLEWIGD (SEQ ID NO: 414) | IYPGGGYTNYNE (SEQ ID NO: 382) | KFKGKATLTADTSSSTAYMQLSSLTSEDSAVYFC (SEQ ID NO: 395) | ARVTPAS (SEQ ID NO: 139) | WGQGTSLTVSS (SEQ ID NO: 708) |
| M294 | 33_63 | QVQLQQSGAELVRPGTSVKISCKAS (SEQ ID NO: 596) | GYTFTNYW (SEQ ID NO: 309) | LGWVKQRPGHGLEWIGD (SEQ ID NO: 416) | IYPGGGYTNYNE (SEQ ID NO: 382) | KFKGKATLTADTSSSTAYMQLSSLTSEDSAVYFC (SEQ ID NO: 395) | ARVTPAS (SEQ ID NO: 139) | WGQGTTLTVSS (SEQ ID NO: 709) |
| M295 | 33_63 | QVQLQQSGAELVRPGTSVKISCKAS (SEQ ID NO: 596) | GYTFTNYW (SEQ ID NO: 309) | LGWVKQRPGHGLEWIGD (SEQ ID NO: 416) | IYPGGGYTNYNE (SEQ ID NO: 382) | EFKGKATLTADTSSSTAYMQLSSLTSEDSAVYFC (SEQ ID NO: 217) | ARVTPAS (SEQ ID NO: 139) | WGQGTTLTVSS (SEQ ID NO: 709) |

TABLE 14A-continued

| ID | Epitope | H FR1 AA | H CDR1 AA | H FR2 AA | H CDR2 AA | H FR3 AA | H CDR3 AA | H FR4 AA |
|---|---|---|---|---|---|---|---|---|
| M296 | 44_56 | QIQLQQSGAELVRPGT SVKISCKAS (SEQ ID NO: 504) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTV TVSS (SEQ ID NO: 713) |
| M297 | 44_56 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTL TVSS (SEQ ID NO: 709) |
| M298 | 44_56 | QIQLQQSGAELVRPGT SVKISCKAS (SEQ ID NO: 504) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTSL TVSS (SEQ ID NO: 708) |
| M299 | 44_56 | QVQLQQSGAELVRPGT SVKISCRAS (SEQ ID NO: 597) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLSSL TSEDSAVYFC (SEQ ID NO: 395) | ARVTPAS (SEQ ID NO: 139) | WGQGTTV TVSS (SEQ ID NO: 713) |
| M300 | 44_56 | QVQLQQSGAELVRPGT SVKISCKAS (SEQ ID NO: 596) | GYTFTN YW (SEQ ID NO: 309) | LGWVKQRPGHGL EWIGD (SEQ ID NO: 416) | IYPGGGY TNYNE (SEQ ID NO: 382) | EFKGKATLTADTSSSTAYMQLSSL TSEDSAVYFC (SEQ ID NO: 217) | ARVTPAS (SEQ ID NO: 139) | WGQGTTL TVSS (SEQ ID NO: 709) |
| M301 | 44_56 | QIQLQQSGAELVRPGT SVKISCKAS (SEQ ID NO: 504) | GYTFTN YW (SEQ ID NO: 309) | LGWVKQRPGHGL EWIGD (SEQ ID NO: 416) | IYPGGGY TNYNE (SEQ ID NO: 382) | KFKGKATLTADTSSSTAYMQLXSL TSEDSAVYFC (SEQ ID NO: 396) | ARVTPAS (SEQ ID NO: 139) | WGQGTTL TVSS (SEQ ID NO: 709) |

TABLE 14B

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M1 | 33_63 | DVVLTQTPLSLPVSLGDQ ASISCRSS (SEQ ID NO: 202) | QSIVHSN GNTY (SEQ ID NO: 569) | LEWYLQKPGQP PKLLIY (SEQ ID NO: 408) | KVS (SEQ ID NO: 461) | NRFSGVPDRFSGSGSGTDFTLKIS RVEAEDLGVYYC (SEQ ID NO: 406) | FQGSHVP T (SEQ ID NO: 257) | FGGGTK LEIK (SEQ ID NO: 249) |
| M2 | 33_63 | DVVVTQTPLSLPVSLGDQ ASISCRSS (SEQ ID NO: 212) | QSLVHSN GNTY (SEQ ID NO: 571) | LEWYLQKPGQS PKLLIY (SEQ ID NO: 409) | KVS (SEQ ID NO: 406) | NRFSGVPDRFSGSGSGTDFTLKIS RVEAEDLGVYYC (SEQ ID NO: 461) | FQGSHVP PT (SEQ ID NO: 255) | FGGGTK LEMK (SEQ ID NO: 250) |
| M3 | 44_56 | DVVVTQTPLSLPVSLGDQ ASISCRSS (SEQ ID NO: 212) | QSLVHSN GNTY (SEQ ID NO: 571) | LEWYLQKPGQS PKLLIY (SEQ ID NO: 409) | KVS (SEQ ID NO: 406) | NRFSGVPDRFSGSGSGTDFILKIS RVEAEDLGVYYC (SEQ ID NO: 461) | FQGSHVP PT (SEQ ID NO: 255) | FGGGTK LEMK (SEQ ID NO: 250) |
| M4 | 44_56 | DVVLTQTPLSLPVSLGDQ ASISCRSS (SEQ ID NO: 202) | QSIVHSN GNTY (SEQ ID NO: 569) | LEWYLQKPGQS PKLLIY (SEQ ID NO: 409) | KVS (SEQ ID NO: 406) | NRFSGVPDRFSGSGSGTDFTLKIS RVEAEDLGVYYC (SEQ ID NO: 461) | FQGSHVP PT (SEQ ID NO: 255) | FGGGTK LEIK (SEQ ID NO: 249) |
| M5 | 147_156 | DVVMTQTPLSLPVSLGDQ ASISCRSS (SEQ ID NO: 209) | QSIVHSN GNTY (SEQ ID NO: 569) | LEWYLQKPGQS PKLLIY (SEQ ID NO: 409) | KVS (SEQ ID NO: 406) | NRFSGVPDRFSGSGSGTDFTLKIS RVEAEDLGVYYC (SEQ ID NO: 461) | FQGSHVP PT (SEQ ID NO: 255) | FGGGTK LEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M6 | 44_56 | DVVLTQTPLSLPVSLGDQASISCRSS (SEQ ID NO: 202) | QSIVHSNGNTY (SEQ ID NO: 569) | LEWYLQKPGQSPKLLIY (SEQ ID NO: 409) | KVS (SEQ ID NO: 406) | NRFSGVPDRFSGSGSGTDFTLKISRVGAEDLGVYYC (SEQ ID NO: 462) | FQGSHVPPT (SEQ ID NO: 255) | FGGGTKLEMK (SEQ ID NO: 250) |
| M7 | 6_130 | DVVLTQTPLSLPVSLGDQASISCRSS (SEQ ID NO: 202) | QSIVHSNGNTY (SEQ ID NO: 569) | LEWYLQKPGQSPKLLIY (SEQ ID NO: 409) | KVS (SEQ ID NO: 406) | NRFSGVPDRFSGSGSGTDFTLKISRVEAEDLGVYYC (SEQ ID NO: 461) | FQGSHVPPT (SEQ ID NO: 255) | FGGGTKLEIK (SEQ ID NO: 249) |
| M8 | 6_163 | DVVMTQTPLSLPVSLGDQASISCRSS (SEQ ID NO: 209) | QSIVHSNGNTY (SEQ ID NO: 569) | LEWYLQKPGQSPKLLIY (SEQ ID NO: 409) | KVS (SEQ ID NO: 406) | NRFSGVPDRFSGSGSGTDFTLKISRVEAEDLGVYYC (SEQ ID NO: 461) | FQGSHVPPT (SEQ ID NO: 255) | FGGGTKLEIK (SEQ ID NO: 249) |
| M9 | 147_157 | DVVMTQTPLSLPVSLGDQASISCRSS (SEQ ID NO: 209) | QSIVHSNGNTY (SEQ ID NO: 569) | LEWYLQKPGQSPKLLIY (SEQ ID NO: 409) | KVS (SEQ ID NO: 406) | NRFSGVPDRFSGSGSGTDFTLKISRVEAEDLGVYYC (SEQ ID NO: 461) | FQGSHVPPT (SEQ ID NO: 255) | FGGGTKLEMK (SEQ ID NO: 250) |
| M10 | 147_157 | DIQMTQSPASLSASVGESVTITCRAS (SEQ ID NO: 165) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLRINSLQPEDFGTYYC (SEQ ID NO: 673) | QHHYGSPYT (SEQ ID NO: 495) | FGGGTKLEIK (SEQ ID NO: 249) |
| M11 | 147_157 | DIQMTQTTSSLSASLGDRVTISCRAS (SEQ ID NO: 176) | QDISNY (SEQ ID NO: 485) | LNWYQQKQDGTVKLLIY (SEQ ID NO: 419) | HTS (SEQ ID NO: 317) | RLQSGVPSRFIGSGSGIDYSLTISNLEQEDIATYFC (SEQ ID NO: 627) | QQSNSLPPT (SEQ ID NO: 529) | FGGGTKLEIK (SEQ ID NO: 249) |
| M12 | 33_63 | DVVVTQTPLSLPVSLGDQASISCRSS (SEQ ID NO: 212) | QSLVHSNGNTY (SEQ ID NO: 571) | LEWYLQKPGQSPKLLIY (SEQ ID NO: 409) | KVS (SEQ ID NO: (406) | NRFSGVPDRFSGSGSGTDFTLKISRVEAEDLGVYYC (SEQ ID NO: 461) | FQGSHVPPT (SEQ ID NO: 255) | FGGGTKLEMK (SEQ ID NO: 250) |
| M13 | 33_63 | DVVLTQTPLSLPVSLGDQASISCRSS (SEQ ID NO: 202) | QSIVHSNGNTY (SEQ ID NO: 569) | LEWYLQKPGQPPKLLIY (SEQ ID NO: 408) | KVS (SEQ ID NO: 406) | NRFSGVPDRFSGSGSGTDFTLKISRVEAEDLGVYYC (SEQ ID NO: 461) | FQGSHVPTF (SEQ ID NO: 258) | GGGGTKLEIK (SEQ ID NO: 278) |
| M14 | 33_63 | DVVMTQTPLSLPVSLGDQASISCRSS (SEQ ID NO: 209) | QSIVHSNGNTY (SEQ ID NO: 569) | LEWYLQKPGQSPKLLIY (SEQ ID NO: 409) | KVS (SEQ ID NO: 406) | NRFSGVPDRFSGSGSGTDFTLKISRVEAEDLGVYYC (SEQ ID NO: 461) | FQGSHVPPT (SEQ ID NO: 255) | FGGGTKLEMK (SEQ ID NO: 250) |
| M15 | 33_63 | DVVMTQTPLSLPVNLGDQASISCRSS (SEQ ID NO: 208) | QSIVHSNGNTY (SEQ ID NO: 569) | LEWYLQKPGQSPKLLIY (SEQ ID NO: 409) | KVS (SEQ ID NO: 406) | NRFSGVPDRFSGSGSGTDFTLKISRVEAEDLGIYYC (SEQ ID NO: 460) | FQGSHVPPT (SEQ ID NO: 255) | FGGGTKLEIK (SEQ ID NO: 249) |
| M16 | 33_63 | DVVLTQTPLSLPVSLGDQASISCRSS (SEQ ID NO: 202) | QSIVHSNGNTY (SEQ ID NO: 569) | LEWYLQKPGQSPKLLIY (SEQ ID NO: 409) | KVS (SEQ ID NO: 406) | NRFSGVPDRFSGSGSGTDFTLKISRVEAEDLGVYYC (SEQ ID NO: 461) | FQGSHVPPT (SEQ ID NO: 255) | FGGGTKLEIK (SEQ ID NO: 249) |
| M17 | 33_63 | DVVLTQTPLSLPVSLGDQASISCRSS (SEQ ID NO: 202) | QSIVHSNGNTY (SEQ ID NO: 569) | LEWYLQKPGQSPKLLIY (SEQ ID NO: 409) | KVS (SEQ ID NO: 406) | NRFSGVPDRFSGSGSGTDFTLKISRVEAEDLGVYYC (SEQ ID NO: 461) | FQGSHVPPT (SEQ ID NO: 255) | FGGGTKLEIK (SEQ ID NO: 249) |
| M18 | 44_56 | DVVMTQTPLSLPVSLGDQASISCRSS (SEQ ID NO: 209) | QSIVHSNGNTY (SEQ ID NO: 569) | LEWYLQKPGQSPKLLIY (SEQ ID NO: 409) | KVS (SEQ ID NO: 406) | NRFSGVPDRFSGSGSGTDFTLKISRVEAEDLGVYYC (SEQ ID NO: 461) | FQGSHVPPT (SEQ ID NO: 255) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M19 | 44_56 | DVVVTQTPLSLPVSLGDQASISCRSS (SEQ ID NO: 212) | QSIVHSNGNTY (SEQ ID NO: 569) | LEWYLQKPGQSPKLLIY (SEQ ID NO: 409) | KVS (SEQ ID NO: 406) | NRFSGVPDRFSGSGSGTDFTLKISRVEAEDLGVYYC (SEQ ID NO: 461) | FQGSHVPRT (SEQ ID NO: 256) | FGGGTKLEIK (SEQ ID NO: 249) |
| M20 | 33_63 | DIQMTQSQKFMSTSVGDRVSVTCKAS (SEQ ID NO: 172) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPLT (SEQ ID NO: 549) | FGGGTKLEIK (SEQ ID NO: 249) |
| M21 | 33_63 | DIQMTQSPKFLDVSAGDRVTITCKAS (SEQ ID NO: 169) | QSVNND (SEQ ID NO: 572) | VVWYQQKPGQSPKLLIY (SEQ ID NO: 696) | YAS (SEQ ID NO: 717) | NRYTGVPDRFTGSGYGTDFTFTISTVQAEDLAVYFC (SEQ ID NO: 464) | QQAYWSPYT (SEQ ID NO: 517) | FGGGTKLEMK (SEQ ID NO: 250) |
| M22 | 44_56 | EIVMTQSPPTLSLSPGERVTLSCKAS (SEQ ID NO: 221) | QDVNTA (SEQ ID NO: 486) | VAWYQQKPGQAPRLLIY (SEQ ID NO: 687) | WAS (SEQ ID NO: 698) | TRHIGVPSRFSGSGSGTDFTLTISSLQPEDFATYYC (SEQ ID NO: 681) | QQHYSSPWT (SEQ ID NO: 524) | FGGGTKVEIK (SEQ ID NO: 252) |
| M23 | 44_56 | EIVMTQSPPTLSLSPGERVTLSCKAS (SEQ ID NO: 221) | QDVNTA (SEQ ID NO: 486) | VAWYQQKQGQAPRLLIY (SEQ ID NO: 690) | WAS (SEQ ID NO: 698) | TRHIGVPSRFSGSGSGTDFTLTISSLQPEDFATYYC (SEQ ID NO: 681) | QQHYSSPWT (SEQ ID NO: 524) | FGGGTKVEIK (SEQ ID NO: 252) |
| M24 | 6_130 | DVVMTQTTSSLSASLGDRVTITCRAS (SEQ ID NO: 211) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQGNTLPPT (SEQ ID NO: 520) | FGEGTKLEIK (SEQ ID NO: 248) |
| M25 | 33_63 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | YTS (SEQ ID NO: 727) | RLHSGVPSRFSGSGSGTDYSLTISNLEQEDIATYFC (SEQ ID NO: 626) | QQGNTLPLT (SEQ ID NO: 519) | FGAGTKLEMK (SEQ ID NO: 247) |
| M26 | 6_163 | DIQMTQTTSSLSASLGDRVTISCRAS (SEQ ID NO: 176) | QYISNY (SEQ ID NO: 617) | LNWYQQRPDGTVKLLIY (SEQ ID NO: 420) | YTS (SEQ ID NO: 727) | RLHSGVPSRFSGSGSGTDYSLTISNLEQEDIATYFC (SEQ ID NO: 626) | QQGNTLPPT (SEQ ID NO: 520) | FGGGTKLEMK (SEQ ID NO: 250) |
| M27 | 33_63 | DIQMTQSTSSLSASLGDRVTISCRAS (SEQ ID NO: 173) | QDISNY (SEQ ID NO: 485) | LNWYQQKPDGTVKLLIY (SEQ ID NO: 418) | YTS (SEQ ID NO: 727) | RLHSGVPSRFSGSGSGTDYSLTISNLEQEDIATYFC (SEQ ID NO: 626) | QQGNTLPPT (SEQ ID NO: 520) | FGGGTKLEIK (SEQ ID NO: 249) |
| M28 | 33_63 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFTGSGSGTDYSLTISNLEQEDIATYFC (SEQ ID NO: 627) | QQSNSLPPT (SEQ ID NO: 529) | FGGGTKLEIK (SEQ ID NO: 249) |
| M29 | 33_63 | DVVMTQTTSSLSASLGDRVTITCRAS (SEQ ID NO: 211) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQGNTLPPT (SEQ ID NO: 520) | FGGGTKLEIK (SEQ ID NO: 249) |
| M30 | 33_63 | DIQMTQTTSSLSASLGDRVTITCRAS (SEQ ID NO: 177) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQGNTLPPT (SEQ ID NO: 520) | FGGGTKLEIK (SEQ ID NO: 249) |

TABLE 14B-continued

| ID | Epitope | L FR1 AA | L CDR1 AA | L FR2 AA | L CDR2 AA | L FR3 AA | L CDR3 AA | L FR4 AA |
|---|---|---|---|---|---|---|---|---|
| M31 | 44_56 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFTGSGSGTDYSLTISNLEQEDIATYFC (SEQ ID NO: 627) | QQSNSLPPT (SEQ ID NO: 529) | FGGGTKLEIK (SEQ ID NO: 249) |
| M32 | 44_56 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFIGSGSGIDYSLTISNLEQEDIATYFC (SEQ ID NO: 627) | QQSNSLPPT (SEQ ID NO: 529) | FGGGTKLEIK (SEQ ID NO: 249) |
| M33 | 44_56 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFIGSGSGIDYSLTISNLEQEDIATYFC (SEQ ID NO: 627) | QQSNSLPPT (SEQ ID NO: 529) | FGGGTKLEIK (SEQ ID NO: 249) |
| M34 | 44_56 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFIGSGSGIDYSLTISNLEQEDIATYFC (SEQ ID NO: 627) | QQSNSLPPT (SEQ ID NO: 529) | FGGGTKLEIK (SEQ ID NO: 249) |
| M35 | 44_56 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFIGSGSGIDYSLTISNLEQEDIATYFC (SEQ ID NO: 627) | QQSNSLPPT (SEQ ID NO: 529) | FGGGTKLEIK (SEQ ID NO: 249) |
| M36 | 44_56 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFIGSGSGIDYSLTISNLEQEDIATYFC (SEQ ID NO: 627) | QQSNSLPPT (SEQ ID NO: 529) | FGGGTKLEIK (SEQ ID NO: 249) |
| M37 | 44_56 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFIGSGSGIDYSLTISNLEQEDIATYFC (SEQ ID NO: 627) | QQSNSLPPT (SEQ ID NO: 529) | FGGGTKLEIK (SEQ ID NO: 249) |
| M38 | 44_56 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFTGSGSGTDYSLTISNLEQEDIATYFC (SEQ ID NO: 627) | QQSNSLPPT (SEQ ID NO: 529) | FGGGTKLEIK (SEQ ID NO: 249) |
| M39 | 44_56 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFTGSGSGTDYSLTISNLEQEDIATYFC (SEQ ID NO: 627) | QQSNSLPPT (SEQ ID NO: 529) | FGGGTKLEIK (SEQ ID NO: 249) |
| M40 | 44_56 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFTGSGSGTDYSLTISNLEQEDIATYFC (SEQ ID NO: 627) | QQSNSLPPT (SEQ ID NO: 529) | FGGGTKLEIK (SEQ ID NO: 249) |
| M41 | 44_56 | DIQMTQSTSSLSASLGDRVTITCRAS (SEQ ID NO: 174) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQSNTLPPT (SEQ ID NO: 530) | FGGGTKLEIK (SEQ ID NO: 249) |
| M42 | 44_56 | DIQMTQSTSSLSASLGDRVTITCRAS (SEQ ID NO: 174) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQSNTLPPT (SEQ ID NO: 530) | FGGGTKLEIK (SEQ ID NO: 249) |
| M43 | 44_56 | DVVMTQTTSSLSASLGDRVKLLIY (SEQ ID NO: 211) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQGNTLPPT (SEQ ID NO: 520) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M44 | 44_56 | DIQMTQSTSSLSASLGDRVTITCRAS (SEQ ID NO: 186) | QDISNY (SEQ ID NO: 485) | LNWYQQKPDGTVKLLIY (SEQ ID NO: 418) | YTS (SEQ ID NO: 727) | RLHSGVPSRFSGSESGTDYSLTISNLEQEDIATYFC (SEQ ID NO: 626) | QQGNTLPPT (SEQ ID NO: 520) | FGGGTKLEIK (SEQ ID NO: 249) |
| M45 | 44_56 | DIQMTQSTSSLSASLGDRVTITCRAS (SEQ ID NO: 211) 520) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQGNTLPPT (SEQ ID NO: 520) | FGGGTKLEIK (SEQ ID NO: 249) |
| M46 | 44_56 | DIQMTQSTSSLSASLGDRVTITCRAS (SEQ ID NO: 174) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQGNTLPPT (SEQ ID NO: 520) | FGGGTKLEIK (SEQ ID NO: 249) |
| M47 | 57_63 | DIQMTQSTSSLSASLGDRVTITCRAS (SEQ ID NO: 176) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 627) | QQSNSLPPT (SEQ ID NO: 529) | FGGGTKLEIK (SEQ ID NO: 249) |
| M48 | 6_130 | DIQMTQSTSSLSASLGDRVTITCRAS (SEQ ID NO: 176) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 627) | QQSNSLPPT (SEQ ID NO: 529) | FGGGTKLEIK (SEQ ID NO: 249) |
| M49 | 6_130 | DIQMTQSTSSLSASLGDRVTITCRAS (SEQ ID NO: 177) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 627) | QQSNSLPPT (SEQ ID NO: 529) | FGGGTKLEIK (SEQ ID NO: 249) |
| M50 | 6_130 | DIQMTQSTSSLSASLGDRVTITCRAS (SEQ ID NO: 174) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQGNTLPPT (SEQ ID NO: 520) | FGGGTKLEIK (SEQ ID NO: 249) |
| M51 | 6_163 | DIQMTQSTSSLSASLGDRVTITCRAS (SEQ ID NO: 174) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQSNTLPPT (SEQ ID NO: 530) | FGGGTKLEIK (SEQ ID NO: 249) |
| M52 | 6_163 | DIQMTQSTSSLSASLGDRVTITCRAS (SEQ ID NO: 174) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQGNTLPPT (SEQ ID NO: 520) | FGGGTKLEIK (SEQ ID NO: 249) |
| M53 | 57_63 | DIQMTQTTSSLSASLGDRVTITCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFTGSGSGTDYSLTISNLEQEDIATYFC (SEQ ID NO: 627) | QQSNSLPPT (SEQ ID NO: 529) | FGGGTKLEIK (SEQ ID NO: 249) |
| M54 | 33_63 | DIQMTQSTSSLSASLGDRVTITCRAS (SEQ ID NO: 174) | QDISNY (SEQ ID NO: 485) | LNWYQQKPDGTVKLLIY (SEQ ID NO: 418) | HTS (SEQ ID NO: 317) | RLHSGVPSRFSGSESGTDYSLTISNLEQEDIATYFC (SEQ ID NO: 624) | QQSNTLPPT (SEQ ID NO: 530) | FGGGTKLEIK (SEQ ID NO: 249) |
| M55 | 147_157 | DIQMTQSTSSLSASLGDRVTITCRAS (SEQ ID NO: 176) | QDISNY (SEQ ID NO: 485) | LNWYQQKPDGTVKLLIY (SEQ ID NO: 418) | YTS (SEQ ID NO: 727) | RLHSGVPSRFSGSGSGTDYSLTISNLEQEDIATYFC (SEQ ID NO: 626) | QQGNTLPPT (SEQ ID NO: 520) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M56 | 147_157 | DIQMTQSTSSLSASLGDR VTITCRAS (SEQ ID NO: 174) | QDISNY (SEQ ID NO: 485) | LNWYQQKPDGT VKLLIY (SEQ ID NO: 418) | HTS (SEQ ID NO: 317) | RLHSGVPSRFSGSESGTDYSLTIS NLEQEDIATYFC (SEQ ID NO: 624) | QQSNTLP PT (SEQ ID NO: 530) | FGGGTK LEIK (SEQ ID NO: 249) |
| M57 | 147_157 | DIQMTQSTSSLSASLGDR VTITCRAS (SEQ ID NO: 173) | QDISNY (SEQ ID NO: 485) | LNWYQQKPDGT VKLLIY (SEQ ID NO: 418) | YTS (SEQ ID NO: 727) | RLHSGVPSRFSGSGSGTDYSLTIS NLEQEDIATYFC (SEQ ID NO: 626) | QQGNTLP PT (SEQ ID NO: 520) | FGGGTK LEIK (SEQ ID NO: 249) |
| M58 | 33_63 | DIQMTQSTSSLSASLGDR VTITCRAS (SEQ ID NO: 176) | QDISNY (SEQ ID NO: 485) | LNWYQQKPDGT VKLLIY (SEQ ID NO: 418) | YTS (SEQ ID NO: 727) | RLHSGVPSRFSGSGSGTDYSLTIS NLEQEDIATYFC (SEQ ID NO: 626) | QQGNTLP PT (SEQ ID NO: 520) | FGGGTK LEIK (SEQ ID NO: 249) |
| M59 | 33_63 | DIQMTQSTSSLSASLGDR VTITCRAS (SEQ ID NO: 174) | QDISNY (SEQ ID NO: 485) | LNWYQQKPDGT VKLLIY (SEQ ID NO: 418) | HTS (SEQ ID NO: 317) | RLHSGVPSRFSGSESGTDYSLTIS NLEQEDIATYFC (SEQ ID NO: 624) | QQSNTLP PT (SEQ ID NO: 530) | FGGGTK LEIK (SEQ ID NO: 249) |
| M60 | 33_63 | DVVMTQTTSSLSASLGDR VTITCRAS (SEQ ID NO: 211) | QDISNY (SEQ ID NO: 485) | LNWYQQKPDGT VKLLIY (SEQ ID NO: 418) | HTS (SEQ ID NO: 317) | RLHSGVPSRFSGSESGTDYSLTIS NLEQEDIATYFC (SEQ ID NO: 624) | QQGNTLP PT (SEQ ID NO: 520) | FGGGTK LEIK (SEQ ID NO: 249) |
| M61 | 33_63 | DVVMTQSPASLSASVGET VTITCRAS (SEQ ID NO: 204) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |
| M62 | 33_63 | DIQMTQSPASLSASVGET VTITCRAS (SEQ ID NO: 168) | ENIYSY (SEQ ID NO: 224) | LEWYQQKQGKS PQLLVY (SEQ ID NO: 413) | NAK (SEQ ID NO: 450) | TLVEGVPSRFSGSGSGTQFSLKIN SLQPEDFGSYYC (SEQ ID NO: 678) | QHHYDTP YT (SEQ ID NO: 493) | FGGGTK LEIK (SEQ ID NO: 249) |
| M63 | 33_63 | DIQMTQSPASLSASVGET VTITCRAS (SEQ ID NO: 168) | ENIYSY (SEQ ID NO: 224) | LEWYQQKQGKS PQLLVY (SEQ ID NO: 413) | NAK (SEQ ID NO: 450) | TLVEGVPSRFSGSGSGTQFSLKIN SLQPEDFGSYYC (SEQ ID NO: 678) | QHHYDTP YT (SEQ ID NO: 493) | FGGGTK LEIK (SEQ ID NO: 249) |
| M64 | 33_63 | DIQMTQTTSSLSASLGDR VTITCRAS (SEQ ID NO: 176) | QYISNY (SEQ ID NO: 617) | LNWYQQRQDGT VKLLIY (SEQ ID NO: 421) | YTS (SEQ ID NO: 727) | RLHSGVPSRFSGSGSGTDYSLTIS NLEQEDIATYFC (SEQ ID NO: 626) | QQGNTLP PT (SEQ ID NO: 520) | FGGGTK LEMK (SEQ ID NO: 250) |
| M65 | 33_63 | DIVMTQTTSSLSASLGDR VTITCGAS (SEQ ID NO: 187) | QDISNY (SEQ ID NO: 485) | LNWYQQKQDGT VKLLIY (SEQ ID NO: 419) | HTS (SEQ ID NO: 317) | RLHSGVPSRFSGSEPGTDYSLTIS NLEQEDIATYFC (SEQ ID NO: 623) | QQGNTLP PT (SEQ ID NO: 520) | FGGGTK LEIK (SEQ ID NO: 249) |
| M66 | 33_63 | DIQMTQSTSSLSASLGDR VTITCRAS (SEQ ID NO: 174) | QDISNY (SEQ ID NO: 485) | LNWYQQKQDGT VKLLIY (SEQ ID NO: 419) | HTS (SEQ ID NO: 317) | RLHSGVPSRFSGSESGTDYSLTIS NLEQEDIATYFC (SEQ ID NO: 624) | QQGNTLP PT (SEQ ID NO: 520) | FGGGTK LEIK (SEQ ID NO: 249) |
| M67 | 33_63 | DIQMTQTTSSLSASLGDR VTISCRAS (SEQ ID NO: 176) | QDISNY (SEQ ID NO: 485) | LNWYQQKPDGT VKLLIY (SEQ ID NO: 418) | HTS (SEQ ID NO: 317) | RLQSGVPSRFTGSGSGTDYSLTIS NLEQEDIATYFC (SEQ ID NO: 627) | QQSNSLP PT (SEQ ID NO: 529) | FGGGTK LEIK (SEQ ID NO: 249) |
| M68 | 33_63 | DIVMTQTTSSLSASLGDR VTISCRAS (SEQ ID NO: 186) | QDISNY (SEQ ID NO: 485) | LNWYQQKPDGT VKLLIY (SEQ ID NO: 418) | YTS (SEQ ID NO: 727) | RLHSGVPSRFSGSGSGTDYSLTIS NLEQEDIATYFC (SEQ ID NO: 626) | QQGNTLP PT (SEQ ID NO: 520) | FGGGTK LEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M69 | 33_63 | DIQMTQTTSSLSASLGDR VTITCRAS (SEQ ID NO: 177) | QDISNY (SEQ ID NO: 485) | LNWYQQKPDGT VKLLIY (SEQ ID NO: 418) | HTS (SEQ ID NO: 317) | RLHSGVPSRFSGSESGTDYSLTIS NLEQEDIATYFC (SEQ ID NO: 624) | QQGNTLP PT (SEQ ID NO: 520) | FGGGTK LEIK (SEQ ID NO: 249) |
| M70 | 33_63 | DIQMTQTTSSLSASLGDR VTITCRAS (SEQ ID NO: 177) | QDISNY (SEQ ID NO: 485) | LNWYQQKPDGT VKLLIY (SEQ ID NO: 418) | HTS (SEQ ID NO: 317) | RLHSGVPSRFSGSESGTDYSLTIS NLEQEDIATYFC (SEQ ID NO: 624) | QQGNTLP PT (SEQ ID NO: 520) | FGGGTK LEIK (SEQ ID NO: 249) |
| M71 | 33_63 | DIQMTQTTSSLSASLGDR VTISCRAS (SEQ ID NO: 176) | QDISNY (SEQ ID NO: 485) | LNWYQQKPDGT VKLLIY (SEQ ID NO: 418) | HTS (SEQ ID NO: 317) | RLQSGVPSRFTGSGSGTDYSLTIS NLEQEDIATYFC (SEQ ID NO: 627) | QQSNSLP PT (SEQ ID NO: 529) | FGGGTK LEIK (SEQ ID NO: 249) |
| M72 | 33_63 | DIQMTQTTSSLSASLGDR VTITCRAS (SEQ ID NO: 177) | QDISNY (SEQ ID NO: 485) | LNWYQQKQDGT VKLLIY (SEQ ID NO: 419) | HTS (SEQ ID NO: 317) | RLHSGVPSRFSGSESGTDYSLTIS NLEQEDIATYFC (SEQ ID NO: 624) | QQGNTLP PT (SEQ ID NO: 520) | FGGGTK LEIK (SEQ ID NO: 249) |
| M73 | 44_56 | DIQMTQTTSSLSASLGDR VTISCRAS (SEQ ID NO: 176) | QDISNY (SEQ ID NO: 485) | LNWYQQKPDGT VKLLIY (SEQ ID NO: 418) | HTS (SEQ ID NO: 317) | RLQSGVPSRFTGSGSGTDYSLTIS NLEQEDIATYFC (SEQ ID NO: 627) | QQSNSLP PT (SEQ ID NO: 529) | FGGGTK LEIK (SEQ ID NO: 249) |
| M74 | 44_56 | DIQMTQTTSSLSASLGDR VTISCRAS (SEQ ID NO: 176) | QDISNY (SEQ ID NO: 485) | LNWYQQKPDGT VKLLIY (SEQ ID NO: 418) | YTS (SEQ ID NO: 727) | RLHSGVPSRFSGSGSGTDYSLTIS NLEQEDIATYFC (SEQ ID NO: 626) | QQGNTLP PT (SEQ ID NO: 520) | FGGGTK LEIK (SEQ ID NO: 249) |
| M75 | 6_163 | DIQMTQTTSSLSASLGDR VTISCRAS (SEQ ID NO: 176) | QDISNY (SEQ ID NO: 485) | LNWYQQKPDGT VKLLIY (SEQ ID NO: 418) | YTS (SEQ ID NO: 727) | RLHSGVPSRFSGSGSGADYSLTIS NLEQEDIATYFC (SEQ ID NO: 625) | QQGNTLP PT (SEQ ID NO: 520) | FGAGTK LEIK (SEQ ID NO: 246) |
| M76 | 147_157 | DIQMTQSQKFMSTSVGDR VSVTCKAS (SEQ ID NO: 172) | QNVSTN (SEQ ID NO: 513) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEMK (SEQ ID NO: 250) |
| M77 | 44_56 | DIQMTQSPASLSASVGET VTITCRAS (SEQ ID NO: 168) | ENIHSY (SEQ ID NO: 222) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGTP YT (SEQ ID NO: 496) | FGGGTK LEMK (SEQ ID NO: 250) |
| M78 | 33_63 | DIQMTQSPASLSASVGET VTITCRAS (SEQ ID NO: 168) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYDTP YT (SEQ ID NO: 493) | FGGGTK LEIK (SEQ ID NO: 249) |
| M79 | 57_63 | DVVMTQSPASLSASVGET VTITCRAS (SEQ ID NO: 204) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |
| M80 | 44_56 | DIQMTQSPASLSASVGET VTITCRAS (SEQ ID NO: 168) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M81 | 147_156 | DVQMTQSPASLSASVGETVTITCRAS (SEQ ID NO: 196) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 670) | QHHYDTPYT (SEQ ID NO: 493) | FGGGTKLEIK (SEQ ID NO: 249) |
| M82 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M83 | 33_63 | DIVLTQSPASLSASVGETVTITCRAS (SEQ ID NO: 179) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M84 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M85 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M86 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M87 | 33_63 | DVVMTQSPASLSASVGETVTITCRAS (SEQ ID NO: 204) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M88 | 33_63 | DVVMTQSPASLSASVGESVTITCRAS (SEQ ID NO: 203) | ENSYNY (SEQ ID NO: 225) | LEWYQQKQGKSPQLLVY (SEQ ID NO: 413) | NAK (SEQ ID NO: 450) | TLAEGVPSRFSGSGFGTQFSLKINSLQPEDFGTYYC (SEQ ID NO: 669) | QHHYGTPYT (SEQ ID NO: 496) | FGGGTKLEIK (SEQ ID NO: 249) |
| M89 | 33_63 | DVVMTQSPASLSASVGETVTITCRAS (SEQ ID NO: 204) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEMK (SEQ ID NO: 250) |
| M90 | 33_63 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M91 | 33_63 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M92 | 33_63 | DIQMTQSPASLSASVGETVTITCRAS (SEQ ID NO: 196) | ENSYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M93 | 33_63 | DVQMTQSPASLSASVGETVTITCRAS (SEQ ID NO: 196) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 670) | QHHYDTPYT (SEQ ID NO: 493) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M94 | 33_63 | DIQMTQSPASLSASVGETVTITCRAS (SEQ ID NO: 196) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QQHYGTPYT (SEQ ID NO: 523) | FGGGTKLEIK (SEQ ID NO: 249) |
| M95 | 44_56 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M96 | 44_56 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M97 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M98 | 147_156 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M99 | 147_156 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M100 | 147_156 | DIQMTQSPASLSASVGESVTITCRAS (SEQ ID NO: 165) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYGSPYT (SEQ ID NO: 495) | FGGGTKLEIK (SEQ ID NO: 249) |
| M101 | 44_56 | DIQMTQSPASLSASVGESVTITCRAS (SEQ ID NO: 165) | ENIYSY (SEQ ID NO: 224) | LEWSQQKQGKSPQLLVY (SEQ ID NO: 407) | NAK (SEQ ID NO: 450) | TLPEGVPSRFSGSGSGTQFSLKISSLQPEDFGTYYC (SEQ ID NO: 676) | QHHYGIPYT (SEQ ID NO: 494) | FGGGTKLEIK (SEQ ID NO: 249) |
| M102 | 57_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M103 | 57_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTRFSLKINSLQPEDFGSYYC (SEQ ID NO: 674) | QHHYDTPYT (SEQ ID NO: 493) | FGGGTKLEIK (SEQ ID NO: 249) |
| M104 | 6_130 | DIQMTQSPASLSASVGETVTITCRAS (SEQ ID NO: 168) | ENIHSY (SEQ ID NO: 22) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYGTPYT (SEQ ID NO: 496) | FGGGTKLEMK (SEQ ID NO: 250) |
| M105 | 6_130 | DIQMTQTPASLSASVGETVTITCRAS (SEQ ID NO: 175) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTQLEIK (SEQ ID NO: 254) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M106 | 6_130 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLTEGVPSRFSGSGSGTQFSLKINSLQPEDFGTYYC (SEQ ID NO: 677) | QQHYGTPYT (SEQ ID NO: 523) | FGGGTKLEIK (SEQ ID NO: 249) |
| M107 | 6_130 | DIQMTQTTSSLSASLGDRVTITCRAS (SEQ ID NO: 176) | QDISNY (SEQ ID NO: 485) | LNWYQQKPDGTVKLLIY (SEQ ID NO: 418) | YTS (SEQ ID NO: 727) | RLHSGVPSRFSGSGSGTDYSLTISNLEQEDIATYFC (SEQ ID NO: 626) | QQGNTLPWT (SEQ ID NO: 522) | FGGGTKLEIK (SEQ ID NO: 249) |
| M108 | 6_163 | DVVMTQSPASLSASVGETVTITCRAS (SEQ ID NO: 204) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M109 | 77_89 | DVVMTQSPASLSASVGETVTITCRAS (SEQ ID NO: 204) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M110 | 77_89 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M111 | 77_89 | DIQMTQSPASLSASVGESVTITCRAS (SEQ ID NO: 165) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYGSPYT (SEQ ID NO: 495) | FGGGTKLEIK (SEQ ID NO: 249) |
| M112 | 77_89 | DVQMTQSPSSMYASLGERVTITCKAS (SEQ ID NO: 199) | QDINSY (SEQ ID NO: 484) | LSWFQQKPGKSPKTLIY (SEQ ID NO: 427) | RAN (SEQ ID NO: 618) | RLVDGAPSRFSGSGSGQDYSLTISSLEYEDMGIYYC (SEQ ID NO: 628) | LQYDEFPYT (SEQ ID NO: 425) | FGGGTKLEIK (SEQ ID NO: 249) |
| M113 | 77_89 | DVQMTQSPSSMYASLGERVTFTCKAS (SEQ ID NO: 198) | QDINRY (SEQ ID NO: 483) | LSWFQQKPGKSPKTLIY (SEQ ID NO: 427) | RAN (SEQ ID NO: 618) | RLVDGVPSRFSGSGSGQNYSLTISSLEYEDMGIYYC (SEQ ID NO: 632) | LQYDEFPYT (SEQ ID NO: 425) | FGGGTKLEIK (SEQ ID NO: 249) |
| M114 | 57_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M115 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTRFSLKINSLQPEDFGSYYC (SEQ ID NO: 674) | QHHYDTPYT (SEQ ID NO: 493) | FGGGTKLEIK (SEQ ID NO: 249) |
| M116 | 57_63 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M117 | 147_157 | DVVMTQSPASLSASVGETVTITCRAS (SEQ ID NO: 204) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M118 | 147_157 | DIQMTQSPASLSASVGESVTITCRAS (SEQ ID NO: 165) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLRINSLQPEDFGTYYC (SEQ ID NO: 673) | QHHYGSPYT (SEQ ID NO: 495) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M119 | 147_157 | DVVMTQSPASLSASVGETVTITCRAS (SEQ ID NO: 204) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M120 | 147_157 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M121 | 147_157 | DVVMTQSPASLSASVGETVTITCRAS (SEQ ID NO: 204) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M122 | 147_157 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M123 | 147_157 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M124 | 147_157 | DIQMTQTPASLSASVGETVTITCRAS (SEQ ID NO: 175) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTQLEIK (SEQ ID NO: 254) |
| M125 | 147_157 | DVVMTQSPASLSASVGETVTITCRAS (SEQ ID NO: 204) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGTYYC (SEQ ID NO: 679) | QHHYDTPYT (SEQ ID NO: 493) | FGGGTKLEIK (SEQ ID NO: 251) |
| M126 | 147_157 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 250) |
| M127 | 147_157 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEMK (SEQ ID NO: 250) |
| M128 | 147_157 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QQHYGTPYT (SEQ ID NO: 523) | FGGGTKLEIK (SEQ ID NO: 249) |
| M129 | 147_157 | DIVMTQTTSSLSASLGDRVTITCGAS (SEQ ID NO: 187) | QDISNY (SEQ ID NO: 485) | LNWYQQKQDGTVKLLIY (SEQ ID NO: 419) | HTS (SEQ ID NO: 317) | RLHSGVPSRFSGSEPGTDYSLTISNLEQEDIATYFC (SEQ ID NO: 623) | QQGNTLPPT (SEQ ID NO: 520) | FGGGTKLEIK (SEQ ID NO: 249) |
| M130 | 147_157 | DIQMTQTTSSLSASLGDRVTITCRAS (SEQ ID NO: 176) | QDISNY (SEQ ID NO: 485) | LNWYQQKQDGTVKLLIY (SEQ ID NO: 419) | HTS (SEQ ID NO: 317) | RLQSGVPSRFTGSGSGTDYSLTISNLEQEDIATYFC (SEQ ID NO: 627) | QQSNSLPPT (SEQ ID NO: 529) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M131 | 33_63 | DIVMTQSPASLSASVGESVTITCRAS (SEQ ID NO: 181) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLRINSLQPEDFGTYYC (SEQ ID NO: 673) | QHHYGSPYT (SEQ ID NO: 495) | FGGGTKLEIK (SEQ ID NO: 249) |
| M132 | 33_63 | DVVMTQSPASLSASVGETVTITCRAS (SEQ ID NO: 204) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M133 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M134 | 33_63 | DVVMTQSPASLSASVGETVTITCRAS (SEQ ID NO: 204) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M135 | 33_63 | DIQMTQSPASLSASVGESVTITCRAS (SEQ ID NO: 165) | ENIYSY (SEQ ID NO: 224) | LEWSQQKQGKSPQLLVY (SEQ ID NO: 407) | NAK (SEQ ID NO: 450) | TLPEGVPSRFSGSGSGTQFSLKISSLQPEDFGTYYC (SEQ ID NO: 676) | QHHYGIPYT (SEQ ID NO: 494) | FGGGTKLEIK (SEQ ID NO: 249) |
| M136 | 33_63 | DVVMTQSPASLSASVGETVTITCRAS (SEQ ID NO: 204) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M137 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M138 | 33_63 | DIVLTQSPASLSASVGETVTITCRAS (SEQ ID NO: 179) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M139 | 33_63 | DIQMTQSPASLSASVGESVTITCRAS (SEQ ID NO: 165) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYGSPYT (SEQ ID NO: 495) | FGGGTKLEIK (SEQ ID NO: 250) |
| M140 | 33_63 | DIQMTQSPASLSASVGESVTITCRAS (SEQ ID NO: 165) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLRINSLQPEDFGTYYC (SEQ ID NO: 673) | QHHYGTPYT (SEQ ID NO: 496) | FGGGTKLEIK (SEQ ID NO: 249) |
| M141 | 33_63 | DVVMTQTPSSLSASLGERVTITCKAS (SEQ ID NO: 210) | QDINSY (SEQ ID NO: 484) | LSWFQQKPGKSPKTLIY (SEQ ID NO: 427) | RAN (SEQ ID NO: 618) | RLVDGVPSRFSGSGSGQDYSLTISSLEYEDMGIYYC (SEQ ID NO: 630) | LQYDEFPYT (SEQ ID NO: 425) | FGGGTKLEIK (SEQ ID NO: 249) |
| M142 | 33_63 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M143 | 33_63 | DVVMTQSPASLSASVGETVTITCRAS (SEQ ID NO: 204) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M144 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M145 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M146 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M147 | 33_63 | DIQMTQSPASLSASVGESVTITCRAS (SEQ ID NO: 165) | ENIYSY (SEQ ID NO: 224) | LEWYQQKKGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYGSPYT (SEQ ID NO: 495) | FGGGTKLEIK (SEQ ID NO: 249) |
| M148 | 33_63 | DTTVTQSPSSMYASLGERVTITCKAS (SEQ ID NO: 192) | QDINNF (SEQ ID NO: 481) | LSWFQQKPGKSPQTLIY (SEQ ID NO: 428) | RAN (SEQ ID NO: 618) | RLVDGVPSRFSGSGSGQDYSLTISSLEYEDLGIYYC (SEQ ID NO: 629) | LQYDEFPWT (SEQ ID NO: 424) | FGGGTKLEIK (SEQ ID NO: 249) |
| M149 | 33_63 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QQHYGTPYT (SEQ ID NO: 523) | FGGGTKLEIK (SEQ ID NO: 249) |
| M150 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M151 | 33_63 | DIQMTQSPASLSASVGETVTITCRAS (SEQ ID NO: 168) | ENSYSY (SEQ ID NO: 26) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M152 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M153 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M154 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M155 | 44_56 | DIQMTQSPASLSASVGESVTITCRAS (SEQ ID NO: 165) | ENIYSY (SEQ ID NO: 224) | LEWYQQKKGKSPQLLVY (SEQ ID NO: 411) | NAK (SEQ ID NO: 450) | TLAEGVPSRFSGSGSGTQFSLKINSLQPEDFGSYYC (SEQ ID NO: 670) | QHHYGSPYT (SEQ ID NO: 495) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M156 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M157 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M158 | 44_56 | DIVMTQSPASLSASVGESVTITCRAS (SEQ ID NO: 181) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLRINSLQPEDFGTYYC (SEQ ID NO: 673) | QHHYGSPYT (SEQ ID NO: 495) | FGGGTKLEIK (SEQ ID NO: 249) |
| M159 | 44_56 | DIVMTQSPASLSASVGESVTITCRAS (SEQ ID NO: 181) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLRINSLQPEDFGTYYC (SEQ ID NO: 673) | QHHYGSPYT (SEQ ID NO: 495) | FGGGTKLEIK (SEQ ID NO: 249) |
| M160 | 44_56 | DIVMTQSPASLSASVGESVTITCRAS (SEQ ID NO: 181) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLRINSLQPEDFGTYYC (SEQ ID NO: 673) | QHHYGSPYT (SEQ ID NO: 495) | FGGGTKLEIK (SEQ ID NO: 249) |
| M161 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M162 | 44_56 | DIQMTQTPASLSASVGETVTITCRAS (SEQ ID NO: 175) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTQLEIK (SEQ ID NO: 254) |
| M163 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M164 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M165 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M166 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTRFSLKINSLQPEDFGSYYC (SEQ ID NO: 674) | QHHYDTPYT (SEQ ID NO: 493) | FGGGTKLEIK (SEQ ID NO: 249) |
| M167 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTRFSLKINSLQPEDFGSYYC (SEQ ID NO: 674) | QHHYDTPYT (SEQ ID NO: 493) | FGGGTKLEIK (SEQ ID NO: 249) |
| M168 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M169 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M170 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M171 | 44_56 | DIQMTQTTSSLSASLGDRVTITCRAS (SEQ ID NO: 176) | QDISNY (SEQ ID NO: 485) | LNWYQQKQDGTVKLLIY (SEQ ID NO: 419) | HTS (SEQ ID NO: 317) | RLQSGVPSRFTGSGSGTDYSLTISNLEQEDIATYFC (SEQ ID NO: 627) | QQSNSLPPT (SEQ ID NO: 529) | FGGGTKLEIK (SEQ ID NO: 249) |
| M172 | 44_56 | EIVMTQSPPTLSLSPGERVTLSCKAS (SEQ ID NO: 221) | QDVNTA (SEQ ID NO: 486) | VAWYQQKQGQAPRLLIY (SEQ ID NO: 690) | WAS (SEQ ID NO: 698) | TRHTGVPSRFSGSGSGTDFTLTISSLQPEDFATYYC (SEQ ID NO: 681) | QQHYSSPWT (SEQ ID NO: 524) | FGGGTKVEIK (SEQ ID NO: 252) |
| M173 | 33_63 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M174 | 33_63 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M175 | 33_63 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M176 | 44_56 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M177 | 44_56 | DIQMTQSPASLSASVGETVTITCRAS (SEQ ID NO: 168) | ENSYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M178 | 44_56 | DVQMNQSPSSMYASLGERVTITCKAS (SEQ ID NO: 194) | QDINNF (SEQ ID NO: 481) | LSWFQQKPGKSPQTLIY (SEQ ID NO: 428) | RAN (SEQ ID NO: 618) | RLVDGVPSRFSGSGSGQHYSLTISGLEYEDLGIYYC (SEQ ID NO: 631) | LQYDEFPWT (SEQ ID NO: 424) | FGGGTKLEIK (SEQ ID NO: 249) |
| M179 | 44_56 | DVQMNQSPSSMYASLGERVTITCKAS (SEQ ID NO: 194) | QDINNF (SEQ ID NO: 481) | LSWFQQKQGKSPQTLIY (SEQ ID NO: 429) | RAN (SEQ ID NO: 618) | RLVDGVPSRFSGSGSGQHYSLTISGLEYEDLGIYYC (SEQ ID NO: 631) | LQYDEFPWT (SEQ ID NO: 424) | FGGGTKLEIK (SEQ ID NO: 249) |
| M180 | 44_56 | DVQMTQSPPSLSASVGETVTITCRAS (SEQ ID NO: 197) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M181 | 33_63 | DIVMTQSPASLSASVGETVTITCRAS (SEQ ID NO: 182) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQSEDFGSYYC (SEQ ID NO: 672) | QHHYSTPYT (SEQ ID NO: 498) | FGGGTKLEIK (SEQ ID NO: 249) |
| M182 | 33_63 | DIVMTQSPASLSASVGETVTITCRAS (SEQ ID NO: 182) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M183 | 33_63 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEMK (SEQ ID NO: 250) |
| M184 | 33_63 | DIQMTQSTSSLSASLGDRVTITCRAS (SEQ ID NO: 173) | QDISNY (SEQ ID NO: 485) | LNWYQQKPDGTVKLLIY (SEQ ID NO: 418) | YTS (SEQ ID NO: 727) | RLHSGVPSRFSGSGSGTDYSLTISNLEQEDIATYFC (SEQ ID NO: 626) | QQGNTLPPT (SEQ ID NO: 520) | FGGGTKLEMK (SEQ ID NO: 250) |
| M185 | 44_56 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M186 | 6_130 | DVVMTQSPASLSASVGESVTITCRAS (SEQ ID NO: 203) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLRINSLQPEDFGTYYC (SEQ ID NO: 673) | QHHYGSPYT (SEQ ID NO: 495) | FGGGTKLEIK (SEQ ID NO: 249) |
| M187 | 6_130 | DIQMTQTTSSLSASLGDRVTITCRAS (SEQ ID NO: 176) | QDISNY (SEQ ID NO: 485) | LNWYQQKPDGTVKLLIY (SEQ ID NO: 418) | YTS (SEQ ID NO: 727) | RLHIGIPSRFSGSGSGTDYSLTISNLEQEDIATYFC (SEQ ID NO: 622) | QQGNTLPST (SEQ ID NO: 521) | FGGGTKLEIK (SEQ ID NO: 249) |
| M188 | 6_163 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYGTPYT (SEQ ID NO: 496) | FGGGTKLEIK (SEQ ID NO: 249) |
| M189 | 6_163 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M190 | 77_89 | DIQMTQSPASLSASVGESVTITCRTS (SEQ ID NO: 166) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLRINSLQPEDFGTYYC (SEQ ID NO: 673) | QHHYGSPYT (SEQ ID NO: 495) | FGGGTKLEIK (SEQ ID NO: 250) |
| M191 | 77_89 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYGTPYT (SEQ ID NO: 496) | FGGGTKLEIK (SEQ ID NO: 249) |
| M192 | 57_63 | DIVMTQSPASLSASVGETVTITCRAS (SEQ ID NO: 182) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 250) |
| M193 | 147_157 | DIQMTQSPASLSASVGESVTITCRAS (SEQ ID NO: 165) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYGSPYT (SEQ ID NO: 495) | FGGGTKLEMK (SEQ ID NO: 250) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M194 | 33_63 | DIQMTQSPASLSASVGES VTITCRAS (SEQ ID NO: 165) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGSP YT (SEQ ID NO: 495) | FGGGTK LEMK (SEQ ID NO: 250) |
| M195 | 44_56 | DIQMTQSPASLSASVGES VTITCRAS (SEQ ID NO: 165) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGSP YT (SEQ ID NO: 495) | FGGGTK LEMK (SEQ ID NO: 250) |
| M196 | 44_56 | DIQMTQSPASLSASVGES VTITCRAS (SEQ ID NO: 165) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGSP YT (SEQ ID NO: 495) | FGGGTK LEIK (SEQ ID NO: 250) |
| M197 | 44_56 | DIQMTQSPASLSASVGES VTITCRAS (SEQ ID NO: 165) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGSP YT (SEQ ID NO: 495) | FGGGTK LEMK (SEQ ID NO: 250) |
| M198 | 147_157 | DIQMTQSPASLSASVGET VTITCRAS (SEQ ID NO: 168) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEMK (SEQ ID NO: 250) |
| M199 | 147_157 | DIQMTQSPASLSASVGES VTITCRAS (SEQ ID NO: 165) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGSP YT (SEQ ID NO: 495) | FGGGTK LEIK (SEQ ID NO: 249) |
| M200 | 33_63 | DIQMTQSPASLSASVGET VTITCRAS (SEQ ID NO: 168) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYDTP YT (SEQ ID NO: 493) | FGGGTK LEIK (SEQ ID NO: 249) |
| M201 | 33_63 | DIQMTQTPASLSASVGET VTITCRAS (SEQ ID NO: 175) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |
| M202 | 33_63 | DIGMTQSPASLSASVGET VTITCRAS (SEQ ID NO: 164) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |
| M203 | 33_63 | DIQMTQSPASLSASVGES VTITCRAS (SEQ ID NO: 165) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLRIN SLQPEDFGTYYC (SEQ ID NO: 673) | QHHYGSP YT (SEQ ID NO: 495) | FGGGTK LEIK (SEQ ID NO: 249) |
| M204 | 33_63 | DIVMTQSPASLSASVGET VTITCRAS (SEQ ID NO: 182) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYDTP YT (SEQ ID NO: 493) | FGGGTK LEIK (SEQ ID NO: 249) |
| M205 | 33_63 | DIQMTQSPASLSASVGET VTITCRAS (SEQ ID NO: 168) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M206 | 33_63 | DIQMTQSPASLSASVGES VTITCRAS (SEQ ID NO: 165) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGSP YT (SEQ ID NO: 495) | FGGGTK LEIK (SEQ ID NO: 249) |
| M207 | 33_63 | DIQMTQSPASLSASVGES VTITCRAS (SEQ ID NO: 165) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGSP YT (SEQ ID NO: 495) | FGGGTK LEMK (SEQ ID NO: 250) |
| M208 | 33_63 | DVVMTQSPASLSASVGET VTITCRAS (SEQ ID NO: 204) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYDTP YT (SEQ ID NO: 493) | FGGGTK LEIK (SEQ ID NO: 249) |
| M209 | 33_63 | DIQMTQSPASLSASVGES VTITCRAS (SEQ ID NO: 165) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGSP YT (SEQ ID NO: 495) | FGGGTK LEIK (SEQ ID NO: 249) |
| M210 | 33_63 | DVVMTQSPASLSASVGES VTITCRAS (SEQ ID NO: 203) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGSP YT (SEQ ID NO: 495) | FGGGTK LEIK (SEQ ID NO: 249) |
| M211 | 33_63 | DIQMTQTPASLSASVGET VTITCRAS (SEQ ID NO: 175) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |
| M212 | 33_63 | DIQMTQSPASLSASVGET VTITCRAS (SEQ ID NO: 168) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |
| M213 | 44_56 | DIQMTQSPASLSASVGET VTITCRAS (SEQ ID NO: 168) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |
| M214 | 44_56 | DIQMTQSPASLSASVGET VTITCRAS (SEQ ID NO: 168) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |
| M215 | 44_56 | DIQMTQSPASLSASVGES VTITCRAS (SEQ ID NO: 165) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGSP YT (SEQ ID NO: 495) | FGGGTK LEIK (SEQ ID NO: 249) |
| M216 | 44_56 | DIQMTQSPASLSASVGES VTITCRAS (SEQ ID NO: 165) | ENIYSY (SEQ ID NO: 224) | LEWYQQKQGKS PQLLVY (SEQ ID NO: 413) | NAK (SEQ ID NO: 450) | TLAEGVPSRFSGSGSGTQFSLKIN SLQPEDFGSYYC (SEQ ID NO: 670) | QHHYGSP YT (SEQ ID NO: 495) | FGGGTK LEIK (SEQ ID NO: 249) |
| M217 | 44_56 | DIVMTQSQKFMSTSVGDR VTITCRAS (SEQ ID NO: 184) | QNVGTN (SEQ ID NO: 512) | VAWYQQKQGQS PKALIY (SEQ ID NO: 691) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M218 | 33_63 | DIQMTQSPASLSASVGET VTITCRAS (SEQ ID NO: 168) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M219 | 6_163 | DIQMTQSQKFMSTSVGDRVTITCRAS (SEQ ID NO: 172) | QNVGTN (SEQ ID NO: 512) | VAWYQQKIGQSPKALIY (SEQ ID NO: 686) | SAS (SEQ ID NO: 637) | YRYSGVPDRFTGSGSGTDFTLTISSVKSEDLAEYFC (SEQ ID NO: 723) | HQYNNYPYT (SEQ ID NO: 316) | FGGGTKLEIK (SEQ ID NO: 249) |
| M220 | 33_63 | DIQMTQSQKFMSTSVGDRVSVTCKAS (SEQ ID NO: 172) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | HQYNNYPYT (SEQ ID NO: 316) | FGGGTKLEIK (SEQ ID NO: 249) |
| M221 | 33_63 | DIQMTQSQKFMSTSVGDRVSVTCKAS (SEQ ID NO: 172) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | HQYNNYPYT (SEQ ID NO: 316) | FGGGTKLEIK (SEQ ID NO: 249) |
| M222 | 33_63 | DVVMTQSQKFMSTSVGDRVSVTCKAS (SEQ ID NO: 206) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M223 | 44_56 | DTTVTQSQKFMSTSVGDRVSVTCKAS (SEQ ID NO: 193) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M224 | 147_157 | DIVLTQSQKFMSTSVGDRVSVTCKAS (SEQ ID NO: 180) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEMK (SEQ ID NO: 250) |
| M225 | 147_157 | DVVMTQSQKFMSTSVGDRVSVTCKAS (SEQ ID NO: 206) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M226 | 33_63 | DIQMTQSQKFMSTSVGDRVSVTCKAS (SEQ ID NO: 172) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | HQYNNYPYT (SEQ ID NO: 316) | FGGGTKLEIK (SEQ ID NO: 249) |
| M227 | 33_63 | DVVMTQSQKFMSTSVGDRVSVTCKAS (SEQ ID NO: 206) | QNVGTN (SEQ ID NO: 512) | VAWYQQKQGQSPKALIY (SEQ ID NO: 691) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M228 | 44_56 | DIQMTQSQKFMSTSVGDRVSVTCKAS (SEQ ID NO: 172) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | HQYNNYPYT (SEQ ID NO: 316) | FGGGTKLEIK (SEQ ID NO: 249) |
| M229 | 33_63 | DIVMTQSQKFMSTSVGDRVSVTCKAS (SEQ ID NO: 184) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M230 | 147_157 | DIQMTQSQKFMSTSVGDRVSVTCKAS (SEQ ID NO: 172) | QNVGTN (SEQ ID NO: 512) | VAWYQQKPGQCPKALIY (SEQ ID NO: 688) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M231 | 147_157 | DIQMTQSQKFMSTSVGDRVSVTCKAS (SEQ ID NO: 172) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M232 | 33_63 | DIVMTQSQKFMSTSVGDRVSVTCKAS (SEQ ID NO: 184) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M233 | 33_63 | DIQMTQSQKFMSTSVGDRVSVTCKAS (SEQ ID NO: 172) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M234 | 33_63 | DIVLTQSQKFMSTSVGDRVSVTCKAS (SEQ ID NO: 180) | QNVGTN (SEQ ID NO: 512) | VAWYQQKPGQSPKALIY (SEQ ID NO: 689) | SAS (SEQ ID NO: 637) | YRYSGVPDRFTGRGSGTDFTLTISNVQSEDLADYFC (SEQ ID NO: 724) | QQYNTYPYT (SEQ ID NO: 552) | FGGGTKLEIK (SEQ ID NO: 249) |
| M235 | 33_63 | DTTVTQSQKFMSTSVGDRVSVTCKAS (SEQ ID NO: 193) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEMK (SEQ ID NO: 250) |
| M236 | 33_63 | DIQMTQSQKFMSASVGDRVSVTCKAS (SEQ ID NO: 170) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEMK (SEQ ID NO: 250) |
| M237 | 33_63 | DVVMTQSQKFMSTSVGDRVSVTCKAS (SEQ ID NO: 206) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEMK (SEQ ID NO: 250) |
| M238 | 33_63 | DTTVTQSQKFMSTSVGDRVSVTCKAS (SEQ ID NO: 193) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M239 | 33_63 | DTTVTQSQKFMSTSVGDRVSVTCKAS (SEQ ID NO: 193) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEMK (SEQ ID NO: 250) |
| M240 | 33_63 | DTTVTQSQKFMSTSVGDRVSVTCKAS (SEQ ID NO: 193) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEMK (SEQ ID NO: 250) |
| M241 | 33_63 | HIQMTHSPPPLSASVGETVTLTCRAS (SEQ ID NO: 315) | ENIYNY (SEQ ID NO: 223) | LEWYQQKQGKSPHLLVY (SEQ ID NO: 412) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M242 | 44_56 | DIQMTQSQKFMSTSVGDRVSVTCKAS (SEQ ID NO: 172) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M243 | 44_56 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M244 | 6_130 | DIVLTQSQKFMSTSVGDR VSVTCKAS (SEQ ID NO: 180) | QNVGTN (SEQ ID NO: 512) | VAWYQQRPGQS PKALIY (SEQ ID NO: 692) | SAS (SEQ ID NO: 637) | YRYTGVPDRFTGSGSGTDFTLTIS NVQSEDLAEYFC (SEQ ID NO: 725) | HQYNNYP YT (SEQ ID NO: 316) | FGGGTK LEMK (SEQ ID NO: 250) |
| M245 | 6_130 | DIVLTQSQKFMSTSVGDR VSVTCKAS (SEQ ID NO: 180) | QNVGTN (SEQ ID NO: 512) | VAWYQQKPGQS PKALIY (SEQ ID NO: 689) | SAS (SEQ ID NO: 637) | YRYSGVPDRITGRGSGTDFTLTIS NVQSEDLAEYFC (SEQ ID NO: 719) | QQYNTYP YT (SEQ ID NO: 550) | FGGGTK LEIK (SEQ ID NO: 249) |
| M246 | 6_163 | DIVITQSQKFMSTSVGDR VSVTCKAS (SEQ ID NO: 178) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M247 | 6_163 | DIVMTQSQKFMSTSVGDR VSVTCKAS (SEQ ID NO: 184) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M248 | 6_163 | DIQMTQSQKFMSTSVGDR VSVTCKAS (SEQ ID NO: 172) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M249 | 6_163 | DIVLTQSQKFMSTSVGDR VSVTCKAS (SEQ ID NO: 180) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLVEYFC (SEQ ID NO: 721) | QQYNTYP YT (SEQ ID NO: 552) | FGGGTK LEMK (SEQ ID NO: 250) |
| M250 | 6_163 | DVQMNQSQKFMSTSVGDR VSVTCKAS (SEQ ID NO: 195) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNTYP YT (SEQ ID NO: 552) | FGGGTK LEIK (SEQ ID NO: 249) |
| M251 | 77_89 | DIVMTQSQKFMSTSVGDR VSVTCKAS (SEQ ID NO: 184) | QNVGIN (SEQ ID NO: 511) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNNYP YT (SEQ ID NO: 546) | FGGGTK LEIK (SEQ ID NO: 249) |
| M252 | 77_89 | DIVMTQSQKFMSTSVGDR VSVTCKAS (SEQ ID NO: 172) | QNVGIN (SEQ ID NO: 511) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNNYP YT (SEQ ID NO: 546) | FGGGTK LEIK (SEQ ID NO: 249) |
| M253 | 77_89 | DVQMTQSQKFMSTSVGDR VSVTCKAS (SEQ ID NO: 200) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M254 | 77_89 | DVQMTQSQKFMSTSVGDR VSVTCKAS (SEQ ID NO: 200) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M255 | 77_89 | DIVMTQTQKFMSTSVGGR VSVTCKAS (SEQ ID NO: 185) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M256 | 77_89 | DIVMTQSQKFMSTSVGDR VSVTCKAS (SEQ ID NO: 184) | QNVGIN (SEQ ID NO: 511) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M257 | 77_89 | DIQMTQSQKFMSTSVGDR VSVTCKAS (SEQ ID NO: 172) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEMK (SEQ ID NO: 250) |
| M258 | 77_89 | DIQMTQSQKFMSTSVGDR VSVTCKAS (SEQ ID NO: 172) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M259 | 77_89 | DIVITQSQKFMSTSVGDR VSVTCKAS (SEQ ID NO: 178) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M260 | 77_89 | DVQMTQSQKFMSTSVGDR VSVTCKAS (SEQ ID NO: 200) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M261 | 33_63 | DIQMTQSQKFMSTSVGDR VSVTCKAS (SEQ ID NO: 172) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M262 | 33_63 | DVVMTQSQKFMSTSVGDR VSVTCKAS (SEQ ID NO: 206) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M263 | 147_157 | DIVLTQSQKFMSTSVGDR VSVTCKAS (SEQ ID NO: 180) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M264 | 147_157 | DIQMTQSQKFMSTSVGDR VSVTCKAS (SEQ ID NO: 172) | QNVGTN (SEQ ID NO: 512) | VAWYQQKPGQS PKALIY (SEQ ID NO: 689) | SAS (SEQ ID NO: 637) | YRYSGVPDRFIGSGSGTDFTLTIS NVQSEDLAEYFC (SEQ ID NO: 719) | QQYNSYP YT (SEQ ID NO: 550) | FGGGTK LEMK (SEQ ID NO: 250) |
| M265 | 147_157 | RHCESQSQKFMSTSVGDR VSVTCKAS (SEQ ID NO: 621) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP LT (SEQ ID NO: 549) | FGGGTK LEIK (SEQ ID NO: 249) |
| M266 | 147_157 | DIQMTQSQKFMSTSAGDR VSVTCKAS (SEQ ID NO: 172171 | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M267 | 147_157 | DIVMTQSQKFMSTSVGDR VSVTCKAS (SEQ ID NO: 184) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP LT (SEQ ID NO: 549) | FGGGTK LEIK (SEQ ID NO: 249) |
| M268 | 147_157 | DIVLTQSQKFMSTSVGDR VSVTCKAS (SEQ ID NO: 180) | QNVGTN (SEQ ID NO: 512) | VAWYQQKPGQS PKALIY (SEQ ID NO: 689) | SAS (SEQ ID NO: 637) | YRYSGVPDRITGRGSGTDFTLTIS NVQSEDLADYFC (SEQ ID NO: 724) | QQYNTYP YT (SEQ ID NO: 552) | FGGGTK LEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M269 | 147_157 | DIQMTQTTSSLSASLGDRVTISCRAS (SEQ ID NO: 176) | QDISNY (SEQ ID NO: 485) | LNWYQQKPDGTVKLLIY (SEQ ID NO: 418) | HTS (SEQ ID NO: 317) | RLQSGVPSRFTGSGSGTDYSLTISNLEQEDIATYFC (SEQ ID NO: 627) | QQSNSLPPT (SEQ ID NO: 529) | FGGGTKLEIK (SEQ ID NO: 249) |
| M270 | 147_157 | DIQMTQSPASLSASVGETVTITCRAS (SEQ ID NO: 168) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEMK (SEQ ID NO: 250) |
| M271 | 147_157 | DVVMTQTPASLSASVGETVTITCRAS (SEQ ID NO: 207) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M272 | 147_157 | DVQMTQSQKFMSTSVGDRVSVTCKAS (SEQ ID NO: 200) | QNVGTN (SEQ ID NO: 512) | VAWYQQKQGQSPKALIY (SEQ ID NO: 691) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M273 | 147_157 | DIVMTQSPPTLSLSPGERVTLSCGAS (SEQ ID NO: 183) | RDVNTA (SEQ ID NO: 620) | VAWYQQKQGQAPRLLIY (SEQ ID NO: 690) | WAS (SEQ ID NO: 698) | TRHTGVPSRFGGGGSGTDFTLTISRLQPENFATYYC (SEQ ID NO: 680) | QHHYSSPWT (SEQ ID NO: 497) | FGGGTKLEMK (SEQ ID NO: 250) |
| M274 | 147_157 | DIVMTQSPASLSASVGETVTITCRAS (SEQ ID NO: 182) | ENIYSY (SEQ ID NO: 224) | LEWYQQKQGKSPQLLVY (SEQ ID NO: 413) | NAK (SEQ ID NO: 450) | TLAEGVPSRFSGSGSGTQFSLKINSLQPEDFGSYYC (SEQ ID NO: 670) | QHHYDTPYT (SEQ ID NO: 493) | FGGGTKLEIK (SEQ ID NO: 249) |
| M275 | 33_63 | DIVMTQSPASLSASVGETVTITCRAS (SEQ ID NO: 182) | ENSYSY (SEQ ID NO: 226) | LEWYQQKQGKSPQLLVY (SEQ ID NO: 413) | NAK (SEQ ID NO: 450) | TLAEGVPSRFSGSGSGTQFSLKINSLQPEDFGTYYC (SEQ ID NO: 671) | QHHYGTPYT (SEQ ID NO: 496) | FGGGTKLEIK (SEQ ID NO: 249) |
| M276 | 33_63 | DIQMTQSQKFMSTSVGDRVSVTCKAS (SEQ ID NO: 172) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M277 | 33_63 | DIQMTQSPASLSASVGETVTITCRAS (SEQ ID NO: 168) | ENIYSY (SEQ ID NO: 224) | LEWYQQKQGKSPQLLVY (SEQ ID NO: 413) | NAK (SEQ ID NO: 450) | TLVEGVPSRFSGSGSGTQFSLKINSLQPEDFGSYYC (SEQ ID NO: 678) | QHHYDTPYT (SEQ ID NO: 493) | FGGGTKLEIK (SEQ ID NO: 249) |
| M278 | 33_63 | DIVMTQSQKFMSTSVGDRVSVTCKAS (SEQ ID NO: 184) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSGDLAEYFC (SEQ ID NO: 722) | QQYNSYPYT (SEQ ID NO: 550) | FGGGTKLEIK (SEQ ID NO: 249) |
| M279 | 33_63 | MLVMTQTPLSLPVSLGDQASISCRSS (SEQ ID NO: 441) | QSLVHSNGNTY (SEQ ID NO: 571) | LHWYLQKPGQSPKLLIY (SEQ ID NO: 417) | KVS (SEQ ID NO: 406) | NRFSGVPDRFSVSGSGTDFTLKISRVEAEDLGVYFC (SEQ ID NO: 463) | SQSTHVPPT (SEQ ID NO: 645) | FGGGTKLEIK (SEQ ID NO: 249) |
| M280 | 33_63 | DVVMTQSQKFMSTSVGDRVSVTCKAS (SEQ ID NO: 206) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M281 | 33_63 | DIQMTQSQKFMSTSVGDRVSVTCKAS (SEQ ID NO: 172) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |

TABLE 14B-continued

| ID | Epi-tope | L FR1 AA | L CDR1 AA | L FR2 AA | L CDR2 AA | L FR3 AA | L CDR3 AA | L FR4 AA |
|---|---|---|---|---|---|---|---|---|
| M282 | 33_63 | DVQMTQSQKFMSTSVGDR VSVTCKAS (SEQ ID NO: 200) | QNVGTN (SEQ ID NO: 512) | VAWYQQKQGQS PKALIY (SEQ ID NO: 691) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M283 | 33_63 | DIVMTQSQKFMSTSVGDR VSVTCKAS (SEQ ID NO: 184) | QNVGTN (SEQ ID NO: 512) | VAWYQQKQGQS PKALIY (SEQ ID NO: 691) | SAS (SEQ ID NO: 637) | YRYSGVPDRFTGSGSGTDFTLTIS NVQSGDLAEYFC (SEQ ID NO: 722) | QQYNSYP YT (SEQ ID NO: 550) | FGGGTK LEIK (SEQ ID NO: 249) |
| M284 | 33_63 | DIQMTQSPASLSASVGET VTITCRAS (SEQ ID NO: 168) | ENSYSY (SEQ ID NO: 226) | LEWYQQKQGKS PQLLVY (SEQ ID NO: 413) | NAK (SEQ ID NO: 450) | TLAEGVPSRFSGSGSGTQFSLKIN SLQPEDFGTYYC (SEQ ID NO: 671) | QHHYGTP YT (SEQ ID NO: 496) | FGGGTK LEIK (SEQ ID NO: 249) |
| M285 | 33_63 | DIQMTQSQKFMSTSVGDR VSVTCKAS (SEQ ID NO: 172) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M286 | 33_63 | DIVLTQSQKFMSTSVGDR VSVTCKAS (SEQ ID NO: 172) | QNVGTN (SEQ ID NO: 512) | VAWYQQEPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M287 | 33_63 | DIQMTQSQKFMSTSVGDR VSVTCKAS (SEQ ID NO: 172) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEMK (SEQ ID NO: 250) |
| M288 | 33_63 | DIVLTQSQKFMSTSVGDR VSVTCKAS (SEQ ID NO: 180) | QNVGTN (SEQ ID NO: 512) | VAWYQQEPGQS PKALIY (SEQ ID NO: 685) | SAS (SEQ ID NO: 637) | YRYSGVPDRFTGSGSGTDFTLTIS NVQSEDLAKYFC (SEQ ID NO: 720) | QQYNSYP YT (SEQ ID NO: 550) | FGGGTK LEIK (SEQ ID NO: 249) |
| M289 | 33_63 | DIQMTQSPASLSASVGES VTLTCQAS (SEQ ID NO: 167) | DNIYSY (SEQ ID NO: 189) | LEWYQQKQGKS PQLLVY (SEQ ID NO: 413) | NAK (SEQ ID NO: 450) | TLAXGVPSRFXGSGSGTQFSLKIN SLQPEDFGSYYC (SEQ ID NO: 675) | QHHYGTP YT (SEQ ID NO: 496) | FGGGTK XEMK (SEQ ID NO: 253) |
| M290 | 33_63 | DIQMTQSQKFMSTSVGDR VSVTCKAS (SEQ ID NO: 172) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M291 | 33_63 | DIQMTQSQKFMSTSVGDR VSVTCKAS (SEQ ID NO: 172) | QNVGTN (SEQ ID NO: 512) | VAWYQQKPGQS PKALIY (SEQ ID NO: 689) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |
| M292 | 33_63 | DTTVTQSQKFMSTSVGDR VSVTCKAS (SEQ ID NO: 193) | QNVGTN (SEQ ID NO: 512) | VAWYQQKQGQS PKALIY (SEQ ID NO: 691) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEMK (SEQ ID NO: 250) |
| M293 | 33_63 | DIQMTQSQKFMSTSVGDR VSVTCKAS (SEQ ID NO: 172) | QNVGTN (SEQ ID NO: 512) | VAWYQQKQGQS PKALIY (SEQ ID NO: 691) | SAS (SEQ ID NO: 637) | YRYSGVPDRFTGSGSGTDFTLTIS NVQSEDLAEYFC (SEQ ID NO: 719) | QQYNSYP YT (SEQ ID NO: 550) | FGGGTK LEIK (SEQ ID NO: 249) |

TABLE 14B-continued

| ID | Epitope | L FR1 AA | L CDR1 AA | L FR2 AA | L CDR2 AA | L FR3 AA | L CDR3 AA | L FR4 AA |
|---|---|---|---|---|---|---|---|---|
| M294 | 33_63 | DVQMTQSQKFMSTSVGDRVSVTCKAS (SEQ ID NO: 200) | QNVGTN (SEQ ID NO: 512) | VAWYQQKQGQSPKALIY (SEQ ID NO: 691) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M295 | 33_63 | DVVMTQSPPSLSASVGETVTISCRAS (SEQ ID NO: 205) | GNVHNF (SEQ ID NO: 288) | LTWYQQKQGKSPQLLVY (SEQ ID NO: 430) | NAE (SEQ ID NO: 449) | TLADGVPSRFSGSGSRSQYSLMINSLQPEDFGTYYC (SEQ ID NO: 668) | QHFWNTPPT (SEQ ID NO: 492) | FGGGTKLEIK (SEQ ID NO: 249) |
| M296 | 44_56 | DTTVTQSQKFMSTSVGDRVSVTCKAS (SEQ ID NO: 193) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M297 | 44_56 | DVQMTQSQKFMSTSVGDRVSVTCKAS (SEQ ID NO: 200) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |
| M298 | 44_56 | DVVMTQSQKFMSTSVGDRVSVTCKAS (SEQ ID NO: 206) | QNVGTN (SEQ ID NO: 512) | VAWYQQKPGQSPKALIY (SEQ ID NO: 689) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEMK (SEQ ID NO: 250) |
| M299 | 44_56 | DTTVTQSQKFMSTSVGDRVSVTCKAS (SEQ ID NO: 193) | QNVGTN (SEQ ID NO: 512) | VAWYQQKPGQSPKALIY (SEQ ID NO: 689) | SAS (SEQ ID NO: 637) | YRYSGVPDRFTGSGSGTDFALTISNVQSEDLAEYFC (SEQ ID NO: 719) | QQYNSYPYT (SEQ ID NO: 550) | FGGGTKLEMK (SEQ ID NO: 250) |
| M300 | 44_56 | DVVLTQTPLSLPVSLGDQASISCRSS (SEQ ID NO: 202) | QSIVHSNGNTY (SEQ ID NO: 569) | LEWYLQRPGQSPKLLIY (SEQ ID NO: 410) | KVS (SEQ ID NO: 406) | NRFSGVPDRFSGSGSGTDFTLKISRVEAEDLGVYYC (SEQ ID NO: 461) | FQGSHVPPT (SEQ ID NO: 255) | FGGGTKLEIK (SEQ ID NO: 249) |
| M301 | 44_56 | DIVMTQSQKFMSTSVGDRVSVTCKAS (SEQ ID NO: 184) | QNVGIN (SEQ ID NO: 511) | VAWYQQKQGQSPKALIY (SEQ ID NO: 691) | SAS (SEQ ID NO: 637) | YRYSGVPDRFTGSGSGTDFTLTISNVQSEDLAEYFC (SEQ ID NO: 719) | QQYNSYPYT (SEQ ID NO: 550) | FGGGTKLEIK (SEQ ID NO: 249) |

Sequence analysis suggests that these antibodies derive from clonal lineages that may be grouped as indicated in Table 15A and Table 15B.

TABLE 15A

| # | Baits | CDRH1 | CDRH2 | CDRH3 |
|---|---|---|---|---|
| 1 | 147_156<br>147_157_J2<br>33_63_J1<br>33_63_J2<br>33_63_J3<br>44_56<br>44_56_J1<br>44_56_J2<br>6_130<br>6_163 | GFNIKDYY (SEQ ID NO: 265) | IDPDNGET (SEQ ID NO: 318) | TVFWYGNNYAGFAY (SEQ ID NO: 684) |
| 2 | 147_156<br>147 157J2<br>33_63_J1<br>33_63_J2<br>33_63_J3<br>44_56<br>44_56_J1 | GYTFTDYA (SEQ ID NO: 305)<br>GYTFTRYW (SEQ ID NO: 311)<br>GYSFTSYW | ISTYSGDA SEQ ID NO: 353)<br>INPRTDYTEYNQ (SEQ ID NO: 338)<br>ISTYSGDAIYNQ (SEQ ID NO: 354)<br>ISTYSGDVNYNQ | ARGVTFDI (SEQ ID NO: 120)<br>ARGVTFDY (SEQ ID NO: 122)<br>ARHGYFDY (SEQ ID NO: 124)<br>ARGVTFDS (SEQ ID NO: |

TABLE 15A-continued

| # | Baits | CDRH1 | CDRH2 | CDRH3 |
|---|---|---|---|---|
| | 44_56_J2<br>57_63<br>6_130<br>6_163<br>77_89 | (SEQ ID NO: 299)<br>GYTFSNYW (SEQ ID NO: 304)<br>GYTFTKYW (SEQ ID NO: 308)<br>GYTFNRFW (SEQ ID NO: 303)<br>GYTFTRFW (SEQ ID NO: 310) | (SEQ ID NO: 357)<br>ISTYSGDVSYNQ (SEQ ID NO: 358)<br>IHPSDSETRLNQ (SEQ ID NO: 322)<br>ILPGSGFTNYNE (SEQ ID NO: 331)<br>ISTYSGDALYNQ (SEQ ID NO: 355)<br>INPRTDYT (SEQ ID NO: 337)<br>ISTYSGDV (SEQ ID NO: 356)<br>INPNSDYI (SEQ ID NO: 335)<br>INTYSGDA (SEQ ID NO: 345)<br>INPSTDYI (SEQ ID NO: 340)<br>INPGSDYT (SEQ ID NO: 334)<br>INPSTGYI (SEQ ID NO: 341) | 121)<br>ARSRGIPFAY (SEQ ID NO: 133)<br>ARGGTSVVHFDY (SEQ ID NO: 109)<br>AIHGYFDY (SEQ ID NO: 57)<br>ARGVTSDS (SEQ ID NO: 123)<br>ARGTIIDY (SEQ ID NO: 114)<br>ARGVSFDY (SEQ ID NO: 119)<br>ARGVPFDY (SEQ ID NO: 117)<br>ATGVTFDY (SEQ ID NO: 148)<br>SRGGTSFVHFDY (SEQ ID NO: 646)<br>AXGVTFDY (SEQ ID NO: 155)<br>ARHXYFDY (SEQ ID NO: 125)<br>ARXVTFDY (SEQ ID NO: 144)<br>ATXVTFDS (SEQ ID NO: 152)<br>ARXGYFDY (SEQ ID NO: 143)<br>ARGTVVDY (SEQ ID NO: 115) |
| 3 | 6_163<br>33_63_J3<br>44_56_J2<br>147_157_J2<br>33_63_J1<br>33_63_J2<br>147_157_J1<br>44_56_J1<br>6_130 | GYTFTKYW (SEQ ID NO: 308)<br>GYTFTNYW (SEQ ID NO: 309) | IYPGGDYT (SEQ ID NO: 378)<br>IYPGGDYTNYNE (SEQ ID NO: 379)<br>IYPGGGYA (SEQ ID NO: 380)<br>IYPGGGYT (SEQ ID NO: 381)<br>IYPGGGYTNYNE (SEQ ID NO: 382) | ARVTPAS (SEQ ID NO: 139)<br>ARVTPSS (SEQ ID NO: 140)<br>ARITPAS (SEQ ID NO: 126)<br>ARVSPAS (SEQ ID NO: 138) |

TABLE 15B

| # | Baits | CDRL1 | CDRL2 | CDRL3 |
|---|---|---|---|---|
| 1 | 147_156<br>147_157_J2<br>33_63_J1<br>33_63_J2<br>33_63_J3<br>44_56<br>44_56_J1<br>44_56_J2<br>6_130<br>6_163 | QSIVHSNGNTY (SEQ ID NO: 569)<br>ENIYSY (SEQ ID NO: 224)<br>QDISNY (SEQ ID NO: 485) | KVS (SEQ ID NO: 406)<br>NAK (SEQ ID NO: 450)<br>HTS (SEQ ID NO: 317) | FQGSHVPPT (SEQ ID NO: 255)<br>FQGSHVPT (SEQ ID NO: 257)<br>QHHYGSPYT (SEQ ID NO: 495)<br>QQSNSLPPT (SEQ ID NO: 529) |
| 2 | 147_156<br>147_157_J2<br>33_63_J1<br>33_63_J2<br>33_63_J3<br>44_56<br>44_56_J1<br>44_56_J2<br>57_63<br>6_130<br>6_163<br>77_89 | ENIYSY (SEQ ID NO: 224)<br>QDISNY (SEQ ID NO: 485)<br>ENSYSY (SEQ ID NO: 226)<br>QNVGTN (SEQ ID NO: 512)<br>QSVNND (SEQ ID NO: 572)<br>QYISNY (SEQ ID NO: 617)<br>QDINSY (SEQ ID NO: 484)<br>QDINNF (SEQ ID NO: 481)<br>ENSYNY (SEQ | NAK (SEQ ID NO: 450)<br>YTS (SEQ ID NO: 727)<br>HTS (SEQ ID NO: 317)<br>SAS (SEQ ID NO: 637)<br>YAS (SEQ ID NO: 717)<br>RAN (SEQ ID NO: 618)<br>WAS (SEQ ID NO: 698) | QHHYDTPYT (SEQ ID NO: 493)<br>QHHYGSPYT (SEQ ID NO: 495)<br>QQGNTLPPT (SEQ ID NO: 520)<br>QQSNTLPPT (SEQ ID NO: 530)<br>QHHYGTPYT (SEQ ID NO: 496)<br>QQHYGTPYT (SEQ ID NO: 523)<br>QQSNSLPPT (SEQ ID NO: 529)<br>QQYNSYPLT (SEQ ID NO: 549)<br>QQAYWSPYT (SEQ |

TABLE 15B-continued

| # | Baits | CDRL1 | CDRL2 | CDRL3 |
|---|---|---|---|---|
| | | ID NO: 225)<br>ENIHSY (SEQ ID NO: 222)<br>QDVNTA (SEQ ID NO: 486)<br>QDINRY (SEQ ID NO: 483) | | ID NO: 517)<br>QHHYGIPYT (SEQ ID NO: 494)<br>LQYDEFPYT (SEQ ID NO: 425)<br>LQYDEFPWT (SEQ ID NO: 424)<br>QHHYSTPYT (SEQ ID NO: 498)<br>QQGNTLPLT (SEQ ID NO: 519)<br>QQHYSSPWT (SEQ ID NO: 524)<br>QQYNSYPYT (SEQ ID NO: 550)<br>QQGNTLPWT (SEQ ID NO: 522)<br>QQGNTLPST (SEQ ID NO: 521) |
| 3 | 6_163<br>33_63_J3<br>44_56_J2<br>147_157_J2<br>33_63_J1<br>33_63_J2<br>147_157_J1<br>44_56_J1<br>6_130<br>77_89 | QNVGTN (SEQ ID NO: 512)<br>ENIYNY (SEQ ID NO: 223)<br>ENIYSY (SEQ ID NO: 224)<br>QNVGIN (SEQ ID NO: 511)<br>QDISNY (SEQ ID NO: 485)<br>ENSYSY (SEQ ID NO: 226)<br>RDVNTA (SEQ ID NO: 620)<br>QSLVHSNGNTY (SEQ ID NO: 571)<br>DNIYSY (SEQ ID NO: 189)<br>GNVHNF (SEQ ID NO: 288)<br>QSIVHSNGNTY (SEQ ID NO: 569) | SAS (SEQ ID NO: 637)<br>NAK (SEQ ID NO: 450)<br>HTS (SEQ ID NO: 317)<br>WAS (SEQ ID NO: 698)<br>KVS (SEQ ID NO: 406)<br>NAE (SEQ ID NO: 449) | HQYNNYPYT (SEQ ID NO: 316)<br>QQYNSYPYT (SEQ ID NO: 550)<br>QQYNTYPYT (SEQ ID NO: 552)<br>QHHYGTPYT (SEQ ID NO: 496)<br>QHHYDTPYT (SEQ ID NO: 493)<br>QQYNNYPYT (SEQ ID NO: 546)<br>QQYNSYPLT (SEQ ID NO: 549)<br>QQSNSLPPT (SEQ ID NO: 529)<br>QHHYSSPWT (SEQ ID NO: 497)<br>SQSTHVPPT (SEQ ID NO: 645)<br>QHFWNTPPT (SEQ ID NO: 492)<br>FQGSHVPPT (SEQ ID NO: 255) |

What is claimed is:

1. An engineered polypeptide, wherein the engineered polypeptide shares at least 80% structural and/or dynamic identity to an α-subunit of an IL-2 receptor (CD25) reference target, wherein the CD25 reference target is a portion of CD25 selected from:

| Reference Target No. | CD25 Residues | Sequence |
|---|---|---|
| 1 | 55-63 | SWDNQCQCT (SEQ ID NO: 22) |
| 2 | 13-20:127-132 | ATFKAMA (SEQ ID NO: 23):MVYYQC (SEQ ID NO: 24) |
| 3 | 5-17 | DDPPEIPHATFKA (SEQ ID NO: 25) |
| 4 | 5-11:156-163 | DDPPEIP (SEQ ID NO: 26):RWTQPQLI (SEQ ID NO: 27) |
| 5 | 77-89 | QPEEQKERKTTEM (SEQ ID NO: 28) |
| 6 | 147-157 | VCKMTHGKTRW (SEQ ID NO: 29) |
| 7 | 11-14 | IPHA (SEQ ID NO: 30). |

2. The engineered polypeptide of claim 1, wherein the engineered polypeptide shares at least 80% sequence identity to an amino-acid sequence selected from:

(SEQ ID NO: 1)
CDCQAQWTPGMRAPGYDPYCLNC (SEQ ID NO: 2)
MVYCQPDCTAKCMHGCDRDTMKECCDRLK (SEQ ID NO: 3)
DDCPEVPHATFKGPGQKWEGPGGGDCSK (SEQ ID NO: 4)
DDCIEVPGPAECAERACRAQEERQRQPQCI (SEQ ID NO: 5)
AEEEKIKIEQKERKTTIKLAKEAK (SEQ ID NO: 6)
CHLQIMTHGKIIYVPC (SEQ ID NO: 7)
DDGDRCAKEHEIPHATGEECQKRDKS (SEQ ID NO: 8)
CKQLVIYFTGNSSHSSVFYIYYDC (SEQ ID NO: 9)
GSGDEDCKKFQSDDNWENYTSTRHLTFCDEKRS (SEQ ID NO: 10)
GSGNEEIEKKIKDCTGNSSHSSWEEALECALKK (SEQ ID NO: 11)
GSGDERIERLIKECTGNSSHSSWEEALECALRR (SEQ ID NO: 12)
GSGSHPCAYWRWVIKMTHGKTRWVLELVFCYRD (SEQ ID NO: 13)
GSGKCEEEAKKIASKMTHGKTREEEAEEYLKKC

-continued (SEQ ID NO: 14)
GSGDDESEKRTTERDTRKCTKAKANDNQCQPTE (SEQ ID NO: 15)
GSGSSEWDKWVEEWYKKMCTEAKKNDNQCQPTK (SEQ ID NO: 16)
GSGQCRVWVFRNGDKILYIYEDCDNDNQHQQTL.

3. The engineered polypeptide of claim 1, wherein the structural and/or dynamic identity to the CD25 reference target is determined using the structure of CD25 deposited at Protein Data Bank (PDB) ID NO: 2ERJ, chain A.

4. The engineered polypeptide of claim 1, wherein the engineered polypeptide comprises an N-terminal modification or a C-terminal modification, optionally an N-terminal Biotin-$PEG_2$- or a C-terminal-GSGSGK-Biotin (SEQ ID NO: 846).

5. The engineered polypeptide of claim 1, wherein the CD25 reference target-derived constraints are independently selected from the group consisting of: atomic distances; atomic fluctuations; atomic energies; chemical descriptors; solvent exposures; amino acid sequence similarity; bioinformatic descriptors; non-covalent bonding propensity; phi angles; psi angles; van der Waals radii; secondary structure propensity; amino acid adjacency; and amino acid contact.

6. An engineered polypeptide designed to mimic a selected CD25 epitope, wherein the engineered polypeptide shares at least 80% sequence identity to an amino-acid sequence selected from:

(SEQ ID NO: 1)
CDCQAQWTPGMRAPGYDPYCLNC (SEQ ID NO: 2)
MVYCQPDCTAKCMHGCDRDTMKECCDRLK (SEQ ID NO: 3)
DDCPEVPHATFKGPGQKWEGPGGGDCSK (SEQ ID NO: 4)
DDCIEVPGPAECAERACRAQEERQRQPQCI (SEQ ID NO: 5)
AEEEKIKIEQKERKTTIKLAKEAK (SEQ ID NO: 6)
CHLQIMTHGKIIYVPC (SEQ ID NO: 7)
DDGDRCAKEHEIPHATGEECQKRDKS (SEQ ID NO: 8)
CKQLVIYFTGNSSHSSVFYIYYDC (SEQ ID NO: 9)
GSGDEDCKKFQSDDNWENYTSTRHLTFCDEKRS (SEQ ID NO: 10)
GSGNEEIEKKIKDCTGNSSHSSWEEALECALKK (SEQ ID NO: 11)
GSGDERIERLIKECTGNSSHSSWEEALECALRR (SEQ ID NO: 12)
GSGSHPCAYWRWVIKMTHGKTRWVLELVFCYRD (SEQ ID NO: 13)
GSGKCEEEAKKIASKMTHGKTREEEAEEYLKKC (SEQ ID NO: 14)
GSGDDESEKRTTERDTRKCTKAKANDNQCQPTE (SEQ ID NO: 15)
GSGSSEWDKWVEEWYKKMCTEAKKNDNQCQPTK

-continued (SEQ ID NO: 16)
GSGQCRVWVFRNGDKILYIYEDCDNDNQHQQTL.

7. The engineered polypeptide of claim 6, wherein the engineered polypeptide shares at least 46% structural and/or dynamic identity to a CD25 reference target, wherein the CD25 reference target is a portion of CD25 selected from:

| Reference Target No. | CD25 Residues | Sequence |
|---|---|---|
| 1 | 55-63 | SWDNQCQCT (SEQ ID NO: 22) |
| 2 | 13-20:127-132 | ATFKAMA (SEQ ID NO: 23) . . . MVYYQC (SEQ ID NO: 24) |
| 3 | 5-17 | DDPPEIPHATFKA (SEQ ID NO: 25) |
| 4 | 5-11:156-163 | DDPPEIP (SEQ ID NO: 26) . . . RWTQPQLI (SEQ ID NO: 27) |
| 5 | 77-89 | QPEEQKERKTTEM (SEQ ID NO: 28) |
| 6 | 147-157 | VCKMTHGKTRW (SEQ ID NO: 29) |
| 7 | 11-14 | IPHA (SEQ ID NO: 30) |
| 8 | 44-56 | YMLCTGSSSHSSW (SEQ ID NO: 31). |

8. The engineered polypeptide of claim 6, wherein between 10% to 98% of the amino acids of the engineered polypeptide meet one or more CD25 reference target-derived constraints, wherein the amino acids of the polypeptide that meet the one or more reference target-derived constraints are the underlined residues.

9. The engineered polypeptide of claim 8, wherein the amino acids that meet the one or more CD25 reference target-derived constraints have less than 8.0 Å backbone root-mean-square deviation (RSMD) structural homology with the CD25 reference target.

10. The engineered polypeptide of claim 8, wherein the amino acids that meet the one or more CD25 reference target-derived constraints have a van der Waals surface area overlap with the reference of between 30 $Å^2$ to 3000 $Å^2$.

* * * * *